US011859189B2

(12) United States Patent
Carlin et al.

(10) Patent No.: US 11,859,189 B2
(45) Date of Patent: Jan. 2, 2024

(54) RECOMBINANT BACTERIA ENGINEERED TO TREAT DISEASES ASSOCIATED WITH METHIONINE METABOLISM AND METHODS OF USE THEREOF

(71) Applicants: Synlogic Operating Company, Inc., Cambridge, MA (US); Ginkgo Bioworks, Inc., Boston, MA (US)

(72) Inventors: Dylan Alexander Carlin, Jamaica Plain, MA (US); Vincent M. Isabella, Medford, MA (US); Jonathan McMurry, Boston, MA (US); Theodore Carlton Moore, III, Cambridge, MA (US); Mylene Perreault, Lexington, MA (US); Nathan Schmidt, Milton, MA (US); Mark Simon, Gainesville, FL (US)

(73) Assignees: Synlogic Operating Company, Inc., Cambridge, MA (US); Ginkgo Bioworks, Inc., Boston, MA (US)

( * ) Notice: Subject to any disclaimer, the term of this patent is extended or adjusted under 35 U.S.C. 154(b) by 0 days.

(21) Appl. No.: 17/819,086

(22) Filed: Aug. 11, 2022

(65) Prior Publication Data

US 2023/0063093 A1 Mar. 2, 2023

Related U.S. Application Data

(60) Provisional application No. 63/231,773, filed on Aug. 11, 2021, provisional application No. 63/281,178, filed on Nov. 19, 2021, provisional application No. 63/282,319, filed on Nov. 23, 2021, provisional application No. 63/326,323, filed on Apr. 1, 2022, provisional application No. 63/355,819, filed on Jun. 27, 2022.

(51) Int. Cl.

| | |
|---|---|
| ***C12N 9/88*** | (2006.01) |
| ***C12N 15/52*** | (2006.01) |
| ***A61K 35/741*** | (2015.01) |
| ***C12N 15/70*** | (2006.01) |
| ***C07K 14/245*** | (2006.01) |

(52) U.S. Cl.

CPC ............ *C12N 15/52* (2013.01); *A61K 35/741* (2013.01); *C07K 14/245* (2013.01); *C12N 9/88* (2013.01); *C12N 15/70* (2013.01); *C12Y 401/01057* (2013.01); *C12Y 404/01011* (2013.01)

(58) Field of Classification Search

CPC ....... C12N 9/0014; C12N 9/80; C12P 13/001; C12Y 401/01057; C12Y 404/01011

USPC ................................................. 435/189, 191

See application file for complete search history.

(56) References Cited

U.S. PATENT DOCUMENTS

| | | | |
|---|---|---|---|
| 2008/0005809 | A1 | 1/2008 | Bledig et al. |
| 2009/0100536 | A1 | 4/2009 | Adams et al. |
| 2023/0090705 | A1 | 3/2023 | Isabella et al. |

FOREIGN PATENT DOCUMENTS

| | | | |
|---|---|---|---|
| WO | 2006/069610 | A2 | 7/2006 |
| WO | 2009/127671 | A1 | 10/2009 |
| WO | 2017/123676 | A1 | 7/2017 |
| WO | 2021/163421 | A1 | 8/2021 |

OTHER PUBLICATIONS

By Masaya et al., (J. Biochem. 2017 161, pp. 389-398.*
Okawa et al., (Protein Sci. Jan. 2021, 30:pp. 663-677.*
Nguyen et al. PNAS 2018, 115,45, pp. 1-9.*
Shilling et al. Commun biology , 2020, pp. 1-8.*
Beimfohr ( Int. J. bacterial 2016, pp. 1-10.*
U.S. Appl. No. 17/798,586, filed Aug. 10, 2022, 2023-0090705.
Feng et al., Discovery and characterization of BIsE, a radical S-adenosyl-L-methionine decarboxylase involved in the plasticidin S biosynthetic pathway. PLoS One. Jul. 18, 2013;8(7):e68545, 12 pages.
GenBank Accession No. AB970471, *Streptomyces* sp. 590 KI-2014 gene for L-methionine decarboxylase, complete cds. 2 pages, May 28, 2015.
Liu et al., YjeH is a Novel Exporter of I-Methionine and Branched-Chain Amino Acids in *Escherichia coli*. Appl Environ Microbiol. Nov. 2015; 81(22):7753-66.
International Search Report and Written Opinion for Application No. PCT/US2021/017775, dated May 4, 2021, 11 pages.
International Search Report and Written Opinion for Application No. PCT/Us2022/074826, dated Feb. 14, 2023, 13 pages.

* cited by examiner

*Primary Examiner* — Robert B Mondesi
*Assistant Examiner* — Mohammad Y Meah
(74) *Attorney, Agent, or Firm* — McCarter & English, LLP; Marcie B. Clarke

(57) ABSTRACT

The present disclosure provides host cells, e.g., bacterial cells, that comprise a methionine decarboxylase enzyme for the treatment of diseases and disorders associated with methionine metabolism in a subject. The disclosure further provides pharmaceutical compositions and methods of treating disorders associated with methionine metabolism, such as homocystinuria.

14 Claims, 52 Drawing Sheets

Specification includes a Sequence Listing.

FIG. 1: Homocystinuria Disease Overview

- Homocystinuria - a disorder of methionine metabolism caused by defect in cystathionine β-synthase (CBS)
- Leads to accumulation of homocysteine in blood and urine.
- Homocysteine is toxic to cells. Normal blood levels range between 5-10 μM, 15-20 μM in mild homocystinuria and up to 500 μM in hyperhomocysteinemia.
- Major disease symptoms: arteriosclerosis, skeletal abnormalities, lens dislocation, mental retardation, thrombosis, behavioral disorders and intellectual disabilities.
- Current treatments include vitamin $B_6$, vitamin $B_{12}$, folate, betaine and methionine restricted diet.

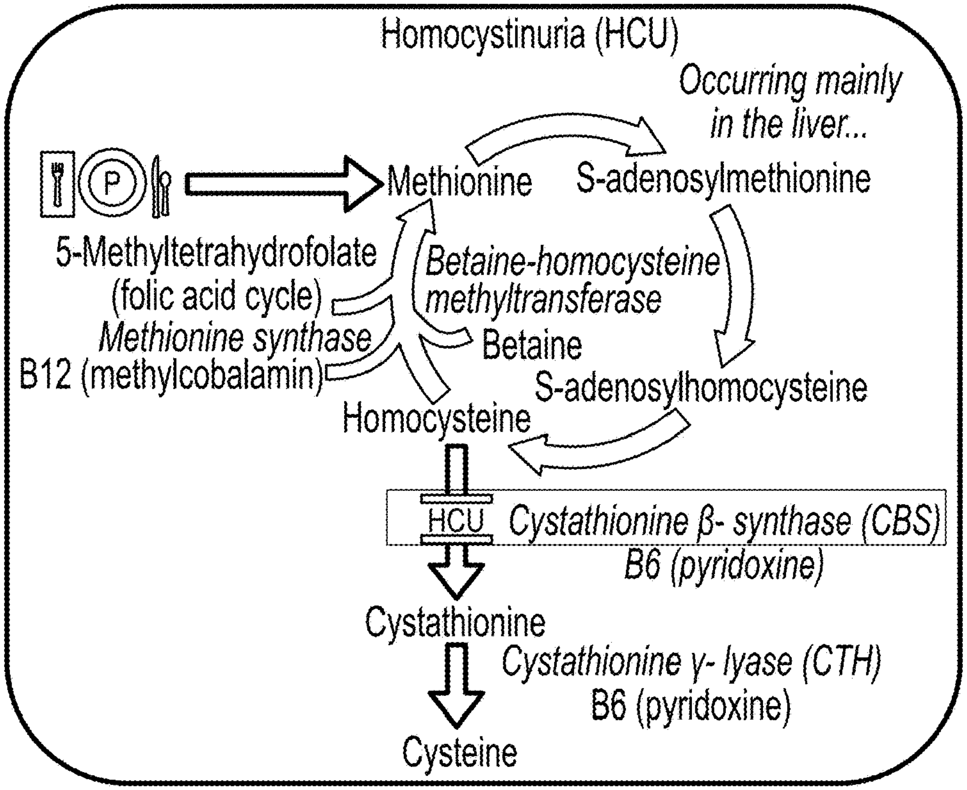

FIG. 2

Synthetic biology for Met consumption in EcN

- Met degradation pathways:

| Pathway |
| --- |
| Methionine-γ-Lyase |
| Meterologous expression of mammalian Met cycle |
| Methionine Decarboxylase (MetDC) |

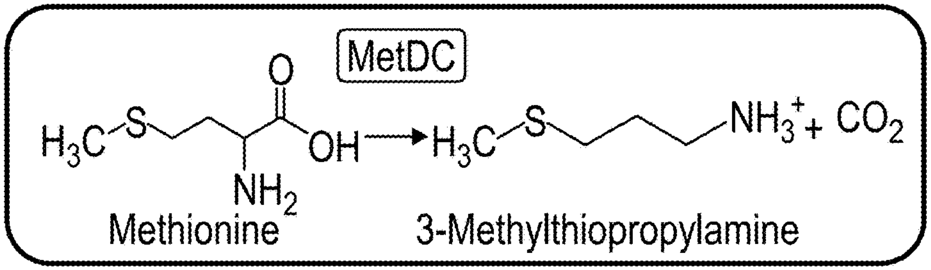

Methionine 3-Methylthiopropylamine

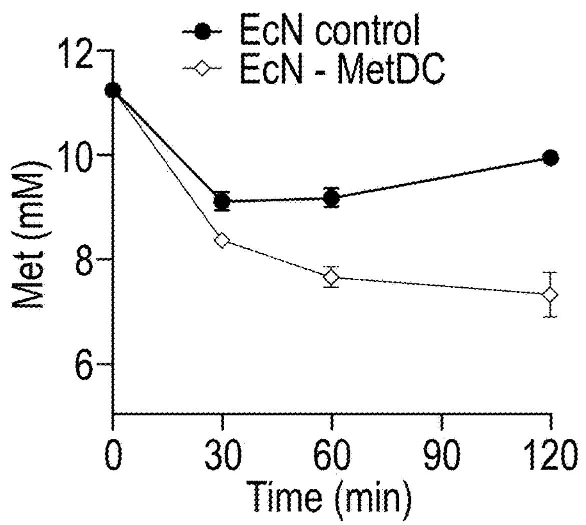

- Methionine decarboxylase from *Streptomyces sp.*590 shows some activity against Met in vitro
- Characteristic odor produced from MetDC-expressing strain (not offensive as is methyl mercaptan)

MetDC-expressing EcN degrade Met

MetDC-expressing EcN (+ accessory genes) degrade Met

Increased Methionine Consumption *In Vitro*

1° MetDC Screen

2° MetDC Screen cysteine cysteine cystine

Slc-/- Male 0.12%

Slc-/- Male 0.62%

RECOMBINANT BACTERIA ENGINEERED TO TREAT DISEASES ASSOCIATED WITH METHIONINE METABOLISM AND METHODS OF USE THEREOF

RELATED APPLICATIONS

The instant application claims priority to U.S. Provisional Application No. 63/231,773, filed on Aug. 11, 2021; U.S. Provisional Application No. 63/281,178 filed Nov. 19, 2021; U.S. Provisional Application No. 63/282,319 filed Nov. 23, 2021; U.S. Provisional Application No. 63/326,323, filed on Apr. 1, 2022; and U.S. Provisional Application No. 63/355,819, filed on Jun. 27, 2022. The entire contents of each of the foregoing applications are expressly incorporated by reference herein.

SEQUENCE LISTING

The instant application contains a Sequence Listing which has been submitted electronically in XML format and is hereby incorporated by reference in its entirety. Said XML copy, created on Aug. 8, 2022, is named 126046-07020_SL.XML and is 750,033 bytes in size.

BACKGROUND

In healthy individuals, acquired dietary methionine is catabolized via the trans-sulfuration pathway, where mammalian cells catabolize methionine into homocysteine via S-Adenosyl-methionine and S-Adenosyl-homocysteine. The cystathionine β-synthase (CBS) enzyme then catalyzes the conversion of homocysteine to cystathionine using vitamin $B_6$ (pyridoxal 5'-phosphate, PLP) as a co-enzyme. Another PLP-dependent enzyme, cystathionine γ-lyase, converts cystathionine into cysteine. Genetic mutations in one or more of these genes can cause metabolic perturbation in the trans-sulfuration pathway that leads to homocystinuria, also known as cystathionine beta synthase deficiency ("CBS deficiency") (Garland et al., *J. Ped. Child Health,* 4(8):557-562, 1999). In homocystinuria patients, CBS enzyme deficiency causes elevated levels of homocysteine and low levels of cystathionine in the serum, which leads to excretion of homocysteine into the urine. Inherited homocystinuria, a serious life-threatening disease, results in high levels of homocysteine in plasma, tissues and urine. Some of the characteristics of the most common form of homocystinuria are myopia (nearsightedness), lens dislocation, higher risk of thromboembolism, and skeletal abnormalities. Homocystinuria may also cause developmental delay/intellectual disability (Mudd et al., *Am. J. Hum. Genet.,* 37:1-31, 1985).

A subpopulation of patients with homocystinuria can be treated with vitamin $B_6$ to increase the residual activity of the CBS enzyme. The $B_6$ non-responsive patients have to drastically limit the intake of dietary methionine to lower the levels of serum homocysteine. Compliance with a life-long low protein diet combined with methionine-free formula, is often poor, especially among the adults (Gupta et al., *J. Inherit Metab. Dis.,* 2016, 39(1):3946; Mudd et al., *Am. J. Hum. Genet.,* 37:1-31, 1985; Orgeron et al., *Prog. Mol. Biol. Transl. Sci.,* 2014, 121:351-376). Hence, other options for treating homocystinuria are needed.

SUMMARY

The present disclosure provides novel optimized enzymes and host cells, e.g., recombinant microorganisms, e.g., bacteria, that have been engineered with optimized genetic circuitry, which allows the recombinant microorganism to have improved methionine consumption and/or 3-MTP production. In particular, the host cells, e.g., recombinant microorganisms, disclosed herein have been engineered to comprise gene sequences encoding one or more optimized methionine catabolism enzymes, e.g., methionine decarboxylase (MetDC) enzymes, and/or one or more methionine importer(s), e.g., MetP or MetNIQ. These optimized host cells, e.g., recombinant microorganisms, demonstrate surprising therapeutic efficacy for modulating and treating diseases associated with methionine metabolism, such as homocystinuria, cystinuria, primary and secondary hypermethioninemia.

In one aspect, disclosed herein is a host cell comprising a heterologous methionine catabolism enzyme gene operably linked to a promoter, wherein the heterologous gene encodes a polypeptide that has at least 90%, 91%, 92%, 93%, 94%, 95%, 96%, 97%, 98%, or 99% identity to, comprises, or consists of any one of SEQ ID NOs: 1053, 1048, 1049, 1050, 1051, 1052, 1053, 1054, 1055, 1124, 1126, or 1128. In one embodiment, the heterologous methionine catabolism enzyme gene is a methionine decarboxylase (metDC) gene that encodes a methionine decarboxylase (MetDC) enzyme. In another embodiment, the heterologous methionine catabolism enzyme gene is a leucine decarboxylase (leuDC) gene that encodes a leucine decarboxylase (LeuDC) enzyme, e.g., that has been modified versus a wild-type LeuDC enzyme to have methionine decarboxylase activity.

In another aspect, the disclosure provides a recombinant bacterial cell comprising a heterologous methionine decarboxylase (metDC) gene operably linked to a promoter, wherein the heterologous metDC gene encodes a polypeptide that has at least 90%, 91%, 92%, 93%, 94%, 95%, 96%, 97%, 98%, or 99% identity to, comprises, or consists of any one of SEQ ID NOs: 1053, 1048, 1049, 1050, 1051, 1052, 1053, 1054, 1055, 1124, 1126, or 1128.

In one aspect, disclosed herein is a host cell comprising a heterologous methionine catabolism enzyme gene operably linked to a promoter, wherein the heterologous metDC gene comprises a sequence that has at least 90%, 91%, 92%, 93%, 94%, 95%, 96%, 97%, 98%, or 99% identity to, comprises, or consists of any one of SEQ ID NOs: 1003, 1018, 1034, 1035, 1036, 1037, 1038, 1039, 1040, 1123, 1125, or 1127. In one embodiment, the heterologous methionine catabolism enzyme gene is a methionine decarboxylase (metDC) gene that encodes a methionine decarboxylase (MetDC) enzyme. In another embodiment, the heterologous methionine catabolism enzyme gene is a leucine decarboxylase (leuDC) gene that encodes a leucine decarboxylase (LeuDC) enzyme, e.g., that has been modified versus a wild-type LeuDC enzyme to have methionine decarboxylase activity.

In another aspect, the disclosure provides a recombinant bacterial cell comprising a heterologous methionine decarboxylase (metDC) gene operably linked to a promoter, wherein the heterologous metDC gene comprises a sequence that has at least 90%, 91%, 92%, 93%, 94%, 95%, 96%, 97%, 98%, or 99% identity to, comprises, or consists of any one of SEQ ID NOs: 1003, 1018, 1034, 1035, 1036, 1037, 1038, 1039, 1040, 1123, 1125, or 1127.

In one embodiment, the recombinant bacterial cell further comprising a heterologous gene encoding a methionine importer. In one embodiment, the heterologous gene encoding the methionine importer is a metP gene. In one embodiment, the heterologous metP gene encodes a polypeptide comprising a sequence having at least 90%, 91%, 92%, 93%, 94%, 95%, 96%, 97%, 98%, or 99% identity to, comprises, or consists of any one of SEQ ID NOs: 1056, 1057, 1061, 1130 or 1132. In one embodiment, the heterologous metP gene comprises a sequence having at least 90%, 91%, 92%, 93%, 94%, 95%, 96%, 97%, 98%, or 99% identity to, comprises, or consists of any one of SEQ ID NO: 1041, 1042, 1044, 1129 or 1131.

In one embodiment, the heterologous gene encoding the methionine importer is an metNIQ gene, wherein the metNIQ gene encodes a MetN protein, a MetI protein, and a MetQ protein. In one embodiment, the heterologous metNIQ gene comprises a sequence having at least 90%, 91%, 92%, 93%, 94%, 95%, 96%, 97%, 98%, or 99% identity to, comprises, or consists of any one of SEQ ID NOs: 1043, 1045, 1046, or 1047. In one embodiment, the MetN protein comprises a sequence having at least 90%, 91%, 92%, 93%, 94%, 95%, 96%, 97%, 98%, or 99% identity to, comprises, or consists of any one of SEQ ID NOs: 1062, 1063, or 1058; wherein the MetI protein comprises a sequence having at least 90%, 91%, 92%, 93%, 94%, 95%, 96%, 97%, 98%, or 99% identity to, comprises, or consists of SEQ ID NO: 1059; and wherein the MetQ protein comprises a sequence having at least 90%, 91%, 92%, 93%, 94%, 95%, 96%, 97%, 98%, or 99% identity to, comprises, or consists of SEQ ID NO: 1060.

In another aspect, the disclosure provides a recombinant bacterial cell comprising a heterologous metNIQ gene operably linked to a promoter, wherein the metNIQ gene encodes a MetN protein, a MetI protein, and a MetQ protein, wherein the MetN protein has a sequence that has at least 90%, 91%, 92%, 93%, 94%, 95%, 96%, 97%, 98%, 99% identity to, comprises, or consists of SEQ ID NO: 1062 or 1063; wherein the MetI protein has a sequence that has at least 90%, 91%, 92%, 93%, 94%, 95%, 96%, 97%, 98%, 99% identity to, comprises, or consists of SEQ ID NO: 1059, and wherein the MetQ protein has a sequence that has at least 90%, 91%, 92%, 93%, 94%, 95%, 96%, 97%, 98%, 99% identity to, comprises, or consists of SEQ ID NO: 1060.

In one embodiment, the heterologous metNIQ gene comprises a sequence having at least 90%, 91%, 92%, 93%, 94%, 95%, 96%, 97%, 98%, or 99% identity to, comprises, or consists of any one of SEQ ID NOs: 1043, 1045, 1046, or 1047.

In one embodiment, the recombinant bacterial cell further comprising a heterologous methionine decarboxylase (metDC) gene that encodes a MetDC protein. In one embodiment, the MetDC protein has a sequence that has at least 90%, 91%, 92%, 93%, 94%, 95%, 96%, 97%, 98%, or 99% identity to, comprises, or consists of any one of SEQ ID NOs: 1048, 1049, 1050, 1051, 1052, 1053, 1054, 1055, 1124, 1126, or 1128. In one embodiment, the heterologous metDC gene comprises a sequence having at least 90%, 91%, 92%, 93%, 94%, 95%, 96%, 97%, 98%, or 99% identity to, comprises, or consists of any one of SEQ ID NOs: 1003, 1018, 1034, 1035, 1036, 1037, 1038, 1039, 1040, 1123, 1125, or 1127.

In one embodiment, the recombinant bacterial cell further comprising genetic modification that reduces export of methionine from the bacterial cell. In one embodiment, the genetic modification is a knock-out of an endogenous methionine efflux pump. In one embodiment, the endogenous methionine efflux pump is encoded by a yjeH gene. In one embodiment, the yjeH gene comprises a sequence having at least 90%, 91%, 92%, 93%, 94%, 95%, 96%, 97%, 98%, or 99% identity to, comprises, or consists of SEQ ID NO: 1014.

In one embodiment, the recombinant bacterial cell further comprising an insertion, deletion or mutation of an endogenous phage gene. In one embodiment, the insertion, deletion or mutation is a deletion of the endogenous phage gene comprising a sequence of SEQ ID NO: 1064.

In one embodiment, the recombinant bacterial cell further comprising a modified endogenous colibactin island. In one embodiment, the modified endogenous colibactin island comprises one or more modified clb sequences selected from the group consisting of clbA (SEQ ID NO: 1065), clbB (SEQ ID NO: 1066), clbC (SEQ ID NO: 1067), clbD (SEQ ID NO: 1068), clbE (SEQ ID NO: 1069), clbF (SEQ ID NO: 1070), clbG (SEQ ID NO: 1071), clbH (SEQ ID NO: 1072), clbI (SEQ ID NO: 1073), clbJ (SEQ ID NO: 1074), clbK (SEQ ID NO: 1075), clbL (SEQ ID NO: 1076), clbM (SEQ ID NO: 1077), clbN (SEQ ID NO: 1078), cibO (SEQ ID NO: 1079), clbP (SEQ ID NO: 1080), clbQ (SEQ ID NO: 1081), clbR (SEQ ID NO: 1082), and clbS (SEQ ID NO: 1803). In one embodiment, the modified endogenous colibactin island comprises a deletion of clbA (SEQ ID NO: 1065), clbB (SEQ ID NO: 1066), clbC (SEQ ID NO: 1067), clbD (SEQ ID NO: 1068), clbE (SEQ ID NO: 1069), clbF (SEQ ID NO: 1070), clbG (SEQ ID NO: 1071), clbH (SEQ ID NO: 1072), clbI (SEQ ID NO: 1073), clbJ (SEQ ID NO: 1074), clbK (SEQ ID NO: 1075), clbL (SEQ ID NO: 1076), clbM (SEQ ID NO: 1077), clbN (SEQ ID NO: 1078), cibO (SEQ ID NO: 1079), clbP (SEQ ID NO: 1080), clbQ (SEQ ID NO: 1081), and clbR (SEQ ID NO: 1082).

In one embodiment, the recombinant bacterial cell further comprising an auxotrophic modification. In one embodiment, the auxotrophy is a modification or deletion in the dapA gene.

In one embodiment, the recombinant bacterial cell comprises two or three copies of the heterologous metDC gene.

In one embodiment, the promoter is an inducible promoter. In one embodiment, the inducible promoter is directly or indirectly induced by environmental conditions specific to the gut of a human. In one embodiment, the inducible promoter is an IPTG-inducible promoter. In one embodiment, the heterologous gene is located on a plasmid or a chromosome in the bacterial cell.

In another aspect, the disclosure provides a recombinant bacterial cell comprising: a heterologous methionine catabolism enzyme gene, e.g., a methionine decarboxylase (metDC) gene, operably linked to a promoter, wherein the heterologous metDC gene encodes a polypeptide that has at least 90%, 91%, 92%, 93%, 94%, 95%, 96%, 97%, 98%, or 99% identity to, comprises, or consists of any one of SEQ ID NOs: 1048, 1049, 1050, 1051, 1052, 1053, 1054, 1055, 1124, 1126, or 1128, a heterologous gene encoding a methionine importer, wherein the heterologous gene encoding the methionine importer is a metP gene, and wherein the metP gene encodes a polypeptide having at least 90%, 91%, 92%, 93%, 94%, 95%, 96%, 97%, 98%, or 99% identity to, comprises, or consists of any one of a polypeptide encoded by SEQ ID NOs: 1056, 1057, 1061, 1130 or 1132, a knock-out of an endogenous methionine efflux pump, wherein the endogenous methionine efflux pump is encoded by a yjeH gene, a phage deletion, and a ΔdapA auxotrophy.

In another aspect, the disclosure provides a recombinant bacterial cell comprising: a heterologous methionine catabolism enzyme gene, e.g., a methionine decarboxylase (metDC) gene, operably linked to a promoter, wherein the heterologous metDC gene comprises a sequence that has at least 90%, 91%, 92%, 93%, 94%, 95%, 96%, 97%, 98%, or 99% identity to, comprises, or consists of any one of SEQ ID NOs: 1003, 1018, 1034, 1035, 1036, 1037, 1038, 1039, 1040, 1123, 1125, or 1127, a heterologous gene encoding a methionine importer, wherein the heterologous gene encoding the methionine importer is a metP gene, and wherein the metP gene comprises a sequence having at least 90%, 91%, 92%, 93%, 94%, 95%, 96%, 97%, 98%, or 99% identity to, comprises, or consists of any one of SEQ ID NOs: 1041, 1042, 1044, 1129 or 1131, a knock-out of an endogenous methionine efflux pump, wherein the endogenous methionine efflux pump is encoded by a yjeH gene, a phage deletion, and a ΔdapA auxotrophy.

In one embodiment, the recombinant bacterial cell comprises two or three copies of the metDC gene.

In one embodiment, the recombinant bacterial cell further comprising a deletion of an endogenous colibactin island.

In another aspect, the disclosure provides a recombinant bacterial cell comprising: a heterologous methionine catabolism enzyme gene, e.g., a methionine decarboxylase (metDC) gene, operably linked to a promoter, wherein the recombinant bacterial cell comprises two or three copies of the metDC gene, wherein the heterologous metDC gene encodes a polypeptide sequence that has at least 90%, 91%, 92%, 93%, 94%, 95%, 96%, 97%, 98%, or 99% identity to, comprises, or consists of SEQ ID NO: 1048, a heterologous gene encoding a methionine importer, wherein the heterologous gene encoding the methionine importer is a metP gene, wherein the metP gene encodes a polypeptide sequence having at least 90%, 91%, 92%, 93%, 94%, 95%, 96%, 97%, 98%, or 99% identity to, comprises, or consists of SEQ ID NO: 1056, a knock-out of an endogenous methionine efflux pump, wherein the endogenous methionine efflux pump is encoded by a yjeH gene, a phage deletion, a ΔdapA auxotrophy, and a deletion of an endogenous colibactin island.

In one embodiment, the recombinant bacterial cell is SYNB1353.

In one embodiment, the recombinant bacterial cell is a recombinant probiotic bacterial cell. In one embodiment, the recombinant bacterial cell is of the species *Escherichia coli* strain Nissle.

In another aspect, the disclosure provides a pharmaceutical composition comprising the recombinant bacterial cell disclosed herein and a pharmaceutically acceptable carrier.

In another aspect, the disclosure provides a method for treating a disease associated with methionine metabolism in a subject, the method comprising administering the pharmaceutical composition disclosed herein to the subject.

In another aspect, the disclosure provides a method for reducing the levels of methionine, cysteine and/or homocysteine in a subject, the method comprising administering to the subject the pharmaceutical composition disclosed herein, thereby reducing the levels of methionine, cysteine, and/or homocysteine in the subject.

In another aspect, the disclosure provides a method for reducing the levels of methionine, homocysteine, cysteine and/or cystine in a subject, the method comprising administering to the subject the pharmaceutical composition disclosed herein, thereby reducing the levels of methionine, homocysteine, cysteine, and/or cystine in the subject.

In one embodiment, the subject has homocystinuria, cystinuria, or a metabolic disease. In one embodiment, the subject has cystinuria, and wherein the method reduces the presence, occurrence, or formation of cystine stones in the subject as compared to the presence, occurrence or formation of cystine stones in the subject before administration of the pharmaceutical composition. In one embodiment, the subject has cystinuria, and wherein the method reduces or reduces an increase in cystine stone number, stone volume, stone area or stone weight as compared to before the administration of the pharmaceutical composition.

In one embodiment, the pharmaceutical composition comprises about $1\times10^{11}$ to about $6\times10^{11}$ live recombinant bacterial cells/mL.

In one embodiment, about 0.1 g to about 1.5 g of methionine are degraded per day. In one embodiment, methionine is metabolized at a rate of about 1.5 μmol/hr/1e9 cells. In one embodiment, methionine is metabolized at a rate of about 1.3 μmol/hr/1e9 cells. In one embodiment, 3-MTP is produced at a rate of about 1.3 μmol/hr/1e9 cells.

In one embodiment, about 0.1 g to about 1.5 g of methionine are degraded when administered to the subject three times per day. In one embodiment, the subject is fed a meal within one hour of administering the pharmaceutical composition. In one embodiment, the subject is fed a meal concurrently with administering the pharmaceutical composition. In one embodiment, the pharmaceutical composition is administered orally.

In one embodiment, the subject is a human subject.

In one embodiment, consumption of methionine is increased in the subject.

In another aspect, the disclosure provides a method for monitoring the effectiveness of a treatment of a subject, the method comprising administering to the subject the recombinant bacterial cell disclosed herein or the pharmaceutical composition disclosed herein, and measuring a level of 3-MTP in urine of the subject.

In one embodiment, an increase in the level of 3-MTP in the urine of the subject after administration as compared to a level of 3-MTP in the urine of a control subject is an indication that the treatment is effective.

In one embodiment, the increase is at least 1.2-fold, 1.5-fold, 2-fold, 2.5-fold, 3-fold, 3.5-fold, 4-fold, 4.5-fold or 5-fold.

In one embodiment, levels of methionine, homocysteine, cysteine or cystine are measured in the plasma or urine of the subject.

In another aspect, the disclosure provides a non-naturally occurring methionine catabolism enzyme comprising a sequence that has at least 90%, 91%, 92%, 93%, 94%, 95%, 96%, 97%, 98%, or 99% identity to, comprises, or consists of any one of SEQ ID NOs: 1048, 1050, 1051, 1053, 1054, 1124, 1126, or 1128.

In another aspect, the disclosure provides a non-naturally occurring MetN protein comprising a sequence that has at least 90%, 91%, 92%, 93%, 94%, 95%, 96%, 97%, 98%, 99% identity to, comprises, or consists of any one of SEQ ID NOs: 1062 or 1063.

In another aspect, the disclosure provides a host cell that comprises a heterologous polynucleotide encoding a methionine catabolism enzyme, e.g., a methionine decarboxylase (MetDC) enzyme, wherein the heterologous polynucleotide comprises a sequence that is at least 90%, 91%, 92%, 93%, 94%, 95%, 96%, 97%, 98%, or 99% identical to, comprises, or consists of any one of SEQ ID NOs: 1003, 1018, 1034, 1035, 1036, 1037, 1038, 1039, 1040, 1123, 1125, or 1127.

In another aspect, the disclosure provides a host cell that comprises a heterologous polynucleotide encoding methionine catabolism enzyme, e.g., a methionine decarboxylase (MetDC) enzyme, wherein the enzyme comprises an amino acid sequence that is at least 90%, 91%, 92%, 93%, 94%, 95%, 96%, 97%, 98%, or 99% identical to, comprises, or consists of a sequence selected from SEQ ID NOs: 1048, 1049, 1050, 1051, 1052, 1053, 1054, 1055, 1124, 1126, and 1128.

In one embodiment, the sequence of the MetDC enzyme comprises one or more amino acid substitutions relative to the sequence of SEQ ID NO: 1049. In one embodiment, the one or more amino acid substitutions are at positions corresponding to position 41, 66, 70, 82, 203, 379, 491 and/or 500 in SEQ ID NO: 1049. In one embodiment, the sequence of the MetDC enzyme comprises: a glutamine (Q) at a position corresponding to position 41 in the sequence of SEQ ID NO: 1049; an asparagine (N) at a position corresponding to position 66 in SEQ ID NO: 1049; an aspartic acid (D) at a position corresponding to position 70 in the sequence of SEQ ID NO: 1049; a histidine (H) at a position corresponding to position 82 in SEQ ID NO: 1049; a histidine (H) at a position corresponding to position 203 in SEQ ID NO: 1049; a glycine (G) at a position corresponding to position 379 in SEQ ID NO: 1049; a leucine (L) at a position corresponding to position 491 in the sequence of SEQ ID NO: 1049; and/or a proline (P) at a position corresponding to position 500 in the sequence of SEQ ID NO: 1049. In one embodiment, the sequence of the MetDC enzyme comprises amino acid substitutions at a position corresponding to: position 66; position 203; position 379; positions 70 and 82; positions 491 and 500; or positions 41 and 70 in the sequence of SEQ ID NO: 1049. In one embodiment, the sequence of the MetDC enzyme comprises the following amino acid substitutions relative to the sequence of SEQ ID NO: 1049: T66N; A203H; H379G; Q70D and N82H; V491L and A500P; or R41Q and Q70D. In another aspect, the disclosure provides a host cell that comprises a heterologous polynucleotide encoding a methionine decarboxylase (MetDC) enzyme, wherein the sequence of the MetDC enzyme comprises one or more amino acid substitutions relative to the sequence of SEQ ID NO: 1049 at positions corresponding to position 41, 66, 70, 82, 203, 379, 491 and/or 500 in SEQ ID NO: 1049.

In one embodiment, the sequence of the MetDC enzyme comprises: a glutamine (Q) at a position corresponding to position 41 in the sequence of SEQ ID NO: 1049; an asparagine (N) at a position corresponding to position 66 in SEQ ID NO: 1049; an aspartic acid (D) at a position corresponding to position 70 in the sequence of SEQ ID NO: 1049; a histidine (H) at a position corresponding to position 82 in SEQ ID NO: 1049; a histidine (H) at a position corresponding to position 203 in SEQ ID NO: 1049; a glycine (G) at a position corresponding to position 379 in SEQ ID NO: 1049; a leucine (L) at a position corresponding to position 491 in the sequence of SEQ ID NO: 1049; and/or a proline (P) at a position corresponding to position 500 in the sequence of SEQ ID NO: 1049. In one embodiment, the sequence of the MetDC enzyme comprises amino acid substitutions at a position corresponding to: position 66; position 203; position 379; positions 70 and 82; positions 491 and 500; or positions 41 and 70 in the sequence of SEQ ID NO: 1049. In one embodiment, the sequence of the MetDC enzyme comprises the following amino acid substitutions relative to the sequence of SEQ ID NO: 1049: T66N; A203H; H379G; Q70D and N82H; V491L and A500P; or R41Q and Q70D.

In one embodiment, the host cell further comprising a heterologous polynucleotide encoding a methionine importer. In one embodiment, the methionine importer is a MetP importer.

In one embodiment, the heterologous polynucleotide encoding the MetP importer comprises a sequence that is at least 90%, 91%, 92%, 93%, 94%, 95%, 96%, 97%, 98%, or 99% identical to, comprises, or consists of any one of SEQ ID NOs: 1041, 1042, 1044, 1129, or 1131.

In one embodiment, the MetP importer comprises an amino acid sequence that is at least 90%, 91%, 92%, 93%, 94%, 95%, 96%, 97%, 98%, or 99% identical to, comprises, or consists of any one of SEQ ID NOs: 1056, 1057, 1061, 1130 or 1132.

In another aspect, the disclosure provides a host cell that comprises a heterologous polynucleotide encoding a MetP importer, wherein the MetP importer comprises an amino acid sequence that is at least 90%, 91%, 92%, 93%, 94%, 95%, 96%, 97%, 98%, or 99% identical to, comprises, or consists of any one of SEQ ID NOs: 1056, 1057, 1061, 1130, or 1132.

In one embodiment, the methionine importer is an MetNIQ importer, wherein the MetNIQ importer comprises a MetN protein, a MetI protein, and a MetQ protein.

In one embodiment, a heterologous polynucleotide encoding the MetNIQ importer comprises a sequence that is at least 90%, 91%, 92%, 93%, 94%, 95%, 96%, 97%, 98%, or 99% identical to, comprises, or consists of SEQ ID NO: 1043, or wherein a heterologous polynucleotide encoding the MetN protein comprises a sequence that is at least 90%, 91%, 92%, 93%, 94%, 95%, 96%, 97%, 98%, or 99% identical to, comprises, or consists of any one of SEQ ID NOs: 1004, 1045, 1046, or 1047; wherein the a heterologous polynucleotide encoding the MetI protein comprises a sequence that is at least 90%, 91%, 92%, 93%, 94%, 95%, 96%, 97%, 98%, or 99% identical to, comprises, or consists of SEQ ID NO: 1005; and wherein a heterologous polynucleotide encoding the MetQ protein comprises a sequence that is at least 90%, 91%, 92%, 93%, 94%, 95%, 96%, 97%, 98%, or 99% identical to, comprises, or consists of SEQ ID NO: 1006.

In one embodiment, the MetN protein comprises an amino acid sequence that is at least 90%, 91%, 92%, 93%, 94%, 95%, 96%, 97%, 98%, or 99% identical to, comprises, or consists of any one of SEQ ID NOs: 1058, 1062, and 1063; wherein the MetI protein comprises an amino acid sequence that is at least 90%, 91%, 92%, 93%, 94%, 95%, 96%, 97%, 98%, or 99% identical to, comprises, or consists of SEQ ID NO: 1059; and wherein the MetQ protein comprises an amino acid sequence that is at least 90%, 91%, 92%, 93%, 94%, 95%, 96%, 97%, 98%, or 99% identical to, comprises, or consists of SEQ ID NO: 1060.

In another aspect, the disclosure provides a host cell comprising a heterologous polynucleotide encoding an MetNIQ importer, wherein the MetNIQ importer comprises MetN protein, a MetI protein, and a MetQ protein, wherein a heterologous polynucleotide encoding the MetN protein comprises a sequence that is at least 90%, 91%, 92%, 93%, 94%, 95%, 96%, 97%, 98%, or 99% identical to, comprises, or consists of any one of SEQ ID NOs: 1045, 1046, or 1047; wherein the a heterologous polynucleotide encoding the MetI protein comprises a sequence that is at least 90%, 91%, 92%, 93%, 94%, 95%, 96%, 97%, 98%, or 99% identical to, comprises, or consists of SEQ ID NO: 1005; and wherein a heterologous polynucleotide encoding the MetQ protein comprises a sequence that is at least 90%, 91%, 92%, 93%, 94%, 95%, 96%, 97%, 98%, or 99% identical to, comprises, or consists of SEQ ID NO: 1006.

In another aspect, the disclosure provides a host cell comprising a heterologous polynucleotide encoding a MetNIQ importer, wherein the MetNIQ importer comprises a MetN protein, a MetI protein, and a MetQ protein, wherein the MetN protein comprises an amino acid sequence that is at least 90%, 91%, 92%, 93%, 94%, 95%, 96%, 97%, 98%, or 99% identical to, comprises, or consists of any one of SEQ ID NOs: 1062 or 1063; wherein the MetI protein comprises an amino acid sequence that is at least 90%, 91%, 92%, 93%, 94%, 95%, 96%, 97%, 98%, or 99% identical to, comprises, or consists of SEQ ID NO: 1059; and wherein the MetQ protein comprises an amino acid sequence that is at least 90%, 91%, 92%, 93%, 94%, 95%, 96%, 97%, 98%, or 99% identical to, comprises, or consists of SEQ ID NO: 1060.

In one embodiment, the host cell further comprising a heterologous polynucleotide encoding a methionine catabolism enzyme, e.g., a methionine decarboxylase (MetDC) enzyme. In one embodiment, the heterologous polynucleotide encoding the enzyme comprises a sequence that is at least 90%, 91%, 92%, 93%, 94%, 95%, 96%, 97%, 98%, or 99% identical to, comprises, or consists of a sequence selected from SEQ ID NOs: 1003, 1018, 1034, 1035, 1036, 1037, 1038, 1039, 1040, 1123, 1125, or 1127.

In one embodiment, the enzyme comprises an amino acid sequence that is at least 90%, 91%, 92%, 93%, 94%, 95%, 96%, 97%, 98%, or 99% identical to, comprises, or consists of a sequence selected from SEQ ID NOs: 1048, 1049, 1050, 1051, 1052, 1053, 1054, 1055, 1124, 1126, or 1128.

In one embodiment, the heterologous polynucleotide is operably linked to a promoter. In one embodiment, the promoter is an inducible promoter. In one embodiment, the inducible promoter is an IPTG-inducible promoter or an inducible promoter that is directly or indirectly induced by environmental conditions specific to the gut of a human.

In one embodiment, the host cell is a plant cell, an algal cell, a yeast cell, a bacterial cell, or an animal cell.

In one embodiment, the host cell is a yeast cell. In one embodiment, the yeast cell is an *Saccharomyces* cell, a *Yarrowia* cell or a *Pichia* cell.

In one embodiment, the host cell is a bacterial cell. In one embodiment, the bacterial cell is a recombinant probiotic bacterial cell.

In one embodiment, the bacterial cell is an *E. coli* cell or a *Bacillus* cell. In one embodiment, the bacterial cell is of the species *Escherichia coli* strain Nissle.

In another aspect, the disclosure provides a method comprising culturing the host cell disclosed herein.

In another aspect, the disclosure provides a method of metabolizing methionine comprising culturing the host cell disclosed herein.

In another aspect, the disclosure provides a non-naturally occurring nucleic acid comprising a sequence that is at least 90%, 91%, 92%, 93%, 94%, 95%, 96%, 97%, 98%, or 99% identical to, comprises, or consists of any one of SEQ ID NOs: 1034, 1035, 1036, 1038, 1039, 1123, 1125, or 1127.

In another aspect, the disclosure provides a non-naturally occurring nucleic acid comprising a sequence that is at least 90%, 91%, 92%, 93%, 94%, 95%, 96%, 97%, 98%, or 99% identical to any one of SEQ ID NOs: 1045, 1046, and 1047.

In another aspect, the disclosure provides a non-naturally occurring nucleic acid comprising a sequence that is at least 90%, 91%, 92%, 93%, 94%, 95%, 96%, 97%, 98%, or 99% identical to any one of SEQ ID NOs: 1129 or 1131.

In another aspect, the disclosure provides a vector comprising the non-naturally occurring nucleic acid disclosed herein.

In another aspect, the disclosure provides an expression cassette comprising the non-naturally occurring nucleic acid disclosed herein.

BRIEF DESCRIPTION OF THE DRAWINGS

FIG. 1 provides an overview for homocystinuria, a disorder of methionine metabolism caused by a defect in cystathionine beta-synthase (CBS), which leads to the accumulation of homocysteine in blood and urine.

FIG. 2 provides an overview of the synthetic biology for methionine consumption in *E. coli* Nissle (ECN).

FIG. 24A depicts a graph showing body weight measured. FIG. 24B depicts a graph showing food intake normalized to body weight. FIG. 24C depicts a graph showing stone volume as obtained by CT scan. FIG. 24D depicts a graph showing bladder weight normalized to body weight.

DETAILED DESCRIPTION

Figure 3:
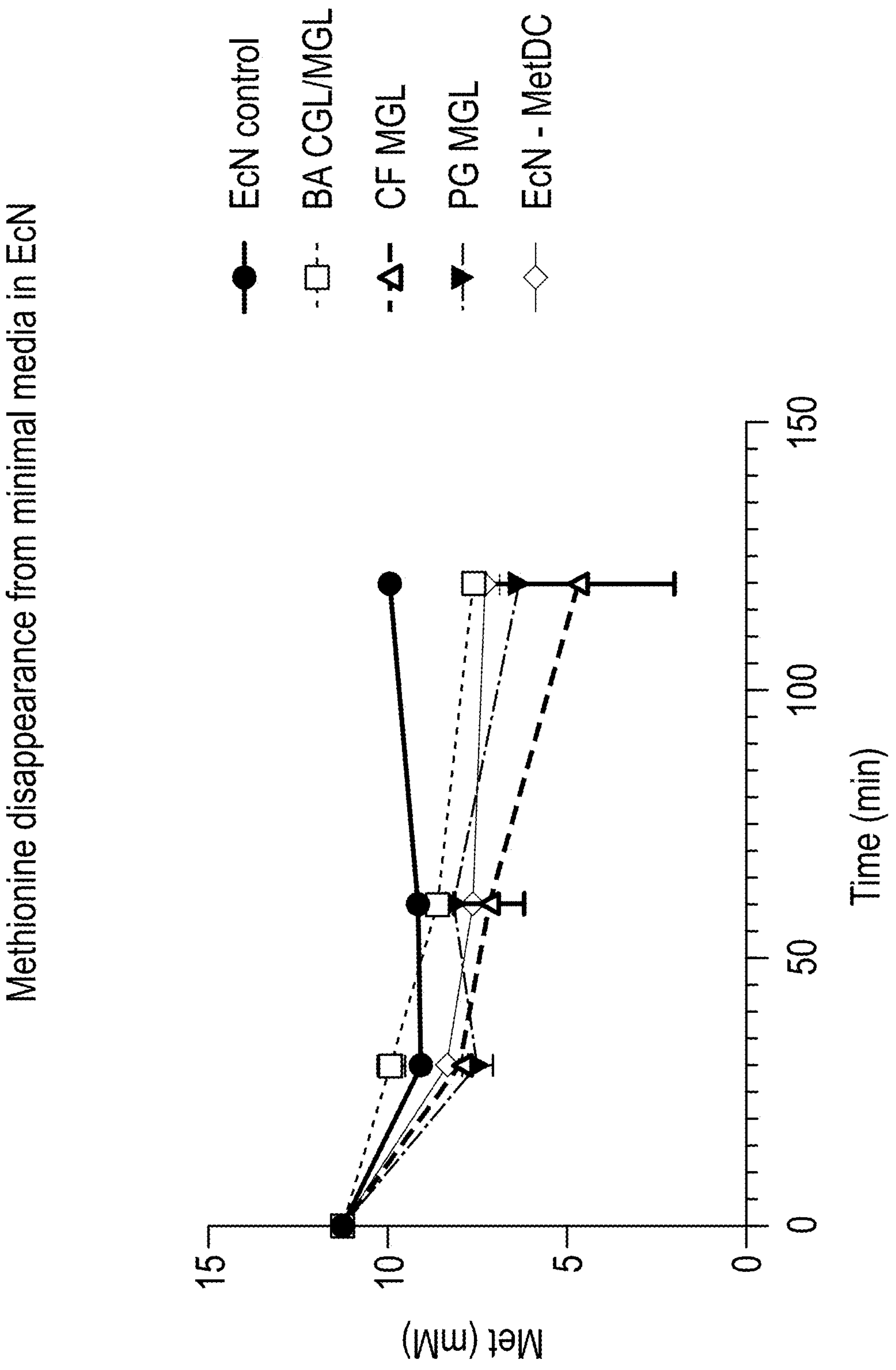
FIG. 3 is a graph depicting methionine disappearance from minimal media in *E. coli* Nissle harboring methionine gamma lyase (MGL) or methionine decarboxylase (MDC) under the control of an anhydrotetracycline (ATC)-inducible promoter. EcN control is wild-type *E. coli* Nissle with no methionine catabolism enzymes. BA CGL/MGL is MGL from *Brevibacterium aurantiacum* (DOI 10.1124/jpet.119.256537). CF MGL is MGL from *Citrobacter freundii*. PG MGL is MGL from *Poprhyromonas gingivalis*. EcN-MetDC is MDC from *Streptomyces* sp. 590.

The present disclosure provides recombinant bacterial cells that have been engineered with optimized genetic circuitry which allow the recombinant bacterial cells to turn on and off an engineered metabolic pathway by sensing a patient's internal environment or by chemical induction during, for example, manufacturing. When turned on, the recombinant bacterial cells complete all of the steps in a metabolic pathway to achieve a therapeutic effect in a host subject and are designed to drive therapeutic effects throughout the body of a host from a point of origin of the microbiome.

Specifically, the present disclosure provides recombinant bacterial cells, pharmaceutical compositions thereof, and methods of modulating and treating diseases associated with amino acid metabolism, such as homocystinuria. Specifically, the recombinant bacteria disclosed herein have been constructed to comprise genetic circuits composed of, for example, a methionine decarboxylase to treat disease, as well as other circuitry in order to guarantee the safety and non-colonization of the subject that is administered the recombinant bacteria, such as auxotrophies, etc. These recombinant bacteria are safe and well tolerated and augment the innate activities of the subject's microbiome to achieve a therapeutic effect.

In some embodiments, a bacterial cell disclosed herein has been genetically engineered to comprise a heterologous gene sequence encoding one or more methionine decarboxylases and is capable of processing (e.g., metabolizing) and reducing levels of methionine. In some embodiments, a bacterial cell disclosed herein has been genetically engineered to comprise a heterologous gene sequence encoding one or more methionine decarboxylases and is capable of processing and reducing levels of methionine in low-oxygen environments, e.g., the gut. Thus, the genetically engineered bacterial cells and pharmaceutical compositions comprising the bacterial cells disclosed herein may be used to convert excess methionine into non-toxic molecules in order to treat and/or prevent diseases associated with amino acid metabolism, such as homocystinuria, cystinuria, primary and secondary hypermethioninemia, cancer, and metabolic syndromes/diseases.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

As used herein, the term "recombinant bacterial cell" or "recombinant bacteria" (also referred to herein as a "genetically engineered bacterial cell") refers to a bacterial cell or bacteria that have been genetically modified from their native state. Similarly, "recombinant microorganism" (or genetically engineered microorganism), or "recombinant host cell" (or genetically engineered host cell), refers to a microorganism or host cell that has been genetically modified from their native state. For instance, a recombinant bacterial cell, microorganism, or host cell may have nucleotide insertions, nucleotide deletions, nucleotide rearrangements, and nucleotide modifications introduced into their DNA. These genetic modifications may be present in the chromosome of the bacteria, bacterial cell, microorganism, or host cell or on a plasmid in the bacteria, bacterial cell, microorganism, or host cell. Recombinant bacterial cells, microorganisms, or host cells of the disclosure may comprise exogenous or heterologous nucleotide sequences on plasmids. Alternatively, recombinant bacterial cells, microorganisms, or host cells may comprise exogenous or heterologous nucleotide sequences stably incorporated into their chromosome(s).

As used herein, the term "gene" refers to a nucleic acid fragment that encodes a protein or fragment thereof, optionally including regulatory sequences preceding (5' non-coding sequences) and following (3' non-coding sequences) the coding sequence. In one embodiment, a "gene" does not include regulatory sequences preceding and following the coding sequence. A "native gene" refers to a gene as found in nature, optionally with its own regulatory sequences preceding and following the coding sequence. A "chimeric gene" refers to any gene that is not a native gene, optionally comprising regulatory sequences preceding and following the coding sequence, wherein the coding sequences and/or the regulatory sequences, in whole or in part, are not found together in nature. Thus, a chimeric gene may comprise regulatory sequences and coding sequences that are derived from different sources, or regulatory and coding sequences that are derived from the same source, but arranged differently than is found in nature. As used herein the term "gene" is also meant to include a codon-optimized gene sequence, which is modified from a native gene sequence, e.g., to reflect the typical codon usage of the host organism, without altering the polypeptide encoded by a gene or nucleic acid molecule. As used herein, the term "gene" may also refer to a gene sequence which encodes a polypeptide that is not naturally occurring. For example, a gene may encode a polypeptide which is derived from a library of engineered, non-naturally occurring polypeptides. As used herein, the term "gene sequence" is meant to refer to a genetic sequence, e.g., a nucleic acid sequence. The gene sequence or genetic sequence is meant to include a complete gene sequence or a partial gene sequence. The gene sequence or genetic sequence is meant to include sequence that encodes a protein or polypeptide and is also meant to include genetic sequence that does not encode a protein or polypeptide, e.g., a regulatory sequence, leader sequence, signal sequence, or other non-protein coding sequence.

As used herein, a "heterologous gene" or "heterologous sequence" refers to a nucleotide sequence that is not normally found in a given cell in nature. As used herein, a heterologous sequence encompasses a nucleic acid sequence that is exogenously introduced into a given cell. "Heterologous gene" includes a native gene, or fragment thereof, that has been introduced into the host cell in a form that is different from the corresponding native gene. For example, a heterologous gene may include a native coding sequence that is a portion of a chimeric gene that is reintroduced into the host cell. A heterologous gene may also include a native gene, or fragment thereof, introduced into a non-native host cell. Alternatively, a heterologous gene may also include a native gene, or fragment thereof, which has been edited within a host cell. Thus, a heterologous gene may be foreign or native to the recipient cell; a nucleic acid sequence that is naturally found in a given cell but expresses an unnatural amount of the nucleic acid and/or the polypeptide which it encodes; and/or two or more nucleic acid sequences that are not found in the same relationship to each other in nature.

As used herein, the term "endogenous gene" refers to a native gene in its natural location in the genome of an organism.

As used herein, the term "transgene" refers to a gene that has been introduced into the host organism, e.g., host bacterial cell, genome.

As used herein, the term "bacteriostatic" or "cytostatic" refers to a molecule or protein which is capable of arresting, retarding, or inhibiting the growth, division, multiplication or replication of a recombinant bacterial cell of the disclosure.

As used herein, the term "bactericidal" refers to a molecule or protein which is capable of killing the recombinant bacterial cell of the disclosure.

As used herein, the term "toxin" refers to a protein, enzyme, or polypeptide fragment thereof, or other molecule which is capable of arresting, retarding, or inhibiting the growth, division, multiplication or replication of the recombinant bacterial cell of the disclosure, or which is capable of killing the recombinant bacterial cell of the disclosure. The term "toxin" is intended to include bacteriostatic proteins and bactericidal proteins. The term "toxin" is intended to include, but not limited to, lytic proteins, bacteriocins (e.g., microcins and colicins), gyrase inhibitors, polymerase inhibitors, transcription inhibitors, translation inhibitors, DNases, and RNases. The term "anti-toxin" or "antitoxin," as used herein, refers to a protein or enzyme which is capable of inhibiting the activity of a toxin. The term anti-toxin is intended to include, but not limited to, immunity modulators, and inhibitors of toxin expression. Examples of toxins and antitoxins are known in the art and described in more detail infra.

As used herein, the term "coding region" refers to a nucleotide sequence that codes for a specific amino acid sequence. The term "regulatory sequence" refers to a nucleotide sequence located upstream (5' non-coding sequences), within, or downstream (3' non-coding sequences) of a coding sequence, and which influences the transcription, RNA processing, RNA stability, or translation of the associated coding sequence. Examples of regulatory sequences include, but are not limited to, promoters, translation leader sequences, effector binding sites, and stem-loop structures. In one embodiment, the regulatory sequence comprises a promoter, e.g., an FNR responsive promoter.

"Operably linked" refers to the association of nucleic acid sequences on a single nucleic acid fragment so that the function of one is affected by the other. A regulatory element is operably linked with a coding sequence when it is capable of affecting the expression of the gene coding sequence, regardless of the distance between the regulatory element and the coding sequence. More specifically, operably linked refers to a nucleic acid sequence, e.g., a gene encoding at least one methionine decarboxylase, that is joined to a regulatory sequence in a manner which allows expression of the nucleic acid sequence, e.g., the gene(s) encoding the methionine decarboxylase. In other words, the regulatory sequence acts in cis. In one embodiment, a gene may be "directly linked" to a regulatory sequence in a manner which allows expression of the gene. In another embodiment, a gene may be "indirectly linked" to a regulatory sequence in a manner which allows expression of the gene. In one embodiment, two or more genes may be directly or indirectly linked to a regulatory sequence in a manner which allows expression of the two or more genes. A regulatory region or sequence is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

A "promoter" as used herein, refers to a nucleotide sequence that is capable of controlling the expression of a coding sequence or gene. Promoters are generally located 5' of the sequence that they regulate. Promoters may be derived in their entirety from a native gene, or be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell- or tissue-specific manner, in response to different environmental or physiological conditions, or in response to specific compounds. Prokaryotic promoters are typically classified into two classes: inducible and constitutive.

An "inducible promoter" refers to a regulatory region that is operably linked to one or more genes, wherein expression of the gene(s) is increased in the presence of an inducer of said regulatory region. An "inducible promoter" refers to a promoter that initiates increased levels of transcription of the coding sequence or gene under its control in response to a stimulus or an exogenous environmental condition. A "directly inducible promoter" refers to a regulatory region, wherein the regulatory region is operably linked to a gene encoding a protein or polypeptide, where, in the presence of an inducer of said regulatory region, the protein or polypeptide is expressed. An "indirectly inducible promoter" refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region may be activated or repressed, thereby activating or repressing expression of the second gene. Both a directly inducible promoter and an indirectly inducible promoter are encompassed by "inducible promoter." Examples of inducible promoters include, but are not limited to, an FNR promoter, a $P_{araC}$ promoter, a $P_{araBAD}$ promoter, a propionate promoter, and a $P_{TetR}$ promoter, each of which are described in more detail herein. Examples of other inducible promoters are provided herein below.

As used herein, a "stably maintained" or "stable" host cell, such as a bacterium, is used to refer to a host cell, such as a bacterial host cell, carrying non-native genetic material, e.g., a methionine decarboxylase, that is incorporated into the host genome or propagated on a self-replicating extra-chromosomal plasmid, such that the non-native genetic material is retained, expressed, and propagated. The stable host cell, such as a stable bacterium, is capable of survival and/or growth in vitro, e.g., in medium, and/or in vivo, e.g., in the gut. For example, the stable host cell, such as a stable bacterium, may be a genetically engineered host cell, such as a bacterium, comprising an amino acid catabolism gene, in which the plasmid or chromosome carrying the amino acid catabolism gene is stably maintained in the host cell, such as a bacterium, such that the methionine decarboxylase can be expressed in the host cell, such as a bacterium, and the host cell, such as a bacterium, is capable of survival and/or growth in vitro and/or in vivo. In some embodiments, copy number affects the stability of expression of the non-native genetic material. In some embodiments, copy number affects the level of expression of the non-native genetic material.

As used herein, the term "expression" refers to the transcription and stable accumulation of sense (mRNA) or anti-sense RNA derived from a nucleic acid, and/or to translation of an mRNA into a polypeptide As used herein, the term "plasmid" or "vector" refers to an extrachromosomal nucleic acid, e.g., DNA, construct that is not integrated into the genome of a host cell, such as a bacterial host cell. Plasmids are usually circular and capable of autonomous replication. Plasmids may be low-copy, medium-copy, or high-copy, as is well known in the art. Plasmids may optionally comprise a selectable marker, such as an antibiotic resistance gene, which helps select for host cells, such as bacterial host cells, containing the plasmid and which ensures that the plasmid is retained in the host cell, such as a bacterial host cell. A plasmid disclosed herein may comprise a nucleic acid sequence encoding a heterologous gene, e.g., a gene encoding at least one methionine decarboxylase.

As used herein, the term "transform" or "transformation" refers to the transfer of a nucleic acid fragment into a host cell, such as a host bacterial cell, resulting in genetically-stable inheritance. Host cells, such as host bacterial cells, comprising the transformed nucleic acid fragment are referred to as "recombinant" or "transgenic" or "transformed" cells or organisms. In some instances where one or more nucleic acid fragments are introduced into a host cell, such as on a plasmid or vector, one or more of the nucleic acid fragments may be retained in the cell, such as by integration into the genome of the cell, while the plasmid or vector itself may be removed from the cell. In such instances, the host cell is considered to be transformed with the nucleic acid fragments that were introduced into the cell regardless of whether the plasmid or vector is retained in the cell or not.

The term "genetic modification," as used herein, refers to any genetic change. Exemplary genetic modifications include those that increase, decrease, or abolish the expression of a gene, including, for example, modifications of native chromosomal or extrachromosomal genetic material. Exemplary genetic modifications also include the introduction of at least one plasmid, modification, mutation, base deletion, base addition, and/or codon modification of chromosomal or extrachromosomal genetic sequence(s), gene over-expression, gene amplification, gene suppression, promoter modification or substitution, gene addition (either single or multi-copy), antisense expression or suppression, or any other change to the genetic elements of a host cell, whether the change produces a change in phenotype or not. Genetic modification can include the introduction of a plasmid, e.g., a plasmid comprising at least one methionine decarboxylase operably linked to a promoter, into a host cell, such as a bacterial host cell. Genetic modification can also involve a targeted replacement in the chromosome, e.g., to replace a native gene promoter with an inducible promoter, regulated promoter, strong promoter, or constitutive promoter. Genetic modification can also involve gene amplification, e.g., introduction of at least one additional copy of a native gene into the chromosome of the cell. Alternatively, chromosomal genetic modification can involve a genetic mutation.

As used herein, the term "genetic mutation" refers to a change or changes in a nucleotide sequence of a gene or related regulatory region that alters the nucleotide sequence as compared to its native or wild-type sequence. Mutations include, for example, substitutions, additions, and deletions, in whole or in part, within the wild-type sequence. Such substitutions, additions, or deletions can be single nucleotide changes (e.g., one or more point mutations), or can be two or more nucleotide changes, which may result in substantial changes to the sequence. Mutations can occur within the coding region of the gene as well as within the non-coding and regulatory sequence of the gene. The term "genetic mutation" is intended to include silent and conservative mutations within a coding region as well as changes which alter the amino acid sequence of the polypeptide encoded by the gene. A genetic mutation in a gene coding sequence may, for example, increase, decrease, or otherwise alter the activity (e.g., enzymatic activity) of the gene's polypeptide product. A genetic mutation in a regulatory sequence may increase, decrease, or otherwise alter the expression of sequences operably linked to the altered regulatory sequence.

It is routine for one of ordinary skill in the art to make mutations in a gene of interest. Mutations include substitutions, insertions, deletions, and/or truncations of one or more specific amino acid residues or of one or more specific nucleotides or codons in the polypeptide or polynucleotide of the exporter of an asparagine. Mutagenesis and directed evolution methods are well known in the art for creating variants. See, e.g., U.S. Pat. Nos. 7,783,428; 6,586,182; 6,117,679; and Ling, et al., 1999, "Approaches to DNA mutagenesis: an overview," *Anal. Biochem.,* 254(2):157-78; Smith, 1985, "In vitro mutagenesis," *Ann. Rev. Genet.,* 19:423-462; Carter, 1986, "Site-directed mutagenesis," *Biochem. J.,* 237:1-7; and Minshull, et al., 1999, "Protein evolution by molecular breeding," *Current Opinion in Chemical Biology,* 3:284-290. For example, the lambda red system can be used to knock-out genes in *E. coli* (see, for example, Datta et al., *Gene,* 379:109-115 (2006)).

The term "inactivated" as applied to a gene refers to any genetic modification that decreases or eliminates the expression of the gene and/or the functional activity of the corresponding gene product (mRNA and/or protein). The term "inactivated" encompasses complete or partial inactivation, suppression, deletion, interruption, blockage, promoter alterations, antisense RNA, dsRNA, or down-regulation of a gene. This can be accomplished, for example, by gene "knockout," inactivation, mutation (e.g., insertion, deletion, point, or frameshift mutations that disrupt the expression or activity of the gene product), or by use of inhibitory RNAs (e.g., sense, antisense, or RNAi technology). A deletion may encompass all or part of a gene's coding sequence. The term "knockout" refers to the deletion of most (at least about 95%, at least about 96%, at least about 97%, at least about 98%, or at least about 99%) or all (100%) of the coding sequence of a gene. In some embodiments, any number of nucleotides can be deleted, from a single base to an entire piece of a chromosome.

"Exogenous environmental condition(s)" or "environmental conditions" refer to settings or circumstances under which the promoter described herein is directly or indirectly induced. The phrase is meant to refer to the environmental conditions external to the engineered microorganism, but endogenous or native to the host subject environment. Thus, "exogenous" and "endogenous" may be used interchangeably to refer to environmental conditions in which the environmental conditions are endogenous to a mammalian body, but external or exogenous to an intact microorganism cell. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, the exogenous environmental conditions are low-oxygen, microaerobic, or anaerobic conditions, such as the environment of the mammalian gut. In some embodiments, exogenous environmental conditions refer to the presence of molecules or metabolites that are specific to the mammalian gut in a healthy or disease-state, e.g., propionate. In some embodiments, the exogenous environmental condition is a tissue-specific or disease-specific metabolite or molecule(s). In some embodiments, the exogenous environmental condition is a low-pH environment. In some embodiments, the genetically engineered microorganism of the disclosure comprises a pH-dependent promoter. In some embodiments, the genetically engineered microorganism of the disclosure comprises an oxygen level-dependent promoter. In some aspects, bacteria have evolved transcription factors that are capable of sensing oxygen levels. Different signaling pathways may be triggered by different oxygen levels and occur with different kinetics.

As used herein, "exogenous environmental conditions" or "environmental conditions" also refers to settings or circumstances or environmental conditions external to the engineered microorganism, which relate to in vitro culture conditions of the microorganism. "Exogenous environmental conditions" may also refer to the conditions during growth, production, and manufacture of the organism. Such conditions include aerobic culture conditions, anaerobic culture conditions, low oxygen culture conditions and other conditions under set oxygen concentrations. Such conditions also include the presence of a chemical and/or nutritional inducer, such as tetracycline, arabinose, IPTG, rhamnose, and the like in the culture medium. Such conditions also include the temperatures at which the microorganisms are grown prior to in vivo administration. For example, using certain promoter systems, certain temperatures are permissive to expression of a payload, while other temperatures are non-permissive. Oxygen levels, temperature and media composition influence such exogenous environmental conditions. Such conditions affect proliferation rate, rate of induction of the payload or gene of interest, e.g., amino acid catabolism gene, other regulators (e.g., FNRS24Y), and overall viability and metabolic activity of the strain during strain production.

In some embodiments, the exogenous environmental condition(s) and/or signal(s) stimulates the activity of an inducible promoter. In some embodiments, the exogenous environmental condition(s) and/or signal(s) that serves to activate the inducible promoter is not naturally present within the gut of a mammal. In some embodiments, the inducible promoter is stimulated by a molecule or metabolite that is administered in combination with the pharmaceutical composition of the disclosure, for example, tetracycline, arabinose, or any biological molecule that serves to activate an inducible promoter. In some embodiments, the exogenous environmental condition(s) and/or signal(s) is added to culture media comprising a recombinant bacterial cell of the disclosure. In some embodiments, the exogenous environmental condition that serves to activate the inducible promoter is naturally present within the gut of a mammal (for example, low oxygen or anaerobic conditions, or biological molecules involved in an inflammatory response). In some embodiments, the loss of exposure to an exogenous environmental condition (for example, in vivo) inhibits the activity of an inducible promoter, as the exogenous environmental condition is not present to induce the promoter (for example, an aerobic environment outside the gut).

An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

Examples of oxygen level-dependent transcription factors include, but are not limited to, FNR, ANR, and DNR. Corresponding FNR-responsive promoters, ANR-responsive promoters, and DNR-responsive promoters are known in the art (see, e.g., Castiglione et al., 2009; Eiglmeier et al., 1989; Galimand et al., 1991; Hasegawa et al., 1998; Hoeren et al., 1993; Salmon et al., 2003). Non-limiting examples are shown in Table 1.

In a non-limiting example, a promoter (PfnrS) was derived from the *E. coli* Nissle fumarate and nitrate reductase gene S (fnrS) that is known to be highly expressed under conditions of low or no environmental oxygen (Durand and Storz, 2010; Boysen et al, 2010). The PfnrS promoter is activated under anaerobic and/or low oxygen conditions by the global transcriptional regulator FNR that is naturally found in Nissle. Under anaerobic and/or low oxygen conditions, FNR forms a dimer and binds to specific sequences in the promoters of specific genes under its control, thereby activating their expression. However, under aerobic conditions, oxygen reacts with iron-sulfur clusters in FNR dimers and converts them to an inactive form. In this way, the PfnrS inducible promoter is adopted to modulate the expression of proteins or RNA. PfnrS is used interchangeably in this application as FNRS, fnrS, FNR, P-FNRS promoter and other such related designations to indicate the promoter PfnrS.

TABLE 1

Examples of transcription factors and responsive genes and regulatory regions

| Transcription factor | Examples of responsive genes, promoters, and/or regulatory regions: |
|---|---|
| FNR | nirB, ydfZ, pdhR, focA, ndH, hlyE, narK, narX, narG, yfiD, tdcD |
| DNR | norb, norC |

As used herein, a "non-native" nucleic acid sequence refers to a nucleic acid sequence not normally present in a host cell, such as a bacterium, e.g., an extra copy of an endogenous sequence, or a heterologous sequence such as a sequence from a different species, strain, or substrain of bacteria, or a sequence that is modified and/or mutated as compared to the unmodified sequence from bacteria of the same subtype. In some embodiments, the non-native nucleic acid sequence is a synthetic, non-naturally occurring sequence (see, e.g., Purcell et al., 2013). The non-native nucleic acid sequence may be a regulatory region, a promoter, a gene, and/or one or more genes in a gene cassette. In some embodiments, "non-native" refers to two or more nucleic acid sequences that are not found in the same relationship to each other in nature. The non-native nucleic acid sequence may be present on a plasmid or chromosome. In addition, multiple copies of any regulatory region, promoter, gene, and/or gene cassette may be present in the host cell, such as a bacterium, wherein one or more copies of the regulatory region, promoter, gene, and/or gene cassette may be mutated or otherwise altered as described herein. In some embodiments, the genetically engineered host cell, such as genetically engineered bacteria, are engineered to comprise multiple copies of the same regulatory region, promoter, gene, and/or gene cassette in order to enhance copy number or to comprise multiple different components of a gene cassette performing multiple different functions. In some embodiments, the genetically engineered host cell, such as genetically engineered bacteria, of the invention comprise a gene encoding a phenylalanine-metabolizing enzyme that is operably linked to a directly or indirectly inducible promoter that is not associated with said gene in nature, e.g., an FNR promoter operably linked to a gene encoding an amino acid metabolism gene.

"Constitutive promoter" refers to a promoter that is capable of facilitating continuous transcription of a coding sequence or gene under its control and/or to which it is operably linked. Constitutive promoters and variants are well known in the art and include, but are not limited to, BBa_J23100, a constitutive *Escherichia coli* $\sigma^S$ promoter (e.g., an osmY promoter (International Genetically Engineered Machine (iGEM) Registry of Standard Biological Parts Name BBa_J45992; BBa_J45993)), a constitutive *Escherichia coli* $\sigma^{32}$ promoter (e.g., htpG heat shock promoter (BBa_J45504)), a constitutive *Escherichia coli* $\sigma^{70}$ promoter (e.g., lacq promoter (BBa_J54200; BBa_J56015), *E. coli* CreABCD phosphate sensing operon promoter (BBa_J64951), GlnRS promoter (BBa_K088007), lacZ promoter (BBa_K119000; BBa_K119001); M13K07 gene I promoter (BBa_M13101); M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), M13110 (BBa_M13110)), a constitutive *Bacillus subtilis* $\sigma^A$ promoter (e.g., promoter veg (BBa_K143013), promoter 43 (BBa_K143013), $P_{liaG}$ (BBa_K823000), $P_{lepA}$ (BBa_K823002), $P_{veg}$ (BBa_K823003)), a constitutive *Bacillus subtilis* $\sigma^B$ promoter (e.g., promoter ctc (BBa_K143010), promoter gsiB (BBa_K143011)), a *Salmonella* promoter (e.g., Pspv2 from *Salmonella* (BBa_K112706), Pspv from *Salmonella* (BBa_K112707)), a bacteriophage T7 promoter (e.g., T7 promoter (BBa_I712074; BBa_I719005; BBa_J34814; BBa_J64997; BBa_K113010; BBa_K113011; BBa_K113012; BBa_R0085; BBa_R0180; BBa_R0181; BBa_R0182; BBa_R0183; BBa_Z0251; BBa_Z0252; BBa_Z0253)), a bacteriophage SP6 promoter (e.g., SP6 promoter (BBa_J64998)), and functional fragments thereof.

"Gut" refers to the organs, glands, tracts, and systems that are responsible for the transfer and digestion of food, absorption of nutrients, and excretion of waste. In humans, the gut comprises the gastrointestinal (GI) tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines.

In some embodiments, the genetically engineered bacteria are active in the gut. In some embodiments, the genetically engineered bacteria are active in the large intestine. In some embodiments, the genetically engineered bacteria are active in the small intestine. In some embodiments, the genetically engineered bacteria are active in the small intestine and in the large intestine. In some embodiments, the genetically engineered bacteria transit through the small intestine. In some embodiments, the genetically engineered bacteria have increased residence time in the small intestine. In some embodiments, the genetically engineered bacteria colonize the small intestine. In some embodiments, the genetically engineered bacteria do not colonize the small intestine. In some embodiments, the genetically engineered bacteria have increased residence time in the gut. In some embodiments, the genetically engineered bacteria colonize the small intestine. In some embodiments, the genetically engineered bacteria do not colonize the gut.

As used herein, the term "low oxygen" is meant to refer to a level, amount, or concentration of oxygen ($O_2$) that is lower than the level, amount, or concentration of oxygen that is present in the atmosphere (e.g., <21% $O_2$; <160 torr $O_2$)). Thus, the term "low oxygen condition or conditions" or "low oxygen environment" refers to conditions or environments containing lower levels of oxygen than are present in the atmosphere. In some embodiments, the term "low oxygen" is meant to refer to the level, amount, or concentration of oxygen ($O_2$) found in a mammalian gut, e.g., lumen, stomach, small intestine, duodenum, jejunum, ileum, large intestine, cecum, colon, distal sigmoid colon, rectum, and anal canal. In some embodiments, the term "low oxygen" is meant to refer to a level, amount, or concentration of $O_2$ that is 0-60 mmHg $O_2$ (0-60 torr $O_2$) (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60 mmHg $O_2$), including any and all incremental fraction(s) thereof (e.g., 0.2 mmHg, 0.5 mmHg $O_2$, 0.75 mmHg $O_2$, 1.25 mmHg $O_2$, 2.175 mmHg $O_2$, 3.45 mmHg $O_2$, 3.75 mmHg $O_2$, 4.5 mmHg $O_2$, 6.8 mmHg 02, 11.35 mmHg 02, 46.3 mmHg 02, 58.75 mmHg, etc., which exemplary fractions are listed here for illustrative purposes and not meant to be limiting in any way). In some embodiments, "low oxygen" refers to about 60 mmHg $O_2$ or less (e.g., 0 to about 60 mmHg 02). The term "low oxygen" may also refer to a range of $O_2$ levels, amounts, or concentrations between 0-60 mmHg 02 (inclusive), e.g., 0-5 mmHg $O_2$, <1.5 mmHg $O_2$, 6-10 mmHg, <8 mmHg, 47-60 mmHg, etc. which listed exemplary ranges are listed here for illustrative purposes and not meant to be limiting in any way. See, for example, Albenberg et al., Gastroenterology, 147 (5): 1055-1063 (2014); Bergofsky et al., J Clin. Invest., 41(11): 1971-1980 (1962); Crompton et al., J Exp. Biol., 43: 473-478 (1965); He et al., PNAS (USA), 96: 4586-4591

(1999); McKeown, Br. J. Radiol., 87:20130676 (2014) (doi: 10.1259/brj.20130676), each of which discusses the oxygen levels found in the mammalian gut of various species and each of which are incorporated by reference herewith in their entireties. In some embodiments, the term "low oxygen" is meant to refer to the level, amount, or concentration of oxygen ($O_2$) found in a mammalian organ or tissue other than the gut, e.g., urogenital tract, tumor tissue, etc. in which oxygen is present at a reduced level, e.g., at a hypoxic or anoxic level. In some embodiments, "low oxygen" is meant to refer to the level, amount, or concentration of oxygen ($O_2$) present in partially aerobic, semi aerobic, microaerobic, nanoaerobic, microoxic, hypoxic, anoxic, and/or anaerobic conditions. For example, Table 2 summarizes the amount of oxygen present in various organs and tissues. In some embodiments, the level, amount, or concentration of oxygen ($O_2$) is expressed as the amount of dissolved oxygen ("DO") which refers to the level of free, non-compound oxygen ($O_2$) present in liquids and is typically reported in milligrams per liter (mg/L), parts per million (ppm; 1 mg/L=1 ppm), or in micromoles (μmole) (1 μmole $O_2$=0.022391 mg/L $O_2$). Fondriest Environmental, Inc., "Dissolved Oxygen", Fundamentals of Environmental Measurements, 19 Nov. 2013. In some embodiments, the term "low oxygen" is meant to refer to a level, amount, or concentration of oxygen ($O_2$) that is about 6.0 mg/L DO or less, e.g., 6.0 mg/L, 5.0 mg/L, 4.0 mg/L, 3.0 mg/L, 2.0 mg/L, 1.0 mg/L, or 0 mg/L, and any fraction therein, e.g., 3.25 mg/L, 2.5 mg/L, 1.75 mg/L, 1.5 mg/L, 1.25 mg/L, 0.9 mg/L, 0.8 mg/L, 0.7 mg/L, 0.6 mg/L, 0.5 mg/L, 0.4 mg/L, 0.3 mg/L, 0.2 mg/L and 0.1 mg/L DO, which exemplary fractions are listed here for illustrative purposes and not meant to be limiting in any way. The level of oxygen in a liquid or solution may also be reported as a percentage of air saturation or as a percentage of oxygen saturation (the ratio of the concentration of dissolved ($O_2$) in the solution to the maximum amount of oxygen that will dissolve in the solution at a certain temperature, pressure, and salinity under stable equilibrium). Well-aerated solutions (e.g., solutions subjected to mixing and/or stirring) without oxygen producers or consumers are 100% air saturated. In some embodiments, the term "low oxygen" is meant to refer to 40% air saturation or less, e.g., 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, and 0% air saturation, including any and all incremental fraction(s) thereof (e.g., 30.25%, 22.70%, 15.5%, 7.7%, 5.0%, 2.8%, 2.0%, 1.65%, 1.0%, 0.9%, 0.8%, 0.75%, 0.68%, 0.5%. 0.44%, 0.3%, 0.25%, 0.2%, 0.1%, 0.08%, 0.075%, 0.058%, 0.04%. 0.032%, 0.025%, 0.01%, etc.) and any range of air saturation levels between 0-40%, inclusive (e.g., 0-5%, 0.05-0.1%, 0.1-0.2%, 0.1-0.5%, 0.5-2.0%, 0-10%, 5-10%, 10-15%, 15-20%, 20-25%, 25-30%, etc.). The exemplary fractions and ranges listed here are for illustrative purposes and not meant to be limiting in any way. In some embodiments, the term "low oxygen" is meant to refer to 9% $O_2$ saturation or less, e.g., 9%, 8%, 7%, 6%, 5%, 4%, 3%, 2%, 1%, 0%, 02 saturation, including any and all incremental fraction(s) thereof (e.g., 6.5%, 5.0%, 2.2%, 1.7%, 1.4%, 0.9%, 0.8%, 0.75%, 0.68%, 0.5%. 0.44%, 0.3%, 0.25%, 0.2%, 0.1%, 0.08%, 0.075%, 0.058%, 0.04%. 0.032%, 0.025%, 0.01%, etc.) and any range of $O_2$ saturation levels between 0-9%, inclusive (e.g., 0-5%, 0.05-0.1%, 0.1-0.2%, 0.1-0.5%, 0.5-2.0%, 0-8%, 5-7%, 0.3-4.2% 02, etc.). The exemplary fractions and ranges listed here are for illustrative purposes and not meant to be limiting in any way.

TABLE 2

| Compartment | Oxygen Tension |
|---|---|
| stomach | ~60 torr (e.g., 58 +/− 15 torr) |
| duodenum and first part of jejunum | ~30 torr (e.g., 32 +/− 8 torr); ~20% oxygen in ambient air |
| Ileum (mid- small intestine) | ~10 torr; ~6% oxygen in ambient air (e.g., 11 +/− 3 torr) |
| Distal sigmoid colon | ~3 torr (e.g., 3 +/− 1 torr) |
| colon | <2 torr |
| Lumen of cecum | <1 torr |
| tumor | <32 torr (most tumors are <15 torr) |

"Microorganism" refers to an organism or microbe of microscopic, submicroscopic, or ultramicroscopic size that typically consists of a single cell. Examples of microorganisms include bacteria, yeast, viruses, parasites, fungi, certain algae, and protozoa. In some aspects, the microorganism is engineered ("engineered microorganism") to produce one or more therapeutic molecules or proteins of interest. In certain aspects, the microorganism is engineered to take up and catabolize certain metabolites or other compounds from its environment, e.g., the gut. In certain aspects, the microorganism is engineered to synthesize certain beneficial metabolites or other compounds (synthetic or naturally occurring) and release them into its environment. In certain embodiments, the engineered microorganism is an engineered bacterium. In certain embodiments, the engineered microorganism is an engineered virus. In certain embodiments, the engineered microorganism is an engineered yeast. When referring to bacteria, engineered bacteria or recombinant bacteria, the embodiments also contemplate other types of microorganisms.

"Host cell" refers to a cell that can be used to express a polynucleotide, such as a polynucleotide that encodes a methionine catabolism enzyme, such as a methionine decarboxylase, and/or a methionine importer.

"Non-pathogenic bacteria" refer to bacteria that are not capable of causing disease or harmful responses in a host. In some embodiments, non-pathogenic bacteria are Gram-negative bacteria. In some embodiments, non-pathogenic bacteria are Gram-positive bacteria. In some embodiments, non-pathogenic bacteria are commensal bacteria, which are present in the indigenous microbiota of the gut. Examples of non-pathogenic bacteria include, but are not limited to, *Bacillus, Bacteroides, Bifidobacterium, Brevibacteria, Clostridium, Enterococcus, Escherichia, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii* (Sonnenborn et al., 2009; Dinleyici et al., 2014; U.S. Pat. Nos. 6,835,376; 6,203,797; 5,589,168; 7,731,976). Naturally pathogenic bacteria may be genetically engineered to provide reduce or eliminate pathogenicity.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria are currently recognized as probiotic. Examples of probiotic bacteria include, but are not limited to, Bifidobacteria, *Escherichia, Lactobacillus*, and *Saccharomyces*, e.g., *Bifidobacterium bifidum, Enterococcus faecium, Escherichia coli, Escherichia coli* strain Nissle, *Lactobacillus acidophilus, Lactobacillus bulgaricus, Lactobacillus paracasei, Lactobacillus plantarum*, and *Saccharomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, the term "auxotroph" or "auxotrophic" refers to an organism that requires a specific factor, e.g., an amino acid, a sugar, or other nutrient, to support its growth. An "auxotrophic modification" is a genetic modification that causes the organism to die in the absence of an exogenously added nutrient essential for survival or growth because it is unable to produce said nutrient. As used herein, the term "essential gene" refers to a gene which is necessary to for cell growth and/or survival. Essential genes are described in more detail infra and include, but are not limited to, DNA synthesis genes (such as thyA), cell wall synthesis genes (such as dapA), and amino acid genes (such as serA and metA).

As used herein, the terms "modulate" and "treat" and their cognates refer to an amelioration of a disease, disorder, and/or condition, or at least one discernible symptom thereof. In another embodiment, "modulate" and "treat" refer to an amelioration of at least one measurable physical parameter, not necessarily discernible by the patient. In another embodiment, "modulate" and "treat" refer to inhibiting the progression of a disease, disorder, and/or condition, either physically (e.g., stabilization of a discernible symptom), physiologically (e.g., stabilization of a physical parameter), or both. In another embodiment, "modulate" and "treat" refer to slowing the progression or reversing the progression of a disease, disorder, and/or condition. As used herein, "prevent" and its cognates refer to delaying the onset or reducing the risk of acquiring a given disease, disorder and/or condition or a symptom associated with such disease, disorder, and/or condition.

Those in need of treatment may include individuals already having a particular medical disease, as well as those at risk of having, or who may ultimately acquire the disease. The need for treatment is assessed, for example, by the presence of one or more risk factors associated with the development of a disease, the presence or progression of a disease, or likely receptiveness to treatment of a subject having the disease. Disorders associated with or involved with amino acid metabolism, e.g., homocystinuria or cystinuria, may be caused by inborn genetic mutations for which there are no known cures. Diseases can also be secondary to other conditions, e.g., an intestinal disorder or a bacterial infection. Treating diseases associated with amino acid metabolism may encompass reducing normal levels of one or more amino acids, reducing excess levels of one or more amino acids, or eliminating one or more amino acids, and does not necessarily encompass the elimination of the underlying disease.

As used herein the terms "disease associated with amino acid metabolism" or a "disorder associated with amino acid metabolism" is a disease or disorder involving the abnormal, e.g., increased, levels of one or more amino acids, e.g., methionine, in a subject. In one embodiment, a disease or disorder associated with amino acid metabolism, e.g., methionine metabolism, is homocystinuria. In another embodiment, a disease or disorder associated with amino acid metabolism, e.g., methionine metabolism, is cancer. In another embodiment, a disease or disorder associated with amino acid metabolism, e.g., methionine metabolism, is a metabolic disease or a metabolic syndrome.

As used herein, the term "amino acid" refers to a class of organic compounds that contain at least one amino group and one carboxyl group. Amino acids include leucine, isoleucine, valine, arginine, lysine, asparagine, serine, glycine, glutamine, tryptophan, methionine, threonine, cysteine, tyrosine, phenylalanine, glutamic acid, aspartic acid, alanine, histidine, and proline.

As used herein, the term "amino acid catabolism" or "amino acid metabolism" refers to the processing, breakdown and/or degradation of an amino acid molecule (e.g., methionine, asparagine, lysine or arginine) into other compounds that are not associated with the disease associated with amino acid metabolism, such as homocystinuria, or other compounds which can be utilized by the bacterial cell.

In another embodiment, the term "methionine catabolism" refers to the processing, breakdown, and/or degradation of methionine into 3-methylthiopropylamine. In yet another embodiment, the term "methionine catabolism" refers to the processing, breakdown, and/or degradation of methionine to sulfate. In one embodiment, the term "methionine catabolism" refers to the processing, breakdown, and/or degradation of methionine into methanethiol and 2-aminobut-2-enoate. In another embodiment, the term "methionine catabolism" refers to the processing, breakdown, and/or degradation of methionine into 3-methylthio-2-oxobutyric acid.

As used herein, the term "importer" is meant to refer to a mechanism, e.g., protein, proteins, or protein complex, for importing a molecule, e.g., amino acid, peptide (di-peptide, tripeptide, polypeptide, etc), toxin, metabolite, substrate, as well as other biomolecules into the microorganism from the extracellular milieu. For example, a methionine importer such as MetP imports methionine into the microorganism.

As used herein, "payload" refers to one or more molecules of interest to be produced by a genetically engineered microorganism, such as bacteria or a virus. In some embodiments, the payload is a therapeutic payload, e.g., an amino acid catabolic enzyme or an amino acid importer polypeptide. In some embodiments, the payload is a regulatory molecule, e.g., a transcriptional regulator such as FNR. In some embodiments, the payload comprises a regulatory element, such as a promoter or a repressor. In some embodiments, the payload comprises an inducible promoter, such as from FNRS. In some embodiments the payload comprises a repressor element, such as a kill switch. In some embodiments, the payload is encoded by a gene or multiple genes or an operon. In alternate embodiments, the payload is produced by a biosynthetic or biochemical pathway, wherein the biosynthetic or biochemical pathway may optionally be endogenous to the microorganism. In some embodiments, the genetically engineered microorganism comprises two or more payloads.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition. A therapeutically effective amount may, for example, be sufficient to treat, prevent, reduce the severity, delay the onset, and/or reduce the risk of occurrence of one or more symptoms of a disease or condition associated with excess amino acid levels. A therapeutically effective amount, as well as a therapeutically effective frequency of administration, can be determined by methods known in the art and discussed below.

As used herein, the term "polypeptide" includes "polypeptide" as well as "polypeptides," and refers to a molecule composed of amino acid monomers linearly linked by amide bonds (i.e., peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms. The term "dipeptide" refers to a peptide of two linked amino acids. The term "tripeptide" refers to a peptide of three linked amino acids. The term "polypeptide" is also intended to refer to the products of post-expression modifications of the polypeptide, including but not limited to glycosylation, acetylation, phosphorylation, amidation, derivatization, proteolytic cleavage, or modification by non-naturally occurring amino acids. A polypeptide may be derived from a natural biological source or produced by recombinant technology. A polypeptide may be a naturally occurring polypeptide or alternatively may be a polypeptide not naturally occurring, such as a polypeptide identified from a library of engineered polypeptides. In other embodiments, the polypeptide is produced by the genetically engineered bacteria or virus of the current invention. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides, which do not possess a defined three-dimensional structure, but rather can adopt a large number of different conformations, are referred to as unfolded. The term "peptide" or "polypeptide" may refer to an amino acid sequence that corresponds to a protein or a portion of a protein or may refer to an amino acid sequence that corresponds with non-protein sequence, e.g., a sequence selected from a regulatory peptide sequence, leader peptide sequence, signal peptide sequence, linker peptide sequence, and other peptide sequence.

An "isolated" polypeptide or a fragment, variant, or derivative thereof refers to a polypeptide that is not in its natural milieu. No particular level of purification is required. Recombinantly produced polypeptides and proteins expressed in host cells, including but not limited to bacterial or mammalian cells, are considered isolated for purposed of the invention, as are native or recombinant polypeptides which have been separated, fractionated, or partially or substantially purified by any suitable technique. Recombinant peptides, polypeptides or proteins refer to peptides, polypeptides or proteins produced by recombinant DNA techniques, i.e. produced from cells, microbial or mammalian, transformed by an exogenous recombinant DNA expression construct encoding the polypeptide. Proteins or peptides expressed in most bacterial cultures will typically be free of glycan. Fragments, derivatives, analogs or variants of the foregoing polypeptides, and any combination thereof are also included as polypeptides. The terms "fragment," "variant," "derivative" and "analog" include polypeptides having an amino acid sequence sufficiently similar to the amino acid sequence of the original peptide and include any polypeptides, which retain at least one or more properties of the corresponding original polypeptide. Fragments of polypeptides of the present invention include proteolytic fragments, as well as deletion fragments. Fragments also include specific antibody or bioactive fragments or immunologically active fragments derived from any polypeptides described herein. Variants may occur naturally or be non-naturally occurring. Non-naturally occurring variants may be produced using mutagenesis methods known in the art. Variant polypeptides may comprise conservative or non-conservative amino acid substitutions, deletions or additions.

Polypeptides also include fusion proteins. As used herein, the term "variant" includes a fusion protein, which comprises a sequence of the original peptide or sufficiently similar to the original peptide. As used herein, the term "fusion protein" refers to a chimeric protein comprising amino acid sequences of two or more different proteins. Typically, fusion proteins result from well known in vitro recombination techniques. Fusion proteins may have a similar structural function (but not necessarily to the same extent), and/or similar regulatory function (but not necessarily to the same extent), and/or similar biochemical function (but not necessarily to the same extent) and/or immunological activity (but not necessarily to the same extent) as the individual original proteins which are the components of the fusion proteins. "Derivatives" include but are not limited to peptides, which contain one or more naturally occurring amino acid derivatives of the twenty standard amino acids. "Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: Ala, Pro, Gly, Gln, Asn, Ser, Thr, Cys, Ser, Tyr, Thr, Val, Ile, Leu, Met, Ala, Phe, Lys, Arg, His, Phe, Tyr, Trp, His, Asp, and Glu.

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the peptides of the invention. Such variants generally retain the functional activity of the peptides of the present invention. Variants include peptides that differ in amino acid sequence from the native and wild-type peptide, respectively, by way of one or more amino acid deletion(s), addition(s), and/or substitution(s). These may be naturally occurring variants as well as artificially designed ones.

As used herein, the term "percent identity" refers to a quantitative measurement of the similarity between two sequences (e.g., nucleic acid or amino acid sequence). In some embodiments, the "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al., *J. Mol. Biol.* 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used. For example, a first nucleic acid sequence may have at least 70%, at least 75%, at least 80%, at least 85%, at least 90%, at least 91%, at least 92%, at least 93%, at least 94%, at least 95%, at least about 96%, at least 97%, at least 98%, at least 99%, or at least 99.5% identity to the sequence of a second nucleic acid. In another example, a first polypeptide may comprise an amino acid sequence that has at least 70%, at least 75%, at least 80%, at least 85%, at least 90%, at least 91%, at least 92%, at least 93%, at least 94%, at least 95%, at least about 96%, at least 97%, at least 98%, at least 99%, or at least 99.5% identity to the amino acid sequence of a second polypeptide.

As used herein, the term "linker", "linker peptide" or "peptide linkers" or "linker" refers to synthetic or non-native or non-naturally-occurring amino acid sequences that connect or link two polypeptide sequences, e.g., that link two polypeptide domains. As used herein the term "synthetic" refers to amino acid sequences that are not naturally occurring. Exemplary linkers are described herein. Additional exemplary linkers are provided in US 20140079701, the contents of which are herein incorporated by reference in its entirety.

As used herein, the term "codon-optimized sequence" refers to a sequence, which was modified from an existing coding sequence, or designed, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism. The term "codon-optimized" refers to the modification of codons in the gene or coding regions of a nucleic acid molecule to reflect the typical codon usage of the host organism without altering the polypeptide encoded by the nucleic acid molecule. Such optimization includes replacing at least one, or more than one, or a significant number, of codons with one or more codons that are more frequently used in the genes of the host organism. A "codon-optimized sequence" refers to a sequence, which was modified from an existing coding sequence, or designed, for example, to improve translation in an expression host cell or organism of a transcript RNA molecule transcribed from the coding sequence, or to improve transcription of a coding sequence. In some embodiments, the improvement of transcription and/or translation involves increasing the level of transcription and/or translation. In some embodiments, the improvement of transcription and/or translation involves decreasing the level of transcription and/or translation. In some embodiments, codon optimization is used to fine-tune the levels of expression from a construct of interest. Codon optimization includes, but is not limited to, processes including selecting codons for the coding sequence to suit the codon preference of the expression host organism. Many organisms display a bias or preference for use of particular codons to code for insertion of a particular amino acid in a growing polypeptide chain. Codon preference or codon bias, differences in codon usage between organisms, is allowed by the degeneracy of the genetic code, and is well documented among many organisms. Codon bias often correlates with the efficiency of translation of messenger RNA (mRNA), which is in turn believed to be dependent, inter alia, on the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

The terms "phage" and "bacteriophage" are used interchangeably herein. Both terms refer to a virus that infects and replicates within a bacterium. As used herein "phage" or bacteriophage" collectively refers to prophage, lysogenic, dormant, temperate, intact, defective, cryptic, and satellite phage, phage tail bacteriocins, tailiocins, and gene transfer agents. As used therein the term "prophage" refers to the genomic material of a bacteriophage, which is integrated into a replicon of the host cell and replicates along with the host. The prophage may be able to produce phages if specifically activated. In some cases, the prophage is not able to produce phages or has never done so (i.e., defective or cryptic prophages). In some cases, prophage also refers to satellite phages. The terms "prophage" and "endogenous phage" are used interchangeably herein. "Endogenous phage" or "endogenous prophage" also refers to a phage that is present in the natural state of a bacterium (and its parental strain). As used herein the term "phage knockout" or "inactivated phage" refers to a phage which has been modified so that it can either no longer produce and/or package phage particles or it produces fewer phage particles than the wild type phage sequence. In some embodiments, the inactivated phage or phage knockout refers to the inactivation of a temperate phage in its lysogenic state, i.e., to a prophage. Such a modification refers to a mutation in the phage; such mutations include insertions, deletions (partial or complete deletion of phage genome), substitutions, inversions, at one or more positions within the phage genome, e.g., within one or more genes within the phage genome. As used herein the adjectives "phage-free", "phage free" and "phageless" are used interchangeably to characterize a bacterium or strain which contains one or more prophages, one or more of which have been modified. The modification can result in a loss of the ability of the prophage to be induced or release phage particles. Alternatively, the modification can result in less efficient or less frequent induction or less efficient or less frequent phage release as compared to the isogenic strain without the modification. Ability to induce and release phage can be measured using a plaque assay as described herein. As used herein phage induction refers to the part of the life cycle of a lysogenic prophage, in which the lytic phage genes are activated, phage particles are produced and lysis occurs.

As used herein a "pharmaceutical composition" refers to a preparation of bacterial cells disclosed herein with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

The articles "a" and "an," as used herein, should be understood to mean "at least one," unless clearly indicated to the contrary. For example, as used herein, "a heterologous gene encoding a methionine decarboxylase" should be understood to mean "at least one heterologous gene encoding at least one methionine decarboxylase." Similarly, as used herein, "a heterologous gene encoding an amino acid importer" should be understood to mean "at least one heterologous gene encoding at least one amino acid importer."

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Host Cells

Any suitable host cell may be used to express any of the enzymes disclosed herein, such as methionine catabolism enzymes (e.g., methionine decarboxylases) and methionine importers. Suitable host cells include, but are not limited to, bacterial cells (e.g., *E. coli* cells), fungal cells (e.g., yeast cells), algal cells, plant cells, insect cells, and animal cells, including mammalian cells.

Suitable yeast host cells include, but are not limited to: *Candida, Hansenula, Saccharomyces, Schizosaccharomyces, Pichia, Kluyveromyces*, and *Yarrowia*. In some embodiments, the yeast cell is *Hansenula polymorpha, Saccharomyces cerevisiae, Saccaromyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica.*

In some embodiments, the yeast strain is an industrial polyploid yeast strain. Other non-limiting examples of fungal cells include cells obtained from *Aspergillus* spp., *Penicillium* spp., *Fusarium* spp., *Rhizopus* spp., *Acremonium* spp., *Neurospora* spp., Sordaria spp., *Magnaporthe* spp., *Allomyces* spp., *Ustilago* spp., *Botrytis* spp., and *Trichoderma* spp.

In certain embodiments, the host cell is an algal cell such as *Chlamydomonas* (e.g., C. *Reinhardtii*) and *Phormidium* (P. sp. ATCC29409).

In some embodiments, the host cell is an animal cell. In some embodiments, the host cell is a mammalian cell, including, for example, a human cell (e.g., 293, HeLa, W138, PER.C6 or Bowes melanoma cells), a mouse cell (e.g., 3T3, NS0, NS1 or Sp2/0), a hamster cell (e.g., CHO or BHK), or a monkey cell (e.g., COS, FRhL or Vero). In some embodiments, the cell is a hybridoma cell line.

In some embodiments, the host cell is a bacterial cell, e.g., a recombinant bacterial cell. The disclosure provides a bacterial cell that comprises a heterologous gene encoding a methionine catabolism enzyme. In some embodiments, the bacterial cell is a non-pathogenic bacterial cell. In some embodiments, the bacterial cell is a commensal bacterial cell. In some embodiments, the bacterial cell is a probiotic bacterial cell.

In certain embodiments, the bacterial cell is selected from the group consisting of a *Bacteroides fragilis, Bacteroides thetaiotaomicron, Bacteroides subtilis, Bifidobacterium animalis, Bifidobacterium bifidum, Bifidobacterium infantis, Bifidobacterium lactis, Clostridium butyricum, Clostridium scindens, Escherichia coli, Lactobacillus acidophilus, Lactobacillus plantarum, Lactobacillus reuteri, Lactococcus lactis*, and *Oxalobacter formigenes* bacterial cell. In one embodiment, the bacterial cell is a *Bacteroides fragilis* bacterial cell. In one embodiment, the bacterial cell is a *Bacteroides thetaiotaomicron* bacterial cell. In one embodiment, the bacterial cell is a *Bacteroides subtilis* bacterial cell. In one embodiment, the bacterial cell is a *Bifidobacterium animalis* bacterial cell. In one embodiment, the bacterial cell is a *Bifidobacterium bifidum* bacterial cell. In one embodiment, the bacterial cell is a *Bifidobacterium infantis* bacterial cell. In one embodiment, the bacterial cell is a *Bifidobacterium lactis* bacterial cell. In one embodiment, the bacterial cell is a *Clostridium butyricum* bacterial cell. In one embodiment, the bacterial cell is a *Clostridium scindens* bacterial cell. In one embodiment, the bacterial cell is an *Escherichia coli* bacterial cell. In one embodiment, the bacterial cell is a *Lactobacillus acidophilus* bacterial cell. In one embodiment, the bacterial cell is a *Lactobacillus plantarum* bacterial cell. In one embodiment, the bacterial cell is a *Lactobacillus reuteri* bacterial cell. In one embodiment, the bacterial cell is a *Lactococcus lactis* bacterial cell. In one embodiment, the bacterial cell is a *Oxalobacter formigenes* bacterial cell. In another embodiment, the bacterial cell does not include *Oxalobacter formigenes.*

In one embodiment, the bacterial cell is a Gram positive bacterial cell. In another embodiment, the bacterial cell is a Gram negative bacterial cell.

In some embodiments, the bacterial cell is *Escherichia coli* strain Nissle 1917 (*E. coli* Nissle), a Gram-positive bacterium of the Enterobacteriaceae family that "has evolved into one of the best characterized probiotics" (Ukena et al., 2007). The strain is characterized by its "complete harmlessness" (Schultz, 2008), and "has GRAS (generally recognized as safe) status" (Reister et al., 2014, emphasis added). Genomic sequencing confirmed that *E. coli* Nissle "lacks prominent virulence factors (e.g., *E. coli* α-hemolysin, P-fimbrial adhesins)" (Schultz, 2008), and *E. coli* Nissle "does not carry pathogenic adhesion factors and does not produce any enterotoxins or cytotoxins, it is not invasive, not uropathogenic" (Sonnenborn et al., 2009). As early as in 1917, *E. coli* Nissle was packaged into medicinal capsules, called Mutaflor, for therapeutic use. *E. coli* Nissle has since been used to treat ulcerative colitis in humans in vivo (Rembacken et al., 1999), to treat inflammatory bowel disease, Crohn's disease, and pouchitis in humans in vivo (Schultz, 2008), and to inhibit enteroinvasive *Salmonella, Legionella, Yersinia*, and *Shigella* in vitro (Altenhoefer et al., 2004). It is commonly accepted that *E. coli* Nissle's "therapeutic efficacy and safety have convincingly been proven" (Ukena et al., 2007).

In one embodiment, the recombinant bacterial cell does not colonize the subject.

One of ordinary skill in the art would appreciate that the genetic modifications disclosed herein may be adapted for other species, strains, and subtypes of bacteria. Furthermore, genes from one or more different species can be introduced into one another, e.g., an amino acid catabolism gene from *Klebsiella quasipneumoniae* can be expressed in *Escherichia coli.*

In some embodiments, the bacterial cell is a genetically engineered bacterial cell. In another embodiment, the bacterial cell is a recombinant bacterial cell. In some embodiments, the disclosure comprises a colony of bacterial cells.

In another aspect, the disclosure provides a recombinant bacterial culture which comprises bacterial cells disclosed herein. In one aspect, the disclosure provides a recombinant bacterial culture which reduces levels of an amino acid, e.g., methionine, in the media of the culture. In one embodiment, the levels of an amino acid are reduced by about 50%, about 75%, or about 100% in the media of the cell culture. In another embodiment, the levels of an amino acid are reduced by about two-fold, three-fold, four-fold, five-fold, six-fold, seven-fold, eight-fold, nine-fold, or ten-fold in the media of the cell culture. In one embodiment, the levels of an amino acid, e.g., methionine, are reduced below the limit of detection in the media of the cell culture.

In some embodiments of the above described genetically engineered bacteria, the gene encoding a methionine decarboxylase is present on a plasmid in the bacterium and operatively linked on the plasmid to the promoter that is induced under low-oxygen or anaerobic conditions. In other embodiments, the gene encoding a methionine decarboxylase is present in the bacterial chromosome and is operatively linked in the chromosome to the promoter that is induced under low-oxygen or anaerobic conditions.

In some embodiments of the above described genetically engineered bacteria, the gene encoding a methionine decarboxylase is present on a plasmid in the bacterium and operatively linked on the plasmid to the promoter that is chemically induced. In other embodiments, the gene encoding a methionine decarboxylase is present in the bacterial chromosome and is operatively linked in the chromosome to the promoter that is chemically induced.

In some embodiments of the above described genetically engineered bacteria, the gene encoding a methionine importer is present on a plasmid in the bacterium and operatively linked on the plasmid to the promoter that is chemically induced. In other embodiments, the gene encoding a methionine importer is present in the bacterial chromosome and is operatively linked in the chromosome to the promoter that is chemically induced.

In some embodiments of the above described genetically engineered bacteria, the gene encoding a methionine decarboxylase is present on a plasmid in the bacterium and operatively linked on the plasmid to the promoter that is chemically induced and the gene encoding a methionine importer is present on a plasmid in the bacterium and operatively linked on the plasmid to the promoter that is chemically induced. In other embodiments, the gene encoding a methionine decarboxylase is present in the bacterial chromosome and is operatively linked in the chromosome to the promoter that is chemically induced and the gene encoding a methionine importer is present in the bacterial chromosome and is operatively linked in the chromosome to the promoter that is chemically induced.

In some embodiments of the above described genetically engineered bacteria, the gene encoding a methionine decarboxylase is present on a plasmid in the bacterium and operatively linked on the plasmid to the promoter that is chemically induced and the gene encoding a methionine importer is present in the bacterial chromosome and is operatively linked in the chromosome to the promoter that is chemically induced. In other embodiments, the gene encoding a methionine decarboxylase is present in the bacterial chromosome and is operatively linked in the chromosome to the promoter that is chemically induced and the gene encoding a methionine importer is present on a plasmid in the bacterium and operatively linked on the plasmid to the promoter that is chemically induced.

In some embodiments, the genetically engineered bacteria is an auxotroph. In one embodiment, the genetically engineered bacteria is an auxotroph selected from a cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1 auxotroph. In some embodiments, the engineered bacteria have more than one auxotrophy, for example, they may be a ΔthyA and ΔdapA auxotroph.

In some embodiments of the above described genetically engineered bacteria, the gene encoding a methionine decarboxylase is present on a plasmid in the bacterium and operatively linked on the plasmid to the promoter that is induced under low-oxygen or anaerobic conditions. In other embodiments, the gene encoding a methionine decarboxylase is present in the bacterial chromosome and is operatively linked in the chromosome to the promoter that is induced under low-oxygen or anaerobic conditions.

A. Methionine Catabolism Enzymes

Methionine catabolism enzymes may be expressed or modified in host cells, such as the bacteria disclosed herein, in order to enhance catabolism of methionine. For example, the genetically engineered bacteria comprising at least one heterologous gene encoding a methionine catabolism enzyme can catabolize methionine to treat a disease associated with methionine, including, but not limited to homocystinuria, cystinuria, primary and secondary hypermethioninemia, cystathionine β-synthase (CBS) deficiency, or cancer, e.g., lymphoblastic leukemia.

As used herein, the term "methionine catabolism enzyme" refers to an enzyme involved in the catabolism of methionine. Specifically, when a methionine catabolism enzyme is expressed in a recombinant bacterial cell, the bacterial cell hydrolyzes more methionine into 3-methylthiopropylamine (3-MTP) when the catabolism enzyme is expressed than unmodified bacteria of the same bacterial subtype under the same conditions. In some embodiments, methionine importers may also be expressed or modified in the recombinant bacteria to enhance methionine import into the cell in order to increase the catabolism of methionine by the methionine catabolism enzyme. In other embodiments, methionine exporters may be knocked-out in the recombinant bacteria to decrease export of methionine and/or increase cytoplasmic concentration of methionine.

In one embodiment, the methionine catabolism enzyme is a methionine decarboxylase (MetDC). In another embodiment, the methionine catabolism enzyme is a leucine decarboxylase (LeuDC) which has been modified to further comprise methionine catabolism activity, e.g., methionine decarboxylase activity. For example, SEQ ID NO: 1053 is a leucine decarboxylase which has been modified as compared to a wild-type leucine decarboxylase sequence at positions N2S, V14A, E16G, H17S, R19W, A30E, K41Q, I45D, R48H, A51P, R65Q, L68C, L90R, N147S, L154V, R156Q, R160G, L170Q, H179S, H185S, E218Q, Y220F, C235R, H240D, K254E, V263M, T269A, V304A, S308V, D310E, A318M, V328S, T372E, S394T, I406P, and D411C as compared to a wild type polypeptide. In one embodiment, the leucine decarboxylase gene encodes a polypeptide that has point mutations N2S, V14A, E16G, H17S, R19W, A30E, K41Q, I45D, R48H, A51P, R65Q, L68C, L90R, N147S, L154V, R156Q, R160G, L170Q, H179S, H185S, E218Q, Y220F, C235R, H240D, K254E, V263M, T269A, V304A, S308V, D310E, A318M, V328S, T372E, S394T, 1406P, and D411C and comprises methionine decarboxylase activity. Accordingly, in some embodiments herein, a leucine decarboxylase enzyme that has been modified to have methionine decarboxylase activity may be referred to as a "methionine decarboxylase (MetDC)" which is encoded by a "methionine decarboxylase (metDC) gene."

In one embodiment, the methionine catabolism enzyme increases the rate of methionine catabolism in the cell. In one embodiment, the methionine catabolism enzyme decreases the level of methionine in the cell. In another embodiment, the methionine catabolism enzyme increases the level of 3-methylthiopropylamine in the cell. In one embodiment, 3-methylthiopropylamine is not toxic to the cell.

Methionine catabolism enzymes are well known to those of skill in the art (see, e.g., Huang et al., *Mar. Drugs,* 13(8):5492-5507, 2015). For example, the adenosylmethionine synthase pathway has been identified in *Anabaena cylindrica*. In the adenosylmethionine synthase pathway, methionine is catabolized into S-adenosyl-L-homocysteine by an S-adenosylmethionine synthase enzyme, followed by conversion of the S-adenosyl-L-homocysteine into $_L$-homocysteine by an adenosylhomocysteinase enzyme. As another example, two methionine aminotransferase enzymes (including Aro8 and Aro9), and one decarboxylase gene (Aro10) have been identified in *Saccharomyces cerevisiae* which catabolize methionine (Yin et al. (2015) FEMS Microbiol. Lett. 362(5) pii: fnu043). Methionine aminotransferase enzymes catabolize methionine and 2-oxo carboxylate into 2-oxo-4-methylthiobutanoate and an L-amino acid.

In some embodiments, a methionine catabolism enzyme is encoded by a gene encoding a methionine catabolism enzyme derived from a bacterial species. In some embodiments, a methionine catabolism enzyme is encoded by a gene encoding a methionine catabolism enzyme derived from a non-bacterial species. In some embodiments, a methionine catabolism enzyme is encoded by a gene derived from a eukaryotic species, e.g., a yeast species or a plant species. In one embodiment, the gene encoding the methionine catabolism enzyme is derived from an organism of the genus or species that includes, but is not limited to, *Klebsiella quasipneumoniae, Bacillus subtilis, Caenorhabditis elegans, Entamoeba histolytica, Bacillus halodurans, Methylobacterium aquaticum, Saccharomyces cerevisiae, Escherichia coli*, and *Anabaena cylindrica.*

In one embodiment, the methionine catabolism enzyme is a methionine decarboxylase (MDC). In one embodiment, the methionine decarboxylase gene is a MDC gene from *Streptomyces* sp. 590. On example of such a MDC gene is described, for example, in Misono et al., *Bull. Inst. Chem. Res., Kyoto Univ.,* 58(3):323-333, 1980. In one embodiment, the methionine decarboxylase gene is a metDC from *Stanieria* sp. NIES-3757. In one embodiment, the methionine decarboxylase gene is a metDC from *Mus musculus*. In one embodiment, the methionine decarboxylase gene is a metDC from *Entamoeba histolytica.*

In one embodiment, the methionine decarboxylase gene encodes a polypeptide with a Q70D mutation referenced by the polypeptide encoded by the gene sequence having the sequence of SEQ ID NO: 1003. In one embodiment, the methionine decarboxylase gene encodes a polypeptide with a N82H mutation referenced by the polypeptide encoded by the gene sequence having the sequence of SEQ ID NO: 1003. In one embodiment, the methionine decarboxylase gene encodes a polypeptide with Q70D N82H mutations referenced by the polypeptide encoded by the gene sequence having the sequence of SEQ ID NO: 1003.

In one embodiment, the methionine decarboxylase gene encodes a polypeptide with a Q70D mutation referenced by the polypeptide encoded by the gene sequence having the sequence of SEQ ID NO: 1018. In one embodiment, the methionine decarboxylase gene encodes a polypeptide with a N82H mutation referenced by the polypeptide encoded by the gene sequence having the sequence of SEQ ID NO: 1018. In one embodiment, the methionine decarboxylase gene encodes a polypeptide with Q70D N82H mutations referenced by the polypeptide encoded by the gene sequence having the sequence of SEQ ID NO: 1018.

In one embodiment, the methionine decarboxylase gene encodes a polypeptide with a V491L mutation referenced by the polypeptide encoded by the gene sequence having the sequence of SEQ ID NO: 1003. In one embodiment, the methionine decarboxylase gene encodes a polypeptide with a A500P mutation referenced by the polypeptide encoded by the gene sequence having the sequence of SEQ ID NO: 1003. In one embodiment, the methionine decarboxylase gene encodes a polypeptide with V491L A500P mutations referenced by the polypeptide encoded by the gene sequence having the sequence of SEQ ID NO: 1003.

In one embodiment, the methionine decarboxylase gene encodes a polypeptide with a V491L mutation referenced by the polypeptide encoded by the gene sequence having the sequence of SEQ ID NO: 1018. In one embodiment, the methionine decarboxylase gene encodes a polypeptide with a A500P mutation referenced by the polypeptide encoded by the gene sequence having the sequence of SEQ ID NO: 1018. In one embodiment, the methionine decarboxylase gene encodes a polypeptide with V491L A500P mutations referenced by the polypeptide encoded by the gene sequence having the sequence of SEQ ID NO: 1018.

In one embodiment, the methionine decarboxylase gene encodes a polypeptide with a R41Q mutation referenced by the polypeptide encoded by the gene sequence having the sequence of SEQ ID NO: 1003. In one embodiment, the methionine decarboxylase gene encodes a polypeptide with a Q70D mutation referenced by the polypeptide encoded by the gene sequence having the sequence of SEQ ID NO: 1003. In one embodiment, the methionine decarboxylase gene encodes a polypeptide with R41Q Q70D mutations referenced by the polypeptide encoded by the gene sequence having the sequence of SEQ ID NO: 1003.

In one embodiment, the methionine decarboxylase gene encodes a polypeptide with a R41Q mutation referenced by the polypeptide encoded by the gene sequence having the sequence of SEQ ID NO: 1018. In one embodiment, the methionine decarboxylase gene encodes a polypeptide with a Q70D mutation referenced by the polypeptide encoded by the gene sequence having the sequence of SEQ ID NO: 1018. In one embodiment, the methionine decarboxylase gene encodes a polypeptide with R41Q Q70D mutations referenced by the polypeptide encoded by the gene sequence having the sequence of SEQ ID NO: 1018.

In one embodiment, the methionine decarboxylase gene encodes a polypeptide with T66N mutation referenced by the polypeptide encoded by the gene sequence having the sequence of SEQ ID NO: 1003. In one embodiment, the methionine decarboxylase gene encodes a polypeptide with A203H mutation referenced by the polypeptide encoded by the gene sequence having the sequence of SEQ ID NO: 1003. In one embodiment, the methionine decarboxylase gene encodes a polypeptide with H379G mutation referenced by the polypeptide encoded by the gene sequence having the sequence of SEQ ID NO: 1003.

In one embodiment, the methionine decarboxylase gene encodes a polypeptide with T66N mutation referenced by the polypeptide encoded by the gene sequence having the sequence of SEQ ID NO: 1018. In one embodiment, the methionine decarboxylase gene encodes a polypeptide with A203H mutation referenced by the polypeptide encoded by the gene sequence having the sequence of SEQ ID NO: 1018. In one embodiment, the methionine decarboxylase gene encodes a polypeptide with H379G mutation referenced by the polypeptide encoded by the gene sequence having the sequence of SEQ ID NO: 1018.

In one embodiment, the methionine decarboxylase gene has at least about 80% identity with the sequence of SEQ ID NO: 1003. Accordingly, in one embodiment, the methionine decarboxylase gene has at least about 90% identity with the sequence of SEQ ID NO: 1003. Accordingly, in one embodiment, the methionine decarboxylase gene has at least about 95% identity with the sequence of SEQ ID NO: 1003. Accordingly, in one embodiment, the methionine decarboxylase gene has at least about 85%, 86%, 87%, 88%, 89%, 90%, 91%, 92%, 93%, 94%, 95%, 96%, 97%, 98%, or 99% identity with the sequence of SEQ ID NO: 1003. In another embodiment, the methionine decarboxylase gene comprises the sequence of SEQ ID NO: 1003. In yet another embodiment the methionine decarboxylase gene consists of the sequence of SEQ ID NO: 1003.

In one embodiment, the methionine decarboxylase gene has at least about 80% identity with the sequence of SEQ ID NO: 1018. Accordingly, in one embodiment, the methionine decarboxylase gene has at least about 90% identity with the sequence of SEQ ID NO: 1018. Accordingly, in one embodiment, the methionine decarboxylase gene has at least about 95% identity with the sequence of SEQ ID NO: 1018. Accordingly, in one embodiment, the methionine decarboxylase gene has at least about 85%, 86%, 87%, 88%, 89%, 90%, 91%, 92%, 93%, 94%, 95%, 96%, 97%, 98%, or 99% identity with the sequence of SEQ ID NO: 1018. In another embodiment, the methionine decarboxylase gene comprises the sequence of SEQ ID NO:1018. In yet another embodiment the methionine decarboxylase gene consists of the sequence of SEQ ID NO: 1018.

In one embodiment, the methionine decarboxylase gene has at least about 80% identity with the sequence of SEQ ID NO: 1034. Accordingly, in one embodiment, the methionine decarboxylase gene has at least about 90% identity with the sequence of SEQ ID NO: 1034. Accordingly, in one embodiment, the methionine decarboxylase gene has at least about 95% identity with the sequence of SEQ ID NO: 1034. Accordingly, in one embodiment, the methionine decarboxylase gene has at least about 85%, 86%, 87%, 88%, 89%, 90%, 91%, 92%, 93%, 94%, 95%, 96%, 97%, 98%, or 99% identity with the sequence of SEQ ID NO: 1034. In another embodiment, the methionine decarboxylase gene comprises the sequence of SEQ ID NO: 1034. In yet another embodiment the methionine decarboxylase gene consists of the sequence of SEQ ID NO: 1034.

In one embodiment, the methionine decarboxylase gene has at least about 80% identity with the sequence of SEQ ID NO: 1035. Accordingly, in one embodiment, the methionine decarboxylase gene has at least about 90% identity with the sequence of SEQ ID NO: 1035. Accordingly, in one embodiment, the methionine decarboxylase gene has at least about 95% identity with the sequence of SEQ ID NO: 1035. Accordingly, in one embodiment, the methionine decarboxylase gene has at least about 85%, 86%, 87%, 88%, 89%, 90%, 91%, 92%, 93%, 94%, 95%, 96%, 97%, 98%, or 99% identity with the sequence of SEQ ID NO: 1035. In another embodiment, the methionine decarboxylase gene comprises the sequence of SEQ ID NO: 1035. In yet another embodiment the methionine decarboxylase gene consists of the sequence of SEQ ID NO: 1035.

In one embodiment, the methionine decarboxylase gene has at least about 80% identity with the sequence of SEQ ID NO: 1036. Accordingly, in one embodiment, the methionine decarboxylase gene has at least about 90% identity with the sequence of SEQ ID NO: 1036. Accordingly, in one embodiment, the methionine decarboxylase gene has at least about 95% identity with the sequence of SEQ ID NO: 1036. Accordingly, in one embodiment, the methionine decarboxylase gene has at least about 85%, 86%, 87%, 88%, 89%, 90%, 91%, 92%, 93%, 94%, 95%, 96%, 97%, 98%, or 99% identity with the sequence of SEQ ID NO: 1036. In another embodiment, the methionine decarboxylase gene comprises the sequence of SEQ ID NO: 1036. In yet another embodiment the methionine decarboxylase gene consists of the sequence of SEQ ID NO: 1036.

In one embodiment, the methionine decarboxylase gene has at least about 80% identity with the sequence of SEQ ID NO: 1037. Accordingly, in one embodiment, the methionine decarboxylase gene has at least about 90% identity with the sequence of SEQ ID NO: 1037. Accordingly, in one embodiment, the methionine decarboxylase gene has at least about 95% identity with the sequence of SEQ ID NO: 1037. Accordingly, in one embodiment, the methionine decarboxylase gene has at least about 85%, 86%, 87%, 88%, 89%, 90%, 91%, 92%, 93%, 94%, 95%, 96%, 97%, 98%, or 99% identity with the sequence of SEQ ID NO: 1037. In another embodiment, the methionine decarboxylase gene comprises the sequence of SEQ ID NO: 1037. In yet another embodiment the methionine decarboxylase gene consists of the sequence of SEQ ID NO: 1037.

In one embodiment, the methionine decarboxylase gene has at least about 80% identity with the sequence of SEQ ID NO: 1039. Accordingly, in one embodiment, the methionine decarboxylase gene has at least about 90% identity with the sequence of SEQ ID NO: 1039. Accordingly, in one embodiment, the methionine decarboxylase gene has at least about 95% identity with the sequence of SEQ ID NO: 1039. Accordingly, in one embodiment, the methionine decarboxylase gene has at least about 85%, 86%, 87%, 88%, 89%, 90%, 91%, 92%, 93%, 94%, 95%, 96%, 97%, 98%, or 99% identity with the sequence of SEQ ID NO: 1039. In another embodiment, the methionine decarboxylase gene comprises the sequence of SEQ ID NO: 1039. In yet another embodiment the methionine decarboxylase gene consists of the sequence of SEQ ID NO: 1039.

In one embodiment, the methionine decarboxylase gene has at least about 80% identity with the sequence of SEQ ID NO: 1040. Accordingly, in one embodiment, the methionine decarboxylase gene has at least about 90% identity with the sequence of SEQ ID NO: 1040. Accordingly, in one embodiment, the methionine decarboxylase gene has at least about 95% identity with the sequence of SEQ ID NO: 1040. Accordingly, in one embodiment, the methionine decarboxylase gene has at least about 85%, 86%, 87%, 88%, 89%, 90%, 91%, 92%, 93%, 94%, 95%, 96%, 97%, 98%, or 99% identity with the sequence of SEQ ID NO: 1040. In another embodiment, the methionine decarboxylase gene comprises the sequence of SEQ ID NO: 1040. In yet another embodiment the methionine decarboxylase gene consists of the sequence of SEQ ID NO: 1040.

In one embodiment, the methionine decarboxylase gene has at least about 80% identity with the sequence of SEQ ID NO: 1123. Accordingly, in one embodiment, the methionine decarboxylase gene has at least about 90% identity with the sequence of SEQ ID NO: 1123. Accordingly, in one embodiment, the methionine decarboxylase gene has at least about 95% identity with the sequence of SEQ ID NO: 1123. Accordingly, in one embodiment, the methionine decarboxylase gene has at least about 85%, 86%, 87%, 88%, 89%, 90%, 91%, 92%, 93%, 94%, 95%, 96%, 97%, 98%, or 99% identity with the sequence of SEQ ID NO: 1123. In another embodiment, the methionine decarboxylase gene comprises the sequence of SEQ ID NO: 1123. In yet another embodiment the methionine decarboxylase gene consists of the sequence of SEQ ID NO: 1123.

In one embodiment, the methionine decarboxylase gene has at least about 80% identity with the sequence of SEQ ID NO: 1125. Accordingly, in one embodiment, the methionine decarboxylase gene has at least about 90% identity with the sequence of SEQ ID NO: 1125. Accordingly, in one embodiment, the methionine decarboxylase gene has at least about 95% identity with the sequence of SEQ ID NO: 1125. Accordingly, in one embodiment, the methionine decarboxylase gene has at least about 85%, 86%, 87%, 88%, 89%, 90%, 91%, 92%, 93%, 94%, 95%, 96%, 97%, 98%, or 99% identity with the sequence of SEQ ID NO: 1125. In another embodiment, the methionine decarboxylase gene comprises the sequence of SEQ ID NO: 1125. In yet another embodiment the methionine decarboxylase gene consists of the sequence of SEQ ID NO: 1125.

In one embodiment, the methionine decarboxylase gene has at least about 80% identity with the sequence of SEQ ID NO: 1127. Accordingly, in one embodiment, the methionine decarboxylase gene has at least about 90% identity with the sequence of SEQ ID NO: 1127. Accordingly, in one embodiment, the methionine decarboxylase gene has at least about 95% identity with the sequence of SEQ ID NO: 1127. Accordingly, in one embodiment, the methionine decarboxylase gene has at least about 85%, 86%, 87%, 88%, 89%, 90%, 91%, 92%, 93%, 94%, 95%, 96%, 97%, 98%, or 99% identity with the sequence of SEQ ID NO: 1127. In another embodiment, the methionine decarboxylase gene comprises the sequence of SEQ ID NO: 1127. In yet another embodiment the methionine decarboxylase gene consists of the sequence of SEQ ID NO: 1127.

In one embodiment, the recombinant bacteria comprise a gene sequence encoding a methionine catabolism enzyme, wherein the methionine catabolism enzyme is a leucine decarboxylase. In some cases, the leucine decarboxylase may have been modified from a wild-type leucine catabolism enzyme to also catabolize methionine, as described herein. Indeed, in some embodiments disclosed herein, a leucine catabolism enzyme that can metabolize methionine is referred to as a "methionine catabolism enzyme" or a "methionine decarboxylase."

In some embodiment, the leucine decarboxylase gene has at least about 80% with the sequence of SEQ ID NO: 1038. Accordingly, in one embodiment, the leucine decarboxylase gene has at least about 90% identity with the sequence of SEQ ID NO: 1038. Accordingly, in one embodiment, the leucine decarboxylase gene has at least about 95% identity with the sequence of SEQ ID NO: 1038. Accordingly, in one embodiment, the leucine decarboxylase gene has at least about 85%, 86%, 87%, 88%, 89%, 90%, 91%, 92%, 93%, 94%, 95%, 96%, 97%, 98%, or 99% identity with the sequence of SEQ ID NO: 1038. In another embodiment, the leucine decarboxylase gene comprises the sequence of SEQ ID NO: 1038. In yet another embodiment the leucine decarboxylase gene consists of the sequence of SEQ ID NO: 1038.

In one embodiment, the leucine decarboxylase gene encodes a polypeptide has at least about 80% identity with SEQ ID NO: 1053. Accordingly, in one embodiment, the leucine decarboxylase gene encodes a polypeptide has at least about 90% identity with SEQ ID NO: 1053. Accordingly, in one embodiment, the leucine decarboxylase gene encodes a polypeptide has at least about 95% identity with SEQ ID NO: 1053. Accordingly, in one embodiment, the leucine decarboxylase gene encodes a polypeptide has at least about 85%, 86%, 87%, 88%, 89%, 90%, 91%, 92%, 93%, 94%, 95%, 96%, 97%, 98%, or 99% identity with SEQ ID NO: 1053. In another embodiment, the leucine decarboxylase gene encodes a polypeptide comprises SEQ ID NO: 1053. In yet another embodiment the leucine decarboxylase gene encodes a polypeptide consists of SEQ ID NO: 1053.

In one embodiment, the leucine decarboxylase gene encodes a polypeptide that has 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 point mutations as compared to a wild type leucine decarboxylase polypeptide. In one embodiment, the leucine decarboxylase gene encodes a polypeptide that has one or more point mutations selected from N2S, V14A, E16G, H17S, R19W, A30E, K41Q, I45D, R48H, A51P, R65Q, L68C, L90R, N147S, L154V, R156Q, R160G, L170Q, H179S, H185S, E218Q, Y220F, C235R, H240D, K254E, V263M, T269A, V304A, S308V, D310E, A318M, V328S, T372E, S394T, 1406P, and D411C as compared to a wild type polypeptide. In one embodiment, the leucine decarboxylase gene encodes a polypeptide that has point mutations N2S, V14A, E16G, H17S, R19W, A30E, K41Q, I45D, R48H, A51P, R65Q, L68C, L90R, N147S, L154V, R156Q, R160G, L170Q, H179S, H185S, E218Q, Y220F, C235R, H240D, K254E, V263M, T269A, V304A, S308V, D310E, A318M, V328S, T372E, S394T, I406P, and D411C as compared to a wild type polypeptide.

In some embodiments, the sequence of a methionine decarboxylase associated with the disclosure comprises one or more amino acid substitutions relative to SEQ ID NO: 1049. In some embodiments, the one or more amino acid substitutions are at a position corresponding to position 41, 66, 70, 82, 203, 379, 491 and/or 500 in SEQ ID NO: 1049.

In some embodiments, a methionine decarboxylase comprises: a glutamine (Q) at a position corresponding to position 41 in the sequence of SEQ ID NO: 1049; an asparagine (N) at a position corresponding to position 66 in SEQ ID NO: 1049; an aspartic acid (D) at a position corresponding to position 70 in the sequence of SEQ ID NO: 1049; a histidine (H) at a position corresponding to position 82 in SEQ ID NO: 1049; a histidine (H) at a position corresponding to position 203 in SEQ ID NO: 1049; a glycine (G) at a position corresponding to position 379 in SEQ ID NO: 1049; a leucine (L) at a position corresponding to position 491 in the sequence of SEQ ID NO: 1049; and/or a proline (P) at a position corresponding to position 500 in the sequence of SEQ ID NO: 1049.

In some embodiments, the sequence of a methionine decarboxylase associated with the disclosure comprises substitutions at a position corresponding to: position 66; position 203; position 379; positions 70 and 82; positions 491 and 500; or positions 41 and 70 in the sequence of SEQ ID NO: 1049. In some embodiments, the sequence of a methionine decarboxylase comprises the following amino acid substitutions relative to the sequence of SEQ ID NO: 1049: T66N; A203H; H379G; Q70D and N82H; V491L and A500P; or R41Q and Q70D.

In one embodiment, the methionine decarboxylase polypeptide has at least about 80% identity with the sequence of any one of SEQ ID NOs: 1048, 1049, 1050, 1051, 1052, 1054, 1055, 1124, 1126, or 1128. Accordingly, in one embodiment, the methionine decarboxylase polypeptide has at least about 90% identity with the sequence of any one of SEQ ID NOs: 1048, 1049, 1050, 1051, 1052, 1054, 1055, 1124, 1126, or 1128. Accordingly, in one embodiment, the methionine decarboxylase polypeptide has at least about 95% identity with the sequence of any one of SEQ ID NOs: 1048, 1049, 1050, 1051, 1052, 1054, 1055, 1124, 1126, or 1128. Accordingly, in one embodiment, the methionine decarboxylase polypeptide has at least about 85%, 86%, 87%, 88%, 89%, 90%, 91%, 92%, 93%, 94%, 95%, 96%, 97%, 98%, or 99% identity with the sequence of any one of SEQ ID NOs: 1048, 1049, 1050, 1051, 1052, 1054, 1055, 1124, 1126, or 1128. In another embodiment, the methionine decarboxylase polypeptide comprises the sequence of any one of SEQ ID NOs: 1048, 1049, 1050, 1051, 1052, 1054, 1055, 1124, 1126, or 1128. In yet another embodiment the methionine decarboxylase polypeptide consists of the sequence of any one of SEQ ID NOs: 1048, 1049, 1050, 1051, 1052, 1054, 1055, 1124, 1126, or 1128.

In one embodiment, the methionine decarboxylase polypeptide has at least about 80% identity with SEQ ID NO: 1048. Accordingly, in one embodiment, the methionine decarboxylase polypeptide has at least about 90% identity with SEQ ID NO: 1048. Accordingly, in one embodiment, the methionine decarboxylase polypeptide has at least about 95% identity with SEQ ID NO: 1048. Accordingly, in one embodiment, the methionine decarboxylase polypeptide has at least about 85%, 86%, 87%, 88%, 89%, 90%, 91%, 92%, 93%, 94%, 95%, 96%, 97%, 98%, or 99% identity with SEQ ID NO: 1048. In another embodiment, the methionine decarboxylase polypeptide comprises SEQ ID NO: 1048. In yet another embodiment the methionine decarboxylase polypeptide consists of SEQ ID NO: 1048.

In one embodiment, the methionine decarboxylase polypeptide has at least about 80% identity with SEQ ID NO: 1049. Accordingly, in one embodiment, the methionine decarboxylase polypeptide has at least about 90% identity with SEQ ID NO: 1049. Accordingly, in one embodiment, the methionine decarboxylase polypeptide has at least about 95% identity with SEQ ID NO: 1049. Accordingly, in one embodiment, the methionine decarboxylase polypeptide has at least about 85%, 86%, 87%, 88%, 89%, 90%, 91%, 92%, 93%, 94%, 95%, 96%, 97%, 98%, or 99% identity with SEQ ID NO: 1049. In another embodiment, the methionine decarboxylase polypeptide comprises SEQ ID NO: 1049. In yet another embodiment the methionine decarboxylase polypeptide consists of SEQ ID NO: 1049.

In one embodiment, the methionine decarboxylase polypeptide has at least about 80% identity with SEQ ID NO: 1050. Accordingly, in one embodiment, the methionine decarboxylase polypeptide has at least about 90% identity with SEQ ID NO: 1050. Accordingly, in one embodiment, the methionine decarboxylase polypeptide has at least about 95% identity with SEQ ID NO: 1050. Accordingly, in one embodiment, the methionine decarboxylase polypeptide has at least about 85%, 86%, 87%, 88%, 89%, 90%, 91%, 92%, 93%, 94%, 95%, 96%, 97%, 98%, or 99% identity with SEQ ID NO: 1050. In another embodiment, the methionine decarboxylase polypeptide comprises SEQ ID NO: 1050. In yet another embodiment the methionine decarboxylase polypeptide consists of SEQ ID NO: 1050.

In one embodiment, the methionine decarboxylase polypeptide has at least about 80% identity with SEQ ID NO: 1051. Accordingly, in one embodiment, the methionine decarboxylase polypeptide has at least about 90% identity with SEQ ID NO: 1051. Accordingly, in one embodiment, the methionine decarboxylase polypeptide has at least about 95% identity with SEQ ID NO: 1051. Accordingly, in one embodiment, the methionine decarboxylase polypeptide has at least about 85%, 86%, 87%, 88%, 89%, 90%, 91%, 92%, 93%, 94%, 95%, 96%, 97%, 98%, or 99% identity with SEQ ID NO: 1051. In another embodiment, the methionine decarboxylase polypeptide comprises SEQ ID NO: 1051. In yet another embodiment the methionine decarboxylase polypeptide consists of SEQ ID NO: 1051.

In one embodiment, the methionine decarboxylase polypeptide has at least about 80% identity with SEQ ID NO: 1052. Accordingly, in one embodiment, the methionine decarboxylase polypeptide has at least about 90% identity with SEQ ID NO: 1052. Accordingly, in one embodiment, the methionine decarboxylase polypeptide has at least about 95% identity SEQ ID NO: 1052. Accordingly, in one embodiment, the methionine decarboxylase polypeptide has at least about 85%, 86%, 87%, 88%, 89%, 90%, 91%, 92%, 93%, 94%, 95%, 96%, 97%, 98%, or 99% identity with SEQ ID NO: 1052. In another embodiment, the methionine decarboxylase polypeptide comprises SEQ ID NO: 1052. In yet another embodiment the methionine decarboxylase polypeptide consists of SEQ ID NO: 1052.

In one embodiment, the methionine decarboxylase polypeptide has at least about 80% identity with SEQ ID NO: 1054. Accordingly, in one embodiment, the methionine decarboxylase polypeptide has at least about 90% identity with SEQ ID NO: 1054. Accordingly, in one embodiment, the methionine decarboxylase polypeptide has at least about 95% identity with SEQ ID NO: 1054. Accordingly, in one embodiment, the methionine decarboxylase polypeptide has at least about 85%, 86%, 87%, 88%, 89%, 90%, 91%, 92%, 93%, 94%, 95%, 96%, 97%, 98%, or 99% identity with SEQ ID NO: 1054. In another embodiment, the methionine decarboxylase polypeptide comprises SEQ ID NO: 1054. In yet another embodiment the methionine decarboxylase polypeptide consists of SEQ ID NO: 1054.

In one embodiment, the methionine decarboxylase polypeptide has at least 1 or 2 point mutations as compared to a wild type polypeptide. In one embodiment, the methionine decarboxylase polypeptide has point mutations H179S and/or V304A as compared to a wild type polypeptide. For example, SEQ ID NO: 1054 (and SEQ ID NO: 1039 encoding SEQ ID NO: 1054) is a methionine decarboxylase with two amino acid substitutions relative to a wild-type sequence.

In one embodiment, the methionine decarboxylase polypeptide has at least about 80% identity with SEQ ID NO: 1055. Accordingly, in one embodiment, the methionine decarboxylase polypeptide has at least about 90% identity with SEQ ID NO: 1055. Accordingly, in one embodiment, the methionine decarboxylase polypeptide has at least about 95% identity with SEQ ID NO: 1055. Accordingly, in one embodiment, the methionine decarboxylase polypeptide has at least about 85%, 86%, 87%, 88%, 89%, 90%, 91%, 92%, 93%, 94%, 95%, 96%, 97%, 98%, or 99% identity with SEQ ID NO: 1055. In another embodiment, the methionine decarboxylase polypeptide comprises SEQ ID NO: 1055. In yet another embodiment the methionine decarboxylase polypeptide consists of SEQ ID NO: 1055.

In one embodiment, the methionine decarboxylase polypeptide has at least about 80% identity with SEQ ID NO: 1124. Accordingly, in one embodiment, the methionine decarboxylase polypeptide has at least about 90% identity with SEQ ID NO: 1124. Accordingly, in one embodiment, the methionine decarboxylase polypeptide has at least about 95% identity with SEQ ID NO: 1124. Accordingly, in one embodiment, the methionine decarboxylase polypeptide has at least about 85%, 86%, 87%, 88%, 89%, 90%, 91%, 92%, 93%, 94%, 95%, 96%, 97%, 98%, or 99% identity with SEQ ID NO: 1124. In another embodiment, the methionine decarboxylase polypeptide comprises SEQ ID NO: 1124. In yet another embodiment the methionine decarboxylase polypeptide consists of SEQ ID NO: 1124.

In one embodiment, the methionine decarboxylase polypeptide has at least about 80% identity with SEQ ID NO: 1126. Accordingly, in one embodiment, the methionine decarboxylase polypeptide has at least about 90% identity with SEQ ID NO: 1126. Accordingly, in one embodiment, the methionine decarboxylase polypeptide has at least about 95% identity with SEQ ID NO: 1126. Accordingly, in one embodiment, the methionine decarboxylase polypeptide has at least about 85%, 86%, 87%, 88%, 89%, 90%, 91%, 92%, 93%, 94%, 95%, 96%, 97%, 98%, or 99% identity with SEQ ID NO: 1126. In another embodiment, the methionine decarboxylase polypeptide comprises SEQ ID NO: 1126. In yet another embodiment the methionine decarboxylase polypeptide consists of SEQ ID NO: 1126.

In one embodiment, the methionine decarboxylase polypeptide has at least about 80% identity with SEQ ID NO: 1128. Accordingly, in one embodiment, the methionine decarboxylase polypeptide has at least about 90% identity with SEQ ID NO: 1128. Accordingly, in one embodiment, the methionine decarboxylase polypeptide has at least about 95% identity with SEQ ID NO: 1128. Accordingly, in one embodiment, the methionine decarboxylase polypeptide has at least about 85%, 86%, 87%, 88%, 89%, 90%, 91%, 92%, 93%, 94%, 95%, 96%, 97%, 98%, or 99% identity with SEQ ID NO: 1128. In another embodiment, the methionine decarboxylase polypeptide comprises SEQ ID NO: 1128. In yet another embodiment the methionine decarboxylase polypeptide consists of SEQ ID NO: 1128.

The present disclosure further comprises genes encoding functional fragments of a methionine decarboxylase enzyme.

Assays for testing the activity of a methionine catabolism enzyme, a methionine catabolism enzyme functional variant, or a methionine catabolism enzyme functional fragment are well known to one of ordinary skill in the art. For example, methionine catabolism can be assessed by expressing the protein, functional variant, or fragment thereof, in a recombinant bacterial cell that lacks endogenous methionine catabolism enzyme activity. Other methods are also well known to one of ordinary skill in the art (see, e.g., Dolzan et al., *FEBS Letters,* 574:141-146, 2004, the entire contents of which are incorporated by reference). Additional methods, i.e., for measuring methionine decarboxylase activity in vitro or in vivo are described in the examples herein.

In some embodiments, the genetically engineered host cell, such as genetically engineered bacteria, comprise a stably maintained plasmid or chromosome carrying a gene for producing a methionine decarboxylase, such that the methionine decarboxylase can be expressed in the host cell, and the host cell is capable of survival and/or growth in vitro, e.g., in medium, and/or in vivo. In some embodiments, a host cell, such as a bacterium, may comprise multiple copies of the gene encoding the methionine decarboxylase. In some embodiments, the gene encoding the methionine decarboxylase is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, the gene encoding the methionine decarboxylase is expressed on a high-copy plasmid. In some embodiments, the high-copy plasmid may be useful for increasing expression of the methionine decarboxylase. In some embodiments, the gene encoding the methionine decarboxylase is expressed on a chromosome.

In some embodiments, the host cells, such as bacteria host cells are genetically engineered to include multiple mechanisms of action (MOAs), e.g., circuits producing multiple copies of the same product (e.g., to enhance copy number) or circuits performing multiple different functions. For example, the genetically engineered host cells, such as genetically engineered bacteria, may include four copies of the gene encoding a particular methionine decarboxylase inserted at four different insertion sites. Alternatively, the genetically engineered host cells, such as genetically engineered bacteria, may include three copies of the gene encoding a particular methionine decarboxylase inserted at three different insertion sites and three copies of the gene encoding a different methionine decarboxylase inserted at three different insertion sites.

In some embodiments, under conditions where the methionine decarboxylase is expressed, the genetically engineered host cells, such as genetically engineered bacteria, of the disclosure produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more of the methionine decarboxylase, and/or transcript of the gene(s) in the operon as compared to unmodified host cells, such as unmodified bacteria, of the same subtype under the same conditions.

In some embodiments, quantitative PCR (qPCR) is used to amplify, detect, and/or quantify mRNA expression levels of the methionine decarboxylase gene(s). Primers specific for methionine decarboxylase the gene(s) may be designed and used to detect mRNA in a sample according to methods known in the art. In some embodiments, a fluorophore is added to a sample reaction mixture that may contain methionine decarboxylase mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle (CT). At least one CT result for each sample is generated, and the CT result(s) may be used to determine mRNA expression levels of the methionine decarboxylase gene(s).

In one embodiment, the host cell, such as a bacterial host cell, comprises a heterologous gene encoding a methionine catabolism enzyme. In one embodiment, the host cell, such as a bacterial host cell, comprises a heterologous gene encoding an importer of methionine. In one embodiment, the host cell, such as a bacterial host cell, comprises a heterologous gene encoding an importer of methionine and a heterologous gene encoding a methionine catabolism enzyme. In one embodiment, the host cell, such as a bacterial host cell, comprises a heterologous gene encoding a methionine catabolism enzyme and a genetic modification that reduces export of methionine. In one embodiment, the host cell, such as a bacterial host cell, comprises a heterologous gene encoding an importer of methionine, a heterologous gene encoding a methionine catabolism enzyme, and a genetic modification that reduces export of methionine. Importers and exporters are described in more detail in the subsections, below.

B. Importers of Methionine

Methionine importers may be expressed or modified in the recombinant host cells, such as recombinant bacteria, described herein in order to enhance methionine import into the cell. Specifically, when the importer of methionine is expressed in the recombinant host cells, such as recombinant bacterial cells, described herein, the bacterial cells import more methionine into the cell when the importer is expressed than unmodified bacteria of the same bacterial subtype under the same conditions. Thus, the genetically engineered bacteria comprising a heterologous gene encoding importer of methionine which may be used to import methionine into the bacteria so that any gene encoding a methionine catabolism enzyme expressed in the organism can catabolize the methionine to treat a disease associated with methionine, such as homocystinuria.

The uptake of methionine into bacterial cells is mediated by proteins well known to those of skill in the art. For example, a methionine importer operon has been identified in *Corynebacterium glutamicum* (Trotschel et al., *J. Bacteriology,* 187(11):3786-3794, 2005). In addition, the high affinity MetD ABC importer system has been characterized in *Escherichia coli* (Kadaba et al. (2008) Science 5886: 250-253; Kadner and Watson (1974) *J. Bacteriol.* 119: 401-9). The MetD importer system is capable of mediating the translocation of several substrates across the bacterial membrane, including methionine. The MetD system of *Escherichia coli* consists of MetN (encoded by metN), which comprises the ATPase domain, MetI (encoded by metI), which comprises the transmembrane domain, and MetQ (encoded by metQ), the cognate binding protein which is located in the periplasm. Orthologues of the genes encoding the *E. coli* MetD importer system have been identified in multiple organisms including, e.g., *Yersinia pestis, Vibrio cholerae, Pasteurella multocida, Haemophilus influenza, Agrobacterium tumefaciens, Sinorhizobium meliloti, Brucella meliloti*, and *Mesorhizobium loti* (Merlin et al. (2002) *J. Bacteriol.* 184: 5513-7).

In one embodiment, the at least one gene encoding an importer of methionine is a metN gene, a metI gene, and/or a metQ gene from *Corynebacterium glutamicum, Escherichia coli*, and *Bacillus subtilis* (Trotschel et al., *J. Bacteriology,* 187(11):3786-3794, 2005).

In one embodiment, the metN gene has at least about 80% identity with the sequence of SEQ ID NO: 1004. Accordingly, in one embodiment, the metN gene has at least about 90% identity with the sequence of SEQ ID NO: 1004. Accordingly, in one embodiment, the metN gene has at least about 95% identity with the sequence of SEQ ID NO: 1004. Accordingly, in one embodiment, the metN gene has at least about 85%, 86%, 87%, 88%, 89%, 90%, 91%, 92%, 93%, 94%, 95%, 96%, 97%, 98%, or 99% identity with the sequence of SEQ ID NO: 1004. In another embodiment, the metN gene comprises the sequence of SEQ ID NO: 1004. In yet another embodiment the metN gene consists of the sequence of SEQ ID NO: 1004.

In one embodiment, the metI gene has at least about 80% identity with the sequence of SEQ ID NO: 1005. Accordingly, in one embodiment, the metI gene has at least about 90% identity with the sequence of SEQ ID NO: 1005. Accordingly, in one embodiment, the metI gene has at least about 95% identity with the sequence of SEQ ID NO: 1005. Accordingly, in one embodiment, the metI gene has at least about 85%, 86%, 87%, 88%, 89%, 90%, 91%, 92%, 93%, 94%, 95%, 96%, 97%, 98%, or 99% identity with the sequence of SEQ ID NO: 1005. In another embodiment, the metI gene comprises the sequence of SEQ ID NO: 1005. In yet another embodiment the metI gene consists of the sequence of SEQ ID NO: 1005.

In one embodiment, the metQ gene has at least about 80% identity with the sequence of SEQ ID NO: 1006. Accordingly, in one embodiment, the metQ gene has at least about 90% identity with the sequence of SEQ ID NO: 1006. Accordingly, in one embodiment, the metQ gene has at least about 95% identity with the sequence of SEQ ID NO: 1006. Accordingly, in one embodiment, the metQ gene has at least about 85%, 86%, 87%, 88%, 89%, 90%, 91%, 92%, 93%, 94%, 95%, 96%, 97%, 98%, or 99% identity with the sequence of SEQ ID NO: 1006. In another embodiment, the metQ gene comprises the sequence of SEQ ID NO: 1006. In yet another embodiment the metQ gene consists of the sequence of SEQ ID NO: 1006.

In one embodiment, the metNIQ gene has at least about 80% identity with the sequence of SEQ ID NO: 1043, 1045, 1046, or 1047. Accordingly, in one embodiment, the metNIQ gene has at least about 90% identity with the sequence of SEQ ID NO: 1043, 1045, 1046, or 1047. Accordingly, in one embodiment, the metNIQ gene has at least about 95% identity with the sequence of SEQ ID NO: 1043, 1045, 1046, or 1047. Accordingly, in one embodiment, the metNIQ gene has at least about 85%, 86%, 87%, 88%, 89%, 90%, 91%, 92%, 93%, 94%, 95%, 96%, 97%, 98%, or 99% identity with the sequence of SEQ ID NO: 1043, 1045, 1046, or 1047. In another embodiment, the metNIQ gene comprises the sequence of SEQ ID NO: 1043, 1045, 1046, or 1047. In yet another embodiment the metNIQ gene consists of the sequence of SEQ ID NO: 1043, 1045, 1046, or 1047.

In one embodiment, the metNIQ gene encodes a polypeptide with a P281G mutation in the MetN polypeptide referenced by the MetN polypeptide encoded the gene sequence having the sequence of SEQ ID NO: 1004. In one embodiment, the metNIQ gene encodes a polypeptide with a P281S mutation in the MetN polypeptide referenced by the MetN polypeptide encoded the gene sequence having the sequence of SEQ ID NO: 1004.

In one embodiment, at least one gene encoding an importer of methionine is a metP gene. In one embodiment, the metP gene is from *Flavobacterium segetis*. In one embodiment, the metP gene is from *Flavobacterium frigoris*. In one embodiment, the metP gene is from *Bacillus subtilis*. In one embodiment, the metP gene is from *Sporomusa termitida*. In one embodiment, the metP gene is from Bacteroidetes bacterium 43-16.

In one embodiment, the metP gene has at least about 80% identity with the sequence of SEQ ID NO: 1041. Accordingly, in one embodiment, the metP gene has at least about 90% identity with the sequence of SEQ ID NO: 1041. Accordingly, in one embodiment, the metP gene has at least about 95% identity with the sequence of SEQ ID NO: 1041. Accordingly, in one embodiment, the metP gene has at least about 85%, 86%, 87%, 88%, 89%, 90%, 91%, 92%, 93%, 94%, 95%, 96%, 97%, 98%, or 99% identity with the sequence of SEQ ID NO: 1041. In another embodiment, the metP gene comprises the sequence of SEQ ID NO: 1041. In yet another embodiment the metP gene consists of the sequence of SEQ ID NO: 1041.

In one embodiment, the metP gene has at least about 80% identity with the sequence of SEQ ID NO: 1042. Accordingly, in one embodiment, the metP gene has at least about 90% identity with the sequence of SEQ ID NO: 1042. Accordingly, in one embodiment, the metP gene has at least about 95% identity with the sequence of SEQ ID NO: 1042. Accordingly, in one embodiment, the metP gene has at least about 85%, 86%, 87%, 88%, 89%, 90%, 91%, 92%, 93%, 94%, 95%, 96%, 97%, 98%, or 99% identity with the sequence of SEQ ID NO: 1042. In another embodiment, the metP gene comprises the sequence of SEQ ID NO: 1042. In yet another embodiment the metP gene consists of the sequence of SEQ ID NO: 1042.

In one embodiment, the metP gene has at least about 80% identity with the sequence of SEQ ID NO: 1044. Accordingly, in one embodiment, the metP gene has at least about 90% identity with the sequence of SEQ ID NO: 1044. Accordingly, in one embodiment, the metP gene has at least about 95% identity with the sequence of SEQ ID NO: 1044. Accordingly, in one embodiment, the metP gene has at least about 85%, 86%, 87%, 88%, 89%, 90%, 91%, 92%, 93%, 94%, 95%, 96%, 97%, 98%, or 99% identity with the sequence of SEQ ID NO: 1044. In another embodiment, the metP gene comprises the sequence of SEQ ID NO: 1044. In yet another embodiment the metP gene consists of the sequence of SEQ ID NO: 1044.

In one embodiment, the metP gene has at least about 80% identity with the sequence of SEQ ID NO: 1129. Accordingly, in one embodiment, the metP gene has at least about 90% identity with the sequence of SEQ ID NO: 1129. Accordingly, in one embodiment, the metP gene has at least about 95% identity with the sequence of SEQ ID NO: 1129. Accordingly, in one embodiment, the metP gene has at least about 85%, 86%, 87%, 88%, 89%, 90%, 91%, 92%, 93%, 94%, 95%, 96%, 97%, 98%, or 99% identity with the sequence of SEQ ID NO: 1129. In another embodiment, the metP gene comprises the sequence of SEQ ID NO: 1129. In yet another embodiment the metP gene consists of the sequence of SEQ ID NO: 1129.

In one embodiment, the metP gene has at least about 80% identity with the sequence of SEQ ID NO: 1131. Accordingly, in one embodiment, the metP gene has at least about 90% identity with the sequence of SEQ ID NO: 1131. Accordingly, in one embodiment, the metP gene has at least about 95% identity with the sequence of SEQ ID NO: 1131. Accordingly, in one embodiment, the metP gene has at least about 85%, 86%, 87%, 88%, 89%, 90%, 91%, 92%, 93%, 94%, 95%, 96%, 97%, 98%, or 99% identity with the sequence of SEQ ID NO: 1131. In another embodiment, the metP gene comprises the sequence of SEQ ID NO: 1131. In yet another embodiment the metP gene consists of the sequence of SEQ ID NO: 1131.

In one embodiment, the MetP is from *Flavobacterium segetis*. In one embodiment, the MetP is from *Flavobacterium frigoris*. In one embodiment, MetP gene is from *Bacillus subtilis*. In one embodiment, MetP gene is from *Sporomusa termitida*. In one embodiment, MetP gene is from Bacteroidetes bacterium 43-16.

In one embodiment, the MetP polypeptide has at least about 80% identity with the sequence of any one of SEQ ID NOs: 1056, 1057, 1061, 1130, or 1132. Accordingly, in one embodiment, the MetP polypeptide has at least about 90% identity with the sequence of any one of SEQ ID NOs: 1056, 1057, 1061, 1130, or 1132. Accordingly, in one embodiment, the MetP polypeptide has at least about 95% identity with the sequence of any one of SEQ ID NOs: 1056, 1057, 1061, 1130, or 1132. Accordingly, in one embodiment, the MetP polypeptide has at least about 85%, 86%, 87%, 88%, 89%, 90%, 91%, 92%, 93%, 94%, 95%, 96%, 97%, 98%, or 99% identity with the sequence of any one of SEQ ID NOs: 1056, 1057, 1061, 1130, or 1132. In another embodiment, the MetP polypeptide comprises the sequence of any one of SEQ ID NOs: 1056, 1057, 1061, 1130, or 1132. In yet another embodiment the MetP polypeptide consists of the sequence of any one of SEQ ID NOs: 1056, 1057, 1061, 1130, or 1132.

In one embodiment, the MetP polypeptide has at least about 80% identity with the sequence of SEQ ID NO: 1056. Accordingly, in one embodiment, the MetP polypeptide has at least about 90% identity with the sequence of SEQ ID NO: 1056. Accordingly, in one embodiment, the MetP polypeptide has at least about 95% identity with the sequence of SEQ ID NO: 1056. Accordingly, in one embodiment, the MetP polypeptide has at least about 85%, 86%, 87%, 88%, 89%, 90%, 91%, 92%, 93%, 94%, 95%, 96%, 97%, 98%, or 99% identity with the sequence of SEQ ID NO: 1056. In another embodiment, the MetP polypeptide comprises the sequence of SEQ ID NO: 1056. In yet another embodiment the MetP polypeptide consists of the sequence of SEQ ID NO: 1056.

In one embodiment, the MetP polypeptide has at least about 80% identity with the sequence of SEQ ID NO: 1057. Accordingly, in one embodiment, the MetP polypeptide has at least about 90% identity with the sequence of SEQ ID NO: 1057. Accordingly, in one embodiment, the MetP polypeptide has at least about 95% identity with the sequence of SEQ ID NO: 1057. Accordingly, in one embodiment, the MetP polypeptide has at least about 85%, 86%, 87%, 88%, 89%, 90%, 91%, 92%, 93%, 94%, 95%, 96%, 97%, 98%, or 99% identity with the sequence of SEQ ID NO: 1057. In another embodiment, the MetP polypeptide comprises the sequence of SEQ ID NO: 1057. In yet another embodiment the MetP polypeptide consists of the sequence of SEQ ID NO: 1057.

In one embodiment, the MetP polypeptide has at least about 80% identity with the sequence of SEQ ID NO: 1061. Accordingly, in one embodiment, the MetP polypeptide has at least about 90% identity with the sequence of SEQ ID NO: 1061. Accordingly, in one embodiment, the MetP polypeptide has at least about 95% identity with the sequence of SEQ ID NO: 1061. Accordingly, in one embodiment, the MetP polypeptide has at least about 85%, 86%, 87%, 88%, 89%, 90%, 91%, 92%, 93%, 94%, 95%, 96%, 97%, 98%, or 99% identity with the sequence of SEQ ID NO: 1061. In another embodiment, the MetP polypeptide comprises the sequence of SEQ ID NO: 1061. In yet another embodiment the MetP polypeptide consists of the sequence of SEQ ID NO: 1061.

In one embodiment, the MetP polypeptide has at least about 80% identity with the sequence of SEQ ID NO: 1130. Accordingly, in one embodiment, the MetP polypeptide has at least about 90% identity with the sequence of SEQ ID NO: 1130. Accordingly, in one embodiment, the MetP polypeptide has at least about 95% identity with the sequence of SEQ ID NO: 1130. Accordingly, in one embodiment, the MetP polypeptide has at least about 85%, 86%, 87%, 88%, 89%, 90%, 91%, 92%, 93%, 94%, 95%, 96%, 97%, 98%, or 99% identity with the sequence of SEQ ID NO: 1130. In another embodiment, the MetP polypeptide comprises the sequence of SEQ ID NO: 1130. In yet another embodiment the MetP polypeptide consists of the sequence of SEQ ID NO: 1130.

In one embodiment, the MetP polypeptide has at least about 80% identity with the sequence of SEQ ID NO: 1132. Accordingly, in one embodiment, the MetP polypeptide has at least about 90% identity with the sequence of SEQ ID NO: 1132. Accordingly, in one embodiment, the MetP polypeptide has at least about 95% identity with the sequence of SEQ ID NO: 1132. Accordingly, in one embodiment, the MetP polypeptide has at least about 85%, 86%, 87%, 88%, 89%, 90%, 91%, 92%, 93%, 94%, 95%, 96%, 97%, 98%, or 99% identity with the sequence of SEQ ID NO: 1132. In another embodiment, the MetP polypeptide comprises the sequence of SEQ ID NO: 1132. In yet another embodiment the MetP polypeptide consists of the sequence of SEQ ID NO: 1132.

In one embodiment, the MetN polypeptide has at least about 80% identity with the sequence of SEQ ID NO: 1058. Accordingly, in one embodiment, the MetN polypeptide has at least about 90% identity with the sequence of SEQ ID NO: 1058. Accordingly, in one embodiment, the MetN polypeptide has at least about 95% identity with the sequence of SEQ ID NO: 1058. Accordingly, in one embodiment, the MetN polypeptide has at least about 85%, 86%, 87%, 88%, 89%, 90%, 91%, 92%, 93%, 94%, 95%, 96%, 97%, 98%, or 99% identity with the sequence of SEQ ID NO: 1058. In another embodiment, the MetN polypeptide comprises the sequence of SEQ ID NO: 1058. In yet another embodiment the MetN polypeptide consists of the sequence of SEQ ID NO: 1058.

In one embodiment, the MetN polypeptide has at least about 80% identity with the sequence of SEQ ID NO: 1062. Accordingly, in one embodiment, the MetN polypeptide has at least about 90% identity with the sequence of SEQ ID NO: 1062. Accordingly, in one embodiment, the MetN polypeptide has at least about 95% identity with the sequence of SEQ ID NO: 1062. Accordingly, in one embodiment, the MetN polypeptide has at least about 85%, 86%, 87%, 88%, 89%, 90%, 91%, 92%, 93%, 94%, 95%, 96%, 97%, 98%, or 99% identity with the sequence of SEQ ID NO: 1062. In another embodiment, the MetN polypeptide comprises the sequence of SEQ ID NO: 1062. In yet another embodiment the MetN polypeptide consists of the sequence of SEQ ID NO: 1062.

In one embodiment, the MetN polypeptide has at least about 80% identity with the sequence of SEQ ID NO: 1063. Accordingly, in one embodiment, the MetN polypeptide has at least about 90% identity with the sequence of SEQ ID NO: 1063. Accordingly, in one embodiment, the MetN polypeptide has at least about 95% identity with the sequence of SEQ ID NO: 1063. Accordingly, in one embodiment, the MetN polypeptide has at least about 85%, 86%, 87%, 88%, 89%, 90%, 91%, 92%, 93%, 94%, 95%, 96%, 97%, 98%, or 99% identity with the sequence of SEQ ID NO: 1063. In another embodiment, the MetN polypeptide comprises the sequence of SEQ ID NO: 1063. In yet another embodiment the MetN polypeptide consists of the sequence of SEQ ID NO: 1063.

In one embodiment, the MetI polypeptide has at least about 80% identity with the sequence of SEQ ID NO: 1059. Accordingly, in one embodiment, the MetI polypeptide has at least about 90% identity with the sequence of SEQ ID NO: 1059. Accordingly, in one embodiment, the MetI polypeptide has at least about 95% identity with the sequence of SEQ ID NO: 1059. Accordingly, in one embodiment, the MetI polypeptide has at least about 85%, 86%, 87%, 88%, 89%, 90%, 91%, 92%, 93%, 94%, 95%, 96%, 97%, 98%, or 99% identity with the sequence of SEQ ID NO: 1059. In another embodiment, the MetI polypeptide comprises the sequence of SEQ ID NO: 1059. In yet another embodiment the MetI polypeptide consists of the sequence of SEQ ID NO: 1059.

In one embodiment, the MetQ polypeptide has at least about 80% identity with the sequence of SEQ ID NO: 1060. Accordingly, in one embodiment, the MetQ polypeptide has at least about 90% identity with the sequence of SEQ ID NO: 1060. Accordingly, in one embodiment, the MetQ polypeptide has at least about 95% identity with the sequence of SEQ ID NO: 1060. Accordingly, in one embodiment, the MetQ polypeptide has at least about 85%, 86%, 87%, 88%, 89%, 90%, 91%, 92%, 93%, 94%, 95%, 96%, 97%, 98%, or 99% identity with the sequence of SEQ ID NO: 1060. In another embodiment, the MetQ polypeptide comprises the sequence of SEQ ID NO: 1060. In yet another embodiment the MetQ polypeptide consists of the sequence of SEQ ID NO: 1060.

In some embodiments, the importer of methionine is encoded by an importer of methionine gene derived from a bacterial genus or species, including but not limited to, *Corynebacterium glutamicum, Escherichia coli*, and *Bacillus subtilis*. In some embodiments, the bacterial species is *Escherichia coli* strain Nissle.

Assays for testing the activity of an importer of methionine, a functional variant of an importer of methionine, or a functional fragment of importer of methionine are well known to one of ordinary skill in the art. For example, import of methionine may be determined using the methods as described in Trotschel et al., *J. Bacteriology,* 187(11): 3786-3794, 2005, the entire contents of which are expressly incorporated by reference herein.

In one embodiment, when the importer of a methionine is expressed in the recombinant bacterial cells described herein, the bacterial cells import 10% more methionine into the bacterial cell when the importer is expressed than unmodified bacteria of the same bacterial subtype under the same conditions. In another embodiment, when the importer of methionine is expressed in the recombinant bacterial cells described herein, the bacterial cells import 20%, 30%, 40%, 50%, 60%, 70%, 80%, 90% or 100% more methionine into the bacterial cell when the importer is expressed than unmodified bacteria of the same bacterial subtype under the same conditions. In yet another embodiment, when the importer of methionine is expressed in the recombinant bacterial cells described herein, the bacterial cells import two-fold more methionine into the cell when the importer is expressed than unmodified bacteria of the same bacterial subtype under the same conditions. In yet another embodiment, when the importer of methionine is expressed in the recombinant bacterial cells described herein, the bacterial cells import three-fold, four-fold, five-fold, six-fold, seven-fold, eight-fold, nine-fold, or ten-fold more methionine into the cell when the importer is expressed than unmodified bacteria of the same bacterial subtype under the same conditions.

C. Exporters of Methionine

Methionine exporters may be modified in the recombinant bacteria described herein in order to reduce methionine export from the cell. Specifically, when the recombinant bacterial cells described herein comprise a genetic modification that reduces export of methionine, the bacterial cells retain more methionine in the bacterial cell than unmodified bacteria of the same bacterial subtype under the same conditions. Thus, the recombinant bacteria comprising a genetic modification that reduces export of methionine may be used to retain more methionine in the bacterial cell so that any methionine catabolism enzyme expressed in the organism, e.g., co-expressed methionine catabolism enzyme, can catabolize the methionine.

Exporters of methionine are well known to one of ordinary skill in the art. For example, the MetE methionine exporter from *Bacillus atrophaeus*, and the BrnFE methionine exporter from *Corynebacterium glutamicum* have been described (Trotschel et al., *J. Bacteriology,* 187(11):3786-3794, 2005). The YjeH methionine exporter from *E. coli* has also been described (Liu et al., 2015*: Applied and Environmental Microbiology,* 81(22):7753-7766).

In one embodiment, the methionine exporter is yjeH. In one embodiment, the yjeH gene has at least about 80% identity with the sequence of SEQ ID NO: 1014. Accordingly, in one embodiment, the yjeH gene has at least about 90% identity with the sequence of SEQ ID NO:1014. Accordingly, in one embodiment, the yjeH gene has at least about 95% identity with the sequence of SEQ ID NO:1014. Accordingly, in one embodiment, the yjeH gene has at least about 85%, 86%, 87%, 88%, 89%, 90%, 91%, 92%, 93%, 94%, 95%, 96%, 97%, 98%, or 99% identity with the sequence of SEQ ID NO:1014. In another embodiment, the yjeH gene comprises the sequence of SEQ ID NO:1014. In yet another embodiment the yjeH gene consists of the sequence of SEQ ID NO:1014. In one embodiment, the yjeH gene is deleted. In another embodiment, a point mutation in the yjeH gene prevents export of methionine from the cell.

In one embodiment, the genetic modification is a mutation in an endogenous gene encoding an exporter of methionine. In another embodiment, the genetic mutation results in an exporter having reduced activity as compared to a wild-type exporter protein. In one embodiment, the activity of the exporter is reduced at least 50%, at least 75%, or at least 100%. In another embodiment, the activity of the exporter is reduced at least two-fold, three-fold, four-fold, or five-fold. In another embodiment, the genetic mutation results in an exporter having no activity and which cannot export methionine from the bacterial cell.

In another embodiment, the genetic modification is a mutation in a promoter of an endogenous gene encoding an exporter of methionine.

In yet another embodiment, the genetic modification is an overexpression of a repressor of an exporter of methionine. In one embodiment, the overexpression of the repressor of the exporter is caused by a mutation which renders the promoter of the repressor constitutively active. In another embodiment, the overexpression of the repressor of the exporter is caused by the insertion of an inducible promoter in front of the repressor so that the expression of the repressor can be induced. Inducible promoters are described in more detail herein.

D. Inducible Promoters

In some embodiments, the host cell, such as a bacterial host cell, comprises a stably maintained plasmid or chromosome carrying the gene(s) encoding the methionine decarboxylase(s) and/or the methionine importers, such that the methionine decarboxylase(s) and/or the methionine importers can be expressed in the host cell, and the host cell is capable of survival and/or growth in vitro, e.g., in medium, and/or in vivo, e.g., in the gut. In some embodiments, the host cell, such as a bacterial host cell, comprises two or more distinct methionine decarboxylase and/or the methionine importer genes or operons. In some embodiments, the host cell, such as a bacterial host cell, comprises three or more distinct methionine decarboxylase and/or methionine importer genes or operons. In some embodiments, the host cell, such as a bacterial host cell, comprises 4, 5, 6, 7, 8, 9, 10, or more distinct methionine decarboxylase and/or methionine importer genes or operons.

In some embodiments, the genetically engineered host cell, such as a genetically engineered bacteria, comprise multiple copies of the same methionine decarboxylase gene(s) or methionine importer genes. In some embodiments, the gene encoding the methionine decarboxylase or methionine importer genes is present on a plasmid and operably linked to a directly or indirectly inducible promoter. In some embodiments, the gene encoding the methionine decarboxylase or methionine importer genes is present on a plasmid and operably linked to a promoter that is induced under low-oxygen or anaerobic conditions. In some embodiments, the gene encoding the methionine decarboxylase or methionine importer genes is present on a chromosome and operably linked to a directly or indirectly inducible promoter. In some embodiments, the gene encoding the methionine decarboxylase or methionine importer genes is present in the chromosome and operably linked to a promoter that is induced under low-oxygen or anaerobic conditions. In some embodiments, the gene encoding the methionine decarboxylase or methionine importer genes is present on a plasmid and operably linked to a promoter that is induced by exposure to tetracycline, arabinose or Isopropyl β-D-1-thiogalactopyranoside (IPTG).

In some embodiments, the inducible promoter is a IPTG inducible promoter, e.g., Ptac. In one embodiment, the IPTG inducible promoter comprises a sequence having at least 90%, 91%, 92%, 93%, 94%, 95%, 96%, 97%, 98%, or 99% identity to, comprises, or consists of SEQ ID NO: 1108. In some embodiments, the recombinant bacterium further comprises a gene sequence encoding a gene sequence encoding a transcriptional regulator, e.g., a repressor IPTG inducible promoter. In some embodiments, the gene sequence encoding a repressor comprises a sequence having at least 90%, 91%, 92%, 93%, 94%, 95%, 96%, 97%, 98%, or 99% identity to, comprises, or consists of SEQ ID NO: 1105. In some embodiments, the repressor comprises a sequence having at least 90%, 91%, 92%, 93%, 94%, 95%, 96%, 97%, 98%, or 99% identity to, comprises, or consists of SEQ ID NO: 1106.

TABLE 3

IPTG inducible promoter and LacI sequences

| Description SEQ ID NO | Sequences |
|---|---|
| LacI in reverse orientation SEQ ID NO: 1105 | TCACTGCCCGCTTTCCAGTCGGGAAACCTGTCGTGCCAGCTGCATTA<br>ATGAATCGGCCAACGCGCGGGGAGAGGCGGTTTGCGTATTGGGCGC<br>CAGGGTGGTTTTTCTTTTCACCAGTGAGACTGGCAACAGCTGATTGC<br>CCTTCACCGCCTGGCCCTGAGAGAGTTGCAGCAAGCGGTCCACGCTG<br>GTTTGCCCCAGCAGGCGAAAATCCTGTTTGATGGTGGTTAACGGCGG<br>GATATAACATGAGCTATCTTCGGTATCGTCGTATCCCACTACCGAGA<br>TATCCGCACCAACGCGCAGCCCGGACTCGGTAATGGCGCGCATTGC<br>GCCCAGCGCCATCTGATCGTTGGCAACCAGCATCGCAGTGGGAACG<br>ATGCCCTCATTCAGCATTTGCATGGTTTGTTGAAAACCGGACATGGC<br>ACTCCAGTCGCCTTCCCGTTCCGCTATCGGCTGAATTTGATTGCGAG<br>TGAGATATTTATGCCAGCCAGCCAGACGCAGACGCGCCGAGACAGA<br>ACTTAATGGGCCCGCTAACAGCGCGATTTGCTGGTGACCCAATGCGA<br>CCAGATGCTCCACGCCCAGTCGCGTACCGTCCTCATGGGAGAAAAT<br>AATACTGTTGATGGGTGTCTGGTCAGAGACATCAAGAAATAACGCC<br>GGAACATTAGTGCAGGCAGCTTCCACAGCAATGGCATCCTGGTCATC<br>CAGCGGATAGTTAATGATCAGCCCACTGACGCGTTGCGCGAGAAGA<br>TTGTGCACCGCCGCTTTACAGGCTTCGACGCCGCTTCGTTCTACCATC<br>GACACCACCACGCTGGCACCCAGTTGATCGGCGCGAGATTTAATCG<br>CCGCGACAATTTGCGACGGCGCGTGCAGGGCCAGACTGGAGGTGGC<br>AACGCCAATCAGCAACGACTGTTTGCCCGCCAGTTGTTGTGCCACGC<br>GGTTGGGAATGTAATTCAGCTCCGCCATCGCCGCTTCCACTTTTTCCC<br>GCGTTTTCGCAGAAACGTGGCTGGCCTGGTTCACCACGCGGGAAAC<br>GGTCTGATAAGAGACACCGGCATACTCTGCGACATCGTATAACGTTA<br>CTGGTTTCAT |
| LacI SEQ ID NO: 1106 | MKPVTLYDVAEYAGVSYQTVSRVVNQASHVSAKTREKVEAAMAELN<br>YIPNRVAQQLAGKQSLLIGVATSSLALHAPSQIVAAIKSRADQLGASVV<br>VSMVERSGVEACKAAVHNLLAQRVSGLIINYPLDDQDAIAVEAACTNV<br>PALFLDVSDQTPINSIIFSHEDGTRLGVEHLVALGHQQIALLAGPLSSVSA<br>RLRLAGWHKYLTRNQIQPIAEREGDWSAMSGFQQTMQMLNEGIVPTA<br>MLVANDQMALGAMRAITESGLRVGADISVVGYDDTEDSSCYIPPLTTIK<br>QDFRLLGQTSVDRLLQLSQGQAVKGNQLLPVSLVKRKTTLAPNTQTAS<br>PRALADSLMQLARQVSRLESGQ |
| PlacI (promoter for lacI in reverse orientation) SEQ ID NO: 1113 | CCGGGCGCTATCATGCCATACCGCGAAAGGTTTTGCGCCATTCGATG<br>G |
| PlacI-RBS - lacI (reverse orientation) SEQ ID NO: 1114 | TCACTGCCCGCTTTCCAGTCGGGAAACCTGTCGTGCCAGCTGCATTA<br>ATGAATCGGCCAACGCGCGGGGAGAGGCGGTTTGCGTATTGGGCGC<br>CAGGGTGGTTTTTCTTTTCACCAGTGAGACTGGCAACAGCTGATTGC<br>CCTTCACCGCCTGGCCCTGAGAGAGTTGCAGCAAGCGGTCCACGCTG<br>GTTTGCCCCAGCAGGCGAAAATCCTGTTTGATGGTGGTTAACGGCGG<br>GATATAACATGAGCTATCTTCGGTATCGTCGTATCCCACTACCGAGA<br>TATCCGCACCAACGCGCAGCCCGGACTCGGTAATGGCGCGCATTGC<br>GCCCAGCGCCATCTGATCGTTGGCAACCAGCATCGCAGTGGGAACG<br>ATGCCCTCATTCAGCATTTGCATGGTTTGTTGAAAACCGGACATGGC<br>ACTCCAGTCGCCTTCCCGTTCCGCTATCGGCTGAATTTGATTGCGAG<br>TGAGATATTTATGCCAGCCAGCCAGACGCAGACGCGCCGAGACAGA<br>ACTTAATGGGCCCGCTAACAGCGCGATTTGCTGGTGACCCAATGCGA<br>CCAGATGCTCCACGCCCAGTCGCGTACCGTCCTCATGGGAGAAAAT<br>AATACTGTTGATGGGTGTCTGGTCAGAGACATCAAGAAATAACGCC<br>GGAACATTAGTGCAGGCAGCTTCCACAGCAATGGCATCCTGGTCATC<br>CAGCGGATAGTTAATGATCAGCCCACTGACGCGTTGCGCGAGAAGA<br>TTGTGCACCGCCGCTTTACAGGCTTCGACGCCGCTTCGTTCTACCATC<br>GACACCACCACGCTGGCACCCAGTTGATCGGCGCGAGATTTAATCG<br>CCGCGACAATTTGCGACGGCGCGTGCAGGGCCAGACTGGAGGTGGC<br>AACGCCAATCAGCAACGACTGTTTGCCCGCCAGTTGTTGTGCCACGC<br>GGTTGGGAATGTAATTCAGCTCCGCCATCGCCGCTTCCACTTTTTCCC<br>GCGTTTTCGCAGAAACGTGGCTGGCCTGGTTCACCACGCGGGAAAC<br>GGTCTGATAAGAGACACCGGCATACTCTGCGACATCGTATAACGTTA<br>CTGGTTTCATATTCACCACCCTGAATTGACTCTCTT**CCGGGCGCTAT**<br>**CATGCCATACCGCGAAAGGTTTTGCGCCATTCGATGG** |
| Ptac (minimal promoter for gene expression - includes -10 and -35 region) SEQ ID NO: 1115 | ttgacaattaatcatcggctcgtataatg |

TABLE 3-continued

IPTG inducible promoter and LacI sequences

| Description SEQ ID NO | Sequences |
|---|---|
| Exemplary spacer region SEQ ID NO: 1116 | CGCGCCGCTTCGTCAGGCCACATAGCTTTCTTGTTCTGATCGGAACG ATCGTTGGCTGtg |
| Exemplary Lac operator SEQ ID NO: 1107 | aattgtgagcgctcacaatt |
| Exemplary pTac promoter comprising -10 and -35 regions and Lac operon SEQ ID NO: 1108 | ttgacaattaatcatcggctcgtataatgtgtggaattgtgagcgctcacaattagctgt |
| Exemplary Operator 1 SEQ ID NO: mi | taacaccgtgcgtgttg |
| Exemplary Operator 2 SEQ ID NO: 1112 | Tacctctggcggtgata |
| Exemplary LacI RBS (reverse orientation) SEQ ID NO: 1117 | ATTCACCACCCTGAATTGACTCTCTT |

In some embodiments, the bacterial cells comprise endogenous gene(s) encoding the IPTG sensing transcriptional regulator, LacI. In some embodiments, the lacI gene is heterologous. In some embodiments, the gene encoding the IPTG level-sensing transcriptional regulator, e.g., LacI, is present on a plasmid. In some embodiments, the gene encoding the IPTG level-sensing transcriptional regulator, e.g., LacI, and the gene encoding the methionine decarboxylase/methionine importer are present on different plasmids. In some embodiments, the gene encoding the IPTG level-sensing transcriptional regulator, e.g., LacI, and the gene encoding the methionine decarboxylase or methionine importer are present on the same plasmid. In some embodiments, the gene encoding the IPTG level-sensing transcriptional regulator, e.g., LacI, is present on a chromosome. In some embodiments, the gene encoding the IPTG level-sensing transcriptional regulator, e.g., LacI, and the gene encoding the methionine decarboxylase or methionine importer are present on different chromosomes. In some embodiments, the gene encoding the IPTG level-sensing transcriptional regulator, e.g., LacI, and the gene encoding the methionine decarboxylase or methionine importer are present on the same chromosome, either at the same or a different insertion site. In some embodiments, expression of the transcriptional regulator is controlled by a different promoter than the promoter that controls expression of the gene encoding the methionine decarboxylase or methionine importer, e.g., a constitutive promoter. In some embodiments, expression of the transcriptional regulator is controlled by the same promoter that controls expression of the methionine decarboxylase or methionine importer. In some embodiments, the transcriptional regulator and the methionine decarboxylase or methionine importer are divergently transcribed from a promoter region.

In some embodiments, the promoter that is operably linked to the gene encoding the methionine decarboxylase or methionine importer is directly induced by exogenous environmental conditions. In some embodiments, the promoter that is operably linked to the gene encoding the methionine decarboxylase or methionine importer is indirectly induced by exogenous environmental conditions. In some embodiments, the promoter is directly or indirectly induced by exogenous environmental conditions specific to the gut of a mammal. In some embodiments, the promoter is directly or indirectly induced by exogenous environmental conditions specific to the small intestine of a mammal. In some embodiments, the promoter is directly or indirectly induced by low-oxygen or anaerobic conditions such as the environment of the mammalian gut. In some embodiments, the promoter is directly or indirectly induced by molecules or metabolites that are specific to the gut of a mammal. In some embodiments, the promoter is directly or indirectly induced by a molecule that is co-administered with the bacterial cell. In one embodiment, the inducible promoter is an anhydrotetracycline (ATC)-inducible promoter. In one embodiment, the inducible promoter is an IPTG promoter. In one embodiment, the IPTG promoter is Ptac.

As used herein the term "pTac" or "pTac promoter" includes the minimal promoter having −35 and −10 regions and at least the lac operator region. As used herein in certain instances, the term "pTac" or "pTac promoter" may also include an RBS in addition the minimal promoter and the Lac operator region. Non-limiting examples of suitable RBSs are listed herein. In a non-limiting example, pTac promoter sequence comprises SEQ ID NO: 1108. In some instances an RBS may be included at the 3' end of SEQ ID NO: 1108. In a non-limiting example, the RBS comprises SEQ ID NO: 1107.

In certain embodiments, the bacterial cell comprises a gene encoding a methionine decarboxylase and/or a methionine importer expressed under the control of a fumarate and nitrate reductase regulator (FNR) responsive promoter. In *E. coli*, FNR is a major transcriptional activator that controls the switch from aerobic to anaerobic metabolism (Unden et al., 1997). In the anaerobic state, FNR dimerizes into an active DNA binding protein that activates hundreds of genes responsible for adapting to anaerobic growth. In the aerobic state, FNR is prevented from dimerizing by oxygen and is inactive. FNR responsive promoters include, but are not limited to, the FNR responsive promoters listed in the chart, below. Underlined sequences are predicted ribosome binding sites, and bolded sequences are restriction sites used for cloning.

TABLE 4

| FNR Responsive Promoter | Sequence |
|---|---|
| SEQ ID NO: 1 | GTCAGCATAACACCCTGACCTCTCATTAATTGTTCATGCCGGGCGGCACTATCGTCGTCCGGCCTTTTCCTCTCTTACTCTGCTACGTACATCTATTTCTATAAATCCGTTCAATTTGTCTGTTTTTTGCACAAACATGAAATATCAGACAATTCCGTGACTTAAGAAAATTTATACAAATCAGCAATATACCCCTTAAGGAGTATATAAAGGTGAATTTGATTTACATCAATAAGCGGGGTTGCTGAATCGTTAAGGTAGGCGGTAATAGAAAAGAAATCGAGGCAAAA |
| SEQ ID NO: 2 | ATTTCCTCTCATCCCATCCGGGGTGAGAGTCTTTTCCCCCGACTTATGGCTCATGCATGCATCAAAAAAGATGTGAGCTTGATCAAAAACAAAAAATATTTCACTCGACAGGAGTATTTATATTGCGCCCGTTACGTGGGCTTCGACTGTAAATCAGAAAGGAGAAAACACCT |
| SEQ ID NO: 3 | GTCAGCATAACACCCTGACCTCTCATTAATTGTTCATGCCGGGCGGCACTATCGTCGTCCGGCCTTTTCCTCTCTTACTCTGCTACGTACATCTATTTCTATAAATCCGTTCAATTTGTCTGTTTTTTGCACAAACATGAAATATCAGACAATTCCGTGACTTAAGAAAATTTATACAAATCAGCAATATACCCCTTAAGGAGTATATAAAGGTGAATTTGATTTACATCAATAAGCGGGGTTGCTGAATCGTTAA**GGATCC**CTCTAGAAATAATTTTGTTTAACTTTAAGAAGGAGATATACAT |
| SEQ ID NO: 4 | CATTTCCTCTCATCCCATCCGGGGTGAGAGTCTTTTCCCCCGACTTATGGCTCATGCATGCATCAAAAAAGATGTGAGCTTGATCAAAAACAAAAAATATTTCACTCGACAGGAGTATTTATATTGCGCCC**GGATCC**CTCTAGAAATAATTTTGTTTAACTTTAAGAAGGAGATATACAT |
| SEQ ID NO: 5 | AGTTGTTCTTATTGGTGGTGTTGCTTTATGGTTGCATCGTAGTAAATGGTTGTAACAAAAGCAATTTTTCCGGCTGTCTGTATACAAAAACGCCGTAAAGTTTGAGCGAAGTCAATAAACTCTCTACCCATTCAGGGCAATATCTCTCTT**GGATCC**CTCTAGAAATAATTTTGTTTAACTTTAAGAAGGAGATATACAT |

In one embodiment, the FNR responsive promoter comprises SEQ ID NO: 1. In another embodiment, the FNR responsive promoter comprises SEQ ID NO: 2. In another embodiment, the FNR responsive promoter comprises SEQ ID NO: 3. In another embodiment, the FNR responsive promoter comprises SEQ ID NO: 4. In yet another embodiment, the FNR responsive promoter comprises SEQ ID NO: 5.

In some embodiments, multiple distinct FNR nucleic acid sequences are inserted in the genetically engineered bacteria. In alternate embodiments, the genetically engineered bacteria comprise a gene encoding a methionine decarboxylase and/or a gene encoding a methionine importer expressed under the control of an alternate oxygen level-dependent promoter, e.g., DNR (Trunk et al., 2010) or ANR (Ray et al., 1997). In these embodiments, expression of the methionine decarboxylase gene or methionine importer gene is particularly activated in a low-oxygen or anaerobic environment, such as in the gut. In one embodiment, the mammalian gut is a human mammalian gut.

In some embodiments, the bacterial cell comprises an oxygen-level dependent transcriptional regulator, e.g., FNR, ANR, or DNR, and corresponding promoter from a different bacterial species. The heterologous oxygen-level dependent transcriptional regulator and promoter increase the transcription of genes operably linked to said promoter, e.g., the gene encoding the methionine decarboxylase or the gene encoding a methionine importer, in a low-oxygen or anaerobic environment, as compared to the native gene(s) and promoter in the bacteria under the same conditions. In certain embodiments, the non-native oxygen-level dependent transcriptional regulator is an FNR protein from *N. gonorrhoeae* (see, e.g., Isabella et al., 2011). In some embodiments, the corresponding wild-type transcriptional regulator is left intact and retains wild-type activity. In alternate embodiments, the corresponding wild-type transcriptional regulator is deleted or mutated to reduce or eliminate wild-type activity.

In some embodiments, the genetically engineered bacteria comprise a wild-type oxygen-level dependent transcriptional regulator, e.g., FNR, ANR, or DNR, and corresponding promoter that is mutated relative to the wild-type promoter from bacteria of the same subtype. The mutated promoter enhances binding to the wild-type transcriptional regulator and increases the transcription of genes operably linked to said promoter, e.g., the gene encoding the methionine decarboxylase or the methionine importer, in a low-oxygen or anaerobic environment, as compared to the wild-type promoter under the same conditions. In some embodiments, the genetically engineered bacteria comprise a wild-type oxygen-level dependent promoter, e.g., FNR, ANR, or DNR promoter, and corresponding transcriptional regulator that is mutated relative to the wild-type transcriptional regulator from bacteria of the same subtype. The mutated transcriptional regulator enhances binding to the wild-type promoter and increases the transcription of genes operably linked to said promoter, e.g., the gene encoding the methionine decarboxylase or the gene encoding the methionine importer, in a low-oxygen or anaerobic environment, as compared to the wild-type transcriptional regulator under the same conditions. In certain embodiments, the mutant oxygen-level dependent transcriptional regulator is an FNR protein comprising amino acid substitutions that enhance dimerization and FNR activity (see, e.g., Moore et al., (2006).

In some embodiments, the bacterial cells comprise multiple copies of the endogenous gene encoding the oxygen level-sensing transcriptional regulator, e.g., the FNR gene. In some embodiments, the gene encoding the oxygen level-sensing transcriptional regulator is present on a plasmid. In some embodiments, the gene encoding the oxygen level-sensing transcriptional regulator and the gene encoding the methionine decarboxylase or methionine importer are present on different plasmids. In some embodiments, the gene encoding the oxygen level-sensing transcriptional regulator and the gene encoding the methionine decarboxylase or methionine importer are present on the same plasmid. In some embodiments, the gene encoding the oxygen level-sensing transcriptional regulator is present on a chromosome. In some embodiments, the gene encoding the oxygen level-sensing transcriptional regulator and the gene encoding the methionine decarboxylase or methionine importer are present on different chromosomes. In some embodiments, the gene encoding the oxygen level-sensing transcriptional regulator and the gene encoding the methionine decarboxylase or methionine importer are present on the same chromosome. In some instances, it may be advantageous to express the oxygen level-sensing transcriptional regulator under the control of an inducible promoter in order to enhance expression stability. In some embodiments, expression of the transcriptional regulator is controlled by a different promoter than the promoter that controls expression of the gene encoding the methionine decarboxylase or methionine importer. In some embodiments, expression of the transcriptional regulator is controlled by the same promoter that controls expression of the methionine decarboxylase or methionine importer. In some embodiments, the transcriptional regulator and the methionine decarboxylase or methionine importer are divergently transcribed from a promoter region.

In some embodiments, any of the gene(s) of the present disclosure may be integrated into the chromosome of a host cell, such as a bacterial chromosome, at one or more integration sites. For example, one or more copies of one or more gene(s) encoding a methionine decarboxylase or methionine importer may be integrated into the chromosome of a host cell, such as a bacterial chromosome. Having multiple copies of the gene or gene(s) integrated into the chromosome allows for greater production of the methionine decarboxylase(s) and also permits fine-tuning of the level of expression. Alternatively, different circuits described herein, such as any of the secretion or exporter circuits, in addition to the therapeutic gene(s) or gene cassette(s) could be integrated into the chromosome of a host cell, such as a bacterial chromosome, at one or more different integration sites to perform multiple different functions.

E. Temperature Dependent Regulation

In some instances, thermoregulators may be advantageous because of strong transcriptional control without the use of external chemicals or specialized media. Thermoregulated protein expression using the mutant cI857 repressor and the pL and/or pR phage λ promoters have been used to engineer recombinant bacterial strains. For example, a gene of interest cloned downstream of the a promoters can be efficiently regulated by the mutant thermolabile cI857 repressor of bacteriophage L. At temperatures below 37° C., cI857 binds to the oL or oR regions of the pR promoter and inhibits transcription by RNA polymerase. At higher temperatures, the functional cI857 dimer is destabilized, binding to the oL or oR DNA sequences is abrogated, and mRNA transcription is initiated. In certain instances, it may be advantageous to reduce, diminish, or shut off production of one or more protein(s) of interest. This can be done in a thermoregulated system by growing a bacterial strain at temperatures at which the temperature regulated system is not optimally active. Temperature regulated expression can then be induced as desired by changing the temperature to a temperature where the system is more active or optimally active.

For example, a thermoregulated promoter may be induced in culture, e.g., grown in a flask, fermenter or other appropriate culture vessel, e.g., used during cell growth, cell expansion, fermentation, recovery, purification, formulation, and/or manufacture. Bacteria comprising gene sequences or gene cassettes either indirectly or directly operably linked to a temperature sensitive system or promoter may, for example, could be induced by temperatures between 37° C. and 42° C. In some instances, the cultures may be grown aerobically. Alternatively, the cultures are grown anaerobically.

In some embodiments, the host cell, such as a bacterial host cell, described herein comprise one or more gene sequence(s) or gene cassette(s) which are directly or indirectly operably linked to a temperature regulated promoter. In some embodiments, the gene sequence(s) or gene cassette(s) are induced in vitro during growth, preparation, or manufacturing of the strain prior to in vivo administration. In some embodiments, the gene sequence(s) are induced upon or during in vivo administration. In some embodiments, the gene sequence(s) are induced during in vitro growth, preparation, or manufacturing of the strain prior to in vivo administration and upon or during in vivo administration. In some embodiments, the genetically engineered host cell, such as genetically engineered bacteria, further comprise gene sequence (s) encoding a transcription factor which is capable of binding to the temperature sensitive promoter. In some embodiments, the transcription factor is a repressor of transcription.

In one embodiment, the thermoregulated promoter is operably linked to a construct having gene sequence(s) or gene cassette(s) encoding one or more protein(s) of interest jointly with a second promoter, e.g., a second constitutive or inducible promoter. In some embodiments, two promoters are positioned proximally to the construct and drive its expression, wherein the thermoregulated promoter is induced under a first set of exogenous conditions, and the second promoter is induced under a second set of exogenous conditions. In a non-limiting example, the first and second conditions may be two sequential culture conditions (i.e., during preparation of the culture in a flask, fermenter or other appropriate culture vessel, e.g., thermoregulation and arabinose or IPTG). In another non-limiting example, the first inducing conditions may be culture conditions, e.g., permissive temperature, and the second inducing conditions may be in vivo conditions. Such in vivo conditions include low-oxygen, microaerobic, or anaerobic conditions, presence of gut metabolites, and/or metabolites administered in combination with the bacterial strain. In some embodiments, one or more thermoregulated promoters drive expression of one or more protein(s) of interest in combination with an oxygen regulated promoter, e.g., FNR, driving the expression of the same gene sequence(s).

In some embodiments, the thermoregulated promoter drives the expression of one or more protein(s) of interest from a low-copy plasmid or a high copy plasmid or a biosafety system plasmid described herein. In some embodiments, the thermoregulated promoter drives the expression of one or more protein(s) of interest from a construct which is integrated into the host cell chromosome, such as a bacterial chromosome. Exemplary insertion sites are described herein.

In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 309. In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 313. In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 316. In some embodiments, the thermoregulated construct further comprises a gene encoding mutant cI857 repressor, which is divergently transcribed from the same promoter as the one or more one or more protein(s) of interest. In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 310. In some embodiments, the genetically engineered bacteria comprise one or more gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with the polypeptide encoded by any of the sequences of SEQ ID NO: 312. In some embodiments, the thermoregulated construct further comprises a gene encoding mutant cI38 repressor, which is divergently transcribed from the same promoter as the one or more one or more protein(s) of interest. In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 314. In some embodiments, the genetically engineered bacteria comprise one or more gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with the polypeptide encoded by any of the sequences of SEQ ID NO: 315.

SEQ ID NOs: 309, 310, and 312-316 are shown in Table 5.

TABLE 5

Inducible promoter construct sequences and related elements

| Description | SEQ ID NO |
|---|---|
| Region comprising Temperature sensitive promoter | SEQ ID NO: 309 |
| mutant cI857 repressor nucleotide sequence | SEQ ID NO: 310 |
| mutant cI857 repressor polypeptide sequence | SEQ ID NO: 312 |
| Pr/Pl promoter | SEQ ID NO: 313 |
| mutant cI38 repressor nucleotide sequence | SEQ ID NO: 314 |
| mutant cI38 repressor polypeptide sequence | SEQ ID NO: 315 |
| Temperature sensitive promoter | SEQ ID NO: 316 |

In some embodiments, the bacterial cells comprise gene(s) encoding a temperature sensing transcriptional regulator/repressor described herein, e.g., cI857 or a mutant thereof. In some embodiments, the gene encoding the temperature sensing transcriptional regulator, is present on a plasmid. In some embodiments, the gene encoding the temperature sensing transcriptional regulator, and the gene encoding the methionine decarboxylase/methionine importer are present on different plasmids. In some embodiments, the gene encoding the temperature sensing transcriptional regulator, and the gene encoding the methionine decarboxylase or methionine importer are present on the same plasmid. In some embodiments, the gene encoding the temperature sensing transcriptional regulator is present on a chromosome. In some embodiments, the gene encoding the temperature sensing transcriptional regulator, and the gene encoding the methionine decarboxylase or methionine importer are present on different chromosomes. In some embodiments, the gene encoding the temperature sensing transcriptional regulator, and the gene encoding the methionine decarboxylase or methionine importer are present on the same chromosome, either at the same or at different insertion sites. In some embodiments, expression of temperature sensing transcriptional regulator is controlled by a different promoter than the promoter that controls expression of the gene encoding the methionine decarboxylase or methionine importer, e.g., a constitutive promoter. In some embodiments, expression of the temperature sensing transcriptional regulator is controlled by the same promoter that controls expression of the methionine decarboxylase or methionine importer. In some embodiments, the temperature sensing transcriptional regulator and the methionine decarboxylase or methionine importer are divergently transcribed from a promoter region.

In any of these embodiments, gene expression may be further optimized by methods known in the art, e.g., by optimizing ribosomal binding sites and/or increasing mRNA stability.

F. Phage Deletion

In some embodiments, the genetically engineered bacteria comprise one or more *E. coli* Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the one or more insertions comprise an antibiotic cassette. In some embodiments, the mutation is a deletion. In some embodiments, the genetically engineered bacteria comprise one or more deletions, which are located in or comprise one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the genetically engineered bacteria comprise a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 1064 is deleted from the Phage 3 genome. In one embodiment, a sequence comprising SEQ ID NO: 1064 is deleted from the Phage 3 genome.

G. Colibactin Island (Also Known as pks Island)

In some embodiments, the engineered bacterium further comprises a modified pks island (colibactin island). Non-limiting examples are described in PCT/US2021/061579, the contents of which are herein incorporated by reference in their entirety. Colibactin is a cyclomodulin that is synthetized by enzymes encoded by the pks genomic island. See Fais 2018. The pks genomic island is "highly conserved" in Enterobacteriaceae. Id. In *Escherichia coli*, a 54-kilobase pks genomic island contains 19 genes, clbA to clbS, and encodes various enzymes that have been described as an "assembly line responsible for colibactin synthesis." Id. The pks genomic island assembly line for colibactin synthesis includes three polyketide synthases (ClbC, ClbI, ClbO), three non-ribosomal peptide synthases (ClbH, ClbJ, ClbN), two hybrid non-ribosomal peptide/polyketide synthases (ClbB, ClbK), and nine accessory, tailoring, and editing proteins. The polyketide synthases, non-ribosomal peptide synthases, and hybrid enzymes "are usually organized in mega-complexes as an assembly line, in which the synthesized compound is transferred from one enzymatic module to the following one." Id. Colibactin undergoes a prodrug activation mechanism that incorporates an N-terminal structural motif, which is removed during the final stage of biosynthesis. In some embodiments, the engineered microorganism, e.g., engineered bacterium, comprises a modified pks island (colibactin island). In some embodiments, the engineered microorganism, e.g., engineered bacterium, comprises a modified clb sequence selected from one or more of the clbA, clbB, clbC, clbD, clbE, clbF, clbG, clbH, clbL, clbJ, clbK, clbL, clbM, clbN, cibO, clbP, clbQ, clbR, and clbS gene sequences, as compared to a suitable control, e.g., the native pks island in an unmodified bacterium of the same strain and/or subtype. In some embodiments, the modified clb sequence is an insertion, a substitution, and/or a deletion as compared to the control. In some embodiments, the modified clb sequence is a deletion of the clb island, e.g., clbA, clbB, clbC, clbD, clbE, clbF, clbG, clbH, clbI, clbJ, clbK, clbL, clbM, clbN, clbO, clbP, clbQ, clbR, and clbS. In one embodiment, the colibactin deletion is the whole island except for the clbS gene, e.g., a deletion of clbA, clbB, clbC, clbD, clbE, clbF, clbG, clbH, clbI, clbJ, clbK, clbL, clbM, clbN, clbO, clbP, clbQ, and clbR.

In some embodiments, the modified endogenous colibactin island comprises one or more modified clb sequences selected from clbA (SEQ ID NO: 1065), clbB (SEQ ID NO: 1066), clbC (SEQ ID NO: 1067), clbD (SEQ ID NO: 1068), clbE (SEQ ID NO: 1069), clbF (SEQ ID NO: 1070), clbG (SEQ ID NO: 1071), clbH (SEQ ID NO: 1072), clbI (SEQ ID NO: 1073), clbJ (SEQ ID NO: 1074), clbK (SEQ ID NO: 1075), clbL (SEQ ID NO: 1076), clbM (SEQ ID NO: 1077), clbN (SEQ ID NO: 1078), clbO (SEQ ID NO: 1079), clbP (SEQ ID NO: 1080), clbQ (SEQ ID NO: 1081), clbR (SEQ ID NO: 1082), or clbS (SEQ ID NO: 1803) gene. In some embodiments, the modified endogenous colibactin island comprises a deletion of clbA (SEQ ID NO: 1065), clbB (SEQ ID NO: 1066), clbC (SEQ ID NO: 1067), clbD (SEQ ID NO: 1068), clbE (SEQ ID NO: 1069), clbF (SEQ ID NO: 1070), clbG (SEQ ID NO: 1071), clbH (SEQ ID NO: 1072), clbI (SEQ ID NO: 1073), clbJ (SEQ ID NO: 1074), clbK (SEQ ID NO: 1075), clbL (SEQ ID NO: 1076), clbM (SEQ ID NO: 1077), clbN (SEQ ID NO: 1078), clbO (SEQ ID NO: 1079), clbP (SEQ ID NO: 1080), clbQ (SEQ ID NO: 1081), and clbR (SEQ ID NO: 1082).

Essential Genes and Auxotrophs

As used herein, the term "essential gene" refers to a gene which is necessary to for cell growth and/or survival. Bacterial essential genes are well known to one of ordinary skill in the art, and can be identified by directed deletion of genes and/or random mutagenesis and screening (see, for example, Zhang and Lin, 2009, DEG 5.0, a database of essential genes in both prokaryotes and eukaryotes, *Nucl. Acids Res.,* 37: D455-D458 and Gerdes et al., Essential genes on metabolic maps, *Curr. Opin. Biotechnol.,* 17(5): 448-456, the entire contents of each of which are expressly incorporated herein by reference).

An "essential gene" may be dependent on the circumstances and environment in which an organism lives. For example, a mutation of, modification of, or excision of an essential gene may result in the recombinant bacteria of the disclosure becoming an auxotroph. An auxotrophic modification is intended to cause bacteria to die in the absence of an exogenously added nutrient essential for survival or growth because they lack the gene(s) necessary to produce that essential nutrient.

An auxotrophic modification is intended to cause bacteria to die in the absence of an exogenously added nutrient essential for survival or growth because they lack the gene(s) necessary to produce that essential nutrient. In some embodiments, any of the genetically engineered bacteria described herein also comprise a deletion or mutation in a gene required for cell survival and/or growth. In one embodiment, the essential gene is an oligonucleotide synthesis gene, for example, thyA. In another embodiment, the essential gene is a cell wall synthesis gene, for example, dapA. In yet another embodiment, the essential gene is an amino acid gene, for example, serA or metA. Any gene required for cell survival and/or growth may be targeted, including but not limited to, cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1, as long as the corresponding wild-type gene product is not produced in the bacteria. For example, thymine is a nucleic acid that is required for bacterial cell growth; in its absence, bacteria undergo cell death. The thyA gene encodes thimidylate synthetase, an enzyme that catalyzes the first step in thymine synthesis by converting dUMP to dTMP (Sat et al., 2003). In some embodiments, the bacterial cell of the disclosure is a thyA auxotroph in which the thyA gene is deleted and/or replaced with an unrelated gene. A thyA auxotroph can grow only when sufficient amounts of thymine are present, e.g., by adding thymine to growth media in vitro, or in the presence of high thymine levels found naturally in the human gut in vivo. In some embodiments, the bacterial cell of the disclosure is auxotrophic in a gene that is complemented when the bacterium is present in the mammalian gut. Without sufficient amounts of thymine, the thyA auxotroph dies. In some embodiments, the auxotrophic modification is used to ensure that the bacterial cell does not survive in the absence of the auxotrophic gene product (e.g., outside of the gut).

Diaminopimelic acid (DAP) is an amino acid synthetized within the lysine biosynthetic pathway and is required for bacterial cell wall growth (Meadow et al., 1959; Clarkson et al., 1971). In some embodiments, any of the genetically engineered bacteria described herein is a dapD auxotroph in which dapD is deleted and/or replaced with an unrelated gene. A dapD auxotroph can grow only when sufficient amounts of DAP are present, e.g., by adding DAP to growth media in vitro. Without sufficient amounts of DAP, the dapD auxotroph dies. In some embodiments, the auxotrophic modification is used to ensure that the bacterial cell does not survive in the absence of the auxotrophic gene product (e.g., outside of the gut).

In other embodiments, the genetically engineered bacterium of the present disclosure is a uraA auxotroph in which uraA is deleted and/or replaced with an unrelated gene. The uraA gene codes for UraA, a membrane-bound importer that facilitates the uptake and subsequent metabolism of the pyrimidine uracil (Andersen et al., 1995). A uraA auxotroph can grow only when sufficient amounts of uracil are present, e.g., by adding uracil to growth media in vitro. Without sufficient amounts of uracil, the uraA auxotroph dies. In some embodiments, auxotrophic modifications are used to ensure that the bacteria do not survive in the absence of the auxotrophic gene product (e.g., outside of the gut).

In complex communities, it is possible for bacteria to share DNA. In very rare circumstances, an auxotrophic bacterial strain may receive DNA from a non-auxotrophic strain, which repairs the genomic deletion and permanently rescues the auxotroph. Therefore, engineering a bacterial strain with more than one auxotroph may greatly decrease the probability that DNA transfer will occur enough times to rescue the auxotrophy. In some embodiments, the genetically engineered bacteria comprise a deletion or mutation in two or more genes required for cell survival and/or growth.

Other examples of essential genes include, but are not limited to yhbV, yagG, hemB, secD, secF, ribD, ribE, thiL, dxs, ispA, dnaX, adk, hemH, lpxH, cysS, fold, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, rnc, ftsB, eno, pyrG, chpR, lgt, fbaA, pgk, yqgD, metK, yqgF, plsC, ygiT, pare, ribB, cca, ygjD, tdcF, yraL, yihA, ftsN, murl, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, dnaC, ribF, lspA, ispH, dapB, folA, imp, yabQ, ftsL, ftsL, murE, murF, mraY, murD, ftsW, murG, murC, ftsQ, ftsA, ftsZ, lpxC, secM, secA, can, folK, hemL, yadR, dapD, map, rpsB, infB, nusA, ftsH, obgE, rpmA, rplU, ispB, murA, yrbB, yrbK, yhbN, rpsL, rplM, degS, mreD, mreC, mreB, accB, accC, yrdC, def fnt, rplQ, rpoA, rpsD, rpsK, rpsM, entD, mrdB, mrdA, nadD, hlepB, rpoE, pssA, yfiO, rplS, trmD, rpsP, ffh, grpE, yfjB, csrA, ispF, ispD, rplW, rplD, rplC, rpsJ, fusA, rpsG, rpsL, trpS, yrfF, asd, rpoH, ftsX, ftsE, ftsY, frr, dxr, ispU, rfaK, kdtA, coaD, rpmB, dfp, dut, gmk, spot, gyrB, dnaN, dnaA, rpmH, rnpA, yidC, tnaB, glmS, glmU, wzyE, hemD, hemC, yigP, ubiB, ubiD, hemG, secY, rplO, rpmD, rpsE, rplR, rplF, rpsH, rpsN, rplE, rplX, rplN, rpsQ, rpmC, rplP, rpsC, rplV, rpsS, rplB, cdsA, yaeL, yaeT, lpxD, fabZ, lpxA, lpxB, dnaE, accA, tilS, proS, yafF, tsf pyrH, olA, rlpB, leuS, lnt, ginS, fldA, cydA, infA, cydC, ftsK, lolA, serS, rpsA, msbA, lpxK, kdsB, mukF, mukE, mukB, asnS, fabA, mviN, rne, yceQ, fabD, fabG, acpP, tmk, holB, lolC, lolD, lolE, purB, ymfK, minE, mind, pth, rsA, ispE, lolB, hemA, prfA, prmC, kdsA, topA, ribA, fabI, racR, dicA, ydfB, tyrS, ribC, ydiL, pheT, pheS, yhhQ, bcsB, glyQ, yibJ, and gpsA. Other essential genes are known to those of ordinary skill in the art.

In some embodiments, the genetically engineered bacterium of the present disclosure is a synthetic ligand-dependent essential gene (SLiDE) bacterial cell. SLiDE bacterial cells are synthetic auxotrophs with a mutation in one or more essential genes that only grow in the presence of a particular ligand (see Lopez and Anderson "Synthetic Auxotrophs with Ligand-Dependent Essential Genes for a BL21 (DE3 Biosafety Strain, "ACS Synthetic Biology (2015) DOI: 10.1021/acssynbio.5b00085, the entire contents of which are expressly incorporated herein by reference).

In some embodiments, the SLiDE bacterial cell comprises a mutation in an essential gene. In some embodiments, the essential gene is selected from the group consisting of pheS, dnaN, tyrS, metG and adk. In some embodiments, the essential gene is dnaN comprising one or more of the following mutations: H191N, R240C, I317S, F319V, L340T, V347I, and S345C. In some embodiments, the essential gene is dnaN comprising the mutations H191N, R240C, I317S, F319V, L340T, V347I, and S345C. In some embodiments, the essential gene is pheS comprising one or more of the following mutations: F125G, P183T, P184A, R186A, and I188L. In some embodiments, the essential gene is pheS comprising the mutations F125G, P183T, P184A, R186A, and I188L. In some embodiments, the essential gene is tyrS comprising one or more of the following mutations: L36V, C38A and F40G. In some embodiments, the essential gene is tyrS comprising the mutations L36V, C38A and F40G. In some embodiments, the essential gene is metG comprising one or more of the following mutations: E45Q, N47R, I49G, and A51C. In some embodiments, the essential gene is metG comprising the mutations E45Q, N47R, I49G, and A51C. In some embodiments, the essential gene is adk comprising one or more of the following mutations: I4L, L5I and L6G. In some embodiments, the essential gene is adk comprising the mutations I4L, L5I and L6G.

In some embodiments, the genetically engineered bacterium is complemented by a ligand. In some embodiments, the ligand is selected from the group consisting of benzothiazole, indole, 2-aminobenzothiazole, indole-3-butyric acid, indole-3-acetic acid, and L-histidine methyl ester. For example, bacterial cells comprising mutations in metG (E45Q, N47R, I49G, and A51C) are complemented by benzothiazole, indole, 2-aminobenzothiazole, indole-3-butyric acid, indole-3-acetic acid or L-histidine methyl ester. Bacterial cells comprising mutations in dnaN (H191N, R240C, I317S, F319V, L340T, V347I, and S345C) are complemented by benzothiazole, indole or 2-aminobenzothiazole. Bacterial cells comprising mutations in pheS (F125G, P183T, P184A, R186A, and I188L) are complemented by benzothiazole or 2-aminobenzothiazole. Bacterial cells comprising mutations in tyrS (L36V, C38A, and F40G) are complemented by benzothiazole or 2-aminobenzothiazole. Bacterial cells comprising mutations in adk (I4L, L5I and L6G) are complemented by benzothiazole or indole.

In some embodiments, the genetically engineered bacterium comprises more than one mutant essential gene that renders it auxotrophic to a ligand. In some embodiments, the bacterial cell comprises mutations in two essential genes. For example, in some embodiments, the bacterial cell comprises mutations in tyrS (L36V, C38A, and F40G) and metG (E45Q, N47R, I49G, and A51C). In other embodiments, the bacterial cell comprises mutations in three essential genes. For example, in some embodiments, the bacterial cell comprises mutations in tyrS (L36V, C38A, and F40G), metG (E45Q, N47R, I49G, and A51C), and pheS (F125G, P183T, P184A, R186A, and I188L).

In some embodiments, the genetically engineered bacterium is a conditional auxotroph whose essential gene(s) is replaced using the arabinose system described herein.

In some embodiments, the genetically engineered bacterium of the disclosure is an auxotroph and also comprises kill-switch circuitry, such as any of the kill-switch components and systems described herein. For example, the recombinant bacteria may comprise a deletion or mutation in an essential gene required for cell survival and/or growth, for example, in a DNA synthesis gene, for example, thyA, cell wall synthesis gene, for example, dapA and/or an amino acid gene, for example, serA or MetA and may also comprise a toxin gene that is regulated by one or more transcriptional activators that are expressed in response to an environmental condition(s) and/or signal(s) (such as the described arabinose system) or regulated by one or more recombinases that are expressed upon sensing an exogenous environmental condition(s) and/or signal(s) (such as the recombinase systems described herein). Other embodiments are described in Wright et al., "GeneGuard: A Modular Plasmid System Designed for Biosafety," ACS Synthetic Biology (2015) 4: 307-16, the entire contents of which are expressly incorporated herein by reference). In some embodiments, the genetically engineered bacterium of the disclosure is an auxotroph and also comprises kill-switch circuitry, such as any of the kill-switch components and systems described herein, as well as another biosecurity system, such a conditional origin of replication (see Wright et al., supra).

Isolated Plasmids

In other embodiments, the disclosure provides an isolated plasmid comprising a first nucleic acid encoding a methionine decarboxylase or methionine importer operably linked to a first inducible promoter. In another embodiment, the disclosure provides an isolated plasmid comprising a second nucleic acid encoding at least one additional methionine decarboxylase or methionine importer. In one embodiment, the first nucleic acid and the second nucleic acid are operably linked to the first promoter. In another embodiment, the second nucleic acid is operably linked to a second inducible promoter. In one embodiment, the first inducible promoter and the second inducible promoter are separate copies of the same inducible promoter. In another embodiment, the first inducible promoter and the second inducible promoter are different inducible promoters. In one embodiment, the first promoter, the second promoter, or the first promoter and the second promoter, are each directly or indirectly induced by low-oxygen or anaerobic conditions. In another embodiment, the first promoter, the second promoter, or the first promoter and the second promoter, are each IPTG inducible. In another embodiment, the first promoter, the second promoter, or the first promoter and second promoter are each regulated by changes in temperature.

In any of the above-described embodiments, the plasmid is a high-copy plasmid. In another embodiment, the plasmid is a low-copy plasmid.

In another aspect, the disclosure provides a recombinant host cell, such as a recombinant bacterial cell, comprising an isolated plasmid described herein. In another embodiment, the disclosure provides a pharmaceutical composition comprising the recombinant bacterial cell.

Integration

In some embodiments, any of the gene(s) or gene cassette(s) of the present disclosure may be integrated into the host cell chromosome, such as a bacterial chromosome, at one or more integration sites. One or more copies of the gene (for example, an amino acid catabolism gene) or gene cassette (for example, a gene cassette comprising an amino acid catabolism gene and an amino acid importer gene) may be integrated into the host cell chromosome, such as a bacterial chromosome. Having multiple copies of the gene or gene cassette integrated into the chromosome allows for greater production of the methionine decarboxylase, and other enzymes of the gene cassette, and also permits fine-tuning of the level of expression. Alternatively, different circuits described herein, such as any of the kill-switch circuits, in addition to the therapeutic gene(s) or gene cassette(s) could be integrated into the host cell chromosome, such as a bacterial chromosome, at one or more different integration sites to perform multiple different functions.

In one non-limiting example, gene sequences encoding MetP and MetDC are integrated to facilitate Met import and metabolism. In one embodiment, metP is derived from *Flavobacterium segetis* and facilitates the uptake of Met into the cell. In one embodiment, MetDC is derived from *Streptomyces* sp. 590 and includes two modifications (Q70D and N82H). In one embodiment, MetP is derived from *Flavobacterium segetis*. In one embodiment, both genes or gene sequences are operably linked to a chemically inducible promoter. In some embodiments, the promoter is induced by the compound Isopropyl β-D-1-thiogalactopyranoside (IPTG) e.g., PTac promoter (see e.g., FIG. 14A).

In some embodiments, the genetically engineered host cell, such as a genetically engineered bacterium, comprises a single integrated copy of metDC. In some embodiments, the genetically engineered host cell, such as a genetically engineered bacterium, comprises two or more integrated copies of metDC. In some embodiments, two or more copies of the metDC gene are present at the same integration site, arranged in a cassette, and operably linked to the same promoter. In some embodiments, two or more copies of the metDC gene are present at the same integration site, arranged in a cassette, and one or more copies of the metDC gene are operably linked to different copies of same promoter or different promoters.

Alternatively, in some embodiments, a genetically engineered host cell, such as a genetically engineered bacterium, may comprise two or more copies of the metDC gene and each copy of the metDC gene may be integrated at distinct sites. In some embodiments, each copy of the metDC gene is linked to a separate promoter at each integration site. In some embodiments, each copy of the metDC gene is operably linked to a different copy of the same promoter. In some embodiments, the promoters are different between two or more copies of the metDC gene. In some embodiments, the promoter is an inducible promoter, e.g., an IPTG inducible promoter. In some embodiments, the genetically engineered host cell, such as a genetically engineered bacterium, comprises a gene cassette comprising a metDC gene operatively linked to an IPTG inducible promoter, e.g., a pTac promoter. In some embodiments, the genetically engineered host cell, such as a genetically engineered bacterium, comprise a Ptac-metDC cassette.

In some embodiments, the genetically engineered host cell, such as a genetically engineered bacterium, comprises a single integrated copy of metP. In some embodiments, the genetically engineered host cell, such as a genetically engineered bacterium, comprises two or more integrated copies of metP. In some embodiments, two or more copies of the metP gene are present at the same integration site, arranged in a cassette, and operably linked to the same promoter. In some embodiments, multiple copies of the metP gene are present at the same integration site, arranged in a cassette, and one or more copies of the metP gene are operably linked to different copies of same promoter or different promoters.

Alternatively, in some embodiments, a genetically engineered host cell, such as a genetically engineered bacterium, may comprise two or more copies of the metP gene and each copy of the metP gene may be integrated at distinct sites. In some embodiments, each copy of the metP gene is linked to a separate promoter at each integration site. In some embodiments, each copy of the metP gene is operably linked to a different copy of the same promoter. In some embodiments, the promoters are different between two or more copies of the metP gene. In some embodiments, the promoter is an inducible promoter, e.g., an IPTG inducible promoter. In some embodiments, the genetically engineered bacterium comprises a gene cassette comprising a metP gene operatively linked to an IPTG inducible promoter, e.g., Ptac. In some embodiments, the genetically engineered bacteria comprise a Ptac-metP cassette.

In one embodiment, both metDC and metP genes are arranged in a cassette.

In some embodiments, the genetically engineered host cell, such as a genetically engineered bacterium, comprises a single integrated copy of metDC and/or metP. In some embodiments, the genetically engineered host cell, such as a genetically engineered bacterium, comprises one or more integrated copies of metDC and one or more integrated copies of metP. In some embodiments, the metDC gene and the metP gene are present at the same integration site, arranged in a cassette, and operably linked to the same promoter. In some embodiments, the metDC gene and the metP gene are present at the same integration site, arranged in a cassette, and the metDC gene and the metP gene are operably linked to different copies of same promoter or different promoters.

In some embodiments, the genetically engineered host cell, such as a genetically engineered bacterium or microorganism, comprises a single integrated copy of a gene cassette comprising metDC and metP. In some embodiments, the genetically engineered host cell, such as a genetically engineered bacterium, comprises two or more integrated copies a gene cassette comprising metDC and metP. In some embodiments, multiple copies of a gene cassette comprising metDC and metP are present at the same integration site, and operably linked to the same promoter. In some embodiments, multiple copies of the gene cassette comprising metDC and metP are present at the same integration site, and one or more copies of the cassette comprising metDC and metP are operably linked to different copies of same promoter or different promoters. In any of these embodiments, the metDC gene and the metP within the gene cassette may be operably linked to the same promoter. Alternatively, in any of these embodiments, the metDC gene and the metP may be each operably linked to a different copy of the same promoter. In another alternative, in any of these embodiments, the metDC gene and the metP may each be operably linked to a different promoter.

Alternatively, in some embodiments, a genetically engineered host cell, such as a genetically engineered bacterium or microorganism, may comprise two or more copies of the gene cassette comprising metDC and metP and each copy of the gene cassette comprising metDC and metP may be integrated at distinct sites. In some embodiments, each copy of the gene cassette comprising metDC and metP is linked to one or more separate promoters at each integration site. In some embodiments, each copy of the gene cassette comprising metDC and metP is operably linked to one or more different copies of the same promoter. In some embodiments, the promoters are different between two or more copies of gene cassette comprising metDC and metP gene. In any of these embodiments, the metDC gene and the metP within the gene cassette may be operably linked to the same promoter. Alternatively, in any of these embodiments, the metDC gene and the metP may be each operably linked to a different copy of the same promoter. In another alternative, in any of these embodiments, the metDC gene and the metP may each be operably linked to a different promoter.

In some embodiments, the promoter is an inducible promoter, e.g., an IPTG inducible promoter, e.g., a Ptac promoter. In some embodiments, the genetically engineered host cell, such as a genetically engineered bacterium or microorganism, comprises gene cassette comprising metDC and metP, wherein metDC and metP are operably linked to the same IPTG inducible promoter. In some embodiments, the genetically engineered host cell, such as a genetically engineered bacterium, comprises gene cassette comprising metDC and metP, wherein metDC and metP are each operably linked to a different copy of an IPTG inducible promoter. In some embodiments metDC and metP are each operably linked to a different copy of a Ptac promoter. In some embodiments, the genetically engineered host cell, such as a genetically engineered bacterium, comprise a Ptac-metP-metDC cassette or a Ptac-metDC-metP-cassette. In some embodiments, the genetically engineered host cell, such as a genetically engineered bacterium or microorganism, comprise a Ptac-metP-Ptac-metDC cassette or a Ptac-metDC-Ptac-metP-cassette.

Alternatively, in some embodiments, a genetically engineered host cell, such as a genetically engineered bacterium, may comprise one or more copies of the metDC gene and one or more copies of the metP gene and the metDC gene and the metP gene may be integrated at distinct sites. In some embodiments, the metP gene and the metDC gene are linked to a separate promoter at each integration site. In some embodiments, the metP gene and the metDC gene are operably linked to a different copy of the same promoter. In some embodiments, the promoters are different between the metP gene and the metDC gene. In some embodiments, the promoter is an inducible promoter, e.g., an IPTG inducible promoter. In some embodiments, the genetically engineered host cell, such as a genetically engineered bacterium, comprises a metDC gene operatively linked to an IPTG inducible promoter, e.g., a pTac promoter and a metP gene operatively linked to a different IPTG inducible promoter, e.g., a pTac promoter. In some embodiments, the genetically engineered host cell, such as a genetically engineered bacterium, comprise a cassette comprising Ptac-metDC cassette and a cassette comprising Ptac-metP.

In some embodiments, the genetically engineered host cell, such as a genetically engineered bacterium or microorganism, further comprise a LacI gene. In some embodiments, the lacI gene is non-native or heterologous. In some embodiments, the lacI gene is native.

In some embodiments, the genetically engineered host cell, such as a genetically engineered bacterium or microorganism, comprises a single integrated copy of lac. In some embodiments, the genetically engineered bacterium comprises two or more integrated copies of lacI. In some embodiments, two or more copies of the lacI gene are present at the same integration site, arranged in a cassette, and operably linked to the same promoter. In some embodiments, two or more copies of the lacI gene are present at the same integration site, arranged in a cassette, and one or more copies of the lacI gene are operably linked to different copies of same promoter or different promoters.

Alternatively, in some embodiments, a genetically engineered host cell, such as a genetically engineered bacterium or microorganism, may comprise two or more copies of the lacI gene and each copy of the lacI gene may be integrated at distinct sites. In some embodiments, each copy of the lacI gene is linked to a separate promoter at each integration site. In some embodiments, each copy of the lacI gene is operably linked to a different copy of the same promoter. In some embodiments, the promoters are different between two or more copies of the lacI gene. In some embodiments, the promoter is a native lacI promoter. In some embodiments, the promoter is a non-native promoter. In some embodiments, the promoter is a constitutive promoter. In some embodiments, the genetically engineered bacterium comprises a gene cassette comprising a lacI gene operatively linked to a constitutive promoter, e.g., a Plac promoter. In some embodiments, the genetically engineered bacteria or microorganism comprise a Plac-lacI cassette.

In some embodiments, the genetically engineered host cell, such as a genetically engineered bacterium or microorganism, comprise a gene cassette having a lacI gene and a metDC and/or metP gene. In some embodiments, the PlacI promoter and the lacI gene sequences are located upstream of a metDC gene, a metP gene or a gene cassette comprising metDC and metP. In some embodiments, the lacI gene is in reverse orientation relative to the metDC gene, metP gene or gene cassette comprising metDC and metP, i.e., LacI is divergently transcribed from a promoter region relative to the metDC gene, metP gene or gene cassette comprising metDC and met. Accordingly, in some embodiments, the genetically engineered host cell, such as a genetically engineered bacterium or microorganism, comprise a lacI-PlacI cassette.

In some embodiments, the genetically engineered host cell, such as a genetically engineered bacterium or microorganism, comprise a lacI-PlacI-Ptac-metDC cassette. In some embodiments, the genetically engineered host cell, such as a genetically engineered bacterium or microorganism, comprise a lacI-PlacI-Ptac-metP cassette. In some embodiments, the genetically engineered host cell, such as a genetically engineered bacterium or microorganism, comprise a lacI-PlacI-Ptac-metP-metDC cassette. In some embodiments, the genetically engineered host cell, such as a genetically engineered bacterium or microorganism, comprise a lacI-PlacI-Ptac-metDC-metP cassette. In some embodiments, the genetically engineered host cell, such as a genetically engineered bacterium or microorganism, comprise a lacI-PlacI-Ptac-metP-Ptac-metDC cassette. In some embodiments, the genetically engineered host cell, such as a genetically engineered bacterium or microorganism, comprise a lacI-PlacI-Ptac-metDC-Ptac-metP-cassette.

In some embodiments, the genetically engineered host cell, such as a genetically engineered bacterium or microorganism, comprise a PlacI-lacI-Ptac-metDC cassette. In some embodiments, the genetically engineered host cell, such as a genetically engineered bacterium or microorganism, comprise a PlacI-lacI-Ptac-metP cassette. In some embodiments, the genetically engineered bacteria or microorganism comprise a PlacI-lacI-Ptac-metP-metDC cassette. In some embodiments, the genetically engineered host cell, such as a genetically engineered bacterium or microorganism, comprise a PlacI-lacI-Ptac-metDC-metP cassette. In some embodiments, the genetically engineered host cell, such as a genetically engineered bacterium or microorganism, comprise a PlacI-lacI-Ptac-metP-Ptac-metDC cassette In some embodiments, the genetically engineered host cell, such as a genetically engineered bacterium or microorganism, comprise a PlacI-lacI-Ptac-metDC-Ptac-metP-cassette.

In more specific embodiments, the genetically engineered host cell, such as a genetically engineered bacterium or microorganism, comprises three integrated copies of a metDC gene. In some embodiments, each of the three copies are integrated at separate integration sites. In some embodiments, the genetically engineered host cell, such as a genetically engineered bacterium, comprises a single integrated copy of metP. In some embodiments, the genetically engineered host cell, such as a genetically engineered bacterium or microorganism, comprises three integrated copies of metDC and one integrated copy of metP. In some embodiments, the genetically engineered host cell, such as a genetically engineered bacterium or microorganism, comprises a single integrated copy of a gene cassette comprising metDC and metP and further comprises a two integrated copies of a metDC gene. In some embodiments, each copy of metDC and metP are operably linked to different copies of the same promoter. In some embodiments, the promoter is an IPTG inducible promoter, e.g., Ptac. In some embodiments, the metDC gene encodes metDC from *Streptomyces* sp. 590, having Q70D and N82H mutations. In some embodiments, the metP gene encodes MetP from *Flavobacterium segetis*. In some embodiments, the gene cassette comprising metDC and metP further comprises lacI. In some embodiments, one copy of a metDC gene is present in a gene cassette which further comprises lac. In some embodiments, a second copy of a metDC gene is not in a gene cassette further comprising lac. In some embodiments, the lacI promoter is a constitutive promoter, e.g., Plac.

In one embodiment, the genetically engineered host cell, such as a genetically engineered bacterium or microorganism, comprises three integrated copies of a metDC gene, integrated at three separate integration sites, wherein one of the three metDC gene copies is present in a cassette further comprising a metP gene. In some embodiments, each of the three copies of the metDC genes and the metP genes, are linked to different copies of the same promoter. In some embodiments, the promoter is an inducible promoter, such as an IPTG inducible promoter, e.g. pTac. In some embodiments, the metDC gene encodes MetDC from *Streptomyces* sp. 590, having Q70D and N82H mutations and the metP gene encodes MetP from *Flavobacterium segetis*.

In any of these embodiments, the genetically engineered host cell, such as a genetically engineered bacterium or microorganism, may further comprise one or more of (1) a deletion in yjeH gene that encodes a Met/branched chain amino acid exporter (2) a deletion of the dapA gene that encodes for dihydrodipicolinate synthase (3) a deletion in the pks island which encodes colibactin and (4) an endogenous Nissle prophage gene deletion.

In one specific embodiment, the host cell, such as a genetically engineered bacterium or microorganism, comprises three copies of a metDC gene derived from *Streptomyces* sp. 590 and comprising two modifications (Q70D and N82H), each integrated at separate integration sites, wherein one of the three metDC gene copies is present in a cassette further comprising metP derived from *Flavobacterium segetis*, wherein the three copies of the metDC gene and the metP gene are each operably linked to separate copies of the same IPTG inducible promoter, wherein the host cell, such as a genetically engineered bacterium or microorganism, further comprises two non-native copies of the lacI gene each operably linked to separate copies of the same constitutive Plac promoter, wherein a first copy is of the lacI gene is present in reverse orientation upstream of the metP-metDC gene cassette and the second copy is present in reverse orientation upstream of a-metDC gene, and wherein the host cell, such as a genetically engineered bacterium or microorganism, further comprises a deletion in yjeH gene, a deletion of the dapA gene, a deletion in the pks island, and an endogenous Nissle prophage gene deletion.

In one embodiment, the genetically engineered host cell, such as a genetically engineered bacterium or microorganism, comprises lacI-PlacI-$P_{tac}$-metDC, $P_{tac}$-metDC, and lacI-PlacI-$P_{tac}$-metP-$P_{tac}$-metDC, wherein the metDC genes encode MetDC from *Streptomyces* sp. 590, having Q70D and N82H mutations and metP gene encoding MetP from *Flavobacterium segetis*, and wherein the bacterium further comprises a deletion in yjeH gene, a deletion of the dapA gene, a deletion in the pks island, and an endogenous Nissle prophage gene deletion.

In Vivo Models

The recombinant host cells, such as recombinant bacteria, may be evaluated in vivo, e.g., in an animal model. Any suitable animal model of a disease or condition associated with amino acid metabolism, such as homocystinuria, may be used.

Pharmaceutical Compositions and Formulations

Pharmaceutical compositions comprising the genetically engineered bacteria described herein may be used to treat, manage, ameliorate, and/or prevent a disorder associated with amino acid catabolism, e.g., homocystinuria. Pharmaceutical compositions comprising one or more genetically engineered bacteria, alone or in combination with prophylactic agents, therapeutic agents, and/or pharmaceutically acceptable carriers are provided.

Pharmaceutical compositions comprising the genetically engineered microorganisms of the invention may be used to treat, manage, ameliorate, and/or prevent a disorder associated with amino acid catabolism or symptom(s) associated with diseases or disorders associated with amino acid catabolism. Pharmaceutical compositions of the invention comprising one or more genetically engineered bacteria, and/or one or more genetically engineered virus, alone or in combination with prophylactic agents, therapeutic agents, and/or pharmaceutically acceptable carriers are provided.

In certain embodiments, the pharmaceutical composition comprises one species, strain, or subtype of bacteria that are engineered to comprise the genetic modifications described herein, e.g., to express a methionine decarboxylase. In alternate embodiments, the pharmaceutical composition comprises two or more species, strains, and/or subtypes of bacteria that are each engineered to comprise the genetic modifications described herein, e.g., to express a methionine decarboxylase.

The pharmaceutical compositions of the invention described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, PA). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered microorganisms may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, intravenous, subcutaneous, immediate-release, pulsatile-release, delayed-release, or sustained release). Suitable dosage amounts for the genetically engineered bacteria may range from about 104 to 1012 bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In on embodiment, the pharmaceutical composition is administered after the subject eats a meal The genetically engineered bacteria may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the genetically engineered bacteria of the invention may be formulated in a solution of sodium bicarbonate, e.g., 1 molar solution of sodium bicarbonate (to buffer an acidic cellular environment, such as the stomach, for example). The genetically engineered bacteria may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The genetically engineered microorganisms may be administered intravenously, e.g., by infusion or injection.

The genetically engineered microorganisms of the disclosure may be administered intrathecally. In some embodiments, the genetically engineered microorganisms of the invention may be administered orally. The genetically engineered microorganisms disclosed herein may be administered topically and formulated in the form of an ointment, cream, transdermal patch, lotion, gel, shampoo, spray, aerosol, solution, emulsion, or other form well known to one of skill in the art. See, e.g., "Remington's Pharmaceutical Sciences," Mack Publishing Co., Easton, PA. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the host cell may be formulated as a hygiene product. For example, the hygiene product may be an antibacterial formulation, or a fermentation product such as a fermentation broth. Hygiene products may be, for example, shampoos, conditioners, creams, pastes, lotions, and lip balms.

The host cells disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the genetically engineered microorganisms are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the genetically engineered microorganisms described herein.

In one embodiment, the genetically engineered microorganisms of the disclosure may be formulated in a composition suitable for administration to adult subjects or pediatric subjects. As is well known in the art, children differ from adults in many aspects, including different rates of gastric emptying, pH, gastrointestinal permeability, etc. (Ivanovska et al., Pediatrics, 134(2):361-372, 2014). Moreover, pediatric formulation acceptability and preferences, such as route of administration and taste attributes, are critical for achieving acceptable pediatric compliance. Thus, in one embodiment, the composition suitable for administration to pediatric subjects may include easy-to-swallow or dissolvable dosage forms, or more palatable compositions, such as compositions with added flavors, sweeteners, or taste blockers. In one embodiment, a composition suitable for administration to pediatric subjects may also be suitable for administration to adults.

In one embodiment, the composition suitable for administration to pediatric subjects may include a solution, syrup, suspension, elixir, powder for reconstitution as suspension or solution, dispersible/effervescent tablet, chewable tablet, gummy candy, lollipop, freezer pop, troche, chewing gum, oral thin strip, orally disintegrating tablet, sachet, soft gelatin capsule, sprinkle oral powder, or granules. In one embodiment, the composition is a gummy candy, which is made from a gelatin base, giving the candy elasticity, desired chewy consistency, and longer shelf-life. In some embodiments, the gummy candy may also comprise sweeteners or flavors.

In one embodiment, the composition suitable for administration to pediatric subjects may include a flavor. As used herein, "flavor" is a substance (liquid or solid) that provides a distinct taste and aroma to the formulation. Flavors also help to improve the palatability of the formulation. Flavors include, but are not limited to, strawberry, vanilla, lemon, grape, bubble gum, and cherry.

In certain embodiments, the genetically engineered microorganisms may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

In another embodiment, the pharmaceutical composition comprising the recombinant bacteria of the invention may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the recombinant bacteria of the invention are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the recombinant bacteria of the invention are well known in the art. For example, see U.S. 2015/0359894 and US 2015/0238545, the entire contents of each of which are expressly incorporated herein by reference. In yet another embodiment, the pharmaceutical composition of the invention is injected into, sprayed onto, or sprinkled onto a food product, such as bread, yogurt, or cheese.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The genetically engineered microorganisms described herein may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The genetically engineered microorganisms may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, LD50, ED50, EC50, and IC50 may be determined, and the dose ratio between toxic and therapeutic effects (LD50/ED50) may be calculated as the therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

The ingredients are supplied either separately or mixed together in unit dosage form, for example, as a dry lyophilized powder or water-free concentrate in a hermetically sealed container such as an ampoule or sachet indicating the quantity of active agent. If the mode of administration is by injection, an ampoule of sterile water for injection or saline can be provided so that the ingredients may be mixed prior to administration.

The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally 0-10% sucrose (optimally 0.5-1.0%). Other suitable cryoprotectants include trehalose and lactose. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

In some embodiments, the genetically engineered viruses are prepared for delivery, taking into consideration the need for efficient delivery and for overcoming the host antiviral immune response. Approaches to evade antiviral response include the administration of different viral serotypes as part of the treatment regimen (serotype switching), formulation, such as polymer coating to mask the virus from antibody recognition and the use of cells as delivery vehicles.

In another embodiment, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

The genetically engineered bacteria of the invention may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Methods of Treatment

Further disclosed herein are methods of treating diseases associated with methionine metabolism. In some embodiments, disclosed herein are methods for reducing, ameliorating, or eliminating one or more symptom(s) associated with these diseases or disorders.

As used herein the terms "disease associated with amino acid metabolism" or a "disorder associated with amino acid metabolism" is a disease or disorder involving the abnormal, e.g., increased, levels of one or more amino acids in a subject. In one embodiment, a disease or disorder associated with amino acid metabolism is homocystinuria, cancer, or a metabolic syndrome/disease. For example, for metabolic indications, a methionine-restricted diet has been shown to increase lifespan, reduce adiposity, decrease systemic inflammation, and improve insulin sensitivity in rodent and some large animal models (see, for example, Dong et al., *EClinicalMedicine,* 2019). For indications in immune-oncology and cancer, there is preclinical data supporting a link between tumoral methionine restriction and antitumor activity (see, for example, Gay et al., *Cancer Medicine,* 2017, 6(6):1437-1452).

In some embodiments, a disease or disorder associated with amino acid metabolism is cystinuria. Cystinuria is a condition in which stones made from cysteine dimers (known as cystine) form in the kidney, ureter, and bladder. The condition is inherited in an autosomal recessive manner. Normally, most cystine dissolves and returns to the bloodstream after entering the kidneys. Subjects with cystinuria have a genetic defect in SLC3A1 or SLC7A9. As a result, cystine builds up in the urine and forms crystals or stones (~10× increase vs healthy subjects). The goal of current treatments is to relieve symptoms and prevent more stones from forming. Treatment involves drinking plenty of water, use drugs that make urine more alkaline, dietary salt/animal protein restriction, kidney/bladder surgery. A large proportion of patients fail to achieve therapeutic success even with adherence to current SOC. Cystinuria is a lifelong condition. Stones often return.

In some embodiments, the disclosure provides methods for reducing, ameliorating, or eliminating one or more symptom(s) associated with these diseases.

The method may comprise preparing a pharmaceutical composition with at least one genetically engineered species, strain, or subtype of bacteria described herein, and administering the pharmaceutical composition to a subject in a therapeutically effective amount. In some embodiments, the genetically engineered bacteria disclosed herein are administered orally, e.g., in a liquid suspension. In some embodiments, the genetically engineered bacteria are lyophilized in a gel cap and administered orally. In some embodiments, the genetically engineered bacteria are administered via a feeding tube or gastric shunt. In some embodiments, the genetically engineered bacteria are administered rectally, e.g., by enema. In some embodiments, the genetically engineered bacteria are administered topically, intraintestinally, intrajejunally, intraduodenally, intraileally, and/or intracolically. In one embodiment, the genetically engineered bacteria are injected directly into a tumor.

In certain embodiments, administering the pharmaceutical composition to the subject reduces the level of an amino acid, e.g., methionine, homocysteine, cysteine or cystine in a subject. In some embodiments, the methods of the present disclosure may reduce the level of an amino acid, e.g., methionine, homocysteine, cysteine or cystine in a subject by at least about 10%, 20%, 25%, 30%, 40%, 50%, 60%, 70%, 75%, 80%, 85%, 90%, 95%, or more as compared to levels in an untreated or control subject. In some embodiments, reduction is measured by comparing the amino acid concentration in a subject before and after administration of the pharmaceutical composition. In some embodiments, the method of treating or ameliorating a disease or disorder allows one or more symptoms of the condition or disorder to improve by at least about 10%, 20%, 30%, 40%, 50%, 60%, 70%, 80%, 90%, 95%, or more as compared to levels in an untreated or control subject, or as compared to levels in the subject prior to administration. Amino acid levels may be measured by methods known in the art (see methionine decarboxylase section, supra).

Before, during, and after the administration of the pharmaceutical composition, methionine concentrations in the subject may be measured in a biological sample, such as blood, serum, plasma, urine, fecal matter, peritoneal fluid, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions to reduce amino acid, e.g., methionine concentrations in a subject to undetectable levels, or to less than about 1%, 2%, 5%, 10%, 20%, 25%, 30%, 40%, 50%, 60%, 70%, 75%, or 80% of the subject's amino acid concentration(s) prior to treatment.

Before, during, and after the administration of the pharmaceutical composition, homocysteine concentrations in the subject may be measured in a biological sample, such as blood, serum, plasma, urine, fecal matter, peritoneal fluid, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions to reduce amino acid, e.g., homocysteine concentrations in a subject to undetectable levels, or to less than about 1%, 2%, 5%, 10%, 20%, 25%, 30%, 40%, 50%, 60%, 70%, 75%, or 80% of the subject's amino acid concentration(s) prior to treatment.

Before, during, and after the administration of the pharmaceutical composition, cysteine concentrations in the subject may be measured in a biological sample, such as blood, serum, plasma, urine, fecal matter, peritoneal fluid, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions to reduce amino acid, e.g., cysteine concentrations in a subject to undetectable levels, or to less than about 1%, 2%, 5%, 10%, 20%, 25%, 30%, 40%, 50%, 60%, 70%, 75%, or 80% of the subject's amino acid concentration(s) prior to treatment.

Before, during, and after the administration of the pharmaceutical composition, cystine concentrations in the subject may be measured in a biological sample, such as blood, serum, plasma, urine, fecal matter, peritoneal fluid, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions to reduce amino acid, e.g., cystine concentrations in a subject to undetectable levels, or to less than about 1%, 2%, 5%, 10%, 20%, 25%, 30%, 40%, 50%, 60%, 70%, 75%, or 80% of the subject's amino acid concentration(s) prior to treatment.

The methods disclosed herein may further comprise isolating a sample from the subject prior to administration of a composition and determining the level of the amino acid(s) in the sample. In some embodiments, the methods may further comprise isolating a sample from the subject after to administration of a composition and determining the level of amino acid(s) in the sample.

In certain embodiments, administering the pharmaceutical composition to the subject prevents or reduces formation, occurrence, or presence of stones in a subject. In some embodiments, the stones are present in the kidney, bladder or urether. In some embodiments, the stones are cystine stones. In some embodiments, the methods of the present disclosure may reduce or reduce/prevent an increase in the formation, occurrence, or presence of a stone, e.g., a cystine stone, in a subject by at least about 10%, 20%, 25%, 30%, 40%, 50%, 60%, 70%, 75%, 80%, 85%, 90%, 95%, or more as compared to levels in an untreated or control subject. In some embodiments, levels of formation, occurrence, or presence of a stone, e.g., a cystine stone, is measured by comparing stone formation, occurrence or presence, respectively, in a subject before and after administration of the pharmaceutical composition, e.g., within a certain time span. In some embodiments, the formation, occurrence, or presence of a stone, e.g., a cystine stone, in a subject may be prevented completely, or completely within a certain time span. In some embodiments, the methods of the present disclosure may reduce or reduce or prevent an increase in cystine stone number, stone volume, stone area or stone weight, e.g., over time, in a subject by at least about 10%, 20%, 25%, 30%, 40%, 50%, 60%, 70%, 75%, 80%, 85%, 90%, 95%, or more as compared to levels in an untreated or control subject. In some embodiments, levels of cystine stone number, volume, area or weight over time are measured by comparing cystine stone number, stone volume, stone area or stone weight, respectively, in a subject before and after administration of the pharmaceutical composition, e.g., within a certain time span. In some embodiments, the methods of the present disclosure may prevent a change, e.g., an increase, in number of cystine stones, stone volume, stone area or stone weight, e.g., over time, in a subject completely, or completely within a certain time span.

In some embodiments, the method of treating or ameliorating a disease or disorder allows the symptom of stone formation, e.g., cystine stone formation, e.g., in a subject having cystinuria, to improve by at least about 10%, 20%, 30%, 40%, 50%, 60%, 70%, 80%, 90%, 95%, or more as compared to levels in an untreated or control subject, or as compared to levels in the subject prior to administration. Presence of stones and stone attributes, e.g. cystine stone number, volume, area and weight may be measured by methods known in the art, e.g., CT scan ultrasound or MRI.

In certain embodiments, the genetically engineered bacteria comprising a methionine decarboxylase is *E. coli* Nissle. The genetically engineered bacteria may be destroyed, e.g., by defense factors in the gut or blood serum (Sonnenborn et al., 2009), or by activation of a kill switch, several hours or days after administration. Thus, the pharmaceutical composition comprising the methionine decarboxylase may be re-administered at a therapeutically effective dose and frequency. In alternate embodiments, the genetically engineered bacteria are not destroyed within hours or days after administration and may propagate and colonize the gut.

The methods disclosed herein may comprise administration of a composition alone or in combination with one or more additional therapies. The pharmaceutical composition may be administered alone or in combination with one or more additional therapeutic agents, including but not limited to, sodium phenylbutyrate, sodium benzoate, and glycerol phenylbutyrate. The methods may also comprise following an amino acid, e.g., methionine, restricted diet, and/or administration of betaine, pyridoxine, and/or other enzyme replacement-based therapies such as OT-58 or AGLE-177. OT-58 represents a therapeutic approach incorporating the use of a modified version of the native human CBS enzyme. The goal of this treatment is to introduce the CBS enzyme into circulation, resulting in reduced Hey levels, increased crystalthionine levels, and normalized cysteine levels. AGLE-177 is an engineered human enzyme designed to degrade both homocysteine and homocysteine (two homocysteine molecules bound together) to lower abnormally high levels of homocysteine in the blood.

Methionine abundance in natural sources of protein ranges from 1-2% (or 1-2 g/100 g protein intake). Assuming the average human subject needs to degrade about 1.0 g methionine per day with meals, and assuming the recombinant bacteria provides 3 hours of activity per dose, that leaves 3× doses per day at $5\times10^{11}$ dose and 1.0 g methionine per day (0.33 g/dose). 0.33 g methionine/dose=2230 μmol methionine. 2230 μmol/3 hours/$5\times10^{11}$ cells leads to 1.49 μmol/hr/$1\times10^9$ cells. The target dose is $5\times10^{11}$ live recombinant bacterial cells/mL.

For human subjects on a low protein diet eating 10 g protein/day, the subject needs to degrade about 0.1-1 g, e.g. 0.1 g, 0.2 g, 0.3 g, 0.4 g, 0.5 g, 0.6 g, 0.7 g, 0.8 g, 0.9 g or 1 g, methionine per day with meals. Assuming the recombinant bacteria provides 3 hours of activity per dose, that leaves 3× doses per day at $5\times10^{11}$ dose and 0.1 g per day (0.033 g/dose). 0.033 g methionine/dose=223 μmol methionine. 223 μmol/3 hours/$5\times10^{11}$ cells leads to 0.15 μmol/hr/$1\times10^9$ cells. The target dose is $5\times10^{11}$ live recombinant bacterial cells/mL.

Accordingly, in one embodiment, the recombinant bacteria disclosed herein has a methionine degradation activity of about 0.1 μmol/hr/$1\times10^9$ cells. Accordingly, in one embodiment, the recombinant bacteria disclosed herein has a methionine degradation activity of about 0.15 μmol/hr/$1\times10^9$ cells. Accordingly, in one embodiment, the recombinant bacteria disclosed herein has a methionine degradation activity of about 0.2 μmol/hr/$1\times10^9$ cells. Accordingly, in one embodiment, the recombinant bacteria disclosed herein has a methionine degradation activity of about 0.25 μmol/hr/$1\times10^9$ cells. Accordingly, in one embodiment, the recombinant bacteria disclosed herein has a methionine degradation activity of about 0.3 μmol/hr/$1\times10^9$ cells. Accordingly, in one embodiment, the recombinant bacteria disclosed herein has a methionine degradation activity of about 0.4 μmol/hr/$1\times10^9$ cells. Accordingly, in one embodiment, the recombinant bacteria disclosed herein has a methionine degradation activity of about 0.5 μmol/hr/$1\times10^9$ cells. Accordingly, in one embodiment, the recombinant bacteria disclosed herein has a methionine degradation activity of about 0.6 μmol/hr/$1\times10^9$ cells. Accordingly, in one embodiment, the recombinant bacteria disclosed herein has a methionine degradation activity of about 0.7 μmol/hr/$1\times10^9$ cells. Accordingly, in one embodiment, the recombinant bacteria disclosed herein has a methionine degradation activity of about 0.8 μmol/hr/$1\times10^9$ cells. Accordingly, in one embodiment, the recombinant bacteria disclosed herein has a methionine degradation activity of about 0.9 μmol/hr/$1\times10^9$ cells. Accordingly, in one embodiment, the recombinant bacteria disclosed herein has a methionine degradation activity of about 1.0 μmol/hr/$1\times10^9$ cells. Accordingly, in one embodiment, the recombinant bacteria disclosed herein has a methionine degradation activity of about 1.10 μmol/ hr/$1\times10^9$ cells. Accordingly, in one embodiment, the recombinant bacteria disclosed herein has a methionine degradation activity of about 1.30 μmol/hr/$1\times10^9$ cells. Accordingly, in one embodiment, the recombinant bacteria disclosed herein has a methionine degradation activity of about 1.30 μmol/hr/$1\times10^9$ cells. Accordingly, in one embodiment, the recombinant bacteria disclosed herein has a methionine degradation activity of about 1.40 μmol/hr/$1\times10^9$ cells. Accordingly, in one embodiment, the recombinant bacteria disclosed herein has a methionine degradation activity of about 1.45 μmol/hr/$1\times10^9$ cells. Accordingly, in one embodiment, the recombinant bacteria disclosed herein has a methionine degradation activity of about 1.50 μmol/hr/$1\times10^9$ cells.

Accordingly, in one embodiment, the recombinant bacteria disclosed herein has a methionine degradation activity of about 0.1 μmol/hr/$1\times10^9$ cells to about 1.5 μmol/hr/$1\times10^9$ cells. Accordingly, in one embodiment, the recombinant bacteria disclosed herein has a methionine degradation activity of about 0.2 μmol/hr/$1\times10^9$ cells to about 1.5 μmol/hr/$1\times10^9$ cells. Accordingly, in one embodiment, the recombinant bacteria disclosed herein has a methionine degradation activity of about 0.1 μmol/hr/$1\times10^9$ cells to about 1.4 μmol/hr/$1\times10^9$ cells. Accordingly, in one embodiment, the recombinant bacteria disclosed herein has a methionine degradation activity of about 0.4 μmol/hr/$1\times10^9$ cells to about 1.1 μmol/hr/$1\times10^9$ cells. Accordingly, in one embodiment, the recombinant bacteria disclosed herein has a methionine degradation activity of about 0.1 μmol/hr/$1\times10^9$ cells to about 1.0 μmol/hr/$1\times10^9$ cells. Accordingly, in one embodiment, the recombinant bacteria disclosed herein has a methionine degradation activity of about 0.5 μmol/hr/$1\times10^9$ cells to about 1.5 μmol/hr/$1\times10^9$ cells. Accordingly, in one embodiment, the recombinant bacteria disclosed herein has a methionine degradation activity of about 0.75 μmol/hr/$1\times10^9$ cells to about 1.25 μmol/hr/$1\times10^9$ cells.

In one embodiment, about 0.1 g to about 1.0 g of methionine are degraded per day. In one embodiment, about 0.01 to about 1.5 g of methionine are degraded per day. In one embodiment, about 0.1 g of methionine are degraded per day. In one embodiment, about 0.2 g of methionine are degraded per day. In one embodiment, about 0.3 g of methionine are degraded per day. In one embodiment, about 0.4 g of methionine are degraded per day. In one embodiment, about 0.5 g of methionine are degraded per day. In one embodiment, about 0.6 g of methionine are degraded per day. In one embodiment, about 0.7 g of methionine are degraded per day. In one embodiment, about 0.8 g of methionine are degraded per day. In one embodiment, about 0.9 g of methionine are degraded per day. In one embodiment, about 1.0 g of methionine are degraded per day. In one embodiment, about 1.1 g of methionine are degraded per day. In one embodiment, about 1.2 g of methionine are degraded per day. In one embodiment, about 1.3 g of methionine are degraded per day. In one embodiment, about 1.4 g of methionine are degraded per day. In one embodiment, about 1.5 g of methionine are degraded per day.

An important consideration in the selection of the one or more additional therapeutic agents is that the agent(s) should be compatible with the genetically engineered bacteria disclosed herein, e.g., the agent(s) must not kill the bacteria. In some embodiments, the pharmaceutical composition is administered with food. In alternate embodiments, the pharmaceutical composition is administered before or after eating food. The pharmaceutical composition may be administered in combination with one or more dietary modifications, e.g., low-protein diet or amino acid supplementation. The dosage of the pharmaceutical composition and the frequency of administration may be selected based on the severity of the symptoms and the progression of the disorder. The appropriate therapeutically effective dose and/or frequency of administration can be selected by a treating clinician.

EXAMPLES

The present disclosure is further illustrated by the following examples which should not be construed as limiting in any way. The contents of all cited references, including literature references, issued patents, and published patent applications, as cited throughout this application are hereby expressly incorporated herein by reference. It should further be understood that the contents of all the figures and tables attached hereto are also expressly incorporated herein by reference.

Example 1: Strain Development and Testing

All strains in this example utilize medium copy plasmids. These plasmids contain either Methionine gamma lyase (MGL) or Methionine decarboxylase (MDC) under the control of an anhydrotetracycline (ATC)-inducible promoter. Plasmids were constructed through TypeIIS cloning of synthesized gBlock fragments (IDT, Coralville, IA) containing these genes, followed by Sanger sequencing for sequence verification. Plasmids were used to transform *E. coli* Nissle (EcN). EcN strains harboring either MGL or MDC plasmids were grown to early log phase and induced for expression with 200 ng/mL ATC. Induction was allowed to proceed for 4 h, at which time cells were harvested by centrifugation and biomass stored in PBS containing 15% glycerol at −80° C. For testing of Methionine degradation activity, frozen biomass was thawed on ice and brought to an OD600=1 in M9 minimal media containing 0.5% glucose and 10 mM methionine and incubated at 37° C. statically. Supernatant samples were removed at 0, 30, 60, and 120 mins to determine the concentration of Methionine remaining over time.

For activated biomass, 2 mL cultures were grown overnight in LB media. Overnight cultures were back-diluted 1:100 in 10-20 mL fresh LB media in 50 mL baffled flasks and grown for 2 hours at 37° C. with shaking at 250 rpm. After 2 hours of growth, induction with 2× anhydrotetracycline (ATC) occurred, and cells were grown an additional four hours at 37° C. with shaking at 250 rpm. After 6 hours of total growth, bacterial cells were pelleted by centrifugation at 8000 rpm for five minutes. The supernatant was removed, cells were placed on ice, and cells were resuspended in PBS buffer. The cells were either frozen at −80° C. or the consumption assay was run.

For the methionine consumption assay, cells were thawed on ice and $OD_{600}$ was measured. The volume of cells equivalent to an OD of 1 were added to 1 mL of M9 minimal media containing 5% glucose in an 1.7 mL tube. The tube was vortexed briefly to evenly distribute the cells, and the tubes were placed at 37° C. with no shaking. 150 μL of cell/media suspension was removed at 0.5, 1.0, 1.5, 2.0 and 4.0 hour time points, spun at high speed for about 1 minute to pellet cells, and 100 μL was added to the well of a 96-well plate (avoiding pellet). The amount of L-methionine was measured using HPLC.

FIG. 3 is a graph depicting methionine disappearance from minimal media in *E. coli* Nissle harboring methionine gamma lyase (MGL) or methionine decarboxylase (MDC also referred to herein as MetDC) under the control of an anhydrotetracycline (ATC)-inducible promoter. EcN control is wild-type *E. coli* Nissle with no methionine catabolism enzymes. BA CGL/MGL is MGL from *Brevibacterium aurantiacum* (DOI 10.1124/jpet.119.256537). CF MGL is MGL from *Citrobacter freundii*. PG MGL is MGL from Poprhyromonas *gingivalis*. EcN-MetDC is MDC from *Streptomyces* sp. 590. These data demonstrate increased disappearance of methionine in the strains comprising a methionine catabolism enzyme as compared to EcN control.

Figure 4:
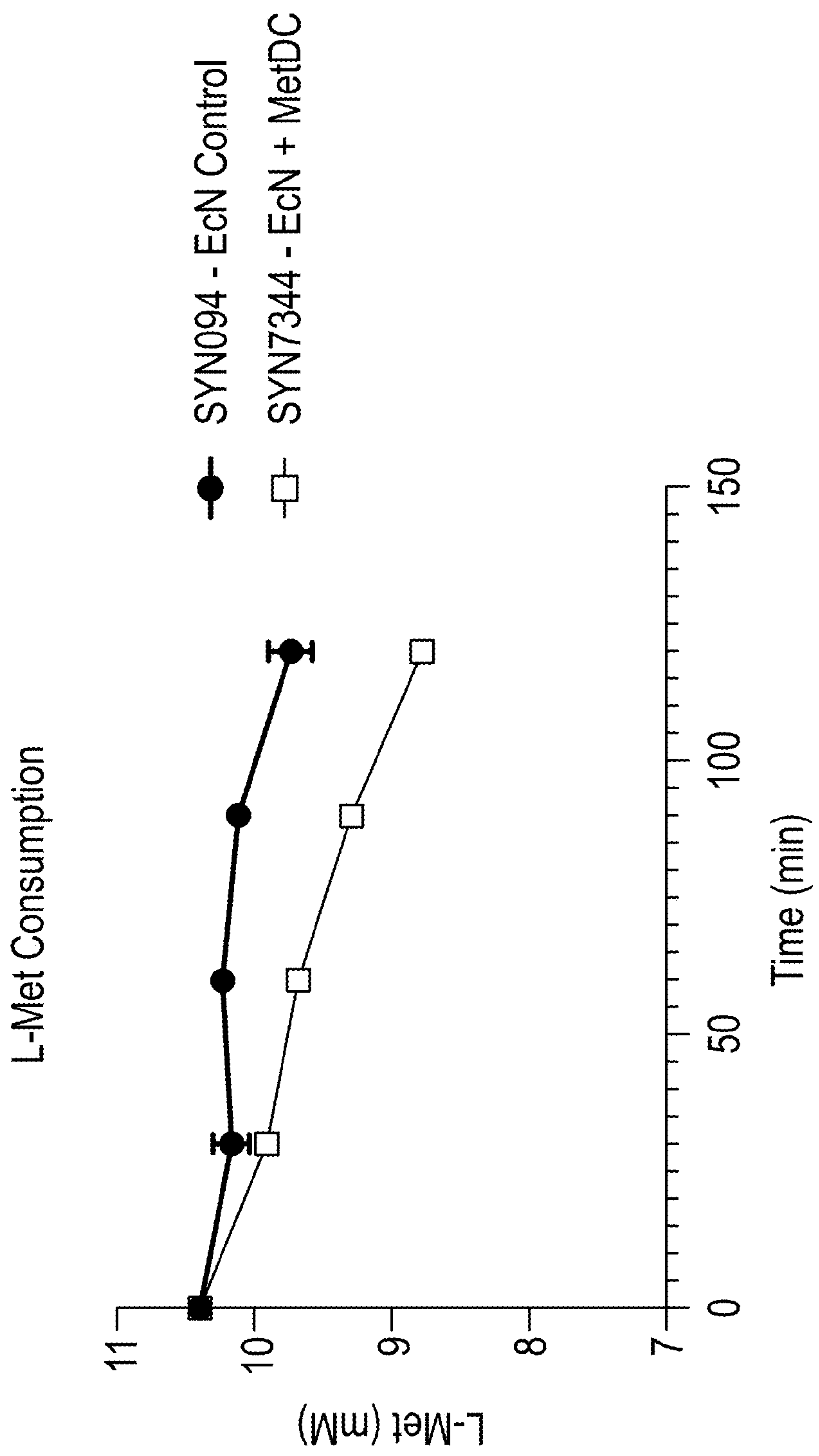
FIG. 4 is a graph depicting L-Met consumption by *E. coli* Nissle, SYN7344 (SpmetDC (SEQ ID NO: 1049), harbouring a medium-copy plasmid encoding an anhydrotetracycline-inducible MetDC compared to the control strain, SYN094.

FIG. 4 is a graph depicting L-Met consumption over time. *E. coli* Nissle, SYN7344, containing a medium copy plasmid (p15A ori) encoding an anhydrotetracycline-inducible MetDC were grown in LB to early log phase followed by induction of MetDC expression for 4 hours. Activated cells were harvested and frozen in PBS buffer containing 15% glycerol at −80° C. On the day of testing, activated biomass was thawed and resuspended to an $OD_{600}$=1 in M9 minimal media containing 0.5% glucose and 10 mM Met. Supernatant samples were removed over 2 hours to quantify Met disappearance. These data demonstrate increased consumption of methionine in the *E. coli* Nissle strains comprising MetDC as compared to *E. coli* Nissle control strains.

The recombinant bacteria may be further modified by knocking out methionine exporters, such as yjeH, an efflux pump known to import methionine out of the cell. Such a knockout will increase the cytoplasmic concentration of methionine to assist in driving methionine degradation reactions. In addition, *E. coli* contains an ABC importer, encoded in the metNIQ operon, known to import methionine into the cell. This importer may also be expressed or over expressed to increase availability of methionine to the recombinant bacteria.

Figure 5:
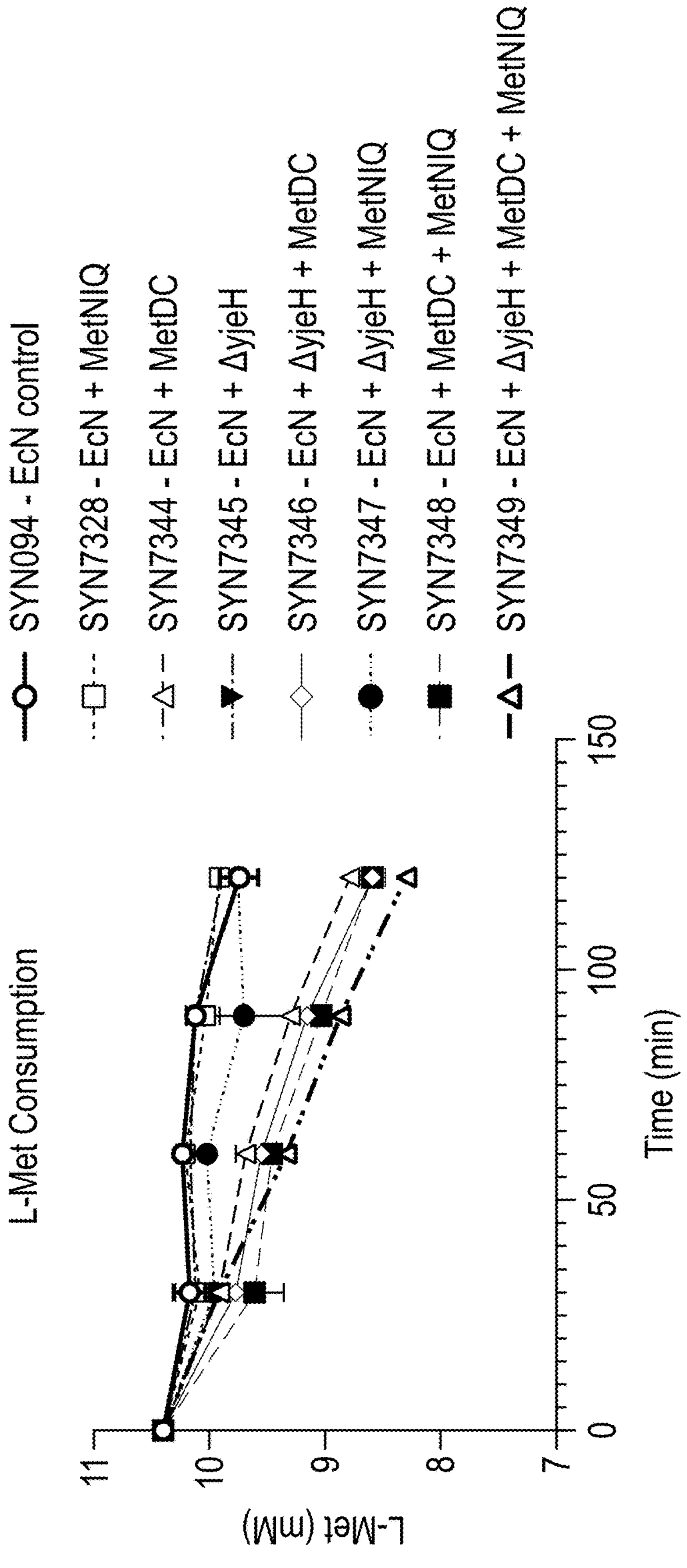
FIG. 5 is a graph depicting L-Met consumption by *E. coli* Nissle strains, SYN094 (control), SYN7328 (metNIQ (SEQ ID NOs: 1058, 1059, and 1060)), SYN7344 (SpmetDC (SEQ ID NO: 1049)), SYN7345 (ΔyjeH), SYN7346 (ΔyjeH, SpmetDC (SEQ ID NO: 1049)), SYN7347 (ΔyjeH, metNIQ (SEQ ID NOs: 1058, 1059, and 1060)), SYN7348 (SpmetDC (SEQ ID NO: 1049), metNIQ (SEQ ID NOs: 1058, 1059, and 1060)), and SYN7349 (ΔyjeH, SpmetDC (SEQ ID NO: 1049), metNIQ (SEQ ID NOs: 1058, 1059, and 1060)).

FIG. 5 is a graph depicting L-Met consumption over time. Strains SYN094 (control), SYN7328 (metNIQ (SEQ ID NOs: 1058, 1059, and 1060)), SYN7344 (SpmetDC (SEQ ID NO: 1049)), SYN7345 (ΔyjeH), SYN7346 (ΔyjeH, SpmetDC (SEQ ID NO: 1049), SYN7347 (ΔyjeH, metNIQ (SEQ ID NOs: 1058, 1059, and 1060)), SYN7348 (SpmetDC (SEQ ID NO: 1049), metNIQ (SEQ ID NOs: 1058, 1059, and 1060)), and SYN7349 (ΔyjeH, SpmetDC (SEQ ID NO: 1049), metNIQ (SEQ ID NOs: 1058, 1059, and 1060)).

The strains used are shown in Table 6 and results in Table 7. EcN containing a medium copy plasmid (p15A ori) encoding an anhydrotetracycline-inducible MetDC and/or a low copy plasmid (pSC101 ori) encoding an anhydrotetracycline-inducible MetNIQ were grown in LB to early log phase followed by induction of MetDC and/or MetNIQ expression for 4 hours. Activated cells were harvested and frozen in formulation buffer containing 15% glycerol at −80° C. On the day of testing, activated biomass was resuspended to an $OD_{600}$=1 in M9 minimal media containing 0.5% glucose and 10 mM Met. Supernatant samples were removed over 2 hours to quantify Met disappearance. Deletion of yjeH and/or addition of metNIQ show an additive effect when tested in combination with metDC.

Expression of the Met importer, metNIQ, increased Met consumption. Similarly, deletion of the Met exporter, yjeH, increased Met consumption. Combining expression of metNIQ and deletion of yjeH with the expression of MetDC lead to an additive effect and greater Met consumption. Increasing internal Met concentration by increasing uptake and decreasing release of Met surprisingly increases whole cell activity.

TABLE 6

| *E. coli* Strains | | |
|---|---|---|
| Strain No. | Background/genotype | Antibiotic resistance |
| SYN7328 | SYN001 (WT EcN); Logic2375(pSC101; Ptet:metNIQ (SEQ ID NOs: 1058, 1059, and 1060) | carbeni - cillin (carb) |
| SYN7344 | SYN001; Logic2279(p15a; Ptet:metDC (SEQ ID NO: 1049)) | kanamycin (kan) |
| SYN7345 | SYN001; ΔyjeH | chloram- phenicol (cam) |
| SYN7346 | SYN001; ΔyjeH; Logic2279(p15a; Ptet:metDC (SEQ ID NO: 1049)) | cam, kan |
| SYN7347 | SYN001; ΔyjeH; Logic2375(pSC101; Ptet: metNIQ (SEQ ID NOs: 1058, 1059, and 1060)) | cam, carb |
| SYN7348 | SYN001; Logic2279(p15a; Ptet: metDC (SEQ ID NO: 1049)); Logic2375(pSC101; Ptet: metNIQ (SEQ ID NOs: 1058, 1059, and 1060)) | kan, carb |
| SYN7349 | SYN001; ΔyjeH; Logic2279(p15a; Ptet: metDC (SEQ ID NO: 1049)); Logic2375(pSC101; Ptet: metNIQ (SEQ ID NOs: 1058, 1059, and 1060)) | cam, carb, kan |

TABLE 7

| Met Consumption | | | | | | |
|---|---|---|---|---|---|---|
| Time (min) | SYN094 - EcN Control | | | SYN7346 - EcN + ΔyjeH + MetDC | | |
| 0 | 10.4384571 | 10.38598365 | 10.4006508 | 10.4384571 | 10.38598365 | 10.4006508 |
| 30 | 10.3239792 | 10.15822805 | 10.04925695 | 9.83632735 | 9.79290835 | 9.71764875 |
| 60 | 10.3105299 | 10.24432475 | 10.17411305 | 9.5354478 | 9.5360832 | 9.59974675 |
| 90 | 10.20976605 | 10.07170775 | 10.104272 | 9.27272755 | 9.1298508 | 9.08238995 |
| 120 | 9.66106285 | 9.9430569 | 9.6527497 | 8.5659333 | 8.59143755 | 8.62101895 |
| | SYN7328 - EcN + MetNIQ | | | SYN7347 - EcN + ΔyjeH + MetNIQ | | |
| 0 | 10.4384571 | 10.38598365 | 10.4006508 | 10.4384571 | 10.38598365 | 10.4006508 |
| 30 | 10.07675565 | 10.1295468 | 10.0716901 | 9.95274675 | 9.9415743 | 9.99951925 |
| 60 | 10.24053 | 10.15007375 | 10.2517907 | 10.0627592 | 9.9935712 | 10.0276357 |
| 90 | 10.1566219 | 10.0433089 | 9.916476 | 9.2044044 | 9.9672374 | 9.96630195 |
| 120 | 9.92157685 | 9.9778627 | 9.8607373 | 9.7831832 | 9.7370814 | 9.76205615 |
| | SYN7344 - EcN + MetDC | | | SYN7348 - EcN + MetDC + MetNIQ | | |
| 0 | 10.4384571 | 10.38598365 | 10.4006508 | 10.4384571 | 10.38598365 | 10.4006508 |
| 30 | 9.94551025 | 9.9600009 | 9.85775445 | 9.3271425 | 9.8031983 | 9.72354385 |
| 60 | 9.59423995 | 9.75471375 | 9.73166285 | 9.5032895 | 9.4215347 | 9.482286 |
| 90 | 9.33654995 | 9.2780402 | 9.3016559 | 9.0206679 | 9.0718176 | 9.02739255 |
| 120 | 8.725101 | 8.8207993 | 8.822176 | 8.4898971 | 8.58314205 | 8.7146875 |
| | SYN7345 - EcN + ΔyjeH | | | SYN7349 - EcN + ΔyjeH + MetDC + MetNIQ | | |
| 0 | 10.4384571 | 10.38598365 | 10.4006508 | 10.4384571 | 10.38598365 | 10.4006508 |
| 30 | 10.1282407 | 10.1477616 | 10.1049427 | 9.9559767 | 9.89644325 | 9.92164745 |
| 60 | 10.1581398 | 10.1230163 | 10.238765 | 9.3027855 | 9.3405565 | 9.37746265 |
| 90 | 10.1263698 | 10.15964005 | 10.1112967 | 8.77976305 | 8.8848688 | 8.9463261 |
| 120 | 9.856113 | 9.90039685 | 9.91575235 | 8.31878035 | 8.3108202 | 8.2659539 |

Example 2: Strain Activity Calculation

Methionine abundance in natural sources of protein ranges from 1-2% (or 1-2 g/100 g protein intake). Assuming the average human subject needs to degrade about 1.0 g methionine per day with meals, and assuming the recombinant bacteria provides 3 hours of activity per dose, that leaves 3× doses per day at $5\times10^{11}$ dose and 1.0 g per day (0.33 g/dose). 0.33 g methionine/dose=2230 μmol methionine. 2230 μmol/3 hours/$5\times10^{11}$ cells leads to 1.49 μmol/hr/$1\times10^{9}$ cells. The target dose is $5\times10^{11}$ live recombinant bacterial cells/mL.

For human subjects on a low protein diet eating 10 g protein/day, the subject needs to degrade about 0.1 g methionine per day with meals. Assuming the recombinant bacteria provides 3 hours of activity per dose, that leaves 3× doses per day at $5\times10^{11}$ dose and 0.1 g per day (0.033 g/dose). 0.033 g methionine/dose=223 μmol methionine. 223 μmol/3 hours/$5\times10^{11}$ cells leads to 0.15 μmol/hr/$1\times10^{9}$ cells. The target dose is $5\times10^{11}$ live recombinant bacterial cells/mL.

The target performance is about 4.0 μmol Met degraded per hour per $1\times10^{9}$ live cells. In one embodiment, the target performance is about 3.5 μmol Met degraded per hour per $1\times10^{9}$ live cells. In one embodiment, the target performance is about 4.5 μmol Met degraded per hour per $1\times10^{9}$ live cells. In one embodiment, the target performance is about 3.5 to about 4.5 μmol Met degraded per hour per $1\times10^{9}$ live cells. In one embodiment, the target performance is about 3.75 to about 4.25 μmol Met degraded per hour per $1\times10^{9}$ live cells. This is approximately five-fold what previous bacteria were able to degrade.

The Met degradation rate for the SYN7344 strain is 0.81 μmol/hr/$1\times10^{9}$ cells. The Met degradation rate for the SYN7346 strain is 0.91 μmol/hr/$1\times10^{9}$ cells. The Met degradation rate for the SYN7348 strain is 0.91 μmol/hr/$1\times10^{9}$ cells. The Met degradation rate for the SYN7349 strain is 1.05 μmol/hr/$1\times10^{9}$ cells.

Example 3: Production and Formulation

Recombinant bacteria are cultured in LB media. 2 mL cultures were grown shaking overnight in 14 mL culture tubes. On the day of biomass preparation, 10 mL of fresh LB in a 50 mL baffled flask was inoculated with overnight culture at a 1:100 back-dilution. Cells were grown for 2 h at 37° C. in a shaking incubator (250 rpm). At 2 h, 200 ng/mL ATC was added for induction of recombinant genes. The induction phase was allowed to continue for 4 h. After induction, cells were spun down in a centrifuge at 5000×g for 10 min, and resuspended in PBS containing 15% glycerol and stored at −80° C. until the day of testing. The current formulation comprises biomass stored in PBS comprising 15% glycerol.

Example 4: Design of In Vivo Study with Acute Mouse Model of Homocystinuria

An in vivo study was designed to evaluate the activity of the recombinant bacterial strains in a mouse model of acute hypermethionemia. Briefly, mice were fasted overnight and orally gavaged with a dose of 200 mg/kg of D4-Met (labeled methionine) the following day. Blood samples were taken at 20 minutes, 1, 2 and 5 hours and urine samples at 5 hours post administration. Baseline samples were collected prior to the administration of D4-Met. Mice were kept fasting throughout the study. Intestinal effluent samples were collected at the end of the study after euthanization.

Samples were analyzed using LC-MS/MS for primarily labelled and unlabeled Met and Homocysteine.

Figure 6A:
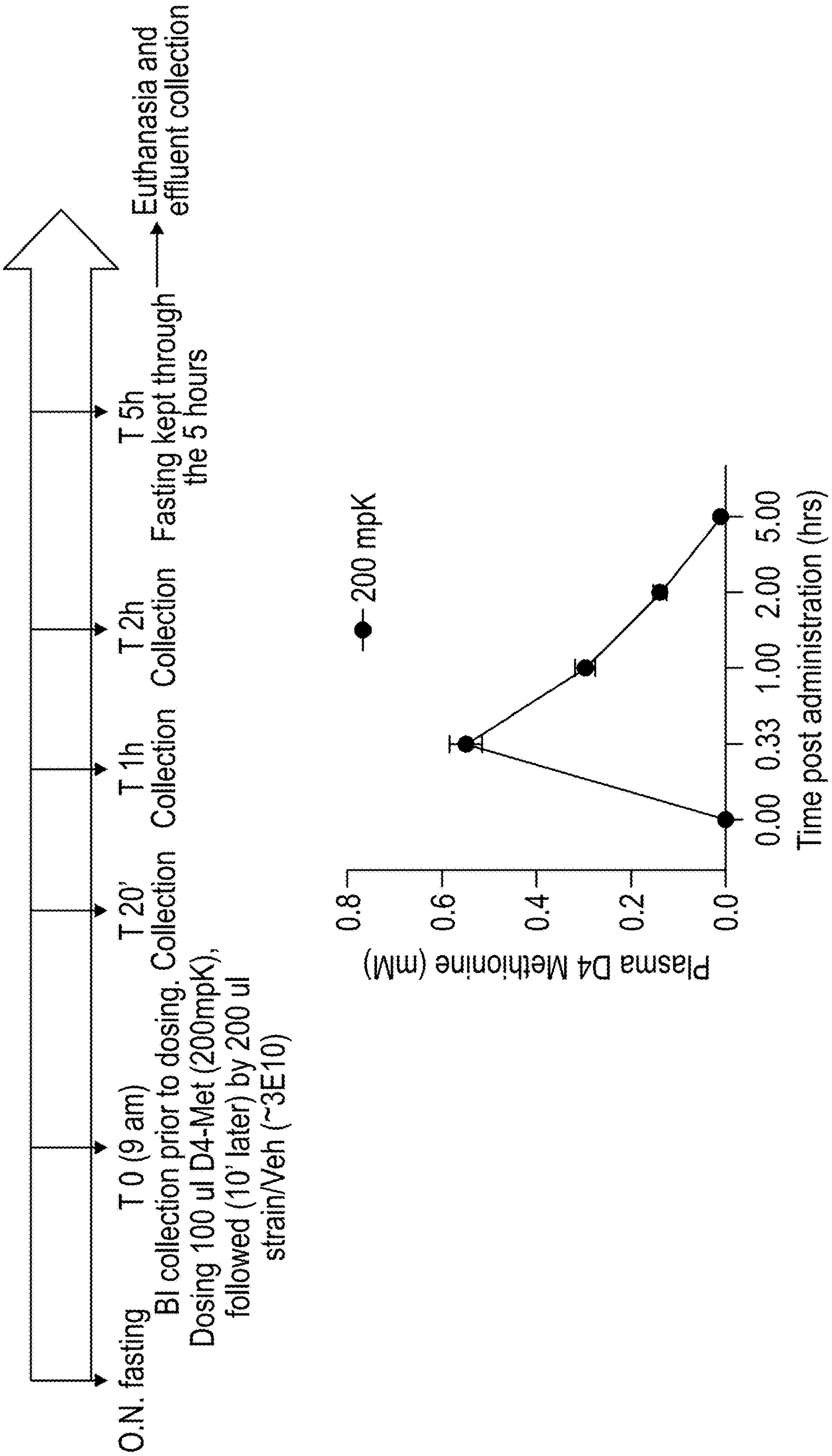
FIG. 6A depicts the plasma exposure of D4-Met (labeled methionine) in mice after receiving an oral dose of 200 mg/kg D4-Met.
Figure 6B:
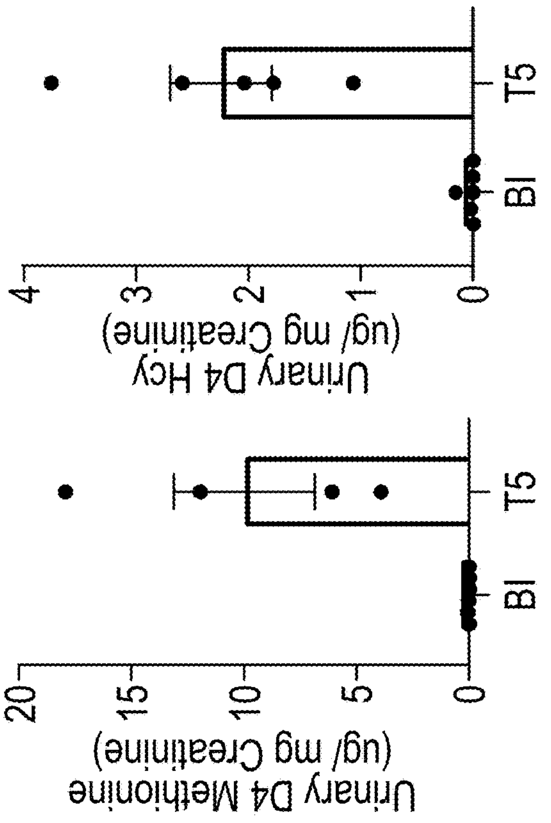
FIG. 6B depicts the level of D4-Met and D4-homocysteine (Hcy) in urine samples. Bl: baseline; T5: 5 hours after dosing.
Figure 6C:
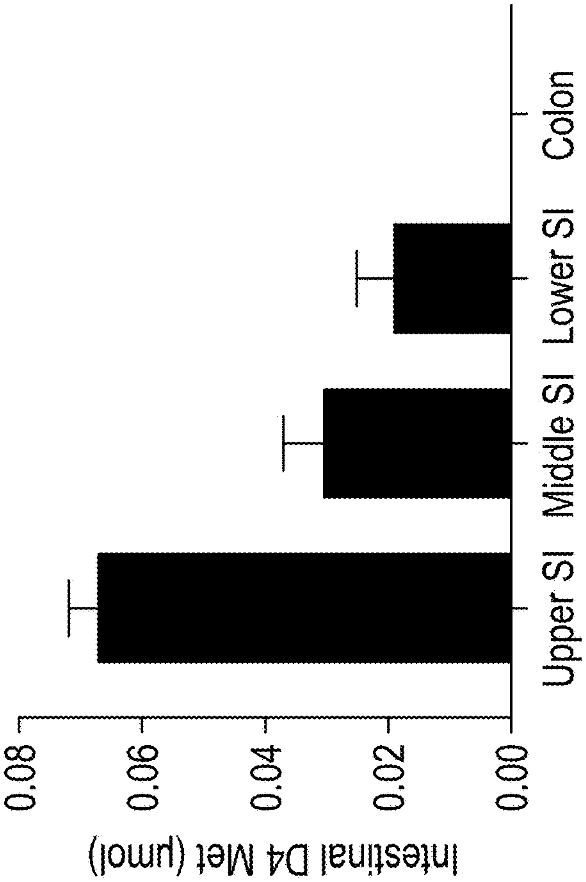
FIG. 6C depicts the level of D4-Met in intestinal effluent samples (upper small intestine, middle small intestine, lower small intestine, colon).
Figure 6D:
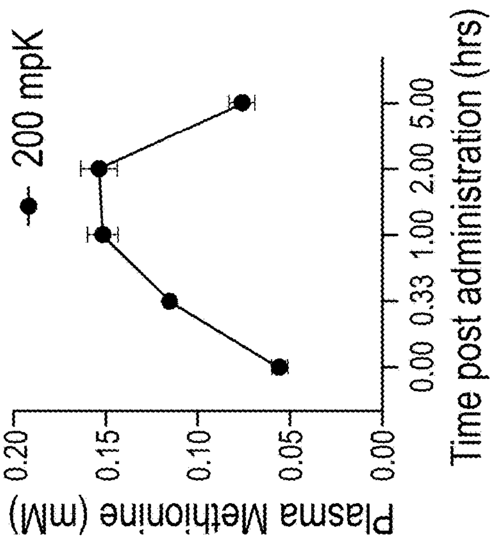
FIG. 6D depicts the plasma level of endogenous methionine in mice.
Figure 6E:
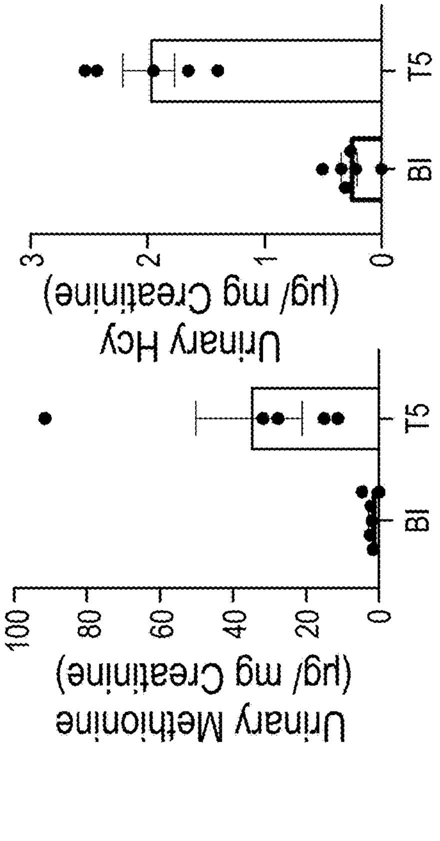
FIG. 6E depicts the level of endogenous methionine and homocysteine in urine samples. Bl: baseline; T5: 5 hours after dosing.
Figure 6F:
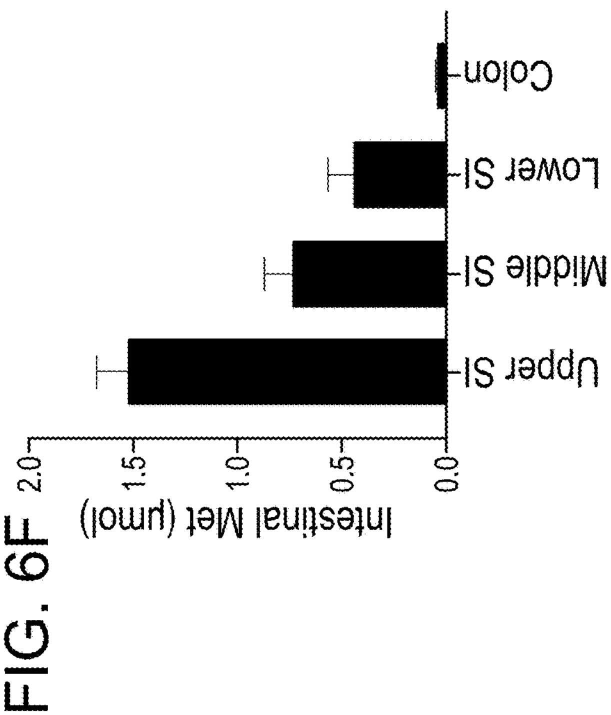
FIG. 6F depicts the level of endogenous methionine in intestinal effluent samples (upper small intestine, middle small intestine, lower small intestine, colon).

As shown in FIG. 6A, the plasma level of D4-Met reached a peak at about 20 minutes post administration, and the level dropped back to the baseline within 5 hours. A significant increase in D4-Met and D4-Hcy urinary excretion was observed in mice at 5 hours post administration (FIG. 6B). The level of D4-Met in different gastrointestinal segments were also measured. As shown in FIG. 6C, the level of D4-Met in the gastrointestinal segments correlated with the expected absorption gradient of methionine, where the upper small intestine had the highest level of D4-Met, followed by the middle small intestine, the lower small intestine and the colon. Similar patterns were observed for the level of endogenous methionine in plasma, urine and intestinal effluent samples (FIGS. 6D-6F). However, the level of endogenous methionine in plasma samples reached a peak at about 2 hours post administration.

Example 5. Evaluation of the Activity of Strain SYN7349 in HCU Mouse Model

The activity of the recombinant bacterial strain, SYN7349 (ΔyjeH; metDC (SEQ ID NO: 1049)); metNIQ (SEQ ID NOs: 1058, 1059, and 1060))), was evaluated in the previously described acute mouse model of HCU based on the oral administration of labeled methionine (D4-Met). Briefly, mice were fasted overnight prior to dose and administered orally using a flexible feeding tube attached to a sterile single use syringe with 100 μL of D4-Met (200 mg/kg) and 200 μl of the recombinant bacterial strains, SYN7349 and/or SYN094 (about $2.8\times10^{10}$ live cells), or the glycerol/PBS vehicle. D4-Met was dosed 10 minutes after administration of the bacterial strains.

Urine samples were collected before dose and 5 hours post dose using free catch method. Gastrointestinal samples were collected at the end of the study after euthanization. Samples were flushed with PBS and effluents were collected from small intestines and colon were collected. The small intestine was divided into three equal sections and effluents from the sections were collected into separate tubes. All samples were kept on ice and stored on 96-well plates at −80° C. for quantification.

Samples were analyzed using LC-MS/MS for primarily labelled and unlabeled Met, Homocysteine and methylthiopropinoic acid (3MTP).

Figure 7A:
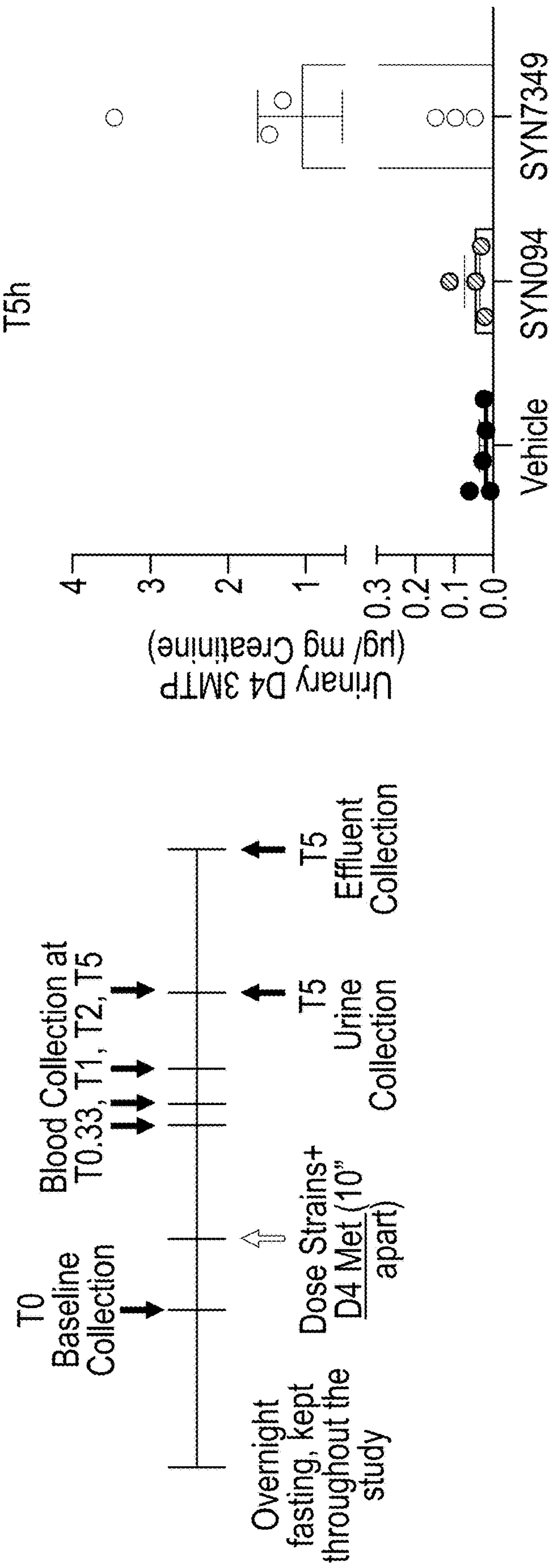
FIG. 7A depicts the level of D4-3MTP detected in urine samples collected from mice after receiving a dose of $2.8\times10^{10}$ recombinant bacterial strain (SYN094 or SYN7349) or a vehicle solution. A dose of 200 mg/kg D4-Met (labeled methionine), was administered to the mice 10 minutes after the bacterial strains.
Figure 7B:
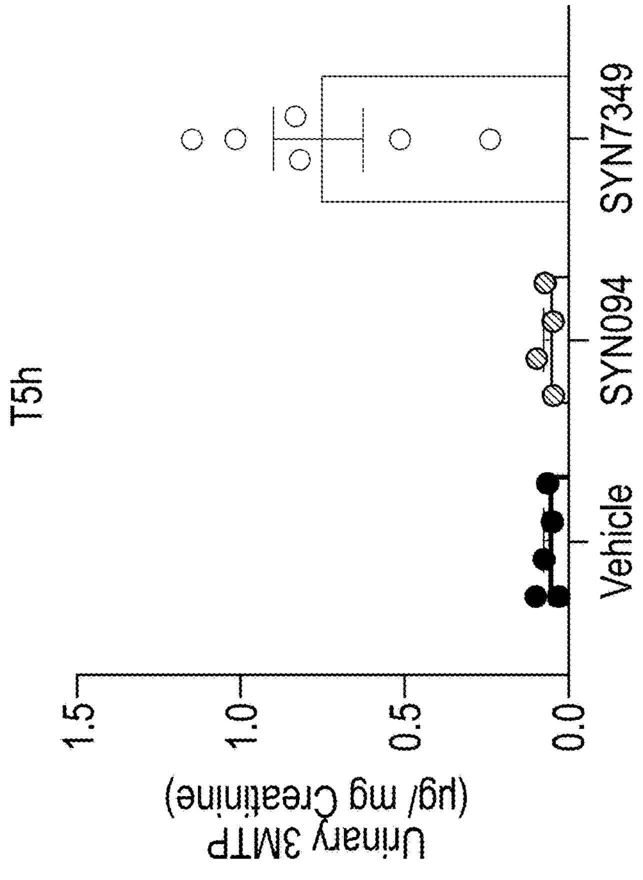
FIG. 7B depicts the level of 3MTP in urine samples after receiving a dose of $2.8\times10^{10}$ recombinant bacterial strain (SYN094 or SYN7349) or a vehicle solution.
Figure 7C:
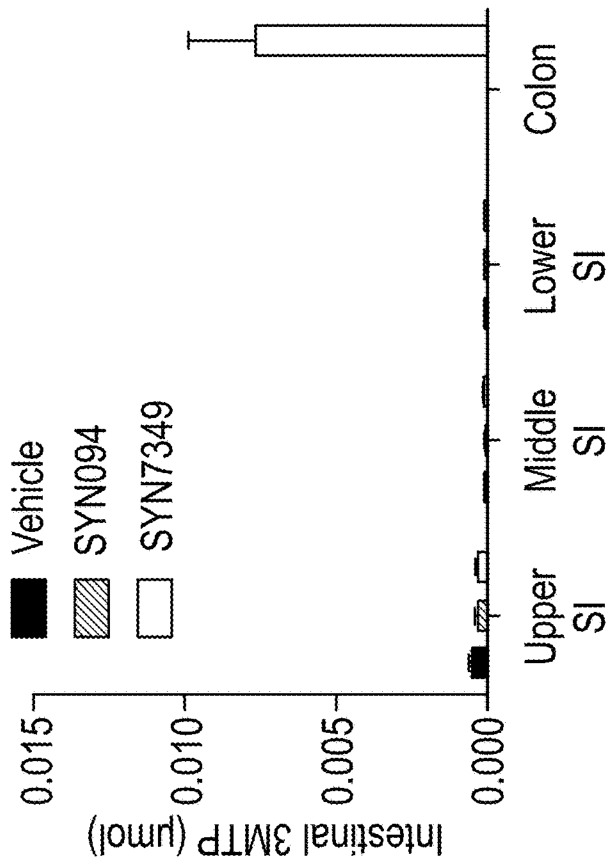
FIG. 7C depicts the level of 3MTP in intestinal effluent samples (upper small intestine, middle small intestine, lower small intestine, colon) after receiving a dose of $2.8\times10^{10}$ recombinant bacterial strain (SYN094 or SYN7349) or a vehicle solution.

Mice receiving the SYN7349 strain excreted a significant higher level of D4-3-methylthiopropinoic acid (3MTP) in urine samples than mice receiving the SYN094 strain or the vehicle control (FIG. 7A). A similar pattern was shown for the elevated endogenous methionine, which is converted into 3MTP (FIG. 7B). In addition, a significant increase in the level of 3MTP in the colon sample of mice receiving the SYN7349 strain was also observed at 5 hours (FIG. 7C), suggesting that mice receiving the SYN7349 strain had a better capacity to consume methionine and excrete the decarboxylated product.

These data demonstrate that the SYN7349 strains are capable of consuming methionine in vivo and are promising therapeutic treatment for metabolic diseases involving dysregulation of methionine metabolism, such as homocystinuria.

Figure 8:
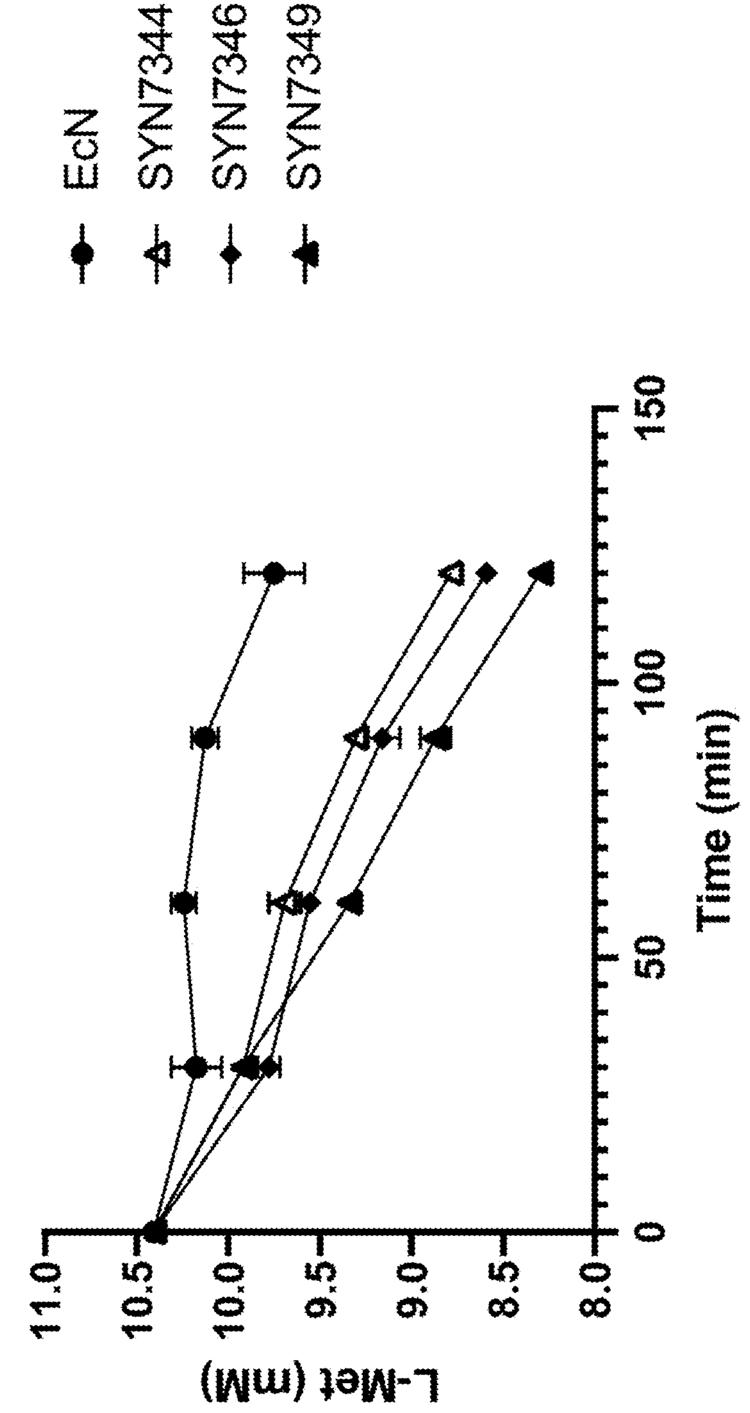
FIG. 8 depicts increased in vitro methionine consumption by strains SYN7344 (metDC (SEQ ID NO: 1049)), SYN7346 (ΔyjeH, metDC (SEQ ID NO: 1049)), and SYN7349 (ΔyjeH, metDC (SEQ ID NO: 1049), metNIQ (SEQ ID NOs: 1058, 1059, 1060)) compared to SYN094 (control).

Example 6. Evaluation of Methionine Consumption and 3-MTP Production Activities of Engineered *E. coli* Strains FIG. 8 is a graph depicting L-Met consumption over time. *E. coli* Nissle strains, SYN7349 (containing a medium copy plasmid (p15A ori) encoding an MetDC (*Streptomyces* sp. 590), a low copy plasmid (pSC101) encoding an endogenous methionine importer (metNIQ), and a knockout of yjeH) and SYN7346 (containing a medium copy plasmid (p15A ori) encoding an MetDC (*Streptomyces* sp. 590), and a knockout of yjeH), were grown in LB to early log phase followed by induction of MetDC expression for 4 hours. Activated cells were harvested and frozen in formulation buffer containing 15% glycerol at −80° C. On the day of testing, activated biomass was resuspended to an $OD_{600}$=1 in M9 minimal media containing 0.5% glucose and 10 mM Met. Supernatant samples were removed over 2 hours to quantify Met disappearance. These data demonstrate increased consumption of methionine in the *E. coli* Nissle strains comprising MetDC or MetDC/MetNIQ as compared to *E. coli* Nissle control strains (SYN094).

Figure 9A:
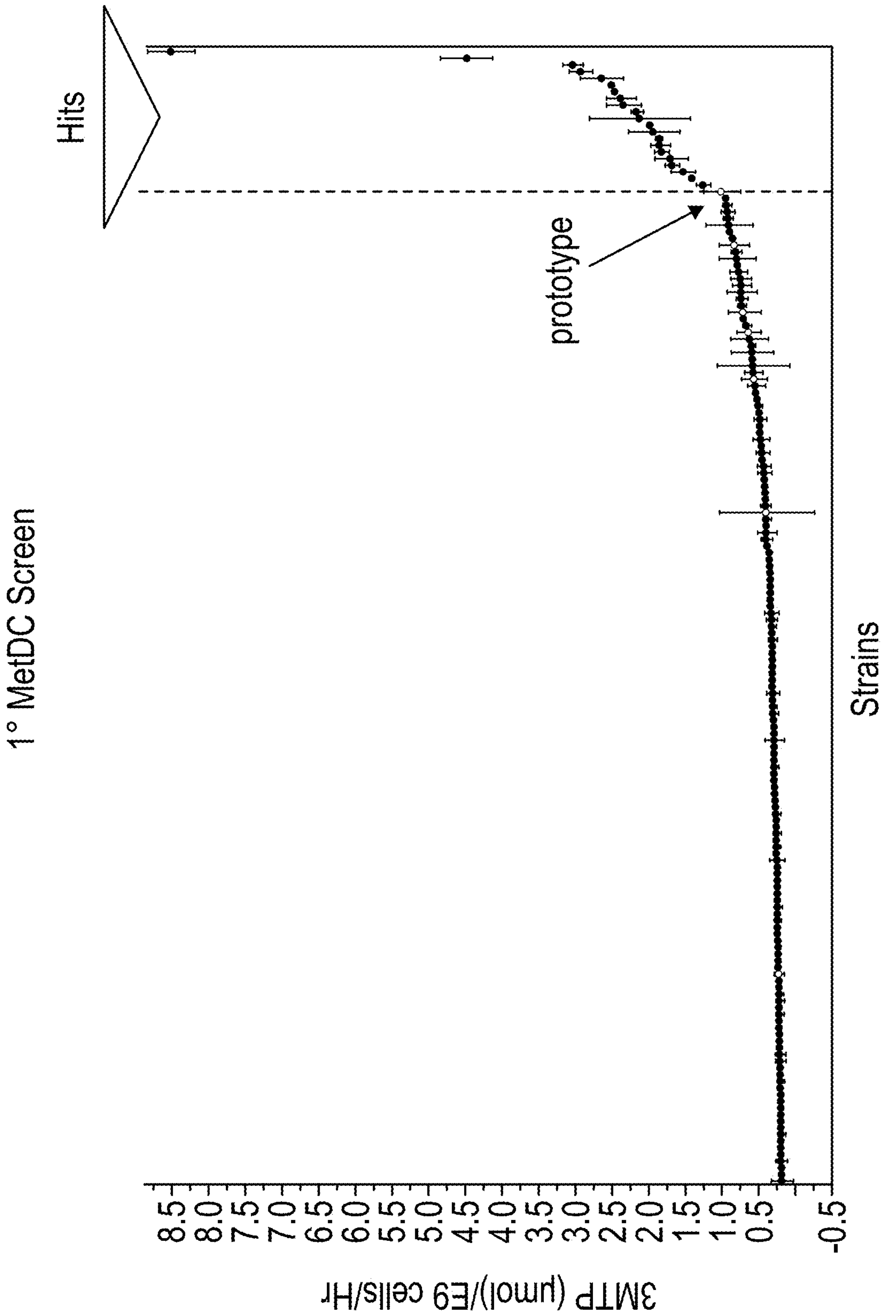
FIG. 9A depicts levels of 3-MTP produced by 173 different metDC candidate genes.
Figure 9B:
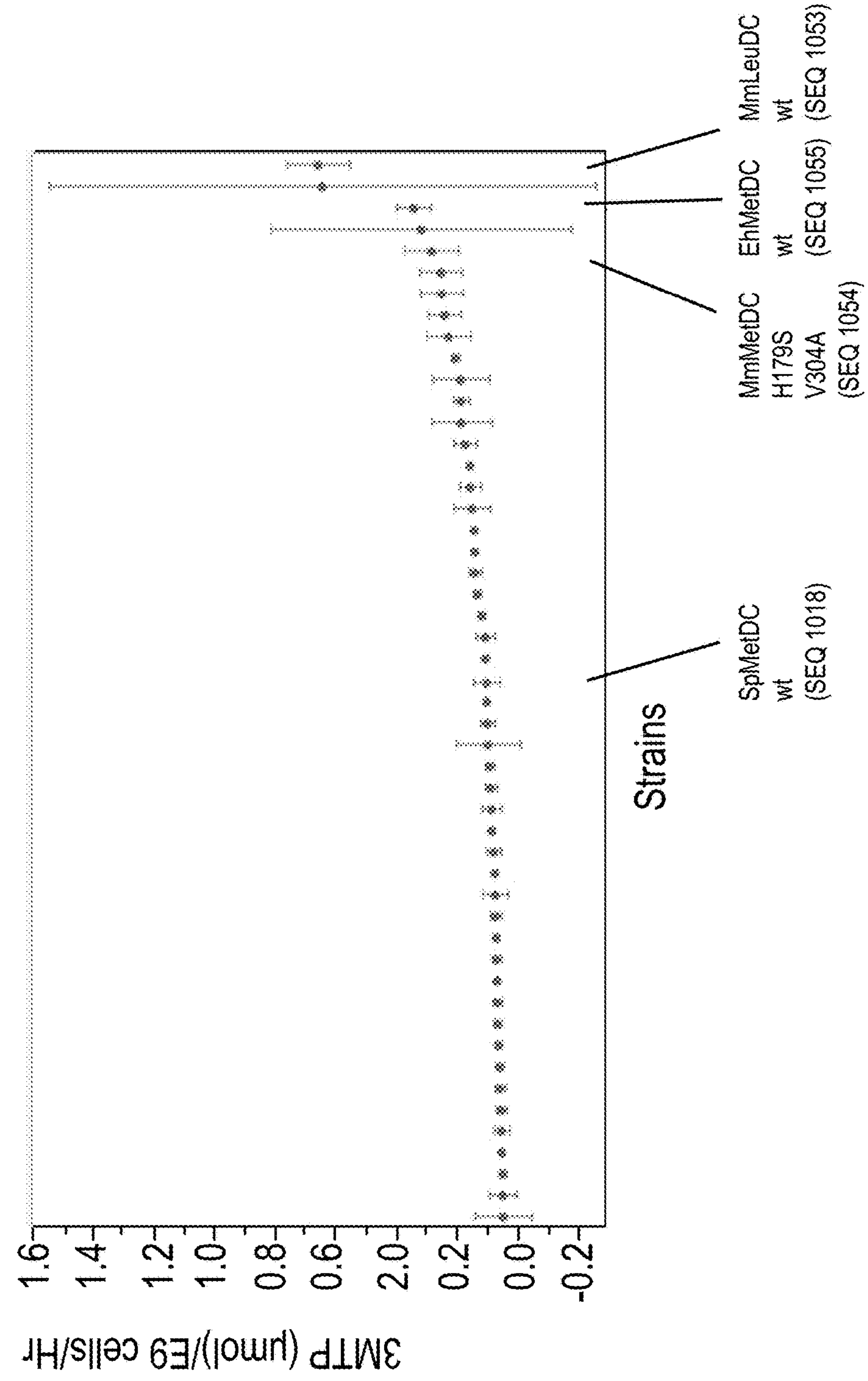
FIG. 9B depicts levels of 3-MTP produced by different metDC genes identified in the MetDC screen.
Figure 9C:
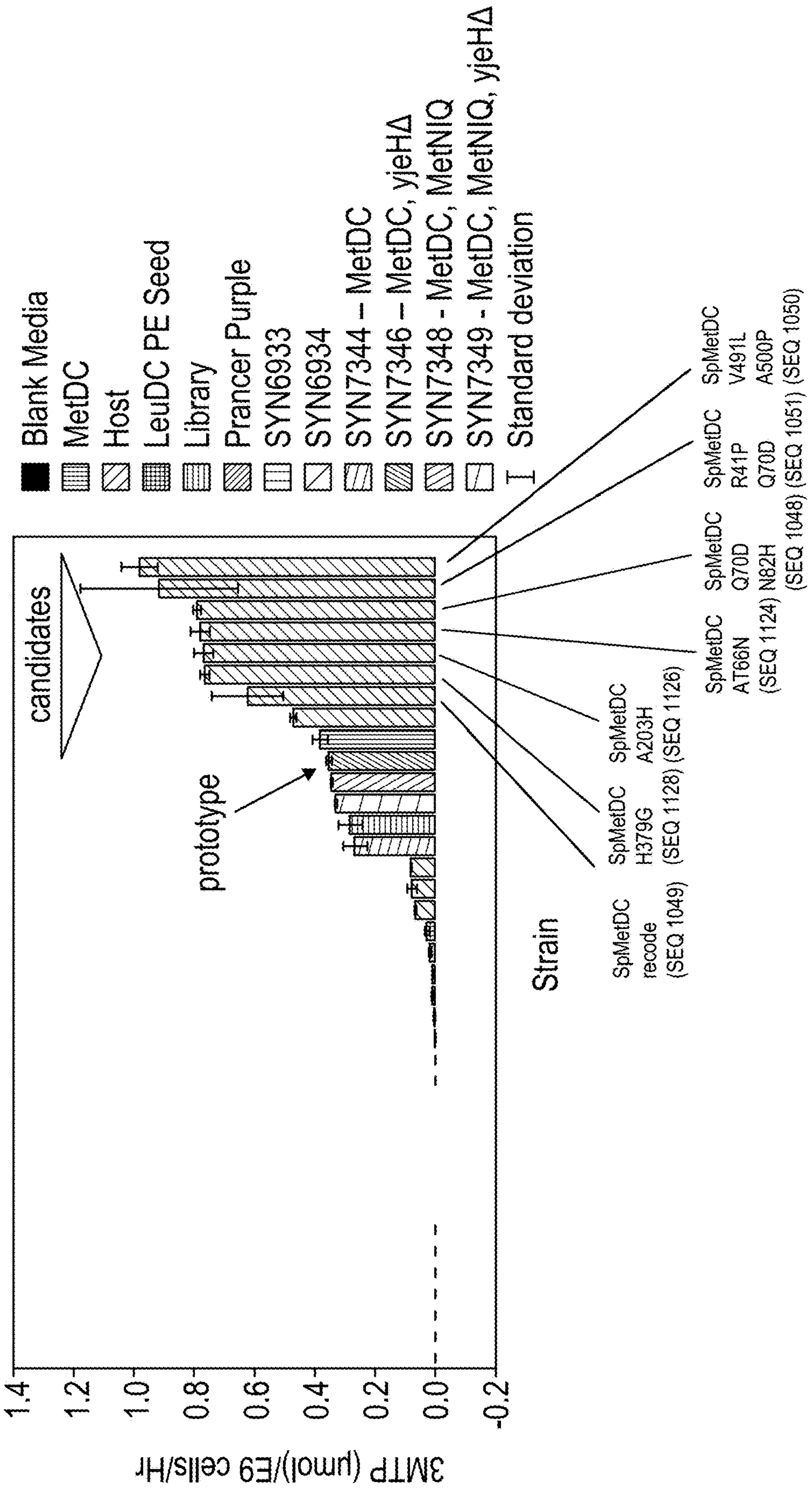
FIG. 9C depicts results from a secondary screen identifying methionine catabolism enzymes (e.g., MetDCs). MetDCs identified in the screen included SpMetDC codon optimized (SEQ ID NO: 1049), SpMetDC H379G (SEQ ID NO: 1128; engineered library), SpMetDC A203H (SEQ ID NO: 1126; engineered library), SpMetDC T66N (SEQ ID NO: 1124; engineered library), SpMetDC Q70D N82H (SEQ ID NO: 1048; engineered library), SpMetDC R41Q Q70D (SEQ ID NO: 1051; engineered library), and SpMetDC V491L A500P (SEQ ID NO: 1050; engineered library).
Figure 9D:
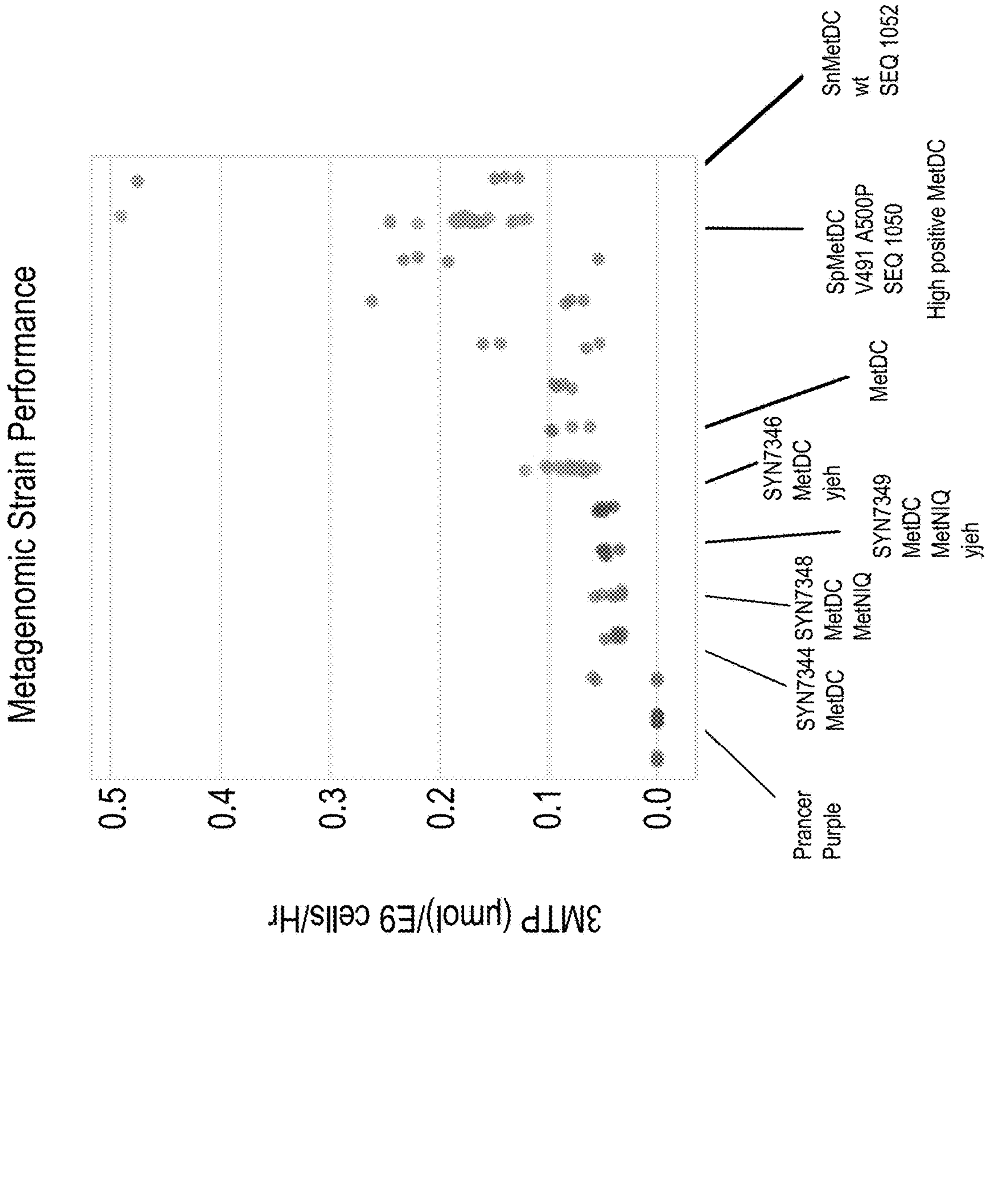
FIG. 9D depicts 3MTP produced by different strains expressing different MetDC proteins identified in the metagenomic screen.

A metagenomic and a protein engineered library were screened for MetDC candidate enzymes having improved activity and for proteins that facilitate import of methionine. FIGS. 9A and 9C depict a primary screen (FIG. 9A) and a secondary screen (FIG. 9C) to identify optimal MetDC candidates. MetDC amino acid decarboxylases were expressed from plasmids in *E. coli* Nissle. These strains were incubated with L-methionine for a set period of time. Samples were taken at the endpoint and analyzed using LCMS for the presence of the decarboxylation product of methionine, 3-methylthiopropylamine (3-MTP), which was used as a measure of activity. Surprisingly, multiple MetDC enzymes identified in the screen showed a multiple fold increase in activity relative to baseline.

Figure 10A:
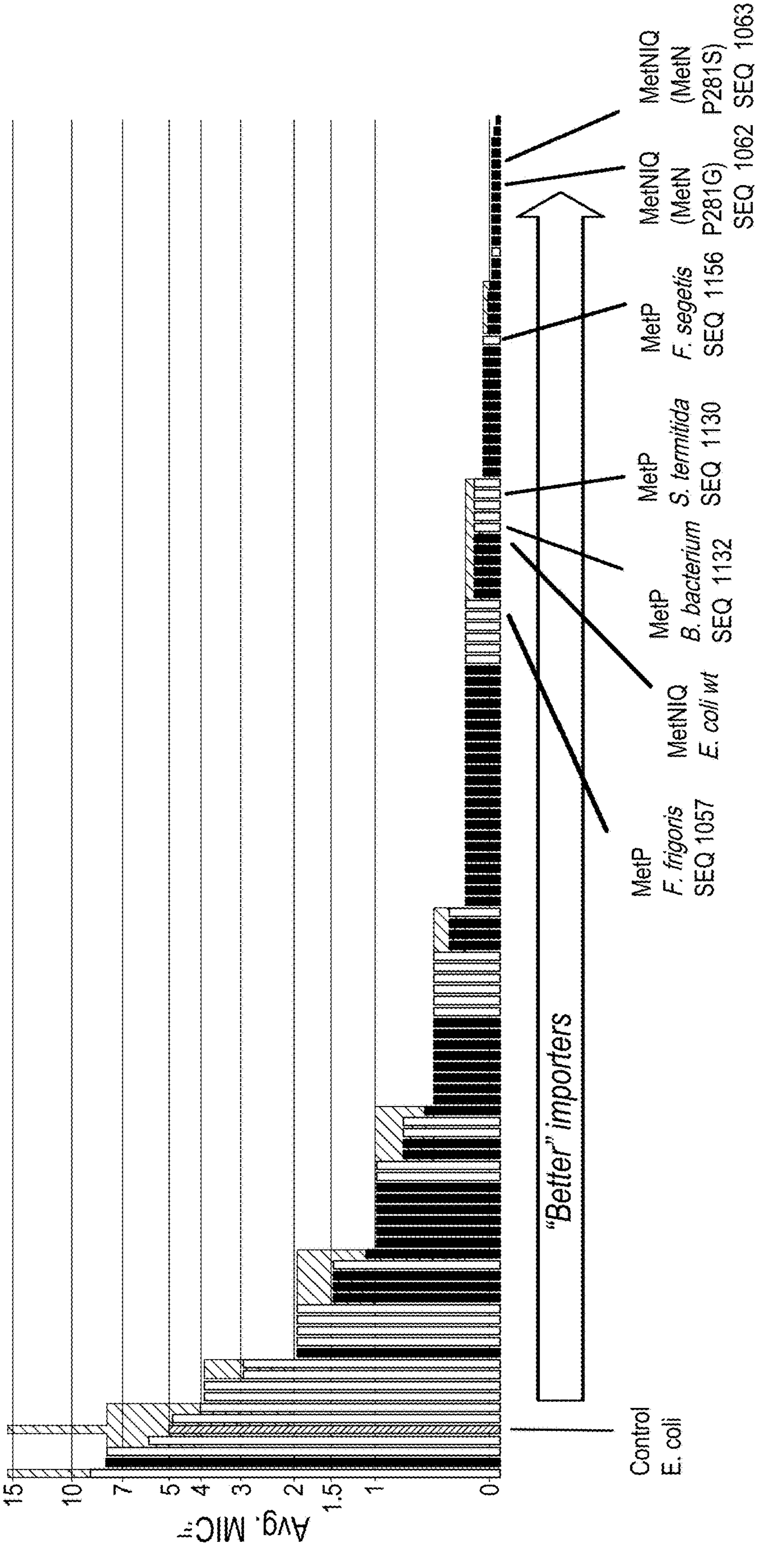
FIG. 10A depicts minimum inhibitory concentrations of a toxic Met analog (norleucine) for metagenomic (MetP) and protein engineered (MetNIQ) importers. Lower MICs are taken to imply higher importer activity.

Screens were also conducted to identify optimal Met importer (MetP or MetNIQ) candidates are shown in FIG. 10A. MetP and MetNIQ amino acid importers were expressed from plasmids in WT *E. coli* Nissle. These strains were subsequently incubated with serial dilutions of norleucine, a toxic methionine analog, in liquid medium. These plates were used to calculate minimum inhibitory concentration of norleucine, under the hypothesis that lower MICs (higher sensitivity to toxin) would correspond to more active methionine importers.

Figure 10C:
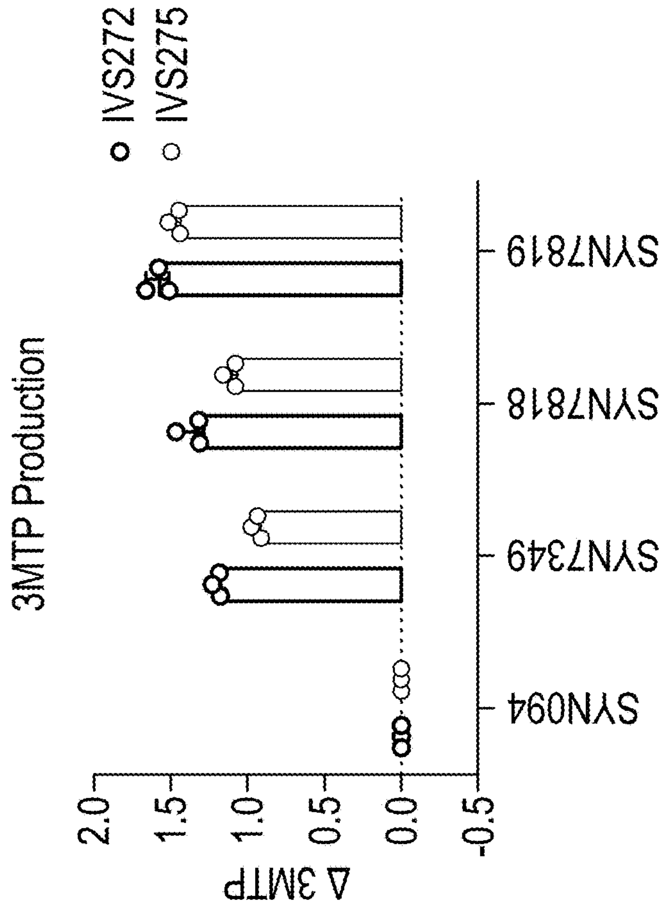
FIG. 10C depicts 3-MTP production comparing SYN7349 (ΔyjeH, metDC (SEQ ID NO: 1049), metNIQ (endogenous)), SYN7818 (ΔyjeH, metDC (SEQ ID NO: 1049), metP (metagenomics library; *F. frigoris*; SEQ ID NO: 1057)), and SYN7819 (ΔyjeH, metDC (SEQ ID NO: 1049), metP (metagenomics library; *F. segetis*; SEQ ID NO: 1056)).
Figure 10B:
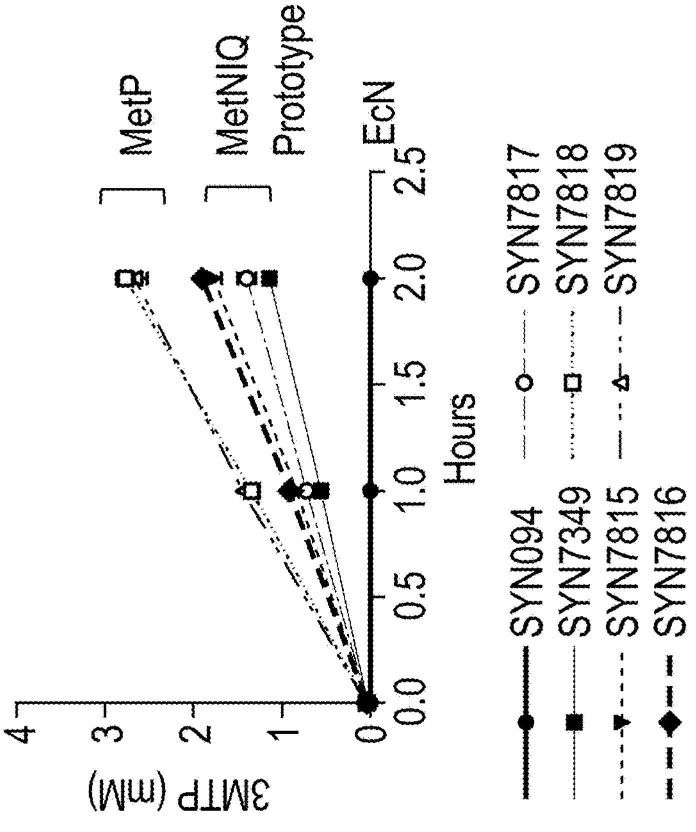
FIG. 10B depicts 3-MTP production by *E. coli* strains with methionine importers, MetP or MetNIQ, added to a MetDC expressing background (SYN7346 (ΔyjeH, metDC (SEQ ID NO: 1049)). Strains with added MetP or MetNIQ improved activity over prototype (SYN7349 (ΔyjeH, metDC (SEQ ID NO: 1049), metNIQ (SEQ ID NOs: 1058, 1059, 1060))). Strains with MetP added are SYN7818 (metP (metagenomics library; *F. frigoris*; SEQ ID NO: 1057)) and SYN7819 (metP (metagenomics library; *F. segetis*; SEQ ID NO: 1056)). Strains with MetNIQ added are SYN7816 (metN(P281G)IQ; SEQ ID NOs: 1062, 1059, and 1060), SYN7817 (metN(P281G)IQ; SEQ ID NOs: 1058, 1059, and 1060), and SYN7815 (metN(P281S)IQ; SEQ ID NOs: 1063, 1059, and 1060).

FIG. 10B is a graph depicting 3-MTP production over time when methionine importers were added to MetDC expressing strains. Genes encoding MetP (SYN7818 or SYN7819) or MetNIQ (SYN7815, SYN7816, or SYN7817) were added to strain expressing MetDC (SYN7346). Both MetP and MetNIQ increased 3-MTP production in comparison to strain containing only MetDC. Assays were performed as described herein.

In vitro Simulation (IVS) assays were performed with SYN094 (control), SYN7349 (ΔyjeH, metDC, metNIQ), SYN7818 (ΔyjeH, metDC, metP((*F. frigoris*)), and SYN7819 (ΔyjeH, metDC, metP((*F. segetis*)) (FIG. 10C). 3-MTP production was increased in SYN7349, SYN7818, and SYN7819 compared to the control strain. Strains with added MetP genes (SYN7818 and SYN7819) showed an increase of 3-MTP production in comparison to SYN7349 with only MetDC. SYN7819 showed approximately a 2-fold increase of 3-MTP production when compared to SYN7349.

Briefly, frozen aliquots were thawed at room temperature, mixed, and placed on ice. Each strain was prepared in 1 mL aliquot at $5\times10^9$ live cells/mL in 0.077 M sodium bicarbonate buffer, pH 7, and 400 uL were aliquoted into 3 wells in a 96-well plate. Samples were incubated in an Anoxic chamber set at 4% $O_2$. 400 uL of Simulated Intestinal Fluid (SIF), with 10 mM Methionine, was added to each well. The plate was incubated for 2 hours at 37° C. with shaking with a breathable plate seal. 100 uL samples were collected at time points 0, 30, 60, 120, and 180 minutes. Each sample was centrifuged at 400 rpm for 5 mins and 90 uL supernatant was collected. The supernatants were stored at −80° C. until LC-MS/MS analysis.

TABLE 8

SIF Experimental Mixture

| Component | Concentration | Volume for One Sample [uL] |
|---|---|---|
| Simulated Gastric Chyme | 1× | 500 |
| Simulated Intestinal Fluid | 1.25× | 275 |
| Pancreatin Solution | 800 Trypsin U/mL in SIF | 125 |
| Bile Salts | 160 mM in SIF | 62.5 |
| CaCl2 Stock Solution | 0.3 M | 1 |
| HCl Stock Solution | 1 M | 7.5 |
| Water | | 29 |
| | Total Volume | 1000 |

Figure 11A:
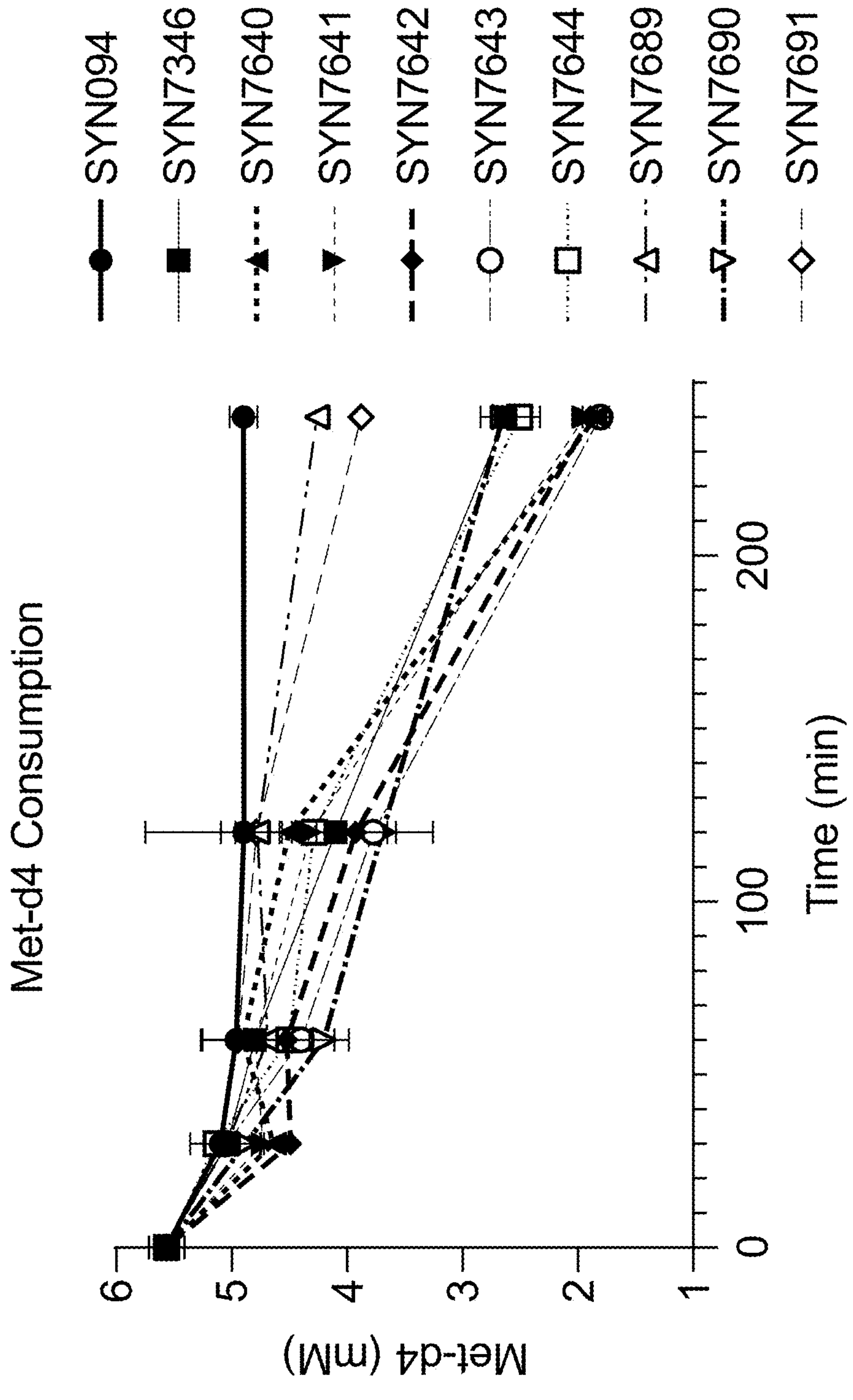
FIGS. 11A and 11B depict graphs showing Met-d4 consumption (FIG. 11A) and 3-MTP-d4 production (FIG. 11B) by *E. coli* Nissle strains: SYN094 (control), SYN7346 (ΔyjeH, metDC SEQ ID NO: 1049), SYN7640 (metDC (SEQ ID NO: 1049), ΔyjeH), SYN7641 (metDC (V491L A500P; SEQ ID NO: 1050; engineered library), ΔyjeH), SYN7642 (metDC (Q70D N82H; SEQ ID NO: 1048; engineered library), ΔyjeH), SYN7643 (metDC (R41Q Q70D; SEQ ID NO: 1051; engineered library), ΔyjeH), SYN7644 (metDC (*Stanieria* sp. NIES-3757; metagenomic library), ΔyjeH), SYN7689 (engineered metDC (*Mus musculus*; SEQ ID NO: 1054; metagenomic library), ΔyjeH), SYN7690 (engineered leuDC (*Mus musculus*; SEQ ID NO: 1053; metagenomic library), ΔyjeH), and SYN7691 (metDC (*Entamoeba histolytica*; SEQ ID NO: 1055; metagenomics library), ΔyjeH).
Figure 11B:
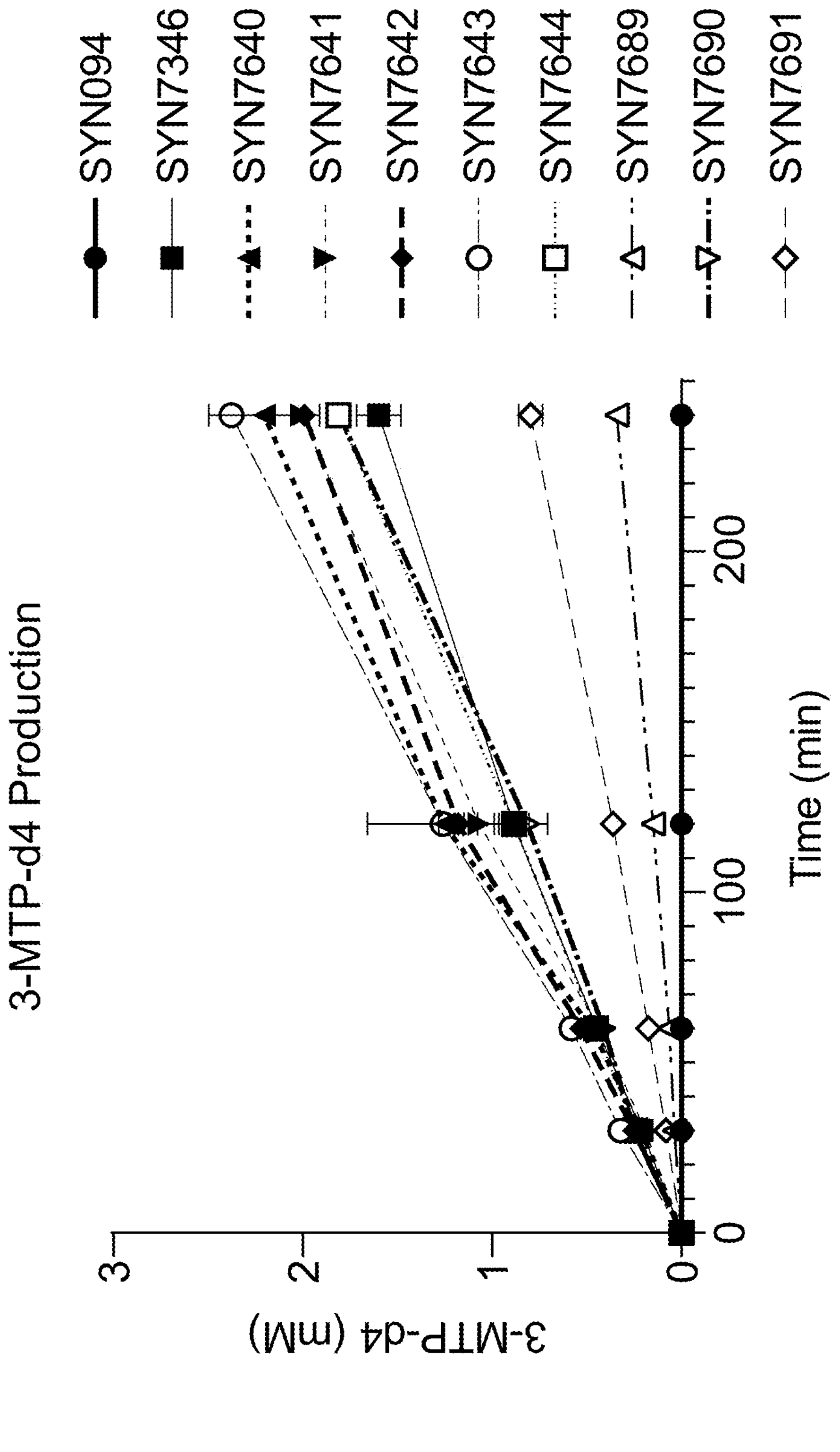
Figure 11C:
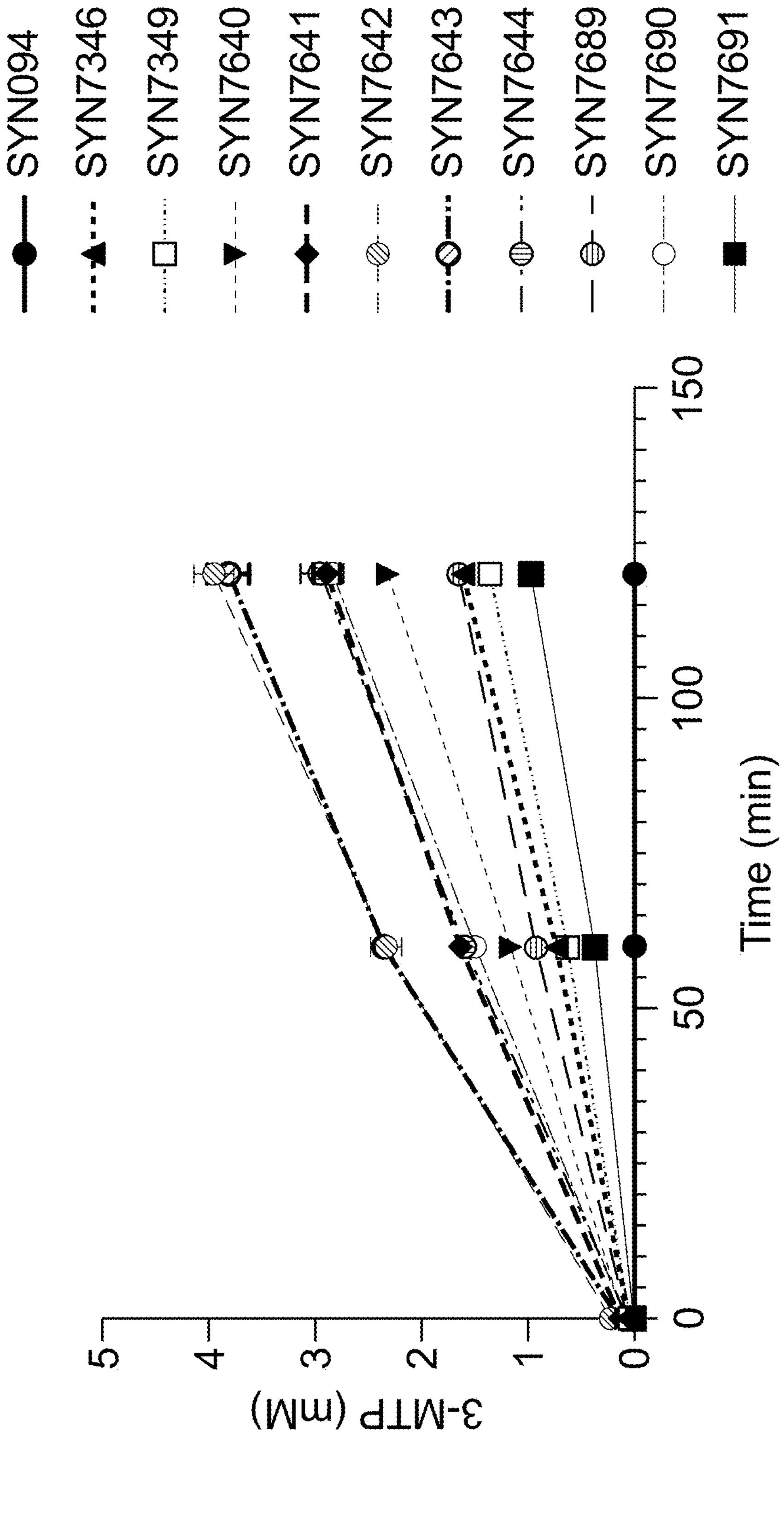
FIG. 11C depicts 3-MTP production of top performing library MetDCs compared to wildtype EcN, and the prototype; the final MetDC selected to move forward (*Streptomyces* sp. 590; Q70D, N82H), a member of the protein engineered library, is in pink. IVS=in vitro gastric simulation.

FIG. 11A is a graph depicting Met-d4 consumption and FIG. 11B is a graph depicting 3-MTP-d4 production by strains containing the identified MetDC proteins from the MetDC screen. SYN094 (control), SYN7346 (ΔyjeH, metDC SEQ ID NO: 1049), SYN7640 (metDC (SEQ ID NO: 1049), ΔyjeH), SYN7641 (metDC (V491L A500P; SEQ ID NO: 1050; engineered library), ΔyjeH), SYN7642 (metDC (Q70D N82H; SEQ ID NO: 1048; engineered library), ΔyjeH), SYN7643 (metDC (R41Q Q70D; SEQ ID NO: 1051; engineered library), ΔyjeH), SYN7644 (metDC (*Stanieria* sp. NIES-3757; metagenomic library), ΔyjeH), SYN7689 (engineered metDC (*Mus musculus*; SEQ ID NO: 1054; metagenomic library), ΔyjeH), SYN7690 (engineered leuDC (*Mus musculus*; SEQ ID NO: 1053; metagenomic library), ΔyjeH), and SYN7691 (metDC (*Entamoeba histolytica*; SEQ ID NO: 1055; metagenomics library), ΔyjeH). MetDC (Q70D N82H) from *Streptomyces* sp. 590 (SYN7642) showed both increased Met-d4 consumption and 3-MTP-d4 production when compared to the control strain and/or prototype strain.

Example 7. Gene Integration into *E. coli* Nissle Genome

Genes encoding MetP and MetDC were integrated to facilitate methionine import and metabolism. The importer metP is derived from *Flavobacterium segetis* and facilitates the uptake of methionine into the cell. MetDC is derived from *Streptomyces* sp. 590 and includes two modifications (Q70D and N82H) to improve its activity at converting methionine to 3-MTP and $CO_2$. Both genes are under the regulatory control of a chemically inducible promoter (Ptac), which is induced by IPTG. To prevent release of methionine from the bacteria in the GI tract once it enters the cell, the yjeH gene that encodes a methionine/branched chain amino acid exporter was deleted. To control growth in vivo and in the environment, strains were engineered to be an auxotrophic strain through deletion of the dapA gene that encodes for dihydrodipicolinate synthase, which is essential for the cell wall. This deletion renders SYNB1353 unable to synthesize DAP, thereby preventing the proper formation of bacterial cell wall unless the strain is supplemented with DAP exogenously.

Figure 12:
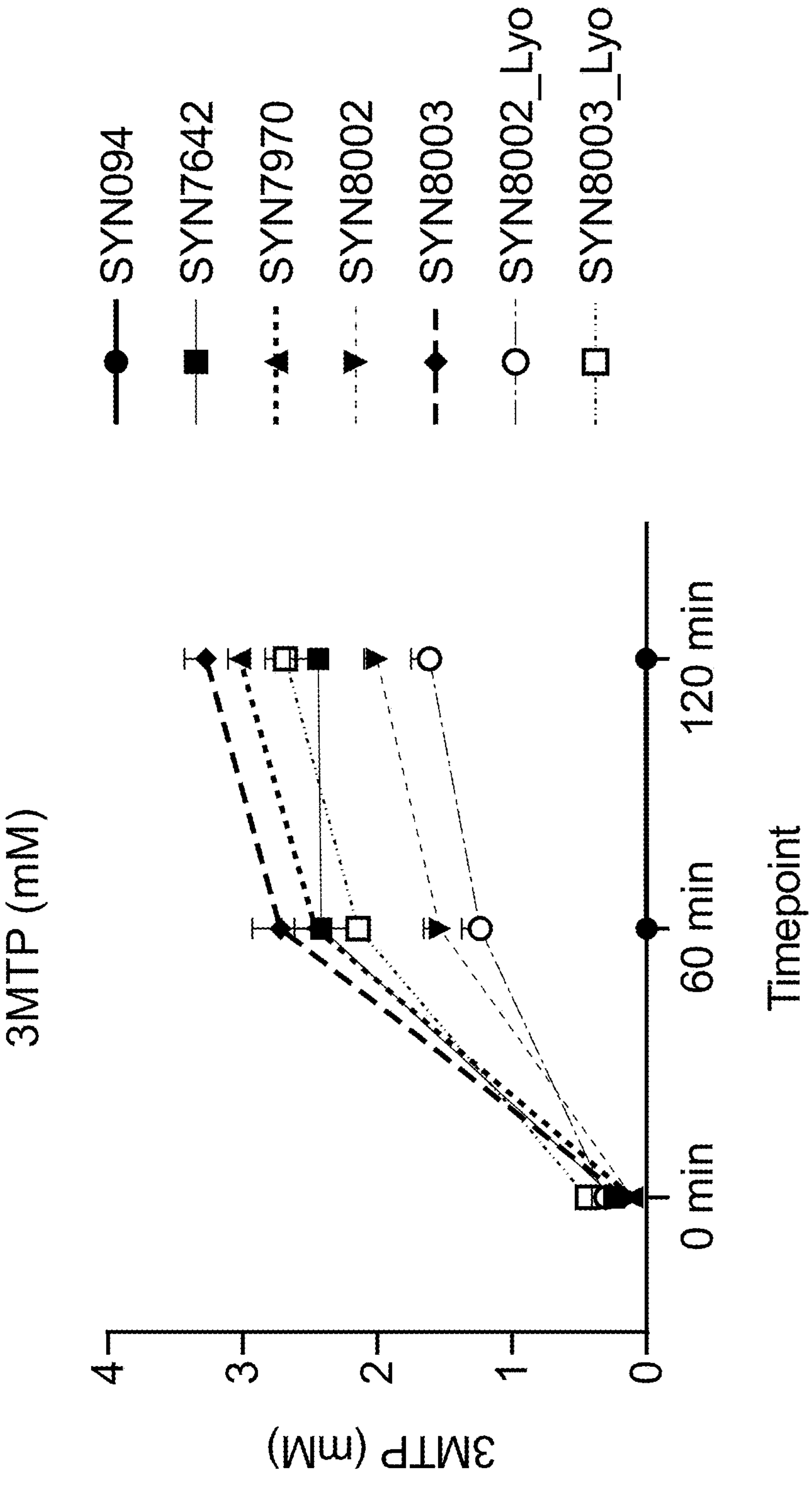
FIG. 12 depicts 3-MTP production by *E. coli* Nissle strains SYN094 (control), SYN7642 (metDC (Q70D N82H; SEQ ID NO: 1048; engineered library)), SYN7970 (2 copies metDC (Q70D N82H; SEQ ID NO: 1048; engineered library), metP (metagenomics library; *F. segetis*; SEQ ID NO: 1056), ΔyjeH, Δdap, Δϕ), SYN8002 (3 copies metDC (Q70D N82H; SEQ ID NO: 1048; engineered library), metP (metagenomics library; *F. segetis*; SEQ ID NO: 1056), ΔyjeH, Δdap, Δϕ), and SYN8003 (3 copies metDC (Q70D N82H; SEQ ID NO: 1048; engineered library), metP (metagenomics library; *F. segetis*; SEQ ID NO: 1056), ΔyjeH, Δdap, Δϕ). Lyo: lyophilized strains. SYN8003 has stronger RBS sites than SYN8002.

IVS assays for 3-MTP production by SYN094 (control), SYN7642 (metDC (Q70D N82H; SEQ ID NO: 1048; engineered library), SYN7970 (2 copies metDC (Q70D N82H; SEQ ID NO: 1048; engineered library), metP (metagenomics library; *F. segetis*; SEQ ID NO: 1056), ΔyjeH, Δdap, Δϕ), SYN8002 (3 copies metDC (Q70D N82H; SEQ ID NO: 1048; engineered library), metP (metagenomics library; *F. segetis*; SEQ ID NO: 1056), ΔyjeH, Δdap, Δϕ), and SYN8003 (3 copies metDC (Q70D N82H; SEQ ID NO: 1048; engineered library), metP (metagenomics library; *F. segetis*; SEQ ID NO: 1056), ΔyjeH, Δdap, Δϕ) showed 3-MTP production (FIG. 12). SYN8003 has three copies of MetDC and one copy of MetP and was shown produce approximately 3-fold more 3-MTP than the control strain. Lyophilization of SYN8003 decreased 3-MTP production by approximately by 1.2-fold. (Note: SYN8002 differs from SYN8003 by the RBS for MetDC. SYN8003 has a stronger RBS).

Figure 13:
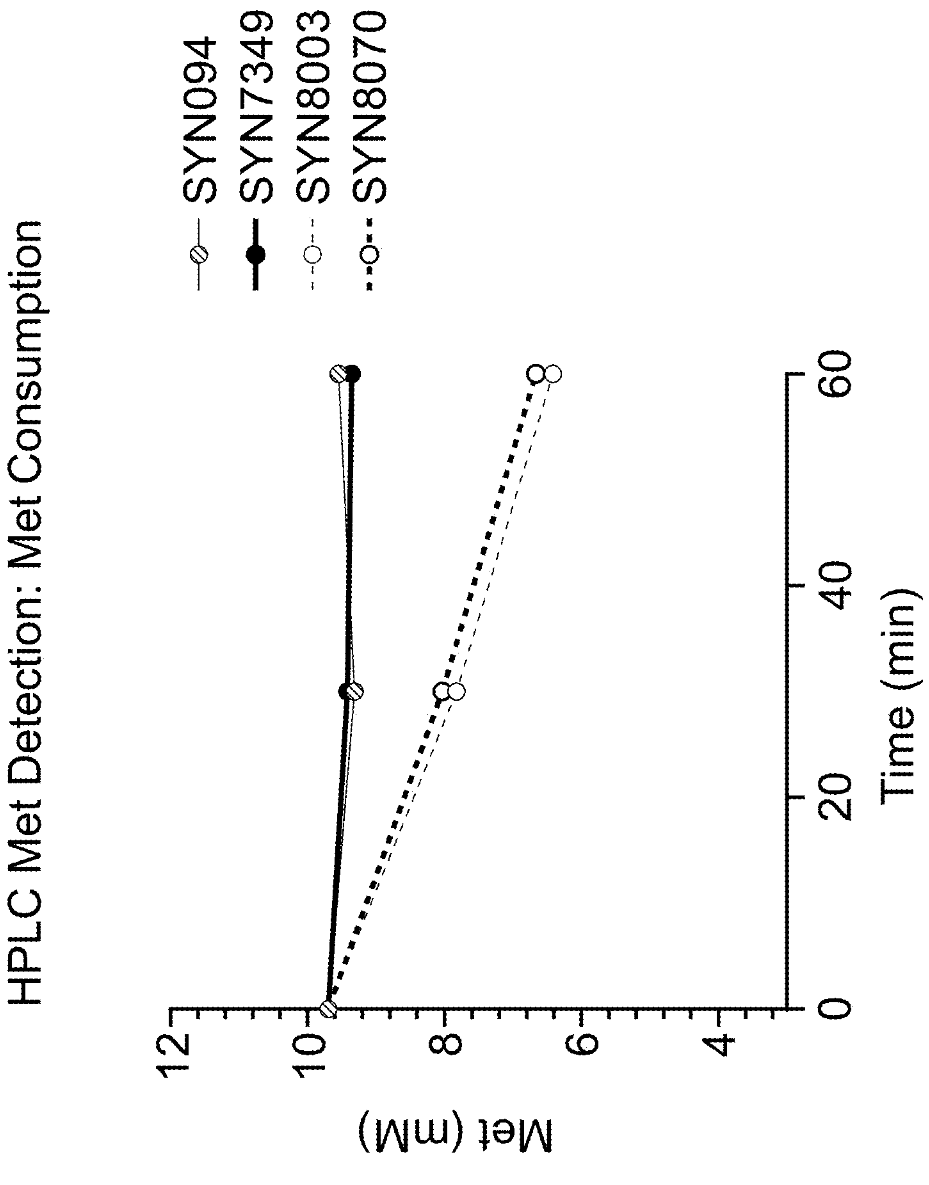
FIG. 13 depicts Met consumption by *E. coli* strains SYN094 (control), SYN7349 (ΔyjeH, metDC (SEQ ID NO: 1049), metNIQ (endogenous)), SYN8003 (3 copies metDC (Q70D N82H; SEQ ID NO: 1048; engineered library), metP (metagenomics library; *F. segetis*; SEQ ID NO: 1056), ΔyjeH, Δdap, Δϕ), and SYN8070 (3 copies metDC (Q70D N82H; SEQ ID NO: 1048; engineered library), metP (metagenomics library; *F. segetis*; SEQ ID NO: 1056), ΔyjeH, Δdap, Δϕ, Δpks).

The pks island (aka colibactin island or clb island), and an endogenous Nissle prophage gene, have also been deleted from the genome. FIG. 13 depicts Met consumption by *E. coli* strains: SYN094 (control), SYN7349 (ΔyjeH, metDC (SEQ ID NO: 1049), metNIQ (endogenous)), SYN8003 (3 copies metDC (Q70D N82H; SEQ ID NO: 1048; engineered library), metP (metagenomics library; *F. segetis*; SEQ ID NO: 1056), ΔyjeH, Δdap, Δϕ), and SYN8070 (3 copies metDC (Q70D N82H; SEQ ID NO: 1048; engineered library), metP (metagenomics library; *F. segetis*; SEQ ID NO: 1056), ΔyjeH, Δdap, Δϕ, Δpks). Both SYN8003 and SYN8070 (aka SYNB1353) showed approximately 1.4 fold to about 1.5-fold decrease of methionine compared to the control strain (SYN094). Deletion of the endogenous clb (colibactin) island (also referred to as pks island) in SYN8070 did not impact methionine consumption in comparison to SYN8003 with an intact clb gene. Strain names SYN8070 and SYNB1353 are used interchangeably herein. Additionally, SYNB1353 was designed as a DAP auxotroph strain by deleting the dapA gene that encodes 4-hydroxy-tetrahydropicolinate synthase, which is essential for bacterial growth. This deletion renders SYNB1353 unable to synthesize DAP, thereby preventing the proper formation of bacterial cell wall unless the strain is supplemented with DAP exogenously.

There are no antibiotic resistance genes in SYNB1353, and whole genome sequencing (PacBio) confirmed that all insertions and deletions in SYNB1353 were created in the proper chromosomal locations and contained the expected sequence identities. Plating on selective media confirmed that SYNB1353 did not grow in the presence of any of the antibiotics used during strain construction and did not grow without exogenously supplied diaminopimelic acid.

Figure 14A:
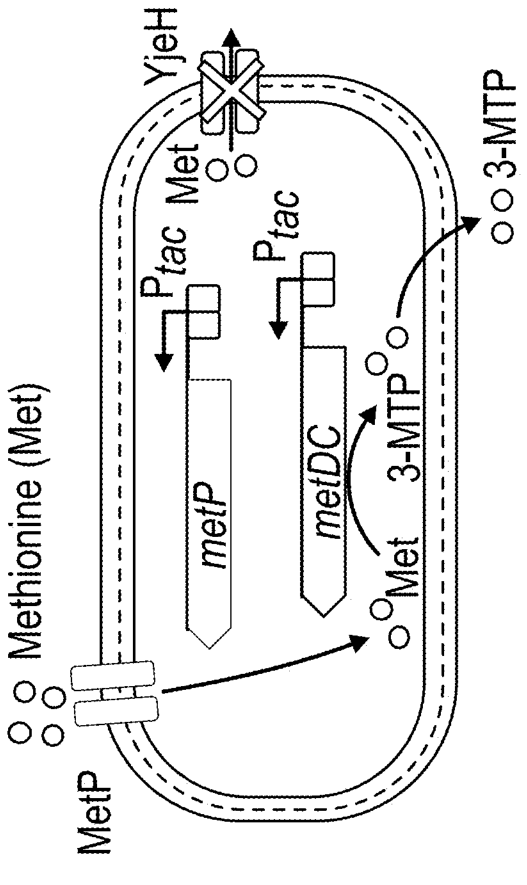
FIG. 14A is a schematic of an exemplary engineered *E. coli* Nissle capable of consuming methionine. Optimal metP and metDC were identified from metagenomic, codebase and protein engineering libraries.

Example 8. Analysis of Methionine Degradation and 3-MTP Production with SYNB1353 In Vitro SYNB1353 comprises a metP gene, metDC gene, and deletion of the yjeH gene, as shown in FIG. 14A. The ability of SYNB1353 to degrade methionine to 3-MTP and $CO_2$ by its engineered pathway was measured.

SYNB1353 and SYN094 were grown and activated in a bioreactor following optimized processes intended to be used for the scale-up of drug product. Activated cell batches were resuspended to the specified live cell count in assay media, and cells were statically incubated at 37° C. Supernatants were collected at defined timepoints, and the quantity of each analyte (methionine and 3-MTP) in each sample was determined by liquid chromatography mass spectrometry (LC-MS/MS). As observed in FIG. 14B, SYNB1353 degraded methionine and produced 3-MTP de novo, as designed. The control strain, SYN094, consumed methionine at a low rate and did not produce any 3-MTP.

Figure 14B:
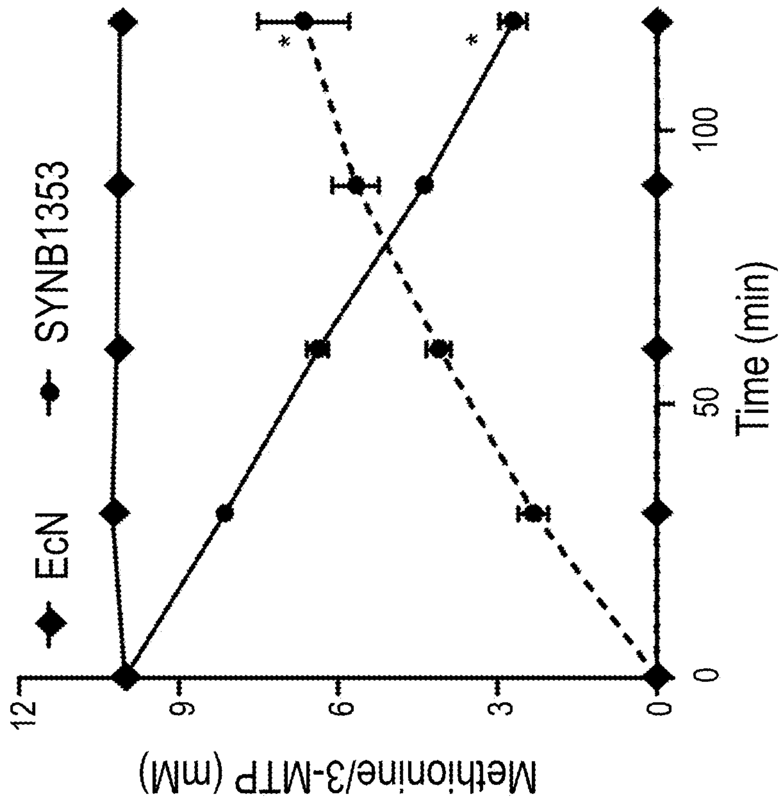
FIG. 14B is a graph showing in vitro methionine consumption (solid line) and 3-MTP production (dotted line) by EcN (unengineered bacteria) or SYNB1353 ((lacI-Ptac, IPTG) 3×metDC (Q70D N82H; SEQ ID NO: 1048; engineered library); 1×metP (metagenomics library; *F. segetis*; SEQ ID NO: 1056); Δϕ; Δdap; ΔyjeH; Δpks). Cells were incubated for the indicated time in M9 medium with 0.5% glucose and 10 mM methionine at 37° C., supernatant was collected for methionine (HPLC) and 3-MTP (LC-MS/MS) measurements. *$p<0.05$ versus EcN. Met: methionine, metP: methionine importer, metDC: methionine decarboxylase, YjeH: methionine exporter.

In vitro Met consumption assays, as described above, show consumption of methionine and production of 3-MTP by SYNB1353 and not the EcN control (FIG. 14B). In vitro, SYNB1353 consumed methionine at a rate of 1.3±0.13 μmol/h/1×$10^9$ live cells and concomitantly produced 3-MTP at a rate of 1.3±0.087 μmol/h/1×$10^9$ live cells.

Example 9. Dose-Response of SYNB1353 in Healthy Mice Receiving a Bolus of D4-Methionine The ability of SYNB1353 to metabolize dietary and gastrointestinal methionine to produce 3-MTP in healthy mice was assessed. Two identical studies were performed, and the data from both studies were combined and shown in FIG. 15D. For each study, male C57BL/6J mice of approximately 8 weeks of age were acclimated for at least 4 days before being placed on study. Mice were fasted overnight and orally administered a single dose of SYN094 (3.5×10^10 live cells, n=18/group) or SYNB1353 (3.0×10^9, 1.0×10^10, 3.5×10^10 live cells, n=18/group). Thirty (30) minutes later, mice received a bolus of 200 mg of D4-methionine (PO) and were immediately placed in metabolic cages (3 per cage) without access to food for a total of 5 hours. Cumulative urine was collected for 3-MTP and creatinine measurements.

Figure 15A:
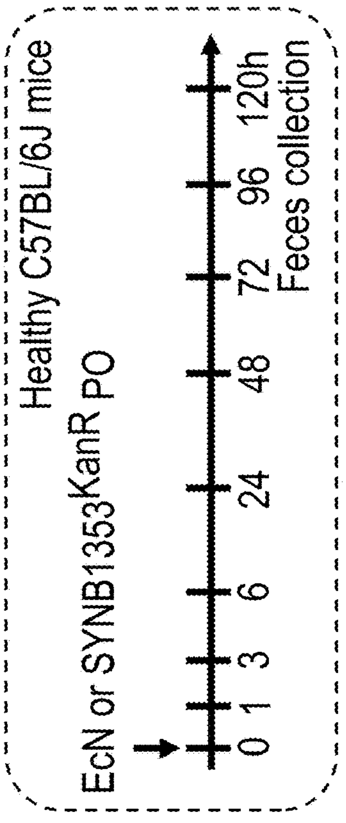
FIG. 15A depicts a schematic of the study design in mice, including administration of EcN or SYNB1353 ((lacI-Ptac, IPTG) 3×metDC (Q70D N82H; SEQ ID NO: 1048; engineered library); 1×metP (metagenomics library; *F. segetis*; SEQ ID NO: 1056); Δϕ; Δdap; ΔyjeH; Δpks) and time points of feces collection.
Figure 15B:
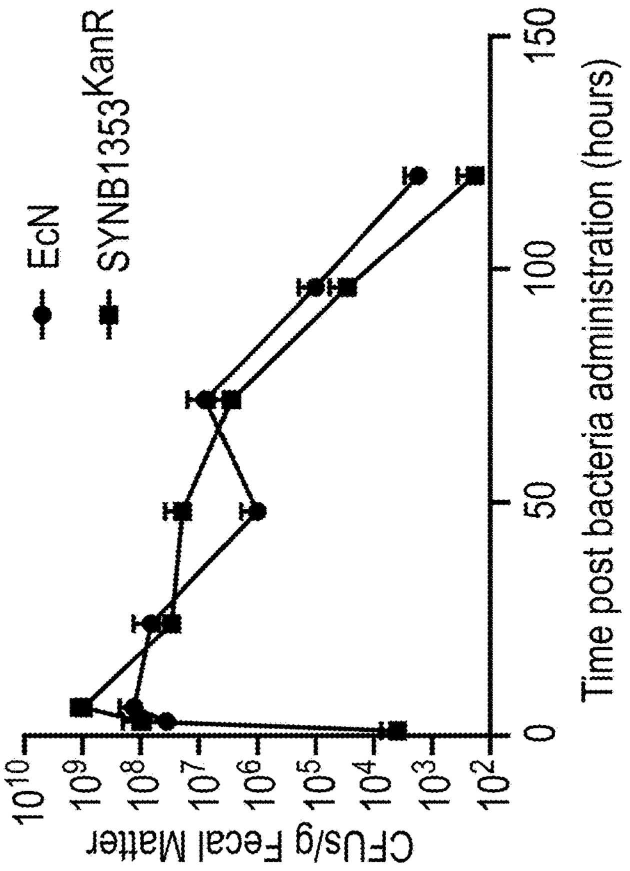
FIG. 15B depicts kinetics of fecal excretion in healthy male mice. Antibiotic resistant EcN or SYNB1353 ((lacI-Ptac, IPTG) 3×metDC (Q70D N82H; SEQ ID NO: 1048; engineered library); 1×metP (metagenomics library; *F. segetis*; SEQ ID NO: 1056); Δϕ; Δdap; ΔyjeH; Δpks) were orally administered at 1e10 CFU and fecal pellets collected at the indicated timepoints for CFU enumeration.
Figure 15C:
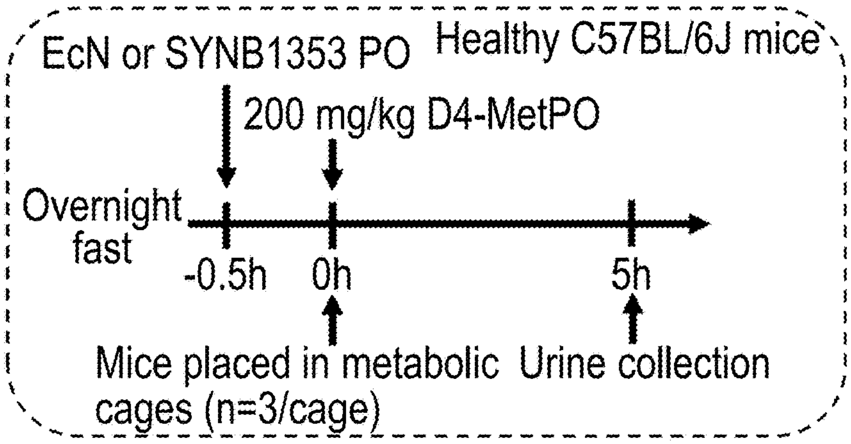
FIG. 15C depicts a schematic of the study design in mice, including administration of EcN or SYNB1353 ((lacI-Ptac, IPTG) 3×metDC (Q70D N82H; SEQ ID NO: 1048; engineered library); 1×metP (metagenomics library; *F. segetis*; SEQ ID NO: 1056); Δϕ; Δdap; ΔyjeH; Δpks) and time points for urine collection.
Figure 15D:
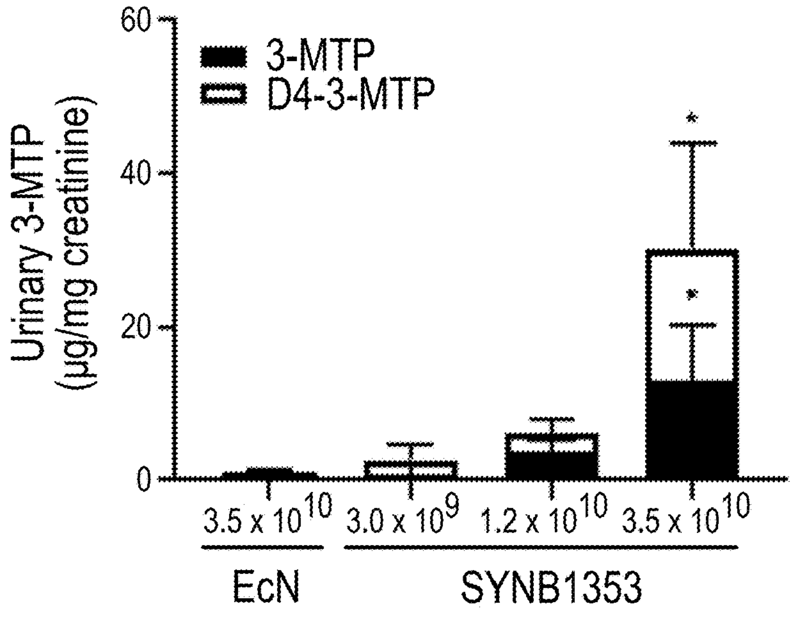
FIG. 15D is a graph showing the effects of SYNB1353 ((lacI-Ptac, IPTG) 3×metDC (Q70D N82H; SEQ ID NO: 1048; engineered library); 1×metP (metagenomics library; *F. segetis*; SEQ ID NO: 1056); Δϕ; Δdap; ΔyjeH; Δpks) on urinary recovery of 3-MTP in healthy mice. Mice received a single oral dose of bacteria followed by 200 mg/kg D4-methionine 30 minutes later. Mice were immediately placed in metabolic cages (n=3/cage) and urine collected 5 hours later. *$p<0.05$ versus EcN. 3-MTP: 3-methylthiopropylamine. Data presented as mean urinary 3-MTP recovery±standard error of the mean (n=18 mice/strain with 3 mice/cage). Statistical analysis was performed using one-way ANOVA followed by Dunnett's multiple comparison test. *$p<0.05$.
Figure 15E:
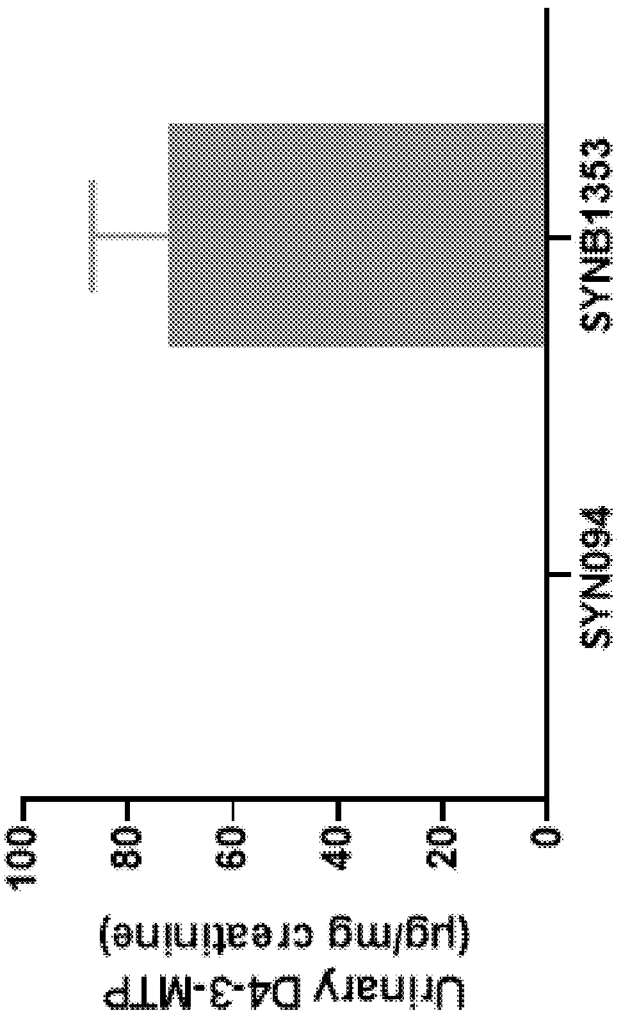
FIG. 15E depicts methionine load challenge at 200 mg/kg. D4-methionine was given at 200 mg/kg to mice via oral gavage at TO. SYNB1353 or SYN094 was administered at TO and T1. Urine was collected at 2 hours and urinary D4-3MTP was measured.

The effects of SYNB1353 on urinary recovery of 3-MTP and D4-3-MTP are shown in FIG. 15D. Urinary 3-MTP, D4-3-MTP, and creatinine were quantified by LC-MS/MS, and the ratio of metabolites to creatinine determined. Overall, the urinary recovery of 3-MTP in healthy mice was low but detectable, and only mice receiving SYNB1353 at 3.5×10^10 live cells registered 3-MTP concentrations above the lower limit of quantitation (LLOQ) of the assay (0.16 μg/mL). SYNB1353 dose-dependently increased the recovery of both 3-MTP and D4-3-MTP, indicating conversion of both endogenous and orally administered methionine by SYNB1353 in the gut. At the highest dose tested, SYNB1353 resulted in a statistically significant 25- and 61-fold increase in urinary recovery of 3-MTP and D4-3-MTP, respectively, as compared to SYN094.

In conclusion, this study indicates that SYNB1353 can dose-dependently convert both endogenous and dietary methionine into 3-MTP.

Example 10. Development of an Acute Model of Homocystinuria in Healthy Nonhuman Primates The objective of this study was to develop an acute model of homocystinuria in nonhuman primates. Male cynomolgus monkeys of approximately 2-5 years of age (average weight of 3.4 kg) were fasted overnight and orally administered a methionine load at 100 or 300 mg/kg, and plasma was collected at 0-, 0.5-, 1-, 2-, 4-, 6-, and 24-hours post-dose for methionine and total homocysteine measurements by LC-MS/MS.

Figure 16A:
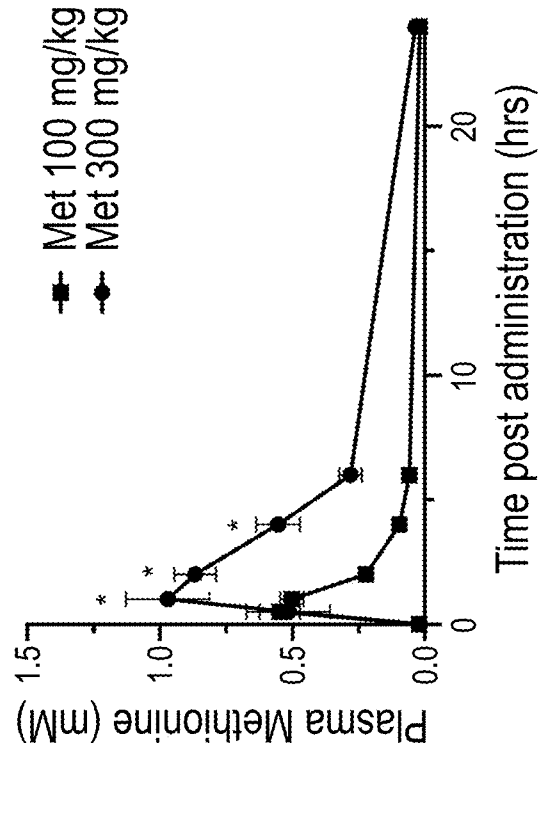
FIGS. 16A and 16B are graphs showing the effects of methionine load (administration of 100 mg/kg or 300 mg/kg methionine (Met)) on plasma Methionine (FIG. 16A) and plasma total homocysteine (FIG. 16B) in healthy nonhuman primates. Data presented as mean±standard error of the mean (n=6/group). Statistical analysis was performed using two-way repeated ANOVA with Sidak's multiple comparison test. *p<0.05 versus 100 mg/kg methionine.
Figure 16B:
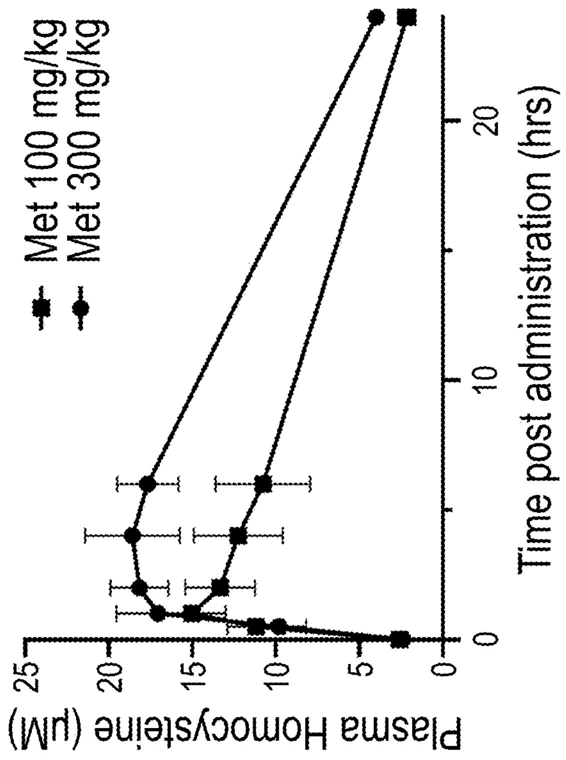

Oral administration of methionine (100 or 300 mg/kg) resulted in a dose-dependent increase in plasma methionine levels, with peak concentration recorded at 30 minutes and 1 hour post dose for 100 mg/kg and 300 mg/kg, respectively (FIG. 16A). Plasma methionine concentrations gradually decreased over time and reached pre-dose levels by 24 hours. The oral methionine load also resulted in a significant elevation in total plasma homocysteine by 30 minutes post dose, but no statistically significant difference between groups was noted (FIG. 16B). By 24 hours, total homocysteine levels had returned to baseline values for both groups. In conclusion, this study indicates that oral administration of a methionine load to nonhuman primates leads to acute homocystinuria.

Example 11. Activity of SYNB1353 on Plasma Methionine and Plasma Homocysteine Levels in Nonhuman Primates Receiving Different Methionine Loads The objective of this study was to assess the ability of SYNB1353 to metabolize methionine in an acute model of homocystinuria in nonhuman primates. SYNB1353 activity was assessed following a single dose of 1×10 live cells compared to vehicle in order to determine the impact of the combined EcN chassis and methionine engineering in this model.

Male cynomolgus monkeys were fasted overnight and orally administered a methionine load (100 or 300 mg/kg) followed by sodium bicarbonate (1.8 mmol), and formulation buffer (vehicle), or SYNB1353 at 1×10 live cells. Plasma was collected at 0, 0.5, 1, 2, 4, and 6-hours post-dose for methionine and total homocysteine measurements and cumulative urine was collected at 6 hours for 3-MTP recovery (and normalized to creatinine levels to account for differences in urinary volumes). Metabolites were measured using LC-MS/MS.

Figure 17A:
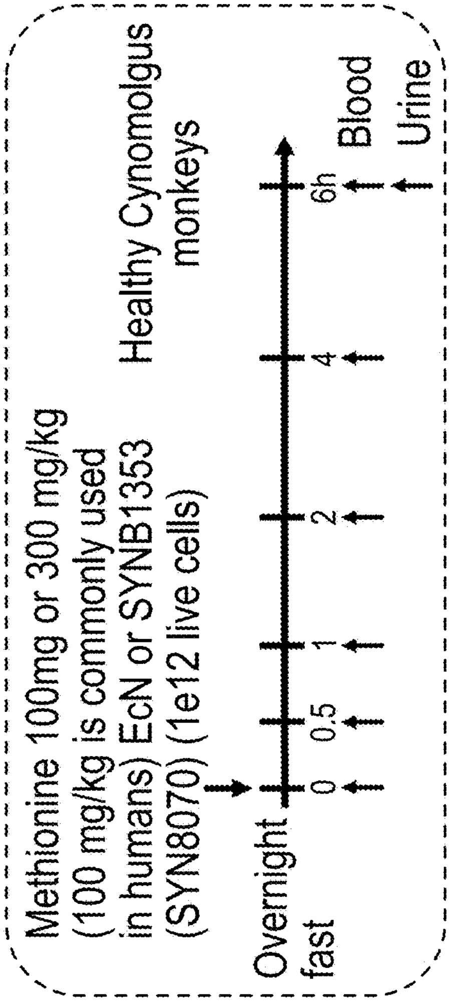
FIG. 17A depicts nonhuman primate study design. Male cynomolgus monkeys (2-5 years old) were fasted overnight and received an oral methionine load (100 or 300 mg/kg) and vehicle or bacteria (1e12 live cells). Plasma was collected throughout, and urine was recovered 6 hours post dosing.
Figure 17B:
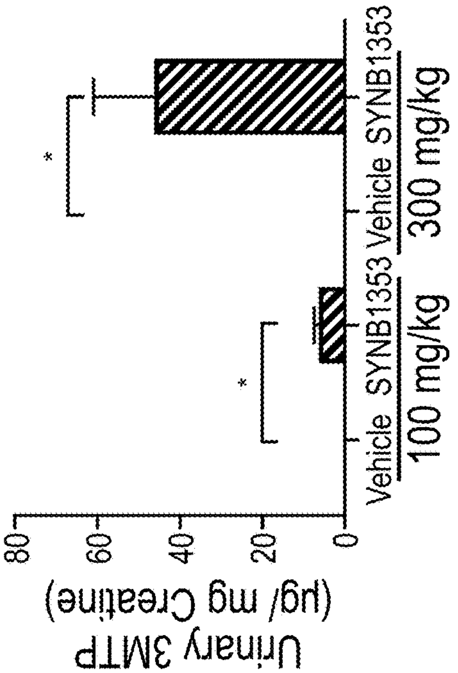
FIGS. 17B-17D are graphs showing SYNB1353 ((lacI-Ptac, IPTG) 3×metDC (Q70D N82H; SEQ ID NO: 1048; engineered library); 1× metP (metagenomics library; *F. segetis*; SEQ ID NO: 1056); Δϕ; Δdap; ΔyjeH; Δpks) is active in a nonhuman primate model of acute homocystinuria as evidenced by (1) urinary 3-MTP recovery at 6 hours post-dosing with vehicle, or SYNB1353 at 1e12 live cells administered concomitantly with 100 mg/kg or 300 mg/kg methionine (FIG. 17B); (2) plasma methionine (FIG. 17C) and plasma homocysteine (FIG. 17D) at 0.5, 1.0, 2.0, 4.0, and 6.0 hours post-dosing with vehicle, or SYNB1353 at 1e12 live cells administered concomitantly with 100 mg/kg or 300 mg/kg. Data presented as mean±standard error of the mean (n=12/group for 100 mg/kg methionine, n=6/group for 300 mg/kg methionine). Statistical analysis was performed using unpaired t-test with Welch's correction (FIG. 17B) and two-way ANOVA with Sidak's multiple comparison test (FIG. 17C, FIG. 17D). *p<0.05.
Figure 17C:
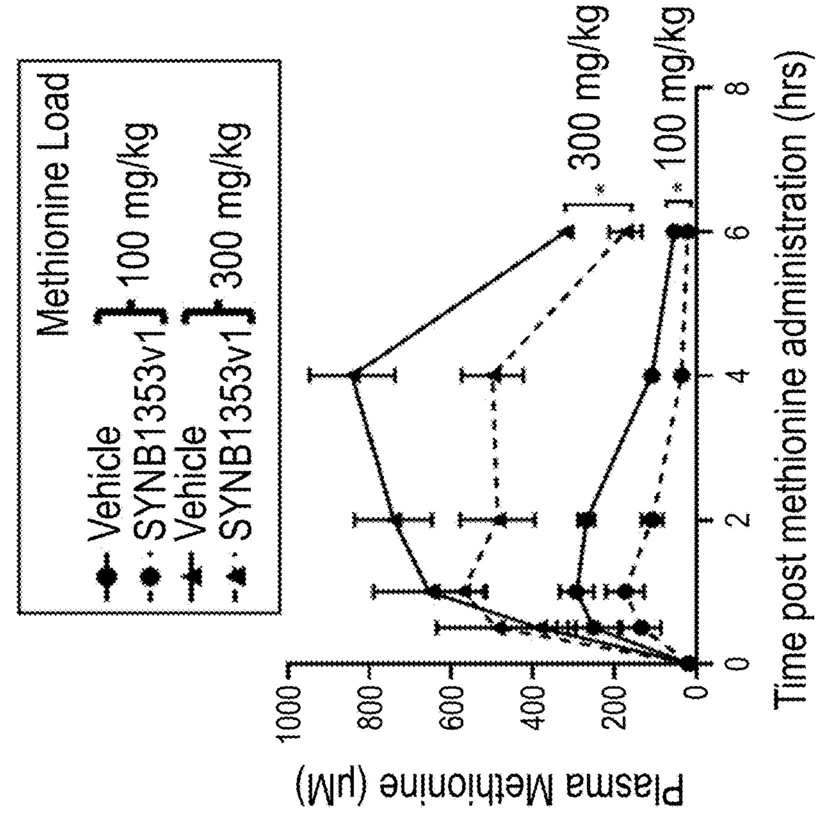
Figure 17D:
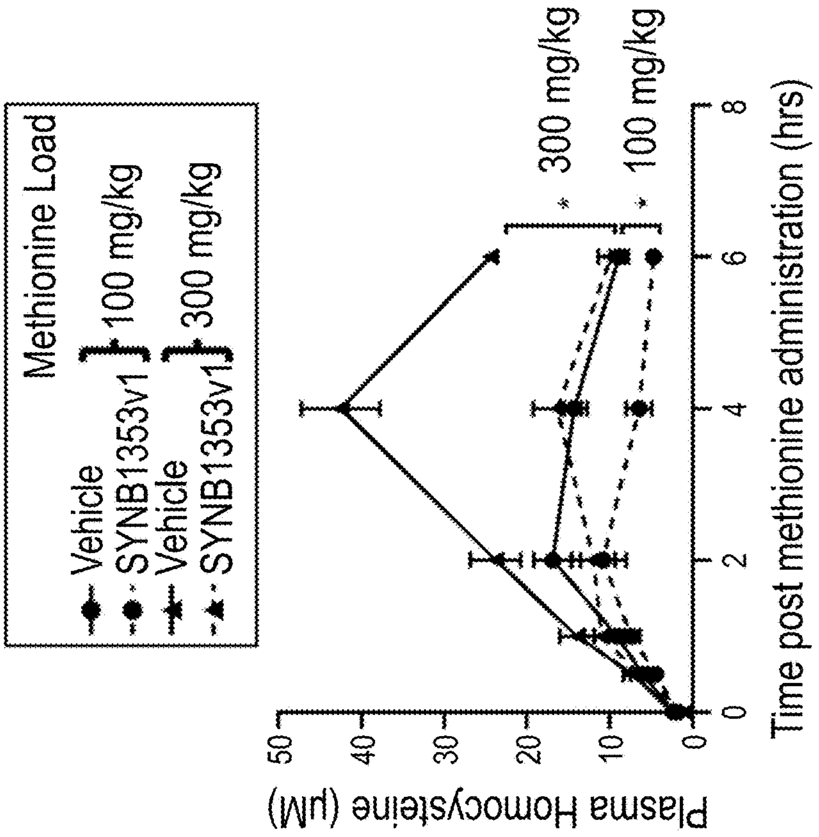

Administration of SYNB1353 resulted in a significant and treatment-related elevation in urinary 3-MTP levels as compared to vehicle, suggesting conversion of methionine by the strain in the gut (FIG. 17B). As shown in FIG. 17C and FIG. 17D, SYNB1353 significantly blunted the plasma appearance of methionine and total homocysteine at both methionine loads, with a 42% and 55% reduction in plasma total homocysteine area under the curve (AUC) compared to vehicle. In conclusion, these data indicate that SYNB1353 is capable of consuming methionine in the gut of nonhuman primates with acute homocystinuria.

Example 12. Dose-Response of SYNB1353 in Nonhuman Primates Receiving a Methionine Load The objective of this study was to evaluate the dose-response of SYNB1353 and assess the specific effect of methionine engineering against a control strain (SYN094) in an acute model of homocystinuria in nonhuman primates.

Male cynomolgus monkeys were fasted overnight and orally administered a methionine load (100 mg/kg) followed by sodium bicarbonate (1.8 mmol), and formulation buffer (vehicle), SYN094, or SYNB1353 at 5×10^11 or 1×10^12 live cells. Two sets of 3 studies were conducted in a cross-over manner so that all 12 colony animals received each treatment. Plasma was collected at 0-, 0.5-, 1-, 2-, 4-, and 6-hours post-dose for methionine and total homocysteine measurements and cumulative urine was collected at 6 hours for 3-MTP recovery (and normalized to creatinine levels to account for differences in urinary volumes). Each set of 3 studies was normalized to its respective vehicle for data representation.

Figure 18A:
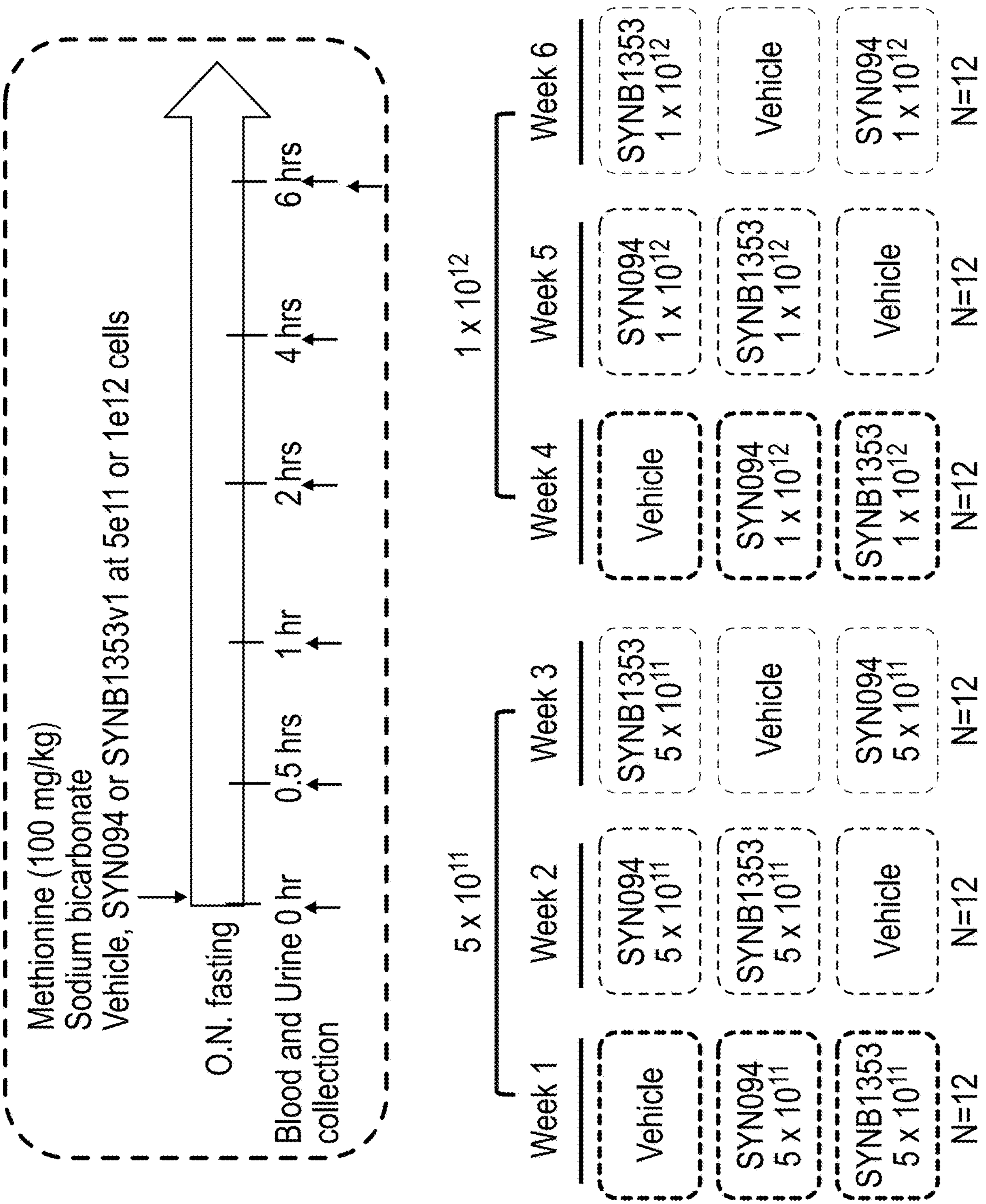
FIGS. 18A-18D depict schematics showing the experimental outline (FIG. 18A) and dose-dependent effect of SYNB1353 ((lacI-Ptac, IPTG) 3×metDC (Q70D N82H; SEQ ID NO: 1048; engineered library); 1× metP (metagenomics library; *F. segetis*; SEQ ID NO: 1056); Δϕ; Δdap; ΔyjeH; Δpks) as evidenced by (1) increased urinary recovery of 3-MTP (FIG. 18B) and decreased plasma methionine (FIG. 18C) and plasma total homocysteine (FIG. 18D) in a nonhuman primate model of acute homocystinuria. 3-MTP: 3-methylthiopropylamine. Data was normalized to the study-respective vehicle and presented as mean±standard error of the mean (n=12/group). Statistical analysis was performed using paired t-test. *p<0.05.
Figure 18B:
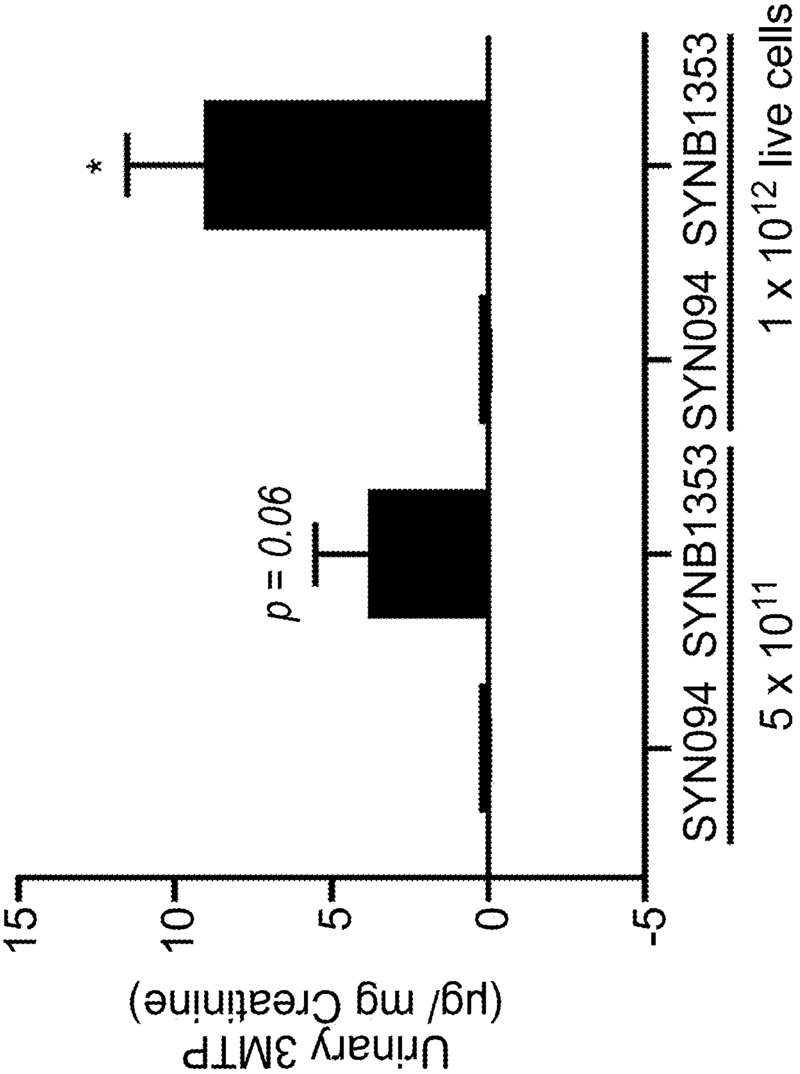
Figure 18C:
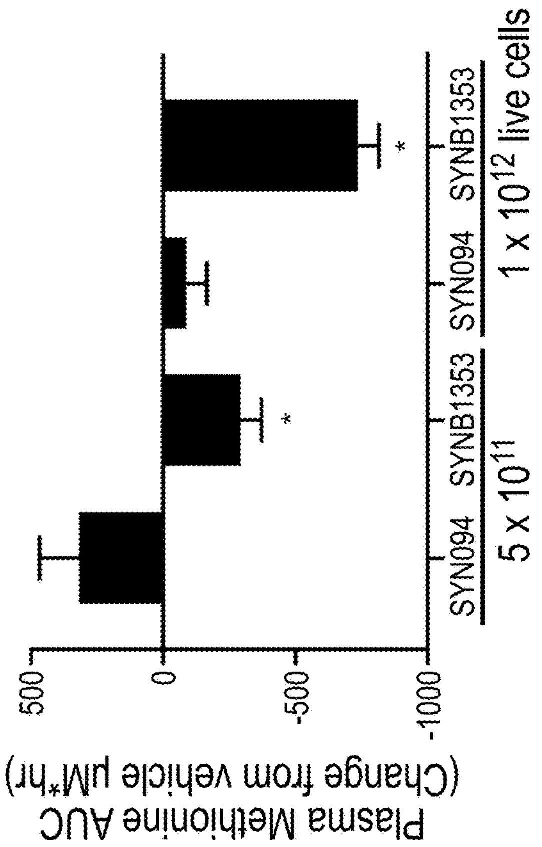
Figure 18D:
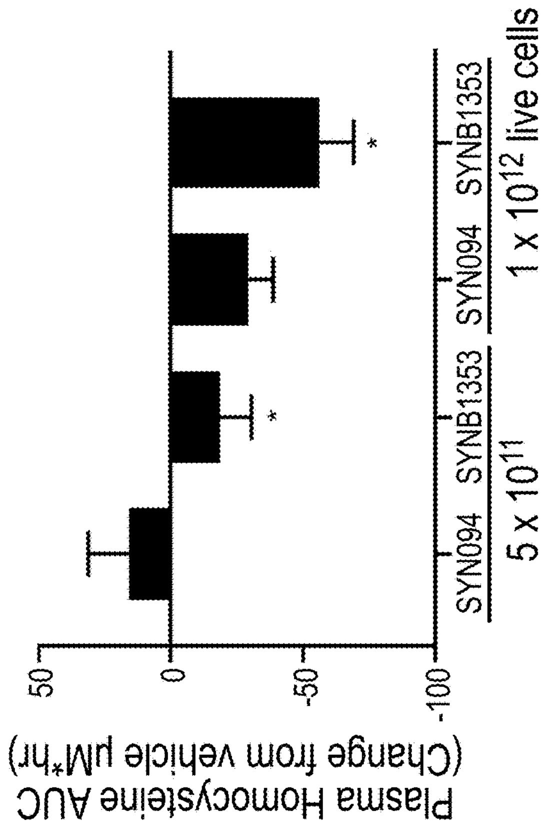
Figure 19A:
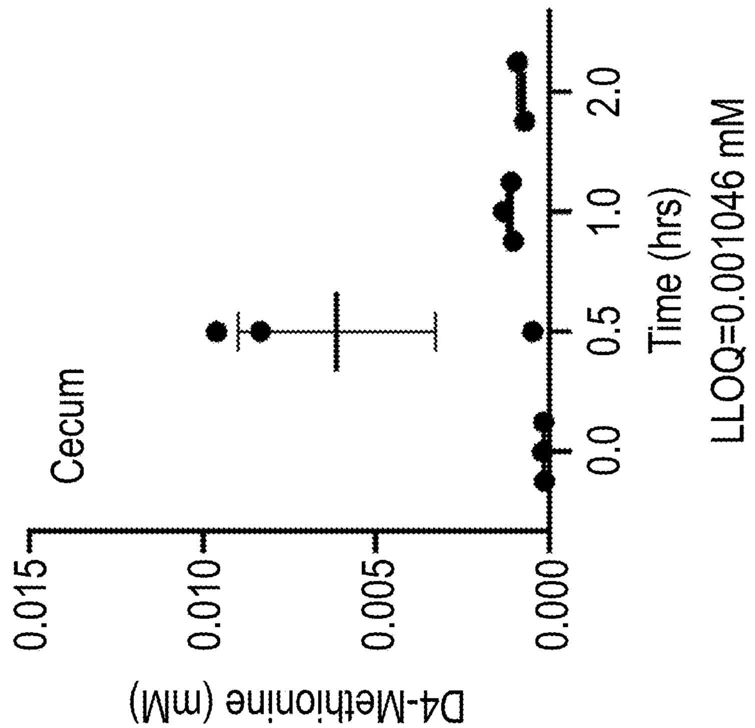
FIGS. 19A-19D are graphs showing levels of D4-methionine over time in the effluents of the cecum (FIG. 19A), and effluents of the colon (FIG. 19B), in the plasma (FIG. 19C) and small intestine effluents (FIG. 19D) of C57BL/6 mice having received a single IP dose of D4-methionine (100 mg/kg).
Figure 19B:
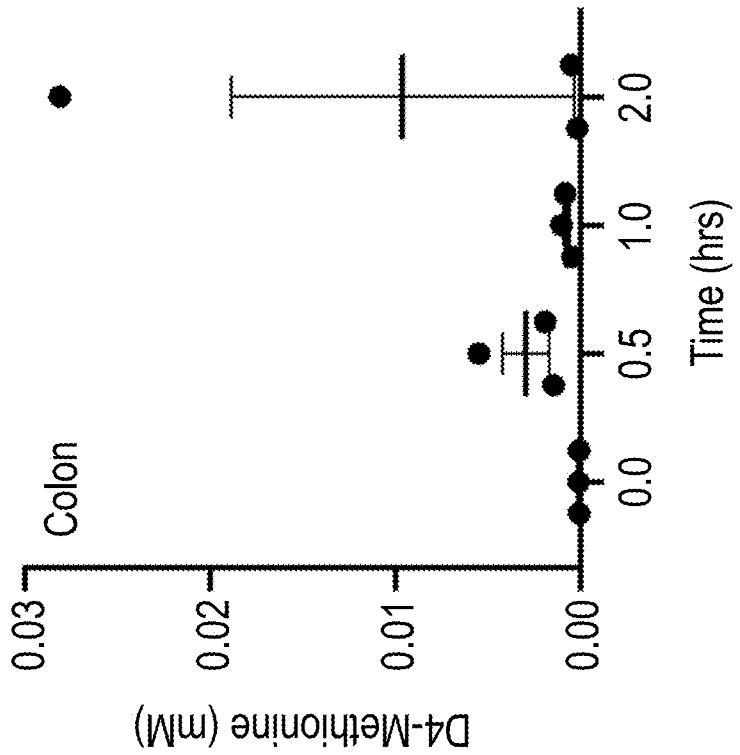
Figure 19D:
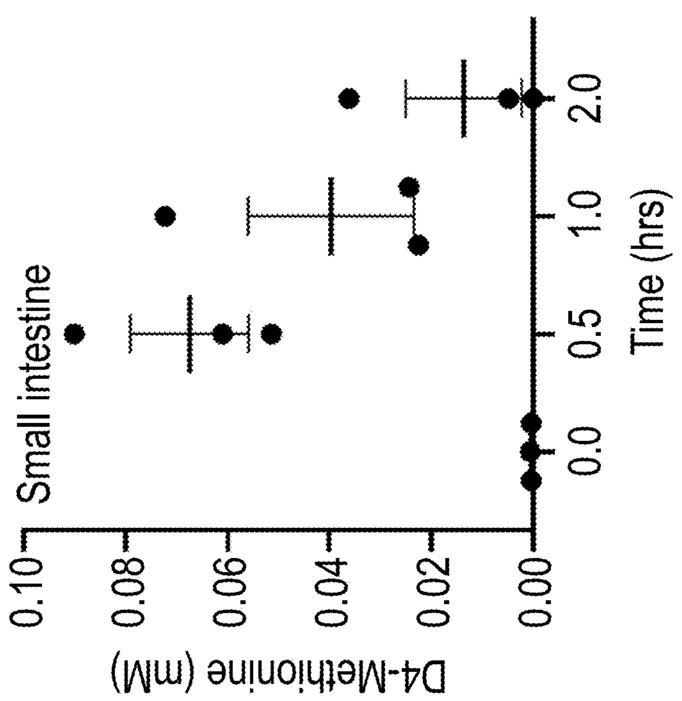
Figure 19C:
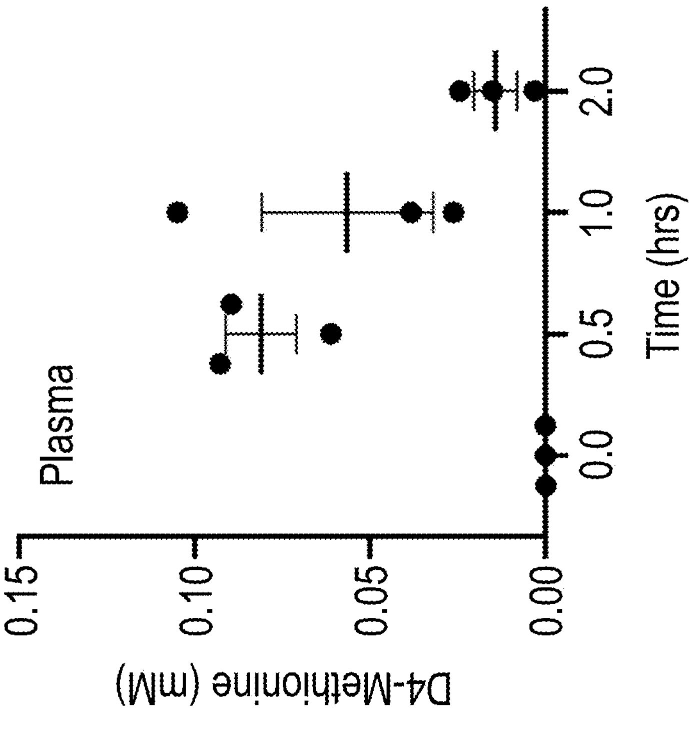

Administration of SYNB1353 resulted in a dose-dependent elevation in urinary 3-MTP levels as compared to SYN094, suggesting that the methionine-metabolizing pathway engineered in SYNB1353, and not the bacterial chassis itself, was responsible for methionine metabolism in the gut (FIG. 18B). As shown in FIG. 18C and FIG. 18D, SYNB1353 dose-dependently blunted the plasma appearance of methionine and total homocysteine in this model as compared to SYN094. In conclusion, these data indicate that the engineering of SYNB1353 is responsible for methionine consumption in the gut of nonhuman primates with acute homocystinuria and results in a dose-dependent blunting of plasma total homocysteine appearance in the blood.

Example 13. In Vivo Evaluation of Methionine Consumption of Engineered *E. coli* Strains after Systemic Administration of Methionine The objectives of this study were to determine (1) whether enterorecirculation of methionine occurs, and (2) whether orally-administered SYNB1353 can consume peripherally administered (IP) labeled methionine in mice.

In a first study, healthy male C57BL/6 mice (n=3/group) were fasted overnight and received a single IP dose of D4-methionine (100 mg/kg). Blood and gut effluents (SI, cecum or colon) were collected at 0, 0.5, 1, or 2 hours post dosing for D4-methionine measurements. Results shown in FIGS. 19A-19D indicate that there is enterorecirculation of methionine from the plasma into the gut.

Figures 20A, 20B, 20C:
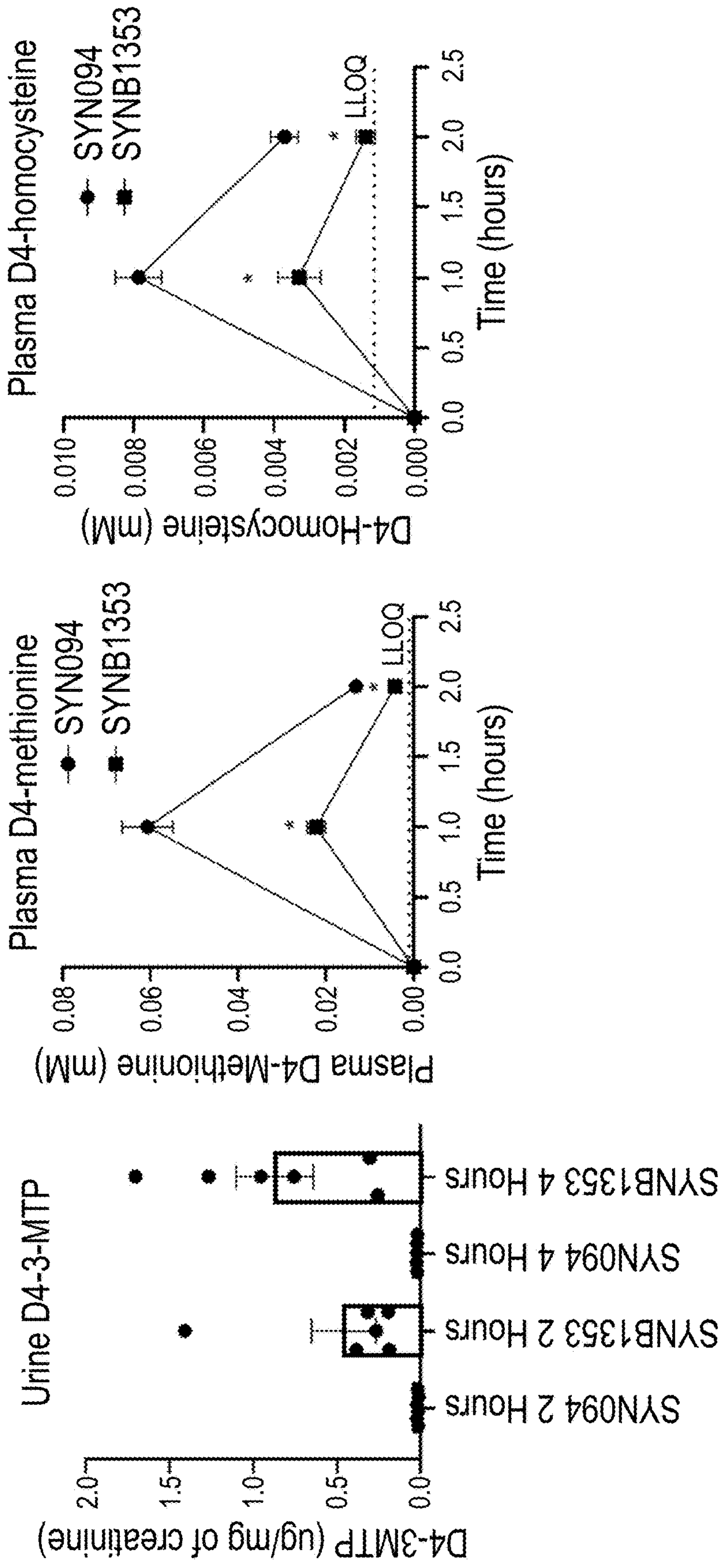
FIG. 20A is a graph showing levels of D4-3-MTP in the urine over time in C57BL/6 mice having received a single IP dose of D4-methionine (100 mg/kg) followed by 2 oral doses of SYN094 (wild type *E. coli* Nissle) or SYNB1353 ((lacI-Ptac, IPTG) 3×metDC (Q70D N82H; SEQ ID NO: 1048; engineered library); 1× metP (metagenomics library; *F. segetis*; SEQ ID NO: 1056); Δϕ; Δdap; ΔyjeH; Δpks) at 0.5 and 1.5 hours post IP injection.
FIGS. 20B and 20C are graphs showing levels of plasma D4-methionine (FIG. 20B) and D4-homocysteine (FIG. 20C) over time in C57BL/6 mice having received a single IP dose of D4-methionine (100 mg/kg) followed by 2 oral doses of SYN094 (wild type *E. coli* Nissle) or SYNB1353 ((lacI-Ptac, IPTG) 3×metDC (Q70D N82H; SEQ ID NO: 1048; engineered library); 1× metP (metagenomics library; *F. segetis*; SEQ ID NO: 1056); Δϕ; Δdap; ΔyjeH; Δpks) at 0.5 and 1.5 hours post IP injection.
Figure 21B:
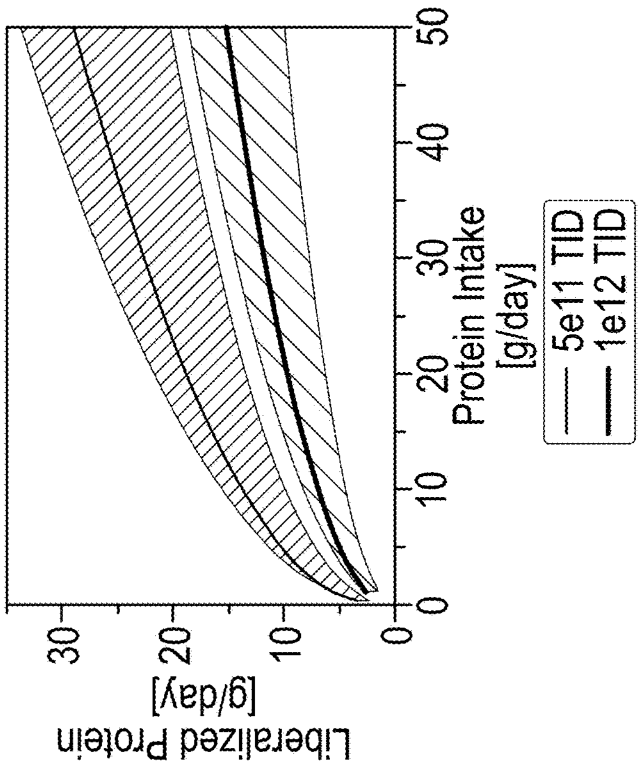
FIG. 21B depicts a graph showing modeling of simulated protein liberalization by SYNB1353 ((lacI-Ptac, IPTG) 3×metDC (Q70D N82H; SEQ ID NO: 1048; engineered library); 1×metP (metagenomics library; *F. segetis*; SEQ ID NO: 1056); Δϕ; Δdap; ΔyjeH; Δpks) dosing at 5e11 or 1e12 live cells TID as a function of current protein intake. Solid lines: best-guess SYNB1353 activity; shaded regions: uncertainty in SYNB1353 activity.
Figure 21A:
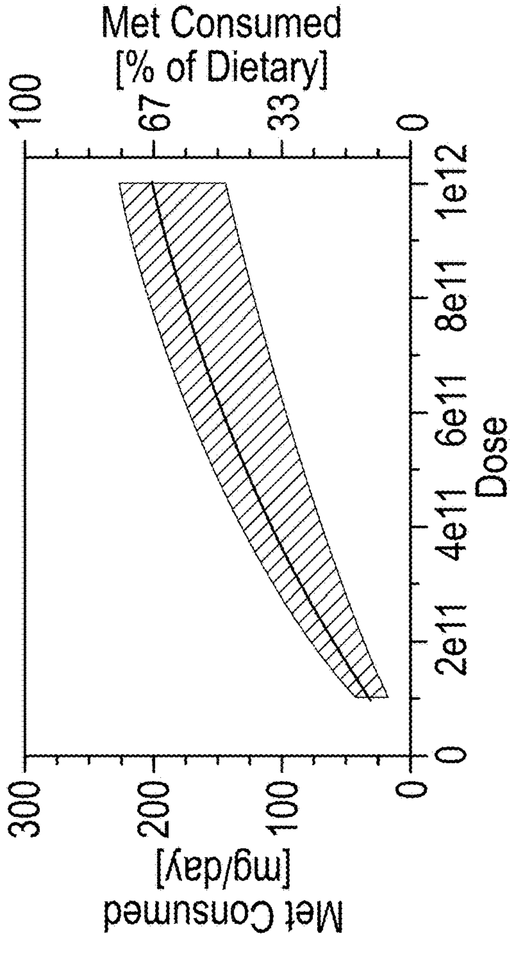
FIG. 21A depicts a graph modeling predicted methionine consumption by SYNB1353 ((lacI-Ptac, IPTG) 3×metDC (Q70D N82H; SEQ ID NO: 1048; engineered library); 1×metP (metagenomics library; *F. segetis*; SEQ ID NO: 1056); Δϕ; Δdap; ΔyjeH; Δpks) as a function of TID dose for an HCU patient consuming 300 mg/day of methionine. Solid line: best-guess SYNB1353 activity; shaded region: uncertainty in SYNB1353 activity.
Figure 21C:
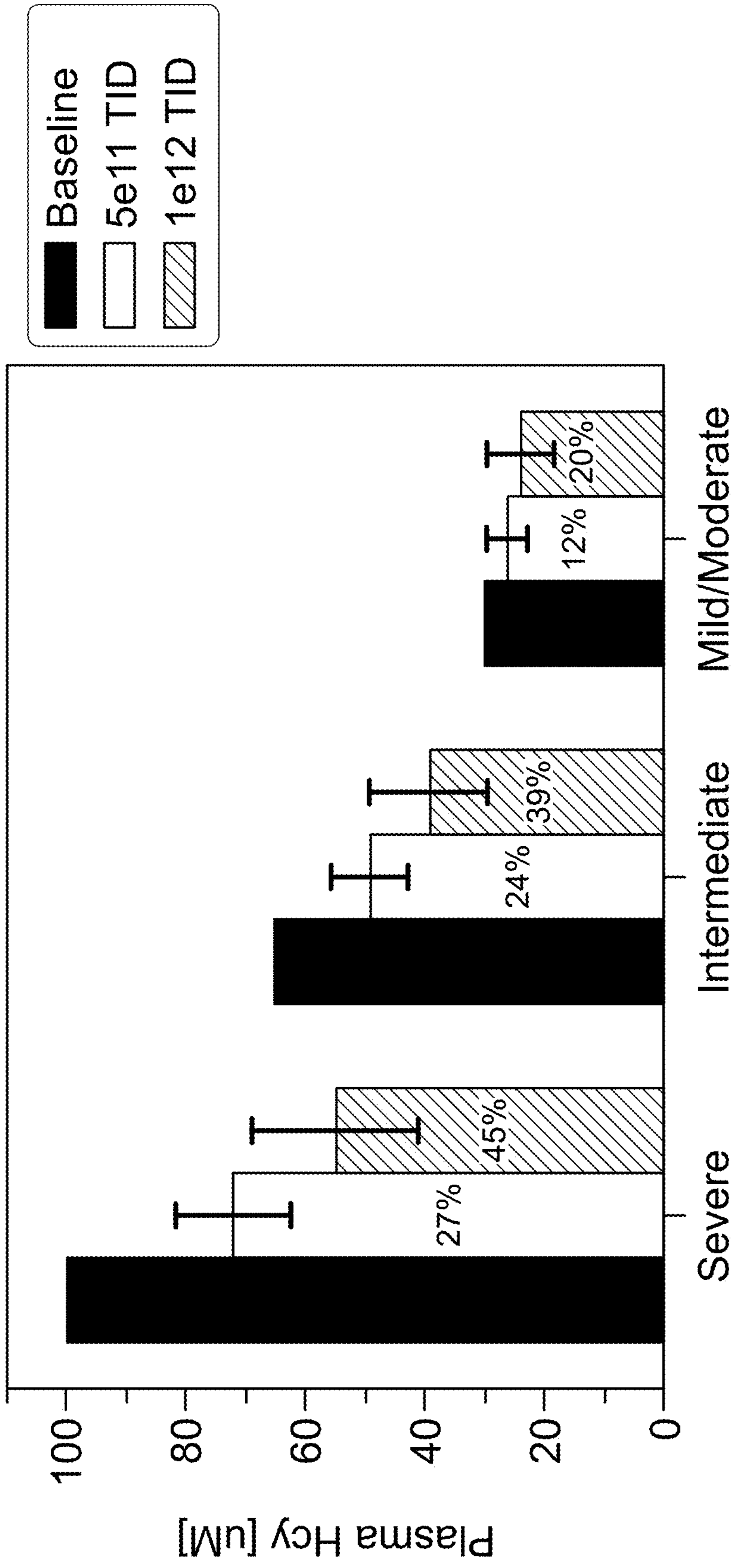
FIG. 21C depicts a graph showing modeling of plasma homocysteine at baseline and after SYNB1353 ((lacI-Ptac, IPTG) 3×metDC (Q70D N82H; SEQ ID NO: 1048; engineered library); 1× metP (metagenomics library; *F. segetis*; SEQ ID NO: 1056); Δϕ; Δdap; ΔyjeH; Δpks) dosing at 5e11 or 1e12 live cells TID as a function of disease severity. Error bars: uncertainty in HCU patient physiology; annotations: percent lowering of plasma homocysteine.
Figure 22A:
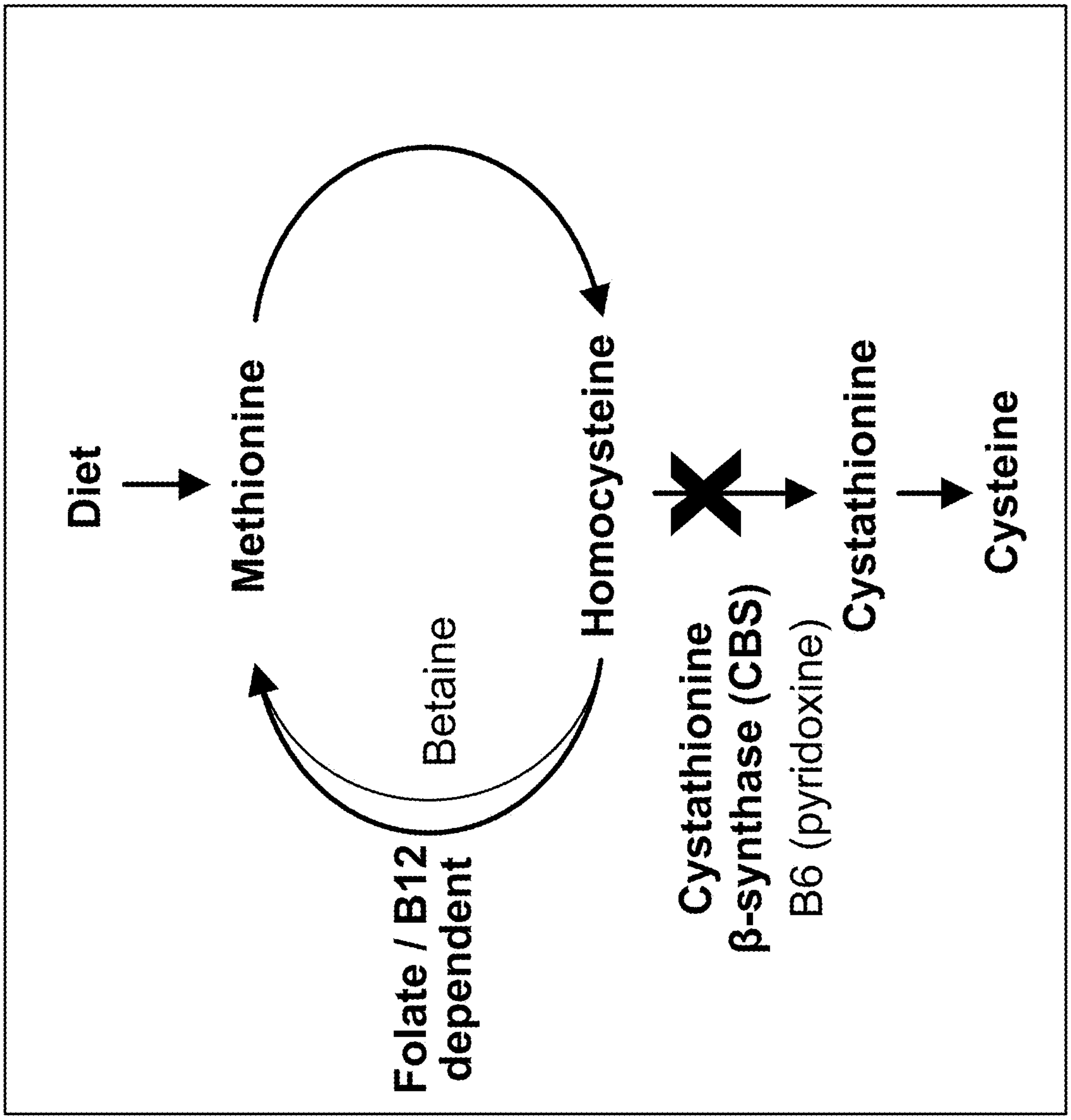
FIG. 22A depicts a schematic showing the pathway for cysteine and cystine production in humans via the metabolism of methionine through a trans-sulfuration pathway.
Figure 22B:
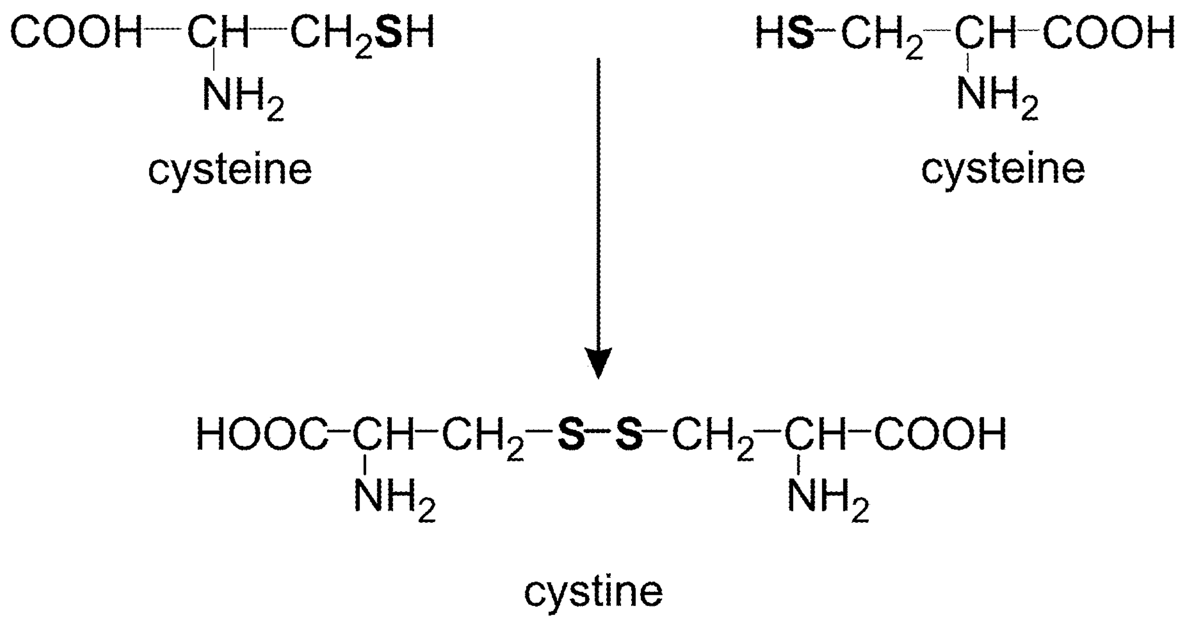
FIG. 22B is a schematic showing the formation of cystine, a cysteine dimer, which builds up in the urine of subjects having cystinuria and forms crystals or stones (urolithiasis).

In a second study, healthy male C57BL/6 mice (n=10-18/group) were fasted overnight and received a single IP dose of D4-Met (100 mg/kg) followed by 2 doses of SYNB1353 PO 0.5 and 1.5 hours later. Blood and urine were collected for D4-Met, D4-tHcy and D4-3-MTP measurements. Results are shown in FIGS. 20A-20C and illustrate that SYNB1353 is capable of consuming peripherally-administered labeled methionine and blunts plasma labeled methionine and labeled homocysteine levels.

Example 14. Effect of Methionine-Restricted Diet in a Mouse Model of Cystinuria Cystinuria is a genetic disorder of amino acid import in the kidney characterized by excessive excretion of cystine, and dibasic amino acids (ornitihine, lysine, and arginine) in the urine, and cystine stone formation in the urinary tract.

Figure 23:
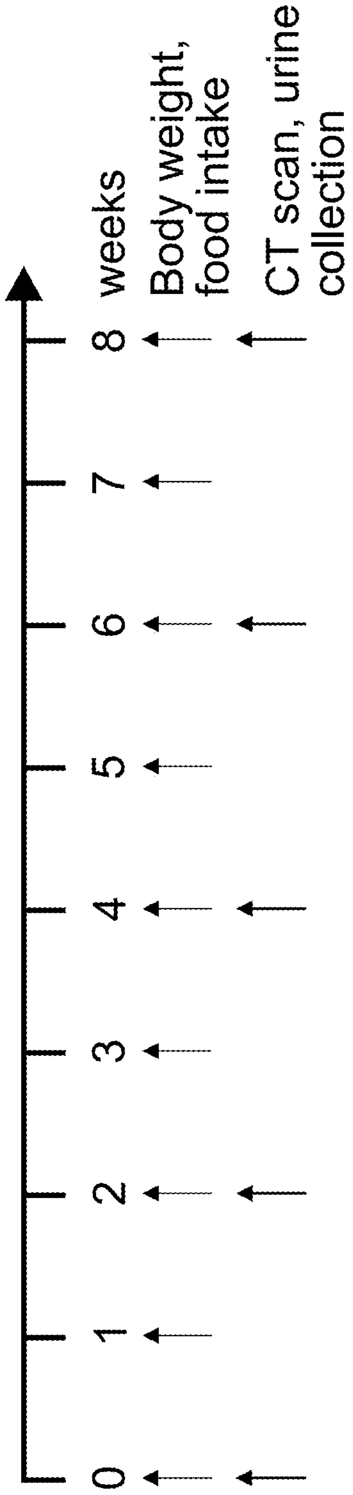
FIG. 23 depicts a schematic showing the outline of a mouse study in which SLC3A1 KO fed a high- (0.62%) or low-methionine (0.12%) diet for 8 weeks. Time points are indicated at which body weight and food intake are measured, urine is collected, and CT scans are performed.

The potential of a methionine consuming strain described herein to treat, prevent, or reduce cystinuria was evaluated by analyzing the effect of a methionine restricted diet in a Slc3a1 knockout (KO) mouse model for cystinuria. Slc3a1 KO mice were subjected to a reduction in the methionine content of diet from the standard 0.62% to 0.12% for eight weeks, and cysteine as well as cystine levels in urine and plasma, and stone formation in the bladder were evaluated according to a scheme shown in FIG. 23.

Cystine stone formation was not observed in any of the twelve mice on the low-methionine diet. In contrast, bladder stones were observed in nine out of twelve mice (75%) on the 0.62% diet. Time of stone formation ranged from 2-8 weeks following diet treatment.

These data suggest that a treatment resulting in a reduction in plasma or urinary methionine, e.g., administration of a methionine-consuming strain described herein, is a promising approach for the treatment of cystinuria.

Methods

Mouse Breeding and Diet Modification

KO mice were generated using Slc−/−×Slc−/− matings and one-half of the male mice from a given litter were used for the 0.12% methionine study and the other half for the 0.62% study. Mice were identified using ear tags. One group of KO mice (N=12, age six weeks) was placed on a diet containing 0.12% methionine and another group on a diet containing 0.62% methionine. A third group of WT mice was placed on the 0.62% methionine diet. Both diets contained 10 kcal % fat. The 0.62% methionine diet is equivalent to the regular mouse diet with respect to methionine content, whereas the 0.12% diet is approximately 20% of regular methionine content.

Computed Tomography

KO mice were scanned by computed tomography (CT) on the Albira PET/CT system (Bruker Corporation) and only mice showing no evidence of stone at the age of six weeks were used for the diet studies. KO mice were then scanned every two weeks and bladder stone volume determined using the VivoQuant software (from Invicro) installed on the CT scanner. WT mice were not scanned.

Body Weight, Food Consumption, and Urine Collection

Mice were weighed and urine collected at baseline. The amount of food added per cage was also weighed. Mice were maintained on the above diets for eight weeks and the amount of food in each cage weighed weekly. There were three or four mice per cage. From these data, the average food consumption per mouse per day was calculated. Water was provided ad libitum, but water consumption was not measured. Mice were then weighed weekly and urine collected every two weeks. Urine samples were stored at −80° C.

Mouse Sacrifice, Blood Collection, and Plasma Separation

Mice were sacrificed using CO2 exposure at the end of the 8-week treatment period and blood was collected by cardiac puncture into heparin (green top tubes) from each of the low- and high-methionine groups and from nine WT mice. Plasma was separated by centrifugation and then stored at −80° C.

A couple of the KO mice on 0.12% methionine diet had lost 20% of their body weights and were therefore euthanized at the recommendations of veterinary staff.

Tissue Fixation and Storage

Kidneys, bladder, and a small portion of the liver were removed from each mouse and placed in 10% formalin.

Bladder Dissection and Stone Enumeration

After three days in formalin, bladders were dissected, and any stones removed and weighed. The dissected bladders were also weighed, photographed and then returned to formalin. Stone number and size distribution (based on surface area of the stone image) were determined using NIH Image J software.

Data Analysis

Where appropriate, data were analyzed using standard statistical techniques and a p value of <0.05 was considered significant.

Results

Body Weight

Figure 24A:
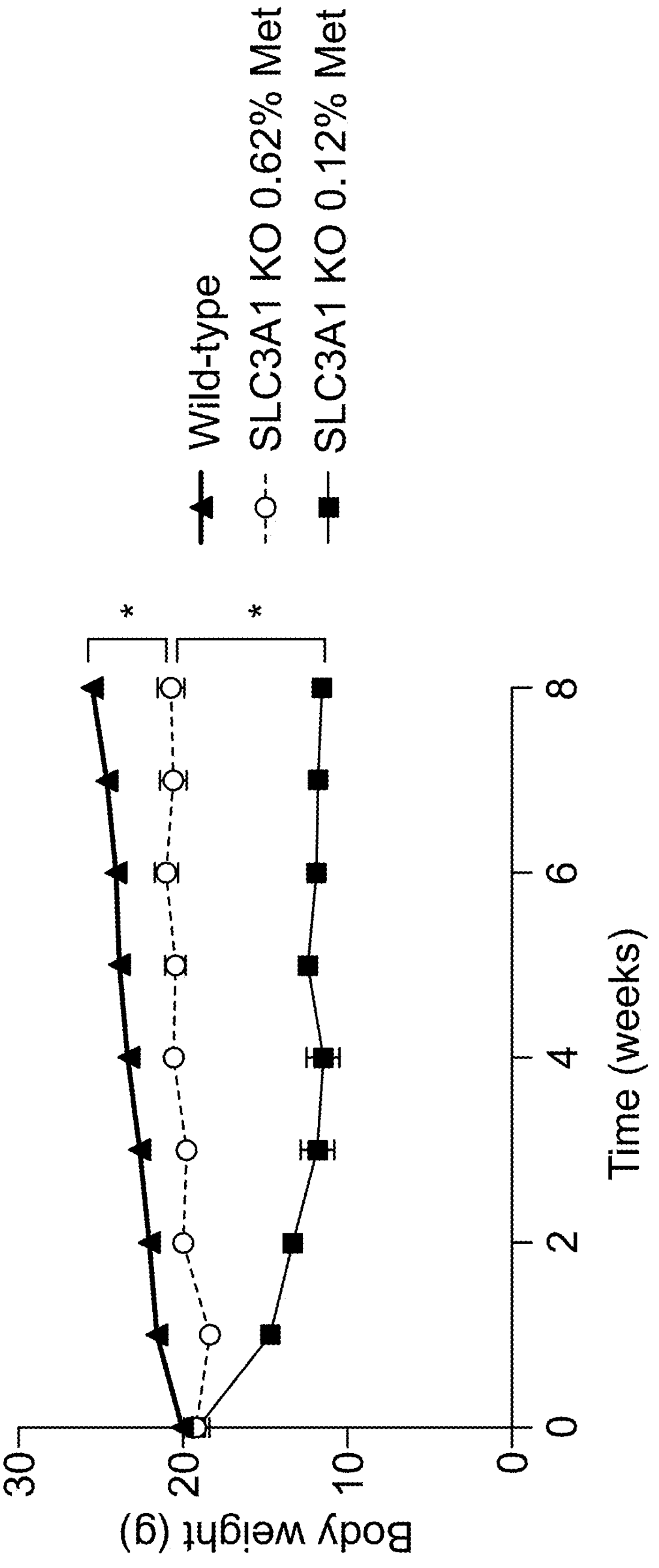
FIGS. 24A-24D depict graphs showing measurements obtained in the mouse study outlined in FIG. 23.

The average body weight in the two KO groups at the start of the study was 19.24 g, but there was a rapid decline in body weight to 14.73 g after one-week on the 0.12% diet (a loss of 23.4% relative to baseline). This was followed by a gradual decline over time, and the weight at eight weeks of treatment was 11.92 g (a loss of 38.0% relative to baseline). As indicated in the Methods section, two mice in this group were sacrificed at 3- and 8-weeks of treatment, respectively. By comparison, body weight of KO mice on the 0.62% diet increased over time, reaching 20.55 g after eight weeks of treatment (an increase of 6.81%). Results are shown in FIG. 24A.

Body weight in the WT mice on the 0.62% diet increased in a linear manner over time (black line), going from 20.48 g at baseline to 25.17 g after eight weeks (an increase of 22.9%).

Food Consumption

Figure 24B:
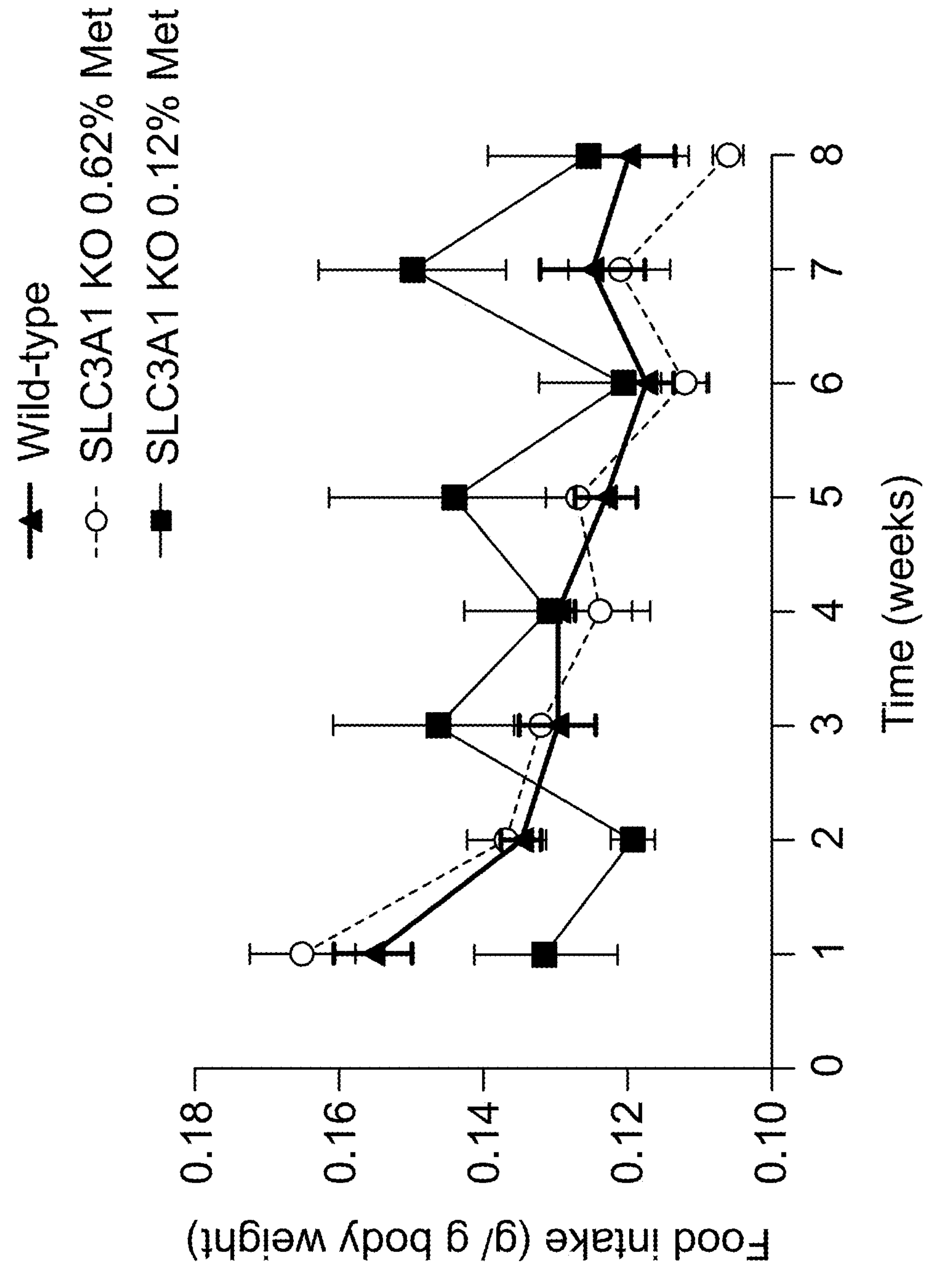

Three cages (with four mice per cage) were set-up for each of the 0.12% and 0.62% diets for the KO mice and four cages (with three mice per cage) were set-up for the 0.62% diet for WT mice. The average food consumption in the three groups was 1.68, 2.57, and 3.00 g/day/mouse, respectively. This may be related to differences in body weight among the three groups. Results normalized to body weight are shown in FIG. 24B.

CT Scanning

Figure 24C:
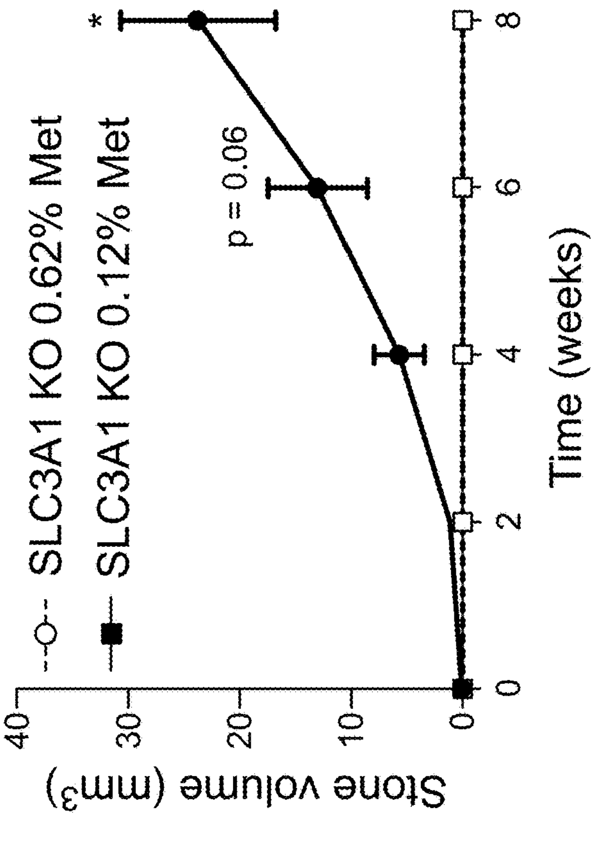

The KO mice on the 0.12 and 0.62% methionine diets were CT scanned every two weeks. Bladder stones were not detected in any mice on the 0.12% diet. Bladder stones were detected by CT in 7 of the 12 KO mice on the 0.62% diet and the onset of stone detection ranged from two weeks to eight weeks of dietary treatment. In two mice, stones were not detected by CT, but small amounts of stone material were present when the bladders were dissected. Therefore, nine of the 12 KO mice on the 0.62% diet demonstrated evidence of stone presence. Results are showing in FIG. 24C and graphs of stone volume versus treatment period were almost parallel, indicating that, once stone formation has started, the rate of stone volume increase was comparable in all seven mice in which stones were detected by CT.

Bladder and Stone Weight

As indicated above, stones were identified in bladders from nine KO mice on the 0.62% methionine diet (7 by CT and two following bladder dissection). In the absence of stones, bladder weight in these mice was typically 16 mg. In the presence of stones, bladders were enlarged, with bladder and stone weights ranging from 19.6-82.1 and 20.2-83.3 mg, respectively, in the seven mice with CT-verified stones.

Figure 24D:
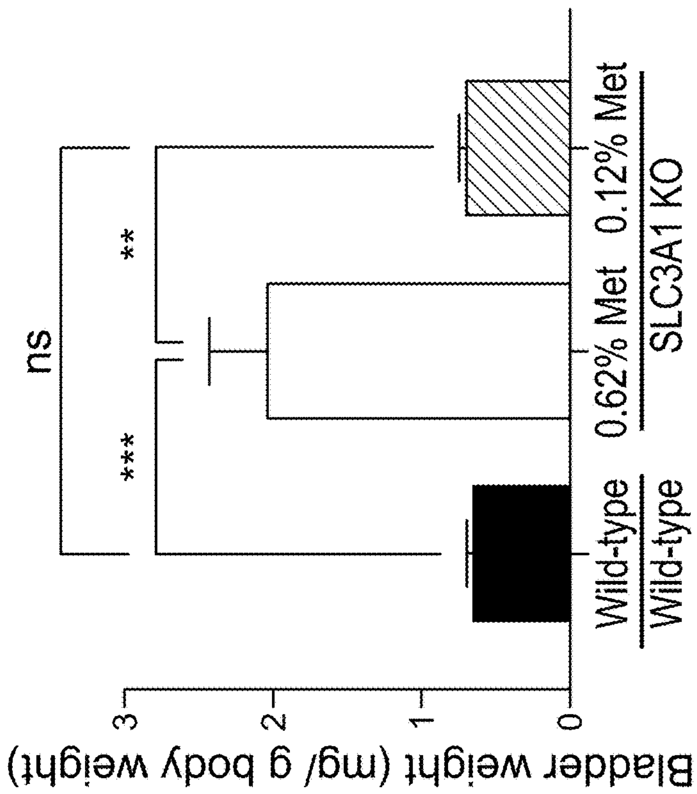

Bladder weight in the 11 KO mice on the 0.12% diet was in the range 5.7-11.0 g (mean=8.38, SD=1.45). Bladder weights normalized to body weight are shown in FIG. 24D.

Figure 25:
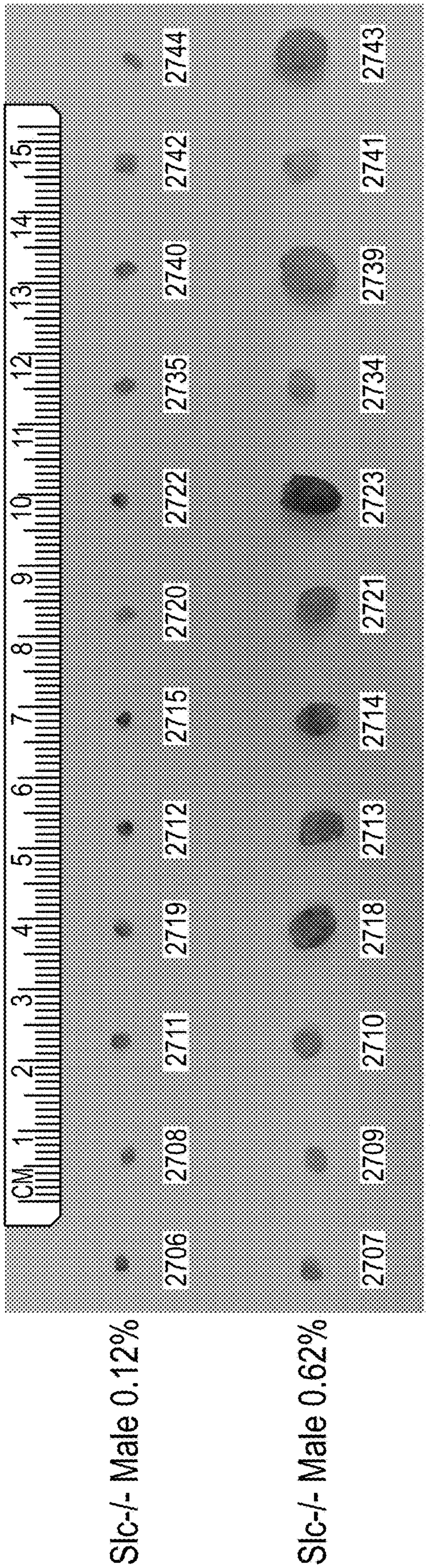
FIG. 25 depicts photographs showing bladder size of SLC3A1 KO mice on low-methionine diet (0.12%) as compared to non-restricted diet (0.62%) at 8 weeks.

Bladder weight in the 12 WT mice on the 0.62% diet was in the range 13.5-23.5 g, but Grubbs' test using GraphPad software (GraphPad.com/quickcalcs/) indicated that the bladder of mouse #2728 (23.5 g) was an outlier ($P<0.05$). It was therefore removed from the data, giving an adjusted mean and SD of 16.36 and 1.70, respectively. The difference in bladder weight of this mouse compared with the others is evident in the photographs of the bladders from KO mice on the 012% and 0.62% methionine diets (FIG. 25).

The difference in bladder weight between the KO mice on the 0.12% diet and WT mice on the 0.62% diet was statistically significant using the unpaired t-test ($P<0.0001$). This is due to the decrease in body weight in the KO mice on the 0.12% diet versus WT mice. As shown in FIG. 24D, when the bladder weight was normalized to total body weight, the difference in bladder weight between KO on 0.12% diet and WT was no longer significant.

Bladder Stone Enumeration

Stones from each of the nine mice were enumerated and the surface area of the stone image determined using NIH Image J software.

Figures 26A, 26B, 26C:
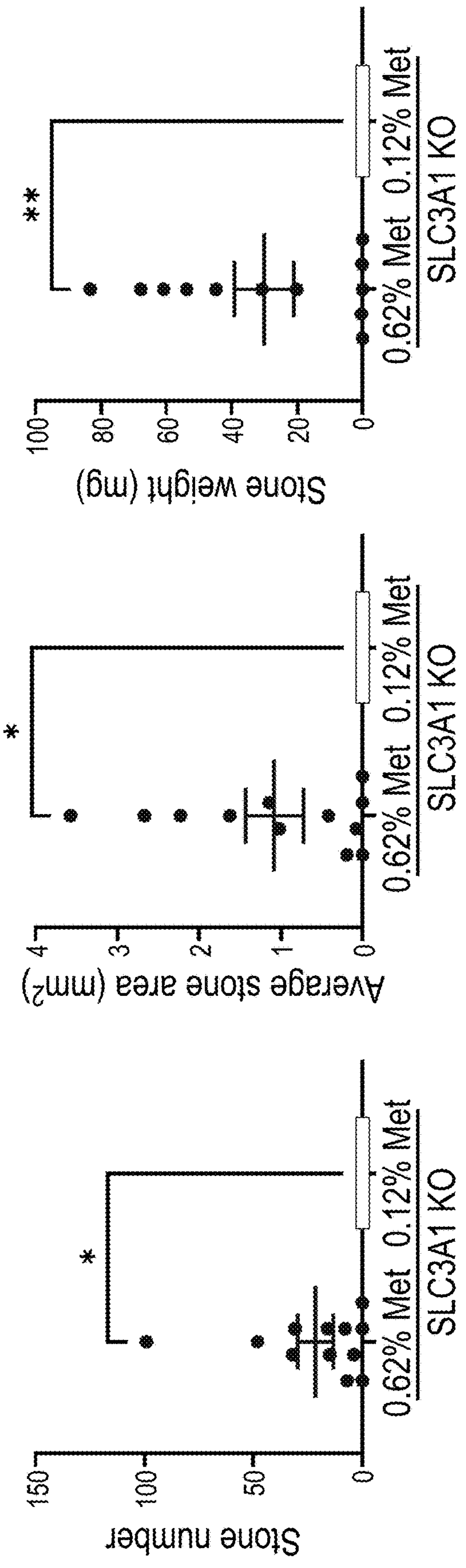
FIGS. 26A-26C depict graphs showing stone number (FIG. 26A), average stone area (FIG. 26B) and stone weight (FIG. 26C) in SLC3A1 KO mice on low-methionine diet (0.12%) and non-restricted diet (0.62%) at 8 weeks.

Stone number, average stone area, and stone weight are summarized in FIGS. 26A-26C. The number of stones per mouse was in the range 4-99 and the average surface area was in the range 0.077-3.574 $mm^2$. Of the 260 stones identified, 137 occupied a surface area within the range 0.00-0.50 mm2 and one stone was at the extreme end (20.01-25.00 $mm^2$).

Conclusion

A diet containing 0.62% methionine promoted stone formation in nine out of 12 KO mice (75%), whereas stones were not observed in any of the 12 KO mice that were on a diet containing 0.12% methionine for 8 weeks. These results indicate that a reduction in methionine levels as a result of methionine restriction leads to a reduction in urolithiasis and provides a rationale for using a methionine consuming strain described herein as a treatment for the reduction of stone formation in a subject having cystinuria.

Example 15. Metabolite Levels in a Mouse Model of Homocystinuria

Urine and plasma samples collected from several mice in each of the three groups in the study described in the previous example, and urinary cystine, cysteine, and methionine levels as well as plasma cysteine levels were measured.

In brief, cysteine, cystine, ornithine, lysine, and arginine were quantitated in mouse plasma and urine by LC-MS/MS. Samples were deprotonated with sulfosalicylic acid then diluted with acetonitrile containing heavy-isotope internal standards for each analyte. To measure total cysteine, separate sample aliquots were first reduced with DL-dithiothreitol. Analytes were separated using hydrophilic interaction chromatography and detected using selected reaction monitoring of compound specific ions. Peaks were integrated and analyte/internal standard area ratios were used to calculate unknown concentrations relative to a standard curve.

Figure 27A:
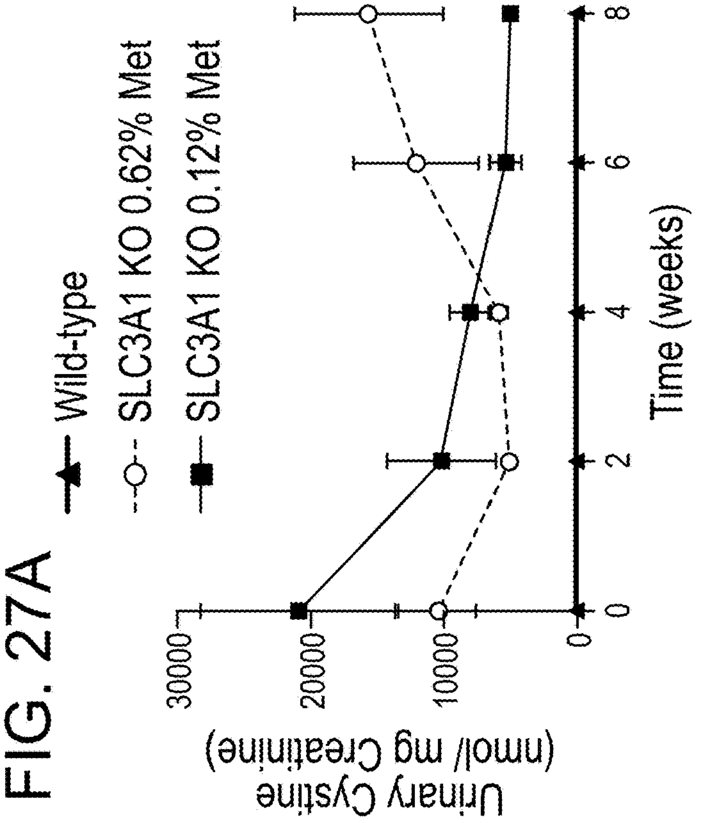
FIGS. 27A-27C depict graphs showing metabolite measurements comparing urinary cystine (FIG. 27A), urinary cysteine (FIG. 27B) and urinary methionine (FIG. 27C) in SLC3A1 KO mice on low-methionine Diet (0.12%), non-restricted diet (0.62%), and wild-type mice non-restricted diet (0.62%).
Figure 27B:
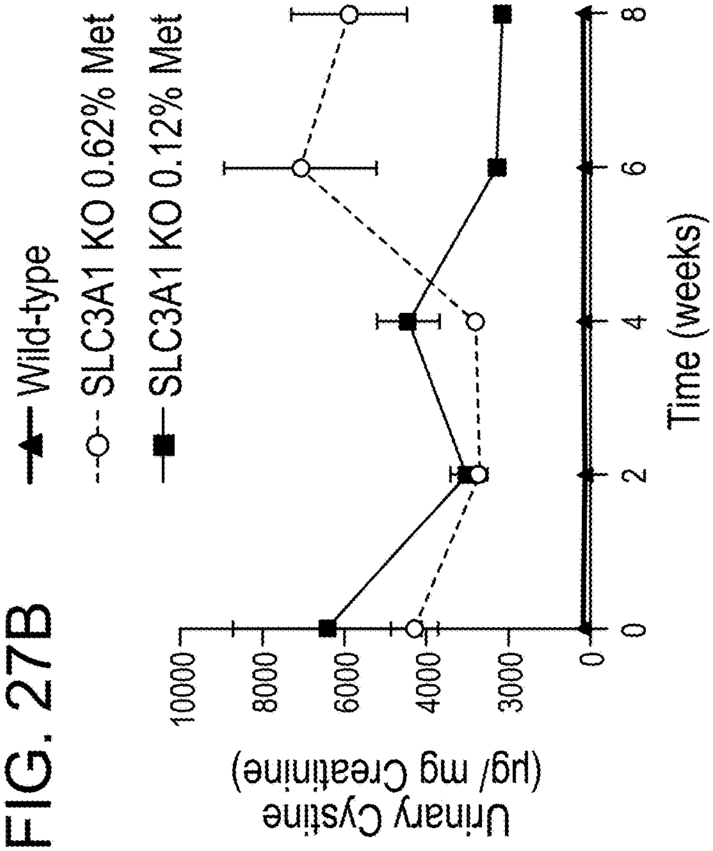
Figure 27C:
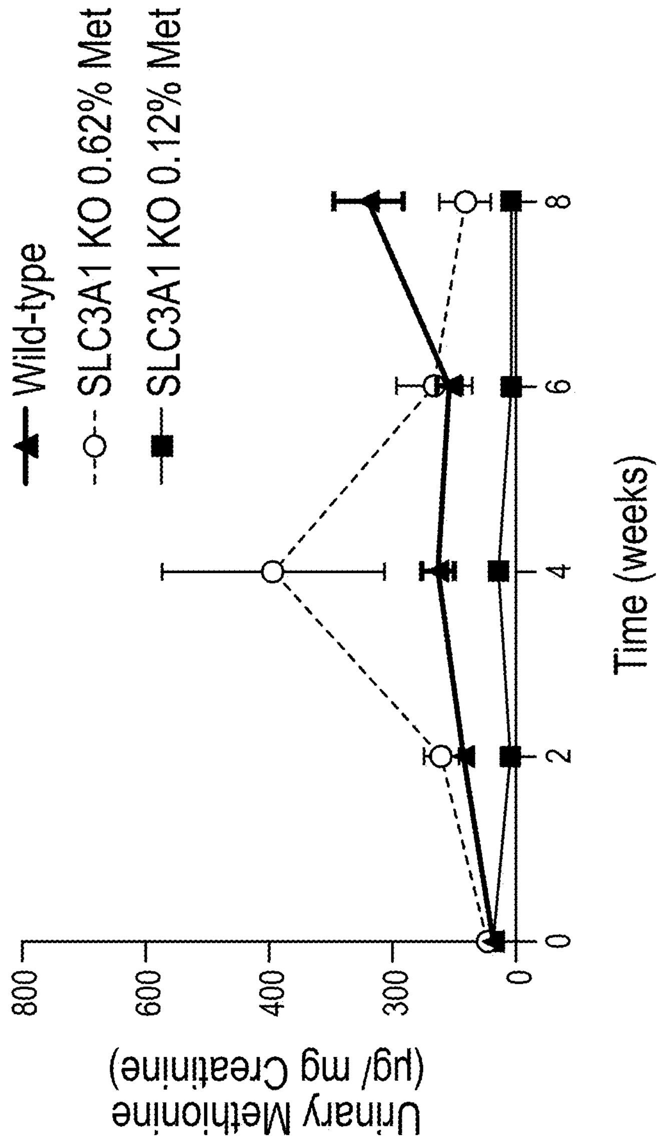
Figure 28:
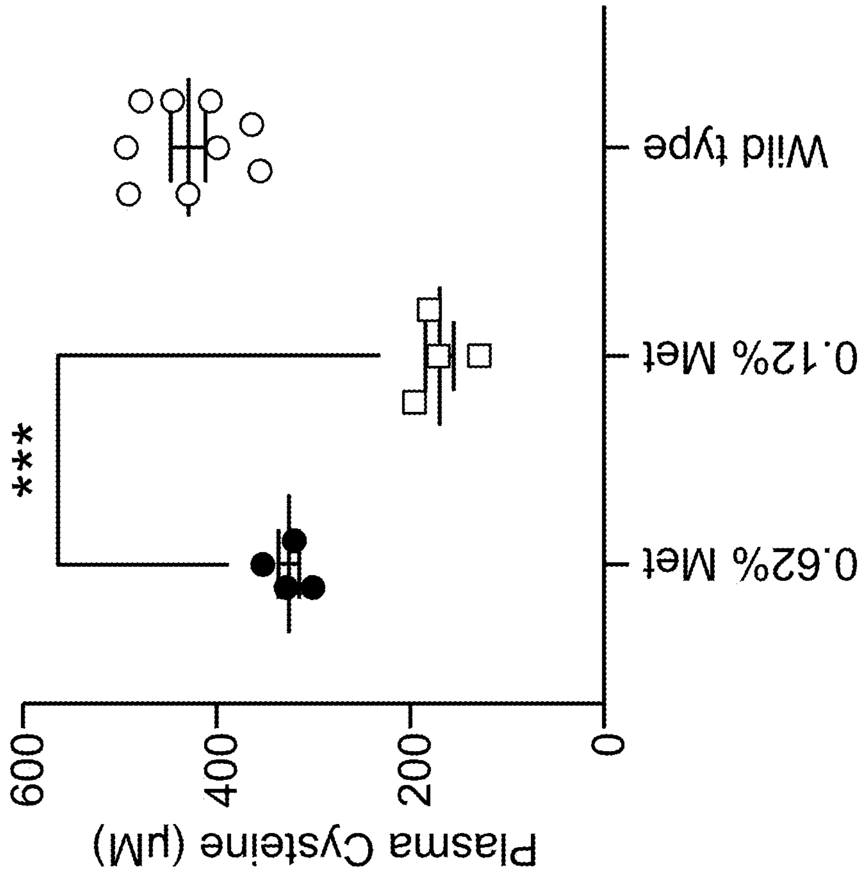
FIG. 28 depicts a graph comparing plasma cysteine in SLC3A1 KO mice on low-methionine diet (0.12%), non-restricted diet (0.62%) and wild-type mice on non-restricted diet (0.62%).
Figure 29B:
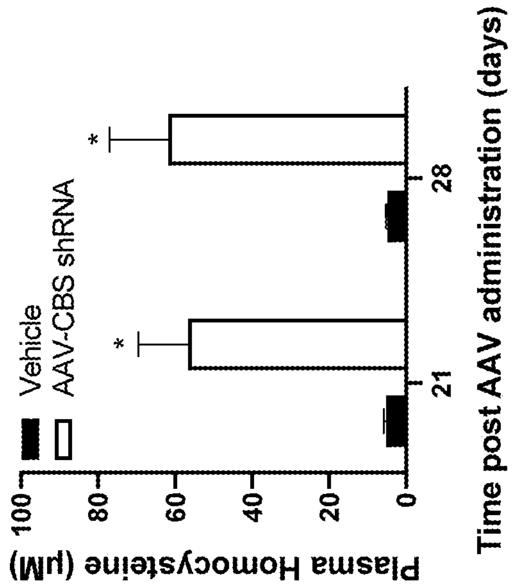
FIG. 29B depicts a bar graph showing significant elevations in plasma homocysteine levels in CBS knockdown mice versus mice treated with vehicle control. Mice received $1\times10^{12}$ genomic copies of an adeno-associated virus containing a shRNA targeting CBS or vehicle intravenously and blood was collected on days 21 and 28 and liver on day 35. Data presented as mean plasma Hcy±SEM (n=9). Statistical analysis was performed using a mixed-effects analysis followed by Sidak's multiple comparison test. *p<0.05, **p<0.01.
Figure 29A:
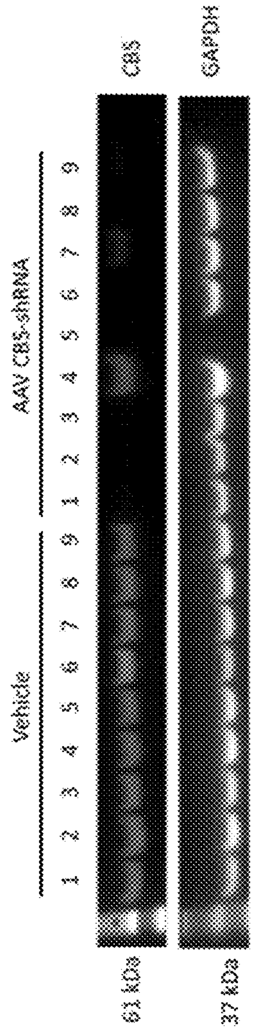
FIG. 29A depicts Western blot showing CBS protein levels in CBS knockdown mice versus mice treated with vehicle control.
Figure 30A:
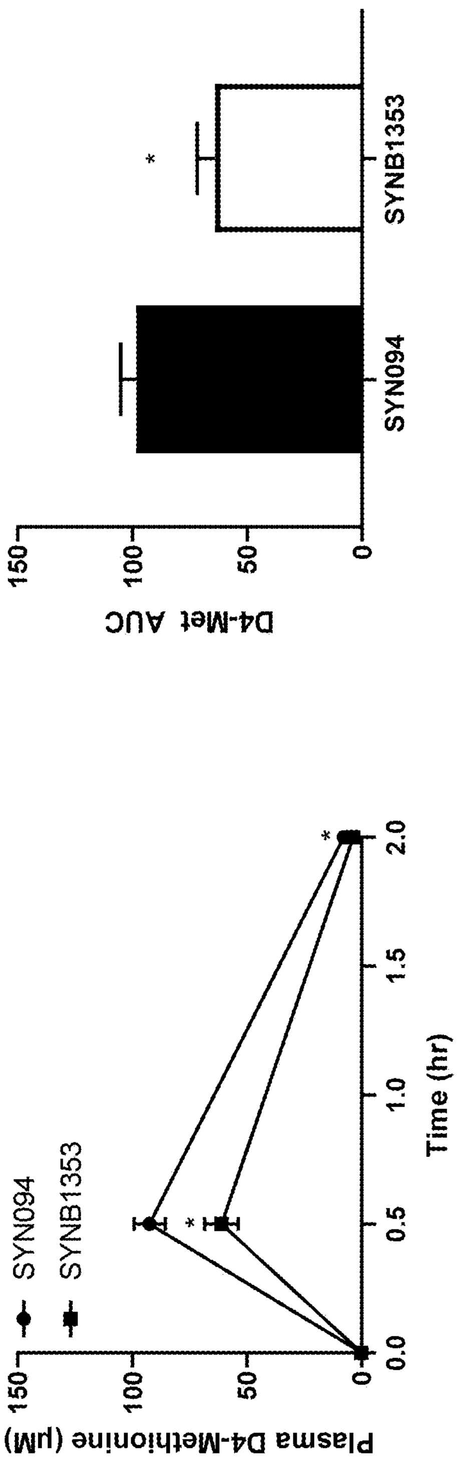
FIGS. 30A and 30B show the effect of SYNB1353 ((lacI-Ptac, IPTG) 3×metDC (Q70D N82H; SEQ ID NO: 1048; engineered library); 1×metP (metagenomics library; *F. segetis*; SEQ ID NO: 1056); Δϕ; Δdap; ΔyjeH; Δpks) (2 doses for a total of $5.4\times10^{10}$ live cells) on plasma labeled methionine (FIG. 30A) and plasma labeled homocysteine (FIG. 30B) after an oral bolus of D4-methionine (50 mg/kg). Mice received 2 doses of SYNB1353 (one hour apart) and blood was collected at 0, 0.5, or 2 hours post methionine (n=8/group). Statistical analysis was performed using two-way ANOVA followed by Sidak's multiple comparison test or unpaired t-test. *p<0.05.
Figure 30B:
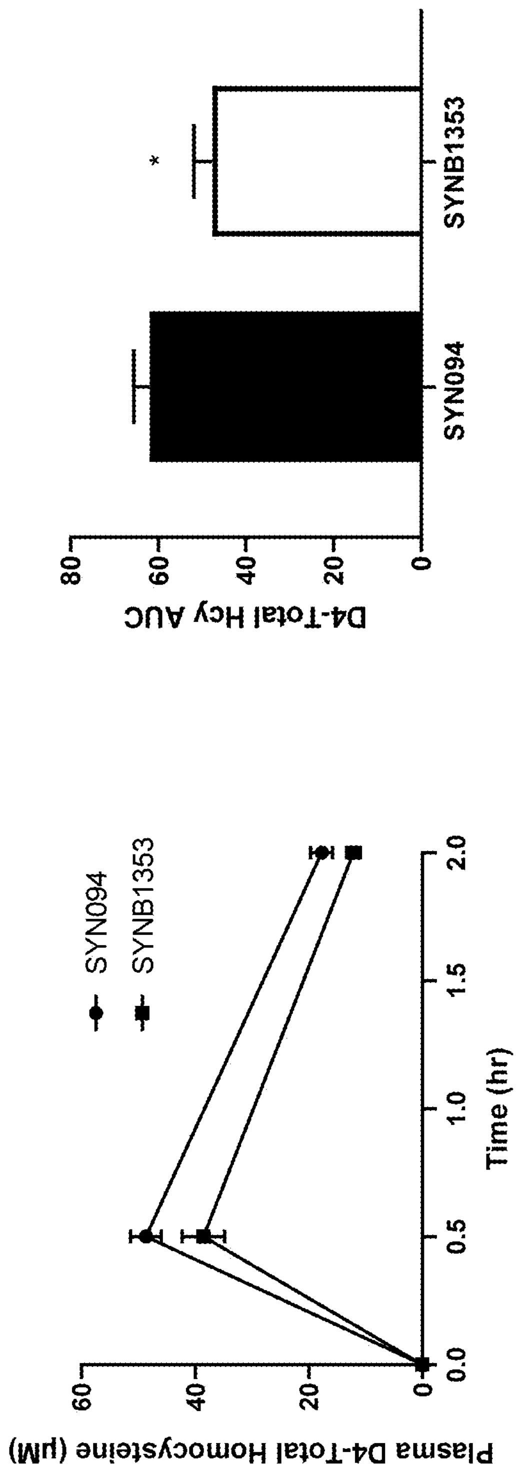
Figure 31A:
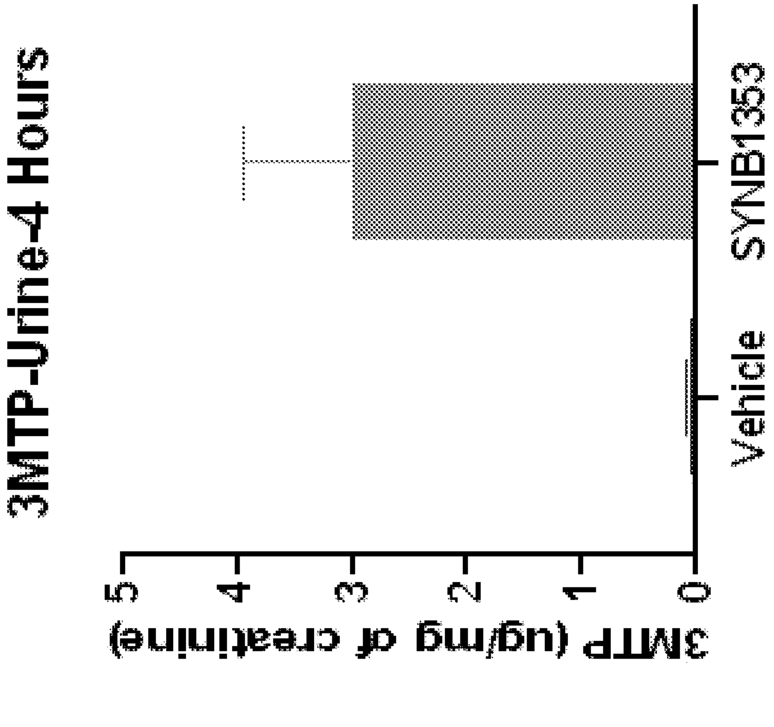
FIGS. 31A and 31B depict whey protein challenge. CBS-knockdown mice were orally dosed with 2750 mg/kg whey protein (~50 mg/kg Met) and either SYNB1353 or vehicle, followed by a second dose of strain or vehicle 2 hours later. Urine was collected at 4 hours (FIG. 31A) and 28 hours (FIG. 31B) to measure 3MTP.
Figure 31B:
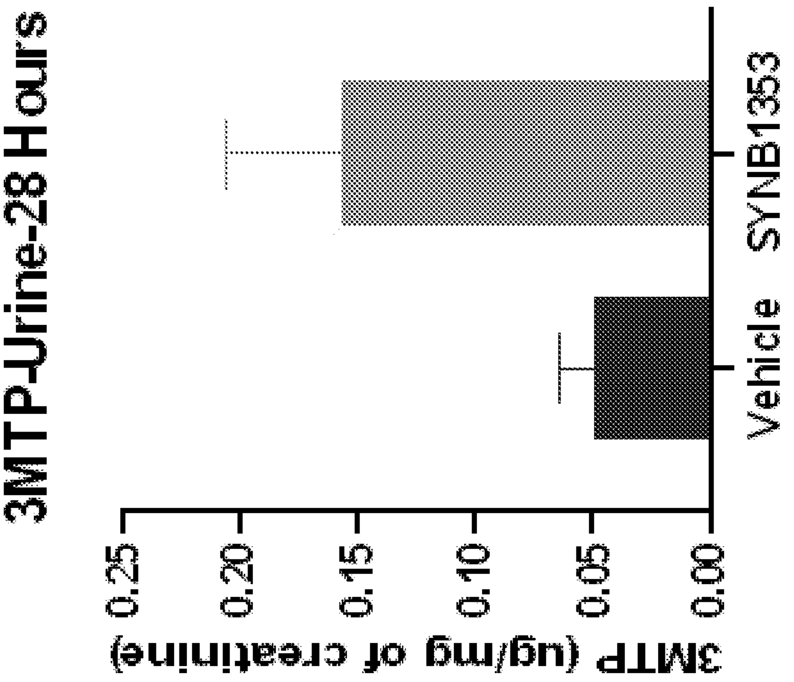

Results of the urine analysis are shown in FIGS. 27A-27C, and results of the plasma analysis is shown in FIG. 28 and demonstrate that methionine restriction in the mouse model of cystinuria lowered urinary cysteine, cystine and methionine levels. Low-Methionine group was also associated with decreased plasma cysteine. These results further support the conclusion that reducing methionine levels in subjects with cystinuria, e.g., by using a methionine consuming strain described herein, can reduce elevated cysteine and cystine in urine and/or plasma and consequently can reduce or prevent cystine stone formation in kidney or bladder in these subjects.

Example 16. Mouse Model of Homocystinuria

Methods

Generation of an Inducible Mouse Model of Homocystinuria

To develop an inducible model of homocystinuria, short hairpin RNA (shRNA) targeting cystathionine β-synthase (CBS) packaged in adeno-associated virus (AAV) particles were purchased from Vector Biolabs (Malvern, PA) and used to inject 6-week-old C57BL/6J male mice. For this experiment, 18 male C57BL/6J mice were group housed and assigned to groups (n=9/group) based on average cage body weight. Mice received a single intravenous dose (tail vein) of vehicle (PBS) or AAV CBS-shRNA ($1\times10^{12}$ genomic copies [GC]) and left unmanipulated for 72 hours. Blood was collected 21- or 28-days post IV dosing for tHcy analysis. Animals were euthanized by CO2 asphyxiation on day 35 and livers were snap-frozen in liquid nitrogen for future analysis.

Liver samples were added to bead-bug tubes and homogenized for 30 seconds in 1 mL of lysis buffer (TPER) with a cocktail of protease inhibitors, followed by a 3-minutes centrifugation at 25,200 g. Protein concentration was determined on the supernatants by the Bradford method, 50 µg of liver homogenate was loaded onto a 4-12% Bis-Tris gel and proteins transferred onto PVDF membranes. Membranes were incubated overnight with a primary rabbit monoclonal antibody against CBS (D8F2P, Cell Signaling Technologies Cat. 14782S) at 1:333 dilution. Membranes were then washed and incubated with anti-rabbit IgG HRP-linked secondary antibody (Cell Signaling Technologies Cat. 70745) at 1:1000 dilution for 60 minutes at room temperature. Protein signal was revealed using ECL Reagent and developed using SignalFire™ ECL Reagent #6883 (Cell Signaling Technologies Cat. 6883S).

Assessment of SYNB1353 Activity in AAV-CBS Mice

ShRNA targeting CBS packaged in AAV particles was administered to 8-week-old C57BL/6J male mice by IV injection ($1\times10^{12}$ genomic copies (GC) of AAV). Six weeks post-AAV injection, mice were orally administered a bolus of labeled methionine (50 mg/kg) with EcN ($2.7\times10^{10}$ live cells, n=8/group) or SYNB1353 ($2.7\times10^{10}$ live cells, n=8/group). One hour later, mice received another dose of bacteria (EcN or SYNB1353 at $2.7\times10^{10}$ live cells) and blood was collected 0, 0.5, or 2 hours post-labeled methionine.

Results

To assess the activity of SYNB1353 on plasma total homocysteine (tHcy) levels in mice, we developed a new model by delivering short hairpin RNA (shRNA) targeting CBS packaged in adeno-associated virus (AAV) particles by intravenous (IV) injection to 6-week-old C57BL/6J male mice. Mice were administered vehicle or $1\times10^{12}$ genomic copies (GC) of AAV by tail vein injection. On days 21 and 28 post AAV injection, blood was collected for total homocysteine determination and livers were harvested on day 35 to assess CBS expression. AAV-targeted delivery of CBS shRNA resulted in substantial lowering of hepatic CBS protein (61 kDa) expression by Western Blot compared to vehicle treated animals. Because of residual CBS protein in one AAV CBS-shRNA, suggesting incomplete CBS knockdown, and lack of housekeeping protein expression (GAPDH) in another, these 2 animals were removed from further analysis. Total homocysteine levels remained low in animals with intact CBS (average 5.1 µM), while downregulation of hepatic CBS expression resulted in a significant 10-12-fold elevation in plasma tHcy.

Short hairpin RNA (shRNA) targeting cystathionine β-synthase (CBS) packaged in adeno-associated virus (AAV) particles was administered to 8-week-old C57BL/6J male mice by intravenous (IV) injection ($1\times10^{12}$ genomic copies (GC) of AAV). Six weeks post-AAV injection, mice were orally administered a bolus of labeled methionine (50 mg/kg) with EcN ($2.7\times10^{10}$ live cells, n=8/group) or SYNB1353 ($2.7\times10^{10}$ live cells, n=8/group). One hour later, mice received another dose of bacteria (EcN or SYNB1353 at $2.7\times10^{10}$ live cells) and blood was collected 0, 0.5, or 2 hours post-labeled methionine. The bolus of labeled methionine resulted in significant elevations in plasma labeled methionine and labeled homocysteine in AAV mice, and SYNB1353 significantly blunted the appearance of both amino acids in plasma as demonstrated by a significant reduction in the area under the curve (AUC) with 35% and 23% for methionine and homocysteine, respectively.

TABLE 9

E. coli Strains

| Strain No. | Background/genotype | Antibiotic resistance |
|---|---|---|
| SYN094 | wt Nissle, strepR | Strep |
| SYN7349 | Logic2279, which is a medium-copy p15a plasmid (pTET, atc induction) expressing a methionine decarboxylase from *Streptomyces* sp. 590 (SEQ ID NO: 1003) to convert methionine into 3-methylthiopropylamine and Logic2375, which is a low-copy pSC101 plasmid (pTET, atc induction) expressing an endogenous methionine importer (metNIQ); yjeH | cam, carb, kan |
| SYN7815 | ΔyjeH, containing Logic2279. Also containing logic2501 with an engineered MetNIQ importer (MetN P281S) (SEQ ID NO: 1047 (metN(P281S)IQ)); (pLacO, IPTG induction) | Cam, kan, spec |
| SYN7816 | Logic2279, methionine decarboxylase from *Streptomyces* sp. 590 (SEQ ID NO: 1003). Also containing plasmid logic2502 with an engineered MetNIQ importer (MetN P281G) (SEQ ID NO: 1045 (metN(P281G)IQ)); (pLacO, IPTG induction); ΔyjeH | Cam, kan, spec |
| SYN7817 | Logic2279, methionine decarboxylase from *Streptomyces* sp. 590 (SEQ ID NO: 1003). Also containing logic2503 with a recoded MetNIQ importer (SEQ ID NO: 1046); (pLacO, IPTG induction); ΔyjeH | Cam, kan, spec |
| SYN7818 | Logic2279, methionine decarboxylase from *Streptomyces* sp. 590 (SEQ ID NO: 1003). Also containing logic2534 with the MetP importer (*F. frigoris*) (SEQ ID NO: 1042); (pLacO I, IPTG induction); ΔyjeH | Cam, kan, spec |
| SYN7819 | Logic2279, methionine decarboxylase from *Streptomyces* sp. 590 (SEQ ID NO: 1003). Also containing logic2535 with the MetP importer (*F. segetis*) (SEQ ID NO: 1041); (pLacO, IPTG induction); ΔyjeH | Cam, kan, spec |

TABLE 9-continued

E. coli Strains

| Strain No. | Background/genotype | Antibiotic resistance |
|---|---|---|
| SYN7346 | Logic2279, methionine decarboxylase from *Streptomyces* sp. 590 (SEQ ID NO: 1003); ΔyjeH | cam, kan |
| SYN7640 | recoded *Streptomyces* MetDC (SEQ ID NO: 1003), pSC101 (pTET, atc induction); ΔyjeH | Cam, kan |
| SYN7641 | protein engineered MetDC (V491L A500P) (SEQ ID NO: 1035) with high 3MTP production, pSC101 (pTET, atc induction); ΔyjeH | Cam, kan |
| SYN7642 | protein engineered MetDC (Q70D N82H) (SEQ ID NO: 1034) with high 3MTP production, pSC101 (pTET, atc induction); ΔyjeH | Cam, kan |
| SYN7643 | protein engineered MetDC (R41Q Q70D) (SEQ ID NO: 1036) with high 3MTP production, pSC101 (pTET, atc induction); ΔyjeH | Cam, kan |
| SYN7644 | *Stanieria* sp. NIES-3757 Methionine decarboxylase (SEQ ID NO: 1037) from MetDC metagenomic library screen with high 3MTP production, pSC101 (pTET, atc induction); ΔyjeH, | Cam kan |
| SYN7689 | SYN7345 containing Logic2491, which expresses an engineered MetDC from *Mus musculus* (SEQ ID NO: 1039). pSC101 (pTET, atc induction); ΔyjeH | Cam kan |
| SYN7690 | SYN7345 containing Logic2492, which expresses an engineered LeuDC from *Mus musculus* (SEQ ID NO: 1038). pSC101 (pTET, atc induction); ΔyjeH | Cam kan |
| SYN7691 | SYN7345 containing Logic2493, which expresses a MetDC from *Entamoeba histolytica* (SEQ ID NO: 1040). pSC101 (pTET, atc induction); ΔyjeH | Cam kan |
| SYN7345 | EcN with endogenous methionine and branched-chain a.a. exporter (yjeH) knocked out. | cam |
| SYN7970 | (lacI-Ptac, IPTG) 2× MetDC (Q70D N82H) (SEQ ID NO: 1034); 1× MetP (*F. segetis*) (SEQ ID NO: 1041); Δdap; ΔyjeH, Δϕ | none |
| SYN8002 | (lacI-Ptac, IPTG) 3× MetDC (Q70D N82H) (SEQ ID NO: 1034); 1× MetP (*F. segetis*) (SEQ ID NO: 1041); Δdap; ΔyjeH; Δϕ | None |
| SYN8003 | (lacI-Ptac, IPTG) 3× MetDC (Q70D N82H) (SEQ ID NO: 1034); 1× MetP (*F. segetis*) (SEQ ID NO: 1041); Δdap; ΔyjeH; Δϕ (stronger RBS than SYN8002) | none |
| SYN8070 | (lacI-Ptac, IPTG) 3× MetDC (Q70D N82H) (SEQ ID NO: 1034); 1× MetP (*F. segetis*) (SEQ ID NO: 1041); Δϕ; Δdap; ΔyjeH; Δpks (integration: thiC/rsd::attB2-lacI-$P_{tac}$-metDC; glmS/pstS::attB5-lacI-$P_{tac}$-metP-$P_{tac}$-metDC; hypothetical protein/yfjJ::attB7-$P_{tac}$-metDC) | None |
| SYNB1353 | (lacI-Ptac, IPTG) 3× MetDC (Q70D N82H) (SEQ ID NO: 1034); 1× MetP (*F. segetis*) (SEQ ID NO: 1041); Δϕ; Δdap; ΔyjeH; Δpks (integration: thiC/rsd::attB2-lacI-$P_{tac}$-metDC; glmS/pstS::attB5-lacI-$P_{tac}$-metP-$P_{tac}$-metDC; hypothetical protein/yfjJ::attB7-$P_{tac}$-metDC) | None |

TABLE 10

Exemplary Methionine Decarboxylase Nucleotide Sequences

| Description SEQ ID NO: | Nucleotide Sequence |
|---|---|
| MetDC Q70D N82H SEQ ID NO: 1034 | ATGtccccgacggcgtttccagcggccgaaacagctactgcccctgcaactgccgtcgatcctgggccagaac tggacggcggagatttcgcccttccagagggcgggctggatgacgatcgtcgcttacgtgcattggacgcagttga cgagtatttgacccgcaagcgcaagcatttggttgggtaccaagctacccaggatatggacggaacggccttggat ttagcccgtttcatgccccacaacatcaacaacctgggagatcctttccagtcgggtgggtataaaccaaatacgaa agtcgttgagcgtgccgtactggactactatgcaaaattgtggcacgcagaacgtccacacgacccagctgaccca gaaagctactggggttacatgttatcgatgggctcaactgagggcaacatgtacgccctgtggaatgcacgtgacta cctgtcgggtaaggctttgattcagcctcccacggcaccatttgacgctgttcgctacgtgaaggctgaccccgatc gccgcaatcctaacgcacaccacccagtcgcattctactcggaggatacccactattcttttgctaaagccgttgcgg tgctgggtgtcgaaactttccacgctgtgggtctggagaaatacgctgacgagtgccccttggtggatccagtaacc ggccttcgtacctggccgaccgaagttccatcgcgcccggggccgtcgggtttaagctgggacggccctggtgag attgatgttgatgcgcttgcagtactggtcgagttcttcgcagcgaagggtcaccccgtcttcgtcaaccttaacttgg ggtctacatttaaaggagcacatgatgacgtacgtgcggtatgtgaacgcttattaccaatcttcgagcgccatggctt agtacaacgtgaagttgtatatgggagctgtccccaaaccggccgccctttagtggatgtacgtcgcggattttggat ccacgtagatggggcacttggggcggggtatgccccttttctgcgtcttgccgccgaagacccggaaggttatggtt ggacccctgaggcagaattacctgagttcgacttcggcttacgtttgccgacggcggggcatggagaagttgatat ggttagcagcatcgccatgagtggacataagtgggcaggcgcgccgtggccatgcggcatctatatgacgaaagt gaaatatcagattagtccaccgtcacagcccgattatattggtgctcctgacacaacatttgccggttcccgtaacgg cttttcgccgttaattttgtgggatcatttatcgcgctactcgtaccgcgaccaggtagagcgcatccgcgaagcaca ggagcttgcagcatatttggaacgccgccttaccgctatggagcgcgagctgggagtggaactttggccagcccg cacaccgggtgctgtaaccgtacgttttcgcaaaccctctgctgagctggttgcgaagtggtccttgtcgtcgcagg |

TABLE 10-continued

Exemplary Methionine Decarboxylase Nucleotide Sequences

| Description<br>SEQ ID NO: | Nucleotide Sequence |
|---|---|
| | atgttttaatggtgccgggtgatgaaactacgcgtcgtagttacgttcatgtgttcgtgatgccttctgttgatcgtgcaa<br>agttagatgcgttgctggcagaattggccgaagatcccgtcatcttgggtgcgccttaa |
| MetDC<br>(*Streptomyces*)<br>SEQ ID NO:<br>1003 | ATGTCCCCGACGGCGTTTCCAGCGGCCGAAACAGCTACTGCCCCTGC<br>AACTGCCGTCGATCCTGGGCCAGAACTGGACGGCGGAGATTTCGCCC<br>TTCCAGAGGGCGGGCTGGATGACGATCGTCGCTTACGTGCATTGGAC<br>GCAGTTGACGAGTATTTGACCCGCAAGCGCAAGCATTTGGTTGGGTA<br>CCAAGCTACCCAGGATATGCAGGGAACGGCCTTGGATTTAGCCCGTT<br>TCATGCCCAACAACATCAACAACCTGGGAGATCCTTTCCAGTCGGGT<br>GGGTATAAACCAAATACGAAAGTCGTTGAGCGTGCCGTACTGGACTA<br>CTATGCAAAATTGTGGCACGCAGAACGTCCACACGACCCAGCTGACC<br>CAGAAAGCTACTGGGGTTACATGTTATCGATGGGCTCAACTGAGGGC<br>AACATGTACGCCCTGTGGAATGCACGTGACTACCTGTCGGGTAAGGC<br>TTTGATTCAGCCTCCCACGGCACCATTTGACGCTGTTCGCTACGTGAA<br>GGCTGACCCCGATCGCCGCAATCCTAACGCACACCACCCAGTCGCAT<br>TCTACTCGGAGGATACCCACTATTCTTTTGCTAAAGCCGTTGCGGTGC<br>TGGGTGTCGAAACTTTCCACGCTGTGGGTCTGGAGAAATACGCTGAC<br>GAGTGCCCCTTGGTGGATCCAGTAACCGGCCTTCGTACCTGGCCGAC<br>CGAAGTTCCATCGCGCCCGGGGCCGTCGGGTTTAAGCTGGGACGGCC<br>CTGGTGAGATTGATGTTGATGCGCTTGCAGTACTGGTCGAGTTCTTCG<br>CAGCGAAGGGTCACCCCGTCTTCGTCAACCTTAACTTGGGGTCTACAT<br>TTAAAGGAGCACATGATGACGTACGTGCGGTATGTGAACGCTTATTA<br>CCAATCTTCGAGCGCCATGGCTTAGTACAACGTGAAGTTGTATATGG<br>GAGCTGTCCCCAAACCGGCCGCCCTTTAGTGGATGTACGTCGCGGAT<br>TTTGGATCCACGTAGATGGGGCACTTGGGGCGGGGTATGCCCCTTTTC<br>TGCGTCTTGCCGCCGAAGACCCGGAAGGTTATGGTTGGACCCCTGAG<br>GCAGAATTACCTGAGTTCGACTTCGGCTTACGTTTGCCGACGGCGGG<br>GCATGGAGAAGTTGATATGGTTAGCAGCATCGCCATGAGTGGACATA<br>AGTGGGCAGGCGCGCCGTGGCCATGCGGCATCTATATGACGAAAGTG<br>AAATATCAGATTAGTCCACCGTCACAGCCCGATTATATTGGTGCTCCT<br>GACACAACATTTGCCGGTTCCCGTAACGGCTTTTCGCCGTTAATTTTG<br>TGGGATCATTTATCGCGCTACTCGTACCGCGACCAGGTAGAGCGCAT<br>CCGCGAAGCACAGGAGCTTGCAGCATATTTGGAACGCCGCCTTACCG<br>CTATGGAGCGCGAGCTGGGAGTGGAACTTTGGCCAGCCCGCACACCG<br>GGTGCTGTAACCGTACGTTTTCGCAAACCCTCTGCTGAGCTGGTTGCG<br>AAGTGGTCCTTGTCGTCGCAGGATGTTTTAATGGTGCCGGGTGATGA<br>AACTACGCGTCGTAGTTACGTTCATGTGTTCGTGATGCCTTCTGTTGA<br>TCGTGCAAAGTTAGATGCGTTGCTGGCAGAATTGGCCGAAGATCCCG<br>TCATCTTGGGTGCGCCTtaa |
| MetDC<br>(*Streptomyces*)<br>SEQ ID NO:<br>1018 | atgagcccgaccgccttccccgccgccgagaccgcgaccgcgcccgcgaccgccgtcgatcccggtccggag<br>ctggacggcggtgacttcgccctccccgagggcggcctggacgacgaccggcggctgcgcgcgctcgacgcc<br>gtggacgagtacctgacccgcaagcgcaagcacctggtcggctaccaggccacccaggacatgcagggcaccg<br>cactggacctcgcccggttcatgccgaacaacatcaacaacctcggcgacccgttccagagcggcggatacaag<br>cccaacaccaaggtcgtcgagcgggccgtgctcgactactacgcgaagctctggcacgccgagcgcccgcacg<br>acccggccgacccggagtcgtactggggctacatgctgtccatgggctcgaccgagggcaacatgtacgccctct<br>ggaacgccagggactacctgagcggcaaggcgctgatccagccgccgaccgccccttcgacgcggtgcgcta<br>cgtcaaggccgaccccgaccgacggaacccgaacgcccaccacccggtggccttctactccgaggacacccac<br>tactccttcgccaaggccgtggccgtcctcggcgtggagaccttccacgccgtcggcctggagaagtacgccgac<br>gagtgcccgctggtcgacccggtgaccgggctgcgcacctggcccaccgaggtgccctcccgcccgggtccgt<br>ccggcctgtcctgggacggccccggcgagatagacgtcgacgccctcgccgtactcgtcgagttcttcgccgcca<br>agggtcacccggtcttcgtcaacctcaacctcggcagcaccttcaagggcgcccacgacgacgtccgcgccgtct<br>gcgagcgcttgctgccgatcttcgagcggcacgggctcgtccagcgcgaggtggtctacggcagctgcccgcag<br>accggccggccgctggtggacgtgcgccgcggcttctggatccacgtggacggcgcgctcggcgccggctacg<br>cgccgttcctgcggctggccgccgaggacccggaagggtacggctggacgcccgaggcggagctgcccgagt<br>tcgacttcggcctgcggctgcccaccgccgggcacggcgaggtggacatggtctcctcgatcgcgatgagcggc<br>cacaagtgggccggcgcgccgtggccgtgcggcatctacatgaccaaggtgaagtaccagatctcgccgccgtc<br>ccagccggactacatcggcgccccggacaccaccttcgccggctcccgcaacggcttctccccgctgatcctctg<br>ggaccacctgtcccggtactcctaccgggaccaggtggagcggatccgcgaggcccaggagctggccgcctac<br>ctggagcggcggctgaccgccatggagcgcgaactcggcgtcgagctctggccggcccgtaccccgggcgcc<br>gtcaccgtacggttccgcaagccgagcgccgagctggtggccaagtggtcgctgtcctcccaggacgtgctgatg<br>gtcccgggcgacgagaccacccggcgcagctacgtgcacgtcttcgtgatgccctcggtcgaccgggccaagct<br>ggacgcgctgctcgccgaactcgccgaggacccggtgatcctgggcgcaccgtag |
| MetDC<br>(V491L<br>A500P)<br>SEQ ID NO:<br>1035 | atgtccccgacggcgtttccagcggccgaaacagctactgcccctgcaactgccgtcgatcctgggccagaactg<br>gacggcggagatttcgcccttccagagggcgggctggatgacgatcgtcgcttacgtgcattggacgcagttgac<br>gagtatttgacccgcaagcgcaagcatttggttgggtaccaagctacccaggatatgcagggaacggccttggattt<br>agcccgtttcatgcccaacaacatcaacaacctgggagatcctttccagtcgggtgggtataaaccaaatacgaaa<br>gtcgttgagcgtgccgtactggactactatgcaaaattgtggcacgcagaacgtccacacgacccagctgacccag<br>aaagctactggggttacatgttatcgatgggctcaactgagggcaacatgtacgccctgtggaatgcacgtgactac<br>ctgtcgggtaaggctttgattcagcctcccacggcaccatttgacgctgttcgctacgtgaaggctgaccccgatcg<br>ccgcaatcctaacgcacaccacccagtcgcattctactcggaggatacccactattcttttgctaaagccgttgcggt<br>gctgggtgtcgaaactttccacgctgtgggtctggagaaatacgctgacgagtgccccttggtggatccagtaacc<br>ggccttcgtacctggccgaccgaagttccatcgcgcccggggccgtcgggtttaagctgggacggccctggtgag<br>attgatgttgatgcgcttgcagtactggtcgagttcttcgcagcgaagggtcaccccgtcttcgtcaaccttaacttgg |

TABLE 10-continued

Exemplary Methionine Decarboxylase Nucleotide Sequences

| Description SEQ ID NO: | Nucleotide Sequence |
|---|---|
| | ggtctacatttaaaggagcacatgatgacgtacgtgcggtatgtgaacgcttattaccaatcttcgagcgccatggctt agtacaacgtgaagttgtatatgggagctgtccccaaaccggccgccctttagtggatgtacgtcgcggattttggat ccacgtagatggggcacttggggcggggtatgccccttttctgcgtcttgccgccgaagacccggaaggttatggtt ggacccctgaggcagaattacctgagttcgacttcggcttacgtttgccgacggcggggcatggagaagttgatat ggttagcagcatcgccatgagtggacataagtgggcaggcgcgccgtggccatgcggcatctatatgacgaaagt gaaatatcagattagtccaccgtcacagcccgattatattggtgctcctgacacaacatttgccggttcccgtaacgg cttttcgccgttaatttgtgggatcatttatcgcgctactcgtaccgcgaccaggtagagcgcatccgcgaagcaca ggagcttgcagcatatttggaacgccgccttaccgctatggagcgcgagctgggagtggaactttggccagcccg cacaccgggtgctctgaccgtacgttttcgcaaaccctctccggagctggttgcgaagtggtccttgtcgtcgcagg atgttttaatggtgccgggtgatgaaactacgcgtcgtagttacgttcatgtgttcgtgatgccttctgttgatcgtgcaa agttagatgcgttgctggcagaattggccgaagatcccgtcatcttgggtgcgccttaa |
| MetDC (R41Q Q70D) SEQ ID NO: 1036 | atgtccccgacggcgtttccagcggccgaaacagctactgcccctgcaactgccgtcgatcctgggccagaactg gacggcggagatttcgcccttccagagggcgggctggatgacgatcagcgcttacgtgcattggacgcagttgac gagtatttgacccgcaagcgcaagcatttggttgggtaccaagctacccaggatatggacggaacggccttggattt agcccgtttcatgcccaacaacatcaacaacctgggagatcctttccagtcgggtgggtataaaccaaatacgaaa gtcgttgagcgtgccgtactggactactatgcaaaattgtggcacgcagaacgtccacacgacccagctgacccag aaagctactggggttacatgttatcgatgggctcaactgagggcaacatgtacgccctgtggaatgcacgtgactac ctgtcgggtaaggctttgattcagcctcccacggcaccatttgacgctgttcgctacgtgaaggctgaccccgatcg ccgcaatcctaacgcacaccacccagtcgcattctactcggaggatacccactattcttttgctaaagccgttgcggt gctgggtgtcgaaactttccacgctgtgggtctggagaaatacgctgacgagtgccccttggtggatccagtaacc ggccttcgtacctggccgaccgaagttccatcgcgcccggggccgtcgggtttaagctgggacggccctggtgag attgatgttgatgcgcttgcagtactggtcgagttcttcgcagcgaagggtcaccccgtcttcgtcaaccttaacttgg ggtctacatttaaaggagcacatgatgacgtacgtgcggtatgtgaacgcttattaccaatcttcgagcgccatggctt agtacaacgtgaagttgtatatgggagctgtccccaaaccggccgccctttagtggatgtacgtcgcggattttggat ccacgtagatggggcacttggggcggggtatgccccttttctgcgtcttgccgccgaagacccggaaggttatggtt ggacccctgaggcagaattacctgagttcgacttcggcttacgtttgccgacggcggggcatggagaagttgatat ggttagcagcatcgccatgagtggacataagtgggcaggcgcgccgtggccatgcggcatctatatgacgaaagt gaaatatcagattagtccaccgtcacagcccgattatattggtgctcctgacacaacatttgccggttcccgtaacgg cttttcgccgttaatttgtgggatcatttatcgcgctactcgtaccgcgaccaggtagagcgcatccgcgaagcaca ggagcttgcagcatatttggaacgccgccttaccgctatggagcgcgagctgggagtggaactttggccagcccg cacaccgggtgctgtaaccgtacgttttcgcaaaccctctgctgagctggttgcgaagtggtccttgtcgtcgcagg atgttttaatggtgccgggtgatgaaactacgcgtcgtagttacgttcatgtgttcgtgatgccttctgttgatcgtgcaa agttagatgcgttgctggcagaattggccgaagatcccgtcatcttgggtgcgccttaa |
| MetDC (*Stanieria* sp. NIES-3757) SEQ ID NO: 1037 | atggggttccagttactgtctaaacataagctgtcagccgaggatcaacagaaacttgaccgcttttatcgtgatattc agacagaagcagaacgattcctgggttacccatgtaacgaactctttgactactccccttgttccggttcctgcaata tccgctgaataacgtcggcgacccgtacctgccgagtaactaccacctgaacacgcacaactttgagtgcgaagta ctggaaatcttccgtaccctgaccgaggctactgaaggttcgacttggggctacgtgaccaacggcggtacggaa ggtaatcattatggtcttttcctggcgagagagctgctgcctgaaggccttgtttactattctcaggatgcgcactactc gatcgataaaatcctgaggtgcctcaacctccgtagcataatgattcgcagccacgacgacggacgcatggacctg gatgatctgcgtgaaactctgcgtatccatcgcgacttgccgccgatcgtttgcgctaccattggtactacaatgaag ggcgctgtagatgacatcgcaggcattaaaaagatcttcaaagatctggcaatacaccgtcactatatccatgctgac gcggccctaggtggcatgattttaccgttcctggataactccccaccgtggaattttaaagctggaatcgactctatcg ctatctccggtcacaaaatggtgggcagtcctatcccgtgtggggttgtcctggctaaaaagtcgaacgttgaacgta ttgcacagagcgtggaatacattggtactctggataccaccctgtctggctcccgtaacgccttgactccgttatttctg tggtacgcgttccacaccgttggtatcgaaggtttcaaacgtatcatcccggcatgcttaaaaatggcggactatgcc atcgctcagctgaacaaaattaaccgcaatgcgtggcgctacccttacagcaacacggtagtcttcgatcgcccaa gccccgaagtgactcgttattggcagctggcttgtcagggcaacctgagccacctaatcaccatgccacacgttaca tctactcaaattgatcatctggttgctgacatcatcgcttctgagccgataccgccgctgccgaccctgtcagttactcc ggcatgcgaactgctgacttctaccccggaccaggatattacgctgatcggcaccgctaatcataatctgctctccg aagtatctaccgccctggctgccgagggtctgtcaattgaaaacctggctgctgtggcggtagaaagcgaggacgt tgaagttgtaaggctccgcgttaacaaccgtgagcgtgcactgcaaatcctgaaccagaacctggatatcggtcgtt gctacggtcaggctcgaccctttggcaacgaagaagcgacgcaggtactgtcccagctggaatatcaaagcgtgg gggaggatgcactactggtccagcttgacgattgccctggcagcctggcggagctgttgaaggattgccgcaacg aagcggtaaaaatccgtaatatccgactgctttggcgtgggcacggtaagggcgtcgtagcaattgctaccacttct ccagatgcgctgaaaacgctgctgaaagaccgtattcttttgagctaa |
| LeuDC (*Mus musculus*) SEQ ID NO: 1038 | ATGtccacacctagtgaagtaaagaaggatttgctgggtgcagcagggtcattatggccgtcggagcccattac gctgggtccaggtgaaagtgcttggcagctggtattgaagaagatccaagagttgagtgacagcggtcatcaagac ccgttcatggttgcagaccttgatgtccttgtgtctcgtcatcagacgttctgtcaagcactgcctagagtacaaccctt ctatgcagtaaagtgcaatagtaacccatgggtgttacgggtgttggcagctcttggcacgggatttgattgtgcttct cagggagaattggagcaagttttgggcttgggtgtagcgccgtcacggataatcttcgcaaatccctgtaaagcagt cagccacattcagtttgcagctcggtgcggtgtgcaattgttgacattcgacagcgaagaggagttaatcaaggttg cgcagtaccatccaggcgcacggttggtgcttcggattcaaacccaggactcacaatcaacgttcccactttccacc aagttcggtgcttctttagaagcatgtggacaccttctgcaggttgccagagagctgggtcttgccgtggtaggtgct agctttcatgtaggaagcgactgccacacacctcagagttttcgtcaggccatcgcagattgtcatcgtgtgttcgag atgggccgtaaggcaggtcatgatatgtcgcttcttgatttgggtggagggttcccaggtgtggaaggttccgaggc gaagtttgaggagatggcaagagtaatcaatgccgctcttgctcagtactttccggaagagactggcatcgaggtga tcgcggaacctggtcgtttctacgctgggtcggtgtgcactgcagctgtgaacatcatcgcgaagaagtctgtcttgg aaccaggtggtcatcgtaagcttatgtactaccttaatgaaggacattacggttctttcagattgttcttgcgtgatccag tgcctcgtattcccatcgtggtgaaagagttcccatccgaaccaccactgtttccttgcactttgtacggtcccacatgt gacgcctatgatcggttgttttccgaagaggtacaattgccagagctggatgttggagattggttgatcttcccagata tgggtgcctatacctcctcaatgtcctcgaccttcaacggatttccaccggccaccgtgtattgcgcaatgtcaccgc agttacgctccctgttggagactgtaccataa |

TABLE 10-continued

Exemplary Methionine Decarboxylase Nucleotide Sequences

| Description<br>SEQ ID NO: | Nucleotide Sequence |
|---|---|
| MetDC<br>(*Mus musculus*)<br>SEQ ID NO:<br>1039 | atgaacacacctagtgaagtaaagaaggatttgctgggtgttgcagaacatttacgtccgtcggagcccattacgct<br>gggtccaggtgcgagtgcttggcagctggtattgaagaagatcaaggagttgagtattagcggtcgtcaagacgct<br>ttcatggttgcagaccttgatgtccttgtgtctcgtcatcggacgttcttacaagcactgcctagagtacaacccttctat<br>gcagtaaagtgcaatagtaacccatgggtgttacttgtgttggcagctcttggcacgggatttgattgtgcttctcagg<br>gagaattggagcaagttttgggcttgggtgtagcgccgtcacggataatcttcgcaaatccctgtaaagcagtcagc<br>cacattcagtttgcagctcggtgcggtgtgcaattgttgacattcgacaatgaagaggagttaatcaagttagcgcgtt<br>accatccacgtgcacggttggtgcttcggattcaaaccctggactcacaatcaacgttcccacttagcaccaagttcg<br>gtgctcacttagaagcatgtggacaccttctgcaggttgccagagagctgggtcttgccgtggtaggtgctagctttc<br>atgtaggaagcgactgccacacacctgagagttaccgtcaggccatcgcagattgtcatcgtgtgttcgagatggg<br>ctgtaaggcaggtcatcacatgtcgcttcttgatttgggtggagggttcccaggtgtgaaaggttccgaggcgaagtt<br>tgaggaggttgcaagagtaatcaataccgctcttgctcagtactttccggaagagactggcatcgaggtgatcgcgg<br>aacctggtcgtttctacgctgggtcggtgtgcactgcagctgtgaacatcatcgccaagaagtctagtttggacccag<br>gtggtcatcgtaagcttgcttactaccttaatgaaggacattacggtgtattcagattgttcttgcgtgatccagtgcctc<br>gtattcccatcgtggtgaaagagttcccatccgaaccaccactgtttccttgcactttgtacggtcccacatgtgacgc<br>ctatgatcggttgttttccaccgaggtacaattgccagagctggatgttggagattggttgatcttcccagatatgggtg<br>cctattcgtcctcaatgtcctcgaccttcaacggatttccaatagccaccgtgtatgatgcaatgtcaccgcagttacg<br>ctccctgttggagactgtaccataa |
| MetDC<br>(*Entamoeba*<br>*histolytica*)<br>SEQ ID NO:<br>1040 | atgaaacaaacgtcccttgaggtgaaggaatttgccttgaatctcatttctcagttcgaaccagaaaaccagcctctg<br>ggtttctggatattcgacaccgaaggcgttgagaaagcggtagaacgctggaaaaagaacatgccgactgtccgtc<br>cctgttttgcagttaaatgcaacccggagccgcacctggtgaaattactggggaactgggttgcggcttcgattgc<br>gctagcctgaacgaaatcaaagaggtactggacttgggttttaatccggaagatatcacttatagtcagaccttcaaa<br>ccgtacaaccagttaattgaagcttcgcatctgggcatcaaccacacgatcgttgattcaatcgacgaagttcaaaaa<br>attgctaaatacgcgcctaagatgggtatcatgattcggatcatggaaaatgacacaagcgcaggccacgtctttgg<br>agagaaattcggtctgcatgatgatgaagttgagatcgtactgaaggaaattaaagacaaaggtctgaacctggac<br>ggcgttcatttccacgttggctctgattcccacaacagcgaagtgtttactaaggcactgaccaaagctcgtaacact<br>gtaaccctggccgaacagttcggcatgaaaccgtacctgatcgacattggtggcgggttctctcaggttgcgccgtt<br>cgaagaatttgctgctaccatcgaaaaaactataaaggaactggaatttccagagcgaactcgtttcattgcagagcc<br>gggtcgctatatggcatcaaatgcctttcaccttgtctcttcgctgcatggtaaaagggtgcgcatccagaacggtaa<br>gaaacagatcgaatacaccagcggcgatgggctgcacggctccttcggctgttgcatctggttcgaaaaacagaa<br>gtcttgcgaatgtataacacaaaaagtaaacgagaacaccaaaatgtatgaaagcatcatctacggcccatcttgca<br>acggttcggacaaagtggccacgcaggagttgccggaaatggagccgggtaaagattggctgctgttccccaata<br>tgggtgcttacactatttccatggcgaccaactttaacggcttcgaagaacgtaaccatgtaatctatacgttaccactc<br>aaaagtactaaaataattcagatccctaaaagcattgaatgcaactccgttccgtctttaaacggaatcccacactacg<br>cgtaa |
| SpMetDC<br>T66N<br>Codon-<br>optimized<br>sequence<br>SEQ ID NO:<br>1123 | atgtccccgacggcgtttccagcggccgaaacagctactgcccctgcaactgccgtcgatcctgggccagaactg<br>gacggcggagatttcgcccttccagagggcgggctggatgacgatcgtcgcttacgtgcattggacgcagttgac<br>gagtatttgacccgcaagcgcaagcatttggttgggtaccaagctaatcaggatatgcagggaacggccttggattt<br>agcccgtttcatgcccaacaacatcaacaacctgggagatcctttccagtcgggtgggtataaaccaaatacgaaa<br>gtcgttgagcgtgccgtactggactactatgcaaaattgtggcacgcagaacgtccacacgacccagctgacccag<br>aaagctactggggttacatgttatcgatgggctcaactgagggcaacatgtacgccctgtggaatgcacgtgactac<br>ctgtcgggtaaggctttgattcagcctcccacggcaccatttgacgctgttcgctacgtgaaggctgaccccgatcg<br>ccgcaatcctaacgcacaccacccagtcgcattctactcggaggatacccactattcttttgctaaagccgttgcggt<br>gctgggtgtcgaaactttccacgctgtgggtctggagaaatacgctgacgagtgccccttggtggatccagtaacc<br>ggccttcgtacctggccgaccgaagttccatcgcgcccggggccgtcgggtttaagctgggacggccctggtgag<br>attgatgttgatgcgcttgcagtactggtcgagttcttcgcagcgaagggtcaccccgtcttcgtcaaccttaacttgg<br>ggtctacatttaaaggagcacatgatgacgtacgtgcggtatgtgaacgcttattaccaatcttcgagcgccatggctt<br>agtacaacgtgaagttgtatatgggagctgtccccaaaccggccgccctttagtggatgtacgtcgcggattttggat<br>ccacgtagatggggcacttggggcggggtatgccccttttctgcgtcttgccgccgaagacccggaaggttatggtt<br>ggacccctgaggcagaattacctgagttcgacttcggcttacgtttgccgacggcggggcatggagaagttgatat<br>ggttagcagcatcgccatgagtggacataagtgggcaggcgcgccgtggccatgcggcatctatatgacgaaagt<br>gaaatatcagattagtccaccgtcacagcccgattatattggtgctcctgacacaacatttgccggttcccgtaacgg<br>cttttcgccgttaattttgtgggatcatttatcgcgctactcgtaccgcgaccaggtagagcgcatccgcgaagcaca<br>ggagcttgcagcatatttggaacgccgccttaccgctatggagcgcgagctgggagtggaactttggccagcccg<br>cacaccgggtgctgtaaccgtacgttttcgcaaaccctctgctgagctggttgcgaagtggtccttgtcgtcgcagg<br>atgttttaatggtgccgggtgatgaaactacgcgtcgtagttacgttcatgtgttcgtgatgccttctgttgatcgtgcaa<br>agttagatgcgttgctggcagaattggccgaagatcccgtcatcttgggtgcgccttaa |
| SpMetDC<br>A203H<br>Codon-<br>optimized<br>sequence<br>SEQ ID NO:<br>1125 | atgtccccgacggcgtttccagcggccgaaacagctactgcccctgcaactgccgtcgatcctgggccagaactg<br>gacggcggagatttcgcccttccagagggcgggctggatgacgatcgtcgcttacgtgcattggacgcagttgac<br>gagtatttgacccgcaagcgcaagcatttggttgggtaccaagctacccaggatatgcagggaacggccttggattt<br>agcccgtttcatgcccaacaacatcaacaacctgggagatcctttccagtcgggtgggtataaaccaaatacgaaa<br>gtcgttgagcgtgccgtactggactactatgcaaaattgtggcacgcagaacgtccacacgacccagctgacccag<br>aaagctactggggttacatgttatcgatgggctcaactgagggcaacatgtacgccctgtggaatgcacgtgactac<br>ctgtcgggtaaggctttgattcagcctcccacggcaccatttgacgctgttcgctacgtgaaggctgaccccgatcg<br>ccgcaatcctaacgcacaccacccagtcgcattctactcggaggatacccactattcttttgctaaagccgttcatgtg<br>ctgggtgtcgaaactttccacgctgtgggtctggagaaatacgctgacgagtgccccttggtggatccagtaaccg<br>gccttcgtacctggccgaccgaagttccatcgcgcccggggccgtcgggtttaagctgggacggccctggtgaga<br>ttgatgttgatgcgcttgcagtactggtcgagttcttcgcagcgaagggtcaccccgtcttcgtcaaccttaacttggg<br>gtctacatttaaaggagcacatgatgacgtacgtgcggtatgtgaacgcttattaccaatcttcgagcgccatggctta<br>gtacaacgtgaagttgtatatgggagctgtccccaaaccggccgccctttagtggatgtacgtcgcggattttggatc<br>cacgtagatggggcacttggggcggggtatgccccttttctgcgtcttgccgccgaagacccggaaggttatggtt<br>ggacccctgaggcagaattacctgagttcgacttcggcttacgtttgccgacggcggggcatggagaagttgatat |

TABLE 10-continued

| Exemplary Methionine Decarboxylase Nucleotide Sequences | |
|---|---|
| Description<br>SEQ ID NO: | Nucleotide Sequence |
| | ggttagcagcatcgccatgagtggacataagtgggcaggcgcgccgtggccatgcggcatctatatgacgaaagt<br>gaaatatcagattagtccaccgtcacagcccgattatattggtgctcctgacacaacatttgccggttcccgtaacgg<br>cttttcgccgttaatttgtgggatcatttatcgcgctactcgtaccgcgaccaggtagagcgcatccgcgaagcaca<br>ggagcttgcagcatatttggaacgccgccttaccgctatggagcgcgagctgggagtggaactttggccagcccg<br>cacaccgggtgctgtaaccgtacgttttcgcaaaccctctgctgagctggttgcgaagtggtccttgtcgtcgcagg<br>atgttttaatggtgccgggtgatgaaactacgcgtcgtagttacgttcatgtgttcgtgatgccttctgttgatcgtgcaa<br>agttagatgcgttgctggcagaattggccgaagatcccgtcatcttgggtgcgccttaa |
| SpMetDC<br>H379G<br>Codon-<br>optimized<br>sequence<br>SEQ ID NO:<br>1127 | atgtccccgacggcgtttccagcggccgaaacagctactgcccctgcaactgccgtcgatcctgggccagaactg<br>gacggcggagatttcgcccttccagagggcgggctggatgacgatcgtcgcttacgtgcattggacgcagttgac<br>gagtatttgacccgcaagcgcaagcatttggttgggtaccaagctacccaggatatgcagggaacggccttggattt<br>agcccgtttcatgcccaacaacatcaacaacctgggagatcctttccagtcgggtgggtataaaccaaatacgaaa<br>gtcgttgagcgtgccgtactggactactatgcaaaattgtggcacgcagaacgtccacacgacccagctgacccag<br>aaagctactggggttacatgttatcgatgggctcaactgagggcaacatgtacgccctgtggaatgcacgtgactac<br>ctgtcgggtaaggctttgattcagcctcccacggcaccatttgacgctgttcgctacgtgaaggctgaccccgatcg<br>ccgcaatcctaacgcacaccacccagtcgcattctactcggaggatacccactattcttttgctaaagccgttgcggt<br>gctgggtgtcgaaactttccacgctgtgggtctggagaaatacgctgacgagtgccccttggtggatccagtaacc<br>ggccttcgtacctggccgaccgaagttccatcgcgcccggggccgtcgggtttaagctgggacggccctggtgag<br>attgatgttgatgcgcttgcagtactggtcgagttcttcgcagcgaagggtcaccccgtcttcgtcaaccttaacttgg<br>ggtctacatttaaaggagcacatgatgacgtacgtgcggtatgtgaacgcttattaccaatcttcgagcgccatggctt<br>agtacaacgtgaagttgtatatgggagctgtccccaaaccggccgccctttagtggatgtacgtcgcggattttggat<br>ccacgtagatggggcacttggggcggggtatgccccttttctgcgtcttgccgccgaagacccggaaggttatggtt<br>ggacccctgaggcagaattacctgagttcgacttcggcttacgtttgccgacggcgggggcggagaagttgatat<br>ggttagcagcatcgccatgagtggacataagtgggcaggcgcgccgtggccatgcggcatctatatgacgaaagt<br>gaaatatcagattagtccaccgtcacagcccgattatattggtgctcctgacacaacatttgccggttcccgtaacgg<br>cttttcgccgttaatttgtgggatcatttatcgcgctactcgtaccgcgaccaggtagagcgcatccgcgaagcaca<br>ggagcttgcagcatatttggaacgccgccttaccgctatggagcgcgagctgggagtggaactttggccagcccg<br>cacaccgggtgctgtaaccgtacgttttcgcaaaccctctgctgagctggttgcgaagtggtccttgtcgtcgcagg<br>atgttttaatggtgccgggtgatgaaactacgcgtcgtagttacgttcatgtgttcgtgatgccttctgttgatcgtgcaa<br>agttagatgcgttgctggcagaattggccgaagatcccgtcatcttgggtgcgccttaa |

TABLE 11

| Exemplary Importer Nucleotide Sequences | |
|---|---|
| Description<br>SEQ ID NO: | Nucleotide Sequence |
| MetP<br>(*F. segetis*)<br>SEQ ID NO:<br>1041 | atggggaccattaacacgaagatctataaatacatgagcatctggaaaacaaaacctctgtccgtgctcttgtctgaa<br>gcaactgaggatgaaaaaggcctgaagcgcactctgtcggcccgttcacttgttgcgctgggtgtcggtgctattat<br>cggcgctggtttattctctctgaccggcatagctgcggcagacaatgctggaccggcagtaaccctgagctttatcct<br>ggcctccgttggttgcgcgttcgctggcctgtgttacgcagaatttgcttctatgattccagttgcgggtagcgcctac<br>acttatagttatgctaccatgggcgagttcgtggcgtggatcatcggttgggatctggtactcgaatacgcattgggc<br>gcagctactgttgccgttagctggtcccagtacgtggacaaattcttgcaaaactacggcatccatattccgaactcta<br>tcctccacgggccgtgggataccaccccggtattatcaatttaccgtcgatatttatcatctgcctgctgagcgtgct<br>gctgattcgtggtactaaagaatctgctctgatcaacaacattctggtaatcctgaaagtcacggttgtcatcgtgttca<br>ttggcctgggctgggggttcatgaactccgcaaaccacacgccctttatcccggttaacgaaggtgaggctctactg<br>tcttctggtgaaatgagtttcctcaacttttcagcagtgactactttggacactacggatggtccggtattcttcgcggc<br>gctggtgtagtattcttcgcatttatcggcttcgacgcggtgagcactgcggcacaggaggccaaggatccgcaga<br>aaggcatgccaatcggtattctgggctcactgatcatttgcaccgttctgtacgtgcttttcgctttcgttctgaccggtc<br>tggaaaactatctaaacttcaaaggtgacgcttctcctgtcaccactgcatttgccaaaacaggctatactttcctgaat<br>agcggtctgacgatcgctatcatagcgggctacacatccgttatgctggtaatgttgatgggtcagtcccgtgtctttt<br>atagtatgtctgtggatggcctgcttccgaagtttttctcgaccctgcataccaaaaacaggactccgtacaaaactaa<br>tttgctgttcatggttttcgtaagcctgttcgctggctttgttccggtcagcgacctgggccatatggtatccatcggtac<br>cctcttcgctttctgcctggtgtgtatcggcgttatcgttatgcgaaaaaccaacccagacgccgttcgcggttttcgtg<br>ttcctttttgtaccggtttcccgattatcggtgtagttatttgtctggttctaatggcgggcctgccgattgaatcttggga<br>acgtctggcgatctggatgattctgggtgtcgtgatctacttcttctactctaaaaagaactctaaactgaataaccccg<br>aataa |
| MetP<br>(*F. frigoris*)<br>SEQ ID NO:<br>1042 | atggggacgatcaatactaagaccaacaaatatatgagcatttggaaaaccaaaccgttgtctgtactgttaaacgag<br>gcctcagaagatgaaaagggcctgaaaggactctgtcctctcgttccctcgtggctctgggtgtcggtgcgatcat<br>tggcgcaggtctgtttagcctaacaggcatcgcagctgcggaacatgctggtccagcggttactctgagtttcatact<br>ggccgctgttggttgtgctttcgcaggcctgtgctacgcggagtttgcgtcgatgatccctgtggctgggtctgcttac<br>acctatagctacgcaaccatgggcgaatttatggcgtggatcattggctgggaccttgtactggaatacgctctgggt<br>gcagcgactgttggtgtatcctggtcccgttacttactggaattgctgaacaaatatggtgttcacctgaacccgaaat<br>tcatctgctctccgtgggagacacttaccctgggcgacggcactattatcgatggcgggtacatcaatctgccggca<br>attctgatcgtgagcgccctcagcttgctgctgattagaggtacccaggaatctgcttctattaacaacatcctggttgt<br>gctgaaagtaatagtcgtgatcatgttcatcgttttaggatgggactatatcgatcccgcaaattactcaccttacatcc<br>cggaaaacaccggcgtaaagggccaattcggttggtcgggtatcgctgcgggtgctggtacggttttctttgccttc<br>attggtttcgacgccgtttccactgcggctcaggaggctaaaaacccgcagaaaggcatgccaattggcatcctgg<br>ggtctttggtaatttgtacgatcctgtacgtcctttttgcccacgttatgacgggcctggtgccgtattataagttcgctg<br>gagatgctaaacccgctgcgacagcattcgcagtcaccggttacagttttctgcaaactggactgattgttgcgatcc |

TABLE 11-continued

Exemplary Importer Nucleotide Sequences

| Description<br>SEQ ID NO: | Nucleotide Sequence |
|---|---|
| | tggctggctatactagcgttatgctggtcatgctgatggggcagagtcgtgttttctacaccatgagcaaagacggtc<br>tgctaccaccgctgttcggtcagatccattcgaaatttcgcactccgtacaagactaacctgttctttatggtattcgtttc<br>tttattcgcgggtttcgtgccggttagcgacctcggccacatggtcagcatcggtaccctcctggcgtttgttcttgtgt<br>gcataggtgtgctggtgatgcgaaaaagatgccagatgctccgcgttctttcaaaccccgttcgttccgtatgtac<br>ccatcgcaggcgtcctggtgtgcacttacctgatgtactccctcccttacgaatcctggattcgcttagtgctttggatg<br>gctatcggcgtagccctgtacttcgtgtatggaaaaagcactcaaaactgaacaatccggataa |
| MetNIQ<br>SEQ ID NO:<br>1043 | atgataaaactttcgaatatcaccaaagtgttccaccagggcacccgcaccatccaggcgttgaacaacgtcagcct<br>gcatgtgccagctggacaaatttatggcgttatcggtgcctcaggcgcgggtaagagtacgcttatacgttgtgtaaa<br>cctgctggagcgcccaaccgagggtagcgtgctggtcgatggccaggaactgaccacgctgtcagaatccgagtt<br>gaccaaagctcgtcgccagattggtatgattttccagcattttaacctgctctcttcgcgtactgtttttggcaacgtggc<br>tctgccgctggagctggacaacacaccgaaagacgagatcaaacgtcgcgtgacggaattgctgtcattggttggt<br>cttggcgataagcatgatagctacccgtcgaatctttccggtgggcagaaacaacgtgtggcgattgcccgtgcatt<br>agccagcaatcccaaagtattgctgtgtgatgaagccaccagcgcgctggacccggcaacgacacgttctattctc<br>gaactgctgaaagacatcaaccgccgtctgggtttgacgattctgttgatcactcacgaaatggacgttgtgaagcg<br>catttgtgattgcgtggcggtcatcagcaatggcgaactgatcgagcaggacacggtaagtgaagtgttctcgcatc<br>cgaaaacgccgctggcgcagaagtttattcagtcgaccctgcatctggatatcccggaagattaccaggaacgtct<br>gcaagcggagccatttactgactgcgtgccgatgctgcgtctggagtttaccggtcaatcggtcgatgccccactgc<br>tttctgaaaccgcgcgtcgtttcaacgtcaacaacaacattattagcgcgcagatggattacgccggtggcgttaagt<br>tcggcatcatgctgactgaaatgcacggcacacaacaagatacgcaagccgccattgcctggctgcaggaacacc<br>atgtaaaagtagaggtactgggttatgtctgagccgatgatgtggctgctggttcgtggcgtatgggaaacgctggc<br>aatgaccttcgtatccggtttttttggctttgtgattggtctgccggttggcgttctgctttatgtcacgcgtccggggca<br>aattattgctaacgcgaagttgtatcgtaccatttctgcgattgtgaacattttccgttccatcccgttcattatcttgctgg<br>tatggatgattccgtttacccgcgttattgtcggtacatcgattggattgcaggcagcgattgttccgttaaccgttggt<br>gcagcaccgtttattgcccgtatggtcgagaacgctctgctggagatcccaaccgggttaattgaagcttcccgcgc<br>aatgggggccacgccaatgcagatcgtccgtaaagtgctgttaccggaagcgttgccgggtctggtgaatgcggc<br>aactatcaccctgattaccctggttggttattccgcgatgggtggtgcagtcggtgccggtggtttaggtcagattggc<br>tatcagtatggctacatcggctacaacgcgacggtgatgaatacggtactggtattgctggtcattctggtttatttaatt<br>cagttcgcaggcgaccgcatcgtccgggctgtcactcgcaagtaacgttcaacacaacataaataattgaagaagg<br>aataaggtatggcgttcaaattcaaaacctttgcggcagtgggagccctgattggatcactggcactggtaggctgc<br>ggtcaggatgaaaaagatccaaaccacattaaagtcggcgtgattgttggtgccgaacagcaggttgcagaagtcg<br>cgcagaaagttgcgaaagacaaatatggcctggacgttgagctggtaaccttcaacgactatgttctgccaaacga<br>agcattgagcaaaggcgatatcgacgccaacgccttccagcataaaccgtaccttgatcagcaactgaaagatcgt<br>ggctacaaactggtcgcagtaggcaacacatttgtttatccgattgctggttactccaagaaaatcaaatcactggatg<br>aactgcaggatggttcgcaggttgccgtgccaaacgacccaactaaccttggtcgttcactgctgctgctgcaaaaa<br>gtgggcttgatcaaactgaaagatggcgttggcctgctgccgaccgttcttgatgttgttgagaacccaaaaaatctg<br>aaaattgttgaactggaagcaccgcagctaccgcgctctctggacgacgcgcaaatcgctctggcagttatcaatac<br>cacctatgccagccagattggcctgactccagcgaaagacggtatctttgtcgaagataaagagtccccgtacgtaa<br>acctgatcgtaacgcgtgaagacaacaaagacgccgaaaacgtgaagaaattcgttcaggcttatcagtctgacga<br>agtttacgaagcagcaaacaaagtgtttaacggcggcgctgttaaaggctggtaa |
| Methionine<br>import system<br>permease<br>protein MetP<br>(*Bacillus*<br>*subtilis*)<br>SEQ ID NO:<br>1044 | atgtttgaga agtattttcc aaatgttgac ttgaccgagt tatggaatgc cacatatgaaactctgtata<br>tgacattgat ttccttactg tttgccttcg taatcggcgt catcctgggattgctgttat tcttaacatc<br>taaggggtct ctttggcaaa ataaagcagt aaattccgttatcgcagccg ttgtcaacat ctttcgttca<br>attcccttcc ttattttaat catcctgcttcttggtttca ctaaattctt agtgggaaca attttgggac<br>caaatgcggc tcttcccgcgttagtcatcg gtagtgctcc cttttatgct cgtctggtcg aaatcgcact<br>tcgtgaagtggacaaaggag tgattgaggc ggcgaaatcg atgggggcta agacgagcac tattattttt<br>aaggttctta tccccgagtc catgcccgcg ctgatttccg gaattacagt gactgcgatt gcattgatcg<br>ggtcaaccgc catcgcagga gctattggtt ctggtggatt gggaaacttagcatacgttg aaggctatca<br>atcgaataat gcggatgtga ccttcgtggc cacagttttcatcctgatta ttgttttcat cattcagatc<br>attggtgacc ttattaccaa catcatcgataaacgc |
| MetNIQ<br>(P281G)<br>SEQ ID NO:<br>1045 | atgataaaactttcgaatatcaccaaagtgttccaccagggcacccgcaccatccaggcgttgaacaacgtcagcct<br>gcatgtgccagctggacaaatttatggcgttatcggtgcctcaggcgcgggtaagagtacgcttatacgttgtgtaaa<br>cctgctggagcgcccaaccgagggtagcgtgctggtcgatggccaggaactgaccacgctgtcagaatccgagtt<br>gaccaaagctcgtcgccagattggtatgattttccagcattttaacctgctctcttcgcgtactgtttttggcaacgtggc<br>tctgccgctggagctggacaacacaccgaaagacgagatcaaacgtcgcgtgacggaattgctgtcattggttggt<br>cttggcgataagcatgatagctacccgtcgaatctttccggtgggcagaaacaacgtgtggcgattgcccgtgcatt<br>agccagcaatcccaaagtattgctgtgtgatgaagccaccagcgcgctggacccggcaacgacacgttctattctc<br>gaactgctgaaagacatcaaccgccgtctgggtttgacgattctgttgatcactcacgaaatggacgttgtgaagcg<br>catttgtgattgcgtggcggtcatcagcaatggcgaactgatcgagcaggacacggtaagtgaagtgttctcgcatc<br>cgaaaacgccgctggcgcagaagtttattcagtcgaccctgcatctggatatcccggaagattaccaggaacgtct<br>gcaagcggagccatttactgactgcgtgccgatgctgcgtctggagtttaccggtcaatcggtcgatgccggcctg<br>ctttctgaaaccgcgcgtcgtttcaacgtcaacaacaacattattagcgcgcagatggattacgccggtggcgttaag<br>ttcggcatcatgctgactgaaatgcacggcacacaacaagatacgcaagccgccattgcctggctgcaagaacac<br>catgtaaaagtagaggtactgggttatgtctgagccgatgatgtggctgctggttcgtggcgtatgggaaacgctgg<br>caatgaccttcgtatccggtttttttggctttgtgattggtctgccggttggcgttctgctttatgtcacgcgtccggggc<br>aaattattgctaacgcgaagttgtatcgtaccatttctgcgattgtgaacattttccgttccatcccgttcattatcttgctg<br>gtatggatgattccgtttacccgcgttattgtcggtacatcgattggattgcaggcagcgattgttccgttaaccgttgg<br>tgcagcaccgtttattgcccgtatggtcgagaacgctctgctggagatcccaaccgggttaattgaagcttcccgcg<br>caatgggggccacgccaatgcagatcgtccgtaaagtgctgttaccggaagcgttgccgggtctggtgaatgcgg<br>caactatcaccctgattaccctggttggttattccgcgatgggtggtgcagtcggtgccggtggtttaggtcagattgg<br>ctatcagtatggctacatcggctacaacgcgacggtgatgaatacggtactggtattgctggtcattctggtttatttaa<br>ttcagttcgcaggcgaccgcatcgtccgggctgtcactcgcaagtaacgttcaacacaacataaataattgaagaag<br>gaataaggtatggcgttcaaattcaaaacctttgcggcagtgggagccctgattggatcactggcactggtaggctg |

TABLE 11-continued

| Exemplary Importer Nucleotide Sequences | |
|---|---|
| Description<br>SEQ ID NO: | Nucleotide Sequence |
| | cggtcaggatgaaaaagatccaaaccacattaaagtcggcgtgattgttggtgccgaacagcaggttgcagaagtc<br>gcgcagaaagttgcgaaagacaaatatggcctggacgttgagctggtaaccttcaacgactatgttctgccaaacg<br>aagcattgagcaaaggcgatatcgacgccaacgccttccagcataaaccgtaccttgatcagcaactgaaagatcg<br>tggctacaaactggtcgcagtaggcaacacatttgtttatccgattgctggttactccaagaaaatcaaatcactggat<br>gaactgcaagatggttcgcaggttgccgtgccaaacgacccaactaaccttggtcgttcactgctgctgctgcaaaa<br>agtgggcttgatcaaactgaaagatggcgttggcctgctgccgaccgttcttgatgttgttgagaacccaaaaaatct<br>gaaaattgttgaactggaagcaccgcagctaccgcgctctctggacgacgcgcaaatcgctctggcagttatcaat<br>accacctatgccagccagattggcctgactccagcgaaagacggtatctttgtcgaagataaagagtccccgtacgt<br>aaacctgatcgtaacgcgtgaagacaacaaagacgccgaaaacgtgaagaaattcgttcaggcttatcagtctgac<br>gaagtttacgaagcagcaaacaaagtgtttaacggcggcgctgttaaaggctggtaa |
| Recoded<br>MetNIQ<br>SEQ ID NO:<br>1046 | atgataaaactttcgaatatcaccaaagtgttccaccagggcacccgcaccatccaggcgttgaacaacgtcagcct<br>gcatgtgccagctggacaaatttatggcgttatcggtgcctcaggcgcgggtaagagtacgcttatacgttgtgtaaa<br>cctgctggagcgcccaaccgagggtagcgtgctggtcgatggccaggaactgaccacgctgtcagaatccgagtt<br>gaccaaagctcgtcgccagattggtatgattttccagcattttaacctgctctcttcgcgtactgtttttggcaacgtggc<br>tctgccgctggagctggacaacacaccgaaagacgagatcaaacgtcgcgtgacggaattgctgtcattggttggt<br>cttggcgataagcatgatagctacccgtcgaatctttccggtgggcagaaacaacgtgtggcgattgcccgtgcatt<br>agccagcaatcccaaagtattgctgtgtgatgaagccaccagcgcgctggacccggcaacgacacgttctattctc<br>gaactgctgaaagacatcaaccgccgtctgggtttgacgattctgttgatcactcacgaaatggacgttgtgaagcg<br>catttgtgattgcgtggcggtcatcagcaatggcgaactgatcgagcaggacacggtaagtgaagtgttctcgcatc<br>cgaaaacgccgctggcgcagaagtttattcagtcgaccctgcatctggatatcccggaagattaccaggaacgtct<br>gcaagcggagccatttactgactgcgtgccgatgctgcgtctggagtttaccggtcaatcggtcgatgccccactgc<br>tttctgaaaccgcgcgtcgtttcaacgtcaacaacaacattattagcgcgcagatggattacgccggtggcgttaagt<br>tcggcatcatgctgactgaaatgcacggcacacaacaagatacgcaagccgccattgcctggctgcaagaacacc<br>atgtaaaagtagaggtactgggttatgtctgagccgatgatgtggctgctggttcgtggcgtatgggaaacgctggc<br>aatgaccttcgtatccggtttttttggctttgtgattggtctgccggttggcgttctgctttatgtcacgcgtccggggca<br>aattattgctaacgcgaagttgtatcgtaccatttctgcgattgtgaacattttccgttccatcccgttcattatcttgctgg<br>tatggatgattccgtttacccgcgttattgtcggtacatcgattggattgcaggcagcgattgttccgttaaccgttggt<br>gcagcaccgtttattgcccgtatggtcgagaacgctctgctggagatcccaaccgggttaattgaagcttcccgcgc<br>aatgggggccacgccaatgcagatcgtccgtaaagtgctgttaccggaagcgttgccgggtctggtgaatgcggc<br>aactatcaccctgattaccctggttggttattccgcgatgggtggtgcagtcggtgccggtggtttaggtcagattggc<br>tatcagtatggctacatcggctacaacgcgacggtgatgaatacggtactggtattgctggtcattctggtttatttaatt<br>cagttcgcaggcgaccgcatcgtccgggctgtcactcgcaagtaacgttcaacacaacataaataattgaagaagg<br>aataaggtatggcgttcaaattcaaaacctttgcggcagtgggagccctgattggatcactggcactggtaggctgc<br>ggtcaggatgaaaaagatccaaaccacattaaagtcggcgtgattgttggtgccgaacagcaggttgcagaagtcg<br>cgcagaaagttgcgaaagacaaatatggcctggacgttgagctggtaaccttcaacgactatgttctgccaaacga<br>agcattgagcaaaggcgatatcgacgccaacgccttccagcataaaccgtaccttgatcagcaactgaaagatcgt<br>ggctacaaactggtcgcagtaggcaacacatttgtttatccgattgctggttactccaagaaaatcaaatcactggatg<br>aactgcaagatggttcgcaggttgccgtgccaaacgacccaactaaccttggtcgttcactgctgctgctgcaaaaa<br>gtgggcttgatcaaactgaaagatggcgttggcctgctgccgaccgttcttgatgttgttgagaacccaaaaaatctg<br>aaaattgttgaactggaagcaccgcagctaccgcgctctctggacgacgcgcaaatcgctctggcagttatcaatac<br>cacctatgccagccagattggcctgactccagcgaaagacggtatctttgtcgaagataaagagtccccgtacgtaa<br>acctgatcgtaacgcgtgaagacaacaaagacgccgaaaacgtgaagaaattcgttcaggcttatcagtctgacga<br>agtttacgaagcagcaaacaaagtgtttaacggcggcgctgttaaaggctggtaa |
| MetNIQ<br>(P281S)<br>SEQ ID NO:<br>1047 | atgataaaactttcgaatatcaccaaagtgttccaccagggcacccgcaccatccaggcgttgaacaacgtcagcct<br>gcatgtgccagctggacaaatttatggcgttatcggtgcctcaggcgcgggtaagagtacgcttatacgttgtgtaaa<br>cctgctggagcgcccaaccgagggtagcgtgctggtcgatggccaggaactgaccacgctgtcagaatccgagtt<br>gaccaaagctcgtcgccagattggtatgattttccagcattttaacctgctctcttcgcgtactgtttttggcaacgtggc<br>tctgccgctggagctggacaacacaccgaaagacgagatcaaacgtcgcgtgacggaattgctgtcattggttggt<br>cttggcgataagcatgatagctacccgtcgaatctttccggtgggcagaaacaacgtgtggcgattgcccgtgcatt<br>agccagcaatcccaaagtattgctgtgtgatgaagccaccagcgcgctggacccggcaacgacacgttctattctc<br>gaactgctgaaagacatcaaccgccgtctgggtttgacgattctgttgatcactcacgaaatggacgttgtgaagcg<br>catttgtgattgcgtggcggtcatcagcaatggcgaactgatcgagcaggacacggtaagtgaagtgttctcgcatc<br>cgaaaacgccgctggcgcagaagtttattcagtcgaccctgcatctggatatcccggaagattaccaggaacgtct<br>gcaagcggagccatttactgactgcgtgccgatgctgcgtctggagtttaccggtcaatcggtcgatgcctccctgc<br>tttctgaaaccgcgcgtcgtttcaacgtcaacaacaacattattagcgcgcagatggattacgccggtggcgttaagt<br>tcggcatcatgctgactgaaatgcacggcacacaacaagatacgcaagccgccattgcctggctgcaagaacacc<br>atgtaaaagtagaggtactgggttatgtctgagccgatgatgtggctgctggttcgtggcgtatgggaaacgctggc<br>aatgaccttcgtatccggtttttttggctttgtgattggtctgccggttggcgttctgctttatgtcacgcgtccggggca<br>aattattgctaacgcgaagttgtatcgtaccatttctgcgattgtgaacattttccgttccatcccgttcattatcttgctgg<br>tatggatgattccgtttacccgcgttattgtcggtacatcgattggattgcaggcagcgattgttccgttaaccgttggt<br>gcagcaccgtttattgcccgtatggtcgagaacgctctgctggagatcccaaccgggttaattgaagcttcccgcgc<br>aatgggggccacgccaatgcagatcgtccgtaaagtgctgttaccggaagcgttgccgggtctggtgaatgcggc<br>aactatcaccctgattaccctggttggttattccgcgatgggtggtgcagtcggtgccggtggtttaggtcagattggc<br>tatcagtatggctacatcggctacaacgcgacggtgatgaatacggtactggtattgctggtcattctggtttatttaatt<br>cagttcgcaggcgaccgcatcgtccgggctgtcactcgcaagtaacgttcaacacaacataaataattgaagaagg<br>aataaggtatggcgttcaaattcaaaacctttgcggcagtgggagccctgattggatcactggcactggtaggctgc<br>ggtcaggatgaaaaagatccaaaccacattaaagtcggcgtgattgttggtgccgaacagcaggttgcagaagtcg<br>cgcagaaagttgcgaaagacaaatatggcctggacgttgagctggtaaccttcaacgactatgttctgccaaacga<br>agcattgagcaaaggcgatatcgacgccaacgccttccagcataaaccgtaccttgatcagcaactgaaagatcgt<br>ggctacaaactggtcgcagtaggcaacacatttgtttatccgattgctggttactccaagaaaatcaaatcactggatg<br>aactgcaagatggttcgcaggttgccgtgccaaacgacccaactaaccttggtcgttcactgctgctgctgcaaaaa<br>gtgggcttgatcaaactgaaagatggcgttggcctgctgccgaccgttcttgatgttgttgagaacccaaaaaatctg<br>aaaattgttgaactggaagcaccgcagctaccgcgctctctggacgacgcgcaaatcgctctggcagttatcaatac |

TABLE 11-continued

| Exemplary Importer Nucleotide Sequences | |
|---|---|
| Description SEQ ID NO: | Nucleotide Sequence |
| | cacctatgccagccagattggcctgactccagcgaaagacggtatctttgtcgaagataaagagtccccgtacgtaa<br>acctgatcgtaacgcgtgaagacaacaaagacgccgaaaacgtgaagaaattcgttcaggcttatcagtctgacga<br>agtttacgaagcagcaaacaaagtgtttaacggcggcgctgttaaaggctggtaa |
| *Sporomusa termitida* MetP - Codon-optimized sequence SEQ ID NO: 1129 | atgaacttttccgcactaaatgtattgacaagttaaaagaaggcgcagagcagcaaggtttgaaaaagagtctggg<br>ggctaccgatctgatccttctgggtatcggatgcatcattggcacaggcatcttcgttctgacgggcgtcgcggctgc<br>aaattatgccggtccgggtataatgctgtccttcgtgatctcgggtctggcgtgcgcttttgcagctctggcctacgcg<br>gaactagctgctatggttccaattgctggcagcgcgtacacttattcttacgccgcgttaggcgaaatcgtagcatgg<br>attgtaggttggaacctgatcctcgagtacagcgttgggtcttcagctgtggccgcgggttggtccggctacatggta<br>ggcctgctgaaaagcggtggtatcgaactgcctaaagctttcaccgcagttccggctgatggtggtttggtgaacttg<br>ccggccatgttaattgctctgctgctgtcggttctgctagtccgtggcaccaaagaatctgtgactctgaataaggtcc<br>tggttgtgattaaactggcagcggttttcatctttctggctctggcgggccccaaagtaaacccggctaactggtccc<br>ctctgatgccgtatgggttctctggtgtagcggcgggtgcagccattatctttttcgcttacatcggcttcgacgcagta<br>gctaccgctgctgaagagtgccggaacccgaaacgagacttaccagcaggtatcatcgggtcactggttatctgca<br>ctatactgtatattgttgttgcgggcgtcctgactggcgtcgttccgtaccagcagctcaacaacgctgaaccggttg<br>catacgctctgagagcgatcggctacaatttcgggtctgctctcgttggtaccggagctatcgccggcattacgaca<br>gtgctgcttgtcctgatgtatggtcagacccgcatcttctttgcaatgagccgtgatggcctgatcccggctcgtatct<br>gtaaagtacatccacgttatggaactcctcacataattaccatggcagcgggtatcgcagttgctctgattgcaggtttt<br>acacctatcggcattatcgcggaactgactaacatcggcaccttgttcgcgttcgtggtagccgccatcggtgtactg<br>gtgctcaggtacacccgcccggacatcccgcgtagctttaagtgcccggctgtcaaagtgattgctccgctggctgt<br>tctgtcctgcggatacctgatggccaatctgccagcagagacttggatccgcttcggtatctggtccgccattggctt<br>cgtcgtttactttgtttattcttatcaccatagcgttctgaacaaagcggaagtggctgggaaggaataa |
| *Bacteroidetes bacterium* 43-16 MetP - Codon-optimized sequence SEQ ID NO: 1131 | atgggtatctttgcgaaaaagcagctgaatcaattgattgccgaggcttccgaatctgaaaaaggcttaaaaaagact<br>ctgtcagctggagcactcgtgagtctagggatcggtgccataatcggcgcgggcctgttctctcttacgggcatggc<br>tgctgccgacaacgcaggtccggcggttgtattcagctttatcctggcagctgtcggttgcgggttcgctggtctgtg<br>ttacgcagaatttgcgagcatgattcctgttgctggctccgcatatacatactcttatgctaccatgggcgaactgattg<br>cttggatcatcggttgggatctggtactggagtacgcgctgggtgccgcaaccgttgctgtgtcgtggagccagtac<br>gttaacaaattccttcactccgtcggcatcgacctgccacagtatctattgcatggtccgtgggatgaagtgaacggc<br>gttgcgatgaacggtattattaacctgcccgcgatcatcattgtatgcctgctgtctctgctgctgatacgcggcacta<br>aagagagtgcgctattgaataacatcctggtgatcctgaaagtcgttgtagttttggtcttcatctgtattggctggtcttt<br>catcaacccggctaatcacgaaccgtttattccggttaacgctggtgaagagatggtaaaaagcggtaccatgtcttt<br>ttggagcttcttcacttccgaaagcttcggatcttacggtatctcgggcatcctgcgtggcgctggtgtggttttctttgc<br>atttatcggattcgatgccgttagcaccgctgctcaagaagccaagaacccgcagaaaggcatgccaatcgggatc<br>attggtagtctggttgtgtgcactatcctgtatgtgctcttcgcatacgtactgactggcctggagaactacataaacttt<br>aaaggtaatgcgtccccggttaccaccgcgttcgcacacaccggttatacgtttttaaactctttccttactatggcgat<br>tatcgcaggttacacctcagttatgcttgtaatgctgatgggccagtcccgtgtgttctatagtatgtcggtggacgga<br>ctgctgcctaaaatgttttctgacctgcataagaaaaacaggacaccgtacaagactaacctgatcttcatggtgtttgt<br>ctcactgttcgcaggcttcgttccggtagcagatctggggcacatggtcagcatcggtacattattcgcattcgctctg<br>gtgtgcattggcgttatagtgatgcgcaaaactaatcccgatgccgttagagggttccgtactccgttcgtcccagttc<br>tccctatcctgggtgtcttagtatgtgtagtactgatgctgggcctgccgaaagaatcctgggaacgtttggccatctg<br>gcttggtttgggcctgattatctactttgcttacagcaagaaaaactctaaaattggaaacaaataa |

TABLE 12

| Exemplary Methionine Decarboxylase Amino Acid Sequences | |
|---|---|
| Description SEQ ID NO: | Amino Acid Sequence |
| MetDC Q70D N82H SEQ ID NO: 1048 | MSPTAFPAAETATAPATAVDPGPELDGGDFALPEGGLDDDRRLRALDAV<br>DEYLTRKRKHLVGYQATQDMDGTALDLARFMPHNINNLGDPFQSGGY<br>KPNTKVVERAVLDYYAKLWHAERPHDPADPESYWGYMLSMGSTEGN<br>MYALWNARDYLSGKALIQPPTAPFDAVRYVKADPDRRNPNAHHPVAFY<br>SEDTHYSFAKAVAVLGVETFHAVGLEKYADECPLVDPVTGLRTWPTEV<br>PSRPGPSGLSWDGPGEIDVDALAVLVEFFAAKGHPVFVNLNLGSTFKGA<br>HDDVRAVCERLLPIFERHGLVQREVVYGSCPQTGRPLVDVRRGFWIHVD<br>GALGAGYAPFLRLAAEDPEGYGWTPEAELPEFDFGLRLPTAGHGEVDM<br>VSSIAMSGHKWAGAPWPCGIYMTKVKYQISPPSQPDYIGAPDTTFAGSR<br>NGFSPLILWDHLSRYSYRDQVERIREAQELAAYLERRLTAMERELGVEL<br>WPARTPGAVTVRFRKPSAELVAKWSLSSQDVLMVPGDETTRRSYVHVF<br>VMPSVDRAKLDALLAELAEDPVILGAP |
| MetDC (*Streptomyces*) SEQ ID NO: 1049 | MSPTAFPAAETATAPATAVDPGPELDGGDFALPEGGLDDDRRLRALDAV<br>DEYLTRKRKHLVGYQATQDMQGTALDLARFMPNNINNLGDPFQSGGY<br>KPNTKVVERAVLDYYAKLWHAERPHDPADPESYWGYMLSMGSTEGN<br>MYALWNARDYLSGKALIQPPTAPFDAVRYVKADPDRRNPNAHHPVAFY<br>SEDTHYSFAKAVAVLGVETFHAVGLEKYADECPLVDPVTGLRTWPTEV<br>PSRPGPSGLSWDGPGEIDVDALAVLVEFFAAKGHPVFVNLNLGSTFKGA<br>HDDVRAVCERLLPIFERHGLVQREVVYGSCPQTGRPLVDVRRGFWIHVD<br>GALGAGYAPFLRLAAEDPEGYGWTPEAELPEFDFGLRLPTAGHGEVDM<br>VSSIAMSGHKWAGAPWPCGIYMTKVKYQISPPSQPDYIGAPDTTFAGSR |

TABLE 12-continued

Exemplary Methionine Decarboxylase Amino Acid Sequences

| Description SEQ ID NO: | Amino Acid Sequence |
|---|---|
| | NGFSPLILWDHLSRYSYRDQVERIREAQELAAYLERRLTAMERELGVEL<br>WPARTPGAVTVRFRKPSAELVAKWSLSSQDVLMVPGDETTRRSYVHVF<br>VMPSVDRAKLDALLAELAEDPVILGAP |
| MetDC (V491L A500P) SEQ ID NO: 1050 | MSPTAFPAAETATAPATAVDPGPELDGGDFALPEGGLDDDRRLRALDAV<br>DEYLTRKRKHLVGYQATQDMQGTALDLARFMPNNINNLGDPFQSGGY<br>KPNTKVVERAVLDYYAKLWHAERPHDPADPESYWGYMLSMGSTEGN<br>MYALWNARDYLSGKALIQPPTAPFDAVRYVKADPDRRNPNAHHPVAFY<br>SEDTHYSFAKAVAVLGVETFHAVGLEKYADECPLVDPVTGLRTWPTEV<br>PSRPGPSGLSWDGPGEIDVDALAVLVEFFAAKGHPVFVNLNLGSTFKGA<br>HDDVRAVCERLLPIFERHGLVQREVVYGSCPQTGRPLVDVRRGFWIHVD<br>GALGAGYAPFLRLAAEDPEGYGWTPEAELPEFDFGLRLPTAGHGEVDM<br>VSSIAMSGHKWAGAPWPCGIYMTKVKYQISPPSQPDYIGAPDTTFAGSR<br>NGFSPLILWDHLSRYSYRDQVERIREAQELAAYLERRLTAMERELGVEL<br>WPARTPGALTVRFRKPSPELVAKWSLSSQDVLMVPGDETTRRSYVHVF<br>VMPSVDRAKLDALLAELAEDPVILGAP |
| MetDC (R41Q Q70D) SEQ ID NO: 1051 | MSPTAFPAAETATAPATAVDPGPELDGGDFALPEGGLDDDQRLRALDA<br>VDEYLTRKRKHLVGYQATQDMDGTALDLARFMPNNINNLGDPFQSGG<br>YKPNTKVVERAVLDYYAKLWHAERPHDPADPESYWGYMLSMGSTEGN<br>MYALWNARDYLSGKALIQPPTAPFDAVRYVKADPDRRNPNAHHPVAFY<br>SEDTHYSFAKAVAVLGVETFHAVGLEKYADECPLVDPVTGLRTWPTEV<br>PSRPGPSGLSWDGPGEIDVDALAVLVEFFAAKGHPVFVNLNLGSTFKGA<br>HDDVRAVCERLLPIFERHGLVQREVVYGSCPQTGRPLVDVRRGFWIHVD<br>GALGAGYAPFLRLAAEDPEGYGWTPEAELPEFDFGLRLPTAGHGEVDM<br>VSSIAMSGHKWAGAPWPCGIYMTKVKYQISPPSQPDYIGAPDTTFAGSR<br>NGFSPLILWDHLSRYSYRDQVERIREAQELAAYLERRLTAMERELGVEL<br>WPARTPGAVTVRFRKPSAELVAKWSLSSQDVLMVPGDETTRRSYVHVF<br>VMPSVDRAKLDALLAELAEDPVILGAP |
| MetDC (*Stanieria* sp. NIES-3757) SEQ ID NO: 1052 | MGFQLLSKHKLSAEDQQKLDRFYRDIQTEAERFLGYPCNELFDYSPLFRF<br>LQYPLNNVGDPYLPSNYHLNTHNFECEVLEIFRTLTEATEGSTWGYVTN<br>GGTEGNHYGLFLARELLPEGLVYYSQDAHYSIDKILRCLNLRSIMIRSHD<br>DGRMDLDDLRETLRIHRDLPPIVCATIGTTMKGAVDDIAGIKKIFKDLAIH<br>RHYIHADAALGGMILPFLDNSPPWNFKAGIDSIAISGHKMVGSPIPCGVV<br>LAKKSNVERIAQSVEYIGTLDTTLSGSRNALTPLFLWYAFHTVGIEGFKRI<br>IPACLKMADYAIAQLNKINRNAWRYPYSNTVVFDRPSPEVTRYWQLAC<br>QGNLSHLITMPHVTSTQIDHLVADIIASEPIPPLPTLSVTPACELLTSTPDQ<br>DITLIGTANHNLLSEVSTALAAEGLSIENLAAVAVESEDVEVVRLRVNNR<br>ERALQILNQNLDIGRCYGQARPFGNEEATQVLSQLEYQSVGEDALLVQL<br>DDCPGSLAELLKDCRNEAVKIRNIRLLWRGHGKGVVAIATTSPDALKTL<br>LKDRILLS |
| LeuDC (*Mus musculus*) SEQ ID NO: 1053 | MSTPSEVKKDLLGAAGSLWPSEPITLGPGESAWQLVLKKIQELSDSGHQ<br>DPFMVADLDVLVSRHQTFCQALPRVQPFYAVKCNSNPWVLRVLAALGT<br>GFDCASQGELEQVLGLGVAPSRIIFANPCKAVSHIQFAARCGVQLLTFDS<br>EEELIKVAQYHPGARLVLRIQTQDSQSTFPLSTKFGASLEACGHLLQVAR<br>ELGLAVVGASFHVGSDCHTPQSFRQAIADCHRVFEMGRKAGHDMSLLD<br>LGGGFPGVEGSEAKFEEMARVINAALAQYFPEETGIEVIAEPGRFYAGSV<br>CTAAVNIIAKKSVLEPGGHRKLMYYLNEGHYGSFRLFLRDPVPRIPIVVK<br>EFPSEPPLFPCTLYGPTCDAYDRLFSEEVQLPELDVGDWLIFPDMGAYTS<br>SMSSTFNGFPPATVYCAMSPQLRSLLETVP |
| MetDC (*Mus musculus*) SEQ ID NO: 1054 | MNTPSEVKKDLLGVAEHLRPSEPITLGPGASAWQLVLKKIKELSISGRQD<br>AFMVADLDVLVSRHRTFLQALPRVQPFYAVKCNSNPWVLLVLAALGTG<br>FDCASQGELEQVLGLGVAPSRIIFANPCKAVSHIQFAARCGVQLLTFDNE<br>EELIKLARYHPRARLVLRIQTLDSQSTFPLSTKFGAHLEACGHLLQVARE<br>LGLAVVGASFHVGSDCHTPESYRQAIADCHRVFEMGCKAGHHMSLLDL<br>GGGFPGVKGSEAKFEEVARVINTALAQYFPEETGIEVIAEPGRFYAGSVC<br>TAAVNIIAKKSSLDPGGHRKLAYYLNEGHYGVFRLFLRDPVPRIPIVVKE<br>FPSEPPLFPCTLYGPTCDAYDRLFSTEVQLPELDVGDWLIFPDMGAYSSS<br>MSSTFNGFPIATVYDAMSPQLRSLLETVP |
| MetDC (*Entamoeba histolytica*) SEQ ID NO: 1055 | MKQTSLEVKEFALNLISQFEPENQPLGFWIFDTEGVEKAVERWKKNMPT<br>VRPCFAVKCNPEPHLVKLLGELGCGFDCASLNEIKEVLDLGFNPEDITYS<br>QTFKPYNQLIEASHLGINHTIVDSIDEVQKIAKYAPKMGIMIRIMENDTSA<br>GHVFGEKFGLHDDEVEIVLKEIKDKGLNLDGVHFHVGSDSHNSEVFTKA<br>LTKARNTVTLAEQFGMKPYLIDIGGGFSQVAPFEEFAATIEKTIKELEFPE<br>RTRFIAEPGRYMASNAFHLVSSLHGKRVRIQNGKKQIEYTSGDGLHGSFG<br>CCIWFEKQKSCECITQKVNENTKMYESIIYGPSCNGSDKVATQELPEMEP<br>GKDWLLFPNMGAYTISMATNFNGFEERNHVIYTLPLKSTKIIQIPKSIECN<br>SVPSLNGIPHYA |
| SpMetDC T66N | MSPTAFPAAETATAPATAVDPGPELDGGDFALPEGGLDDDRRLRALDAV<br>DEYLTRKRKHLVGYQANQDMQGTALDLARFMPNNINNLGDPFQSGGY |

TABLE 12-continued

| Exemplary Methionine Decarboxylase Amino Acid Sequences | |
|---|---|
| Description SEQ ID NO: | Amino Acid Sequence |
| SEQ ID NO: 1124 | KPNTKVVERAVLDYYAKLWHAERPHDPADPESYWGYMLSMGSTEGN MYALWNARDYLSGKALIQPPTAPFDAVRYVKADPDRRNPNAHHPVAFY SEDTHYSFAKAVAVLGVETFHAVGLEKYADECPLVDPVTGLRTWPTEV PSRPGPSGLSWDGPGEIDVDALAVLVEFFAAKGHPVFVNLNLGSTFKGA HDDVRAVCERLLPIFERHGLVQREVVYGSCPQTGRPLVDVRRGFWIHVD GALGAGYAPFLRLAAEDPEGYGWTPEAELPEFDFGLRLPTAGHGEVDM VSSIAMSGHKWAGAPWPCGIYMTKVKYQISPPSQPDYIGAPDTTFAGSR NGFSPLILWDHLSRYSYRDQVERIREAQELAAYLERRLTAMERELGVEL WPARTPGAVTVRFRKPSAELVAKWSLSSQDVLMVPGDETTRRSYVHVF VMPSVDRAKLDALLAELAEDPVILGAP |
| SpMetDC A203H SEQ ID NO: 1126 | MSPTAFPAAETATAPATAVDPGPELDGGDFALPEGGLDDDRRLRALDAV DEYLTRKRKHLVGYQATQDMQGTALDLARFMPNNINNLGDPFQSGGY KPNTKVVERAVLDYYAKLWHAERPHDPADPESYWGYMLSMGSTEGN MYALWNARDYLSGKALIQPPTAPFDAVRYVKADPDRRNPNAHHPVAFY SEDTHYSFAKAVHVLGVETFHAVGLEKYADECPLVDPVTGLRTWPTEV PSRPGPSGLSWDGPGEIDVDALAVLVEFFAAKGHPVFVNLNLGSTFKGA HDDVRAVCERLLPIFERHGLVQREVVYGSCPQTGRPLVDVRRGFWIHVD GALGAGYAPFLRLAAEDPEGYGWTPEAELPEFDFGLRLPTAGHGEVDM VSSIAMSGHKWAGAPWPCGIYMTKVKYQISPPSQPDYIGAPDTTFAGSR NGFSPLILWDHLSRYSYRDQVERIREAQELAAYLERRLTAMERELGVEL WPARTPGAVTVRFRKPSAELVAKWSLSSQDVLMVPGDETTRRSYVHVF VMPSVDRAKLDALLAELAEDPVILGAP |
| SpMetDC H379G SEQ ID NO: 1128 | MSPTAFPAAETATAPATAVDPGPELDGGDFALPEGGLDDDRRLRALDAV DEYLTRKRKHLVGYQATQDMQGTALDLARFMPNNINNLGDPFQSGGY KPNTKVVERAVLDYYAKLWHAERPHDPADPESYWGYMLSMGSTEGN MYALWNARDYLSGKALIQPPTAPFDAVRYVKADPDRRNPNAHHPVAFY SEDTHYSFAKAVAVLGVETFHAVGLEKYADECPLVDPVTGLRTWPTEV PSRPGPSGLSWDGPGEIDVDALAVLVEFFAAKGHPVFVNLNLGSTFKGA HDDVRAVCERLLPIFERHGLVQREVVYGSCPQTGRPLVDVRRGFWIHVD GALGAGYAPFLRLAAEDPEGYGWTPEAELPEFDFGLRLPTAGGGEVDM VSSIAMSGHKWAGAPWPCGIYMTKVKYQISPPSQPDYIGAPDTTFAGSR NGFSPLILWDHLSRYSYRDQVERIREAQELAAYLERRLTAMERELGVEL WPARTPGAVTVRFRKPSAELVAKWSLSSQDVLMVPGDETTRRSYVHVF VMPSVDRAKLDALLAELAEDPVILGAP |

TABLE 13

| Exemplary Importer Amino Acid Sequences | |
|---|---|
| Description SEQ ID NO: | Amino Acid Sequence |
| MetP (*F. segetis*) SEQ ID NO: 1056 | MGTINTKIYKYMSIWKTKPLSVLLSEATEDEKGLKRTLSARSLVALGVG AIIGAGLFSLTGIAAADNAGPAVTLSFILASVGCAFAGLCYAEFASMIPVA GSAYTYSYATMGEFVAWIIGWDLVLEYALGAATVAVSWSQYVDKFLQ NYGIHIPNSILHGPWDTTPGIINLPSIFIICLLSVLLIRGTKESALINNILVILK VTVVIVFIGLGWGFMNSANHTPFIPVNEGEALLSSGEMSFLNFFSSDYFG HYGWSGILRGAGVVFFAFIGFDAVSTAAQEAKDPQKGMPIGILGSLIICT VLYVLFAFVLTGLENYLNFKGDASPVTTAFAKTGYTFLNSGLTIAIIAGY TSVMLVMLMGQSRVFYSMSVDGLLPKFFSTLHTKNRTPYKTNLLFMVF VSLFAGFVPVSDLGHMVSIGTLFAFCLVCIGVIVMRKTNPDAVRGFRVPF VPVFPIIGVVICLVLMAGLPIESWERLAIWMILGVVIYFFYSKKNSKLNNP E |
| MetP (*F. frigoris*) SEQ ID NO: 1057 | MGTINTKTNKYMSIWKTKPLSVLLNEASEDEKGLKRTLSSRSLVALGVG AIIGAGLFSLTGIAAAEHAGPAVTLSFILAAVGCAFAGLCYAEFASMIPVA GSAYTYSYATMGEFMAWIIGWDLVLEYALGAATVGVSWSRYLLELLNK YGVHLNPKFICSPWETLTLGDGTIIDGGYINLPAILIVSALSLLLIRGTQES ASINNILVVLKVIVVIMFIVLGWDYIDPANYSPYIPENTGVKGQFGWSGIA AGAGTVFFAFIGFDAVSTAAQEAKNPQKGMPIGILGSLVICTILYVLFAH VMTGLVPYYKFAGDAKPAATAFAVTGYSFLQTGLIVAILAGYTSVMLV MLMGQSRVFYTMSKDGLLPPLFGQIHSKFRTPYKTNLFFMVFVSLFAGF VPVSDLGHMVSIGTLLAFVLVCIGVLVMRKKMPDAPRSFKTPFVPYVPIA GVLVCTYLMYSLPYESWIRLVLWMAIGVALYFVYGKKHSKLNNPD |
| MetN SEQ ID NO: 1058 | MIKLSNITKVFHQGTRTIQALNNVSLHVPAGQIYGVIGASGAGKSTLIRC VNLLERPTEGSVLVDGQELTTLSESELTKARRQIGMIFQHFNLLSSRTVFG NVALPLELDNTPKDEIKRRVTELLSLVGLGDKHDSYPSNLSGGQKQRVAI ARALASNPKVLLCDEATSALDPATTRSILELLKDINRRLGLTILLITHEMD VVKRICDCVAVISNGELIEQDTVSEVFSHPKTPLAQKFIQSTLHLDIPEDY |

TABLE 13-continued

| Exemplary Importer Amino Acid Sequences | |
|---|---|
| Description SEQ ID NO: | Amino Acid Sequence |
| | QERLQAEPFTDCVPMLRLEFTGQSVDAPLLSETARRFNVNNNIISAQMDY AGGVKFGIMLTEMHGTQQDTQAAIAWLQEHHVKVEVLGYV |
| MetI SEQ ID NO: 1059 | MSEPMMWLLVRGVWETLAMTFVSGFFGFVIGLPVGVLLYVTRPGQIIAN AKLYRTISAIVNIFRSIPFIILLVWMIPFTRVIVGTSIGLQAAIVPLTVGAAPF IARMVENALLEIPTGLIEASRAMGATPMQIVRKVLLPEALPGLVNAATIT LITLVGYSAMGGAVGAGGLGQIGYQYGYIGYNATVMNTVLVLLVILVY LIQFAGDRIVRAVTRK |
| MetQ SEQ ID NO: 1060 | MAFKFKTFAAVGALIGSLALVGCGQDEKDPNHIKVGVIVGAEQQVAEV AQKVAKDKYGLDVELVTFNDYVLPNEALSKGDIDANAFQHKPYLDQQL KDRGYKLVAVGNTFVYPIAGYSKKIKSLDELQDGSQVAVPNDPTNLGRS LLLLQKVGLIKLKDGVGLLPTVLDVVENPKNLKIVELEAPQLPRSLDDAQ IALAVINTTYASQIGLTPAKDGIFVEDKESPYVNLIVTREDNKDAENVKK FVQAYQSDEVYEAANKVFNGGAVKGW |
| Methionine import system permease protein MetP (*Bacillus subtilis*) SEQ ID NO: 1061 | MFEKYFPNVDLTELWNATYETLYMTLISLLFAFVIGVILGLLLFLTSKGSL WQNKAVNSVIAAVVNIFRSIPFLILIILLLGFTKFLVGTILGPNAALPALVI GSAPFYARLVEIALREVDKGVIEAAKSMGAKTSTIIFKVLIPESMPALISGI TVTAIALIGSTAIAGAIGSGGLGNLAYVEGYQSNNADVTFVATVFILIIVFI IQIIGDLITNIIDKR |
| MetN (P281G) SEQ ID NO: 1062 | MIKLSNITKVFHQGTRTIQALNNVSLHVPAGQIYGVIGASGAGKSTLIRC VNLLERPTEGSVLVDGQELTTLSESELTKARRQIGMIFQHFNLLSSRTVFG NVALPLELDNTPKDEIKRRVTELLSLVGLGDKHDSYPSNLSGGQKQRVAI ARALASNPKVLLCDEATSALDPATTRSILELLKDINRRLGLTILLITHEMD VVKRICDCVAVISNGELIEQDTVSEVFSHPKTPLAQKFIQSTLHLDIPEDY QERLQAEPFTDCVPMLRLEFTGQSVDAGLLSETARRFNVNNNIISAQMD YAGGVKFGIMLTEMHGTQQDTQAAIAWLQEHHVKVEVLGYV |
| MetN (P281S) SEQ ID NO: 1063 | MIKLSNITKVFHQGTRTIQALNNVSLHVPAGQIYGVIGASGAGKSTLIRC VNLLERPTEGSVLVDGQELTTLSESELTKARRQIGMIFQHFNLLSSRTVFG NVALPLELDNTPKDEIKRRVTELLSLVGLGDKHDSYPSNLSGGQKQRVAI ARALASNPKVLLCDEATSALDPATTRSILELLKDINRRLGLTILLITHEMD VVKRICDCVAVISNGELIEQDTVSEVFSHPKTPLAQKFIQSTLHLDIPEDY QERLQAEPFTDCVPMLRLEFTGQSVDASLLSETARRFNVNNNIISAQMDY AGGVKFGIMLTEMHGTQQDTQAAIAWLQEHHVKVEVLGYV |
| *Sporomusa termitida* MetP SEQ ID NO: 1130 | MNFFRTKCIDKLKEGAEQQGLKKSLGATDLILLGIGCIIGTGIFVLTGVAA ANYAGPGIMLSFVISGLACAFAALAYAELAAMVPIAGSAYTYSYAALGE IVAWIVGWNLILEYSVGSSAVAAGWSGYMVGLLKSGGIELPKAFTAVPA DGGLVNLPAMLIALLLSVLLVRGTKESVTLNKVLVVIKLAAVFIFLALAG PKVNPANWSPLMPYGFSGVAAGAAIIFFAYIGFDAVATAAEECRNPKRD LPAGIIGSLVICTILYIVVAGVLTGVVPYQQLNNAEPVAYALRAIGYNFGS ALVGTGAIAGITTVLLVLMYGQTRIFFAMSRDGLIPARICKVHPRYGTPHI ITMAAGIAVALIAGFTPIGIIAELTNIGTLFAFVVAAIGVLVLRYTRPDIPRS FKCPAVKVIAPLAVLSCGYLMANLPAETWIRFGIWSAIGFVVYFVYSYH HSVLNKAEVAGKE |
| *Bacteroidetes bacterium* 43-16 MetP SEQ ID NO: 1132 | MGIFAKKQLNQLIAEASESEKGLKKTLSAGALVSLGIGAIIGAGLFSLTG MAAADNAGPAVVFSFILAAVGCGFAGLCYAEFASMIPVAGSAYTYSYA TMGELIAWIIGWDLVLEYALGAATVAVSWSQYVNKFLHSVGIDLPQYLL HGPWDEVNGVAMNGIINLPAIIIVCLLSLLLIRGTKESALLNNILVILKVV VVLVFICIGWSFINPANHEPFIPVNAGEEMVKSGTMSFWSFFTSESFGSYG ISGILRGAGVVFFAFIGFDAVSTAAQEAKNPQKGMPIGIIGSLVVCTILYV LFAYVLTGLENYINFKGNASPVTTAFAHTGYTFLNSFLTMAIIAGYTSVM LVMLMGQSRVFYSMSVDGLLPKMFSDLHKKNRTPYKTNLIFMVFVSLF AGFVPVADLGHMVSIGTLFAFALVCIGVIVMRKTNPDAVRGFRTPFVPV LPILGVLVCVVLMLGLPKESWERLAIWLGLGLIIYFAYSKKNSKIGNK |

TABLE 14

| Phage Nucleotide Sequence | |
|---|---|
| Description | SEQ ID NO: |
| Phage 3 | SEQ ID NO: 1064 |

TABLE 15

| Colibactin Nucleotide Sequences | |
|---|---|
| Description | SEQ ID NO: |
| clbA | SEQ ID NO: 1065 |
| clbB | SEQ ID NO: 1066 |
| clbC | SEQ ID NO: 1067 |

TABLE 15-continued

| Colibactin Nucleotide Sequences | |
|---|---|
| Description | SEQ ID NO: |
| clbD | SEQ ID NO: 1068 |
| clbE | SEQ ID NO: 1069 |
| clbF | SEQ ID NO: 1070 |
| clbG | SEQ ID NO: 1071 |
| clbH | SEQ ID NO: 1072 |
| clbI | SEQ ID NO: 1073 |
| clbJ | SEQ ID NO: 1074 |
| clbK | SEQ ID NO: 1075 |
| clbL | SEQ ID NO: 1076 |
| clbM | SEQ ID NO: 1077 |
| clbN | SEQ ID NO: 1078 |
| clbO | SEQ ID NO: 1079 |
| clbP | SEQ ID NO: 1080 |
| clbQ | SEQ ID NO: 1081 |
| clbR | SEQ ID NO: 1082 |
| clbS | SEQ ID NO: 1083 |

TABLE 16

| Colibactin Amino Acid Sequences | |
|---|---|
| Description SEQ ID NO: | Amino Acid Sequence |
| clbA | SEQ ID NO: 1084 |
| clbB | SEQ ID NO: 1085 |
| clbC | SEQ ID NO: 1086 |
| clbD | SEQ ID NO: 1087 |
| clbE | SEQ ID NO: 1088 |
| clbF | SEQ ID NO: 1089 |
| clbG | SEQ ID NO: 1090 |
| clbH | SEQ ID NO: 1091 |
| clbI | SEQ ID NO: 1092 |
| clbJ | SEQ ID NO: 1093 |
| clbK | SEQ ID NO: 1094 |
| clbL | SEQ ID NO: 1095 |
| clbM | SEQ ID NO: 1096 |
| clbN | SEQ ID NO: 1097 |
| clbO | SEQ ID NO: 1098 |
| clbP | SEQ ID NO: 1099 |
| clbQ | SEQ ID NO: 1100 |
| clbR | SEQ ID NO: 1101 |
| clbS | SEQ ID NO: 1102 |

TABLE 17

| Other Exemplary Sequences | |
|---|---|
| Description | Sequence |
| Ptac-metP SEQ ID NO: 1118 | ttgacaattaatcatcggctcgtataatgtgtggaattgtgagcgctcacaattagctgtgaccagaggtaaggaggtaac<br>aaccatgcgagtgttgaagaaacatcttaatcatgctgcggagggtttctaatggggaccattaacacgaagatctataaa<br>tacatgagcatctggaaaacaaaacctctgtccgtgctcttgtctgaagcaactgaggatgaaaaaggcctgaagcgca<br>ctctgtcggcccgttcacttgttgcgctgggtgtcggtgctattatcggcgctggtttattctctctgaccggcatagctgcg<br>gcagacaatgctggaccggcagtaaccctgagctttatcctggcctccgttggttgcgcgttcgctggcctgtgttacgc<br>agaatttgcttctatgattccagttgcgggtagcgcctacacttatagttatgctaccatgggcgagttcgtggcgtggatc<br>atcggttgggatctggtactcgaatacgcattgggcgcagctactgttgccgttagctggtcccagtacgtggacaaattc<br>ttgcaaaactacggcatccatattccgaactctatcctccacgggccgtgggataccacccccggtattatcaatttaccgt<br>cgatatttatcatctgcctgctgagcgtgctgctgattcgtggtactaaagaatctgctctgatcaacaacattctggtaatcc<br>tgaaagtcacggttgtcatcgtgttcattggcctgggctgggggttcatgaactccgcaaaccacacgccctttatcccgg<br>ttaacgaaggtgaggctctactgtcttctggtgaaatgagtttcctcaactttttcagcagtgactactttggacactacggat<br>ggtccggtattcttcgcggcgctggtgtagtattcttcgcatttatcggcttcgacgcggtgagcactgcggcacaggag<br>gccaaggatccgcagaaaggcatgccaatcggtattctgggctcactgatcatttgcaccgttctgtacgtgcttttcgctt<br>tcgttctgaccggtctggaaaactatctaaacttcaaaggtgacgcttctcctgtcaccactgcatttgccaaaacaggcta<br>tactttcctgaatagcggtctgacgatcgctatcatagcgggctacacatccgttatgctggtaatgttgatgggtcagtcc<br>cgtgtcttttatagtatgtctgtggatggcctgcttccgaagtttttctcgaccctgcataccaaaaacaggactccgtacaa<br>aactaatttgctgttcatggttttcgtaagcctgttcgctggctttgttccggtcagcgacctgggccatatggtatccatcgg<br>taccctcttcgctttctgcctggtgtgtatcggcgttatcgttatgcgaaaaaccaacccagacgccgttcgcggttttcgtg<br>ttcctttttgtaccggttttcccgattatcggtgtagttatttgtctggttctaatggcgggcctgccgattgaatcttgggaacg<br>tctggcgatctggatgattctgggtgtcgtgatctacttcttctactctaaaaagaactctaaactgaataaccccgaataa |
| Ptac-metDC SEQ ID NO: 1119 | ttgacaattaatcatcggctcgtataatgtgtggaattgtgagcgctcacaattaagtgaATTGCCAATAACA<br>ATTACTAAGGAGGTTTTTTATGtccccgacggcgtttccagcggccgaaacagctactgcccctgc<br>aactgccgtcgatcctgggccagaactggacggcggagatttcgcccttccagagggcgggctggatgacgatcgtc<br>gcttacgtgcattggacgcagttgacgagtatttgacccgcaagcgcaagcatttggttgggtaccaagctacccaggat<br>atggacggaacggccttggatttagcccgtttcatgccccacaacatcaacaacctgggagatcctttccagtcgggtgg<br>gtataaaccaaatacgaaagtcgttgagcgtgccgtactggactactatgcaaaattgtggcacgcagaacgtccacac<br>gacccagctgacccagaaagctactggggttacatgttatcgatgggctcaactgagggcaacatgtacgccctgtgga<br>atgcacgtgactacctgtcgggtaaggctttgattcagcctcccacggcaccatttgacgctgttcgctacgtgaaggctg<br>accccgatcgccgcaatcctaacgcacaccacccagtcgcattctactcggaggatacccactattcttttgctaaagcc<br>gttgcggtgctgggtgtcgaaactttccacgctgtgggtctggagaaatacgctgacgagtgccccttggtggatccagt<br>aaccggccttcgtacctggccgaccgaagttccatcgcgcccggggccgtcgggtttaagctgggacggccctggtg<br>agattgatgttgatgcgcttgcagtactggtcgagttcttcgcagcgaagggtcaccccgtcttcgtcaaccttaacttggg<br>gtctacatttaaaggagcacatgatgacgtacgtgcggtatgtgaacgcttattaccaatcttcgagcgccatggcttagta<br>caacgtgaagttgtatatgggagctgtccccaaaccggccgccctttagtggatgtacgtcgcggattttggatccacgta<br>gatggggcacttggggcggggtatgccccttttctgcgtcttgccgccgaagacccggaaggttatggttggacccctg<br>aggcagaattacctgagttcgacttcggcttacgtttgccgacggcggggcatggagaagttgatatggttagcagcatc<br>gccatgagtggacataagtgggcaggcgcgccgtggccatgcggcatctatatgacgaaagtgaaatatcagattagt<br>ccaccgtcacagcccgattatattggtgctcctgacacaacatttgccggttcccgtaacggcttttcgccgttaattttgtg<br>ggatcatttatcgcgctactcgtaccgcgaccaggtagagcgcatccgcgaagcacaggagcttgcagcatatttggaa<br>cgccgccttaccgctatggagcgcgagctgggagtggaactttggccagcccgcacaccgggtgctgtaaccgtacgt<br>tttcgcaaaccctctgctgagctggttgcgaagtggtccttgtcgtcgcaggatgttttaatggtgccgggtgatgaaacta<br>cgcgtcgtagttacgttcatgtgttcgtgatgccttctgttgatcgtgcaaagttagatgcgttgctggcagaattggccgaa<br>gatcccgtcatcttgggtgcgccttaa |

TABLE 17-continued

| Other Exemplary Sequences | |
|---|---|
| Description | Sequence |
| yjeH<br>SEQ ID NO:<br>1014 | atgagtggactcaaacaagaactggggctggcccagggcatcggcctactatcgacgtcattattaggcactggcgtgt<br>ttgccgttcctgcgttagctgcgctagtagcaggcaataacagcctgtgggcgtggcccgttttgattatcttagtgttccc<br>gattgcgattgtgtttgcgattctgggtcgccactatcccagcgcaggcggcgtcgcacacttcgtcggtatggcgtttgg<br>ttcgcggcttgagcgagtcaccggctggttgtttttatcggtcattcccgtgggtttgcctgccgcgctacaaattgctgcc<br>ggattcggccaggcaatgtttggctggcatagcgggcaactgttgttggcagaactcggtacgctggcgctggtgtggt<br>atatcggtactcgaggtgccagttccagtgctaatctacaaacagttattgccgggcttatcgtcgcactgattgtcgctatc<br>tggtgggcgggcgatatcaaacctgcgaatatccccttccctgcgccaggaaatatcgaacttaccgggttattcgctgc<br>gttatcagtgatgttctggtgttttgtcggtctggaagcatttgcccatcttgcctcggaatttaaaaatccagagcgtgatttt<br>cctcgtgctttgatgattggcctgctgctggcaggattagtctattggggctgtacggtagtcgtcttacacttcgacgccta<br>tggtgaacaaatggcggcggcagcatcgcttcccaaaattgtagtgcagttattcggtgtaggagcgttatggattgcctg<br>cgtaattggctatctggcctgctttgccagtctcaacatttatatacagagcttcgcccgcctggtctggtcgcaggcgcaa<br>cataatcctgaccattacctggcacgcctctcttctcgccatattccgaataatgccctcaatgcggtgctcggctgctgcg<br>tggtgagcacgttggtgattcatgctttagagatcaatctggacgctcttattatttatgccaatggcatctttattatgatttat<br>ctgttatgcatgctggcaggctgtaaattattgcaaggacgttatcgactactggcagtggttggcgggctattatgcgttct<br>gttactggcaatggtcggctggaaaagtctctacgcgctgatcatgctggcggggttatggctgtttctgccaaaacgaa<br>aaacgccggaaaatggcataaccacataa |
| yjeH K/O<br>(100 bp up<br>and<br>downstream<br>and the scar<br>site in<br>between)<br>SEQ ID NO:<br>1120 | aatgtgaatggcacgattatgcgggatacttacaccaccgacggaatatgaaaatcaatattatcgacggctcagaagtg<br>tctagattatccgtggcgatCTGACATGGGAATTAGCCATGGTCCATATGAATATCCT<br>CCttAGTTCCTATTCCGAAGTTCCTATTCTCTAGAAAGTATAGGAACTTCG<br>AAGCAGCTCCAGCCTACACAATCGCTCAAGACGTGTAATtccggcgtttcgacatt<br>aatcctggcgatcgtctttatgatcaaggcggtcgcggtcatcatcctttcgctggtactcaccatcaaaagtattaccgcc<br>a |
| YjeH Amino<br>acid<br>sequence<br>SEQ ID NO:<br>1121 | MSGLKQELGLAQGIGLLSTSLLGTGVFAVPALAALVAGNNSLWAWPVLIIL<br>VFPIAIVFAILGRHYPSAGGVAHFVGMAFGSRLERVTGWLFLSVIPVGLPAA<br>LQIAAGFGQAMFGWHSGQLLLAELGTLALVWYIGTRGASSSANLQTVIAGL<br>IVALIVAIWWAGDIKPANIPFPAPGNIELTGLFAALSVMFWCFVGLEAFAHL<br>ASEFKNPERDFPRALMIGLLLAGLVYWGCTVVVLHFDAYGEQMAAAASLP<br>KIVVQLFGVGALWIACVIGYLACFASLNIYIQSFARLVWSQAQHNPDHYLA<br>RLSSRHIPNNALNAVLGCCVVSTLVIHALEINLDALIIYANGIFIMIYLLCMLA<br>GCKLLQGRYRLLAVVGGLLCVLLLAMVGWKSLYALIMLAGLWLFLPKRK<br>TPENGITT |
| Exemplary<br>RBS for<br>MetP<br>SEQ ID NO:<br>1109 | gaccagaggtaaggaggtaacaaccatgcgagtgttgaagaaacatcttaatcatgctgcggagggtttcta |
| Exemplary<br>RBS for<br>MetDC<br>SEQ ID NO:<br>1122 | ATTGCCAATAACAATTACTAAGGAGGTTTTTT |

The invention claimed is:

1. A recombinant bacterial cell comprising:

a heterologous methionine decarboxylase (metDC) gene operably linked to a promoter, wherein the heterologous metDC gene encodes a polypeptide comprising SEQ ID NO: 1048.

2. The recombinant bacterial cell of claim 1, wherein the metDC gene comprises a nucleic acid sequence of SEQ ID NO: 1034.

3. The recombinant bacterial cell of claim 1, further comprising a heterologous gene encoding a methionine importer.

4. The recombinant bacterial cell of claim 3, wherein the heterologous gene encoding the methionine importer is a metP gene, and wherein the metP gene encodes a polypeptide that has at least 90% identity to SEQ ID NO: 1056.

5. The recombinant bacterial cell of claim 4, wherein the metP gene encodes a polypeptide comprising SEQ ID NO: 1056.

6. The recombinant bacterial cell of claim 5, wherein the metP gene comprises a nucleic acid sequence of SEQ ID NO: 1041.

7. The recombinant bacterial cell of claim 1, wherein the promoter is an inducible promoter.

8. The recombinant bacterial cell of claim 7, wherein the inducible promoter is an IPTG-inducible promoter.

9. The recombinant bacterial cell of claim 1, wherein the recombinant bacterial cell is a recombinant probiotic bacterial cell.

10. The recombinant bacterial cell of claim 9, wherein the recombinant bacterial cell is of the species *Escherichia coli* strain Nissle.

11. A pharmaceutical composition comprising the recombinant bacterial cell of claim 1 and a pharmaceutically acceptable carrier.

12. A method for reducing the levels of methionine, cysteine and/or homocysteine in a subject, the method comprising administering to the subject the pharmaceutical composition of claim 11, thereby reducing the levels of methionine, cysteine, and/or homocysteine in the subject.

13. The method of claim 12, wherein the subject has homocystinuria, cystinuria, or a metabolic disease.

14. The method of claim 12, wherein the pharmaceutical composition comprises about $1\times10^{11}$ to about $6\times10^{11}$ live recombinant bacterial cells/mL.

* * * * *

SEQUENCE LISTING

```
Sequence total quantity: 1122
SEQ ID NO: 1             moltype = DNA  length = 290
FEATURE                  Location/Qualifiers
source                   1..290
                         mol_type = other DNA
                         organism = synthetic construct
SEQUENCE: 1
gtcagcataa caccctgacc tctcattaat tgttcatgcc gggcggcact atcgtcgtcc  60
ggccttttcc tctcttactc tgctacgtac atctatttct ataaatccgt tcaatttgtc  120
tgtttttgc acaaacatga aatatcagac aattccgtga cttaagaaaa tttatacaaa  180
tcagcaatat accccttaag gagtatataa aggtgaattt gatttacatc aataagcggg  240
gttgctgaat cgttaaggta ggcggtaata gaaaagaaat cgaggcaaaa             290

SEQ ID NO: 2             moltype = DNA  length = 173
FEATURE                  Location/Qualifiers
source                   1..173
                         mol_type = other DNA
                         organism = synthetic construct
SEQUENCE: 2
```

-continued

```
atttcctctc atcccatccg gggtgagagt cttttccccc gacttatggc tcatgcatgc  60
atcaaaaaag atgtgagctt gatcaaaaac aaaaaatatt tcactcgaca ggagtattta  120
tattgcgccc gttacgtggg cttcgactgt aaatcagaaa ggagaaaaca cct         173

SEQ ID NO: 3           moltype = DNA  length = 305
FEATURE                Location/Qualifiers
source                 1..305
                       mol_type = other DNA
                       organism = synthetic construct
SEQUENCE: 3
gtcagcataa caccctgacc tctcattaat tgttcatgcc gggcggcact atcgtcgtcc  60
ggcctttttcc tctcttactc tgctacgtac atctatttct ataaatccgt tcaatttgtc  120
tgtttttgc acaaacatga aatatcagac aattccgtga cttaagaaaa tttatacaaa  180
tcagcaatat accccttaag gagtatataa aggtgaattt gatttacatc aataagcggg  240
gttgctgaat cgttaaggat ccctctagaa ataattttgt ttaactttaa gaaggagata  300
tacat                                                              305

SEQ ID NO: 4           moltype = DNA  length = 180
FEATURE                Location/Qualifiers
source                 1..180
                       mol_type = other DNA
                       organism = synthetic construct
SEQUENCE: 4
catttcctct catcccatcc ggggtgagag tcttttcccc cgacttatgg ctcatgcatg  60
catcaaaaaa gatgtgagct tgatcaaaaa caaaaaatat ttcactcgac aggagtattt  120
atattgcgcc cggatccctc tagaaataat tttgtttaac tttaagaagg agatatacat  180

SEQ ID NO: 5           moltype = DNA  length = 199
FEATURE                Location/Qualifiers
source                 1..199
                       mol_type = other DNA
                       organism = synthetic construct
SEQUENCE: 5
agttgttctt attggtggtg ttgctttatg gttgcatcgt agtaaatggt tgtaacaaaa  60
gcaatttttc cggctgtctg tatacaaaaa cgccgtaaag tttgagcgaa gtcaataaac  120
tctctaccca ttcagggcaa tatctctctt ggatccctct agaaataatt ttgtttaact  180
ttaagaagga gatatacat                                               199

SEQ ID NO: 6           moltype = AA  length = 490
FEATURE                Location/Qualifiers
source                 1..490
                       mol_type = protein
                       organism = Ruminococcus gnavus
SEQUENCE: 6
MSQVIKKKRN TFMIGTEYIL NSTQLEEAIK SFVHDFCAEK HEIHDQPVVV EAKEHQEDKI  60
KQIKIPEKGR PVNEVVSEMM NEVYRYRGDA NHPRFFSFVP GPASSVSWLG DIMTSAYNIH  120
AGGSKLAPMV NCIEQEVLKW LAKQVGFTEN PGGVFVSGGS MANITALTAA RDNKLTDINL  180
HLGTAYISDQ THSSVAKGLR IIGITDSRIR RIPTNSHFQM DTTKLEEAIE TDKKSGYIPF  240
VVIGTAGTTN TGSIDPLTEI SALCKKHDMW FHIDGAYGAS VLLSPKYKSL LTGTGLADSI  300
SWDAHKWLFQ TYGCAMVLVK DIRNLFHSFH VNPEYLKDLE NDIDNVNTWD IGMELTRPAR  360
GLKLWLTLQV LGSDLIGSAI EHGFQLAVWA EEALNPKKDW EIVSPAQMAM INFRYAPKDL  420
TKEEQDILNE KISHRILESG YAAIFTTVLN GKTVLRICAI HPEATQEDMQ HTIDLLDQYG  480
REIYTEMKKA                                                         490

SEQ ID NO: 7           moltype = DNA  length = 18
FEATURE                Location/Qualifiers
source                 1..18
                       mol_type = other DNA
                       organism = synthetic construct
SEQUENCE: 7
ttgttgayry rtcaacwa                                                18

SEQ ID NO: 8           moltype = DNA  length = 15
FEATURE                Location/Qualifiers
source                 1..15
                       mol_type = other DNA
                       organism = synthetic construct
misc_difference        8
                       note = a, c, t, or g
SEQUENCE: 8
ttataatnat tataa                                                   15

SEQ ID NO: 9           moltype = DNA  length = 24
FEATURE                Location/Qualifiers
source                 1..24
                       mol_type = other DNA
                       organism = synthetic construct
SEQUENCE: 9
ggaaaatttt tttaaaaaaa aaac                                         24
```

```
SEQ ID NO: 10          moltype = DNA  length = 1251
FEATURE                Location/Qualifiers
source                 1..1251
                       mol_type = other DNA
                       organism = synthetic construct
SEQUENCE: 10
atgacgaccc gaaatgattg cctagcgttg gatgcacagg acagtctggc tccgctgcgc  60
caacaatttg cgctgccgga gggtgtgata tacctggatg gcaattcgct gggcgcacgt  120
ccggtagctg cgctggctcg cgcgcaggct gtgatcgcag aagaatgggg caacgggttg  180
atccgttcat ggaactctgc gggctggcgt gatctgtctg aacgcctggg taatcgcctg  240
gctaccctga ttggtgcgcg cgatggggaa gtagttgtta ctgataccac ctcgattaat  300
ctgtttaaag tgctgtcagc ggcgctgcgc gtgcaagcta cccgtagccc ggagcgccgt  360
gttatcgtga ctgagacctc gaatttcccg accgacctgt atattgcgga agggttggcg  420
gatatgctgc aacaaggtta cactctgcgt ttggtggatt caccggaaga gctgccacag  480
gctatagatc aggacaccgc ggtggtgatg ctgacgcacg taaattataa aaccggttat  540
atgcacgaca tgcaggctct gaccgcgttg agccacgagt gtggggctct ggcgatttgg  600
gatctggcgc actctgctgg cgctgtgccg gtggacctgc accaagcggg cgcggactat  660
gcgattggct gcacgtacaa atacctgaat ggcggcccgg gttcgcaagc gtttgtttgg  720
gtttcgccgc aactgtgcga cctggtaccg cagccgctgt ctggttggtt cggccatagt  780
cgccaattcg cgatggagcc gcgctacgaa ccttctaacg gcattgctcg ctatctgtgc  840
ggcactcagc ctattactag cttggctatg gtggagtgcg gcctggatgt gtttgcgcag  900
acggatatgg cttcgctgcg ccgtaaaagt ctggcgctga ctgatctgtt catcgagctg  960
gttgaacaac gctgcgctgc acacgaactg accctggtta ctccacgtga acacgcgaaa  1020
cgcggctctc acgtgtcttt tgaacacccc gagggttacg ctgttattca agctctgatt  1080
gatcgtggcg tgatcggcga ttaccgtgag ccacgtatta tgcgtttcgg tttcactcct  1140
ctgtatacta cttttacgga agtttgggat gcagtacaaa tcctgggcga aatcctggat  1200
cgtaagactt gggcgcaggc tcagtttcag gtgcgccact ctgttactta a           1251

SEQ ID NO: 11          moltype = DNA  length = 1354
FEATURE                Location/Qualifiers
source                 1..1354
                       mol_type = other DNA
                       organism = synthetic construct
SEQUENCE: 11
taattcctaa tttttgttga cactctatca ttgatagagt tattttacca ctccctatca  60
gtgatagaga aaagtgaatt atataaaagt gggaggtgcc cgaatgacga cccgaaatga  120
ttgcctagcg ttggatgcac aggacagtct ggctccgctg cgccaacaat ttgcgctgcc  180
ggagggtgtg atatacctgg atggcaattc gctgggcgca cgtccggtag ctgcgctggc  240
tcgcgcgcag gctgtgatcg cagaagaatg gggcaacggg ttgatccgtt catggaactc  300
tgcgggctgg cgtgatctgt ctgaacgcct gggtaatcgc ctggctaccc tgattggtgc  360
gcgcgatggg gaagtagttg ttactgatac cacctcgatt aatctgttta aagtgctgtc  420
agcggcgctg cgcgtgcaag ctacccgtag cccggagcgc cgtgttatcg tgactgagac  480
ctcgaatttc ccgaccgacc tgtatattgc ggaagggttg gcggatatgc tgcaacaagg  540
ttacactctg cgtttggtgg attcaccgga agagctgcca caggctatag atcaggacac  600
cgcggtggtg atgctgacgc acgtaaatta taaaaccggt tatatgcacg acatgcaggc  660
tctgaccgcg ttgagccacg agtgtggggc tctggcgatt tgggatctgg cgcactctgc  720
tggcgctgtg ccggtggacc tgcaccaagc gggcgcggac tatgcgattg gctgcacgta  780
caaatacctg aatggcggcc cgggttcgca agcgtttgtt tgggtttcgc cgcaactgtg  840
cgacctggta ccgcagccgc tgtctggttg gttcggccat agtcgccaat tcgcgatgga  900
gccgcgctac gaaccttcta acggcattgc tcgctatctg tgcggcactc agcctattac  960
tagcttggct atggtggagt gcggcctgga tgtgtttgcg cagacggata tggcttcgct  1020
gcgccgtaaa agtctggcgc tgactgatct gttcatcgag ctggttgaac aacgctgcgc  1080
tgcacacgaa ctgaccctgg ttactccacg tgaacacgcg aaacgcggct ctcacgtgtc  1140
ttttgaacac cccgagggtt acgctgttat tcaagctctg attgatcgtg gcgtgatcgg  1200
cgattaccgt gagccacgta ttatgcgttt cggtttcact cctctgtata ctacttttac  1260
ggaagtttgg gatgcagtac aaatcctggg cgaaatcctg gatcgtaaga cttgggcgca  1320
ggctcagttt caggtgcgcc actctgttac ttaa                              1354

SEQ ID NO: 12          moltype = DNA  length = 1985
FEATURE                Location/Qualifiers
source                 1..1985
                       mol_type = other DNA
                       organism = synthetic construct
SEQUENCE: 12
ttaagaccca ctttcacatt taagttgttt ttctaatccg catatgatca attcaaggcc  60
gaataagaag gctggctctg caccttggtg atcaaataat tcgatagctt gtcgtaataa  120
tggcggcata ctatcagtag taggtgtttc cctttcttct ttagcgactt gatgctcttg  180
atcttccaat acgcaaccta aagtaaaatg ccccacagcg ctgagtgcat ataatgcatt  240
ctctagtgaa aaaccttgtt ggcataaaaa ggctaattga ttttcgagag tttcatactg  300
tttttctgta ggccgtgtac ctaaatgtac ttttgctcca tcgcgatgac ttagtaaagc  360
acatctaaaa cttttagcgt tattacgtaa aaaatcttgc cagctttccc cttctaaagg  420
gcaaaagtga gtatggtgcc tatctaacat ctcaatggct aaggcgtcga gcaaagcccg  480
cttatttttt acatgccaat acaatgtagg ctgctctaca cctagcttct gggcgagttt  540
acgggttgtt aaaccttcga ttccgacctc attaagcagc tctaatgcgc tgttaatcac  600
tttactttta tctaatctag acatcattaa ttcctaattt ttgttgacac tctatcattg  660
atagagttat tttaccactc cctatcagtg atagagaaaa gtgaattata taaaagtggg  720
aggtgcccga atgacgaccc gaaatgattg cctagcgttg gatgcacagg acagtctggc  780
tccgctgcgc caacaatttg cgctgccgga gggtgtgata tacctggatg gcaattcgct  840
```

-continued

```
gggcgcacgt ccggtagctg cgctggctcg cgcgcaggct gtgatcgcag aagaatgggg  900
caacgggttg atccgttcat ggaactctgc gggctggcgt gatctgtctg aacgcctggg  960
taatcgcctg gctaccctga ttggtgcgcg cgatggggaa gtagttgtta ctgataccac  1020
ctcgattaat ctgtttaaag tgctgtcagc ggcgctgcgc gtgcaagcta cccgtagccc  1080
ggagcgccgt gttatcgtga ctgagacctc gaatttcccg accgacctgt atattgcgga  1140
agggttggcg gatatgctgc aacaaggtta cactctgcgt ttggtggatt caccggaaga  1200
gctgccacag gctatagatc aggacaccgc ggtggtgatg ctgacgcacg taaattataa  1260
aaccggttat atgcacgaca tgcaggctct gaccgcgttg agccacgagt gtggggctct  1320
ggcgatttgg gatctggcgc actctgctgg cgctgtgccg gtggacctgc accaagcggg  1380
cgcggactat gcgattggct gcacgtacaa atacctgaat ggcggcccgg gttcgcaagc  1440
gtttgtttgg gtttcgccgc aactgtgcga cctggtaccg cagccgctgt ctggttggtt  1500
cggccatagt cgccaattcg cgatggagcc gcgctacgaa ccttctaacg gcattgctcg  1560
ctatctgtgc ggcactcagc ctattactag cttggctatg gtggagtgcg gcctggatgt  1620
gtttgcgcag acggatatgg cttcgctgcg ccgtaaaagt ctggcgctga ctgatctgtt  1680
catcgagctg gttgaacaac gctgcgctgc acacgaactg accctggtta ctccacgtga  1740
acacgcgaaa cgcggctctc acgtgtcttt tgaacacccc gagggttacg ctgttattca  1800
agctctgatt gatcgtggcg tgatcggcga ttaccgtgag ccacgtatta tgcgtttcgg  1860
tttcactcct ctgtatacta cttttacgga agtttgggat gcagtacaaa tcctgggcga  1920
aatcctggat cgtaagactt gggcgcaggc tcagtttcag gtgcgccact ctgttactta  1980
aggag                                                              1985

SEQ ID NO: 13          moltype = DNA  length = 1398
FEATURE                Location/Qualifiers
source                 1..1398
                       mol_type = other DNA
                       organism = synthetic construct
SEQUENCE: 13
atggagcctt catctttaga actgccagcg gacacggtgc agcgcatcgc ggcggaactg  60
aagtgccatc cgactgatga gcgtgtggcg ctgcatctgg acgaagaaga taaactgcgc  120
cactttcgtg aatgttttta tattcctaaa attcaagact tgccgccggt agatttgagt  180
ctcgttaaca aagatgaaaa cgcgatctac tttctgggca actctctggg tctgcaacca  240
aaaatggtta aaacgtacct ggaggaagaa ctggataaat gggcaaaaat cgcggcttat  300
ggtcacgaag tgggcaagcg tccttggatt actggcgacg agtctattgt gggtttgatg  360
aaagatattg tgggcgcgaa tgaaaaggaa attgcactga tgaatgctct gaccgttaat  420
ctgcacctgc tgatgctgtc ttttttttaaa ccgaccccga aacgctacaa aatactgctg  480
gaagcgaaag cgtttccgtc ggatcactat gctatagaaa gtcaactgca gttgcatggt  540
ctgaatatcg aggaatctat gcgcatgatt aaaccgcgtg agggtgaaga aacgctgcgt  600
attgaagaca ttctggaagt tattgaaaaa gaaggtgatt ctatcgcagt tatactgttt  660
tctggcgtgc acttttatac aggtcagcac ttcaatatcc cggcaatcac taaagcgggg  720
caggcaaaag gctgctatgt tggttttgac ctggcgcatg cagtggggaa tgttgaactg  780
tatctgcacg attggggcgt tgatttcgcg tgttggtgta gctacaaata tctgaacgct  840
ggcgcgggtg gcattgctgg cgcttttatt cacgaaaaac acgcgcacac cattaaaccg  900
gctctggttg gctggttcgg tcatgagctg agtactcgct ttaaaatgga taacaaactg  960
caattgattc cgggtgtttg cggcttccgt atcagcaatc cgccgattct gctggtttgc  1020
agcctgcacg ctagtctgga aatctttaag caggcgacta tgaaagcgct gcgcaaaaaa  1080
tctgtgctgc tgaccggcta tctggagtat ctgatcaaac acaattatgg caaagataaa  1140
gctgcaacta aaaaaccggt agtgaacatt atcacccccct cacacgtgga ggagcgcggt  1200
tgtcagctga ctattacttt cagtgtacct aataaagatg tgttccagga actggaaaaa  1260
cgcggcgttg tttgtgataa acgtaacccg aatggtattc gcgtggctcc tgtgccgctg  1320
tacaattcat tccacgatgt ttataaattc accaacctgc tgacttctat tctcgacagt  1380
gctgagacta aaaattaa                                                1398

SEQ ID NO: 14          moltype = DNA  length = 1501
FEATURE                Location/Qualifiers
source                 1..1501
                       mol_type = other DNA
                       organism = synthetic construct
SEQUENCE: 14
taattcctaa tttttgttga cactctatca ttgatagagt tattttacca ctccctatca  60
gtgatagaga aaagtgaata tcaagacacg aggaggtaag attatggagc cttcatcttt  120
agaactgcca gcggacacgg tgcagcgcat cgcggcggaa ctgaagtgcc atccgactga  180
tgagcgtgtg gcgctgcatc tggacgaaga agataaactg cgccactttc gtgaatgttt  240
ttatattcct aaaattcaag acttgccgcc ggtagatttg agtctcgtta acaaagatga  300
aaacgcgatc tactttctgg gcaactctct gggtctgcaa ccaaaaatgg ttaaaacgta  360
cctggaggaa gaactggata aatgggcaaa aatcgcggct tatggtcacg aagtgggcaa  420
gcgtccttgg attactggcg acgagtctat tgtgggtttg atgaaagata ttgtgggcgc  480
gaatgaaaag gaaattgcac tgatgaatgc tctgaccgtt aatctgcacc tgctgatgct  540
gtcttttttt aaaccgaccc cgaaacgcta caaaatactg ctggaagcga aagcgtttcc  600
gtcggatcac tatgctatag aaagtcaact gcagttgcat ggtctgaata tcgaggaatc  660
tatgcgcatg attaaaccgc gtgagggtga agaaacgctg cgtattgaag acattctgga  720
agttattgaa aaagaaggtg attctatcgc agttatactg ttttctggcg tgcactttta  780
tacaggtcag cacttcaata tcccggcaat cactaaagcg gggcaggcaa aaggctgcta  840
tgttggtttt gacctggcgc atgcagtggg gaatgttgaa ctgtatctgc acgattgggg  900
cgttgatttc gcgtgttggt gtagctacaa atatctgaac gctggcgcgg gtggcattgc  960
tggcgctttt attcacgaaa aacacgcgca caccattaaa ccggctctgg ttggctggtt  1020
cggtcatgag ctgagtactc gctttaaaat ggataacaaa ctgcaattga ttccgggtgt  1080
ttgcggcttc cgtatcagca atccgccgat tctgctggtt tgcagcctgc acgctagtct  1140
ggaaatcttt aagcaggcga ctatgaaagc gctgcgcaaa aaatctgtgc tgctgaccgg  1200
ctatctggag tatctgatca aacacaatta tggcaaagat aaagctgcaa ctaaaaaacc  1260
```

```
ggtagtgaac attatcaccc cctcacacgt ggaggagcgc ggttgtcagc tgactattac  1320
tttcagtgta cctaataaag atgtgttcca ggaactggaa aaacgcggcg ttgtttgtga  1380
taaacgtaac ccgaatggta ttcgcgtggc tcctgtgccg ctgtacaatt cattccacga  1440
tgtttataaa ttcaccaacc tgctgacttc tattctcgac agtgctgaga ctaaaaatta  1500
a                                                                  1501

SEQ ID NO: 15          moltype = DNA  length = 2127
FEATURE                Location/Qualifiers
source                 1..2127
                       mol_type = other DNA
                       organism = synthetic construct
SEQUENCE: 15
taagacccac tttcacattt aagttgtttt tctaatccgc atatgatcaa ttcaaggccg  60
aataagaagg ctggctctgc accttggtga tcaaataatt cgatagcttg tcgtaataat  120
ggcggcatac tatcagtagt aggtgtttcc ctttcttctt tagcgacttg atgctcttga  180
tcttccaata cgcaacctaa agtaaaatgc cccacagcgc tgagtgcata taatgcattc  240
tctagtgaaa aaccttgttg gcataaaaag gctaattgat tttcgagagt ttcatactgt  300
ttttctgtag gccgtgtacc taaatgtact tttgctccat cgcgatgact tagtaaagca  360
catctaaaac ttttagcgtt attacgtaaa aaatcttgcc agctttcccc ttctaaaggg  420
caaaagtgag tatggtgcct atctaacatc tcaatggcta aggcgtcgag caaagcccgc  480
ttatttttta catgccaata caatgtaggc tgctctacac ctagcttctg ggcgagttta  540
cgggttgtta aaccttcgat tccgacctca ttaagcagct ctaatgcgct gttaatcact  600
ttacttttat ctaatctaga catcattaat tcctaatttt tgttgacact ctatcattga  660
tagagttatt ttaccactcc ctatcagtga tagagaaaag tgaatatcaa gacacgagga  720
ggtaagatta tggagccttc atctttagaa ctgccagcgg acacggtgca gcgcatcgcg  780
gcggaactga agtgccatcc gactgatgag cgtgtggcgc tgcatctgga cgaagaagat  840
aaactgcgcc actttcgtga atgtttttat attcctaaaa ttcaagactt gccgccggta  900
gatttgagtc tcgttaacaa agatgaaaac gcgatctact ttctgggcaa ctctctgggt  960
ctgcaaccaa aaatggttaa aacgtacctg gaggaagaac tggataaatg ggcaaaaatc  1020
gcggcttatg gtcacgaagt gggcaagcgt ccttggatta ctggcgacga gtctattgtg  1080
ggtttgatga aagatattgt gggcgcgaat gaaaaggaaa ttgcactgat gaatgctctg  1140
accgttaatc tgcacctgct gatgctgtct ttttttaaac cgaccccgaa acgctacaaa  1200
atactgctgg aagcgaaagc gtttccgtcg gatcactatg ctatagaaag tcaactgcag  1260
ttgcatggtc tgaatatcga ggaatctatg cgcatgatta aaccgcgtga gggtgaagaa  1320
acgctgcgta ttgaagacat tctggaagtt attgaaaaag aaggtgattc tatcgcagtt  1380
atactgtttt ctggcgtgca cttttataca ggtcagcact tcaatatccc ggcaatcact  1440
aaagcggggc aggcaaaagg ctgctatgtt ggttttgacc tggcgcatgc agtggggaat  1500
gttgaactgt atctgcacga ttggggcgtt gatttcgcgt gttggtgtag ctacaaatat  1560
ctgaacgctg gcgcgggtgg cattgctggc gcttttattc acgaaaaaca cgcgcacacc  1620
attaaaccgg ctctggttgg ctggttcggt catgagctga gtactcgctt taaaatggat  1680
aacaaactgc aattgattcc gggtgtttgc ggcttccgta tcagcaatcc gccgattctg  1740
ctggtttgca gcctgcacgc tagtctggaa atctttaagc aggcgactat gaaagcgctg  1800
cgcaaaaaat ctgtgctgct gaccggctat ctggagtatc tgatcaaaca caattatggc  1860
aaagataaag ctgcaactaa aaaaccggta gtgaacatta tcaccccctc acacgtggag  1920
gagcgcggtt gtcagctgac tattactttc agtgtaccta ataaagatgt gttccaggaa  1980
ctggaaaaac gcggcgttgt ttgtgataaa cgtaacccga atggtattcg cgtggctcct  2040
gtgccgctgt acaattcatt ccacgatgtt tataaattca ccaacctgct gacttctatt  2100
ctcgacagtg ctgagactaa aaattaa                                      2127

SEQ ID NO: 16          moltype = DNA  length = 64
FEATURE                Location/Qualifiers
source                 1..64
                       mol_type = other DNA
                       organism = synthetic construct
SEQUENCE: 16
ggaaaatttt tttaaaaaaa aaacttgaca gctagctcag tccttggtat aatgctagca  60
cgaa                                                               64

SEQ ID NO: 17          moltype = DNA  length = 25
FEATURE                Location/Qualifiers
source                 1..25
                       mol_type = other DNA
                       organism = synthetic construct
SEQUENCE: 17
ttatataaaa gtgggaggtg cccga                                        25

SEQ ID NO: 18          moltype = DNA  length = 94
FEATURE                Location/Qualifiers
source                 1..94
                       mol_type = other DNA
                       organism = synthetic construct
SEQUENCE: 18
ggaaaatttt tttaaaaaaa aaacttgaca gctagctcag tccttggtat aatgctagca  60
cgaagtgaat tatataaaag tgggaggtgc ccga                              94

SEQ ID NO: 19          moltype = DNA  length = 951
FEATURE                Location/Qualifiers
source                 1..951
                       mol_type = genomic DNA
```

-continued

```
                         organism = Escherichia coli
SEQUENCE: 19
caaatatcac ataatcttaa catatcaata aacacagtaa agtttcatgt gaaaaacatc  60
aaacataaaa tacaagctcg gaatacgaat cacgctatac acattgctaa caggaatgag  120
attatctaaa tgaggattga tatattaatt ggacatacta gtttttttca tcaaaccagt  180
agagataact tccttcacta tctcaatgag gaagaaataa aacgctatga tcagtttcat  240
tttgtgagtg ataaagaact ctatatttta agccgtatcc tgctcaaaac agcactaaaa  300
agatatcaac ctgatgtctc attacaatca tggcaattta gtacgtgcaa atatggcaaa  360
ccatttatag tttttcctca gttggcaaaa aagatttttt tacctttcca tactatagat  420
acagtagccg tgctattagt tctcactgcg agcttggtgt cgatattgaa caaatagaga  480
tttagacaac tctatctgaa tatcagtcag catttttttac tccacaggaa gctactacat  540
agtttcactt cctcgttatg aaggtcaatt actttttgga aatgtggacg ctcaaagagc  600
ttacatcaat atcgaggtaa ggcctatctt taggactgga ttgtattgaa tttcatttaa  660
caaataaaaa ctaactcaaa tatagaggtt cacctgttta tttctctcaa tggaaaatat  720
gtaactcatt tctcgcatta gcctctccac tcatcacccc taaaataact attgagctat  780
ttcctatgca gtcccaactt tatcaccacg actatcagct aattcattcg tcaaatgggc  840
agaattgaat cgccacggat aatctagaca cttctgagcc gtcgataata ttgattttca  900
tattccgtcg gtggtgtaag tatcccgcat aatcgtgcca ttcacattta g           951

SEQ ID NO: 20            moltype = DNA  length = 424
FEATURE                  Location/Qualifiers
source                   1..424
                         mol_type = other DNA
                         organism = synthetic construct
SEQUENCE: 20
ggatgggggg aaacatggat aagttcaaag aaaaaaaccc gttatctctg cgtgaaagac  60
aagtattgcg catgctggca caaggtgatg agtactctca aatatcacat aatcttaaca  120
tatcaataaa cacagtaaag tttcatgtga aaaacatcaa acataaaata caagctcgga  180
atacgaatca cgctatacac attgctaaca ggaatgagat tatctaaatg aggattgatg  240
tgtaggctgg agctgcttcg aagttcctat actttctaga gaataggaac ttcggaatag  300
gaacttcgga ataggaacta aggaggatat tcatatgtcg tcaaatgggc agaattgaat  360
cgccacggat aatctagaca cttctgagcc gtcgataata ttgattttca tattccgtcg  420
gtgg                                                               424

SEQ ID NO: 21            moltype = DNA  length = 1225
FEATURE                  Location/Qualifiers
source                   1..1225
                         mol_type = other DNA
                         organism = synthetic construct
SEQUENCE: 21
ggaaaatttt tttaaaaaaa aaacttgaca gctagctcag tccttggtat aatgctagca  60
cgaagtgaat tatataaaag tgggaggtgc ccgaatgacg acccgaaatg attgcctagc  120
gttggatgca caggacagtc tggctccgct gcgccaacaa tttgcgctgc cggagggtgt  180
gatatacctg gatggcaatt cgctgggcgc acgtccggta gctgcgctgg ctcgcgcgca  240
ggctgtgatc gcagaagaat ggggcaacgg gttgatccgt tcatggaact ctgcgggctg  300
gcgtgatctg tctgaacgcc tgggtaatcg cctggctacc ctgattggtg cgcgcgatgg  360
ggaagtagtt gttactgata ccacctcgat taatctgttt aaagtgctgt cagcggcgct  420
gcgcgtgcaa gctacccgta gcccggagcg ccgtgttatc gtgactgaga cctcgaattt  480
cccgaccgac ctgtatattg cggaagggtt ggcggatatg ctgcaacaag gttacactct  540
gcgtttggtg gattcaccgg aagagctgcc acaggctata gatcaggaca ccgcggtggt  600
gatgctgacg cacgtaaatt ataaaaccgg ttatatgcac gacatgcagg ctctgaccgc  660
gttgagccac gagtgtgggg ctctggcgat ttgggatctg gcgcactctg ctggcgctgt  720
gccggtggac ctgcaccaag cgggcgcgga ctatgcgatt ggctgcacgt acaaatacct  780
gaatggcggc ccgggttcgc aagcgtttgt ttgggtttcg ccgcaactgt gcgacctggt  840
accgcagccg ctgtctggtt ggttcggcca tagtcgccaa ttcgcgatgg agccgcgcta  900
cgaaccttct aacggcattg ctcgctatct gtgcggcact cagcctatta ctagcttggc  960
tatggtggag tgcggcctgg atgtgtttgc gcagacggat atggcttcgc tgcgccgtaa  1020
aagtctggcg ctgactgatc tgttcatcga gctggttgaa caacgctgcg ctgcacacga  1080
actgaccctg gttactccac gtgaacacgc gaaacgcggc tctcacgtgt cttttgaaca  1140
ccccgagggt tacgctgtta ttcaagctct gattgatcgt ggcgtgatcg gcgattaccg  1200
tgagccacgt attatgcgtt tcggt                                        1225

SEQ ID NO: 22            moltype = DNA  length = 66
FEATURE                  Location/Qualifiers
source                   1..66
                         mol_type = other DNA
                         organism = synthetic construct
SEQUENCE: 22
ataagtgcct tcccatcaaa aaaatattct caacataaaa aactttgtgt aatacttgta  60
acgcta                                                             66

SEQ ID NO: 23            moltype = DNA  length = 25
FEATURE                  Location/Qualifiers
source                   1..25
                         mol_type = other DNA
                         organism = synthetic construct
SEQUENCE: 23
ttatataaaa gtgggaggtg cccga                                        25
```

-continued

```
SEQ ID NO: 24          moltype = DNA  length = 96
FEATURE                Location/Qualifiers
source                 1..96
                       mol_type = other DNA
                       organism = synthetic construct
SEQUENCE: 24
ataagtgcct tcccatcaaa aaaatattct caacataaaa aactttgtgt aatacttgta  60
acgctagtga attatataaa agtgggaggt gcccga                            96

SEQ ID NO: 25          moltype = DNA  length = 1347
FEATURE                Location/Qualifiers
source                 1..1347
                       mol_type = other DNA
                       organism = synthetic construct
SEQUENCE: 25
ataagtgcct tcccatcaaa aaaatattct caacataaaa aactttgtgt aatacttgta  60
acgctagtga attatataaa agtgggaggt gcccgaatga cgacccgaaa tgattgccta  120
gcgttggatg cacaggacag tctggctccg ctgcgccaac aatttgcgct gccggagggt  180
gtgatatacc tggatggcaa ttcgctgggc gcacgtccgg tagctgcgct ggctcgcgcg  240
caggctgtga tcgcagaaga atggggcaac gggttgatcc gttcatggaa ctctgcgggc  300
tggcgtgatc tgtctgaacg cctgggtaat cgcctggcta ccctgattgg tgcgcgcgat  360
ggggaagtag ttgttactga taccacctcg attaatctgt ttaaagtgct gtcagcggcg  420
ctgcgcgtgc aagctacccg tagcccggag cgccgtgtta tcgtgactga gacctcgaat  480
ttcccgaccg acctgtatat tgcggaaggg ttggcggata tgctgcaaca aggttacact  540
ctgcgtttgg tggattcacc ggaagagctg ccacaggcta tagatcagga caccgcggtg  600
gtgatgctga cgcacgtaaa ttataaaacc ggttatatgc acgacatgca ggctctgacc  660
gcgttgagcc acgagtgtgg ggctctggcg atttgggatc tggcgcactc tgctggcgct  720
gtgccggtgg acctgcacca agcgggcgcg gactatgcga ttggctgcac gtacaaatac  780
ctgaatggcg gcccgggttc gcaagcgttt gtttgggttt cgccgcaact gtgcgacctg  840
gtaccgcagc cgctgtctgg ttggttcggc catagtcgcc aattcgcgat ggagccgcgc  900
tacgaacctt ctaacggcat tgctcgctat ctgtgcggca ctcagcctat tactagcttg  960
gctatggtgg agtgcggcct ggatgtgttt gcgcagacgg atatggcttc gctgcgccgt  1020
aaaagtctgg cgctgactga tctgttcatc gagctggttg aacaacgctg cgctgcacac  1080
gaactgaccc tggttactcc acgtgaacac gcgaaacgcg gctctcacgt gtcttttgaa  1140
cacccccgagg gttacgctgt tattcaagct ctgattgatc gtggcgtgat cggcgattac  1200
cgtgagccac gtattatgcg tttcggtttc actcctctgt atactacttt tacggaagtt  1260
tgggatgcag tacaaatcct gggcgaaatc ctggatcgta agacttgggc gcaggctcag  1320
tttcaggtgc gccactctgt tacttaa                                      1347

SEQ ID NO: 26          moltype = DNA  length = 2372
FEATURE                Location/Qualifiers
source                 1..2372
                       mol_type = genomic DNA
                       organism = Clostridium sporogenes
SEQUENCE: 26
ctctagaaat aattttgttt aactttaaga aggagatata catatgaatt atcagaacga  60
cgatttacgc atcaaagaaa tcaaagagtt acttcctcct gtcgcattgc tggaaaaatt  120
ccccgctact gaaaatgccg cgaatacggt cgcccatgcc cgaaaagcga tccataagat  180
cctgaaaggt aatgatgatc gcctgttggt ggtgattggc ccatgctcaa ttcatgatcc  240
tgtcgcggct aaagagtatg ccactcgctt gctgacgctg cgtgaagagc tgcaagatga  300
gctggaaatc gtgatgcgcg tctattttga aaagccgcgt actacggtgg gctggaaagg  360
gctgattaac gatccgcata tggataacag cttccagatc aacgacggtc tgcgtattgc  420
ccgcaaattg ctgctcgata ttaacgacag cggtctgcca gcggcgggtg aattcctgga  480
tatgatcacc ctacaatatc tcgctgacct gatgagctgg ggcgcaattg gcgcacgtac  540
caccgaatcg caggtgcacc gcgaactggc gtctggtctt tcttgtccgg taggtttcaa  600
aaatggcact gatggtacga ttaaagtggc tatcgatgcc attaatgccg ccggtgcgcc  660
gcactgcttc ctgtccgtaa cgaaatgggg gcattcggcg attgtgaata ccagcggtaa  720
cggcgattgc catatcattc tgcgcggcgg taaagagcct aactacagcg cgaagcacgt  780
tgctgaagtg aaagaagggc tgaacaaagc aggcctgcca gcgcaggtga tgatcgattt  840
cagccatgct aactcgtcaa aacaattcaa aaagcagatg gatgtttgta ctgacgtttg  900
ccagcagatt gccggtggcg aaaaggccat tattggcgtg atggtggaaa gccatctggt  960
ggaaggcaat cagagcctcg agagcgggga accgctggcc tacggtaaga gcatcaccga  1020
tgcctgcatt ggctgggatg ataccgatgc tctgttacgt caactggcga gtgcagtaaa  1080
agcgcgtcgc gggtaatact taagaaggag atatacatat gaaattttgg cgcaagtata  1140
cgcaacagga gatggatgag aaaatcacag aatcgcttga gaagacatta aattacgata  1200
acacgaaaac catcggcatc ccaggtacta agctggatga tactgtattt tatgacgatc  1260
actccttcgt taagcactct ccctatttac gtacgttcat ccaaaaccct aatcacattg  1320
gttgtcacac gtacgataaa gcagacatct tgtttggcgg cacgtttgac atcgaacgcg  1380
aactgattca gcttttggcc atcgatgtct taaacggaaa tgatgaggaa ttcgatggat  1440
atgtgacaca ggggggaacc gaggcgaata ttcaggcaat gtgggtttat cgtaactatt  1500
tcaaaaaaga acgtaaagca aaacatgagg aaatcgcaat catcacgagc gcggataccc  1560
attacagtgc atataagggg agcgacttgc tgaacattga tattatcaag gtcccagtag  1620
acttctattc gcgtaagatc caggagaaca cgttagactc gattgtcaag gaggcgaagg  1680
aaattggaaa gaagtacttc attgtcatct caaacatggg tacgactatg tttggcagtg  1740
tagacgaccc tgatctttat gctaacattt ttgataagta taacttagaa tacaaaatcc  1800
acgtcgatgg agcttttggg ggtttcattt atcctatcga taataaggag tgcaaaacag  1860
atttctcgaa caagaacgtc tcatccatca cgcttgacgg tcacaaaatg cttcaagccc  1920
cctatgggac tggtatcttc gtgtcacgta agaacttgat ccataacacc ctgacaaagg  1980
aagcaacgta tattgaaaac ctggacgtta ccctgagtgg gtcccgctcc ggatccaacg  2040
```

-continued

```
ccgttgcgat ctggatggtt ttagcctctt atggccccta cgggtggatg gagaagatta  2100
acaagttgcg caatcgcact aagtggcttt gcaagcagct taacgacatg cgcatcaaat  2160
actataagga ggatagcatg aatatcgtca cgattgaaga gcaatacgta aataaagaga  2220
ttgcagagaa atacttcctt gtgcctgaag tacacaatcc taccaacaat tggtacaaga  2280
ttgtagtcat ggaacatgtt gaacttgaca tcttgaactc ccttgtttat gatttacgta  2340
aattcaacaa ggagcacctg aaggcaatgt ga                                2372

SEQ ID NO: 27          moltype = DNA  length = 1254
FEATURE                Location/Qualifiers
source                 1..1254
                       mol_type = genomic DNA
                       organism = Clostridium sporogenes
SEQUENCE: 27
atgaaatttt ggcgcaagta tacgcaacag gagatggatg agaaaatcac agaatcgctt  60
gagaagacat taaattacga taacacgaaa accatcggca tcccaggtac taagctggat  120
gatactgtat tttatgacga tcactccttc gttaagcact ctccctattt acgtacgttc  180
atccaaaacc ctaatcacat tggttgtcac acgtacgata aagcagacat cttgtttggc  240
ggcacgtttg acatcgaacg cgaactgatt cagcttttgg ccatcgatgt cttaaacgga  300
aatgatgagg aattcgatgg atatgtgaca cagggggaa ccgaggcgaa tattcaggca  360
atgtgggttt atcgtaacta tttcaaaaaa gaacgtaaag caaaacatga ggaaatcgca  420
atcatcacga gcgcggatac ccattacagt gcatataagg ggagcgactt gctgaacatt  480
gatattatca aggtcccagt agacttctat tcgcgtaaga tccaggagaa cacgttagac  540
tcgattgtca aggaggcgaa ggaaattgga aagaagtact tcattgtcat ctcaaacatg  600
ggtacgacta tgtttggcag tgtagacgac cctgatcttt atgctaacat ttttgataag  660
tataacttag aatacaaaat ccacgtcgat ggagcttttg gggtttcat ttatcctatc  720
gataataagg agtgcaaaac agatttctcg aacaagaacg tctcatccat cacgcttgac  780
ggtcacaaaa tgcttcaagc cccctatggg actggtatct tcgtgtcacg taagaacttg  840
atccataaca ccctgacaaa ggaagcaacg tatattgaaa acctggacgt taccctgagt  900
gggtcccgct ccggatccaa cgccgttgcg atctggatgg ttttagcctc ttatggcccc  960
tacgggtgga tggagaagat taacaagttg cgcaatcgca ctaagtggct ttgcaagcag  1020
cttaacgaca tgcgcatcaa atactataag gaggatagca tgaatatcgt cacgattgaa  1080
gagcaatacg taaataaaga gattgcagag aaatacttcc ttgtgcctga agtacacaat  1140
cctaccaaca attggtacaa gattgtagtc atggaacatg ttgaacttga catcttgaac  1200
tcccttgttt atgatttacg taaattcaac aaggagcacc tgaaggcaat gtga        1254

SEQ ID NO: 28          moltype = AA  length = 417
FEATURE                Location/Qualifiers
source                 1..417
                       mol_type = protein
                       organism = Clostridium sporogenes
SEQUENCE: 28
MKFWRKYTQQ EMDEKITESL EKTLNYDNTK TIGIPGTKLD DTVFYDDHSF VKHSPYLRTF  60
IQNPNHIGCH TYDKADILFG GTFDIERELI QLLAIDVLNG NDEEFDGYVT QGGTEANIQA  120
MWVYRNYFKK ERKAKHEEIA IITSADTHYS AYKGSDLLNI DIIKVPVDFY SRKIQENTLD  180
SIVKEAKEIG KKYFIVISNM GTTMFGSVDD PDLYANIFDK YNLEYKIHVD GAFGGFIYPI  240
DNKECKTDFS NKNVSSITLD GHKMLQAPYG TGIFVSRKNL IHNTLTKEAT YIENLDVTLS  300
GSRSGSNAVA IWMVLASYGP YGWMEKINKL RNRTKWLCKQ LNDMRIKYYK EDSMNIVTIE  360
EQYVNKEIAE KYFLVPEVHN PTNNWYKIVV MEHVELDILN SLVYDLRKFN KEHLKAM     417

SEQ ID NO: 29          moltype = DNA  length = 60
FEATURE                Location/Qualifiers
source                 1..60
                       mol_type = other DNA
                       organism = synthetic construct
SEQUENCE: 29
tagaactgat gcaaaaagtg ctcgacgaag gcacacagat gtgtaggctg gagctgcttc  60

SEQ ID NO: 30          moltype = DNA  length = 60
FEATURE                Location/Qualifiers
source                 1..60
                       mol_type = other DNA
                       organism = synthetic construct
SEQUENCE: 30
gtttcgtaat tagatagcca ccggcgcttt aatgcccgga catatgaata tcctccttag  60

SEQ ID NO: 31          moltype = DNA  length = 52
FEATURE                Location/Qualifiers
source                 1..52
                       mol_type = other DNA
                       organism = synthetic construct
SEQUENCE: 31
caacacgttt cctgaggaac catgaaacag tatttagaac tgatgcaaaa ag          52

SEQ ID NO: 32          moltype = DNA  length = 46
FEATURE                Location/Qualifiers
source                 1..46
                       mol_type = other DNA
                       organism = synthetic construct
SEQUENCE: 32
```

```
cgcacactgg cgtcggctct ggcaggatgt ttcgtaatta gatagc                46

SEQ ID NO: 33          moltype = DNA  length = 1096
FEATURE                Location/Qualifiers
source                 1..1096
                       mol_type = other DNA
                       organism = synthetic construct
SEQUENCE: 33
ctctagaaat aattttgttt aactttaaga aggagatata catatgaatt atcagaacga  60
cgatttacgc atcaaagaaa tcaaagagtt acttcctcct gtcgcattgc tggaaaaatt  120
ccccgctact gaaaatgccg cgaatacggt cgcccatgcc cgaaaagcga tccataagat  180
cctgaaaggt aatgatgatc gcctgttggt ggtgattggc ccatgctcaa ttcatgatcc  240
tgtcgcggct aaagagtatg ccactcgctt gctgacgctg cgtgaagagc tgcaagatga  300
gctggaaatc gtgatgcgcg tctattttga aaagccgcgt actacggtgg gctggaaagg  360
gctgattaac gatccgcata tggataacag cttccagatc aacgacggtc tgcgtattgc  420
ccgcaaattg ctgctcgata ttaacgacag cggtctgcca gcggcgggtg aattcctgga  480
tatgatcacc ctacaatatc tcgctgacct gatgagctgg ggcgcaattg gcgcacgtac  540
caccgaatcg caggtgcacc gcgaactggc gtctggtctt tcttgtccgg taggtttcaa  600
aaatggcact gatggtacga ttaaagtggc tatcgatgcc attaatgccg ccggtgcgcc  660
gcactgcttc ctgtccgtaa cgaaatgggg gcattcggcg attgtgaata ccagcggtaa  720
cggcgattgc catatcattc tgcgcggcgg taaagagcct aactacagcg cgaagcacgt  780
tgctgaagtg aaagaagggc tgaacaaagc aggcctgcca gcgcaggtga tgatcgattt  840
cagccatgct aactcgtcaa aacaattcaa aaagcagatg gatgtttgta ctgacgtttg  900
ccagcagatt gccggtggcg aaaaggccat tattggcgtg atggtggaaa gccatctggt  960
ggaaggcaat cagagcctcg agagcgggga accgctggcc tacggtaaga gcatcaccga  1020
tgcctgcatt ggctgggatg ataccgatgc tctgttacgt caactggcga gtgcagtaaa  1080
agcgcgtcgc gggtaa                                                  1096

SEQ ID NO: 34          moltype = DNA  length = 1053
FEATURE                Location/Qualifiers
source                 1..1053
                       mol_type = other DNA
                       organism = synthetic construct
SEQUENCE: 34
atgaattatc agaacgacga tttacgcatc aaagaaatca aagagttact tcctcctgtc  60
gcattgctgg aaaaattccc cgctactgaa aatgccgcga atacggtcgc ccatgcccga  120
aaagcgatcc ataagatcct gaaaggtaat gatgatcgcc tgttggtggt gattggccca  180
tgctcaattc atgatcctgt cgcggctaaa gagtatgcca ctcgcttgct gacgctgcgt  240
gaagagctgc aagatgagct ggaaatcgtg atgcgcgtct attttgaaaa gccgcgtact  300
acggtgggct ggaaagggct gattaacgat ccgcatatgg ataacagctt ccagatcaac  360
gacggtctgc gtattgcccg caaattgctg ctcgatatta acgacagcgg tctgccagcg  420
gcgggtgaat tcctggatat gatcacccta caatatctcg ctgacctgat gagctggggc  480
gcaattggcg cacgtaccac cgaatcgcag gtgcaccgcg aactggcgtc tggtctttct  540
tgtccggtag gtttcaaaaa tggcactgat ggtacgatta aagtggctat cgatgccatt  600
aatgccgccg gtgcgccgca ctgcttcctg tccgtaacga aatgggggca ttcggcgatt  660
gtgaatacca gcggtaacgg cgattgccat atcattctgc gcggcggtaa agagcctaac  720
tacagcgcga agcacgttgc tgaagtgaaa gaagggctga acaaagcagg cctgccagcg  780
caggtgatga tcgatttcag ccatgctaac tcgtcaaaac aattcaaaaa gcagatggat  840
gtttgtactg acgtttgcca gcagattgcc ggtggcgaaa aggccattat tggcgtgatg  900
gtggaaagcc atctggtgga aggcaatcag agcctcgaga gcggggaacc gctggcctac  960
ggtaagagca tcaccgatgc ctgcattggc tgggatgata ccgatgctct gttacgtcaa  1020
ctggcgagtg cagtaaaagc gcgtcgcggg taa                               1053

SEQ ID NO: 35          moltype = DNA  length = 2351
FEATURE                Location/Qualifiers
source                 1..2351
                       mol_type = other DNA
                       organism = synthetic construct
SEQUENCE: 35
ctctagaaat aattttgttt aactttaaga aggagatata catatgaatt atcagaacga  60
cgatttacgc atcaaagaaa tcaaagagtt acttcctcct gtcgcattgc tggaaaaatt  120
ccccgctact gaaaatgccg cgaatacggt cgcccatgcc cgaaaagcga tccataagat  180
cctgaaaggt aatgatgatc gcctgttggt ggtgattggc ccatgctcaa ttcatgatcc  240
tgtcgcggct aaagagtatg ccactcgctt gctgacgctg cgtgaagagc tgcaagatga  300
gctggaaatc gtgatgcgcg tctattttga aaagccgcgt actacggtgg gctggaaagg  360
gctgattaac gatccgcata tggataacag cttccagatc aacgacggtc tgcgtattgc  420
ccgcaaattg ctgctcgata ttaacgacag cggtctgcca gcggcgggtg aattcctgga  480
tatgatcacc ctacaatatc tcgctgacct gatgagctgg ggcgcaattg gcgcacgtac  540
caccgaatcg caggtgcacc gcgaactggc gtctggtctt tcttgtccgg taggtttcaa  600
aaatggcact gatggtacga ttaaagtggc tatcgatgcc attaatgccg ccggtgcgcc  660
gcactgcttc ctgtccgtaa cgaaatgggg gcattcggcg attgtgaata ccagcggtaa  720
cggcgattgc catatcattc tgcgcggcgg taaagagcct aactacagcg cgaagcacgt  780
tgctgaagtg aaagaagggc tgaacaaagc aggcctgcca gcgcaggtga tgatcgattt  840
cagccatgct aactcgtcaa aacaattcaa aaagcagatg gatgtttgta ctgacgtttg  900
ccagcagatt gccggtggcg aaaaggccat tattggcgtg atggtggaaa gccatctggt  960
ggaaggcaat cagagcctcg agagcgggga accgctggcc tacggtaaga gcatcaccga  1020
tgcctgcatt ggctgggatg ataccgatgc tctgttacgt caactggcga gtgcagtaaa  1080
agcgcgtcgc gggtaatact taagaaggag atatacatat ggcaaaggta tcgctggaga  1140
aagacaagat taagtttctg ctggtagaag gcgtgcacca aaaggcgctg gaaagccttc  1200
```

-continued

```
gtgcagctgg ttacaccaac atcgaatttc acaaaggcgc gctggatgat gaacaattaa  1260
aagaatccat ccgcgatgcc cacttcatcg gcctgcgatc ccgtacccat ctgactgaag  1320
acgtgatcaa cgccgcagaa aaactggtcg ctattggctg tttctgtatc ggaacaaatc  1380
aggttgatct ggatgcggcg gcaaagcgcg ggatcccggt atttaacgca ccgttctcaa  1440
atacgcgctc tgttgcggag ctggtgattg gcgaactgct gctgctattg cgcggcgtgc  1500
cagaagccaa tgctaaagcg catcgtggcg tgtggaacaa actggcggcg ggttcttttg  1560
aagcgcgcgg caaaaagctg ggtatcatcg gctacggtca tattggtacg caattgggca  1620
ttctggctga atcgctggga atgtatgttt acttttatga tattgaaaac aaactgccgc  1680
tgggcaacgc cactcaggta cagcatcttt ctgacctgct gaatatgagc gatgtggtga  1740
gtctgcatgt accagagaat ccgtccacca aaaatatgat gggcgcgaaa gagatttcgc  1800
taatgaagcc cggctcgctg ctgattaatg cttcgcgcgg tactgtggtg gatattccag  1860
cgctgtgtga cgcgctggcg agcaaacatc tggcgggggc ggcaatcgac gtattcccga  1920
cggaaccggc gaccaatagc gatccattta cctctccgct gtgtgaattc gacaatgtcc  1980
ttctgacgcc acacattggc ggttcgactc aggaagcgca ggagaatatc ggcttggaag  2040
ttgcgggtaa attgatcaag tattctgaca atggctcaac gctctctgcg gtgaacttcc  2100
cggaagtctc gctgccactg cacggtgggc gtcgtctgat gcacatccac gaaaaccgtc  2160
cgggcgtgct aactgcgctc aacaaaattt ttgccgagca gggcgtcaac atcgccgcgc  2220
aatatctaca aacttccgcc cagatgggtt atgtagttat tgatattgaa gccgacgaag  2280
acgttgccga aaaagcgctg caggcaatga aagctattcc gggtaccatt cgcgcccgtc  2340
tgctgtacta a                                                        2351

SEQ ID NO: 36          moltype = DNA  length = 1233
FEATURE                Location/Qualifiers
source                 1..1233
                       mol_type = other DNA
                       organism = synthetic construct
SEQUENCE: 36
atggcaaagg tatcgctgga gaaagacaag attaagtttc tgctggtaga aggcgtgcac  60
caaaaggcgc tggaaagcct tcgtgcagct ggttacacca acatcgaatt tcacaaaggc  120
gcgctggatg atgaacaatt aaaagaatcc atccgcgatg cccacttcat cggcctgcga  180
tcccgtaccc atctgactga agacgtgatc aacgccgcag aaaaactggt cgctattggc  240
tgtttctgta tcggaacaaa tcaggttgat ctggatgcgg cggcaaagcg cgggatcccg  300
gtatttaacg caccgttctc aaatacgcgc tctgttgcgg agctggtgat tggcgaactg  360
ctgctgctat tgcgcggcgt gccagaagcc aatgctaaag cgcatcgtgg cgtgtggaac  420
aaactggcgg cgggttcttt tgaagcgcgc ggcaaaaagc tgggtatcat cggctacggt  480
catattggta cgcaattggg cattctggct gaatcgctgg gaatgtatgt ttacttttat  540
gatattgaaa acaaactgcc gctgggcaac gccactcagg tacagcatct ttctgacctg  600
ctgaatatga gcgatgtggt gagtctgcat gtaccagaga atccgtccac caaaaatatg  660
atgggcgcga aagagatttc gctaatgaag cccggctcgc tgctgattaa tgcttcgcgc  720
ggtactgtgg tggatattcc agcgctgtgt gacgcgctgg cgagcaaaca tctggcgggg  780
gcggcaatcg acgtattccc gacggaaccg gcgaccaata gcgatccatt tacctctccg  840
ctgtgtgaat tcgacaatgt ccttctgacg ccacacattg gcggttcgac tcaggaagcg  900
caggagaata tcggcttgga agttgcgggt aaattgatca agtattctga caatggctca  960
acgctctctg cggtgaactt cccggaagtc tcgctgccac tgcacggtgg gcgtcgtctg  1020
atgcacatcc acgaaaaccg tccgggcgtg ctaactgcgc tcaacaaaat ttttgccgag  1080
cagggcgtca acatcgccgc gcaatatcta caaacttccg cccagatggg ttatgtagtt  1140
attgatattg aagccgacga agacgttgcc gaaaaagcgc tgcaggcaat gaaagctatt  1200
ccgggtacca ttcgcgcccg tctgctgtac taa                                1233

SEQ ID NO: 37          moltype = DNA  length = 2621
FEATURE                Location/Qualifiers
source                 1..2621
                       mol_type = genomic DNA
                       organism = Catharanthus roseus
SEQUENCE: 37
ctctagaaat aattttgttt aactttaaga aggagatata catatgaatt atcagaacga  60
cgatttacgc atcaaagaaa tcaaagagtt acttcctcct gtcgcattgc tggaaaaatt  120
ccccgctact gaaaatgccg cgaatacggt cgcccatgcc cgaaaagcga tccataagat  180
cctgaaaggt aatgatgatc gcctgttggt ggtgattggc ccatgctcaa ttcatgatcc  240
tgtcgcggct aaagagtatg ccactcgctt gctgacgctg cgtgaagagc tgcaagatga  300
gctggaaatc gtgatgcgcg tctattttga aaagccgcgt actacggtgg gctggaaagg  360
gctgattaac gatccgcata tggataacag cttccagatc aacgacggtc tgcgtattgc  420
ccgcaaattg ctgctcgata ttaacgacag cggtctgcca gcggcgggtg aattcctgga  480
tatgatcacc ctacaatatc tcgctgacct gatgagctgg ggcgcaattg gcgcacgtac  540
caccgaatcg caggtgcacc gcgaactggc gtctggtctt tcttgtccgg taggtttcaa  600
aaatggcact gatggtacga ttaaagtggc tatcgatgcc attaatgccg ccggtgcgcc  660
gcactgcttc ctgtccgtaa cgaaatgggg gcattcggcg attgtgaata ccagcggtaa  720
cggcgattgc catatcattc tgcgcggcgg taaagagcct aactacagcg cgaagcacgt  780
tgctgaagtg aaagaagggc tgaacaaagc aggcctgcca gcgcaggtga tgatcgattt  840
cagccatgct aactcgtcaa aacaattcaa aaagcagatg gatgtttgta ctgacgtttg  900
ccagcagatt gccggtggcg aaaaggccat tattggcgtg atggtggaaa gccatctggt  960
ggaaggcaat cagagcctcg agagcgggga accgctggcc tacggtaaga gcatcaccga  1020
tgcctgcatt ggctgggatg ataccgatgc tctgttacgt caactggcga gtgcagtaaa  1080
agcgcgtcgc gggtaatact taagaaggag atatacatat gggttctatt gactcgacga  1140
atgtggccat gtctaattct cctgttggcg agtttaagcc ccttgaagca gaagagttcc  1200
gtaaacaggc acaccgcatg gtggatttta ttgcggatta ttacaagaac gtagaaacat  1260
acccggtcct ttccgaggtt gaacccggct atctgcgcaa acgtattccc gaaaccgcac  1320
catacctgcc ggagccactt gatgatatta tgaaggatat tcaaaaggac attatccccg  1380
gaatgacgaa ctggatgtcc ccgaactttt acgccttctt cccggccaca gttagctcag  1440
```

```
cagctttctt gggggaaatg ctttcaacgg cccttaacag cgtaggattt acctgggtca  1500
gttccccggc agcgactgaa ttagagatga tcgttatgga ttggcttgcg caaattttga  1560
aacttccaaa aagctttatg ttctccggaa ccggggggtgg tgtcatccaa aacactacgt  1620
cagagtcgat cttgtgcact attatcgcgg cccgtgaacg cgccttggaa aaattgggcc  1680
ctgattcaat tggtaagctt gtctgctatg ggtccgatca aacgcacaca atgtttccga  1740
aaacctgtaa gttagcagga atttatccga ataatatccg ccttatccct accacggtag  1800
aaaccgactt tggcatctca ccgcaggtac ttcgcaagat ggtcgaagac gacgtcgctg  1860
cggggtacgt tcccttattt ttgtgtgcca ccttgggaac gacatcaact acggcaacag  1920
atcctgtaga ttcgctgtcc gaaatcgcaa acgagtttgg tatctggatt catgtcgacg  1980
ccgcatatgc tggatcggct tgcatctgcc cagaatttcg tcactacctt gatggcatcg  2040
aacgtgtgga ttccttatcg ctgtctcccc acaaatggct tttagcatat ctggattgca  2100
cgtgcttgtg ggtaaaacaa cctcacctgc tgcttcgcgc tttaacgact aatcccgaat  2160
acttgaagaa taaacagagt gatttagata aggtcgtgga ttttaagaac tggcagatcg  2220
caacaggacg taagttccgc tctttaaaac tttggttaat tctgcgttcc tacggggtag  2280
ttaacctgca aagtcatatc cgtagtgatg tagcgatggg gaagatgttt gaggaatggg  2340
tccgttccga tagccgcttt gaaatcgtcg tgccacgtaa tttttcgctt gtatgctttc  2400
gcttgaaacc ggatgtatct agtttacatg tcgaggaggt caacaagaag ttgttggata  2460
tgcttaactc caccggtcgc gtatatatga cgcatacaat tgttggcgga atctatatgt  2520
tacgtttggc tgtaggtagc agcttgacag aggaacatca cgtgcgccgc gtttgggact  2580
tgatccagaa gcttacggac gacctgctta aagaggcgtg a                      2621

SEQ ID NO: 38           moltype = DNA  length = 1503
FEATURE                 Location/Qualifiers
source                  1..1503
                        mol_type = genomic DNA
                        organism = Catharanthus roseus
SEQUENCE: 38
atgggttcta ttgactcgac gaatgtggcc atgtctaatt ctcctgttgg cgagtttaag  60
ccccttgaag cagaagagtt ccgtaaacag gcacaccgca tggtggattt tattgcggat  120
tattacaaga acgtagaaac atacccggtc ctttccgagg ttgaacccgg ctatctgcgc  180
aaacgtattc ccgaaaccgc accatacctg ccggagccac ttgatgatat tatgaaggat  240
attcaaaagg acattatccc cggaatgacg aactggatgt ccccgaactt ttacgccttc  300
ttcccggcca cagttagctc agcagctttc ttgggggaaa tgctttcaac ggcccttaac  360
agcgtaggat ttacctgggt cagttccccg gcagcgactg aattagagat gatcgttatg  420
gattggcttg cgcaaatttt gaaacttcca aaaagcttta tgttctccgg aaccgggggt  480
ggtgtcatcc aaaacactac gtcagagtcg atcttgtgca ctattatcgc ggcccgtgaa  540
cgcgccttgg aaaaattggg ccctgattca attggtaagc ttgtctgcta tgggtccgat  600
caaacgcaca caatgtttcc gaaaacctgt aagttagcag gaatttatcc gaataatatc  660
cgccttatcc ctaccacggt agaaaccgac tttggcatct caccgcaggt acttcgcaag  720
atggtcgaag acgacgtcgc tgcggggtac gttcccttat ttttgtgtgc caccttggga  780
acgacatcaa ctacggcaac agatcctgta gattcgctgt ccgaaatcgc aaacgagttt  840
ggtatctgga ttcatgtcga cgccgcatat gctggatcgg cttgcatctg cccagaattt  900
cgtcactacc ttgatggcat cgaacgtgtg gattccttat cgctgtctcc ccacaaatgg  960
cttttagcat atctggattg cacgtgcttg tgggtaaaac aacctcacct gctgcttcgc  1020
gctttaacga ctaatcccga atacttgaag aataaacaga gtgatttaga taaggtcgtg  1080
gattttaaga actggcagat cgcaacagga cgtaagttcc gctctttaaa actttggtta  1140
attctgcgtt cctacggggt agttaacctg caaagtcata tccgtagtga tgtagcgatg  1200
gggaagatgt ttgaggaatg ggtccgttcc gatagccgct ttgaaatcgt cgtgccacgt  1260
aatttttcgc ttgtatgctt tcgcttgaaa ccggatgtat ctagtttaca tgtcgaggag  1320
gtcaacaaga agttgttgga tatgcttaac tccaccggtc gcgtatatat gacgcataca  1380
attgttggcg gaatctatat gttacgtttg gctgtaggta gcagcttgac agaggaacat  1440
cacgtgcgcc gcgtttggga cttgatccag aagcttacgg acgacctgct taaagaggcg  1500
tga                                                                1503

SEQ ID NO: 39           moltype = DNA  length = 5377
FEATURE                 Location/Qualifiers
source                  1..5377
                        mol_type = other DNA
                        organism = synthetic construct
SEQUENCE: 39
ctctagaaat aattttgttt aactttaaga aggagatata catatgaatt atcagaacga  60
cgatttacgc atcaaagaaa tcaaagagtt acttcctcct gtcgcattgc tggaaaaatt  120
ccccgctact gaaaatgccg cgaatacggt cgcccatgcc cgaaaagcga tccataagat  180
cctgaaaggt aatgatgatc gcctgttggt ggtgattggc ccatgctcaa ttcatgatcc  240
tgtcgcggct aaagagtatg ccactcgctt gctgacgctg cgtgaagagc tgcaagatga  300
gctggaaatc gtgatgcgcg tctattttga aaagccgcgt actacggtgg gctggaaagg  360
gctgattaac gatccgcata tggataacag cttccagatc aacgacggtc tgcgtattgc  420
ccgcaaattg ctgctcgata ttaacgacag cggtctgcca gcggcgggtg aattcctgga  480
tatgatcacc ctacaatatc tcgctgacct gatgagctgg ggcgcaattg gcgcacgtac  540
caccgaatcg caggtgcacc gcgaactggc gtctggtctt tcttgtccgg taggtttcaa  600
aaatggcact gatggtacga ttaaagtggc tatcgatgcc attaatgccg ccggtgcgcc  660
gcactgcttc ctgtccgtaa cgaaatgggg gcattcggcg attgtgaata ccagcggtaa  720
cggcgattgc catatcattc tgcgcggcgg taaagagcct aactacagcg cgaagcacgt  780
tgctgaagtg aaagaagggc tgaacaaagc aggcctgcca gcgcaggtga tgatcgattt  840
cagccatgct aactcgtcaa aacaattcaa aaagcagatg gatgtttgta ctgacgtttg  900
ccagcagatt gccggtggcg aaaaggccat tattggcgtg atggtggaaa gccatctggt  960
ggaaggcaat cagagcctcg agagcgggga accgctggcc tacggtaaga gcatcaccga  1020
tgcctgcatt ggctgggatg ataccgatgc tctgttacgt caactggcga gtgcagtaaa  1080
agcgcgtcgc gggtaatact taagaaggag atatacatat gctgttattc gagactgtgc  1140
```

-continued

```
gtgaaatggg tcatgagcaa gtccttttct gtcatagcaa gaatcccgag atcaaggcaa  1200
ttatcgcaat ccacgatacc accttaggac cggctatggg cgcaactcgt atcttacctt  1260
atattaatga ggaggctgcc ctgaaagatg cattacgtct gtcccgcgga atgacttaca  1320
aagcagcctg cgccaatatt cccgccgggg gcggcaaagc cgtcatcatc gctaaccccg  1380
aaaacaagac cgatgacctg ttacgcgcat acggccgttt cgtggacagc ttgaacggcc  1440
gtttcatcac cgggcaggac gttaacatta cgcccgacga cgttcgcact atttcgcagg  1500
agactaagta cgtggtaggc gtctcagaaa agtcgggagg gccggcacct atcacctctc  1560
tgggagtatt tttaggcatc aaagccgctg tagagtcgcg ttggcagtct aaacgcctgg  1620
atggcatgaa agtggcggtg caaggacttg ggaacgtagg aaaaaaatctt tgtcgccatc  1680
tgcatgaaca cgatgtacaa ctttttgtgt ctgatgtcga tccaatcaag gccgaggaag  1740
taaaacgctt attcggggcg actgttgtcg aaccgactga aatctattct ttagatgttg  1800
atattttgc accgtgtgca cttgggggta ttttgaatag ccataccatc ccgttcttac  1860
aagcctcaat catcgcagga gcagcgaata accagctgga gaacgagcaa cttcattcgc  1920
agatgcttgc gaaaaagggt attctttact caccagacta cgttatcaat gcaggaggac  1980
ttatcaatgt ttataacgaa atgatcggat atgacgagga aaaagcattc aaacaagttc  2040
ataacatcta cgatacgtta ttagcgattt tcgaaattgc aaaagaacaa ggtgtaacca  2100
ccaacgacgc ggcccgtcgt ttagcagagg atcgtatcaa caactccaaa cgctcaaaga  2160
gtaaagcgat tgcggcgtga aatgtaagaa ggagatatac atatgcgtac accctactgt  2220
gtcgccgatt atcttttaga tcgtctgacg gactgcgggg ccgatcacct gtttggcgta  2280
ccgggcgatt acaacttgca gtttctggac cacgtcattg actcaccaga tatctgctgg  2340
gtagggtgtg cgaacgagct taacgcgagc tacgctgctg acggatatgc gcgttgtaaa  2400
ggctttgctg cacttcttac taccttcggg gtcggtgagt tatcggcgat gaacggtatc  2460
gcaggctcgt acgctgagca cgtcccggta ttacacattg tgggagctcc gggtaccgca  2520
gctcaacagc gcggagaact gttacaccac acgctgggcg acggagaatt ccgccacttt  2580
taccatatgt ccgagccaat tactgtagcc caggctgtac ttacagagca aaatgcctgt  2640
tacgagatcg accgtgtttt gaccacgatg cttcgcgagc gccgtcccgg gtatttgatg  2700
ctgccagccg atgttgccaa aaaagctgcg acgcccccag tgaatgccct gacgcataaa  2760
caagctcatg ccgattccgc ctgtttaaag gcttttcgcg atgcagctga aaataaatta  2820
gccatgtcga aacgcaccgc cttgttggcg gactttctgg tcctgcgcca tggccttaaa  2880
cacgcccttc agaaatgggt caaagaagtc ccgatggccc acgctacgat gcttatgggt  2940
aaggggattt ttgatgaacg tcaagcggga ttttatggaa cttattccgg ttcggcgagt  3000
acgggggcgg taaaggaagc gattgaggga gccgacacag ttctttgcgt ggggacacgt  3060
ttcaccgata cactgaccgc tggattcaca caccaactta ctccggcaca aacgattgag  3120
gtgcaacccc atgcggctcg cgtgggggat gtatggttta cgggcattcc aatgaatcaa  3180
gccattgaga ctcttgtcga gctgtgcaaa cagcacgtcc acgcaggact gatgagttcg  3240
agctctgggg cgattccttt tccacaacca gatggtagtt taactcaaga aaacttctgg  3300
cgcacattgc aaaccttat ccgcccaggt gatatcatct tagcagacca gggtacttca  3360
gcctttggag caattgacct gcgcttacca gcagacgtga actttattgt gcagccgctg  3420
tgggggtcta ttggttatac tttagctgcg gccttcggag cgcagacagc gtgtccaaac  3480
cgtcgtgtga tcgtattgac aggagatgga gcagcgcagt tgaccattca ggagttaggc  3540
tcgatgttac gcgataagca gcaccccatt atcctggtcc tgaacaatga ggggtataca  3600
gttgaacgcg ccattcatgg tgcggaacaa cgctacaatg acatcgcttt atggaattgg  3660
acgcacatcc cccaagcctt atcgttagat ccccaatcgg aatgttggcg tgtgtctgaa  3720
gcagagcaac tggctgatgt tctggaaaaa gttgctcatc atgaacgcct gtcgttgatc  3780
gaggtaatgt tgcccaaggc cgatatccct ccgttactgg gagccttgac caaggcttta  3840
gaagcctgca acaacgctta aaggttaaga aggagatata catatgccca ccttgaactt  3900
ggacttaccc aacggtatta agagcacgat tcaggcagac cttttcatca ataataagtt  3960
tgtgccggcg cttgatggga aaacgttcgc aactattaat ccgtctacgg ggaaagagat  4020
cggacaggtg gcagaggctt cggcgaagga tgtggatctt gcagttaagg ccgcgcgtga  4080
ggcgtttgaa actacttggg gggaaaacac gccaggtgat gctcgtggcc gtttactgat  4140
taagcttgct gagttggtgg aagcgaatat tgatgagtta gcggcaattg aatcactgga  4200
caatgggaaa gcgttctcta ttgctaagtc attcgacgta gctgctgtgg ccgcaaactt  4260
acgttactac ggcggttggg ctgataaaaa ccacggtaaa gtcatggagg tagacacaaa  4320
gcgcctgaac tatacccgcc acgagccgat cggggtttgc ggacaaatca ttccgtggaa  4380
tttcccgctt ttgatgtttg catggaagct gggtcccgct ttagccacag ggaacacaat  4440
tgtgttaaag actgccgagc agactccctt aagtgctatc aagatgtgtg aattaatcgt  4500
agaagccggc tttccgcccg gagtagttaa tgtgatctcg ggattcggac cggtggcggg  4560
ggccgcgatc tcgcaacaca tggacatcga taagattgcc tttacaggat cgacattggt  4620
tggccgcaac attatgaagg cagctgcgtc gactaactta aaaaaggtta cacttgagtt  4680
aggaggaaaa tccccgaata tcattttcaa agatgccgac cttgaccaag ctgttcgctg  4740
gagcgccttc ggtatcatgt ttaaccacgg acaatgctgc tgcgctggat cgcgcgtata  4800
tgtggaagaa tccatctatg acgccttcat ggaaaaaatg actgcgcatt gtaaggcgct  4860
tcaagttgga gatcctttca gcgcgaacac cttccaagga ccacaagtct cgcagttaca  4920
atacgaccgt atcatggaat acatcgaatc agggaaaaaa gatgcaaatc ttgctttagg  4980
cggcgttcgc aaagggaatg aggggtattt cattgagcca actattttta cagacgtgcc  5040
gcacgacgcg aagattgcca aagaggagat cttcggtcca gtggttgttg tgtcgaaatt  5100
taaggacgaa aaagatctga tccgtatcgc aaatgattct atttatggtt tagctgcggc  5160
agtcttttcc cgcgacatca gccgcgcgat cgagacagca cacaaactga aagcaggcac  5220
ggtctgggtc aactgctata atcagcttat tccgcaggtg ccattcggag ggtataaggc  5280
ttccggtatc ggccgtgagt tgggggaata tgccttgtct aattacacaa atatcaaggc  5340
cgtccacgtt aacctttctc aaccggcgcc catttga                           5377
```

```
SEQ ID NO: 40          moltype = DNA  length = 1080
FEATURE                Location/Qualifiers
source                 1..1080
                       mol_type = other DNA
                       organism = synthetic construct
SEQUENCE: 40
taagaaggag atatacatat gctgttattc gagactgtgc gtgaaatggg tcatgagcaa  60
```

```
gtccttttct gtcatagcaa gaatcccgag atcaaggcaa ttatcgcaat ccacgatacc  120
accttaggac cggctatggg cgcaactcgt atcttacctt atattaatga ggaggctgcc  180
ctgaaagatg cattacgtct gtcccgcgga atgacttaca aagcagcctg cgccaatatt  240
cccgccgggg gcggcaaagc cgtcatcatc gctaaccccg aaaacaagac cgatgacctg  300
ttacgcgcat acggccgttt cgtggacagc ttgaacggcc gtttcatcac cgggcaggac  360
gttaacatta cgcccgacga cgttcgcact atttcgcagg agactaagta cgtggtaggc  420
gtctcagaaa agtcgggagg gccggcacct atcacctctc tgggagtatt tttaggcatc  480
aaagccgctg tagagtcgcg ttggcagtct aaacgcctgg atggcatgaa agtggcggtg  540
caaggacttg ggaacgtagg aaaaaatctt tgtcgccatc tgcatgaaca cgatgtacaa  600
ctttttgtgt ctgatgtcga tccaatcaag gccgaggaag taaaacgctt attcggggcg  660
actgttgtcg aaccgactga aatctattct ttagatgttg atatttttgc accgtgtgca  720
cttgggggta ttttgaatag ccataccatc ccgttcttac aagcctcaat catcgcagga  780
gcagcgaata accagctgga gaacgagcaa cttcattcgc agatgcttgc gaaaaagggt  840
attctttact caccagacta cgttatcaat gcaggaggac ttatcaatgt ttataacgaa  900
atgatcggat atgacgagga aaaagcattc aaacaagttc ataacatcta cgatacgtta  960
ttagcgattt tcgaaattgc aaaagaacaa ggtgtaacca ccaacgacgc ggcccgtcgt  1020
ttagcagagg atcgtatcaa caactccaaa cgctcaaaga gtaaagcgat tgcggcgtga  1080
```

```
SEQ ID NO: 41          moltype = DNA  length = 1674
FEATURE                Location/Qualifiers
source                 1..1674
                       mol_type = other DNA
                       organism = synthetic construct
SEQUENCE: 41
gaaggagata tacatatgcg tacaccctac tgtgtcgccg attatctttt agatcgtctg  60
acggactgcg gggccgatca cctgtttggc gtaccgggcg attacaactt gcagtttctg  120
gaccacgtca ttgactcacc agatatctgc tgggtagggt gtgcgaacga gcttaacgcg  180
agctacgctg ctgacggata tgcgcgttgt aaaggctttg ctgcacttct tactaccttc  240
ggggtcggtg agttatcggc gatgaacggt atcgcaggct cgtacgctga gcacgtcccg  300
gtattacaca ttgtgggagc tccgggtacc gcagctcaac agcgcggaga actgttacac  360
cacacgctgg gcgacggaga attccgccac ttttaccata tgtccgagcc aattactgta  420
gcccaggctg tacttacaga gcaaaatgcc tgttacgaga tcgaccgtgt tttgaccacg  480
atgcttcgcg agcgccgtcc cgggtatttg atgctgccag ccgatgttgc caaaaaagct  540
gcgacgcccc cagtgaatgc cctgacgcat aaacaagctc atgccgattc cgcctgttta  600
aaggcttttc gcgatgcagc tgaaaataaa ttagccatgt cgaaacgcac cgccttgttg  660
gcggactttc tggtcctgcg ccatggcctt aaacacgccc ttcagaaatg ggtcaaagaa  720
gtcccgatgg cccacgctac gatgcttatg ggtaagggga tttttgatga acgtcaagcg  780
ggattttatg gaacttattc cggttcggcg agtacggggg cggtaaagga agcgattgag  840
ggagccgaca cagttctttg cgtggggaca cgtttcaccg atacactgac cgctggattc  900
acacaccaac ttactccggc acaaacgatt gaggtgcaac cccatgcggc tcgcgtgggg  960
gatgtatggt ttacgggcat tccaatgaat caagccattg agactcttgt cgagctgtgc  1020
aaacagcacg tccacgcagg actgatgagt tcgagctctg ggcgattcc  ttttccacaa  1080
ccagatggta gtttaactca agaaaacttc tggcgcacat tgcaaacctt tatccgccca  1140
ggtgatatca tcttagcaga ccagggtact tcagcctttg gagcaattga cctgcgctta  1200
ccagcagacg tgaactttat tgtgcagccg ctgtgggggt ctattggtta tactttagct  1260
gcggccttcg gagcgcagac agcgtgtcca aaccgtcgtg tgatcgtatt gacaggagat  1320
ggagcagcgc agttgaccat tcaggagtta ggctcgatgt tacgcgataa gcagcacccc  1380
attatcctgg tcctgaacaa tgaggggtat acagttgaac gcgccattca tggtgcggaa  1440
caacgctaca atgacatcgc tttatggaat tggacgcaca tcccccaagc cttatcgtta  1500
gatccccaat cggaatgttg gcgtgtgtct gaagcagagc aactggctga tgttctggaa  1560
aaagttgctc atcatgaacg cctgtcgttg atcgaggtaa tgttgcccaa ggccgatatc  1620
cctccgttac tgggagcctt gaccaaggct ttagaagcct gcaacaacgc ttaa        1674
```

```
SEQ ID NO: 42          moltype = DNA  length = 1509
FEATURE                Location/Qualifiers
source                 1..1509
                       mol_type = other DNA
                       organism = synthetic construct
SEQUENCE: 42
gaaggagata tacatatgcc caccttgaac ttggacttac ccaacggtat taagagcacg  60
attcaggcag accttttcat caataataag tttgtgccgg cgcttgatgg gaaaacgttc  120
gcaactatta atccgtctac ggggaaagag atcggacagg tggcagaggc ttcggcgaag  180
gatgtggatc ttgcagttaa ggccgcgcgt gaggcgtttg aaactacttg gggggaaaac  240
acgccaggtg atgctcgtgg ccgtttactg attaagcttg ctgagttggt ggaagcgaat  300
attgatgagt tagcggcaat tgaatcactg gacaatggga aagcgttctc tattgctaag  360
tcattcgacg tagctgctgt ggccgcaaac ttacgttact acggcggttg ggctgataaa  420
aaccacggta aagtcatgga ggtagacaca aagcgcctga actataccccg ccacgagccg  480
atcggggttt gcggacaaat cattccgtgg aatttcccgc ttttgatgtt tgcatggaag  540
ctgggtcccg ctttagccac agggaacaca attgtgttaa agactgccga gcagactccc  600
ttaagtgcta tcaagatgtg tgaattaatc gtagaagccg gctttccgcc cggagtagtt  660
aatgtgatct cgggattcgg accggtggcg ggggccgcga tctcgcaaca catggacatc  720
gataagattg cctttacagg atcgacattg gttggccgca acattatgaa ggcagctgcg  780
tcgactaact taaaaaaggt tacacttgag ttaggaggaa aatccccgaa tatcattttc  840
aaagatgccg accttgacca agctgttcgc tggagcgcct tcggtatcat gtttaaccac  900
ggacaatgct gctgcgctgg atcgcgcgta tatgtggaag aatccatcta tgacgccttc  960
atggaaaaaa tgactgcgca ttgtaaggcg cttcaagttg gagatccttt cagcgcgaac  1020
accttccaag gaccacaagt ctcgcagtta caatacgacc gtatcatgga atacatcgaa  1080
tcagggaaaa aagatgcaaa tcttgcttta ggcggcgttc gcaaagggaa tgaggggtat  1140
ttcattgagc caactatttt tacagacgtg ccgcacgacg cgaagattgc caaagaggag  1200
```

-continued

```
atcttcggtc cagtggttgt tgtgtcgaaa tttaaggacg aaaaagatct gatccgtatc  1260
gcaaatgatt ctatttatgg tttagctgcg gcagtctttt cccgcgacat cagccgcgcg  1320
atcgagacag cacacaaact gaaagcaggc acggtctggg tcaactgcta taatcagctt  1380
attccgcagg tgccattcgg agggtataag gcttccggta tcggccgtga gttgggggaa  1440
tatgccttgt ctaattacac aaatatcaag gccgtccacg ttaacctttc tcaaccggcg  1500
cccatttga                                                          1509

SEQ ID NO: 43          moltype = DNA  length = 6573
FEATURE                Location/Qualifiers
source                 1..6573
                       mol_type = other DNA
                       organism = synthetic construct
SEQUENCE: 43
ctctagaaat aattttgttt aactttaaga aggagatata catatgcaaa cacaaaaacc  60
gactctcgaa ctgctaacct gcgaaggcgc ttatcgcgac aacccgactg cgctttttca  120
ccagttgtgt ggggatcgtc cggcaacgct gctgctggaa tccgcagata tcgacagcaa  180
agatgattta aaaagcctgc tgctggtaga cagtgcgctg cgcattacag cattaagtga  240
cactgtcaca atccaggcgc tttccggcaa tggagaagcc ctgttgacac tactggataa  300
cgccttgcct gcgggtgtgg aaaatgaaca atcaccaaac tgccgcgtac tgcgcttccc  360
gcctgtcagt ccactgctgg atgaagacgc ccgcttatgc tccctttcgg tttttgacgc  420
tttccgctta ttacagaatc tgttgaatgt accgaaggaa gaacgagaag caatgttctt  480
cggcggcctg ttctcttatg accttgtggc gggatttgaa aatttaccgc aactgtcagc  540
ggaaaatagc tgccctgatt tctgttttta tctcgctgaa acgctgatgg tgattgacca  600
tcagaaaaaa agcactcgta ttcaggccag cctgtttgct ccgaatgaag aagaaaaaca  660
acgtctcact gctcgcctga acgaactacg tcagcaactg accgaagccg cgccgccgct  720
gccggtggtt tccgtgccgc atatgcgttg tgaatgtaac cagagcgatg aagagttcgg  780
tggtgtagtg cgtttgttgc aaaaagcgat tcgcgccgga gaaattttcc aggtggtgcc  840
atctcgccgt ttctctctgc cctgcccgtc accgctggca gcctattacg tgctgaaaaa  900
gagtaatccc agcccgtaca tgttttttat gcaggataat gatttcaccc tgtttggcgc  960
gtcgccggaa agttcgctca agtatgacgc caccagccgc cagattgaga tttacccgat  1020
tgccggaaca cgtccacgcg gtcgtcgtgc cgatggttcg ctggacagag acctcgacag  1080
ccgcatcgaa ctggagatgc gtaccgatca taaagagctt tctgaacatc tgatgctggt  1140
ggatctcgcc cgtaatgacc tggcacgcat ttgcacaccc ggcagccgct acgtcgccga  1200
tctcaccaaa gttgaccgtt actcttacgt gatgcaccta gtctcccgcg ttgttggtga  1260
gctgcgccac gatctcgacg ccctgcacgc ttaccgcgcc tgtatgaata tggggacgtt  1320
aagcggtgca ccgaaagtac gcgctatgca gttaattgcc gaagcagaag gtcgtcgacg  1380
cggcagctac ggcggcgcgg taggttattt taccgcgcat ggcgatctcg acacctgcat  1440
tgtgatccgc tcggcgctgg tggaaaacgg tatcgccacc gtgcaagccg gtgctggcgt  1500
agtccttgat tctgttccgc agtcggaagc cgacgaaact cgtaataaag cccgcgctgt  1560
actgcgcgct attgccaccg cgcatcatgc acaggagacg ttctaatggc tgacattctg  1620
ctgctcgata atatcgactc ttttacgtac aacctggcag atcagttgcg cagcaatggt  1680
cataacgtgg tgatttaccg caaccatatt ccggcgcaga ccttaattga acgcctggcg  1740
acgatgagca atccggtgct gatgctttct cctggccccg gtgtgccgag cgaagccggt  1800
tgtatgccgg aactcctcac ccgcttgcgt ggcaagctgc caattattgg catttgcctc  1860
ggacatcagg cgattgtcga agcttacggg ggctatgtcg gtcaggcggg cgaaattctt  1920
cacggtaaag cgtcgagcat tgaacatgac ggtcaggcga tgtttgccgg attaacaaac  1980
ccgctgccag tggcgcgtta tcactcgctg gttggcagta acattccggc cggtttaacc  2040
atcaacgccc attttaatgg catggtgatg gcggtgcgtc acgatgcaga tcgcgtttgt  2100
ggattccagt tccatccgga atccattctt actacccagg gcgctcgcct gctggaacaa  2160
acgctggcct gggcgcagca gaaactagag ccaaccaaca cgctgcaacc gattctggaa  2220
aaactgtatc aggcacagac gcttagccaa caagaaagcc accagctgtt ttcagcggtg  2280
gtacgtggcg agctgaagcc ggaacaactg gcggcggcgc tggtgagcat gaaaattcgc  2340
ggtgaacacc cgaacgagat cgccggggca gcaaccgcgc tactggaaaa cgccgcgcca  2400
ttcccgcgcc cggattatct gtttgccgat atcgtcggta ctggcggtga cggcagcaac  2460
agcatcaata tttctaccgc cagtgcgttt gtcgccgcgg cctgcgggct gaaagtggcg  2520
aaacacggca accgtagcgt ctccagtaaa tccggctcgt cggatctgct ggcggcgttc  2580
ggtattaatc ttgatatgaa cgccgataaa tcgcgccagg cgctggatga gttaggcgtc  2640
tgtttcctct ttgcgccgaa gtatcacacc ggattccgcc atgcgatgcc ggttcgccag  2700
caactgaaaa cccgcactct gttcaacgtg ctgggaccat tgattaaccc ggcgcatccg  2760
ccgctggcgc taattggtgt ttatagtccg gaactggtgc tgccgattgc cgaaaccttg  2820
cgcgtgctgg ggtatcaacg cgcggcagtg gtgcacagcg gcgggatgga tgaagtttca  2880
ttacacgcgc cgacaatcgt tgccgaacta catgacggcg aaattaagag ctatcaattg  2940
accgctgaag attttggcct gacaccctac caccaggagc aattggcagg cggaacaccg  3000
gaagaaaacc gtgacatttt aacacgcttg ttacaaggta aaggcgacgc cgcccatgaa  3060
gcagccgtcg cggcgaatgt cgccatgtta atgcgcctgc atggccatga agatctgcaa  3120
gccaatgcgc aaaccgttct tgaggtactg cgcagtggtt ccgcttacga cagagtcacc  3180
gcactggcgg cacgagggta aatgatgcaa accgttttag cgaaaatcgt cgcagacaag  3240
gcgatttggg tagaaacccg caaagagcag caaccgctgg ccagttttca gaatgaggtt  3300
cagccgagca cgcgacattt ttatgatgca cttcagggcg cacgcacggc gtttattctg  3360
gagtgtaaaa aagcgtcgcc gtcaaaaggc gtgatccgtg atgatttcga tccggcacgc  3420
attgccgcca tttataaaca ttacgcttcg gcaatttcag tgctgactga tgagaaatat  3480
tttcagggga gctttgattt cctccccatc gtcagccaaa tcgccccgca gccgatttta  3540
tgtaaagact tcattatcga tccttaccag atctatctgg cgcgctatta ccaggccgat  3600
gcctgcttat taatgctttc agtactggat gacgaacaat atcgccagct tgcagccgtc  3660
gcccacagtc tggagatggg tgtgctgacc gaagtcagta atgaagagga actggagcgc  3720
gccattgcat tgggggcaaa ggtcgttggc atcaacaacc gcgatctgcg cgatttgtcg  3780
attgatctca accgtacccg cgagcttgcg ccgaaactgg ggcacaacgt gacggtaatc  3840
agcgaatccg gcatcaatac ttacgctcag gtgcgcgagt taagccactt cgctaacggc  3900
tttctgattg gttcggcgtt gatggcccat gacgatttga acgccgccgt gcgtcgggtg  3960
```

-continued

```
ttgctgggtg agaataaagt atgtggcctg acacgtgggc aagatgctaa agcagcttat  4020
gacgcgggcg cgatttacgg tgggttgatt tttgttgcga catcaccgcg ttgcgtcaac  4080
gttgaacagg cgcaggaagt gatggctgca gcaccgttgc agtatgttgg cgtgttccgc  4140
aatcacgata ttgccgatgt ggcggacaaa gctaaggtgt tatcgctggc ggcagtgcaa  4200
ctgcatggta atgaagatca gctgtatatc gacaatctgc gtgaggctct gccagcacac  4260
gtcgccatct ggaaggcttt aagtgtcggt gaaactcttc ccgcgcgcga ttttcagcac  4320
atcgataaat atgtattcga caacggtcag ggcgggagcg gacaacgttt cgactggtca  4380
ctattaaatg gtcaatcgct tggcaacgtt ctgctggcgg ggggcttagg cgcagataac  4440
tgcgtggaag cggcacaaac cggctgcgcc gggcttgatt ttaattctgc tgtagagtcg  4500
caaccgggta tcaaagacgc acgtcttttg gcctcggttt tccagacgct gcgcgcatat  4560
taaggaaagg aacaatgaca acattactta accccta ttt tggtgagttt ggcggcatgt  4620
acgtgccaca aatcctgatg cctgctctgc gccagctgga agaagctttt gtcagcgcgc  4680
aaaaagatcc tgaatttcag gctcagttca acgacctgct gaaaaactat gccgggcgtc  4740
caaccgcgct gaccaaatgc cagaacatta cagccgggac gaacaccacg ctgtatctga  4800
agcgcgaaga tttgctgcac ggcggcgcgc ataaaactaa ccaggtgctc ggtcaggctt  4860
tactggcgaa gcggatgggt aaaactgaaa ttattgccga aaccggtgcc ggtcagcatg  4920
gcgtggcgtc ggcccttgcc agcgccctgc tcggcctgaa atgccgaatt tatatgggtg  4980
ccaaagacgt tgaacgccag tcgcccaacg ttttccggat gcgcttaatg ggtgcggaag  5040
tgatcccggt acatagcggt tccgcgaccc tgaaagatgc ctgtaatgag gcgctacgcg  5100
actggtccgg cagttatgaa accgcgcact atatgctggg taccgcagct ggcccgcatc  5160
cttacccgac cattgtgcgt gagtttcagc ggatgattgg cgaagaaacg aaagcgcaga  5220
ttctggaaag agaaggtcgc ctgccggatg ccgttatcgc ctgtgttggc ggtggttcga  5280
atgccatcgg tatgtttgca gatttcatca acgaaaccga cgtcggcctg attggtgtgg  5340
agcctggcgg ccacggtatc gaaactggcg agcacggcgc accgttaaaa catggtcgcg  5400
tgggcatcta tttcggtatg aaagcgccga tgatgcaaac cgaagacggg caaattgaag  5460
agtcttactc catttctgcc gggctggatt tcccgtccgt cggcccgcaa catgcgtatc  5520
tcaacagcac tggacgcgct gattacgtgt ctattaccga cgatgaagcc ctggaagcct  5580
ttaaaacgct ttgcctgcat gaagggatca tcccggcgct ggaatcctcc cacgccctgg  5640
cccatgcgct gaaaatgatg cgcgaaaatc cggaaaaaga gcagctactg gtggttaacc  5700
tttccggtcg cggcgataaa gacatcttca ccgttcacga tattttgaaa gcacgagggg  5760
aaatctgatg gaacgctacg aatctctgtt tgcccagttg aaggagcgca aagaaggcgc  5820
attcgttcct ttcgtcaccc tcggtgatcc gggcattgag cagtcgttga aaattatcga  5880
tacgctaatt gaagccggtg ctgacgcgct ggagttaggc atccccttct ccgacccact  5940
ggcggatggc ccgacgattc aaaacgccac actgcgtgct tttgcggcgg gagtaacccc  6000
ggcgcagtgc tttgagatgc tggcactcat tcgccagaag cacccgacca ttcccatcgg  6060
ccttttgatg tatgccaacc tggtgtttaa caaaggcatt gatgagtttt atgccgagtg  6120
cgagaaagtc ggcgtcgatt cggtgctggt tgccgatgtg cccgtggaag agtccgcgcc  6180
cttccgccag gccgcgttgc gtcataatgt cgcacctatc tttatttgcc cgccgaatgc  6240
cgacgatgat ttgctgcgcc agatagcctc ttacggtcgt ggttacacct atttgctgtc  6300
gcgagcgggc gtgaccggcg cagaaaaccg cgccgcgtta cccctcaatc atctggttgc  6360
gaagctgaaa gagtacaacg ctgcgcctcc attgcaggga tttggtattt ccgcccccga  6420
tcaggtaaaa gccgcgattg atgcaggagc tgcgggcgcg atttctggtt cggccatcgt  6480
taaaatcatc gagcaacata ttaatgagcc agagaaaatg ctggcggcac tgaaagcttt  6540
tgtacaaccg atgaaagcgg cgacgcgcag tta                                 6573
```

SEQ ID NO: 44 moltype = DNA length = 1562
FEATURE Location/Qualifiers
source 1..1562
mol_type = other DNA
organism = synthetic construct
SEQUENCE: 44

```
atgcaaacac aaaaaccgac tctcgaactg ctaacctgcg aaggcgctta tcgcgacaac  60
ccgactgcgc tttttcacca gttgtgtggg gatcgtccgg caacgctgct gctggaatcc  120
gcagatatcg acagcaaaga tgatttaaaa agcctgctgc tggtagacag tgcgctgcgc  180
attacagcat taagtgacac tgtcacaatc caggcgcttt ccggcaatgg agaagccctg  240
ttgacactac tggataacgc cttgcctgcg ggtgtggaaa atgaacaatc accaaactgc  300
cgcgtactgc gcttcccgcc tgtcagtcca ctgctggatg aagacgcccg cttatgctcc  360
ctttcggttt ttgacgcttt ccgcttatta cagaatctgt tgaatgtacc gaaggaagaa  420
cgagaagcaa tgttcttcgg cggcctgttc tcttatgacc ttgtggcggg atttgaaaat  480
ttaccgcaac tgtcagcgga aaatagctgc cctgatttct gtttttatct cgctgaaacg  540
ctgatggtga ttgaccatca gaaaaaaagc actcgtattc aggccagcct gtttgctccg  600
aatgaagaag aaaaacaacg tctcactgct cgcctgaacg aactacgtca gcaactgacc  660
gaagccgcgc cgccgctgcc ggtggtttcc gtgccgcata tgcgttgtga atgtaaccag  720
agcgatgaag agttcggtgg tgtagtgcgt ttgttgcaaa aagcgattcg cgccggagaa  780
attttccagg tggtgccatc tcgccgtttc tctctgccct gcccgtcacc gctggcagcc  840
tattacgtgc tgaaaaagag taatcccagc ccgtacatgt tttttatgca ggataatgat  900
ttcaccctgt ttggcgcgtc gccggaaagt tcgctcaagt atgacgccac cagccgccag  960
attgagattt acccgattgc cggaacacgt ccacgcggtc gtcgtgccga tggttcgctg  1020
gacagagacc tcgacagccg catcgaactg gagatgcgta ccgatcataa agagctttct  1080
gaacatctga tgctggtgga tctcgcccgt aatgacctgg cacgcatttg cacacccggc  1140
agccgctacg tcgccgatct caccaaagtt gaccgttact cttacgtgat gcacctagtc  1200
tcccgcgttg ttggtgagct gcgccacgat ctcgacgccc tgcacgctta ccgcgcctgt  1260
atgaatatgg ggacgttaag cggtgcaccg aaagtacgcg ctatgcagtt aattgccgaa  1320
gcagaaggtc gtcgacgcgg cagctacggc ggcgcggtag gttattttac cgcgcatggc  1380
gatctcgaca cctgcattgt gatccgctcg gcgctggtgg aaaacggtat cgccaccgtg  1440
caagccggtg ctggcgtagt ccttgattct gttccgcagt cggaagccga cgaaactcgt  1500
aataaagccc gcgctgtact gcgcgctatt gccaccgcgc atcatgcaca ggagacgttc  1560
ta                                                                  1562
```

```
SEQ ID NO: 45          moltype = DNA  length = 1596
FEATURE                Location/Qualifiers
source                 1..1596
                       mol_type = other DNA
                       organism = synthetic construct
SEQUENCE: 45
atggctgaca ttctgctgct cgataatatc gactctttta cgtacaacct ggcagatcag  60
ttgcgcagca atggtcataa cgtggtgatt taccgcaacc atattccggc gcagacctta  120
attgaacgcc tggcgacgat gagcaatccg gtgctgatgc tttctcctgg ccccggtgtg  180
ccgagcgaag ccggttgtat gccggaactc ctcacccgct tgcgtggcaa gctgccaatt  240
attggcattt gcctcggaca tcaggcgatt gtcgaagctt acgggggcta tgtcggtcag  300
gcgggcgaaa ttcttcacgg taaagcgtcg agcattgaac atgacggtca ggcgatgttt  360
gccggattaa caaacccgct gccagtggcg cgttatcact cgctggttgg cagtaacatt  420
ccggccggtt taaccatcaa cgcccatttt aatggcatgg tgatggcggt gcgtcacgat  480
gcagatcgcg tttgtggatt ccagttccat ccggaatcca ttcttactac ccagggcgct  540
cgcctgctgg aacaaacgct ggcctgggcg cagcagaaac tagagccaac caacacgctg  600
caaccgattc tggaaaaact gtatcaggca cagacgctta gccaacaaga aagccaccag  660
ctgttttcag cggtggtacg tggcgagctg aagccggaac aactggcggc ggcgctggtg  720
agcatgaaaa ttcgcggtga acacccgaac gagatcgccg gggcagcaac cgcgctactg  780
gaaaacgccg cgccattccc gcgcccggat tatctgtttg ccgatatcgt cggtactggc  840
ggtgacggca gcaacagcat caatatttct accgccagtg cgtttgtcgc cgcggcctgc  900
gggctgaaag tggcgaaaca cggcaaccgt agcgtctcca gtaaatccgg ctcgtcggat  960
ctgctggcgg cgttcggtat taatcttgat atgaacgccg ataaatcgcg ccaggcgctg  1020
gatgagttag gcgtctgttt cctctttgcg ccgaagtatc acaccggatt ccgccatgcg  1080
atgccggttc gccagcaact gaaaacccgc actctgttca acgtgctggg accattgatt  1140
aacccggcgc atccgccgct ggcgctaatt ggtgtttata gtccggaact ggtgctgccg  1200
attgccgaaa ccttgcgcgt gctggggtat caacgcgcgg cagtggtgca cagcggcggg  1260
atggatgaag tttcattaca cgcgccgaca atcgttgccg aactacatga cggcgaaatt  1320
aagagctatc aattgaccgc tgaagatttt ggcctgacac cctaccacca ggagcaattg  1380
gcaggcggaa caccggaaga aaaccgtgac attttaacac gcttgttaca aggtaaaggc  1440
gacgccgccc atgaagcagc cgtcgcggcg aatgtcgcca tgttaatgcg cctgcatggc  1500
catgaagatc tgcaagccaa tgcgcaaacc gttcttgagg tactgcgcag tggttccgct  1560
tacgacagag tcaccgcact ggcggcacga gggtaa                           1596

SEQ ID NO: 46          moltype = DNA  length = 355
FEATURE                Location/Qualifiers
source                 1..355
                       mol_type = other DNA
                       organism = synthetic construct
SEQUENCE: 46
tgtggctttt atgaaaatca cacagtgatc acaaatttta aacagagcac aaaatgctgc  60
ctcgaaatga gggcgggaaa ataaggttat cagccttgtt ttctccctca ttacttgaag  120
gatatgaagc taaaaccctt ttttataaag catttgtccg aattcggaca taatcaaaaa  180
agcttaatta agatcaattt gatctacatc tctttaacca acaatatgta agatctcaac  240
tatcgcatcc gtggattaat tcaattataa cttctctcta acgctgtgta tcgtaacggt  300
aacactgtag aggggagcac attgatgcga attcattaaa gaggagaaag gtacc       355

SEQ ID NO: 47          moltype = DNA  length = 228
FEATURE                Location/Qualifiers
source                 1..228
                       mol_type = other DNA
                       organism = synthetic construct
SEQUENCE: 47
ttccgaaaat tcctggcgag cagataaata agaattgttc ttatcaatat atctaactca  60
ttgaatcttt attagttttg tttttcacgc ttgttaccac tattagtgtg ataggaacag  120
ccagaatagc ggaacacata gccggtgcta tacttaatct cgttaattac tgggacataa  180
catcaagagg atatgaaatt cgaattcatt aaagaggaga aaggtacc               228

SEQ ID NO: 48          moltype = DNA  length = 334
FEATURE                Location/Qualifiers
source                 1..334
                       mol_type = other DNA
                       organism = synthetic construct
SEQUENCE: 48
gcttagatca ggtgattgcc ctttgtttat gagggtgttg taatccatgt cgttgttgca  60
tttgtaaggg caacacctca gcctgcaggc aggcactgaa gataccaaag ggtagttcag  120
attacacggt cacctggaaa gggggccatt ttactttttta tcgccgctgg cggtgcaaag  180
ttcacaaagt tgtcttacga aggttgtaag gtaaaactta tcgatttgat aatggaaacg  240
cattagccga atcggcaaaa attggttacc ttacatctca tcgaaaacac ggaggaagta  300
tagatgcgaa ttcattaaag aggagaaagg tacc                              334

SEQ ID NO: 49          moltype = DNA  length = 134
FEATURE                Location/Qualifiers
source                 1..134
                       mol_type = other DNA
                       organism = synthetic construct
SEQUENCE: 49
ctcgagttca ttatccatcc tccatcgcca cgatagttca tggcgatagg tagaatagca  60
atgaacgatt atccctatca agcattctga ctgataattg ctcacacgaa ttcattaaag  120
```

-continued

```
aggagaaagg tacc                                                    134

SEQ ID NO: 50          moltype = DNA  length = 36
FEATURE                Location/Qualifiers
source                 1..36
                       mol_type = other DNA
                       organism = synthetic construct
SEQUENCE: 50
atatcgtcgc agcccacagc aacacgtttc ctgagg                            36

SEQ ID NO: 51          moltype = DNA  length = 47
FEATURE                Location/Qualifiers
source                 1..47
                       mol_type = other DNA
                       organism = synthetic construct
SEQUENCE: 51
aagaatttaa cggagggcaa aaaaaaccga cgcacactgg cgtcggc                47

SEQ ID NO: 52          moltype = DNA  length = 1359
FEATURE                Location/Qualifiers
source                 1..1359
                       mol_type = other DNA
                       organism = synthetic construct
SEQUENCE: 52
atgcaaaccg ttttagcgaa aatcgtcgca gacaaggcga tttgggtaga aacccgcaaa  60
gagcagcaac cgctggccag ttttcagaat gaggttcagc cgagcacgcg acatttttat  120
gatgcacttc agggcgcacg cacggcgttt attctggagt gtaaaaaagc gtcgccgtca  180
aaaggcgtga tccgtgatga tttcgatccg gcacgcattg ccgccattta taaacattac  240
gcttcggcaa tttcagtgct gactgatgag aaatattttc aggggagctt tgatttcctc  300
cccatcgtca gccaaatcgc cccgcagccg attttatgta aagacttcat tatcgatcct  360
taccagatct atctggcgcg ctattaccag gccgatgcct gcttattaat gctttcagta  420
ctggatgacg aacaatatcg ccagcttgca gccgtcgccc acagtctgga gatgggtgtg  480
ctgaccgaag tcagtaatga agaggaactg gagcgcgcca ttgcattggg ggcaaaggtc  540
gttggcatca acaaccgcga tctgcgcgat ttgtcgattg atctcaaccg tacccgcgag  600
cttgcgccga aactggggca caacgtgacg gtaatcagcg aatccggcat caatacttac  660
gctcaggtgc gcgagttaag ccacttcgct aacggctttc tgattggttc ggcgttgatg  720
gcccatgacg atttgaacgc cgccgtgcgt cgggtgttgc tgggtgagaa taaagtatgt  780
ggcctgacac gtgggcaaga tgctaaagca gcttatgacg cgggcgcgat ttacggtggg  840
ttgatttttg ttgcgacatc accgcgttgc gtcaacgttg aacaggcgca ggaagtgatg  900
gctgcagcac cgttgcagta tgttggcgtg ttccgcaatc acgatattgc cgatgtggcg  960
gacaaagcta aggtgttatc gctggcggca gtgcaactgc atggtaatga agatcagctg  1020
tatatcgaca atctgcgtga ggctctgcca gcacacgtcg ccatctggaa ggctttaagt  1080
gtcggtgaaa ctcttcccgc gcgcgatttt cagcacatcg ataaatatgt attcgacaac  1140
ggtcagggcg ggagcggaca acgtttcgac tggtcactat taaatggtca atcgcttggc  1200
aacgttctgc tggcgggggg cttaggcgca gataactgcg tggaagcggc acaaaccggc  1260
tgcgccgggc ttgattttaa ttctgctgta gagtcgcaac cgggtatcaa agacgcacgt  1320
cttttggcct cggttttcca gacgctgcgc gcatattaa                         1359

SEQ ID NO: 53          moltype = DNA  length = 1193
FEATURE                Location/Qualifiers
source                 1..1193
                       mol_type = other DNA
                       organism = synthetic construct
SEQUENCE: 53
atgacaacat tacttaaccc ctattttggt gagtttggcg gcatgtacgt gccacaaatc  60
ctgatgcctg ctctgcgcca gctggaagaa gcttttgtca gcgcgcaaaa agatcctgaa  120
tttcaggctc agttcaacga cctgctgaaa aactatgccg ggcgtccaac cgcgctgacc  180
aaatgccaga acattacagc cgggacgaac accacgctgt atctgaagcg cgaagatttg  240
ctgcacggcg gcgcgcataa aactaaccag gtgctcggtc aggctttact ggcgaagcgg  300
atgggtaaaa ctgaaattat tgccgaaacc ggtgccggtc agcatggcgt ggcgtcggcc  360
cttgccagcg ccctgctcgg cctgaaatgc cgaatttata tgggtgccaa agacgttgaa  420
cgccagtcgc ccaacgtttt ccggatgcgc ttaatgggtg cggaagtgat cccggtacat  480
agcggttccg cgaccctgaa agatgcctgt aatgaggcgc tacgcgactg gtccggcagt  540
tatgaaaccg cgcactatat gctgggtacc gcagctggcc cgcatcctta cccgaccatt  600
gtgcgtgagt ttcagcggat gattggcgaa gaaacgaaag cgcagattct ggaaagagaa  660
ggtcgcctgc cggatgccgt tatcgcctgt gttggcggtg gttcgaatgc catcggtatg  720
tttgcagatt tcatcaacga aaccgacgtc ggcctgattg gtgtggagcc tggcggccac  780
ggtatcgaaa ctggcgagca cggcgcaccg ttaaaacatg gtcgcgtggg catctatttc  840
ggtatgaaag cgccgatgat gcaaaccgaa gacgggcaaa ttgaagagtc ttactccatt  900
tctgccgggc tggatttccc gtccgtcggc ccgcaacatg cgtatctcaa cagcactgga  960
cgcgctgatt acgtgtctat taccgacgat gaagccctgg aagcctttaa aacgctttgc  1020
ctgcatgaag ggatcatccc ggcgctggaa tcctcccacg ccctggccca tgcgctgaaa  1080
atgatgcgcg aaaatccgga aaaagagcag ctactggtgg ttaacctttc cggtcgcggc  1140
gataaagaca tcttcaccgt tcacgatatt ttgaaagcac gaggggaaat ctg         1193

SEQ ID NO: 54          moltype = DNA  length = 807
FEATURE                Location/Qualifiers
source                 1..807
                       mol_type = other DNA
```

```
                         organism = synthetic construct
SEQUENCE: 54
atggaacgct acgaatctct gtttgcccag ttgaaggagc gcaaagaagg cgcattcgtt  60
cctttcgtca ccctcggtga tccgggcatt gagcagtcgt tgaaaattat cgatacgcta  120
attgaagccg gtgctgacgc gctggagtta ggcatcccct tctccgaccc actggcggat  180
ggcccgacga ttcaaaacgc cacactgcgt gcttttgcgg cgggagtaac cccggcgcag  240
tgctttgaga tgctggcact cattcgccag aagcacccga ccattcccat cggccttttg  300
atgtatgcca acctggtgtt taacaaaggc attgatgagt tttatgccga gtgcgagaaa  360
gtcggcgtcg attcggtgct ggttgccgat gtgcccgtgg aagagtccgc gcccttccgc  420
caggccgcgt tgcgtcataa tgtcgcacct atctttattt gcccgccgaa tgccgacgat  480
gatttgctgc gccagatagc ctcttacggt cgtggttaca cctatttgct gtcgcgagcg  540
ggcgtgaccg gcgcagaaaa ccgcgccgcg ttacccctca atcatctggt tgcgaagctg  600
aaagagtaca acgctgcgcc tccattgcag ggatttggta tttccgcccc ggatcaggta  660
aaagccgcga ttgatgcagg agctgcgggc gcgatttctg gttcggccat cgttaaaatc  720
atcgagcaac atattaatga gccagagaaa atgctggcgg cactgaaagc ttttgtacaa  780
ccgatgaaag cggcgacgcg cagttaa                                    807

SEQ ID NO: 55            moltype = DNA  length = 6574
FEATURE                  Location/Qualifiers
source                   1..6574
                         mol_type = other DNA
                         organism = synthetic construct
SEQUENCE: 55
ctctagaaat aattttgttt aactttaaga aggagatata catatgcaaa cacaaaaacc  60
gactctcgaa ctgctaacct gcgaaggcgc ttatcgcgac aacccgactg cgctttttca  120
ccagttgtgt ggggatcgtc cggcaacgct gctgctggaa ttcgcagata tcgacagcaa  180
agatgattta aaaagcctgc tgctggtaga cagtgcgctg cgcattacag cattaagtga  240
cactgtcaca atccaggcgc tttccggcaa tggagaagcc ctgttgacac tactggataa  300
cgccttgcct gcgggtgtgg aaaatgaaca atcaccaaac tgccgcgtac tgcgcttccc  360
gcctgtcagt ccactgctgg atgaagacgc ccgcttatgc tccctttcgg tttttgacgc  420
tttccgctta ttacagaatc tgttgaatgt accgaaggaa gaacgagaag caatgttctt  480
cggcggcctg ttctcttatg accttgtggc gggatttgaa aatttaccgc aactgtcagc  540
ggaaaatagc tgccctgatt tctgttttta tctcgctgaa acgctgatgg tgattgacca  600
tcagaaaaaa agcactcgta ttcaggccag cctgtttgct ccgaatgaag aagaaaaaca  660
acgtctcact gctcgcctga acgaactacg tcagcaactg accgaagccg cgccgccgct  720
gccggtggtt tccgtgccgc atatgcgttg tgaatgtaac cagagcgatg aagagttcgg  780
tggtgtagtg cgtttgttgc aaaaagcgat tcgcgccgga gaaattttcc aggtggtgcc  840
atctcgccgt ttctctctgc cctgcccgtc accgctggca gcctattacg tgctgaaaaa  900
gagtaatccc agcccgtaca tgttttttat gcaggataat gatttcaccc tgtttggcgc  960
gtcgccggaa agttcgctca agtatgacgc caccagccgc cagattgaga tttacccgat  1020
tgccggaaca cgtccacgcg gtcgtcgtgc cgatggttcg ctggacagag acctcgacag  1080
ccgcatcgaa ctggagatgc gtaccgatca taaagagctt tctgaacatc tgatgctggt  1140
ggatctcgcc cgtaatgacc tggcacgcat ttgcacaccc ggcagccgct acgtcgccga  1200
tctcaccaaa gttgaccgtt actcttacgt gatgcaccta gtctcccgcg ttgttggtga  1260
gctgcgccac gatctcgacg ccctgcacgc ttaccgcgcc tgtatgaata tggggacgtt  1320
aagcggtgca ccgaaagtac gcgctatgca gttaattgcc gaagcagaag gtcgtcgacg  1380
cggcagctac ggcggcgcgg taggttattt taccgcgcat ggcgatctcg acacctgcat  1440
tgtgatccgc tcggcgctgg tggaaaacgg tatcgccacc gtgcaagccg gtgctggcgt  1500
agtccttgat tctgttccgc agtcggaagc cgacgaaact cgtaataaag cccgcgctgt  1560
actgcgcgct attgccaccg cgcatcatgc acaggagacg ttctaatggc tgacattctg  1620
ctgctcgata atatcgactc ttttacgtac aacctggcag atcagttgcg cagcaatggt  1680
cataacgtgg tgatttaccg caaccatatt ccggcgcaga ccttaattga acgcctggcg  1740
acgatgagca atccggtgct gatgctttct cctggccccg gtgtgccgag cgaagccggt  1800
tgtatgccgg aactcctcac ccgcttgcgt ggcaagctgc caattattgg catttgcctc  1860
ggacatcagg cgattgtcga agcttacggg ggctatgtcg gtcaggcggg cgaaattctt  1920
cacggtaaag cgtcgagcat tgaacatgac ggtcaggcga tgtttgccgg attaacaaac  1980
ccgctgccag tggcgcgtta tcactcgctg gttggcagta acattccggc cggtttaacc  2040
atcaacgccc attttaatgg catggtgatg gcggtgcgtc acgatgcaga tcgcgtttgt  2100
ggattccagt tccatccgga atccattctt actacccagg gcgctcgcct gctggaacaa  2160
acgctggcct gggcgcagca gaaactagag ccaaccaaca cgctgcaacc gattctggaa  2220
aaactgtatc aggcacagac gcttagccaa caagaaagcc accagctgtt ttcagcggtg  2280
gtacgtggcg agctgaagcc ggaacaactg gcggcggcgc tggtgagcat gaaaattcgc  2340
ggtgaacacc cgaacgagat cgccggggca gcaaccgcgc tactggaaaa cgccgcgcca  2400
ttcccgcgcc cggattatct gtttgccgat atcgtcggta ctggcggtga cggcagcaac  2460
agcatcaata tttctaccgc cagtgcgttt gtcgccgcgg cctgcgggct gaaagtggcg  2520
aaacacggca accgtagcgt ctccagtaaa tccggctcgt cggatctgct ggcggcgttc  2580
ggtattaatc ttgatatgaa cgccgataaa tcgcgccagg cgctggatga gttaggcgtc  2640
tgtttcctct ttgcgccgaa gtatcacacc ggattccgcc atgcgatgcc ggttcgccag  2700
caactgaaaa cccgcactct gttcaacgtg ctgggaccat tgattaaccc ggcgcatccg  2760
ccgctggcgc taattggtgt ttatagtccg gaactggtgc tgccgattgc cgaaaccttg  2820
cgcgtgctgg ggtatcaacg cgcggcagtg gtgcacagcg gcgggatgga tgaagtttca  2880
ttacacgcgc cgacaatcgt tgccgaacta catgacggcg aaattaagag ctatcaattg  2940
accgctgaag attttggcct gacaccctac caccaggagc aattggcagg cggaacaccg  3000
gaagaaaacc gtgacatttt aacacgcttg ttacaaggta aaggcgacgc cgcccatgaa  3060
gcagccgtcg cggcgaatgt cgccatgtta atgcgcctgc atggccatga agatctgcaa  3120
gccaatgcgc aaaccgttct tgaggtactg cgcagtggtt ccgcttacga cagagtcacc  3180
gcactggcgg cacgagggta aatgatgcaa accgttttag cgaaaatcgt cgcagacaag  3240
gcgatttggg tagaaacccg caaagagcag caaccgctgg ccagttttca gaatgaggtt  3300
cagccgagca cgcgacattt ttatgatgca cttcagggcg cacgcacggc gtttattctg  3360
```

-continued

```
gagtgtaaaa aagcgtcgcc gtcaaaaggc gtgatccgtg atgatttcga tccggcacgc  3420
attgccgcca tttataaaca ttacgcttcg gcaatttcag tgctgactga tgagaaatat  3480
tttcagggga gctttgattt cctccccatc gtcagccaaa tcgccccgca gccgatttta  3540
tgtaaagact tcattatcga tccttaccag atctatctgg cgcgctatta ccaggccgat  3600
gcctgcttat taatgctttc agtactggat gacgaacaat atcgccagct tgcagccgtc  3660
gcccacagtc tggagatggg tgtgctgacc gaagtcagta atgaagagga actggagcgc  3720
gccattgcat tgggggcaaa ggtcgttggc atcaacaacc gcgatctgcg cgatttgtcg  3780
attgatctca accgtacccg cgagcttgcg ccgaaactgg ggcacaacgt gacggtaatc  3840
agcgaatccg gcatcaatac ttacgctcag gtgcgcgagt taagccactt cgctaacggc  3900
tttctgattg gttcggcgtt gatggcccat gacgatttga acgccgccgt gcgtcgggtg  3960
ttgctgggtg agaataaagt atgtggcctg acacgtgggc aagatgctaa agcagcttat  4020
gacgcgggcg cgatttacgg tgggttgatt tttgttgcga catcaccgcg ttgcgtcaac  4080
gttgaacagg cgcaggaagt gatggctgca gcaccgttgc agtatgttgg cgtgttccgc  4140
aatcacgata ttgccgatgt ggcggacaaa gctaaggtgt tatcgctggc ggcagtgcaa  4200
ctgcatggta atgaagatca gctgtatatc gacaatctgc gtgaggctct gccagcacac  4260
gtcgccatct ggaaggcttt aagtgtcggt gaaactcttc ccgcgcgcga ttttcagcac  4320
atcgataaat atgtattcga caacggtcag ggcgggagcg gacaacgttt cgactggtca  4380
ctattaaatg gtcaatcgct tggcaacgtt ctgctggcgg ggggcttagg cgcagataac  4440
tgcgtggaag cggcacaaac cggctgcgcc gggcttgatt ttaattctgc tgtagagtcg  4500
caaccgggta tcaaagacgc acgtcttttg gcctcggttt tccagacgct gcgcgcatat  4560
taaggaaagg aacaatgaca acattactta acccctattt tggtgagttt ggcggcatgt  4620
acgtgccaca aatcctgatg cctgctctgc gccagctgga agaagctttt gtcagcgcgc  4680
aaaaagatcc tgaatttcag gctcagttca acgacctgct gaaaaactat gccgggcgtc  4740
caaccgcgct gaccaaatgc cagaacatta cagccgggac gaacaccacg ctgtatctga  4800
agcgcgaaga tttgctgcac ggcggcgcgc ataaaactaa ccaggtgctc ggtcaggctt  4860
tactggcgaa gcggatgggt aaaactgaaa ttattgccga aaccggtgcc ggtcagcatg  4920
gcgtggcgtc ggcccttgcc agcgccctgc tcggcctgaa atgccgaatt tatatgggtg  4980
ccaaagacgt tgaacgccag tcgcccaacg ttttccggat gcgcttaatg ggtgcggaag  5040
tgatcccggt acatagcggt tccgcgaccc tgaaagatgc ctgtaatgag gcgctacgcg  5100
actggtccgg cagttatgaa accgcgcact atatgctggg taccgcagct ggcccgcatc  5160
cttacccgac cattgtgcgt gagtttcagc ggatgattgg cgaagaaacg aaagcgcaga  5220
ttctggaaag agaaggtcgc ctgccggatg ccgttatcgc ctgtgttggc ggtggttcga  5280
atgccatcgg tatgtttgca gatttcatca acgaaaccga cgtcggcctg attggtgtgg  5340
agcctggcgg ccacggtatc gaaactggcg agcacggcgc accgttaaaa catggtcgcg  5400
tgggcatcta tttcggtatg aaagcgccga tgatgcaaac cgaagacggg caaattgaag  5460
agtcttactc catttctgcc gggctggatt tcccgtccgt cggcccgcaa catgcgtatc  5520
tcaacagcac tggacgcgct gattacgtgt ctattaccga cgatgaagcc ctggaagcct  5580
ttaaaacgct ttgcctgcat gaagggatca tcccggcgct ggaatcctcc cacgccctgg  5640
cccatgcgct gaaaatgatg cgcgaaaatc cggaaaaaga gcagctactg gtggttaacc  5700
tttccggtcg cggcgataaa gacatcttca ccgttcacga tattttgaaa gcacgagggg  5760
aaatctgatg gaacgctacg aatctctgtt tgcccagttg aaggagcgca aagaaggcgc  5820
attcgttcct ttcgtcaccc tcggtgatcc gggcattgag cagtcgttga aaattatcga  5880
tacgctaatt gaagccggtg ctgacgcgct ggagttaggc atccccttct ccgacccact  5940
ggcggatggc ccgacgattc aaaacgccac actgcgtgct tttgcggcgg gagtaacccc  6000
ggcgcagtgc tttgagatgc tggcactcat tcgccagaag cacccgacca ttcccatcgg  6060
ccttttgatg tatgccaacc tggtgtttaa caaaggcatt gatgagtttt atgccgagtg  6120
cgagaaagtc ggcgtcgatt cggtgctggt tgccgatgtg cccgtggaag agtccgcgcc  6180
cttccgccag gccgcgttgc gtcataatgt cgcacctatc tttatttgcc cgccgaatgc  6240
cgacgatgat ttgctgcgcc agatagcctc ttacggtcgt ggttacacct atttgctgtc  6300
gcgagcgggc gtgaccggcg cagaaaaccg cgccgcgtta cccctcaatc atctggttgc  6360
gaagctgaaa gagtacaacg ctgcgcctcc attgcaggga tttggtattt ccgccccgga  6420
tcaggtaaaa gccgcgattg atgcaggagc tgcgggcgcg atttctggtt cggccatcgt  6480
taaaatcatc gagcaacata ttaatgagcc agagaaaatg ctggcggcac tgaaagcttt  6540
tgtacaaccg atgaaagcgg cgacgcgcag ttaa                             6574
```

```
SEQ ID NO: 56          moltype = DNA  length = 1562
FEATURE                Location/Qualifiers
source                 1..1562
                       mol_type = other DNA
                       organism = synthetic construct
SEQUENCE: 56
atgcaaacac aaaaaccgac tctcgaactg ctaacctgcg aaggcgctta tcgcgacaac  60
ccgactgcgc tttttcacca gttgtgtggg gatcgtccgg caacgctgct gctggaattc  120
gcagatatcg acagcaaaga tgatttaaaa agcctgctgc tggtagacag tgcgctgcgc  180
attacagcat taagtgacac tgtcacaatc caggcgcttt ccggcaatgg agaagccctg  240
ttgacactac tggataacgc cttgcctgcg ggtgtggaaa atgaacaatc accaaactgc  300
cgcgtactgc gcttcccgcc tgtcagtcca ctgctggatg aagacgcccg cttatgctcc  360
ctttcggttt ttgacgcttt ccgcttatta cagaatctgt tgaatgtacc gaaggaagaa  420
cgagaagcaa tgttcttcgg cggcctgttc tcttatgacc ttgtggcggg atttgaaaat  480
ttaccgcaac tgtcagcgga aaatagctgc cctgatttct gtttttatct cgctgaaacg  540
ctgatggtga ttgaccatca gaaaaaaagc actcgtattc aggccagcct gtttgctccg  600
aatgaagaag aaaaacaacg tctcactgct cgcctgaacg aactacgtca gcaactgacc  660
gaagccgcgc cgccgctgcc ggtggtttcc gtgccgcata tgcgttgtga atgtaaccag  720
agcgatgaag agttcggtgg tgtagtgcgt ttgttgcaaa aagcgattcg cgccggagaa  780
attttccagg tggtgccatc tcgccgtttc tctctgccct gcccgtcacc gctggcagcc  840
tattacgtgc tgaaaaagag taatcccagc ccgtacatgt tttttatgca ggataatgat  900
ttcaccctgt ttggcgcgtc gccggaaagt tcgctcaagt atgacgccac cagccgccag  960
attgagattt acccgattgc cggaacacgt ccacgcggtc gtcgtgccga tggttcgctg  1020
gacagagacc tcgacagccg catcgaactg gagatgcgta ccgatcataa agagctttct  1080
```

-continued

```
gaacatctga tgctggtgga tctcgcccgt aatgacctgg cacgcatttg cacacccggc  1140
agccgctacg tcgccgatct caccaaagtt gaccgttact cttacgtgat gcacctagtc  1200
tcccgcgttg ttggtgagct gcgccacgat ctcgacgccc tgcacgctta ccgcgcctgt  1260
atgaatatgg ggacgttaag cggtgcaccg aaagtacgcg ctatgcagtt aattgccgaa  1320
gcagaaggtc gtcgacgcgg cagctacggc ggcgcggtag gttattttac cgcgcatggc  1380
gatctcgaca cctgcattgt gatccgctcg gcgctggtgg aaaacggtat cgccaccgtg  1440
caagccggtg ctggcgtagt ccttgattct gttccgcagt cggaagccga cgaaactcgt  1500
aataaagccc gcgctgtact gcgcgctatt gccaccgcgc atcatgcaca ggagacgttc  1560
ta                                                                 1562

SEQ ID NO: 57          moltype = DNA  length = 7615
FEATURE                Location/Qualifiers
source                 1..7615
                       mol_type = other DNA
                       organism = synthetic construct
SEQUENCE: 57
ctctagaaat aattttgttt aactttaaga aggagatata catatgaatt atcagaacga  60
cgatttacgc atcaaagaaa tcaaagagtt acttcctcct gtcgcattgc tggaaaaatt  120
ccccgctact gaaaatgccg cgaatacggt cgcccatgcc cgaaaagcga tccataagat  180
cctgaaaggt aatgatgatc gcctgttggt ggtgattggc ccatgctcaa ttcatgatcc  240
tgtcgcggct aaagagtatg ccactcgctt gctgacgctg cgtgaagagc tgcaagatga  300
gctggaaatc gtgatgcgcg tctattttga aaagccgcgt actacggtgg gctggaaagg  360
gctgattaac gatccgcata tggataacag cttccagatc aacgacggtc tgcgtattgc  420
ccgcaaattg ctgctcgata ttaacgacag cggtctgcca gcggcgggtg aattcctgga  480
tatgatcacc ctacaatatc tcgctgacct gatgagctgg ggcgcaattg gcgcacgtac  540
caccgaatcg caggtgcacc gcgaactggc gtctggtctt tcttgtccgg taggtttcaa  600
aaatggcact gatggtacga ttaaagtggc tatcgatgcc attaatgccg ccggtgcgcc  660
gcactgcttc ctgtccgtaa cgaaatgggg gcattcggcg attgtgaata ccagcggtaa  720
cggcgattgc catatcattc tgcgcggcgg taaagagcct aactacagcg cgaagcacgt  780
tgctgaagtg aaagaagggc tgaacaaagc aggcctgcca gcgcaggtga tgatcgattt  840
cagccatgct aactcgtcaa aacaattcaa aaagcagatg gatgtttgta ctgacgtttg  900
ccagcagatt gccggtggcg aaaaggccat tattggcgtg atggtggaaa gccatctggt  960
ggaaggcaat cagagcctcg agagcgggga accgctggcc tacggtaaga gcatcaccga  1020
tgcctgcatt ggctgggatg ataccgatgc tctgttacgt caactggcga gtgcagtaaa  1080
agcgcgtcgc gggtaatact taagaaggag atatacatat gctgttattc gagactgtgc  1140
gtgaaatggg tcatgagcaa gtccttttct gtcatagcaa gaatcccgag atcaaggcaa  1200
ttatcgcaat ccacgatacc accttaggac cggctatggg cgcaactcgt atcttacctt  1260
atattaatga ggaggctgcc ctgaaagatg cattacgtct gtcccgcgga atgacttaca  1320
aagcagcctg cgccaatatt cccgccgggg gcggcaaagc cgtcatcatc gctaaccccg  1380
aaaacaagac cgatgacctg ttacgcgcat acggccgttt cgtggacagc ttgaacggcc  1440
gtttcatcac cgggcaggac gttaacatta cgcccgacga cgttcgcact atttcgcagg  1500
agactaagta cgtggtaggc gtctcagaaa agtcgggagg gccggcacct atcacctctc  1560
tgggagtatt tttaggcatc aaagccgctg tagagtcgcg ttggcagtct aaacgcctgg  1620
atggcatgaa agtggcggtg caaggacttg ggaacgtagg aaaaaatctt tgtcgccatc  1680
tgcatgaaca cgatgtacaa ctttttgtgt ctgatgtcga tccaatcaag gccgaggaag  1740
taaaacgctt attcggggcg actgttgtcg aaccgactga aatctattct ttagatgttg  1800
atatttttgc accgtgtgca cttgggggta ttttgaatag ccataccatc ccgttcttac  1860
aagcctcaat catcgcagga gcagcgaata accagctgga gaacgagcaa cttcattcgc  1920
agatgcttgc gaaaaagggt attctttact caccagacta cgttatcaat gcaggaggac  1980
ttatcaatgt ttataacgaa atgatcggat atgacgagga aaaagcattc aaacaagttc  2040
ataacatcta cgatacgtta ttagcgattt tcgaaattgc aaaagaacaa ggtgtaacca  2100
ccaacgacgc ggcccgtcgt ttagcagagg atcgtatcaa caactccaaa cgctcaaaga  2160
gtaaagcgat tgcggcgtga aatgtaagaa ggagatatac atatggaaaa caacaccaat  2220
atgttctctg gagtgaaggt gatcgaactg gccaacttta tcgctgctcc ggcggcaggt  2280
cgcttctttg ctgatggggg agcagaagta attaagatcg aatctccagc aggcgacccg  2340
ctgcgctaca cggccccatc agaaggacgc ccgctttctc aagaggaaaa cacaacgtat  2400
gatttggaaa acgcgaataa gaaagcaatt gttctgaact taaaatcgga aaaaggaaag  2460
aaaattcttc acgagatgct tgctgaggca gacatcttgt taacaaattg gcgcacgaaa  2520
gcgttagtca aacaggggtt agattacgaa acactgaaag agaagtatcc aaaattggta  2580
tttgcacaga ttacaggata cggggagaaa ggacccgaca aagacctgcc tggtttcgac  2640
tacacggcgt tttcgcccg cggaggagtc tccggtacat tatatgaaaa aggaactgtc  2700
cctcctaatg tggtaccggg tctgggtgac caccaggcag gaatgttctt agctgccggt  2760
atggctggtg cgttgtataa ggccaaaacc accggacaag gcgacaaagt caccgttagt  2820
ctgatgcata gcgcaatgta cggcctggga atcatgattc aggcagccca gtacaaggac  2880
catgggctgg tgtacccgat caaccgtaat gaaacgccta atcctttcat cgtttcatac  2940
aagtccaaag atgattactt tgtccaagtt tgcatgcctc cctatgatgt gttttatgat  3000
cgctttatga cggccttagg acgtgaagac ttggtaggtg acgaacgcta caataagatc  3060
gagaacttga aggatggtcg cgcaaaagaa gtctattcca tcatcgaaca acaaatggta  3120
acgaagacga aggacgaatg ggacaagatt tttcgtgatg cagacattcc attcgctatt  3180
gcccaaacgt gggaagatct tttagaagac gagcaggcat gggccaacga ctacctgtat  3240
aaaatgaagt atcccacagg caacgaacgt gccctggtac gtttacctgt gttcttcaaa  3300
gaagctggac ttcctgaata caaccagtcg ccacagattg ctgagaatac cgtggaagtg  3360
ttaaaggaga tgggatatac cgagcaagaa attgaggagc ttgagaaaga caaagacatc  3420
atggtacgta aagagaaatg aaggttaaga aggagatata catatgtcag accgcaacaa  3480
agaagtgaaa gaaaagaagg ctaaacacta tctgcgcgag atcacagcta aacactacaa  3540
ggaagcgtta gaggctaaag agcgtgggga gaaagtgggt tggtgtgcct ctaacttccc  3600
ccaagagatt gcaaccacgt tgggtgtaaa ggttgtttat cccgaaaacc acgccgccgc  3660
cgtagcggca cgtggcaatg ggcaaaatat gtgcgaacac gcggaggcta tgggattcag  3720
taatgatgtg tgtggatatg cacgtgtaaa tttagccgta atggacatcg gccatagtga  3780
```

-continued

```
agatcaacct attccaatgc ctgatttcgt tctgtgctgt aataatatct gcaatcagat  3840
gattaaatgg tatgaacaca ttgcaaaaac gttggatatt cctatgatcc ttatcgatat  3900
tccatataat actgagaaca cggtgtctca ggaccgcatt aagtacatcc gcgcccagtt  3960
cgatgacgct atcaagcaac tggaagaaat cactggcaaa aagtgggacg agaataaatt  4020
cgaagaagtg atgaagattt cgcaagaatc ggccaagcaa tggttacgcg ccgcgagcta  4080
cgcgaaatac aaaccatcac cgttttcggg ctttgacctt tttaatcaca tggctgtagc  4140
cgtttgtgct cgcggcaccc aggaagccgc cgatgcattc aaaatgttag cagatgaata  4200
tgaagagaac gttaagacag gaaagtctac ttatcgcggc gaggagaagc agcgtatctt  4260
gttcgagggc atcgcttgtt ggccttatct gcgccacaag ttgacgaaac tgagtgaata  4320
tggaatgaac gtcacagcta cggtgtacgc cgaagctttt ggggttattt acgaaaacat  4380
ggatgaactg atggccgctt acaataaagt gcctaactca atctccttcg agaacgcgct  4440
gaagatgcgt cttaatgccg ttacaagcac caatacagaa ggggctgtta tccacattaa  4500
tcgcagttgt aagctgtggt caggattctt atacgaactg gcccgtcgtt tggaaaagga  4560
gacggggatc cctgttgttt cgttcgacgg agatcaagcg gatccccgta acttctccga  4620
ggctcaatat gacactcgca tccaaggttt aaatgaggtg atggtcgcga aaaaagaagc  4680
agagtgagct ttaagaagga gatatacata tgtcgaatag tgacaagttt tttaacgact  4740
tcaaggacat tgtggaaaac ccaaagaagt atatcatgaa gcatatggaa caaacgggac  4800
aaaaagccat cggttgcatg cctttataca ccccagaaga gcttgtctta gcggcgggta  4860
tgtttcctgt tggagtatgg ggctcgaata ctgagttgtc aaaagccaag acctactttc  4920
cggcttttat ctgttctatc ttgcaaacta ctttagaaaa cgcattgaat ggggagtatg  4980
acatgctgtc tggtatgatg atcacaaact attgcgattc gctgaaatgt atgggacaaa  5040
acttcaaact tacagtggaa aatatcgaat tcatcccggt tacggttcca caaaaccgca  5100
agatggaggc gggtaaagaa tttctgaaat cccagtataa aatgaatatc gaacaactgg  5160
aaaaaatctc agggaataag atcactgacg agagcttgga gaaggctatt gaaatttacg  5220
atgagcaccg taaagtcatg aacgatttct ctatgcttgc gtccaagtac cctggtatca  5280
ttacgccaac gaaacgtaac tacgtgatga agtcagcgta ttatatggac aagaaagaac  5340
atacagagaa ggtacgtcag ttgatggatg aaatcaaggc cattgagcct aaaccattcg  5400
aaggaaaacg cgtgattacc actgggatca ttgcagattc ggaggacctt ttgaaaatct  5460
tggaggagaa taacattgct atcgtgggag atgatattgc acacgagtct cgccaatacc  5520
gcactttgac ccggaggcc aacacaccta tggaccgtct tgctgaacaa tttgcgaacc  5580
gcgagtgttc gacgttgtat gaccctgaaa aaaaacgtgg acagtatatt gtcgagatgg  5640
caaaagagcg taaggccgac ggaatcatct tcttcatgac aaaattctgc gatcccgaag  5700
aatacgatta ccctcagatg aaaaaagact tcgaagaagc cggtattccc cacgttctga  5760
ttgagacaga catgcaaatg aagaactacg aacaagctcg caccgctatt caagcatttt  5820
cagaaaccct ttgacgctta agaaggagat atacatatgc gtgctgtctt aatcgagaag  5880
tcagatgaca cccagagtgt ttcagttacg gagttggctg aagaccaatt acccgaaggt  5940
gacgtccttg tggatgtcgc gtacagcaca ttgaattaca aggatgctct tgcgattact  6000
ggaaaagcac ccgttgtacg ccgttttcct atggtccccg gaattgactt tactgggact  6060
gtcgcacaga gttcccatgc tgatttcaag ccaggcgacc gcgtaattct gaacggatgg  6120
ggagttggtg agaaacactg gggcggtctt gcagaacgcg cacgcgtacg tggggactgg  6180
cttgtcccgt tgccagcccc cttagacttg cgccaggctg caatgattgg cactgcgggg  6240
tacacagcta tgctgtgcgt gcttgccctt gagcgccatg gagtcgtacc tgggaacggc  6300
gagattgtcg tctcaggcgc agcaggaggg gtaggttctg tagcaaccac actgttagca  6360
gccaaaggct acgaagtggc cgccgtgacc gggcgcgcaa gcgaggccga atatttacgc  6420
ggattaggcg ccgcgtcggt cattgatcgc aatgaattaa cggggaaggt gcgtccatta  6480
gggcaggaac gctgggcagg aggaatcgat gtagcaggat caaccgtact tgctaatatg  6540
ttgagcatga tgaaataccg tggcgtggtg gcggcctgtg gcctggcggc tggaatggac  6600
ttgcccgcgt ctgtcgcccc ttttattctg cgtggtatga ctttggcagg ggtagattca  6660
gtcatgtgcc ccaaaactga tcgtctggct gcttgggcac gcctggcatc cgacctggac  6720
cctgcaaagc tggaagagat gacaactgaa ttaccgttct ctgaggtgat tgaaacggct  6780
ccgaagttct tggatggaac agtgcgtggg cgtattgtca ttccggtaac accttgatac  6840
ttaagaagga gatatacata tgaaaatctt ggcatactgc gtccgcccag acgaggtaga  6900
ctcctttaag aaatttagtg aaaagtacgg gcatacagtt gatcttattc cagactcttt  6960
tggacctaat gtcgctcatt tggcgaaggg ttacgatggg atttctattc tgggcaacga  7020
cacgtgtaac cgtgaggcac tggagaagat caaggattgc gggatcaaat atctggcaac  7080
ccgtacagcc ggagtgaaca acattgactt cgatgcagca aaggagttcg gtattaacgt  7140
ggctaatgtt cccgcatatt cccccaactc ggtcagcgaa tttaccattg gattggcatt  7200
aagtctgacg cgtaagattc catttgccct gaaacgcgtg gaactgaaca attttgcgct  7260
tggcggcctt attggtgtgg aattgcgtaa cttaacttta ggagtcatcg gtactggtcg  7320
catcggattg aaagtgattg agggcttctc tgggtttgga atgaaaaaaa tgatcggtta  7380
tgacattttt gaaaatgaag aagcaaagaa gtacatcgaa tacaaatcat tagacgaagt  7440
ttttaaagag gctgatatta tcactctgca tgcgcctctg acagacgaca actatcatat  7500
gattggtaaa gaatccattg ctaaaatgaa ggatggggta tttattatca acgcagcgcg  7560
tggagcctta atcgatagtg aggccctgat tgaagggtta aaatcgggga agatt        7615
```

```
SEQ ID NO: 58           moltype = DNA  length = 1239
FEATURE                 Location/Qualifiers
source                  1..1239
                        mol_type = other DNA
                        organism = synthetic construct
SEQUENCE: 58
atggaaaaca acaccaatat gttctctgga gtgaaggtga tcgaactggc caactttatc  60
gctgctccgg cggcaggtcg cttctttgct gatgggggag cagaagtaat taagatcgaa  120
tctccagcag gcgacccgct gcgctacacg gccccatcag aaggacgccc gctttctcaa  180
gaggaaaaca caacgtatga tttggaaaac gcgaataaga aagcaattgt tctgaactta  240
aaatcggaaa aaggaaagaa aattcttcac gagatgcttg ctgaggcaga catcttgtta  300
acaaattggc gcacgaaagc gttagtcaaa caggggttag attacgaaac actgaaagag  360
aagtatccaa aattggtatt tgcacagatt acaggatacg gggagaaagg acccgacaaa  420
gacctgcctg gtttcgacta cacggcgttt ttcgcccgcg gaggagtctc cggtacatta  480
```

-continued

```
tatgaaaaag gaactgtccc tcctaatgtg gtaccgggtc tgggtgacca ccaggcagga  540
atgttcttag ctgccggtat ggctggtgcg ttgtataagg ccaaaaccac cggacaaggc  600
gacaaagtca ccgttagtct gatgcatagc gcaatgtacg gcctgggaat catgattcag  660
gcagcccagt acaaggacca tgggctggtg tacccgatca accgtaatga aacgcctaat  720
cctttcatcg tttcatacaa gtccaaagat gattactttg tccaagtttg catgcctccc  780
tatgatgtgt tttatgatcg ctttatgacg gccttaggac gtgaagactt ggtaggtgac  840
gaacgctaca ataagatcga gaacttgaag gatggtcgcg caaaagaagt ctattccatc  900
atcgaacaac aaatggtaac gaagacgaag gacgaatggg acaagatttt tcgtgatgca  960
gacattccat tcgctattgc ccaaacgtgg gaagatcttt tagaagacga gcaggcatgg  1020
gccaacgact acctgtataa aatgaagtat cccacaggca acgaacgtgc cctggtacgt  1080
ttacctgtgt tcttcaaaga agctggactt cctgaataca accagtcgcc acagattgct  1140
gagaataccg tggaagtgtt aaaggagatg ggatataccg agcaagaaat tgaggagctt  1200
gagaaagaca aagacatcat ggtacgtaaa gagaaatga                        1239
```

```
SEQ ID NO: 59           moltype = DNA  length = 1224
FEATURE                 Location/Qualifiers
source                  1..1224
                        mol_type = other DNA
                        organism = synthetic construct
SEQUENCE: 59
atgtcagacc gcaacaaaga agtgaaagaa aagaaggcta aacactatct gcgcgagatc  60
acagctaaac actacaagga agcgttagag gctaaagagc gtggggagaa agtgggttgg  120
tgtgcctcta acttccccca agagattgca accacgttgg gtgtaaaggt tgtttatccc  180
gaaaaccacg ccgccgccgt agcggcacgt ggcaatgggc aaaatatgtg cgaacacgcg  240
gaggctatgg gattcagtaa tgatgtgtgt ggatatgcac gtgtaaattt agccgtaatg  300
gacatcggcc atagtgaaga tcaacctatt ccaatgcctg atttcgttct gtgctgtaat  360
aatatctgca atcagatgat taaatggtat gaacacattg caaaaacgtt ggatattcct  420
atgatcctta tcgatattcc atataatact gagaacacgg tgtctcagga ccgcattaag  480
tacatccgcg cccagttcga tgacgctatc aagcaactgg aagaaatcac tggcaaaaag  540
tgggacgaga ataaattcga agaagtgatg aagatttcgc aagaatcggc caagcaatgg  600
ttacgcgccg cgagctacgc gaaatacaaa ccatcaccgt tttcgggctt tgaccttttt  660
aatcacatgg ctgtagccgt ttgtgctcgc ggcacccagg aagccgccga tgcattcaaa  720
atgttagcag atgaatatga agagaacgtt aagacaggaa agtctactta tcgcggcgag  780
gagaagcagc gtatcttgtt cgagggcatc gcttgttggc cttatctgcg ccacaagttg  840
acgaaactga gtgaatatgg aatgaacgtc acagctacgg tgtacgccga agcttttggg  900
gttatttacg aaaacatgga tgaactgatg gccgcttaca ataaagtgcc taactcaatc  960
tccttcgaga acgcgctgaa gatgcgtctt aatgccgtta caagcaccaa tacagaaggg  1020
gctgttatcc acattaatcg cagttgtaag ctgtggtcag gattcttata cgaactggcc  1080
cgtcgtttgg aaaaggagac ggggatccct gttgtttcgt tcgacggaga tcaagcggat  1140
ccccgtaact tctccgaggc tcaatatgac actcgcatcc aaggtttaaa tgaggtgatg  1200
gtcgcgaaaa aagaagcaga gtga                                        1224
```

```
SEQ ID NO: 60           moltype = DNA  length = 1124
FEATURE                 Location/Qualifiers
source                  1..1124
                        mol_type = other DNA
                        organism = synthetic construct
SEQUENCE: 60
atgtcgaata gtgacaagtt ttttaacgac ttcaaggaca ttgtggaaaa cccaaagaag  60
tatatcatga agcatatgga acaaacggga caaaaagcca tcggttgcat gcctttatac  120
accccagaag agcttgtctt agcggcgggt atgtttcctg ttggagtatg ggctcgaat  180
actgagttgt caaaagccaa gacctacttt ccggctttta tctgttctat cttgcaaact  240
actttagaaa acgcattgaa tggggagtat gacatgctgt ctggtatgat gatcacaaac  300
tattgcgatt cgctgaaatg tatgggacaa aacttcaaac ttacagtgga aaatatcgaa  360
ttcatcccgg ttacggttcc acaaaaccgc aagatggagg cgggtaaaga atttctgaaa  420
tcccagtata aaatgaatat cgaacaactg gaaaaaatct cagggaataa gatcactgac  480
gagagcttgg agaaggctat tgaaatttac gatgagcacc gtaaagtcat gaacgatttc  540
tctatgcttg cgtccaagta ccctggtatc attacgccaa cgaaacgtaa ctacgtgatg  600
aagtcagcgt attatatgga caagaaagaa catacagaga aggtacgtca gttgatggat  660
gaaatcaagg ccattgagcc taaaccattc gaaggaaaac gcgtgattac cactgggatc  720
attgcagatt cggaggacct tttgaaaatc ttggaggaga ataacattgc tatcgtggga  780
gatgatattg cacacgagtc tcgccaatac cgcactttga ccccggaggc caacacacct  840
atggaccgtc ttgctgaaca atttgcgaac cgcgagtgtt cgacgttgta tgaccctgaa  900
aaaaaacgtg gacagtatat tgtcgagatg gcaaaagagc gtaaggccga cggaatcatc  960
ttcttcatga caaaattctg cgatcccgaa gaatacgatt accctcagat gaaaaaagac  1020
ttcgaagaag ccggtattcc ccacgttctg attgagacag acatgcaaat gaagaactac  1080
gaacaagctc gcaccgctat tcaagcattt tcagaaaccc tttg                  1124
```

```
SEQ ID NO: 61           moltype = DNA  length = 981
FEATURE                 Location/Qualifiers
source                  1..981
                        mol_type = other DNA
                        organism = synthetic construct
SEQUENCE: 61
atgcgtgctg tcttaatcga gaagtcagat gacacccaga gtgtttcagt tacggagttg  60
gctgaagacc aattacccga aggtgacgtc cttgtggatg tcgcgtacag cacattgaat  120
tacaaggatg ctcttgcgat tactggaaaa gcacccgttg tacgccgttt tcctatggtc  180
cccggaattg actttactgg gactgtcgca cagagttccc atgctgattt caagccaggc  240
gaccgcgtaa ttctgaacgg atggggagtt ggtgagaaac actggggcgg tcttgcagaa  300
```

```
cgcgcacgcg tacgtgggga ctggcttgtc ccgttgccag ccccettaga cttgcgccag  360
gctgcaatga ttggcactgc ggggtacaca gctatgctgt gcgtgcttgc ccttgagcgc  420
catggagtcg tacctgggaa cggcgagatt gtcgtctcag gcgcagcagg aggggtaggt  480
tctgtagcaa ccacactgtt agcagccaaa ggctacgaag tggccgccgt gaccgggcgc  540
gcaagcgagg ccgaatattt acgcggatta ggcgccgcgt cggtcattga tcgcaatgaa  600
ttaacgggga aggtgcgtcc attagggcag gaacgctggg caggaggaat cgatgtagca  660
ggatcaaccg tacttgctaa tatgttgagc atgatgaaat accgtggcgt ggtggcggcc  720
tgtggcctgg cggctggaat ggacttgccc gcgtctgtcg cccctttat tctgcgtggt  780
atgactttgg caggggtaga ttcagtcatg tgccccaaaa ctgatcgtct ggctgcttgg  840
gcacgcctgg catccgacct ggaccctgca aagctggaag agatgacaac tgaattaccg  900
ttctctgagg tgattgaaac ggctccgaag ttcttggatg gaacagtgcg tgggcgtatt  960
gtcattccgg taacaccttg a                                            981
```

```
SEQ ID NO: 62          moltype = DNA  length = 996
FEATURE                Location/Qualifiers
source                 1..996
                       mol_type = other DNA
                       organism = synthetic construct
SEQUENCE: 62
atgaaaatct tggcatactg cgtccgccca gacgaggtag actcctttaa gaaatttagt  60
gaaaagtacg ggcatacagt tgatcttatt ccagactctt ttggacctaa tgtcgctcat  120
ttggcgaagg gttacgatgg gatttctatt ctgggcaacg acacgtgtaa ccgtgaggca  180
ctggagaaga tcaaggattg cggatcaaa tatctggcaa cccgtacagc cggagtgaac  240
aacattgact tcgatgcagc aaaggagttc ggtattaacg tggctaatgt tcccgcatat  300
tcccccaact cggtcagcga atttaccatt ggattggcat taagtctgac gcgtaagatt  360
ccatttgccc tgaaacgcgt ggaactgaac aattttgcgc ttggcggcct tattggtgtg  420
gaattgcgta acttaacttt aggagtcatc ggtactggtc gcatcggatt gaaagtgatt  480
gagggcttct ctgggtttgg aatgaaaaaa atgatcggtt atgacatttt tgaaaatgaa  540
gaagcaaaga agtacatcga atacaaatca ttagacgaag tttttaaaga ggctgatatt  600
atcactctgc atgcgcctct gacagacgac aactatcata tgattggtaa agaatccatt  660
gctaaaatga aggatggggt atttattatc aacgcagcgc gtggagcctt aatcgatagt  720
gaggccctga ttgaagggtt aaaatcgggg aagattgcgg gcgcggctct ggatagctat  780
gagtatgagc aaggtgtctt tcacaacaat aagatgaatg aaattatgca ggatgatacc  840
ttggaacgtc tgaaatcttt tcccaacgtc gtgatcacgc cgcatttggg tttttatact  900
gatgaggcgg tttccaatat ggtagagatc acactgatga accttcagga attcgagttg  960
aaaggaacct gtaagaacca gcgtgtttgt aaatga                           996
```

```
SEQ ID NO: 63          moltype = DNA  length = 8008
FEATURE                Location/Qualifiers
source                 1..8008
                       mol_type = other DNA
                       organism = synthetic construct
SEQUENCE: 63
ctctagaaat aattttgttt aactttaaga aggagatata catatgaatt atcagaacga  60
cgatttacgc atcaaagaaa tcaaagagtt acttcctcct gtcgcattgc tggaaaaatt  120
ccccgctact gaaaatgccg cgaatacggt cgcccatgcc cgaaaagcga tccataagat  180
cctgaaaggt aatgatgatc gcctgttggt ggtgattggc ccatgctcaa ttcatgatcc  240
tgtcgcggct aaagagtatg ccactcgctt gctgacgctg cgtgaagagc tgcaagatga  300
gctggaaatc gtgatgcgcg tctattttga aaagccgcgt actacggtgg gctggaaagg  360
gctgattaac gatccgcata tggataacag cttccagatc aacgacggtc tgcgtattgc  420
ccgcaaattg ctgctcgata ttaacgacag cggtctgcca gcggcgggtg aattcctgga  480
tatgatcacc ctacaatatc tcgctgacct gatgagctgg ggcgcaattg gcgcacgtac  540
caccgaatcg caggtgcacc gcgaactggc gtctggtctt tcttgtccgg taggtttcaa  600
aaatggcact gatggtacga ttaaagtggc tatcgatgcc attaatgccg ccggtgcgcc  660
gcactgcttc ctgtccgtaa cgaaatgggg gcattcggcg attgtgaata ccagcggtaa  720
cggcgattgc catatcattc tgcgcggcgg taaagagcct aactacagcg cgaagcacgt  780
tgctgaagtg aaagaagggc tgaacaaagc aggcctgcca gcgcaggtga tgatcgattt  840
cagccatgct aactcgtcaa aacaattcaa aaagcagatg gatgtttgta ctgacgtttg  900
ccagcagatt gccggtggcg aaaaggccat tattggcgtg atggtggaaa gccatctggt  960
ggaaggcaat cagagcctcg agagcgggga accgctggcc tacggtaaga gcatcaccga  1020
tgcctgcatt ggctgggatg ataccgatgc tctgttacgt caactggcga gtgcagtaaa  1080
agcgcgtcgc gggtaatact taagaaggag atatacatat gctgttattc gagactgtgc  1140
gtgaaatggg tcatgagcaa gtccttttct gtcatagcaa gaatcccgag atcaaggcaa  1200
ttatcgcaat ccacgatacc accttaggac cggctatggg cgcaactcgt atcttacctt  1260
atattaatga ggaggctgcc ctgaaagatg cattacgtct gtcccgcgga atgacttaca  1320
aagcagcctg cgccaatatt cccgccgggg gcggcaaagc cgtcatcatc gctaaccccg  1380
aaaacaagac cgatgacctg ttacgcgcat acggccgttt cgtggacagc ttgaacggcc  1440
gtttcatcac cgggcaggac gttaacatta cgcccgacga cgttcgcact atttcgcagg  1500
agactaagta cgtggtaggc gtctcagaaa agtcgggagg gccggcacct atcacctctc  1560
tgggagtatt tttaggcatc aaagccgctg tagagtcgcg ttggcagtct aaacgcctgg  1620
atggcatgaa agtggcggtg caaggacttg ggaacgtagg aaaaaatctt tgtcgccatc  1680
tgcatgaaca cgatgtacaa ctttttgtgt ctgatgtcga tccaatcaag gccgaggaag  1740
taaaacgctt attcggggcg actgttgtcg aaccgactga aatctattct ttagatgttg  1800
atatttttgc accgtgtgca cttgggggta ttttgaatag ccataccatc ccgttcttac  1860
aagcctcaat catcgcagga gcagcgaata accagctgga gaacgagcaa cttcattcgc  1920
agatgcttgc gaaaaagggt attctttact caccagacta cgttatcaat gcaggaggac  1980
ttatcaatgt ttataacgaa atgatcggat atgacgagga aaaagcattc aaacaagttc  2040
ataacatcta cgatacgtta ttagcgattt tcgaaattgc aaaagaacaa ggtgtaacca  2100
ccaacgacgc ggcccgtcgt ttagcagagg atcgtatcaa caactccaaa cgctcaaaga  2160
```

-continued

```
gtaaagcgat tgcggcgtga aatgtaagaa ggagatatac atatggaaaa caacaccaat  2220
atgttctctg gagtgaaggt gatcgaactg gccaacttta tcgctgctcc ggcggcaggt  2280
cgcttctttg ctgatggggg agcagaagta attaagatcg aatctccagc aggcgacccg  2340
ctgcgctaca cggccccatc agaaggacgc ccgctttctc aagaggaaaa cacaacgtat  2400
gatttggaaa acgcgaataa gaaagcaatt gttctgaact taaaatcgga aaaaggaaag  2460
aaaattcttc acgagatgct tgctgaggca gacatcttgt taacaaattg gcgcacgaaa  2520
gcgttagtca aacaggggtt agattacgaa acactgaaag agaagtatcc aaaattggta  2580
tttgcacaga ttacaggata cggggagaaa ggacccgaca aagacctgcc tggtttcgac  2640
tacacggcgt ttttcgcccg cggaggagtc tccggtacat tatatgaaaa aggaactgtc  2700
cctcctaatg tggtaccggg tctgggtgac caccaggcag gaatgttctt agctgccggt  2760
atggctggtg cgttgtataa ggccaaaacc accggacaag gcgacaaagt caccgttagt  2820
ctgatgcata gcgcaatgta cggcctggga atcatgattc aggcagccca gtacaaggac  2880
catgggctgg tgtacccgat caaccgtaat gaaacgccta atcctttcat cgtttcatac  2940
aagtccaaag atgattactt tgtccaagtt tgcatgcctc cctatgatgt gttttatgat  3000
cgctttatga cggccttagg acgtgaagac ttggtaggtg acgaacgcta caataagatc  3060
gagaacttga aggatggtcg cgcaaaagaa gtctattcca tcatcgaaca acaaatggta  3120
acgaagacga aggacgaatg ggacaagatt tttcgtgatg cagacattcc attcgctatt  3180
gcccaaacgt gggaagatct tttagaagac gagcaggcat gggccaacga ctacctgtat  3240
aaaatgaagt atcccacagg caacgaacgt gccctggtac gtttacctgt gttcttcaaa  3300
gaagctggac ttcctgaata caaccagtcg ccacagattg ctgagaatac cgtggaagtg  3360
ttaaaggaga tgggatatac cgagcaagaa attgaggagc ttgagaaaga caaagacatc  3420
atggtacgta aagagaaatg aaggttaaga aggagatata catatgtcag accgcaacaa  3480
agaagtgaaa gaaaagaagg ctaaacacta tctgcgcgag atcacagcta aacactacaa  3540
ggaagcgtta gaggctaaag agcgtgggga gaaagtgggt tggtgtgcct ctaacttccc  3600
ccaagagatt gcaaccacgt tgggtgtaaa ggttgtttat cccgaaaacc acgccgccgc  3660
cgtagcggca cgtggcaatg ggcaaaatat gtgcgaacac gcggaggcta tgggattcag  3720
taatgatgtg tgtggatatg cacgtgtaaa tttagccgta atggacatcg gccatagtga  3780
agatcaacct attccaatgc ctgatttcgt tctgtgctgt aataatatct gcaatcagat  3840
gattaaatgg tatgaacaca ttgcaaaaac gttggatatt cctatgatcc ttatcgatat  3900
tccatataat actgagaaca cggtgtctca ggaccgcatt aagtacatcc gcgcccagtt  3960
cgatgacgct atcaagcaac tggaagaaat cactggcaaa aagtgggacg agaataaatt  4020
cgaagaagtg atgaagattt cgcaagaatc ggccaagcaa tggttacgcg ccgcgagcta  4080
cgcgaaatac aaaccatcac cgttttcggg ctttgacctt tttaatcaca tggctgtagc  4140
cgtttgtgct cgcggcaccc aggaagccgc cgatgcattc aaaatgttag cagatgaata  4200
tgaagagaac gttaagacag gaaagtctac ttatcgcggc gaggagaagc agcgtatctt  4260
gttcgagggc atcgcttgtt ggccttatct gcgccacaag ttgacgaaac tgagtgaata  4320
tggaatgaac gtcacagcta cggtgtacgc cgaagctttt ggggttattt acgaaaacat  4380
ggatgaactg atggccgctt acaataaagt gcctaactca atctccttcg agaacgcgct  4440
gaagatgcgt cttaatgccg ttacaagcac caatacagaa ggggctgtta tccacattaa  4500
tcgcagttgt aagctgtggt caggattctt atacgaactg gcccgtcgtt tggaaaagga  4560
gacggggatc cctgttgttt cgttcgacgg agatcaagcg gatccccgta acttctccga  4620
ggctcaatat gacactcgca tccaaggttt aaatgaggtg atggtcgcga aaaaagaagc  4680
agagtgagct ttaagaagga gatatacata tgtcgaatag tgacaagttt tttaacgact  4740
tcaaggacat tgtggaaaac ccaaagaagt atatcatgaa gcatatggaa caaacgggac  4800
aaaaagccat cggttgcatg cctttataca ccccagaaga gcttgtctta gcggcgggta  4860
tgtttcctgt tggagtatgg ggctcgaata ctgagttgtc aaaagccaag acctactttc  4920
cggcttttat ctgttctatc ttgcaaacta ctttagaaaa cgcattgaat ggggagtatg  4980
acatgctgtc tggtatgatg atcacaaact attgcgattc gctgaaatgt atgggacaaa  5040
acttcaaact tacagtggaa aatatcgaat tcatcccggt tacggttcca caaaaccgca  5100
agatggaggc gggtaaagaa tttctgaaat cccagtataa aatgaatatc gaacaactgg  5160
aaaaaatctc agggaataag atcactgacg agagcttgga gaaggctatt gaaatttacg  5220
atgagcaccg taaagtcatg aacgatttct ctatgcttgc gtccaagtac cctggtatca  5280
ttacgccaac gaaacgtaac tacgtgatga agtcagcgta ttatatggac aagaaagaac  5340
atacagagaa ggtacgtcag ttgatggatg aaatcaaggc cattgagcct aaaccattcg  5400
aaggaaaacg cgtgattacc actgggatca ttgcagattc ggaggacctt ttgaaaatct  5460
tggaggagaa taacattgct atcgtgggag atgatattgc acacgagtct cgccaatacc  5520
gcactttgac ccggaggcc aacacaccta tggaccgtct tgctgaacaa tttgcgaacc  5580
gcgagtgttc gacgttgtat gaccctgaaa aaaaacgtgg acagtatatt gtcgagatgg  5640
caaaagagcg taaggccgac ggaatcatct tcttcatgac aaaattctgc gatcccgaag  5700
aatacgatta ccctcagatg aaaaaagact tcgaagaagc cggtattccc cacgttctga  5760
ttgagacaga catgcaaatg aagaactacg aacaagctcg caccgctatt caagcatttt  5820
cagaaaccct ttgacgctta agaaggagat atacatatgt tctttacgga gcaacacgaa  5880
cttattcgca aactggcgcg tgactttgcc gaacaggaaa tcgagcctat cgcagacgaa  5940
gtagataaaa ccgcagagtt cccaaaagaa atcgtgaaga agatggctca aaatggattt  6000
ttcggcatta aaatgcctaa agaatacgga ggggcgggtg cggataaccg cgcttatgtc  6060
actattatgg aggaaatttc acgtgcttcc ggggtagcgg gtatctacct gagctcgccg  6120
aacagtttgt taggaactcc cttcttattg gtcggaaccg atgagcaaaa agaaaagtac  6180
cttaagccta tgatccgcgg cgagaagact ctggcgttcg ccctgacaga gcctggtgct  6240
ggctctgatg cgggtgcgtt ggctactact gcccgtgaag agggcgacta ttatatctta  6300
aatggccgca agacgtttat tacaggggct cctattagcg acaatattat tgtgttcgca  6360
aaaaccgata tgagcaaagg gaccaaaggt atcaccactt tcattgtgga ctcaaagcag  6420
gaaggggtaa gttttggtaa gccagaggac aaaatgggaa tgattggttg tccgacaagc  6480
gacatcatct tggaaaacgt taaagttcat aagtccgaca tcttgggaga agtcaataag  6540
gggtttatta ccgcgatgaa aacactttcc gttggtcgta tcggagtggc gtcacaggcg  6600
cttggaattg cacaggccgc cgtagatgag gcggtaaagt acgccaagca acgtaaacaa  6660
ttcaatcgcc caatcgcgaa atttcaggcc attcaattta aacttgccaa tatggagact  6720
aaattaaatg ccgctaaact tcttgtttat aacgcagcgt acaaaatgga ttgtggagaa  6780
aaagccgaca aggaagcctc tatggctaaa tactttgctg ctgaatcagc gatccaaatc  6840
gttaacgacg cgctgcaaat ccatggcggg tatggctata tcaaagacta caagattgaa  6900
```

-continued

```
cgtttgtacc gcgatgtgcg tgtgatcgct atttatgagg gcacttccga ggtccaacag  6960
atggttatcg cgtccaatct gctgaagtaa tacttaagaa ggagatatac atatgaaaat  7020
cttggcatac tgcgtccgcc cagacgaggt agactccttt aagaaattta gtgaaaagta  7080
cgggcataca gttgatctta ttccagactc ttttggacct aatgtcgctc atttggcgaa  7140
gggttacgat gggatttcta ttctgggcaa cgacacgtgt aaccgtgagg cactggagaa  7200
gatcaaggat tgcgggatca aatatctggc aacccgtaca gccggagtga acaacattga  7260
cttcgatgca gcaaaggagt tcggtattaa cgtggctaat gttcccgcat attcccccaa  7320
ctcggtcagc gaatttacca ttggattggc attaagtctg acgcgtaaga ttccatttgc  7380
cctgaaacgc gtggaactga acaattttgc gcttggcggc cttattggtg tggaattgcg  7440
taacttaact ttaggagtca tcggtactgg tcgcatcgga ttgaaagtga ttgagggctt  7500
ctctgggttt ggaatgaaaa aaatgatcgg ttatgacatt tttgaaaatg aagaagcaaa  7560
gaagtacatc gaatacaaat cattagacga agtttttaaa gaggctgata ttatcactct  7620
gcatgcgcct ctgacagacg acaactatca tatgattggt aaagaatcca ttgctaaaat  7680
gaaggatggg gtatttatta tcaacgcagc gcgtggagcc ttaatcgata gtgaggccct  7740
gattgaaggg ttaaaatcgg ggaagattgc gggcgcggct ctggatagct atgagtatga  7800
gcaaggtgtc tttcacaaca ataagatgaa tgaaattatg caggatgata ccttggaacg  7860
tctgaaatct tttcccaacg tcgtgatcac gccgcatttg ggttttata ctgatgaggc  7920
ggtttccaat atggtagaga tcacactgat gaaccttcag gaattcgagt tgaaaggaac  7980
ctgtaagaac cagcgtgttt gtaaatga                                     8008
```

```
SEQ ID NO: 64          moltype = DNA  length = 1134
FEATURE                Location/Qualifiers
source                 1..1134
                       mol_type = other DNA
                       organism = synthetic construct
SEQUENCE: 64
atgttcttta cggagcaaca cgaacttatt cgcaaactgg cgcgtgactt tgccgaacag  60
gaaatcgagc ctatcgcaga cgaagtagat aaaaccgcag agttcccaaa agaaatcgtg  120
aagaagatgg ctcaaaatgg atttttcggc attaaaatgc ctaaagaata cggaggggcg  180
ggtgcggata accgcgctta tgtcactatt atggaggaaa tttcacgtgc ttccggggta  240
gcgggtatct acctgagctc gccgaacagt ttgttaggaa ctcccttctt attggtcgga  300
accgatgagc aaaaagaaaa gtaccttaag cctatgatcc gcggcgagaa gactctggcg  360
ttcgccctga cagagcctgg tgctggctct gatgcgggtg cgttggctac tactgcccgt  420
gaagagggcg actattatat cttaaatggc cgcaagacgt ttattacagg ggctcctatt  480
agcgacaata ttattgtgtt cgcaaaaacc gatatgagca aagggaccaa aggtatcacc  540
actttcattg tggactcaaa gcaggaaggg gtaagttttg gtaagccaga ggacaaaatg  600
ggaatgattg gttgtccgac aagcgacatc atcttggaaa acgttaaagt tcataagtcc  660
gacatcttgg gagaagtcaa taaggggttt attaccgcga tgaaaacact ttccgttggt  720
cgtatcggag tggcgtcaca ggcgcttgga attgcacagg ccgccgtaga tgaggcggta  780
aagtacgcca agcaacgtaa acaattcaat cgcccaatcg cgaaatttca ggccattcaa  840
tttaaacttg ccaatatgga gactaaatta aatgccgcta aacttcttgt ttataacgca  900
gcgtacaaaa tggattgtgg agaaaaagcc gacaaggaag cctctatggc taaatacttt  960
gctgctgaat cagcgatcca aatcgttaac gacgcgctgc aaatccatgg cgggtatggc  1020
tatatcaaag actacaagat tgaacgtttg taccgcgatg tgcgtgtgat cgctatttat  1080
gagggcactt ccgaggtcca acagatggtt atcgcgtcca atctgctgaa gtaa        1134
```

```
SEQ ID NO: 65          moltype = DNA  length = 117
FEATURE                Location/Qualifiers
source                 1..117
                       mol_type = other DNA
                       organism = synthetic construct
SEQUENCE: 65
atccccatca ctcttgatgg agatcaattc cccaagctgc tagagcgtta ccttgccctt  60
aaacattagc aatgtcgatt tatcagaggg ccgacaggct cccacaggag aaaaccg     117
```

```
SEQ ID NO: 66          moltype = DNA  length = 108
FEATURE                Location/Qualifiers
source                 1..108
                       mol_type = other DNA
                       organism = synthetic construct
SEQUENCE: 66
ctcttgatcg ttatcaattc ccacgctgtt tcagagcgtt accttgccct taaacattag  60
caatgtcgat ttatcagagg gccgacaggc tcccacagga gaaaaccg               108
```

```
SEQ ID NO: 67          moltype = DNA  length = 433
FEATURE                Location/Qualifiers
source                 1..433
                       mol_type = other DNA
                       organism = synthetic construct
SEQUENCE: 67
cggcccgatc gttgaacata gcggtccgca ggcggcactg cttacagcaa acggtctgta  60
cgctgtcgtc tttgtgatgt gcttcctgtt aggtttcgtc agccgtcacc gtcagcataa  120
caccctgacc tctcattaat tgctcatgcc ggacggcact atcgtcgtcc ggccttttcc  180
tctcttcccc cgctacgtgc atctatttct ataaacccgc tcattttgtc tattttttgc  240
acaaacatga aatatcagac aattccgtga cttaagaaaa tttatacaaa tcagcaatat  300
acccattaag gagtatataa aggtgaattt gatttacatc aataagcggg gttgctgaat  360
cgttaaggta ggcggtaata gaaaagaaat cgaggcaaaa atgtttgttt aactttaaga  420
aggagatata cat                                                     433
```

-continued

```
SEQ ID NO: 68          moltype = DNA  length = 290
FEATURE                Location/Qualifiers
source                 1..290
                       mol_type = other DNA
                       organism = synthetic construct
SEQUENCE: 68
gtcagcataa caccctgacc tctcattaat tgctcatgcc ggacggcact atcgtcgtcc  60
ggccttttcc tctcttcccc cgctacgtgc atctatttct ataaacccgc tcattttgtc  120
tattttttgc acaaacatga aatatcagac aattccgtga cttaagaaaa tttatacaaa  180
tcagcaatat acccattaag gagtatataa aggtgaattt gatttacatc aataagcggg  240
gttgctgaat cgttaaggta ggcggtaata gaaaagaaat cgaggcaaaa             290

SEQ ID NO: 69          moltype = DNA  length = 207
FEATURE                Location/Qualifiers
source                 1..207
                       mol_type = other DNA
                       organism = synthetic construct
SEQUENCE: 69
agttgttctt attggtggtg ttgctttatg gttgcatcgt agtaaatggt tgtaacaaaa  60
gcaatttttc cggctgtctg tatacaaaaa cgccgcaaag tttgagcgaa gtcaataaac  120
tctctaccca ttcagggcaa tatctctctt ggatccaaag tgaactctag aaataatttt  180
gtttaacttt aagaaggaga tatacat                                      207

SEQ ID NO: 70          moltype = DNA  length = 390
FEATURE                Location/Qualifiers
source                 1..390
                       mol_type = other DNA
                       organism = synthetic construct
SEQUENCE: 70
tcgtctttgt gatgtgcttc ctgttaggtt tcgtcagccg tcaccgtcag cataacaccc  60
tgacctctca ttaattgctc atgccggacg gcactatcgt cgtccggcct tttcctctct  120
tcccccgcta cgtgcatcta tttctataaa cccgctcatt ttgtctattt tttgcacaaa  180
catgaaatat cagacaattc cgtgacttaa gaaaatttat acaaatcagc aatataccca  240
ttaaggagta tataaaggtg aatttgattt acatcaataa gcggggttgc tgaatcgtta  300
aggtagaaat gtgatctagt tcacatttgc ggtaatagaa aagaaatcga ggcaaaaatg  360
tttgtttaac tttaagaagg agatatacat                                   390

SEQ ID NO: 71          moltype = DNA  length = 200
FEATURE                Location/Qualifiers
source                 1..200
                       mol_type = other DNA
                       organism = synthetic construct
SEQUENCE: 71
agttgttctt attggtggtg ttgctttatg gttgcatcgt agtaaatggt tgtaacaaaa  60
gcaatttttc cggctgtctg tatacaaaaa cgccgcaaag tttgagcgaa gtcaataaac  120
tctctaccca ttcagggcaa tatctctcaa atgtgatcta gttcacattt tttgtttaac  180
tttaagaagg agatatacat                                              200

SEQ ID NO: 72          moltype =   length =
SEQUENCE: 72
000

SEQ ID NO: 73          moltype =   length =
SEQUENCE: 73
000

SEQ ID NO: 74          moltype =   length =
SEQUENCE: 74
000

SEQ ID NO: 75          moltype =   length =
SEQUENCE: 75
000

SEQ ID NO: 76          moltype =   length =
SEQUENCE: 76
000

SEQ ID NO: 77          moltype =   length =
SEQUENCE: 77
000

SEQ ID NO: 78          moltype =   length =
SEQUENCE: 78
000

SEQ ID NO: 79          moltype =   length =
SEQUENCE: 79
000
```

SEQ ID NO: 80 moltype = length =
SEQUENCE: 80
000

SEQ ID NO: 81 moltype = length =
SEQUENCE: 81
000

SEQ ID NO: 82 moltype = length =
SEQUENCE: 82
000

SEQ ID NO: 83 moltype = length =
SEQUENCE: 83
000

SEQ ID NO: 84 moltype = length =
SEQUENCE: 84
000

SEQ ID NO: 85 moltype = length =
SEQUENCE: 85
000

SEQ ID NO: 86 moltype = length =
SEQUENCE: 86
000

SEQ ID NO: 87 moltype = length =
SEQUENCE: 87
000

SEQ ID NO: 88 moltype = length =
SEQUENCE: 88
000

SEQ ID NO: 89 moltype = length =
SEQUENCE: 89
000

SEQ ID NO: 90 moltype = length =
SEQUENCE: 90
000

SEQ ID NO: 91 moltype = length =
SEQUENCE: 91
000

SEQ ID NO: 92 moltype = length =
SEQUENCE: 92
000

SEQ ID NO: 93 moltype = length =
SEQUENCE: 93
000

SEQ ID NO: 94 moltype = length =
SEQUENCE: 94
000

SEQ ID NO: 95 moltype = length =
SEQUENCE: 95
000

SEQ ID NO: 96 moltype = DNA length = 1470
FEATURE Location/Qualifiers
source 1..1470
mol_type = other DNA
organism = synthetic construct
SEQUENCE: 96
atgagtcaag tgattaagaa gaaacgtaac acctttatga tcggaacgga gtacattctt 60
aacagtacac aattggagga agcgattaaa tcattcgtac atgatttctg cgcagagaag 120
catgagatcc atgatcaacc tgtggtagta gaagctaaag aacatcagga ggacaaaatc 180
aaacaaatca aaatcccgga aaagggacgt cctgtaaatg aagtcgtttc tgagatgatg 240
aatgaagtgt atcgctaccg cggagacgcc aaccatcctc gcttttttc ttttgtgccc 300
ggacctgcaa gcagtgtgtc gtggttgggg gatattatga cgtccgccta caatattcat 360
gctggaggct caaagctggc accgatggtt aactgcattg agcaggaagt tctgaagtgg 420
ttagcaaagc aagtggggtt cacagaaaat ccaggtggcg tatttgtgtc gggcggttca 480

-continued

```
atggcgaata ttacggcact tactgcggct cgtgacaata aactgaccga cattaacctt  540
catttgggaa ctgcttatat tagtgaccag actcatagtt cagttgcgaa aggattacgc  600
attattggaa tcactgacag tcgcatccgt cgcattccca ctaactccca cttccagatg  660
gataccacca agctggagga agccatcgag accgacaaga agtctggcta cattccgttc  720
gtcgttatcg gaacagcagg taccaccaac actggttcga ttgaccccct gacagaaatc  780
tctgcgttat gtaagaagca tgacatgtgg tttcatatcg acggagcgta tggagctagt  840
gttctgctgt cacctaagta caagagcctt cttaccggaa ccggcttggc tgacagtatt  900
tcgtgggatg ctcataaatg gttgttccaa acgtacggct gtgcaatggt acttgtcaaa  960
gatatccgta atttattcca ctcttttcat gtgaatcccg agtatcttaa ggatctggaa  1020
aacgacatcg ataacgttaa tacatgggac atcggcatgg agctgacgcg ccctgcacgc  1080
ggtcttaaat tgtggcttac tttacaggtc cttggatctg acttgattgg gagtgccatt  1140
gaacacggtt tccagctggc agtttgggct gaggaagcat tgaatccaaa gaaagactgg  1200
gagatcgttt ctccagctca gatggctatg attaatttcc gttatgcccc taaggattta  1260
accaaagagg aacaggatat tctgaatgaa aagatctccc accgcatttt agagagcgga  1320
tacgctgcaa ttttcactac tgtattaaac ggcaagaccg ttttacgcat ctgtgcaatt  1380
cacccggagg caactcaaga ggatatgcaa cacacaatcg acttattaga ccaatacggt  1440
cgtgaaatct ataccgagat gaagaaagcg                                   1470

SEQ ID NO: 97          moltype = AA  length = 444
FEATURE                Location/Qualifiers
source                 1..444
                       mol_type = protein
                       organism = Cryptococcus deuterogattii
SEQUENCE: 97
MTATTISIET VPQAPAAGTK TNGTSGKYNP RTYLSDRAKV TEIDGSDAGR PNPDTFPFNS  60
ITLNLKPPLG LPESSNNMPV SITIEDPDLA TALQYAPSAG IPKLREWLAD LQAHVHERPR  120
GDYAISVGSG SQDLMFKGFQ AVLNPGDPVL LETPMYSGVL PALRILKADY AEVDVDDQGL  180
SAKNLEKVLS EWPADKKRPR VLYTSPIGSN PSGCSASKER KLEVLKVCKK YDVLIFEDDP  240
YYYLAQELIP SYFALEKQVY PEGGHVVRFD SFSKLLSAGM RLGFATGPKE ILHAIDVSTA  300
GANLHTSAVS QGVALRLMQY WGIEGFLAHG RAVAKLYTER RAQFEATAHK YLDGLATWVS  360
PVAGMFLWID LRPAGIEDSY ELIRHEALAK GVLGVPGMAF YPTGRKSSHV RVSFSIVDLE  420
DESDLGFQRL AEAIKDKRKA LGLA                                         444

SEQ ID NO: 98          moltype = DNA  length = 1332
FEATURE                Location/Qualifiers
source                 1..1332
                       mol_type = other DNA
                       organism = synthetic construct
SEQUENCE: 98
atgacggcaa ctacaatttc tattgagacc gtacctcagg ccccggcggc ggggaccaaa  60
actaatggga cttcaggaaa atacaacccc cgcacttacc tgtccgaccg cgccaaagtc  120
actgagattg atggatctga cgccggtcgc cccaatcccg atactttccc atttaactcg  180
attaccttaa atttgaaacc acctttaggc ttgcccgaga gttcaaataa catgccggtc  240
tctatcacga ttgaagaccc cgatttagcg acggccttac aatatgcacc tagcgccggt  300
attcctaagc tgcgcgaatg gctggctgac ttacaagctc acgttcatga gcgcccccgt  360
ggcgattatg ccatctcggt cgggtcgggg tcacaggatt tgatgtttaa gggcttccaa  420
gctgtcttga atccaggtga tccagtcctt ctggaaaccc caatgtattc aggtgttctg  480
ccagcgctgc gcattctgaa ggcggattat gcagaagttg atgtagacga ccaggggtta  540
tctgctaaaa accttgaaaa agttttatca gagtggcccg cagataagaa gcgtcctcgt  600
gtcctgtata cgtcgccaat cggctccaat ccttccggat gttcagcatc caaggaacgc  660
aagttagagg tactgaaagt ctgtaagaag tacgatgtgc tgatcttcga agacgatccg  720
tattattacc ttgctcaaga gcttattcca tcctattttg cgttggaaaa acaagtttat  780
ccggagggtg ggcacgttgt acgctttgac tcatttagta aattgctttc tgctgggatg  840
cgcttgggat ttgctacagg gccgaaggaa attcttcatg cgattgacgt cagtacagca  900
ggcgcaaatt tacatacttc agcggtctct caaggtgtcg ctcttcgcct gatgcagtat  960
tgggggatcg agggattcct tgcacatggc cgcgcggtgg ccaaacttta cacggagcgc  1020
cgcgctcagt tcgaggcaac cgcacataag tacctggacg ggctggccac ttgggtatct  1080
cccgtagcgg gaatgttttt atggatcgat cttcgtccag caggaatcga agattcttac  1140
gaattaattc gccatgaagc attagccaaa ggcgttttag gcgttccagg gatggcgttt  1200
tatccgacag gccgtaagtc ttcccatgtt cgtgtcagtt tcagtatcgt cgacctggaa  1260
gacgaatctg accttggttt tcaacgcctg gctgaagcta ttaaggataa acgcaaggct  1320
ttagggctgg ct                                                      1332

SEQ ID NO: 99          moltype = AA  length = 500
FEATURE                Location/Qualifiers
source                 1..500
                       mol_type = protein
                       organism = Catharanthus roseus
SEQUENCE: 99
MGSIDSTNVA MSNSPVGEFK PLEAEEFRKQ AHRMVDFIAD YYKNVETYPV LSEVEPGYLR  60
KRIPETAPYL PEPLDDIMKD IQKDIIPGMT NWMSPNFYAF FPATVSSAAF LGEMLSTALN  120
SVGFTWVSSP AATELEMIVM DWLAQILKLP KSFMFSGTGG GVIQNTTSES ILCTIIAARE  180
RALEKLGPDS IGKLVCYGSD QTHTMFPKTC KLAGIYPNNI RLIPTTVETD FGISPQVLRK  240
MVEDDVAAGY VPLFLCATLG TTSTTATDPV DSLSEIANEF GIWIHVDAAY AGSACICPEF  300
RHYLDGIERV DSLSLSPHKW LLAYLDCTCL WVKQPHLLLR ALTTNPEYLK NKQSDLDKVV  360
DFKNWQIATG RKFRSLKLWL ILRSYGVVNL QSHIRSDVAM GKMFEEWVRS DSRFEIVVPR  420
NFSLVCFRLK PDVSSLHVEE VNKKLLDMLN STGRVYMTHT IVGGIYMLRL AVGSSLTEEH  480
HVRRVWDLIQ KLTDDLLKEA                                              500
```

```
SEQ ID NO: 100          moltype = AA  length = 757
FEATURE                 Location/Qualifiers
source                  1..757
                        mol_type = protein
                        organism = Escherichia coli
SEQUENCE: 100
MGSPSLYSAR KTTLALAVAL SFAWQAPVFA HGGEAHMVPM DKTLKEFGAD VQWDDYAQLF  60
TLIKDGAYVK VKPGAQTAIV NGQPLALQVP VVMKDNKAWV SDTFINDVFQ SGLDQTFQVE  120
KRPHPLNALT ADEIKQAVEI VKASADFKPN TRFTEISLLP PDKEAVWAFA LENKPVDQPR  180
KADVIMLDGK HIIEAVVDLQ NNKLLSWQPI KDAHGMVLLD DFASVQNIIN NSEEFAAAVK  240
KRGITDAKKV ITTPLTVGYF DGKDGLKQDA RLLKVISYLD VGDGNYWAHP IENLVAVVDL  300
EQKKIVKIEE GPVVPVPMTA RPFDGRDRVA PAVKPMQIIE PEGKNYTITG DMIHWRNWDF  360
HLSMNSRVGP MISTVTYNDN GTKRKVMYEG SLGGMIVPYG DPDIGWYFKA YLDSGDYGMG  420
TLTSPIARGK DAPSNAVLLN ETIADYTGVP MEIPRAIAVF ERYAGPEYKH QEMGQPNVST  480
ERRELVVRWI STVGNYDYIF DWIFHENGTI GIDAGATGIE AVKGVKAKTM HDETAKDDTR  540
YGTLIDHNIV GTTHQHIYNF RLDLDVDGEN NSLVAMDPVV KPNTAGGPRT STMQVNQYNI  600
GNEQDAAQKF DPGTIRLLSN PNKENRMGNP VSYQIIPYAG GTHPVAKGAQ FAPDEWIYHR  660
LSFMDKQLWV TRYHPGERFP EGKYPNRSTH DTGLGQYSKD NESLDNTDAV VWMTTGTTHV  720
ARAEEWPIMP TEWVHTLLKP WNFFDETPTL GALKKDK                         757

SEQ ID NO: 101          moltype = AA  length = 1368
FEATURE                 Location/Qualifiers
source                  1..1368
                        mol_type = protein
                        organism = Arabidopsis thaliana
SEQUENCE: 101
MGEKAIDEDK VEAMKSSKTS LVFAINGQRF ELELSSIDPS TTLVDFLRNK TPFKSVKLGC  60
GEGGCGACVV LLSKYDPLLE KVDEFTISSC LTLLCSIDGC SITTSDGLGN SRVGFHAVHE  120
RIAGFHATQC GFCTPGMSVS MFSALLNADK SHPPPRSGFS NLTAVEAEKA VSGNLCRCTG  180
YRPLVDACKS FAADVDIEDL GFNAFCKKGE NRDEVLRRLP CYDHTSSHVC TFPEFLKKEI  240
KNDMSLHSRK YRWSSPVSVS ELQGLLEVEN GLSVKLVAGN TSTGYYKEEK ERKYERFIDI  300
RKIPEFTMVR SDEKGVELGA CVTISKAIEV LREEKNVSVL AKIATHMEKI ANRFVRNTGT  360
IGGNIMMAQR KQFPSDLATI LVAAQATVKI MTSSSSQEQF TLEEFLQQPP LDAKSLLLSL  420
EIPSWHSAKK NGSSEDSILL FETYRAAPRP LGNALAFLNA AFSAEVTEAL DGIVVNDCQL  480
VFGAYGTKHA HRAKKVEEFL TGKVISDEVL MEAISLLKDE IVPDKGTSNP GYRSSLAVTF  540
LFEFFGSLTK KNAKTTNGWL NGGCKEIGFD QNVESLKPEA MLSSAQQIVE NQEHSPVGKG  600
ITKAGACLQA SGEAVYVDDI PAPENCLYGA FIYSTMPLAR IKGIRFKQNR VPEGVLGIIT  660
YKDIPKGGQN IGTNGFFTSD LLFAEEVTHC AGQIIAFLVA DSQKHADIAA NLVVIDYDTK  720
DLKPPILSLE EAVENFSLFE VPPPLRGYPV GDITKGMDEA EHKILGSKIS FGSQYFFYME  780
TQTALAVPDE DNCMVVYSST QTPEFVHQTI AGCLGVPENN VRVITRRVGG GFGGKAVKSM  840
PVAAACALAA SKMQRPVRTY VNRKTDMITT GGRHPMKVTY SVGFKSNGKI TALDVEVLLD  900
AGLTEDISPL MPKGIQGALM KYDWGALSFN VKVCKTNTVS RTALRAPGDV QGSYIGEAII  960
EKVASYLSVD VDEIRKVNLH TYESLRLFHS AKAGEFSEYT LPLLWDRIDE FSGFNKRRKV  1020
VEEFNASNKW RKRGISRVPA VYAVNMRSTP GRVSVLGDGS IVVEVQGIEI GQGLWTKVKQ  1080
MAAYSLGLIQ CGTTSDELLK KIRVIQSDTL SMVQGSMTAG STTSEASSEA VRICCDGLVE  1140
RLLPVKTALV EQTGGPVTWD SLISQAYQQS INMSVSSKYM PDSTGEYLNY GIAASEVEVN  1200
VLTGETTILR TDIIYDCGKS LNPAVDLGQI EGAFVQGLGF FMLEEFLMNS DGLVVTDSTW  1260
TYKIPTVDTI PRQFNVEILN SGQHKNRVLS SKASGEPPLL LAASVHCAVR AAVKEARKQI  1320
LSWNSNKQGT DMYFELPVPA TMPIVKEFCG LDVVEKYLEW KIQQRKNV              1368

SEQ ID NO: 102          moltype = AA  length = 513
FEATURE                 Location/Qualifiers
source                  1..513
                        mol_type = protein
                        organism = Saccharomyces cerevisiae
SEQUENCE: 102
MTAGSAPPVD YTSLKKNFQP FLSRRVENRS LKSFWDASDI SDDVIELAGG MPNERFFPIE  60
SMDLKISKVP FNDNPKWHNS FTTAHLDLGS PSELPIARSF QYAETKGLPP LLHFVKDFVS  120
RINRPAFSDE TESNWDVILS GGSNDSMFKV FETICDESTT VMIEEFTFTP AMSNVEATGA  180
KVIPIKMNLT FDRESQGIDV EYLTQLLDNW STGPYKDLNK PRVLYTIATG QNPTGMSVPQ  240
WKREKIYQLA QRHDFLIVED DPYGYLYFPS YNPQEPLENP YHSSDLTTER YLNDFLMKSF  300
LTLDTDARVI RLETFSKIFA PGLRLSFIVA NKFLLQKILD LADITTRAPS GTSQAIVYST  360
IKAMAESNLS SSLSMKEAMF EGWIRWIMQI ASKYNHRKNL TLKALYETES YQAGQFTVME  420
PSAGMFIIIK INWGNFDRPD DLPQQMDILD KFLLKNGVKV VLGYKMAVCP NYSKQNSDFL  480
RLTIAYARDD DQLIEASKRI GSGIKEFFDN YKS                             513

SEQ ID NO: 103          moltype = AA  length = 396
FEATURE                 Location/Qualifiers
source                  1..396
                        mol_type = protein
                        organism = Escherichia coli
SEQUENCE: 103
MFENITAAPA DPILGLADLF RADERPGKIN LGIGVYKDET GKTPVLTSVK KAEQYLLENE  60
TTKNYLGIDG IPEFGRCTQE LLFGKGSALI NDKRARTAQT PGGTGALRVA ADFLAKNTSV  120
KRVWVSNPSW PNHKSVFNSA GLEVREYAYY DAENHTLDFD ALINSLNEAQ AGDVVLFHGC  180
CHNPTGIDPT LEQWQTLAQL SVEKGWLPLF DFAYQGFARG LEEDAEGLRA FAAMHKELIV  240
ASSYSKNFGL YNERVGACTL VAADSETVDR AFSQMKAAIR ANYSNPPAHG ASVVATILSN  300
DALRAIWEQE LTDMRQRIQR MRQLFVNTLQ EKGANRDFSF IIKQNGMFSF SGLTKEQVLR  360
LREEFGVYAV ASGRVNVAGM TPDNMAPLCE AIVAVL                          396
```

-continued

```
SEQ ID NO: 104         moltype = AA  length = 391
FEATURE                Location/Qualifiers
source                 1..391
                       mol_type = protein
                       organism = Arabidopsis thaliana
SEQUENCE: 104
MVKLENSRKP EKISNKNIPM SDFVVNLDHG DPTAYEEYWR KMGDRCTVTI RGCDLMSYFS  60
DMTNLCWFLE PELEDAIKDL HGVVGNAATE DRYIVVGTGS TQLCQAAVHA LSSLARSQPV  120
SVVAAAPFYS TYVEETTYVR SGMYKWEGDA WGFDKKGPYI ELVTSPNNPD GTIRETVVNR  180
PDDDEAKVIH DFAYYWPHYT PITRRQDHDI MLFTFSKITG HAGSRIGWAL VKDKEVAKKM  240
VEYIIVNSIG VSKESQVRTA KILNVLKETC KSESESENFF KYGREMMKNR WEKLREVVKE  300
SDAFTLPKYP EAFCNYFGKS LESYPAFAWL GTKEETDLVS ELRRHKVMSR AGERCGSDKK  360
HVRVSMLSRE DVFNVFLERL ANMKLIKSID L                                391

SEQ ID NO: 105         moltype = AA  length = 504
FEATURE                Location/Qualifiers
source                 1..504
                       mol_type = protein
                       organism = Streptomyces sp.
SEQUENCE: 105
MTAPLQDSDG PDDAIGGPKQ VTVIGAGIAG LVTAYELERL GHHVQIIEGS DDIGGRIHTH  60
RFSGAGGPGP FAEMGAMRIP AGHRLTMHYI AELGLQNQVR EFRTLFSDDA AYLPSSAGYL  120
RVREAHDTLV DEFATGLPSA HYRQDTLLFG AWLDASIRAI APRQFYDGLH NDIGVELLNL  180
VDDIDLTPYR CGTARNRIDL HALFADHPRV RASCPPRLER FLDDVLDETS SSIVRLKDGM  240
DELPRRLASR IRGKISLGQE VTGIDVHDDT VTLTVRQGLR TVTRTCDYVV CTIPFTVLRT  300
LRLTGFDQDK LDIVHETKYW PATKIAFHCR EPFWEKDGIS GGASFTGGHV RQTYYPPAEG  360
DPALGAVLLA SYTIGPDAEA LARMDEAERD ALVAKELSVM HPELRRPGMV LAVAGRDWGA  420
RRWSRGAATV RWGQEAALRE AERRECARPQ KGLFFAGEHC SSKPAWIEGA IESAIDAAHE  480
IEWYEPRASR VFAASRLSRS DRSA                                        504

SEQ ID NO: 106         moltype = AA  length = 552
FEATURE                Location/Qualifiers
source                 1..552
                       mol_type = protein
                       organism = Enterobacter cloacae
SEQUENCE: 106
MRTPYCVADY LLDRLTDCGA DHLFGVPGDY NLQFLDHVID SPDICWVGCA NELNASYAAD  60
GYARCKGFAA LLTTFGVGEL SAMNGIAGSY AEHVPVLHIV GAPGTAAQQR GELLHHTLGD  120
GEFRHFYHMS EPITVAQAVL TEQNACYEID RVLTTMLRER RPGYLMLPAD VAKKAATPPV  180
NALTHKQAHA DSACLKAFRD AAENKLAMSK RTALLADFLV LRHGLKHALQ KWVKEVPMAH  240
ATMLMGKGIF DERQAGFYGT YSGSASTGAV KEAIEGADTV LCVGTRFTDT LTAGFTHQLT  300
PAQTIEVQPH AARVGDVWFT GIPMNQAIET LVELCKQHVH AGLMSSSSGA IPFPQPDGSL  360
TQENFWRTLQ TFIRPGDIIL ADQGTSAFGA IDLRLPADVN FIVQPLWGSI GYTLAAAFGA  420
QTACPNRRVI VLTGDGAAQL TIQELGSMLR DKQHPIILVL NNEGYTVERA IHGAEQRYND  480
IALWNWTHIP QALSLDPQSE CWRVSEAEQL ADVLEKVAHH ERLSLIEVML PKADIPPLLG  540
ALTKALEACN NA                                                     552

SEQ ID NO: 107         moltype = AA  length = 497
FEATURE                Location/Qualifiers
source                 1..497
                       mol_type = protein
                       organism = Ustilago maydis
SEQUENCE: 107
MPTLNLDLPN GIKSTIQADL FINNKFVPAL DGKTFATINP STGKEIGQVA EASAKDVDLA  60
VKAAREAFET TWGENTPGDA RGRLLIKLAE LVEANIDELA AIESLDNGKA FSIAKSFDVA  120
AVAANLRYYG GWADKNHGKV MEVDTKRLNY TRHEPIGVCG QIIPWNFPLL MFAWKLGPAL  180
ATGNTIVLKT AEQTPLSAIK MCELIVEAGF PPGVVNVISG FGPVAGAAIS QHMDIDKIAF  240
TGSTLVGRNI MKAAASTNLK KVTLELGGKS PNIIFKDADL DQAVRWSAFG IMFNHGQCCC  300
AGSRVYVEES IYDAFMEKMT AHCKALQVGD PFSANTFQGP QVSQLQYDRI MEYIESGKKD  360
ANLALGGVRK GNEGYFIEPT IFTDVPHDAK IAKEEIFGPV VVVSKFKDEK DLIRIANDSI  420
YGLAAAVFSR DISRAIETAH KLKAGTVWVN CYNQLIPQVP FGGYKASGIG RELGEYALSN  480
YTNIKAVHVN LSQPAPI                                                497

SEQ ID NO: 108         moltype = AA  length = 415
FEATURE                Location/Qualifiers
source                 1..415
                       mol_type = protein
                       organism = Arabidopsis thaliana
SEQUENCE: 108
MEFVTETLGK RIHDPYVEET RCLMIPGPII VGSGPSGLAT AACLKSRDIP SLILERSTCI  60
ASLWQHKTYD RLRLHLPKDF CELPLMPFPS SYPTYPTKQQ FVQYLESYAE HFDLKPVFNQ  120
TVEEAKFDRR CGLWRVRTTG GKKDETMEYV SRWLVVATGE NAEEVMPEID GIPDFGGPIL  180
HTSSYKSGEI FSEKKILVVG CGNSGMEVCL DLCNFNALPS LVVRDSVHVL PQEMLGISTF  240
GISTSLLKWF PVHVVDRFLL RMSRLVLGDT DRLGLVRPKL GPLERKIKCG KTPVLDVGTL  300
AKIRSGHIKV YPELKRVMHY SAEFVDGRVD NFDAIILATG YKSNVPMWLK GVNMFSEKDG  360
FPHKPFPNGW KGESGLYAVG FTKLGLLGAA IDAKKIAEDI EVQRHFLPLA RPQHC       415

SEQ ID NO: 109         moltype = AA  length = 557
```

```
FEATURE                Location/Qualifiers
source                 1..557
                       mol_type = protein
                       organism = Pseudomonas savastanoi
SEQUENCE: 109
MYDHFNSPSI DILYDYGPFL KKCEMTGGIG SYSAGTPTPR VAIVGAGISG LVAATELLRA  60
GVKDVVLYES RDRIGGRVWS QVFDQTRPRY IAEMGAMRFP PSATGLFHYL KKFGISTSTT  120
FPDPGVVDTE LHYRGKRYHW PAGKKPPELF RRVYEGWQSL LSEGYLLEGG SLVAPLDITA  180
MLKSGRLEEA AIAWQGWLNV FRDCSFYNAI VCIFTGRHPP GGDRWARPED FELFGSLGIG  240
SGGFLPVFQA GFTEILRMVI NGYQSDQRLI PDGISSLAAR LADQSFDGKA LRDRVCFSRV  300
GRISREAEKI IIQTEAGEQR VFDRVIVTSS NRAMQMIHCL TDSESFLSRD VARAVRETHL  360
TGSSKLFILT RTKFWIKNKL PTTIQSDGLV RGVYCLDYQP DEPEGHGVVL LSYTWEDDAQ  420
KMLAMPDKKT RCQVLVDDLA AIHPTFASYL LPVDGDYERY VLHHDWLTDP HSAGAFKLNY  480
PGEDVYSQRL FFQPMTANSP NKDTGLYLAG CSCSFAGGWI EGAVQTALNS ACAVLRSTGG  540
QLSKGNPLDC INASYRY                                                 557

SEQ ID NO: 110         moltype = AA  length = 455
FEATURE                Location/Qualifiers
source                 1..455
                       mol_type = protein
                       organism = Pseudomonas savastanoi
SEQUENCE: 110
MHEIITLESL CQALADGEIA AAELRERALD TEARLARLNC FIREGDAVSQ FGEADHAMKG  60
TPLWGMPVSF KDNICVRGLP LTAGTRGMSG FVSDQDAAIV SQLRALGAVV AGKNNMHELS  120
FGVTSINPHW GTVGNPVAPG YCAGGSSGGS AAAVASGIVP LSVGTDTGGS IRIPAAFCGI  180
TGFRPTTGRW STAGIIPVSH TKDCVGLLTR TAGDAGFLYG LLSGKQQSFP LSRTAPCRIG  240
LPVSMWSDLD GEVERACVNA LSLLRKTGFE FIEIDDADIV ELNQTLTFTV PLYEFFADLA  300
QSLLSLGWKH GIHHIFAQVD DANVKGIINH HLGEGAIKPA HYLSSLQNGE LLKRKMDELF  360
ARHNIELLGY PTVPCRVPHL DHADRPEFFS QAIRNTDLAS NAMLPSITIP VGPEGRLPVG  420
LSFDALRGRD ALLLSRVSAI EQVLGFVRKV LPHTT                             455

SEQ ID NO: 111         moltype = AA  length = 353
FEATURE                Location/Qualifiers
source                 1..353
                       mol_type = protein
                       organism = Nostoc punctiforme
SEQUENCE: 111
MLLFETVREM GHEQVLFCHS KNPEIKAIIA IHDTTLGPAM GATRILPYIN EEAALKDALR  60
LSRGMTYKAA CANIPAGGGK AVIIANPENK TDDLLRAYGR FVDSLNGRFI TGQDVNITPD  120
DVRTISQETK YVVGVSEKSG GPAPITSLGV FLGIKAAVES RWQSKRLDGM KVAVQGLGNV  180
GKNLCRHLHE HDVQLFVSDV DPIKAEEVKR LFGATVVEPT EIYSLDVDIF APCALGGILN  240
SHTIPFLQAS IIAGAANNQL ENEQLHSQML AKKGILYSPD YVINAGGLIN VYNEMIGYDE  300
EKAFKQVHNI YDTLLAIFEI AKEQGVTTND AARRLAEDRI NNSKRSKSKA IAA         353

SEQ ID NO: 112         moltype = AA  length = 541
FEATURE                Location/Qualifiers
source                 1..541
                       mol_type = protein
                       organism = Arabidopsis thaliana
SEQUENCE: 112
MNTFTSNSSD LTTTATETSS FSTLYLLSTL QAFVAITLVM LLKKLMTDPN KKKPYLPPGP  60
TGWPIIGMIP TMLKSRPVFR WLHSIMKQLN TEIACVKLGN THVITVTCPK IAREILKQQD  120
ALFASRPLTY AQKILSNGYK TCVITPFGDQ FKKMRKVVMT ELVCPARHRW LHQKRSEEND  180
HLTAWVYNMV KNSGSVDFRF MTRHYCGNAI KKLMFGTRTF SKNTAPDGGP TVEDVEHMEA  240
MFEALGFTFA FCISDYLPML TGLDLNGHEK IMRESSAIMD KYHDPIIDER IKMWREGKRT  300
QIEDFLDIFI SIKDEQGNPL LTADEIKPTI KELVMAAPDN PSNAVEWAMA EMVNKPEILR  360
KAMEEIDRVV GKERLVQESD IPKLNYVKAI LREAFRLHPV AAFNLPHVAL SDTTVAGYHI  420
PKGSQVLLSR YGLGRNPKVW ADPLCFKPER HLNECSEVTL TENDLRFISF STGKRGCAAP  480
ALGTALTTMM LARLLQGFTW KLPENETRVE LMESSHDMFL AKPLVMVGDL RLPEHLYPTV  540
K                                                                  541

SEQ ID NO: 113         moltype = AA  length = 543
FEATURE                Location/Qualifiers
source                 1..543
                       mol_type = protein
                       organism = Arabidopsis thaliana
SEQUENCE: 113
MDTLASNSSD LTTKSSLGMS SFTNMYLLTT LQALAALCFL MILNKIKSSS RNKKLHPLPP  60
GPTGFPIVGM IPAMLKNRPV FRWLHSLMKE LNTEIACVRL GNTHVIPVTC PKIAREIFKQ  120
QDALFASRPL TYAQKILSNG YKTCVITPFG EQFKKMRKVI MTEIVCPARH RWLHDNRAEE  180
TDHLTAWLYN MVKNSEPVDL RFVTRHYCGN AIKRLMFGTR TFSEKTEADG GPTLEDIEHM  240
DAMFEGLGFT FAFCISDYLP MLTGLDLNGH EKIMRESSAI MDKYHDPIID ERIKMWREGK  300
RTQIEDFLDI FISIKDEAGQ PLLTADEIKP TIKELVMAAP DNPSNAVEWA IAEMINKPEI  360
LHKAMEEIDR VVGKERFVQE SDIPKLNYVK AIIREAFRLH PVAAFNLPHV ALSDTTVAGY  420
HIPKGSQVLL SRYGLGRNPK VWSDPLSFKP ERHLNECSEV TLTENDLRFI SFSTGKRGCA  480
APALGTAITT MMLARLLQGF KWKLAGSETR VELMESSHDM FLSKPLVLVG ELRLSEDLYP  540
MVK                                                                543

SEQ ID NO: 114         moltype = AA  length = 503
```

-continued

```
FEATURE               Location/Qualifiers
source                1..503
                      mol_type = protein
                      organism = Arabidopsis thaliana
SEQUENCE: 114
MSNIQEMEMI LSISLCLTTL ITLLLLRRFL KRTATKVNLP PSPWRLPVIG NLHQLSLHPH  60
RSLRSLSLRY GPLMLLHFGR VPILVVSSGE AAQEVLKTHD HKFANRPRSK AVHGLMNGGR  120
DVVFAPYGEY WRQMKSVCIL NLLTNKMVES FEKVREDEVN AMIEKLEKAS SSSSSENLSE  180
LFITLPSDVT SRVALGRKHS EDETARDLKK RVRQIMELLG EFPIGEYVPI LAWIDGIRGF  240
NNKIKEVSRG FSDLMDKVVQ EHLEASNDKA DFVDILLSIE KDKNSGFQVQ RNDIKFMILD  300
MFIGGTSTTS TLLEWTMTEL IRSPKSMKKL QDEIRSTIRP HGSYIKEKEV ENMKYLKAVI  360
KEVLRLHPSL PMILPRLLSE DVKVKGYNIA AGTEVIINAW AIQRDTAIWG PDAEEFKPER  420
HLDSGLDYHG KNLNYIPFGS GRRICPGINL ALGLAEVTVA NLVGRFDWRV EAGPNGDQPD  480
LTEAIGIDVC RKFPLIAFPS SVV                                         503

SEQ ID NO: 115        moltype = AA  length = 560
FEATURE               Location/Qualifiers
source                1..560
                      mol_type = protein
                      organism = Arabidopsis thaliana
SEQUENCE: 115
MAHLQRTFPT EMSKGRASFP KGFLFGTASS SYQYEGAVNE GARGQSVWDH FSNRFPHRIS  60
DSSDGNVAVD FYHRYKEDIK RMKDINMDSF RLSIAWPRVL PYGKRDRGVS EEGIKFYNDV  120
IDELLANEIT PLVTIFHWDI PQDLEDEYGG FLSEQIIDDF RDYASLCFER FGDRVSLWCT  180
MNEPWVYSVA GYDTGRKAPG RCSKYVNGAS VAGMSGYEAY IVSHNMLLAH AEAVEVFRKC  240
DHIKNGQIGI AHNPLWYEPY DPSDPDDVEG CNRAMDFMLG WHQHPTACGD YPETMKKSVG  300
DRLPSFTPEQ SKKLIGSCDY VGINYYSSLF VKSIKHVDPT QPTWRTDQGV DWMKTNIDGK  360
QIAKQGGSEW SFTYPTGLRN ILKYVKKTYG NPPILITENG YGEVAEQSQS LYMYNPSIDT  420
ERLEYIEGHI HAIHQAIHED GVRVEGYYVW SLLDNFEWNS GYGVRYGLYY IDYKDGLRRY  480
PKMSALWLKE FLRFDQEDDS STSKKEEKKE SYGKQLLHSV QDSQFVHSIK DSGALPAVLG  540
SLFVVSATVG TSLFFKGANN                                             560

SEQ ID NO: 116        moltype = AA  length = 346
FEATURE               Location/Qualifiers
source                1..346
                      mol_type = protein
                      organism = Arabidopsis thaliana
SEQUENCE: 116
MSSTKDMSTV QNATPFNGVA PSTTVRVTIV QSSTVYNDTP ATIDKAEKYI VEAASKGAEL  60
VLFPEGFIGG YPRGFRFGLA VGVHNEEGRD EFRKYHASAI HVPGPEVARL ADVARKNHVY  120
LVMGAIEKEG YTLYCTVLFF SPQGQFLGKH RKLMPTSLER CIWGQGDGST IPVYDTPIGK  180
LGAAICWENR MPLYRTALYA KGIELYCAPT ADGSKEWQSS MLHIAIEGGC FVLSACQFCQ  240
RKHFPDHPDY LFTDWYDDKE HDSIVSQGGS VIISPLGQVL AGPNFESEGL VTADIDLGDI  300
ARAKLYFDSV GHYSRPDVLH LTVNEHPRKS VTFVTKVEKA EDDSNK                346

SEQ ID NO: 117        moltype = AA  length = 403
FEATURE               Location/Qualifiers
source                1..403
                      mol_type = protein
                      organism = Homo sapiens
SEQUENCE: 117
MAHAMENSWT ISKEYHIDEE VGFALPNPQE NLPDFYNDWM FIAKHLPDLI ESGQLRERVE  60
KLNMLSIDHL TDHKSQRLAR LVLGCITMAY VWGKGHGDVR KVLPRNIAVP YCQLSKKLEL  120
PPILVYADCV LANWKKKDPN KPLTYENMDV LFSFRDGDCS KGFFLVSLLV EIAAASAIKV  180
IPTVFKAMQM QERDTLLKAL LEIASCLEKA LQVFHQIHDH VNPKAFFSVL RIYLSGWKGN  240
PQLSDGLVYE GFWEDPKEFA GGSAGQSSVF QCFDVLLGIQ QTAGGGHAAQ FLQDMRRYMP  300
PAHRNFLCSL ESNPSVREFV LSKGDAGLRE AYDACVKALV SLRSYHLQIV TKYILIPASQ  360
QPKENKTSED PSKLEAKGTG GTDLMNFLKT VRSTTEKSLL KEG                   403

SEQ ID NO: 118        moltype = AA  length = 406
FEATURE               Location/Qualifiers
source                1..406
                      mol_type = protein
                      organism = Homo sapiens
SEQUENCE: 118
MSGCPFLGNN FGYTFKKLPV EGSEEDKSQT GVNRASKGGL IYGNYLHLEK VLNAQELQSE  60
TKGNKIHDEH LFIITHQAYE LWFKQILWEL DSVREIFQNG HVRDERNMLK VVSRMHRVSV  120
ILKLLVQQFS ILETMTALDF NDFREYLSPA SGFQSLQFRL LENKIGVLQN MRVPYNRRHY  180
RDNFKGEENE LLLKSEQEKT LLELVEAWLE RTPGLEPHGF NFWGKLEKNI TRGLEEEFIR  240
IQAKEESEEK EEQVAEFQKQ KEVLLSLFDE KRHEHLLSKG ERRLSYRALQ GALMIYFYRE  300
EPRFQVPFQL LTSLMDIDSL MTKWRYNHVC MVHRMLGSKA GTGGSSGYHY LRSTVSDRYK  360
VFVDLFNLST YLIPRHWIPK MNPTIHKFLY TAEYCDSSYF SSDESD                406

SEQ ID NO: 119        moltype = AA  length = 453
FEATURE               Location/Qualifiers
source                1..453
                      mol_type = protein
                      organism = Saccharomyces cerevisiae
SEQUENCE: 119
```

-continued

```
MNNTSITGPQ VLHRTKMRPL PVLEKYCISP HHGFLDDRLP LTRLSSKKYM KWEEIVADLP  60
SLLQEDNKVR SVIDGLDVLD LDETILGDVR ELRRAYSILG FMAHAYIWAS GTPRDVLPEC  120
IARPLLETAH ILGVPPLATY SSLVLWNFKV TDECKKTETG CLDLENITTI NTFTGTVDES  180
WFYLVSVRFE KIGSACLNHG LQILRAIRSG DKGDANVIDG LEGLAATIER LSKALMEMEL  240
KCEPNVFYFK IRPFLAGWTN MSHMGLPQGV RYGAEGQYRI FSGGSNAQSS LIQTLDILLG  300
VKHTANAAHS SQGDSKINYL DEMKKYMPRE HREFLYHLES VCNIREYVSR NASNRALQEA  360
YGRCISMLKI FRDNHIQIVT KYIILPSNSK QHGSNKPNVL SPIEPNTKAS GCLGHKVASS  420
KTIGTGGTRL MPFLKQCRDE TVATADIKNE DKN                              453

SEQ ID NO: 120         moltype = AA  length = 305
FEATURE                Location/Qualifiers
source                 1..305
                       mol_type = protein
                       organism = Mus musculus
SEQUENCE: 120
MAFPSLSAGQ NPWRNLSSEE LEKQYSPSRW VIHTKPEEVV GNFVQIGSQA TQKARATRRN  60
QLDVPYGDGE GEKLDIYFPD EDSKAFPLFL FLHGGYWQSG SKDDSAFMVN PLTAQGIVVV  120
IVAYDIAPKG TLDQMVDQVT RSVVFLQRRY PSNEGIYLCG HSAGAHLAAM VLLARWTKHG  180
VTPNLQGFLL VSGIYDLEPL IATSQNDPLR MTLEDAQRNS PQRHLDVVPA QPVAPACPVL  240
VLVGQHDSPE FHRQSKEFYE TLLRVGWKAS FQQLRGVDHF DIIENLTRED DVLTQIILKT  300
VFQKL                                                             305

SEQ ID NO: 121         moltype = AA  length = 444
FEATURE                Location/Qualifiers
source                 1..444
                       mol_type = protein
                       organism = Saccharomyces cerevisiae
SEQUENCE: 121
MKQRFIRQFT NLMSTSRPKV VANKYFTSNT AKDVWSLTNE AAAKAANNSK NQGRELINLG  60
QGFFSYSPPQ FAIKEAQKAL DIPMVNQYSP TRGRPSLINS LIKLYSPIYN TELKAENVTV  120
TTGANEGILS CLMGLLNAGD EVIVFEPFFD QYIPNIELCG GKVVYVPINP PKELDQRNTR  180
GEEWTIDFEQ FEKAITSKTK AVIINTPHNP IGKVFTREEL TTLGNICVKH NVVIISDEVY  240
EHLYFTDSFT RIATLSPEIG QLTLTVGSAG KSFAATGWRI GWVLSLNAEL LSYAAKAHTR  300
ICFASPSPLQ EACANSINDA LKIGYFEKMR QEYINKFKIF TSIFDELGLP YTAPEGTYFV  360
LVDFSKVKIP EDYPYPEEIL NKGKDFRISH WLINELGVVA IPPTEFYIKE HEKAAENLLR  420
FAVCKDDAYL ENAVERLKLL KDYL                                        444

SEQ ID NO: 122         moltype = AA  length = 430
FEATURE                Location/Qualifiers
source                 1..430
                       mol_type = protein
                       organism = Homo sapiens
SEQUENCE: 122
MALLHSGRVL PGIAAAFHPG LAAAASARAS SWWTHVEMGP PDPILGVTEA FKRDTNSKKM  60
NLGVGAYRDD NGKPYVLPSV RKAEAQIAAK NLDKEYLPIG GLAEFCKASA ELALGENSEV  120
LKSGRFVTVQ TISGTGALRI GASFLQRFFK FSRDVFLPKP TWGNHTPIFR DAGMQLQGYR  180
YYDPKTCGFD FTGAVEDISK IPEQSVLLLH ACAHNPTGVD PRPEQWKEIA TVVKKRNLFA  240
FFDMAYQGFA SGDGDKDAWA VRHFIEQGIN VCLCQSYAKN MGLYGERVGA FTMVCKDADE  300
AKRVESQLKI LIRPMYSNPP LNGARIAAAI LNTPDLRKQW LQEVKVMADR IIGMRTQLVS  360
NLKKEGSTHN WQHITDQIGM FCFTGLKPEQ VERLIKEFSI YMTKDGRISV AGVTSSNVGY  420
LAHAIHQVTK                                                        430

SEQ ID NO: 123         moltype = AA  length = 425
FEATURE                Location/Qualifiers
source                 1..425
                       mol_type = protein
                       organism = unidentified
SEQUENCE: 123
MNYARFITAA SAARNPSPIR TMTDILSRGP KSMISLAGGL PNPNMFPFKT AVITVENGKT  60
IQFGEEMMKR ALQYSPSAGI PELLSWLKQL QIKLHNPPTI HYPPSQGQMD LCVTSGSQQG  120
LCKVFEMIIN PGDNVLLDEP AYSGTLQSLH PLGCNIINVA SDESGIVPDS LRDILSRWKP  180
EDAKNPQKNT PKFLYTVPNG NNPTGNSLTS ERKKEIYELA RKYDFLIIED DPYYFLQFNK  240
FRVPTFLSMD VDGRVIRADS FSKIISSGLR IGFLTGPKPL IERVILHIQV STLHPSTFNQ  300
LMISQLLHEW GEEGFMAHVD RVIDFYSNQK DAILAAADKW LTGLAEWHVP AAGMFLWIKV  360
KGINDVKELI EEKAVKMGVL MLPGNAFYVD SSAPSPYLRA SFSSASPEQM DVAFQVLAQL  420
IKESL                                                             425

SEQ ID NO: 124         moltype = AA  length = 422
FEATURE                Location/Qualifiers
source                 1..422
                       mol_type = protein
                       organism = Homo sapiens
SEQUENCE: 124
MAKQLQARRL DGIDYNPWVE FVKLASEHDV VNLGQGFPDF PPPDFAVEAF QHAVSGDFML  60
NQYTKTFGYP PLTKILASFF GELLGQEIDP LRNVLVTVGG YGALFTAFQA LVDEGDEVII  120
IEPFFDCYEP MTMMAGGRPV FVSLKPGPIQ NGELGSSSNW QLDPMELAGK FTSRTKALVL  180
NTPNNPLGKV FSREELELVA SLCQQHDVVC ITDEVYQWMV YDGHQHISIA SLPGMWERTL  240
TIGSAGKTFS ATGWKVGWVL GPDHIMKHLR TVHQNSVFHC PTQSQAAVAE SFEREQLLFR  300
QPSSYFVQFP QAMQRCRDHM IRSLQSVGLK PIIPQGSYFL ITDISDFKRK MPDLPGAVDE  360
```

-continued

```
PYDRRFVKWM IKNKGLVAIP VSIFYSVPHQ KHFDHYIRFC FVKDEATLQA MDEKLRKWKV  420
EL                                                                422

SEQ ID NO: 125          moltype = AA  length = 454
FEATURE                 Location/Qualifiers
source                  1..454
                        mol_type = protein
                        organism = Homo sapiens
SEQUENCE: 125
MFLAQRSLCS LSGRAKFLKT ISSSKILGFS TSAKMSLKFT NAKRIEGLDS NVWIEFTKLA  60
ADPSVVNLGQ GFPDISPPTY VKEELSKIAA IDSLNQYTRG FGHPSLVKAL SYLYEKLYQK  120
QIDSNKEILV TVGAYGSLFN TIQALIDEGD EVILIVPFYD CYEPMVRMAG ATPVFIPLRS  180
KPVYGKRWSS SDWTLDPQEL ESKFNSKTKA IILNTPHNPL GKVYNREELQ VIADLCIKYD  240
TLCISDEVYE WLVYSGNKHL KIATFPGMWE RTITIGSAGK TFSVTGWKLG WSIGPNHLIK  300
HLQTVQQNTI YTCATPLQEA LAQAFWIDIK RMDDPECYFN SLPKELEVKR DRMVRLLESV  360
GLKPIVPDGG YFIIADVSLL DPDLSDMKNN EPYDYKFVKW MTKHKKLSAI PVSAFCNSET  420
KSQFEKFVRF CFIKKDSTLD AAEEIIKAWS VQKS                             454

SEQ ID NO: 126          moltype = AA  length = 471
FEATURE                 Location/Qualifiers
source                  1..471
                        mol_type = protein
                        organism = Escherichia coli
SEQUENCE: 126
MENFKHLPEP FRIRVIEPVK RTTRAYREEA IIKSGMNPFL LDSEDVFIDL LTDSGTGAVT  60
QSMQAAMMRG DEAYSGSRSY YALAESVKNI FGYQYTIPTH QGRGAEQIYI PVLIKKREQE  120
KGLDRSKMVA FSNYFFDTTQ GHSQINGCTV RNVYIKEAFD TGVRYDFKGN FDLEGLERGI  180
EEVGPNNVPY IVATITSNSA GGQPVSLANL KAMYSIAKKY DIPVVMDSAR FAENAYFIKQ  240
REAEYKDWTI EQITRETYKY ADMLAMSAKK DAMVPMGGLL CMKDDSFFDV YTECRTLCVV  300
QEGFPTYGGL EGGAMERLAV GLYDGMNLDW LAYRIAQVQY LVDGLEEIGV VCQQAGGHAA  360
FVDAGKLLPH IPADQFPAQA LACELYKVAG IRAVEIGSFL LGRDPKTGKQ LPCPAELLRL  420
TIPRATYTQT HMDFIIEAFK HVKENAANIK GLTFTYEPKV LRHFTAKLKE V           471

SEQ ID NO: 127          moltype = AA  length = 412
FEATURE                 Location/Qualifiers
source                  1..412
                        mol_type = protein
                        organism = Clostridium sporogenes
SEQUENCE: 127
MENNTNMFSG VKVIELANFI AAPAAGRFFA DGGAEVIKIE SPAGDPLRYT APSEGRPLSQ  60
EENTTYDLEN ANKKAIVLNL KSEKGKKILH EMLAEADILL TNWRTKALVK QGLDYETLKE  120
KYPKLVFAQI TGYGEKGPDK DLPGFDYTAF FARGGVSGTL YEKGTVPPNV VPGLGDHQAG  180
MFLAAGMAGA LYKAKTTGQG DKVTVSLMHS AMYGLGIMIQ AAQYKDHGLV YPINRNETPN  240
PFIVSYKSKD DYFVQVCMPP YDVFYDRFMT ALGREDLVGD ERYNKIENLK DGRAKEVYSI  300
IEQQMVTKTK DEWDKIFRDA DIPFAIAQTW EDLLEDEQAW ANDYLYKMKY PTGNERALVR  360
LPVFFKEAGL PEYNQSPQIA ENTVEVLKEM GYTEQEIEEL EKDKDIMVRK EK          412

SEQ ID NO: 128          moltype = AA  length = 407
FEATURE                 Location/Qualifiers
source                  1..407
                        mol_type = protein
                        organism = Clostridium sporogenes
SEQUENCE: 128
MSDRNKEVKE KKAKHYLREI TAKHYKEALE AKERGEKVGW CASNFPQEIA TTLGVKVVYP  60
ENHAAAVAAR GNGQNMCEHA EAMGFSNDVC GYARVNLAVM DIGHSEDQPI PMPDFVLCCN  120
NICNQMIKWY EHIAKTLDIP MILIDIPYNT ENTVSQDRIK YIRAQFDDAI KQLEEITGKK  180
WDENKFEEVM KISQESAKQW LRAASYAKYK PSPFSGFDLF NHMAVAVCAR GTQEAADAFK  240
MLADEYEENV KTGKSTYRGE EKQRILFEGI ACWPYLRHKL TKLSEYGMNV TATVYAEAFG  300
VIYENMDELM AAYNKVPNSI SFENALKMRL NAVTSTNTEG AVIHINRSCK LWSGFLYELA  360
RRLEKETGIP VVSFDGDQAD PRNFSEAQYD TRIQGLNEVM VAKKEAE                407

SEQ ID NO: 129          moltype = AA  length = 374
FEATURE                 Location/Qualifiers
source                  1..374
                        mol_type = protein
                        organism = Clostridium sporogenes
SEQUENCE: 129
MSNSDKFFND FKDIVENPKK YIMKHMEQTG QKAIGCMPLY TPEELVLAAG MFPVGVWGSN  60
TELSKAKTYF PAFICSILQT TLENALNGEY DMLSGMMITN YCDSLKCMGQ NFKLTVENIE  120
FIPVTVPQNR KMEAGKEFLK SQYKMNIEQL EKISGNKITD ESLEKAIEIY DEHRKVMNDF  180
SMLASKYPGI ITPTKRNYVM KSAYYMDKKE HTEKVRQLMD EIKAIEPKPF EGKRVITTGI  240
IADSEDLLKI LEENNIAIVG DDIAHESRQY RTLTPEANTP MDRLAEQFAN RECSTLYDPE  300
KKRGQYIVEM AKERKADGII FFMTKFCDPE EYDYPQMKKD FEEAGIPHVL IETDMQMKNY  360
EQARTAIQAF SETL                                                   374

SEQ ID NO: 130          moltype = AA  length = 377
FEATURE                 Location/Qualifiers
source                  1..377
                        mol_type = protein
```

```
                            organism = Clostridium sporogenes
SEQUENCE: 130
MFFTEQHELI RKLARDFAEQ EIEPIADEVD KTAEFPKEIV KKMAQNGFFG IKMPKEYGGA    60
GADNRAYVTI MEEISRASGV AGIYLSSPNS LLGTPFLLVG TDEQKEKYLK PMIRGEKTLA   120
FALTEPGAGS DAGALATTAR EEGDYYILNG RKTFITGAPI SDNIIVFAKT DMSKGTKGIT   180
TFIVDSKQEG VSFGKPEDKM GMIGCPTSDI ILENVKVHKS DILGEVNKGF ITAMKTLSVG   240
RIGVASQALG IAQAAVDEAV KYAKQRKQFN RPIAKFQAIQ FKLANMETKL NAAKLLVYNA   300
AYKMDCGEKA DKEASMAKYF AAESAIQIVN DALQIHGGYG YIKDYKIERL YRDVRVIAIY   360
EGTSEVQQMV IASNLLK                                                 377

SEQ ID NO: 131          moltype = AA  length = 331
FEATURE                 Location/Qualifiers
source                  1..331
                        mol_type = protein
                        organism = Clostridium sporogenes
SEQUENCE: 131
MKILAYCVRP DEVDSFKKFS EKYGHTVDLI PDSFGPNVAH LAKGYDGISI LGNDTCNREA    60
LEKIKDCGIK YLATRTAGVN NIDFDAAKEF GINVANVPAY SPNSVSEFTI GLALSLTRKI   120
PFALKRVELN NFALGGLIGV ELRNLTLGVI GTGRIGLKVI EGFSGFGMKK MIGYDIFENE   180
EAKKYIEYKS LDEVFKEADI ITLHAPLTDD NYHMIGKESI AKMKDGVFII NAARGALIDS   240
EALIEGLKSG KIAGAALDSY EYEQGVFHNN KMNEIMQDDT LERLKSFPNV VITPHLGFYT   300
DEAVSNMVEI TLMNLQEFEL KGTCKNQRVC K                                 331

SEQ ID NO: 132          moltype = AA  length = 334
FEATURE                 Location/Qualifiers
source                  1..334
                        mol_type = protein
                        organism = Clostridium sporogenes
SEQUENCE: 132
MKILMYSVRE HEKPAIKKWL EANPGVQIDL CNNALSEDTV CKAKEYDGIA IQQTNSIGGK    60
AVYSTLKEYG IKQIASRTAG VDMIDLKMAS DSNILVTNVP AYSPNAIAEL AVTHTMNLLR   120
NIKTLNKRIA YGDYRWSADL IAREVRSVTV GVVGTGKIGR TSAKLFKGLG ANVIGYDAYP   180
DKKLEENNLL TYKESLEDLL READVVTLHT PLLESTKYMI NKNNLKYMKP DAFIVNTGRG   240
GIINTEDLIE ALEQNKIAGA ALDTFENEGL FLNKVVDPTK LPDSQLDKLL KMDQVLITHH   300
VGFFTTTAVQ NIVDTSLDSV VEVLKTNNSV NKVN                              334

SEQ ID NO: 133          moltype = AA  length = 326
FEATURE                 Location/Qualifiers
source                  1..326
                        mol_type = protein
                        organism = Rhodobacter sphaeroides
SEQUENCE: 133
MRAVLIEKSD DTQSVSVTEL AEDQLPEGDV LVDVAYSTLN YKDALAITGK APVVRRFPMV    60
PGIDFTGTVA QSSHADFKPG DRVILNGWGV GEKHWGGLAE RARVRGDWLV PLPAPLDLRQ   120
AAMIGTAGYT AMLCVLALER HGVVPGNGEI VVSGAAGGVG SVATTLLAAK GYEVAAVTGR   180
ASEAEYLRGL GAASVIDRNE LTGKVRPLGQ ERWAGGIDVA GSTVLANMLS MMKYRGVVAA   240
CGLAAGMDLP ASVAPFILRG MTLAGVDSVM CPKTDRLAAW ARLASDLDPA KLEEMTTELP   300
FSEVIETAPK FLDGTVRGRI VIPVTP                                       326

SEQ ID NO: 134          moltype =    length =
SEQUENCE: 134
000

SEQ ID NO: 135          moltype =    length =
SEQUENCE: 135
000

SEQ ID NO: 136          moltype =    length =
SEQUENCE: 136
000

SEQ ID NO: 137          moltype =    length =
SEQUENCE: 137
000

SEQ ID NO: 138          moltype =    length =
SEQUENCE: 138
000

SEQ ID NO: 139          moltype =    length =
SEQUENCE: 139
000

SEQ ID NO: 140          moltype =    length =
SEQUENCE: 140
000

SEQ ID NO: 141          moltype =    length =
SEQUENCE: 141
```

```
000

SEQ ID NO: 142         moltype =   length =
SEQUENCE: 142
000

SEQ ID NO: 143         moltype =   length =
SEQUENCE: 143
000

SEQ ID NO: 144         moltype =   length =
SEQUENCE: 144
000

SEQ ID NO: 145         moltype =   length =
SEQUENCE: 145
000

SEQ ID NO: 146         moltype =   length =
SEQUENCE: 146
000

SEQ ID NO: 147         moltype =   length =
SEQUENCE: 147
000

SEQ ID NO: 148         moltype =   length =
SEQUENCE: 148
000

SEQ ID NO: 149         moltype =   length =
SEQUENCE: 149
000

SEQ ID NO: 150         moltype =   length =
SEQUENCE: 150
000

SEQ ID NO: 151         moltype =   length =
SEQUENCE: 151
000

SEQ ID NO: 152         moltype = DNA  length = 30
FEATURE                Location/Qualifiers
source                 1..30
                       mol_type = other DNA
                       organism = synthetic construct
SEQUENCE: 152
gtttatacat aggcgagtac tctgttatgg                                   30

SEQ ID NO: 153         moltype = DNA  length = 30
FEATURE                Location/Qualifiers
source                 1..30
                       mol_type = other DNA
                       organism = synthetic construct
SEQUENCE: 153
agaggttcca actttcacca taatgaaaca                                   30

SEQ ID NO: 154         moltype = DNA  length = 30
FEATURE                Location/Qualifiers
source                 1..30
                       mol_type = other DNA
                       organism = synthetic construct
SEQUENCE: 154
taaacaacta acggacaatt ctacctaaca                                   30

SEQ ID NO: 155         moltype = DNA  length = 30
FEATURE                Location/Qualifiers
source                 1..30
                       mol_type = other DNA
                       organism = synthetic construct
SEQUENCE: 155
acatcaagcc aaattaaaca ggattaacac                                   30

SEQ ID NO: 156         moltype = DNA  length = 30
FEATURE                Location/Qualifiers
source                 1..30
                       mol_type = other DNA
                       organism = synthetic construct
```

```
SEQUENCE: 156
gaggtaaaat agtcaacacg cacggtgtta                                   30

SEQ ID NO: 157         moltype = DNA  length = 30
FEATURE                Location/Qualifiers
source                 1..30
                       mol_type = other DNA
                       organism = synthetic construct
SEQUENCE: 157
caggccggaa taactcccta taatgcgcca                                   30

SEQ ID NO: 158         moltype = DNA  length = 30
FEATURE                Location/Qualifiers
source                 1..30
                       mol_type = other DNA
                       organism = synthetic construct
SEQUENCE: 158
ggctagctca gtcctaggta cagtgctagc                                   30

SEQ ID NO: 159         moltype = DNA  length = 30
FEATURE                Location/Qualifiers
source                 1..30
                       mol_type = other DNA
                       organism = synthetic construct
SEQUENCE: 159
agctagctca gtcctaggta ttatgctagc                                   30

SEQ ID NO: 160         moltype = DNA  length = 30
FEATURE                Location/Qualifiers
source                 1..30
                       mol_type = other DNA
                       organism = synthetic construct
SEQUENCE: 160
agctagctca gtcctaggta ctgtgctagc                                   30

SEQ ID NO: 161         moltype = DNA  length = 30
FEATURE                Location/Qualifiers
source                 1..30
                       mol_type = other DNA
                       organism = synthetic construct
SEQUENCE: 161
agctagctca gtcctaggga ttatgctagc                                   30

SEQ ID NO: 162         moltype = DNA  length = 30
FEATURE                Location/Qualifiers
source                 1..30
                       mol_type = other DNA
                       organism = synthetic construct
SEQUENCE: 162
agctagctca gtcctaggta ttgtgctagc                                   30

SEQ ID NO: 163         moltype = DNA  length = 30
FEATURE                Location/Qualifiers
source                 1..30
                       mol_type = other DNA
                       organism = synthetic construct
SEQUENCE: 163
ggctagctca gtcctaggta ctatgctagc                                   30

SEQ ID NO: 164         moltype = DNA  length = 30
FEATURE                Location/Qualifiers
source                 1..30
                       mol_type = other DNA
                       organism = synthetic construct
SEQUENCE: 164
ggctagctca gtcctaggta tagtgctagc                                   30

SEQ ID NO: 165         moltype = DNA  length = 30
FEATURE                Location/Qualifiers
source                 1..30
                       mol_type = other DNA
                       organism = synthetic construct
SEQUENCE: 165
ggctagctca gccctaggta ttatgctagc                                   30

SEQ ID NO: 166         moltype = DNA  length = 30
FEATURE                Location/Qualifiers
source                 1..30
                       mol_type = other DNA
```

```
                        organism = synthetic construct
SEQUENCE: 166
agctagctca gtcctaggta taatgctagc                                            30

SEQ ID NO: 167          moltype = DNA  length = 30
FEATURE                 Location/Qualifiers
source                  1..30
                        mol_type = other DNA
                        organism = synthetic construct
SEQUENCE: 167
agctagctca gtcctaggga ctgtgctagc                                            30

SEQ ID NO: 168          moltype = DNA  length = 30
FEATURE                 Location/Qualifiers
source                  1..30
                        mol_type = other DNA
                        organism = synthetic construct
SEQUENCE: 168
ggctagctca gtcctaggta caatgctagc                                            30

SEQ ID NO: 169          moltype = DNA  length = 30
FEATURE                 Location/Qualifiers
source                  1..30
                        mol_type = other DNA
                        organism = synthetic construct
SEQUENCE: 169
ggctagctca gtcctaggta tagtgctagc                                            30

SEQ ID NO: 170          moltype = DNA  length = 30
FEATURE                 Location/Qualifiers
source                  1..30
                        mol_type = other DNA
                        organism = synthetic construct
SEQUENCE: 170
agctagctca gtcctaggga ttatgctagc                                            30

SEQ ID NO: 171          moltype = DNA  length = 30
FEATURE                 Location/Qualifiers
source                  1..30
                        mol_type = other DNA
                        organism = synthetic construct
SEQUENCE: 171
ggctagctca gtcctaggga ttatgctagc                                            30

SEQ ID NO: 172          moltype = DNA  length = 30
FEATURE                 Location/Qualifiers
source                  1..30
                        mol_type = other DNA
                        organism = synthetic construct
SEQUENCE: 172
ggctagctca gtcctaggta caatgctagc                                            30

SEQ ID NO: 173          moltype = DNA  length = 30
FEATURE                 Location/Qualifiers
source                  1..30
                        mol_type = other DNA
                        organism = synthetic construct
SEQUENCE: 173
agctagctca gcccttggta caatgctagc                                            30

SEQ ID NO: 174          moltype = DNA  length = 30
FEATURE                 Location/Qualifiers
source                  1..30
                        mol_type = other DNA
                        organism = synthetic construct
SEQUENCE: 174
agctagctca gtcctaggga ctatgctagc                                            30

SEQ ID NO: 175          moltype = DNA  length = 30
FEATURE                 Location/Qualifiers
source                  1..30
                        mol_type = other DNA
                        organism = synthetic construct
SEQUENCE: 175
agctagctca gtcctaggga ttgtgctagc                                            30

SEQ ID NO: 176          moltype = DNA  length = 30
FEATURE                 Location/Qualifiers
source                  1..30
```

```
                      mol_type = other DNA
                      organism = synthetic construct
SEQUENCE: 176
ggctagctca gtcctaggta ttgtgctagc                                  30

SEQ ID NO: 177        moltype = DNA  length = 30
FEATURE               Location/Qualifiers
source                1..30
                      mol_type = other DNA
                      organism = synthetic construct
SEQUENCE: 177
agctagctca gtcctaggta taatgctagc                                  30

SEQ ID NO: 178        moltype = DNA  length = 30
FEATURE               Location/Qualifiers
source                1..30
                      mol_type = other DNA
                      organism = synthetic construct
SEQUENCE: 178
ggctagctca gtcctaggta ttatgctagc                                  30

SEQ ID NO: 179        moltype = DNA  length = 30
FEATURE               Location/Qualifiers
source                1..30
                      mol_type = other DNA
                      organism = synthetic construct
SEQUENCE: 179
ggctagctca gtcctaggta caatgctagc                                  30

SEQ ID NO: 180        moltype = DNA  length = 30
FEATURE               Location/Qualifiers
source                1..30
                      mol_type = other DNA
                      organism = synthetic construct
SEQUENCE: 180
aaagtgtgac gccgtgcaaa taatcaatgt                                  30

SEQ ID NO: 181        moltype = DNA  length = 30
FEATURE               Location/Qualifiers
source                1..30
                      mol_type = other DNA
                      organism = synthetic construct
SEQUENCE: 181
gacgaatact taaaatcgtc atacttattt                                  30

SEQ ID NO: 182        moltype = DNA  length = 30
FEATURE               Location/Qualifiers
source                1..30
                      mol_type = other DNA
                      organism = synthetic construct
SEQUENCE: 182
aaacctttcg cggtatggca tgatagcgcc                                  30

SEQ ID NO: 183        moltype = DNA  length = 30
FEATURE               Location/Qualifiers
source                1..30
                      mol_type = other DNA
                      organism = synthetic construct
SEQUENCE: 183
tgatagcgcc cggaagagag tcaattcagg                                  30

SEQ ID NO: 184        moltype = DNA  length = 30
FEATURE               Location/Qualifiers
source                1..30
                      mol_type = other DNA
                      organism = synthetic construct
SEQUENCE: 184
ttatttaccg tgacgaacta attgctcgtg                                  30

SEQ ID NO: 185        moltype = DNA  length = 30
FEATURE               Location/Qualifiers
source                1..30
                      mol_type = other DNA
                      organism = synthetic construct
SEQUENCE: 185
catacgccgt tatacgttgt ttacgctttg                                  30

SEQ ID NO: 186        moltype = DNA  length = 30
FEATURE               Location/Qualifiers
```

-continued

```
source                  1..30
                        mol_type = other DNA
                        organism = synthetic construct
SEQUENCE: 186
ttatgcttcc ggctcgtatg ttgtgtggac                                   30

SEQ ID NO: 187          moltype = DNA  length = 30
FEATURE                 Location/Qualifiers
source                  1..30
                        mol_type = other DNA
                        organism = synthetic construct
SEQUENCE: 187
ttatgcttcc ggctcgtatg gtgtgtggac                                   30

SEQ ID NO: 188          moltype = DNA  length = 30
FEATURE                 Location/Qualifiers
source                  1..30
                        mol_type = other DNA
                        organism = synthetic construct
SEQUENCE: 188
ggctagctca gtcctaggta ctatgctagc                                   30

SEQ ID NO: 189          moltype = DNA  length = 30
FEATURE                 Location/Qualifiers
source                  1..30
                        mol_type = other DNA
                        organism = synthetic construct
SEQUENCE: 189
atatatatat atatataatg gaagcgtttt                                   30

SEQ ID NO: 190          moltype = DNA  length = 30
FEATURE                 Location/Qualifiers
source                  1..30
                        mol_type = other DNA
                        organism = synthetic construct
SEQUENCE: 190
atatatatat atatataatg gaagcgtttt                                   30

SEQ ID NO: 191          moltype = DNA  length = 30
FEATURE                 Location/Qualifiers
source                  1..30
                        mol_type = other DNA
                        organism = synthetic construct
SEQUENCE: 191
ccccgaaagc ttaagaatat aattgtaagc                                   30

SEQ ID NO: 192          moltype = DNA  length = 30
FEATURE                 Location/Qualifiers
source                  1..30
                        mol_type = other DNA
                        organism = synthetic construct
SEQUENCE: 192
ccccgaaagc ttaagaatat aattgtaagc                                   30

SEQ ID NO: 193          moltype = DNA  length = 30
FEATURE                 Location/Qualifiers
source                  1..30
                        mol_type = other DNA
                        organism = synthetic construct
SEQUENCE: 193
tgacaatata tatatatata taatgctagc                                   30

SEQ ID NO: 194          moltype = DNA  length = 30
FEATURE                 Location/Qualifiers
source                  1..30
                        mol_type = other DNA
                        organism = synthetic construct
SEQUENCE: 194
acaatatata tatatatata taatgctagc                                   30

SEQ ID NO: 195          moltype = DNA  length = 30
FEATURE                 Location/Qualifiers
source                  1..30
                        mol_type = other DNA
                        organism = synthetic construct
SEQUENCE: 195
aatatatata tatatatata taatgctagc                                   30

SEQ ID NO: 196          moltype = DNA  length = 30
```

```
FEATURE                 Location/Qualifiers
source                  1..30
                        mol_type = other DNA
                        organism = synthetic construct
SEQUENCE: 196
tatatatata tatatatata taatgctagc                                    30

SEQ ID NO: 197          moltype = DNA  length = 30
FEATURE                 Location/Qualifiers
source                  1..30
                        mol_type = other DNA
                        organism = synthetic construct
SEQUENCE: 197
tatatatata tatatatata taatgctagc                                    30

SEQ ID NO: 198          moltype = DNA  length = 30
FEATURE                 Location/Qualifiers
source                  1..30
                        mol_type = other DNA
                        organism = synthetic construct
SEQUENCE: 198
aaaaaaaaaa aaaaaaaata taatgctagc                                    30

SEQ ID NO: 199          moltype = DNA  length = 30
FEATURE                 Location/Qualifiers
source                  1..30
                        mol_type = other DNA
                        organism = synthetic construct
SEQUENCE: 199
aaaaaaaaaa aaaaaaaata taatgctagc                                    30

SEQ ID NO: 200          moltype = DNA  length = 30
FEATURE                 Location/Qualifiers
source                  1..30
                        mol_type = other DNA
                        organism = synthetic construct
SEQUENCE: 200
ggaattgtga gcggataaca atttcacaca                                    30

SEQ ID NO: 201          moltype = DNA  length = 30
FEATURE                 Location/Qualifiers
source                  1..30
                        mol_type = other DNA
                        organism = synthetic construct
SEQUENCE: 201
ggaattgtga gcggataaca atttcacaca                                    30

SEQ ID NO: 202          moltype = DNA  length = 30
FEATURE                 Location/Qualifiers
source                  1..30
                        mol_type = other DNA
                        organism = synthetic construct
SEQUENCE: 202
ggaattgtga gcggataaca atttcacaca                                    30

SEQ ID NO: 203          moltype = DNA  length = 30
FEATURE                 Location/Qualifiers
source                  1..30
                        mol_type = other DNA
                        organism = synthetic construct
SEQUENCE: 203
ggaattgtga gcggataaca atttcacaca                                    30

SEQ ID NO: 204          moltype = DNA  length = 30
FEATURE                 Location/Qualifiers
source                  1..30
                        mol_type = other DNA
                        organism = synthetic construct
SEQUENCE: 204
ggaattgtga gcggataaca atttcacaca                                    30

SEQ ID NO: 205          moltype = DNA  length = 30
FEATURE                 Location/Qualifiers
source                  1..30
                        mol_type = other DNA
                        organism = synthetic construct
SEQUENCE: 205
ggaattgtga gcggataaca atttcacaca                                    30
```

-continued

```
SEQ ID NO: 206          moltype = DNA  length = 30
FEATURE                 Location/Qualifiers
source                  1..30
                        mol_type = other DNA
                        organism = synthetic construct
SEQUENCE: 206
ggaattgtga gcggataaca atttcacaca                                   30

SEQ ID NO: 207          moltype = DNA  length = 30
FEATURE                 Location/Qualifiers
source                  1..30
                        mol_type = other DNA
                        organism = synthetic construct
SEQUENCE: 207
ggaattgtga gcggataaca atttcacaca                                   30

SEQ ID NO: 208          moltype = DNA  length = 30
FEATURE                 Location/Qualifiers
source                  1..30
                        mol_type = other DNA
                        organism = synthetic construct
SEQUENCE: 208
ggaattgtga gcggataaca atttcacaca                                   30

SEQ ID NO: 209          moltype = DNA  length = 30
FEATURE                 Location/Qualifiers
source                  1..30
                        mol_type = other DNA
                        organism = synthetic construct
SEQUENCE: 209
ggaattgtga gcggataaca atttcacaca                                   30

SEQ ID NO: 210          moltype = DNA  length = 30
FEATURE                 Location/Qualifiers
source                  1..30
                        mol_type = other DNA
                        organism = synthetic construct
SEQUENCE: 210
ggaattgtga gcggataaca atttcacaca                                   30

SEQ ID NO: 211          moltype = DNA  length = 30
FEATURE                 Location/Qualifiers
source                  1..30
                        mol_type = other DNA
                        organism = synthetic construct
SEQUENCE: 211
ggaattgtga gcggataaca atttcacaca                                   30

SEQ ID NO: 212          moltype = DNA  length = 30
FEATURE                 Location/Qualifiers
source                  1..30
                        mol_type = other DNA
                        organism = synthetic construct
SEQUENCE: 212
ggaattgtga gcggataaca atttcacaca                                   30

SEQ ID NO: 213          moltype = DNA  length = 30
FEATURE                 Location/Qualifiers
source                  1..30
                        mol_type = other DNA
                        organism = synthetic construct
SEQUENCE: 213
ggaattgtga gcggataaca atttcacaca                                   30

SEQ ID NO: 214          moltype = DNA  length = 30
FEATURE                 Location/Qualifiers
source                  1..30
                        mol_type = other DNA
                        organism = synthetic construct
SEQUENCE: 214
gattaaagag gagaaatact agagtactag                                   30

SEQ ID NO: 215          moltype = DNA  length = 30
FEATURE                 Location/Qualifiers
source                  1..30
                        mol_type = other DNA
                        organism = synthetic construct
SEQUENCE: 215
caccttcggg tgggcctttc tgcgtttata                                   30
```

```
SEQ ID NO: 216          moltype = DNA  length = 30
FEATURE                 Location/Qualifiers
source                  1..30
                        mol_type = other DNA
                        organism = synthetic construct
SEQUENCE: 216
caccttcggg tgggcctttc tgcgtttata                                   30

SEQ ID NO: 217          moltype = DNA  length = 30
FEATURE                 Location/Qualifiers
source                  1..30
                        mol_type = other DNA
                        organism = synthetic construct
SEQUENCE: 217
caccttcggg tgggcctttc tgcgtttata                                   30

SEQ ID NO: 218          moltype = DNA  length = 30
FEATURE                 Location/Qualifiers
source                  1..30
                        mol_type = other DNA
                        organism = synthetic construct
SEQUENCE: 218
caccttcggg tgggcctttc tgcgtttata                                   30

SEQ ID NO: 219          moltype = DNA  length = 30
FEATURE                 Location/Qualifiers
source                  1..30
                        mol_type = other DNA
                        organism = synthetic construct
SEQUENCE: 219
ggctagctca gtcctaggta cagtgctagc                                   30

SEQ ID NO: 220          moltype = DNA  length = 30
FEATURE                 Location/Qualifiers
source                  1..30
                        mol_type = other DNA
                        organism = synthetic construct
SEQUENCE: 220
tgctagctac tagagattaa agaggagaaa                                   30

SEQ ID NO: 221          moltype = DNA  length = 30
FEATURE                 Location/Qualifiers
source                  1..30
                        mol_type = other DNA
                        organism = synthetic construct
SEQUENCE: 221
ttgtgagcgg ataacaagat actgagcaca                                   30

SEQ ID NO: 222          moltype = DNA  length = 30
FEATURE                 Location/Qualifiers
source                  1..30
                        mol_type = other DNA
                        organism = synthetic construct
SEQUENCE: 222
ttgtgagcgg ataacaagat actgagcaca                                   30

SEQ ID NO: 223          moltype = DNA  length = 30
FEATURE                 Location/Qualifiers
source                  1..30
                        mol_type = other DNA
                        organism = synthetic construct
SEQUENCE: 223
ttgtgagcgg ataacaagat actgagcaca                                   30

SEQ ID NO: 224          moltype = DNA  length = 30
FEATURE                 Location/Qualifiers
source                  1..30
                        mol_type = other DNA
                        organism = synthetic construct
SEQUENCE: 224
ggctagctca gtcctaggta cagtgctagc                                   30

SEQ ID NO: 225          moltype = DNA  length = 30
FEATURE                 Location/Qualifiers
source                  1..30
                        mol_type = other DNA
                        organism = synthetic construct
SEQUENCE: 225
```

-continued

```
agctagctca gtcctaggta ttatgctagc                                   30

SEQ ID NO: 226         moltype = DNA  length = 30
FEATURE                Location/Qualifiers
source                 1..30
                       mol_type = other DNA
                       organism = synthetic construct
SEQUENCE: 226
agctagctca gtcctaggta ctgtgctagc                                   30

SEQ ID NO: 227         moltype = DNA  length = 30
FEATURE                Location/Qualifiers
source                 1..30
                       mol_type = other DNA
                       organism = synthetic construct
SEQUENCE: 227
agctagctca gtcctaggga ttatgctagc                                   30

SEQ ID NO: 228         moltype = DNA  length = 30
FEATURE                Location/Qualifiers
source                 1..30
                       mol_type = other DNA
                       organism = synthetic construct
SEQUENCE: 228
ggctagctca gtcctaggta tagtgctagc                                   30

SEQ ID NO: 229         moltype = DNA  length = 30
FEATURE                Location/Qualifiers
source                 1..30
                       mol_type = other DNA
                       organism = synthetic construct
SEQUENCE: 229
ggctagctca gtcctaggga ttatgctagc                                   30

SEQ ID NO: 230         moltype = DNA  length = 30
FEATURE                Location/Qualifiers
source                 1..30
                       mol_type = other DNA
                       organism = synthetic construct
SEQUENCE: 230
ggctagctca gtcctaggta caatgctagc                                   30

SEQ ID NO: 231         moltype = DNA  length = 30
FEATURE                Location/Qualifiers
source                 1..30
                       mol_type = other DNA
                       organism = synthetic construct
SEQUENCE: 231
agctagctca gtcctaggga ttgtgctagc                                   30

SEQ ID NO: 232         moltype = DNA  length = 30
FEATURE                Location/Qualifiers
source                 1..30
                       mol_type = other DNA
                       organism = synthetic construct
SEQUENCE: 232
ggctagctca gtcctaggta ttgtgctagc                                   30

SEQ ID NO: 233         moltype = DNA  length = 30
FEATURE                Location/Qualifiers
source                 1..30
                       mol_type = other DNA
                       organism = synthetic construct
SEQUENCE: 233
cctgttttta tgttattctc tctgtaaagg                                   30

SEQ ID NO: 234         moltype = DNA  length = 30
FEATURE                Location/Qualifiers
source                 1..30
                       mol_type = other DNA
                       organism = synthetic construct
SEQUENCE: 234
aaatatttgc ttatacaatc ttcctgtttt                                   30

SEQ ID NO: 235         moltype = DNA  length = 30
FEATURE                Location/Qualifiers
source                 1..30
                       mol_type = other DNA
                       organism = synthetic construct
```

```
SEQUENCE: 235
gctgataaac cgatacaatt aaaggctcct                                  30

SEQ ID NO: 236         moltype = DNA  length = 30
FEATURE                Location/Qualifiers
source                 1..30
                       mol_type = other DNA
                       organism = synthetic construct
SEQUENCE: 236
ctcttctcag cgtcttaatc taagctatcg                                  30

SEQ ID NO: 237         moltype = DNA  length = 30
FEATURE                Location/Qualifiers
source                 1..30
                       mol_type = other DNA
                       organism = synthetic construct
SEQUENCE: 237
atgagccagt tcttaaaatc gcataaggta                                  30

SEQ ID NO: 238         moltype = DNA  length = 30
FEATURE                Location/Qualifiers
source                 1..30
                       mol_type = other DNA
                       organism = synthetic construct
SEQUENCE: 238
ctattgattg tgacaaaata aacttattcc                                  30

SEQ ID NO: 239         moltype = DNA  length = 30
FEATURE                Location/Qualifiers
source                 1..30
                       mol_type = other DNA
                       organism = synthetic construct
SEQUENCE: 239
gtttcgcgct tggtataatc gctgggggtc                                  30

SEQ ID NO: 240         moltype = DNA  length = 30
FEATURE                Location/Qualifiers
source                 1..30
                       mol_type = other DNA
                       organism = synthetic construct
SEQUENCE: 240
ctttgcttct gactataata gtcagggtaa                                  30

SEQ ID NO: 241         moltype = DNA  length = 30
FEATURE                Location/Qualifiers
source                 1..30
                       mol_type = other DNA
                       organism = synthetic construct
SEQUENCE: 241
aaaccgatac aattaaaggc tcctgctagc                                  30

SEQ ID NO: 242         moltype = DNA  length = 30
FEATURE                Location/Qualifiers
source                 1..30
                       mol_type = other DNA
                       organism = synthetic construct
SEQUENCE: 242
caccacactg atagtgctag tgtagatcac                                  30

SEQ ID NO: 243         moltype = DNA  length = 30
FEATURE                Location/Qualifiers
source                 1..30
                       mol_type = other DNA
                       organism = synthetic construct
SEQUENCE: 243
gccggaataa ctccctataa tgcgccacca                                  30

SEQ ID NO: 244         moltype = DNA  length = 30
FEATURE                Location/Qualifiers
source                 1..30
                       mol_type = other DNA
                       organism = synthetic construct
SEQUENCE: 244
ttgacaagct tttcctcagc tccgtaaact                                  30

SEQ ID NO: 245         moltype = DNA  length = 30
FEATURE                Location/Qualifiers
source                 1..30
                       mol_type = other DNA
```

```
                        organism = synthetic construct
SEQUENCE: 245
ggtttcaaaa ttgtgatcta tatttaacaa                                    30

SEQ ID NO: 246          moltype = DNA  length = 30
FEATURE                 Location/Qualifiers
source                  1..30
                        mol_type = other DNA
                        organism = synthetic construct
SEQUENCE: 246
ggtttcaaaa ttgtgatcta tatttaacaa                                    30

SEQ ID NO: 247          moltype = DNA  length = 30
FEATURE                 Location/Qualifiers
source                  1..30
                        mol_type = other DNA
                        organism = synthetic construct
SEQUENCE: 247
tctattccaa taaagaaatc ttcctgcgtg                                    30

SEQ ID NO: 248          moltype = DNA  length = 30
FEATURE                 Location/Qualifiers
source                  1..30
                        mol_type = other DNA
                        organism = synthetic construct
SEQUENCE: 248
gaccgaatat atagtggaaa cgtttagatg                                    30

SEQ ID NO: 249          moltype = DNA  length = 30
FEATURE                 Location/Qualifiers
source                  1..30
                        mol_type = other DNA
                        organism = synthetic construct
SEQUENCE: 249
ccacatcctg tttttaacct taaaatggca                                    30

SEQ ID NO: 250          moltype = DNA  length = 30
FEATURE                 Location/Qualifiers
source                  1..30
                        mol_type = other DNA
                        organism = synthetic construct
SEQUENCE: 250
aaaaatgggc tcgtgttgta caataaatgt                                    30

SEQ ID NO: 251          moltype = DNA  length = 30
FEATURE                 Location/Qualifiers
source                  1..30
                        mol_type = other DNA
                        organism = synthetic construct
SEQUENCE: 251
aaaaaaagcg cgcgattatg taaaatataa                                    30

SEQ ID NO: 252          moltype = DNA  length = 30
FEATURE                 Location/Qualifiers
source                  1..30
                        mol_type = other DNA
                        organism = synthetic construct
SEQUENCE: 252
aattgcagta ggcatgacaa aatggactca                                    30

SEQ ID NO: 253          moltype = DNA  length = 30
FEATURE                 Location/Qualifiers
source                  1..30
                        mol_type = other DNA
                        organism = synthetic construct
SEQUENCE: 253
caagcttttc ctttataata gaatgaatga                                    30

SEQ ID NO: 254          moltype = DNA  length = 30
FEATURE                 Location/Qualifiers
source                  1..30
                        mol_type = other DNA
                        organism = synthetic construct
SEQUENCE: 254
tctaagctag tgtattttgc gtttaatagt                                    30

SEQ ID NO: 255          moltype = DNA  length = 30
FEATURE                 Location/Qualifiers
source                  1..30
```

```
                        mol_type = other DNA
                        organism = synthetic construct
SEQUENCE: 255
aatgggctcg tgttgtacaa taaatgtagt                                    30

SEQ ID NO: 256          moltype = DNA  length = 30
FEATURE                 Location/Qualifiers
source                  1..30
                        mol_type = other DNA
                        organism = synthetic construct
SEQUENCE: 256
atccttatcg ttatgggtat tgtttgtaat                                    30

SEQ ID NO: 257          moltype = DNA  length = 30
FEATURE                 Location/Qualifiers
source                  1..30
                        mol_type = other DNA
                        organism = synthetic construct
SEQUENCE: 257
taaaagaatt gtgagcggga atacaacaac                                    30

SEQ ID NO: 258          moltype = DNA  length = 30
FEATURE                 Location/Qualifiers
source                  1..30
                        mol_type = other DNA
                        organism = synthetic construct
SEQUENCE: 258
aaaaaaagcg cgcgattatg taaaatataa                                    30

SEQ ID NO: 259          moltype = DNA  length = 30
FEATURE                 Location/Qualifiers
source                  1..30
                        mol_type = other DNA
                        organism = synthetic construct
SEQUENCE: 259
tacaaaataa ttcccctgca aacattatca                                    30

SEQ ID NO: 260          moltype = DNA  length = 30
FEATURE                 Location/Qualifiers
source                  1..30
                        mol_type = other DNA
                        organism = synthetic construct
SEQUENCE: 260
tacaaaataa ttcccctgca aacattatcg                                    30

SEQ ID NO: 261          moltype = DNA  length = 30
FEATURE                 Location/Qualifiers
source                  1..30
                        mol_type = other DNA
                        organism = synthetic construct
SEQUENCE: 261
agggaataca agctacttgt tctttttgca                                    30

SEQ ID NO: 262          moltype = DNA  length = 23
FEATURE                 Location/Qualifiers
source                  1..23
                        mol_type = other DNA
                        organism = synthetic construct
SEQUENCE: 262
taatacgact cactataggg aga                                           23

SEQ ID NO: 263          moltype = DNA  length = 28
FEATURE                 Location/Qualifiers
source                  1..28
                        mol_type = other DNA
                        organism = synthetic construct
SEQUENCE: 263
gaatttaata cgactcacta tagggaga                                      28

SEQ ID NO: 264          moltype = DNA  length = 19
FEATURE                 Location/Qualifiers
source                  1..19
                        mol_type = other DNA
                        organism = synthetic construct
SEQUENCE: 264
taatacgact cactatagg                                                19

SEQ ID NO: 265          moltype = DNA  length = 30
FEATURE                 Location/Qualifiers
```

```
source                 1..30
                       mol_type = other DNA
                       organism = synthetic construct
SEQUENCE: 265
gagtcgtatt aatacgactc actatagggg                                   30

SEQ ID NO: 266         moltype = DNA  length = 30
FEATURE                Location/Qualifiers
source                 1..30
                       mol_type = other DNA
                       organism = synthetic construct
SEQUENCE: 266
agtgagtcgt actacgactc actatagggg                                   30

SEQ ID NO: 267         moltype = DNA  length = 30
FEATURE                Location/Qualifiers
source                 1..30
                       mol_type = other DNA
                       organism = synthetic construct
SEQUENCE: 267
gagtcgtatt aatacgactc tctatagggg                                   30

SEQ ID NO: 268         moltype = DNA  length = 18
FEATURE                Location/Qualifiers
source                 1..18
                       mol_type = other DNA
                       organism = synthetic construct
SEQUENCE: 268
taatacgact cactatag                                                18

SEQ ID NO: 269         moltype = DNA  length = 23
FEATURE                Location/Qualifiers
source                 1..23
                       mol_type = other DNA
                       organism = synthetic construct
SEQUENCE: 269
taatacgact cactataggg aga                                          23

SEQ ID NO: 270         moltype = DNA  length = 23
FEATURE                Location/Qualifiers
source                 1..23
                       mol_type = other DNA
                       organism = synthetic construct
SEQUENCE: 270
ttatacgact cactataggg aga                                          23

SEQ ID NO: 271         moltype = DNA  length = 23
FEATURE                Location/Qualifiers
source                 1..23
                       mol_type = other DNA
                       organism = synthetic construct
SEQUENCE: 271
gaatacgact cactataggg aga                                          23

SEQ ID NO: 272         moltype = DNA  length = 23
FEATURE                Location/Qualifiers
source                 1..23
                       mol_type = other DNA
                       organism = synthetic construct
SEQUENCE: 272
taatacgtct cactataggg aga                                          23

SEQ ID NO: 273         moltype = DNA  length = 23
FEATURE                Location/Qualifiers
source                 1..23
                       mol_type = other DNA
                       organism = synthetic construct
SEQUENCE: 273
tcatacgact cactataggg aga                                          23

SEQ ID NO: 274         moltype = DNA  length = 30
FEATURE                Location/Qualifiers
source                 1..30
                       mol_type = other DNA
                       organism = synthetic construct
SEQUENCE: 274
taatacgact cactataggg agaccacaac                                   30

SEQ ID NO: 275         moltype = DNA  length = 30
```

```
FEATURE                Location/Qualifiers
source                 1..30
                       mol_type = other DNA
                       organism = synthetic construct
SEQUENCE: 275
taattgaact cactaaaggg agaccacagc                                     30

SEQ ID NO: 276         moltype = DNA  length = 30
FEATURE                Location/Qualifiers
source                 1..30
                       mol_type = other DNA
                       organism = synthetic construct
SEQUENCE: 276
cgaagtaata cgactcacta ttagggaaga                                     30

SEQ ID NO: 277         moltype = DNA  length = 19
FEATURE                Location/Qualifiers
source                 1..19
                       mol_type = other DNA
                       organism = synthetic construct
SEQUENCE: 277
atttaggtga cactataga                                                 19

SEQ ID NO: 278         moltype = DNA  length = 30
FEATURE                Location/Qualifiers
source                 1..30
                       mol_type = other DNA
                       organism = synthetic construct
SEQUENCE: 278
acaaacacaa atacacacac taaattaata                                     30

SEQ ID NO: 279         moltype = DNA  length = 30
FEATURE                Location/Qualifiers
source                 1..30
                       mol_type = other DNA
                       organism = synthetic construct
SEQUENCE: 279
ccaagcatac aatcaactat ctcatataca                                     30

SEQ ID NO: 280         moltype = DNA  length = 30
FEATURE                Location/Qualifiers
source                 1..30
                       mol_type = other DNA
                       organism = synthetic construct
SEQUENCE: 280
gatacaggat acagcggaaa caacttttaa                                     30

SEQ ID NO: 281         moltype = DNA  length = 30
FEATURE                Location/Qualifiers
source                 1..30
                       mol_type = other DNA
                       organism = synthetic construct
SEQUENCE: 281
tttcaagcta taccaagcat acaatcaact                                     30

SEQ ID NO: 282         moltype = DNA  length = 30
FEATURE                Location/Qualifiers
source                 1..30
                       mol_type = other DNA
                       organism = synthetic construct
SEQUENCE: 282
cctttgcagc ataaattact atacttctat                                     30

SEQ ID NO: 283         moltype = DNA  length = 30
FEATURE                Location/Qualifiers
source                 1..30
                       mol_type = other DNA
                       organism = synthetic construct
SEQUENCE: 283
cctttgcagc ataaattact atacttctat                                     30

SEQ ID NO: 284         moltype = DNA  length = 30
FEATURE                Location/Qualifiers
source                 1..30
                       mol_type = other DNA
                       organism = synthetic construct
SEQUENCE: 284
cctttgcagc ataaattact atacttctat                                     30
```

```
SEQ ID NO: 285         moltype = DNA  length = 30
FEATURE                Location/Qualifiers
source                 1..30
                       mol_type = other DNA
                       organism = synthetic construct
SEQUENCE: 285
cctttgcagc ataaattact atacttctat                                  30

SEQ ID NO: 286         moltype = DNA  length = 30
FEATURE                Location/Qualifiers
source                 1..30
                       mol_type = other DNA
                       organism = synthetic construct
SEQUENCE: 286
cctttgcagc ataaattact atacttctat                                  30

SEQ ID NO: 287         moltype = DNA  length = 30
FEATURE                Location/Qualifiers
source                 1..30
                       mol_type = other DNA
                       organism = synthetic construct
SEQUENCE: 287
ttatctactt tttacaacaa atataaaaca                                  30

SEQ ID NO: 288         moltype = DNA  length = 30
FEATURE                Location/Qualifiers
source                 1..30
                       mol_type = other DNA
                       organism = synthetic construct
SEQUENCE: 288
acaaacacaa atacacacac taaattaata                                  30

SEQ ID NO: 289         moltype = DNA  length = 30
FEATURE                Location/Qualifiers
source                 1..30
                       mol_type = other DNA
                       organism = synthetic construct
SEQUENCE: 289
gtttcgaata aacacacata aacaaacaaa                                  30

SEQ ID NO: 290         moltype = DNA  length = 30
FEATURE                Location/Qualifiers
source                 1..30
                       mol_type = other DNA
                       organism = synthetic construct
SEQUENCE: 290
ccaagcatac aatcaactat ctcatataca                                  30

SEQ ID NO: 291         moltype = DNA  length = 30
FEATURE                Location/Qualifiers
source                 1..30
                       mol_type = other DNA
                       organism = synthetic construct
SEQUENCE: 291
accatcaaag gaagctttaa tcttctcata                                  30

SEQ ID NO: 292         moltype = DNA  length = 30
FEATURE                Location/Qualifiers
source                 1..30
                       mol_type = other DNA
                       organism = synthetic construct
SEQUENCE: 292
agaacccact gcttactggc ttatcgaaat                                  30

SEQ ID NO: 293         moltype = DNA  length = 30
FEATURE                Location/Qualifiers
source                 1..30
                       mol_type = other DNA
                       organism = synthetic construct
SEQUENCE: 293
ggccgttttt ggcttttttg ttagacgaag                                  30

SEQ ID NO: 294         moltype = DNA  length = 66
FEATURE                Location/Qualifiers
source                 1..66
                       mol_type = other DNA
                       organism = synthetic construct
SEQUENCE: 294
ataagtgcct tcccatcaaa aaaatattct caacataaaa aactttgtgt aatacttgta  60
```

-continued

```
acgcta                                                          66

SEQ ID NO: 295          moltype = DNA  length = 52
FEATURE                 Location/Qualifiers
source                  1..52
                        mol_type = other DNA
                        organism = synthetic construct
SEQUENCE: 295
aaaaagagta ttgacttcgc atctttttgt acctataata gattcattgc ta          52

SEQ ID NO: 296          moltype = DNA  length = 59
FEATURE                 Location/Qualifiers
source                  1..59
                        mol_type = other DNA
                        organism = synthetic construct
SEQUENCE: 296
ggaaaatttt tttaaaaaaa aaactttaca gctagctcag tcctaggtat tatgctagc   59

SEQ ID NO: 297          moltype = DNA  length = 59
FEATURE                 Location/Qualifiers
source                  1..59
                        mol_type = other DNA
                        organism = synthetic construct
SEQUENCE: 297
ggaaaatttt tttaaaaaaa aaactttacg gctagctcag ccctaggtat tatgctagc   59

SEQ ID NO: 298          moltype = DNA  length = 64
FEATURE                 Location/Qualifiers
source                  1..64
                        mol_type = other DNA
                        organism = synthetic construct
SEQUENCE: 298
ggaaaatttt tttaaaaaaa aaacttgaca gctagctcag tccttggtat aatgctagca  60
cgaa                                                            64

SEQ ID NO: 299          moltype =   length =
SEQUENCE: 299
000

SEQ ID NO: 300          moltype =   length =
SEQUENCE: 300
000

SEQ ID NO: 301          moltype =   length =
SEQUENCE: 301
000

SEQ ID NO: 302          moltype =   length =
SEQUENCE: 302
000

SEQ ID NO: 303          moltype =   length =
SEQUENCE: 303
000

SEQ ID NO: 304          moltype =   length =
SEQUENCE: 304
000

SEQ ID NO: 305          moltype =   length =
SEQUENCE: 305
000

SEQ ID NO: 306          moltype =   length =
SEQUENCE: 306
000

SEQ ID NO: 307          moltype =   length =
SEQUENCE: 307
000

SEQ ID NO: 308          moltype =   length =
SEQUENCE: 308
000

SEQ ID NO: 309          moltype = DNA  length = 222
FEATURE                 Location/Qualifiers
source                  1..222
                        mol_type = other DNA
```

```
                         organism = synthetic construct
SEQUENCE: 309
acgttaaatc tatcaccgca agggataaat atctaacacc gtgcgtgttg actattttac  60
ctctggcggt gataatggtt gcatagctgt caccggatgt gctttccggt ctgatgagtc  120
cgtgaggacg aaacagcctc tacaaataat tttgtttaaa acaacaccca ctaagataac  180
tctagaaata attttgttta actttaagaa ggagatatac at                     222

SEQ ID NO: 310           moltype = DNA  length = 714
FEATURE                  Location/Qualifiers
source                   1..714
                         mol_type = other DNA
                         organism = synthetic construct
SEQUENCE: 310
tcagccaaac gtctcttcag gccactgact agcgataact ttccccacaa cggaacaact  60
ctcattgcat gggatcattg ggtactgtgg gtttagtggt tgtaaaaaca cctgaccgct  120
atccctgatc agtttcttga aggtaaactc atcaccccca agtctggcta tgcagaaatc  180
acctggctca acagcctgct cagggtcaac gagaattaac attccgtcag gaaagcttgg  240
cttggagcct gttggtgcgg tcatggaatt accttcaacc tcaagccaga atgcagaatc  300
actggctttt ttggttgtgc ttacccatct ctccgcatca cctttggtaa aggttctaag  360
cttaggtgag aacatccctg cctgaacatg agaaaaaaca gggtactcat actcacttct  420
aagtgacggc tgcatactaa ccgcttcata catctcgtag atttctctgg cgattgaagg  480
gctaaattct tcaacgctaa ctttgagaat ttttgtaagc aatgcggcgt tataagcatt  540
taatgcattg atgccattaa ataaagcacc aacgcctgac tgccccatcc ccatcttgtc  600
tgcgacagat tcctgggata agccaagttc atttttcttt ttttcataaa ttgctttaag  660
gcgacgtgcg tcctcaagct gctcttgtgt taatggtttc ttttttgtgc tcat        714

SEQ ID NO: 311           moltype =   length =
SEQUENCE: 311
000

SEQ ID NO: 312           moltype = AA  length = 237
FEATURE                  Location/Qualifiers
source                   1..237
                         mol_type = protein
                         organism = synthetic construct
SEQUENCE: 312
MSTKKKPLTQ EQLEDARRLK AIYEKKKNEL GLSQESVADK MGMGQSGVGA LFNGINALNA  60
YNAALLTKIL KVSVEEFSPS IAREIYEMYE AVSMQPSLRS EYEYPVFSHV QAGMFSPKLR  120
TFTKGDAERW VSTTKKASDS AFWLEVEGNS MTAPTGSKPS FPDGMLILVD PEQAVEPGDF  180
CIARLGGDEF TFKKLIRDSG QVFLQPLNPQ YPMIPCNESC SVVGKVIASQ WPEETFG     237

SEQ ID NO: 313           moltype = DNA  length = 84
FEATURE                  Location/Qualifiers
source                   1..84
                         mol_type = other DNA
                         organism = synthetic construct
SEQUENCE: 313
acgttaaatc tatcaccgca agggataaat atctaacacc gtgcgtgttg actattttac  60
ctctggcggt gataatggtt gcat                                          84

SEQ ID NO: 314           moltype = DNA  length = 714
FEATURE                  Location/Qualifiers
source                   1..714
                         mol_type = other DNA
                         organism = synthetic construct
SEQUENCE: 314
atgagcacaa aaaagaaacc attaacacaa gagcagcttg aggacgcacg tcgccttaaa  60
gcaatttatg aaaaaaagaa aaatgaactt ggcttatccc aggaatctgt cgcagacaag  120
atggggatgg ggcagtcagg cgttggtgcc ttatttaatg gcatcaatgc attaaatgct  180
tataacgccg catcgcttac aagaattctc aaagttagcg ttgaagaatt tagcccttca  240
atcgccagag aaatctacga gatgtatgaa gcggttagta tgcagccgtc acttagaagt  300
gagtatgagt accctgtttt ttctcatgtt caggcaggga tgctctcacc tgagcttaga  360
acctttacca aaggtggtgc ggaaaggtgg gtaagcacaa ccaaaaaagc cagtgattct  420
gcattctggc ttgaggttga aggtaattcc atgacagcac caacaggctc caagccaagc  480
tttcctgacg gaatgttaat tctcgttgac cctgagcagg ctgttgagcc aggtgatttc  540
tgcatagcca gactcggggg tggtgagttt accttcaaga aactgatcag ggatagcggt  600
caggtgtttt tacaaccact aaacccacag tacccaatga tcccatgcaa tgagagttgt  660
tccgttgtgg ggaaagttat cgctagtcag tggcctgaag agacgtttgg ctga        714

SEQ ID NO: 315           moltype = AA  length = 237
FEATURE                  Location/Qualifiers
source                   1..237
                         mol_type = protein
                         organism = synthetic construct
SEQUENCE: 315
MSTKKKPLTQ EQLEDARRLK AIYEKKKNEL GLSQESVADK MGMGQSGVGA LFNGINALNA  60
YNAASLTRIL KVSVEEFSPS IAREIYEMYE AVSMQPSLRS EYEYPVFSHV QAGMLSPELR  120
TFTKGGAERW VSTTKKASDS AFWLEVEGNS MTAPTGSKPS FPDGMLILVD PEQAVEPGDF  180
CIARLGGGEF TFKKLIRDSG QVFLQPLNPQ YPMIPCNESC SVVGKVIASQ WPEETFG     237
```

-continued

```
SEQ ID NO: 316          moltype = DNA  length = 183
FEATURE                 Location/Qualifiers
source                  1..183
                        mol_type = other DNA
                        organism = synthetic construct
SEQUENCE: 316
aaatctatca ccgcaaggga taaatatcta acaccgtgcg tgttgactat tttacctctg  60
gcggtgataa tggttgcata gctgtcaccg gatgtgcttt ccggtctgat gagtccgtga  120
ggacgaaaca gcctctacaa ataattttgt ttaaaacaac acccactaag ataaggtaga  180
aac                                                                183

SEQ ID NO: 317          moltype =   length =
SEQUENCE: 317
000

SEQ ID NO: 318          moltype =   length =
SEQUENCE: 318
000

SEQ ID NO: 319          moltype =   length =
SEQUENCE: 319
000

SEQ ID NO: 320          moltype =   length =
SEQUENCE: 320
000

SEQ ID NO: 321          moltype =   length =
SEQUENCE: 321
000

SEQ ID NO: 322          moltype =   length =
SEQUENCE: 322
000

SEQ ID NO: 323          moltype =   length =
SEQUENCE: 323
000

SEQ ID NO: 324          moltype =   length =
SEQUENCE: 324
000

SEQ ID NO: 325          moltype =   length =
SEQUENCE: 325
000

SEQ ID NO: 326          moltype =   length =
SEQUENCE: 326
000

SEQ ID NO: 327          moltype =   length =
SEQUENCE: 327
000

SEQ ID NO: 328          moltype =   length =
SEQUENCE: 328
000

SEQ ID NO: 329          moltype =   length =
SEQUENCE: 329
000

SEQ ID NO: 330          moltype =   length =
SEQUENCE: 330
000

SEQ ID NO: 331          moltype =   length =
SEQUENCE: 331
000

SEQ ID NO: 332          moltype =   length =
SEQUENCE: 332
000

SEQ ID NO: 333          moltype =   length =
SEQUENCE: 333
000
```

-continued

SEQ ID NO: 334 moltype = length =
SEQUENCE: 334
000

SEQ ID NO: 335 moltype = length =
SEQUENCE: 335
000

SEQ ID NO: 336 moltype = length =
SEQUENCE: 336
000

SEQ ID NO: 337 moltype = length =
SEQUENCE: 337
000

SEQ ID NO: 338 moltype = length =
SEQUENCE: 338
000

SEQ ID NO: 339 moltype = length =
SEQUENCE: 339
000

SEQ ID NO: 340 moltype = length =
SEQUENCE: 340
000

SEQ ID NO: 341 moltype = length =
SEQUENCE: 341
000

SEQ ID NO: 342 moltype = length =
SEQUENCE: 342
000

SEQ ID NO: 343 moltype = length =
SEQUENCE: 343
000

SEQ ID NO: 344 moltype = length =
SEQUENCE: 344
000

SEQ ID NO: 345 moltype = length =
SEQUENCE: 345
000

SEQ ID NO: 346 moltype = length =
SEQUENCE: 346
000

SEQ ID NO: 347 moltype = length =
SEQUENCE: 347
000

SEQ ID NO: 348 moltype = length =
SEQUENCE: 348
000

SEQ ID NO: 349 moltype = length =
SEQUENCE: 349
000

SEQ ID NO: 350 moltype = length =
SEQUENCE: 350
000

SEQ ID NO: 351 moltype = length =
SEQUENCE: 351
000

SEQ ID NO: 352 moltype = length =
SEQUENCE: 352
000

SEQ ID NO: 353 moltype = length =
SEQUENCE: 353

000

SEQ ID NO: 354 moltype = length =
SEQUENCE: 354
000

SEQ ID NO: 355 moltype = length =
SEQUENCE: 355
000

SEQ ID NO: 356 moltype = length =
SEQUENCE: 356
000

SEQ ID NO: 357 moltype = length =
SEQUENCE: 357
000

SEQ ID NO: 358 moltype = length =
SEQUENCE: 358
000

SEQ ID NO: 359 moltype = length =
SEQUENCE: 359
000

SEQ ID NO: 360 moltype = length =
SEQUENCE: 360
000

SEQ ID NO: 361 moltype = length =
SEQUENCE: 361
000

SEQ ID NO: 362 moltype = length =
SEQUENCE: 362
000

SEQ ID NO: 363 moltype = length =
SEQUENCE: 363
000

SEQ ID NO: 364 moltype = length =
SEQUENCE: 364
000

SEQ ID NO: 365 moltype = length =
SEQUENCE: 365
000

SEQ ID NO: 366 moltype = length =
SEQUENCE: 366
000

SEQ ID NO: 367 moltype = length =
SEQUENCE: 367
000

SEQ ID NO: 368 moltype = length =
SEQUENCE: 368
000

SEQ ID NO: 369 moltype = length =
SEQUENCE: 369
000

SEQ ID NO: 370 moltype = length =
SEQUENCE: 370
000

SEQ ID NO: 371 moltype = length =
SEQUENCE: 371
000

SEQ ID NO: 372 moltype = length =
SEQUENCE: 372
000

SEQ ID NO: 373 moltype = length =

-continued

SEQUENCE: 373
000

SEQ ID NO: 374 moltype = length =
SEQUENCE: 374
000

SEQ ID NO: 375 moltype = length =
SEQUENCE: 375
000

SEQ ID NO: 376 moltype = length =
SEQUENCE: 376
000

SEQ ID NO: 377 moltype = length =
SEQUENCE: 377
000

SEQ ID NO: 378 moltype = length =
SEQUENCE: 378
000

SEQ ID NO: 379 moltype = length =
SEQUENCE: 379
000

SEQ ID NO: 380 moltype = length =
SEQUENCE: 380
000

SEQ ID NO: 381 moltype = length =
SEQUENCE: 381
000

SEQ ID NO: 382 moltype = length =
SEQUENCE: 382
000

SEQ ID NO: 383 moltype = length =
SEQUENCE: 383
000

SEQ ID NO: 384 moltype = length =
SEQUENCE: 384
000

SEQ ID NO: 385 moltype = length =
SEQUENCE: 385
000

SEQ ID NO: 386 moltype = length =
SEQUENCE: 386
000

SEQ ID NO: 387 moltype = length =
SEQUENCE: 387
000

SEQ ID NO: 388 moltype = length =
SEQUENCE: 388
000

SEQ ID NO: 389 moltype = length =
SEQUENCE: 389
000

SEQ ID NO: 390 moltype = length =
SEQUENCE: 390
000

SEQ ID NO: 391 moltype = length =
SEQUENCE: 391
000

SEQ ID NO: 392 moltype = length =
SEQUENCE: 392
000

SEQ ID NO: 393 moltype = length =
SEQUENCE: 393
000

SEQ ID NO: 394 moltype = length =
SEQUENCE: 394
000

SEQ ID NO: 395 moltype = length =
SEQUENCE: 395
000

SEQ ID NO: 396 moltype = length =
SEQUENCE: 396
000

SEQ ID NO: 397 moltype = length =
SEQUENCE: 397
000

SEQ ID NO: 398 moltype = length =
SEQUENCE: 398
000

SEQ ID NO: 399 moltype = length =
SEQUENCE: 399
000

SEQ ID NO: 400 moltype = length =
SEQUENCE: 400
000

SEQ ID NO: 401 moltype = length =
SEQUENCE: 401
000

SEQ ID NO: 402 moltype = length =
SEQUENCE: 402
000

SEQ ID NO: 403 moltype = length =
SEQUENCE: 403
000

SEQ ID NO: 404 moltype = length =
SEQUENCE: 404
000

SEQ ID NO: 405 moltype = length =
SEQUENCE: 405
000

SEQ ID NO: 406 moltype = length =
SEQUENCE: 406
000

SEQ ID NO: 407 moltype = length =
SEQUENCE: 407
000

SEQ ID NO: 408 moltype = length =
SEQUENCE: 408
000

SEQ ID NO: 409 moltype = length =
SEQUENCE: 409
000

SEQ ID NO: 410 moltype = length =
SEQUENCE: 410
000

SEQ ID NO: 411 moltype = length =
SEQUENCE: 411
000

SEQ ID NO: 412 moltype = length =
SEQUENCE: 412
000

SEQ ID NO: 413 moltype = length =
SEQUENCE: 413
000

SEQ ID NO: 414 moltype = length =
SEQUENCE: 414
000

SEQ ID NO: 415 moltype = length =
SEQUENCE: 415
000

SEQ ID NO: 416 moltype = length =
SEQUENCE: 416
000

SEQ ID NO: 417 moltype = length =
SEQUENCE: 417
000

SEQ ID NO: 418 moltype = length =
SEQUENCE: 418
000

SEQ ID NO: 419 moltype = length =
SEQUENCE: 419
000

SEQ ID NO: 420 moltype = length =
SEQUENCE: 420
000

SEQ ID NO: 421 moltype = length =
SEQUENCE: 421
000

SEQ ID NO: 422 moltype = length =
SEQUENCE: 422
000

SEQ ID NO: 423 moltype = length =
SEQUENCE: 423
000

SEQ ID NO: 424 moltype = length =
SEQUENCE: 424
000

SEQ ID NO: 425 moltype = length =
SEQUENCE: 425
000

SEQ ID NO: 426 moltype = length =
SEQUENCE: 426
000

SEQ ID NO: 427 moltype = length =
SEQUENCE: 427
000

SEQ ID NO: 428 moltype = length =
SEQUENCE: 428
000

SEQ ID NO: 429 moltype = length =
SEQUENCE: 429
000

SEQ ID NO: 430 moltype = length =
SEQUENCE: 430
000

SEQ ID NO: 431 moltype = length =
SEQUENCE: 431
000

SEQ ID NO: 432 moltype = length =
SEQUENCE: 432

000

SEQ ID NO: 433 moltype = length =
SEQUENCE: 433
000

SEQ ID NO: 434 moltype = length =
SEQUENCE: 434
000

SEQ ID NO: 435 moltype = length =
SEQUENCE: 435
000

SEQ ID NO: 436 moltype = length =
SEQUENCE: 436
000

SEQ ID NO: 437 moltype = length =
SEQUENCE: 437
000

SEQ ID NO: 438 moltype = length =
SEQUENCE: 438
000

SEQ ID NO: 439 moltype = length =
SEQUENCE: 439
000

SEQ ID NO: 440 moltype = length =
SEQUENCE: 440
000

SEQ ID NO: 441 moltype = length =
SEQUENCE: 441
000

SEQ ID NO: 442 moltype = length =
SEQUENCE: 442
000

SEQ ID NO: 443 moltype = length =
SEQUENCE: 443
000

SEQ ID NO: 444 moltype = length =
SEQUENCE: 444
000

SEQ ID NO: 445 moltype = length =
SEQUENCE: 445
000

SEQ ID NO: 446 moltype = length =
SEQUENCE: 446
000

SEQ ID NO: 447 moltype = length =
SEQUENCE: 447
000

SEQ ID NO: 448 moltype = length =
SEQUENCE: 448
000

SEQ ID NO: 449 moltype = length =
SEQUENCE: 449
000

SEQ ID NO: 450 moltype = length =
SEQUENCE: 450
000

SEQ ID NO: 451 moltype = length =
SEQUENCE: 451
000

SEQ ID NO: 452 moltype = length =

-continued

SEQUENCE: 452
000

SEQ ID NO: 453 moltype = length =
SEQUENCE: 453
000

SEQ ID NO: 454 moltype = length =
SEQUENCE: 454
000

SEQ ID NO: 455 moltype = length =
SEQUENCE: 455
000

SEQ ID NO: 456 moltype = length =
SEQUENCE: 456
000

SEQ ID NO: 457 moltype = length =
SEQUENCE: 457
000

SEQ ID NO: 458 moltype = length =
SEQUENCE: 458
000

SEQ ID NO: 459 moltype = length =
SEQUENCE: 459
000

SEQ ID NO: 460 moltype = length =
SEQUENCE: 460
000

SEQ ID NO: 461 moltype = length =
SEQUENCE: 461
000

SEQ ID NO: 462 moltype = length =
SEQUENCE: 462
000

SEQ ID NO: 463 moltype = length =
SEQUENCE: 463
000

SEQ ID NO: 464 moltype = length =
SEQUENCE: 464
000

SEQ ID NO: 465 moltype = length =
SEQUENCE: 465
000

SEQ ID NO: 466 moltype = length =
SEQUENCE: 466
000

SEQ ID NO: 467 moltype = length =
SEQUENCE: 467
000

SEQ ID NO: 468 moltype = length =
SEQUENCE: 468
000

SEQ ID NO: 469 moltype = length =
SEQUENCE: 469
000

SEQ ID NO: 470 moltype = length =
SEQUENCE: 470
000

SEQ ID NO: 471 moltype = length =
SEQUENCE: 471
000

SEQ ID NO: 472 moltype = length =
SEQUENCE: 472
000

SEQ ID NO: 473 moltype = length =
SEQUENCE: 473
000

SEQ ID NO: 474 moltype = length =
SEQUENCE: 474
000

SEQ ID NO: 475 moltype = length =
SEQUENCE: 475
000

SEQ ID NO: 476 moltype = length =
SEQUENCE: 476
000

SEQ ID NO: 477 moltype = length =
SEQUENCE: 477
000

SEQ ID NO: 478 moltype = length =
SEQUENCE: 478
000

SEQ ID NO: 479 moltype = length =
SEQUENCE: 479
000

SEQ ID NO: 480 moltype = length =
SEQUENCE: 480
000

SEQ ID NO: 481 moltype = length =
SEQUENCE: 481
000

SEQ ID NO: 482 moltype = length =
SEQUENCE: 482
000

SEQ ID NO: 483 moltype = length =
SEQUENCE: 483
000

SEQ ID NO: 484 moltype = length =
SEQUENCE: 484
000

SEQ ID NO: 485 moltype = length =
SEQUENCE: 485
000

SEQ ID NO: 486 moltype = length =
SEQUENCE: 486
000

SEQ ID NO: 487 moltype = length =
SEQUENCE: 487
000

SEQ ID NO: 488 moltype = length =
SEQUENCE: 488
000

SEQ ID NO: 489 moltype = length =
SEQUENCE: 489
000

SEQ ID NO: 490 moltype = length =
SEQUENCE: 490
000

SEQ ID NO: 491 moltype = length =
SEQUENCE: 491
000

-continued

SEQ ID NO: 492 moltype = length =
SEQUENCE: 492
000

SEQ ID NO: 493 moltype = length =
SEQUENCE: 493
000

SEQ ID NO: 494 moltype = length =
SEQUENCE: 494
000

SEQ ID NO: 495 moltype = length =
SEQUENCE: 495
000

SEQ ID NO: 496 moltype = length =
SEQUENCE: 496
000

SEQ ID NO: 497 moltype = length =
SEQUENCE: 497
000

SEQ ID NO: 498 moltype = length =
SEQUENCE: 498
000

SEQ ID NO: 499 moltype = length =
SEQUENCE: 499
000

SEQ ID NO: 500 moltype = length =
SEQUENCE: 500
000

SEQ ID NO: 501 moltype = length =
SEQUENCE: 501
000

SEQ ID NO: 502 moltype = length =
SEQUENCE: 502
000

SEQ ID NO: 503 moltype = length =
SEQUENCE: 503
000

SEQ ID NO: 504 moltype = length =
SEQUENCE: 504
000

SEQ ID NO: 505 moltype = length =
SEQUENCE: 505
000

SEQ ID NO: 506 moltype = length =
SEQUENCE: 506
000

SEQ ID NO: 507 moltype = length =
SEQUENCE: 507
000

SEQ ID NO: 508 moltype = length =
SEQUENCE: 508
000

SEQ ID NO: 509 moltype = length =
SEQUENCE: 509
000

SEQ ID NO: 510 moltype = length =
SEQUENCE: 510
000

SEQ ID NO: 511 moltype = length =
SEQUENCE: 511

000

SEQ ID NO: 512 moltype = length =
SEQUENCE: 512
000

SEQ ID NO: 513 moltype = length =
SEQUENCE: 513
000

SEQ ID NO: 514 moltype = length =
SEQUENCE: 514
000

SEQ ID NO: 515 moltype = length =
SEQUENCE: 515
000

SEQ ID NO: 516 moltype = length =
SEQUENCE: 516
000

SEQ ID NO: 517 moltype = length =
SEQUENCE: 517
000

SEQ ID NO: 518 moltype = length =
SEQUENCE: 518
000

SEQ ID NO: 519 moltype = length =
SEQUENCE: 519
000

SEQ ID NO: 520 moltype = length =
SEQUENCE: 520
000

SEQ ID NO: 521 moltype = length =
SEQUENCE: 521
000

SEQ ID NO: 522 moltype = length =
SEQUENCE: 522
000

SEQ ID NO: 523 moltype = length =
SEQUENCE: 523
000

SEQ ID NO: 524 moltype = length =
SEQUENCE: 524
000

SEQ ID NO: 525 moltype = length =
SEQUENCE: 525
000

SEQ ID NO: 526 moltype = length =
SEQUENCE: 526
000

SEQ ID NO: 527 moltype = length =
SEQUENCE: 527
000

SEQ ID NO: 528 moltype = length =
SEQUENCE: 528
000

SEQ ID NO: 529 moltype = length =
SEQUENCE: 529
000

SEQ ID NO: 530 moltype = length =
SEQUENCE: 530
000

SEQ ID NO: 531 moltype = length =

SEQUENCE: 531
000

SEQ ID NO: 532 moltype = length =
SEQUENCE: 532
000

SEQ ID NO: 533 moltype = length =
SEQUENCE: 533
000

SEQ ID NO: 534 moltype = length =
SEQUENCE: 534
000

SEQ ID NO: 535 moltype = length =
SEQUENCE: 535
000

SEQ ID NO: 536 moltype = length =
SEQUENCE: 536
000

SEQ ID NO: 537 moltype = length =
SEQUENCE: 537
000

SEQ ID NO: 538 moltype = length =
SEQUENCE: 538
000

SEQ ID NO: 539 moltype = length =
SEQUENCE: 539
000

SEQ ID NO: 540 moltype = length =
SEQUENCE: 540
000

SEQ ID NO: 541 moltype = length =
SEQUENCE: 541
000

SEQ ID NO: 542 moltype = length =
SEQUENCE: 542
000

SEQ ID NO: 543 moltype = length =
SEQUENCE: 543
000

SEQ ID NO: 544 moltype = length =
SEQUENCE: 544
000

SEQ ID NO: 545 moltype = length =
SEQUENCE: 545
000

SEQ ID NO: 546 moltype = length =
SEQUENCE: 546
000

SEQ ID NO: 547 moltype = length =
SEQUENCE: 547
000

SEQ ID NO: 548 moltype = length =
SEQUENCE: 548
000

SEQ ID NO: 549 moltype = length =
SEQUENCE: 549
000

SEQ ID NO: 550 moltype = length =
SEQUENCE: 550
000

-continued

SEQ ID NO: 551 moltype = length =
SEQUENCE: 551
000

SEQ ID NO: 552 moltype = length =
SEQUENCE: 552
000

SEQ ID NO: 553 moltype = length =
SEQUENCE: 553
000

SEQ ID NO: 554 moltype = length =
SEQUENCE: 554
000

SEQ ID NO: 555 moltype = length =
SEQUENCE: 555
000

SEQ ID NO: 556 moltype = length =
SEQUENCE: 556
000

SEQ ID NO: 557 moltype = length =
SEQUENCE: 557
000

SEQ ID NO: 558 moltype = length =
SEQUENCE: 558
000

SEQ ID NO: 559 moltype = length =
SEQUENCE: 559
000

SEQ ID NO: 560 moltype = length =
SEQUENCE: 560
000

SEQ ID NO: 561 moltype = length =
SEQUENCE: 561
000

SEQ ID NO: 562 moltype = length =
SEQUENCE: 562
000

SEQ ID NO: 563 moltype = length =
SEQUENCE: 563
000

SEQ ID NO: 564 moltype = length =
SEQUENCE: 564
000

SEQ ID NO: 565 moltype = length =
SEQUENCE: 565
000

SEQ ID NO: 566 moltype = length =
SEQUENCE: 566
000

SEQ ID NO: 567 moltype = length =
SEQUENCE: 567
000

SEQ ID NO: 568 moltype = length =
SEQUENCE: 568
000

SEQ ID NO: 569 moltype = length =
SEQUENCE: 569
000

SEQ ID NO: 570 moltype = length =
SEQUENCE: 570
000

-continued

SEQ ID NO: 571 moltype = length =
SEQUENCE: 571
000

SEQ ID NO: 572 moltype = length =
SEQUENCE: 572
000

SEQ ID NO: 573 moltype = length =
SEQUENCE: 573
000

SEQ ID NO: 574 moltype = length =
SEQUENCE: 574
000

SEQ ID NO: 575 moltype = length =
SEQUENCE: 575
000

SEQ ID NO: 576 moltype = length =
SEQUENCE: 576
000

SEQ ID NO: 577 moltype = length =
SEQUENCE: 577
000

SEQ ID NO: 578 moltype = length =
SEQUENCE: 578
000

SEQ ID NO: 579 moltype = length =
SEQUENCE: 579
000

SEQ ID NO: 580 moltype = length =
SEQUENCE: 580
000

SEQ ID NO: 581 moltype = length =
SEQUENCE: 581
000

SEQ ID NO: 582 moltype = length =
SEQUENCE: 582
000

SEQ ID NO: 583 moltype = length =
SEQUENCE: 583
000

SEQ ID NO: 584 moltype = length =
SEQUENCE: 584
000

SEQ ID NO: 585 moltype = length =
SEQUENCE: 585
000

SEQ ID NO: 586 moltype = length =
SEQUENCE: 586
000

SEQ ID NO: 587 moltype = length =
SEQUENCE: 587
000

SEQ ID NO: 588 moltype = length =
SEQUENCE: 588
000

SEQ ID NO: 589 moltype = length =
SEQUENCE: 589
000

SEQ ID NO: 590 moltype = length =
SEQUENCE: 590

000

SEQ ID NO: 591 moltype = length =
SEQUENCE: 591
000

SEQ ID NO: 592 moltype = length =
SEQUENCE: 592
000

SEQ ID NO: 593 moltype = length =
SEQUENCE: 593
000

SEQ ID NO: 594 moltype = length =
SEQUENCE: 594
000

SEQ ID NO: 595 moltype = length =
SEQUENCE: 595
000

SEQ ID NO: 596 moltype = length =
SEQUENCE: 596
000

SEQ ID NO: 597 moltype = length =
SEQUENCE: 597
000

SEQ ID NO: 598 moltype = length =
SEQUENCE: 598
000

SEQ ID NO: 599 moltype = length =
SEQUENCE: 599
000

SEQ ID NO: 600 moltype = length =
SEQUENCE: 600
000

SEQ ID NO: 601 moltype = length =
SEQUENCE: 601
000

SEQ ID NO: 602 moltype = length =
SEQUENCE: 602
000

SEQ ID NO: 603 moltype = length =
SEQUENCE: 603
000

SEQ ID NO: 604 moltype = length =
SEQUENCE: 604
000

SEQ ID NO: 605 moltype = length =
SEQUENCE: 605
000

SEQ ID NO: 606 moltype = length =
SEQUENCE: 606
000

SEQ ID NO: 607 moltype = length =
SEQUENCE: 607
000

SEQ ID NO: 608 moltype = length =
SEQUENCE: 608
000

SEQ ID NO: 609 moltype = length =
SEQUENCE: 609
000

SEQ ID NO: 610 moltype = length =

SEQUENCE: 610
000

SEQ ID NO: 611 moltype = length =
SEQUENCE: 611
000

SEQ ID NO: 612 moltype = length =
SEQUENCE: 612
000

SEQ ID NO: 613 moltype = length =
SEQUENCE: 613
000

SEQ ID NO: 614 moltype = length =
SEQUENCE: 614
000

SEQ ID NO: 615 moltype = length =
SEQUENCE: 615
000

SEQ ID NO: 616 moltype = length =
SEQUENCE: 616
000

SEQ ID NO: 617 moltype = length =
SEQUENCE: 617
000

SEQ ID NO: 618 moltype = length =
SEQUENCE: 618
000

SEQ ID NO: 619 moltype = length =
SEQUENCE: 619
000

SEQ ID NO: 620 moltype = length =
SEQUENCE: 620
000

SEQ ID NO: 621 moltype = length =
SEQUENCE: 621
000

SEQ ID NO: 622 moltype = length =
SEQUENCE: 622
000

SEQ ID NO: 623 moltype = length =
SEQUENCE: 623
000

SEQ ID NO: 624 moltype = length =
SEQUENCE: 624
000

SEQ ID NO: 625 moltype = length =
SEQUENCE: 625
000

SEQ ID NO: 626 moltype = length =
SEQUENCE: 626
000

SEQ ID NO: 627 moltype = length =
SEQUENCE: 627
000

SEQ ID NO: 628 moltype = length =
SEQUENCE: 628
000

SEQ ID NO: 629 moltype = length =
SEQUENCE: 629
000

-continued

SEQ ID NO: 630 moltype = length =
SEQUENCE: 630
000

SEQ ID NO: 631 moltype = length =
SEQUENCE: 631
000

SEQ ID NO: 632 moltype = length =
SEQUENCE: 632
000

SEQ ID NO: 633 moltype = length =
SEQUENCE: 633
000

SEQ ID NO: 634 moltype = length =
SEQUENCE: 634
000

SEQ ID NO: 635 moltype = length =
SEQUENCE: 635
000

SEQ ID NO: 636 moltype = length =
SEQUENCE: 636
000

SEQ ID NO: 637 moltype = length =
SEQUENCE: 637
000

SEQ ID NO: 638 moltype = length =
SEQUENCE: 638
000

SEQ ID NO: 639 moltype = length =
SEQUENCE: 639
000

SEQ ID NO: 640 moltype = length =
SEQUENCE: 640
000

SEQ ID NO: 641 moltype = length =
SEQUENCE: 641
000

SEQ ID NO: 642 moltype = length =
SEQUENCE: 642
000

SEQ ID NO: 643 moltype = length =
SEQUENCE: 643
000

SEQ ID NO: 644 moltype = length =
SEQUENCE: 644
000

SEQ ID NO: 645 moltype = length =
SEQUENCE: 645
000

SEQ ID NO: 646 moltype = length =
SEQUENCE: 646
000

SEQ ID NO: 647 moltype = length =
SEQUENCE: 647
000

SEQ ID NO: 648 moltype = length =
SEQUENCE: 648
000

SEQ ID NO: 649 moltype = length =
SEQUENCE: 649
000

SEQ ID NO: 650 moltype = length =
SEQUENCE: 650
000

SEQ ID NO: 651 moltype = length =
SEQUENCE: 651
000

SEQ ID NO: 652 moltype = length =
SEQUENCE: 652
000

SEQ ID NO: 653 moltype = length =
SEQUENCE: 653
000

SEQ ID NO: 654 moltype = length =
SEQUENCE: 654
000

SEQ ID NO: 655 moltype = length =
SEQUENCE: 655
000

SEQ ID NO: 656 moltype = length =
SEQUENCE: 656
000

SEQ ID NO: 657 moltype = length =
SEQUENCE: 657
000

SEQ ID NO: 658 moltype = length =
SEQUENCE: 658
000

SEQ ID NO: 659 moltype = length =
SEQUENCE: 659
000

SEQ ID NO: 660 moltype = length =
SEQUENCE: 660
000

SEQ ID NO: 661 moltype = length =
SEQUENCE: 661
000

SEQ ID NO: 662 moltype = length =
SEQUENCE: 662
000

SEQ ID NO: 663 moltype = length =
SEQUENCE: 663
000

SEQ ID NO: 664 moltype = length =
SEQUENCE: 664
000

SEQ ID NO: 665 moltype = length =
SEQUENCE: 665
000

SEQ ID NO: 666 moltype = length =
SEQUENCE: 666
000

SEQ ID NO: 667 moltype = length =
SEQUENCE: 667
000

SEQ ID NO: 668 moltype = length =
SEQUENCE: 668
000

SEQ ID NO: 669 moltype = length =
SEQUENCE: 669

000

SEQ ID NO: 670 moltype = length =
SEQUENCE: 670
000

SEQ ID NO: 671 moltype = length =
SEQUENCE: 671
000

SEQ ID NO: 672 moltype = length =
SEQUENCE: 672
000

SEQ ID NO: 673 moltype = length =
SEQUENCE: 673
000

SEQ ID NO: 674 moltype = length =
SEQUENCE: 674
000

SEQ ID NO: 675 moltype = length =
SEQUENCE: 675
000

SEQ ID NO: 676 moltype = length =
SEQUENCE: 676
000

SEQ ID NO: 677 moltype = length =
SEQUENCE: 677
000

SEQ ID NO: 678 moltype = length =
SEQUENCE: 678
000

SEQ ID NO: 679 moltype = length =
SEQUENCE: 679
000

SEQ ID NO: 680 moltype = length =
SEQUENCE: 680
000

SEQ ID NO: 681 moltype = length =
SEQUENCE: 681
000

SEQ ID NO: 682 moltype = length =
SEQUENCE: 682
000

SEQ ID NO: 683 moltype = length =
SEQUENCE: 683
000

SEQ ID NO: 684 moltype = length =
SEQUENCE: 684
000

SEQ ID NO: 685 moltype = length =
SEQUENCE: 685
000

SEQ ID NO: 686 moltype = length =
SEQUENCE: 686
000

SEQ ID NO: 687 moltype = length =
SEQUENCE: 687
000

SEQ ID NO: 688 moltype = length =
SEQUENCE: 688
000

SEQ ID NO: 689 moltype = length =

SEQUENCE: 689
000

SEQ ID NO: 690 moltype = length =
SEQUENCE: 690
000

SEQ ID NO: 691 moltype = length =
SEQUENCE: 691
000

SEQ ID NO: 692 moltype = length =
SEQUENCE: 692
000

SEQ ID NO: 693 moltype = length =
SEQUENCE: 693
000

SEQ ID NO: 694 moltype = length =
SEQUENCE: 694
000

SEQ ID NO: 695 moltype = length =
SEQUENCE: 695
000

SEQ ID NO: 696 moltype = length =
SEQUENCE: 696
000

SEQ ID NO: 697 moltype = length =
SEQUENCE: 697
000

SEQ ID NO: 698 moltype = length =
SEQUENCE: 698
000

SEQ ID NO: 699 moltype = length =
SEQUENCE: 699
000

SEQ ID NO: 700 moltype = length =
SEQUENCE: 700
000

SEQ ID NO: 701 moltype = length =
SEQUENCE: 701
000

SEQ ID NO: 702 moltype = length =
SEQUENCE: 702
000

SEQ ID NO: 703 moltype = length =
SEQUENCE: 703
000

SEQ ID NO: 704 moltype = length =
SEQUENCE: 704
000

SEQ ID NO: 705 moltype = length =
SEQUENCE: 705
000

SEQ ID NO: 706 moltype = length =
SEQUENCE: 706
000

SEQ ID NO: 707 moltype = length =
SEQUENCE: 707
000

SEQ ID NO: 708 moltype = length =
SEQUENCE: 708
000

-continued

SEQ ID NO: 709 moltype = length =
SEQUENCE: 709
000

SEQ ID NO: 710 moltype = length =
SEQUENCE: 710
000

SEQ ID NO: 711 moltype = length =
SEQUENCE: 711
000

SEQ ID NO: 712 moltype = length =
SEQUENCE: 712
000

SEQ ID NO: 713 moltype = length =
SEQUENCE: 713
000

SEQ ID NO: 714 moltype = length =
SEQUENCE: 714
000

SEQ ID NO: 715 moltype = length =
SEQUENCE: 715
000

SEQ ID NO: 716 moltype = length =
SEQUENCE: 716
000

SEQ ID NO: 717 moltype = length =
SEQUENCE: 717
000

SEQ ID NO: 718 moltype = length =
SEQUENCE: 718
000

SEQ ID NO: 719 moltype = length =
SEQUENCE: 719
000

SEQ ID NO: 720 moltype = length =
SEQUENCE: 720
000

SEQ ID NO: 721 moltype = length =
SEQUENCE: 721
000

SEQ ID NO: 722 moltype = length =
SEQUENCE: 722
000

SEQ ID NO: 723 moltype = length =
SEQUENCE: 723
000

SEQ ID NO: 724 moltype = length =
SEQUENCE: 724
000

SEQ ID NO: 725 moltype = length =
SEQUENCE: 725
000

SEQ ID NO: 726 moltype = length =
SEQUENCE: 726
000

SEQ ID NO: 727 moltype = length =
SEQUENCE: 727
000

SEQ ID NO: 728 moltype = length =
SEQUENCE: 728
000

SEQ ID NO: 729 moltype = length =
SEQUENCE: 729
000

SEQ ID NO: 730 moltype = length =
SEQUENCE: 730
000

SEQ ID NO: 731 moltype = length =
SEQUENCE: 731
000

SEQ ID NO: 732 moltype = length =
SEQUENCE: 732
000

SEQ ID NO: 733 moltype = length =
SEQUENCE: 733
000

SEQ ID NO: 734 moltype = length =
SEQUENCE: 734
000

SEQ ID NO: 735 moltype = length =
SEQUENCE: 735
000

SEQ ID NO: 736 moltype = length =
SEQUENCE: 736
000

SEQ ID NO: 737 moltype = length =
SEQUENCE: 737
000

SEQ ID NO: 738 moltype = length =
SEQUENCE: 738
000

SEQ ID NO: 739 moltype = length =
SEQUENCE: 739
000

SEQ ID NO: 740 moltype = length =
SEQUENCE: 740
000

SEQ ID NO: 741 moltype = length =
SEQUENCE: 741
000

SEQ ID NO: 742 moltype = length =
SEQUENCE: 742
000

SEQ ID NO: 743 moltype = length =
SEQUENCE: 743
000

SEQ ID NO: 744 moltype = length =
SEQUENCE: 744
000

SEQ ID NO: 745 moltype = length =
SEQUENCE: 745
000

SEQ ID NO: 746 moltype = length =
SEQUENCE: 746
000

SEQ ID NO: 747 moltype = length =
SEQUENCE: 747
000

SEQ ID NO: 748 moltype = length =
SEQUENCE: 748

-continued

000

SEQ ID NO: 749 moltype = length =
SEQUENCE: 749
000

SEQ ID NO: 750 moltype = length =
SEQUENCE: 750
000

SEQ ID NO: 751 moltype = length =
SEQUENCE: 751
000

SEQ ID NO: 752 moltype = length =
SEQUENCE: 752
000

SEQ ID NO: 753 moltype = length =
SEQUENCE: 753
000

SEQ ID NO: 754 moltype = length =
SEQUENCE: 754
000

SEQ ID NO: 755 moltype = length =
SEQUENCE: 755
000

SEQ ID NO: 756 moltype = length =
SEQUENCE: 756
000

SEQ ID NO: 757 moltype = length =
SEQUENCE: 757
000

SEQ ID NO: 758 moltype = length =
SEQUENCE: 758
000

SEQ ID NO: 759 moltype = length =
SEQUENCE: 759
000

SEQ ID NO: 760 moltype = length =
SEQUENCE: 760
000

SEQ ID NO: 761 moltype = length =
SEQUENCE: 761
000

SEQ ID NO: 762 moltype = length =
SEQUENCE: 762
000

SEQ ID NO: 763 moltype = length =
SEQUENCE: 763
000

SEQ ID NO: 764 moltype = length =
SEQUENCE: 764
000

SEQ ID NO: 765 moltype = length =
SEQUENCE: 765
000

SEQ ID NO: 766 moltype = length =
SEQUENCE: 766
000

SEQ ID NO: 767 moltype = length =
SEQUENCE: 767
000

SEQ ID NO: 768 moltype = length =

SEQUENCE: 768
000

SEQ ID NO: 769 moltype = length =
SEQUENCE: 769
000

SEQ ID NO: 770 moltype = length =
SEQUENCE: 770
000

SEQ ID NO: 771 moltype = length =
SEQUENCE: 771
000

SEQ ID NO: 772 moltype = length =
SEQUENCE: 772
000

SEQ ID NO: 773 moltype = length =
SEQUENCE: 773
000

SEQ ID NO: 774 moltype = length =
SEQUENCE: 774
000

SEQ ID NO: 775 moltype = length =
SEQUENCE: 775
000

SEQ ID NO: 776 moltype = length =
SEQUENCE: 776
000

SEQ ID NO: 777 moltype = length =
SEQUENCE: 777
000

SEQ ID NO: 778 moltype = length =
SEQUENCE: 778
000

SEQ ID NO: 779 moltype = length =
SEQUENCE: 779
000

SEQ ID NO: 780 moltype = length =
SEQUENCE: 780
000

SEQ ID NO: 781 moltype = length =
SEQUENCE: 781
000

SEQ ID NO: 782 moltype = length =
SEQUENCE: 782
000

SEQ ID NO: 783 moltype = length =
SEQUENCE: 783
000

SEQ ID NO: 784 moltype = length =
SEQUENCE: 784
000

SEQ ID NO: 785 moltype = length =
SEQUENCE: 785
000

SEQ ID NO: 786 moltype = length =
SEQUENCE: 786
000

SEQ ID NO: 787 moltype = length =
SEQUENCE: 787
000

-continued

SEQ ID NO: 788 moltype = length =
SEQUENCE: 788
000

SEQ ID NO: 789 moltype = length =
SEQUENCE: 789
000

SEQ ID NO: 790 moltype = length =
SEQUENCE: 790
000

SEQ ID NO: 791 moltype = length =
SEQUENCE: 791
000

SEQ ID NO: 792 moltype = length =
SEQUENCE: 792
000

SEQ ID NO: 793 moltype = length =
SEQUENCE: 793
000

SEQ ID NO: 794 moltype = length =
SEQUENCE: 794
000

SEQ ID NO: 795 moltype = length =
SEQUENCE: 795
000

SEQ ID NO: 796 moltype = length =
SEQUENCE: 796
000

SEQ ID NO: 797 moltype = length =
SEQUENCE: 797
000

SEQ ID NO: 798 moltype = length =
SEQUENCE: 798
000

SEQ ID NO: 799 moltype = length =
SEQUENCE: 799
000

SEQ ID NO: 800 moltype = length =
SEQUENCE: 800
000

SEQ ID NO: 801 moltype = length =
SEQUENCE: 801
000

SEQ ID NO: 802 moltype = length =
SEQUENCE: 802
000

SEQ ID NO: 803 moltype = length =
SEQUENCE: 803
000

SEQ ID NO: 804 moltype = length =
SEQUENCE: 804
000

SEQ ID NO: 805 moltype = length =
SEQUENCE: 805
000

SEQ ID NO: 806 moltype = length =
SEQUENCE: 806
000

SEQ ID NO: 807 moltype = length =
SEQUENCE: 807
000

SEQ ID NO: 808 moltype = length =
SEQUENCE: 808
000

SEQ ID NO: 809 moltype = length =
SEQUENCE: 809
000

SEQ ID NO: 810 moltype = length =
SEQUENCE: 810
000

SEQ ID NO: 811 moltype = length =
SEQUENCE: 811
000

SEQ ID NO: 812 moltype = length =
SEQUENCE: 812
000

SEQ ID NO: 813 moltype = length =
SEQUENCE: 813
000

SEQ ID NO: 814 moltype = length =
SEQUENCE: 814
000

SEQ ID NO: 815 moltype = length =
SEQUENCE: 815
000

SEQ ID NO: 816 moltype = length =
SEQUENCE: 816
000

SEQ ID NO: 817 moltype = length =
SEQUENCE: 817
000

SEQ ID NO: 818 moltype = length =
SEQUENCE: 818
000

SEQ ID NO: 819 moltype = length =
SEQUENCE: 819
000

SEQ ID NO: 820 moltype = length =
SEQUENCE: 820
000

SEQ ID NO: 821 moltype = length =
SEQUENCE: 821
000

SEQ ID NO: 822 moltype = length =
SEQUENCE: 822
000

SEQ ID NO: 823 moltype = length =
SEQUENCE: 823
000

SEQ ID NO: 824 moltype = length =
SEQUENCE: 824
000

SEQ ID NO: 825 moltype = length =
SEQUENCE: 825
000

SEQ ID NO: 826 moltype = length =
SEQUENCE: 826
000

SEQ ID NO: 827 moltype = length =
SEQUENCE: 827

000

SEQ ID NO: 828 moltype = length =
SEQUENCE: 828
000

SEQ ID NO: 829 moltype = length =
SEQUENCE: 829
000

SEQ ID NO: 830 moltype = length =
SEQUENCE: 830
000

SEQ ID NO: 831 moltype = length =
SEQUENCE: 831
000

SEQ ID NO: 832 moltype = length =
SEQUENCE: 832
000

SEQ ID NO: 833 moltype = length =
SEQUENCE: 833
000

SEQ ID NO: 834 moltype = length =
SEQUENCE: 834
000

SEQ ID NO: 835 moltype = length =
SEQUENCE: 835
000

SEQ ID NO: 836 moltype = length =
SEQUENCE: 836
000

SEQ ID NO: 837 moltype = length =
SEQUENCE: 837
000

SEQ ID NO: 838 moltype = length =
SEQUENCE: 838
000

SEQ ID NO: 839 moltype = length =
SEQUENCE: 839
000

SEQ ID NO: 840 moltype = length =
SEQUENCE: 840
000

SEQ ID NO: 841 moltype = length =
SEQUENCE: 841
000

SEQ ID NO: 842 moltype = length =
SEQUENCE: 842
000

SEQ ID NO: 843 moltype = length =
SEQUENCE: 843
000

SEQ ID NO: 844 moltype = length =
SEQUENCE: 844
000

SEQ ID NO: 845 moltype = length =
SEQUENCE: 845
000

SEQ ID NO: 846 moltype = length =
SEQUENCE: 846
000

SEQ ID NO: 847 moltype = length =

SEQUENCE: 847
000

SEQ ID NO: 848 moltype = length =
SEQUENCE: 848
000

SEQ ID NO: 849 moltype = length =
SEQUENCE: 849
000

SEQ ID NO: 850 moltype = length =
SEQUENCE: 850
000

SEQ ID NO: 851 moltype = length =
SEQUENCE: 851
000

SEQ ID NO: 852 moltype = length =
SEQUENCE: 852
000

SEQ ID NO: 853 moltype = length =
SEQUENCE: 853
000

SEQ ID NO: 854 moltype = length =
SEQUENCE: 854
000

SEQ ID NO: 855 moltype = length =
SEQUENCE: 855
000

SEQ ID NO: 856 moltype = length =
SEQUENCE: 856
000

SEQ ID NO: 857 moltype = length =
SEQUENCE: 857
000

SEQ ID NO: 858 moltype = length =
SEQUENCE: 858
000

SEQ ID NO: 859 moltype = length =
SEQUENCE: 859
000

SEQ ID NO: 860 moltype = length =
SEQUENCE: 860
000

SEQ ID NO: 861 moltype = length =
SEQUENCE: 861
000

SEQ ID NO: 862 moltype = length =
SEQUENCE: 862
000

SEQ ID NO: 863 moltype = length =
SEQUENCE: 863
000

SEQ ID NO: 864 moltype = length =
SEQUENCE: 864
000

SEQ ID NO: 865 moltype = length =
SEQUENCE: 865
000

SEQ ID NO: 866 moltype = length =
SEQUENCE: 866
000

-continued

SEQ ID NO: 867 moltype = length =
SEQUENCE: 867
000

SEQ ID NO: 868 moltype = length =
SEQUENCE: 868
000

SEQ ID NO: 869 moltype = length =
SEQUENCE: 869
000

SEQ ID NO: 870 moltype = length =
SEQUENCE: 870
000

SEQ ID NO: 871 moltype = length =
SEQUENCE: 871
000

SEQ ID NO: 872 moltype = length =
SEQUENCE: 872
000

SEQ ID NO: 873 moltype = length =
SEQUENCE: 873
000

SEQ ID NO: 874 moltype = length =
SEQUENCE: 874
000

SEQ ID NO: 875 moltype = length =
SEQUENCE: 875
000

SEQ ID NO: 876 moltype = length =
SEQUENCE: 876
000

SEQ ID NO: 877 moltype = length =
SEQUENCE: 877
000

SEQ ID NO: 878 moltype = length =
SEQUENCE: 878
000

SEQ ID NO: 879 moltype = length =
SEQUENCE: 879
000

SEQ ID NO: 880 moltype = length =
SEQUENCE: 880
000

SEQ ID NO: 881 moltype = length =
SEQUENCE: 881
000

SEQ ID NO: 882 moltype = length =
SEQUENCE: 882
000

SEQ ID NO: 883 moltype = length =
SEQUENCE: 883
000

SEQ ID NO: 884 moltype = length =
SEQUENCE: 884
000

SEQ ID NO: 885 moltype = length =
SEQUENCE: 885
000

SEQ ID NO: 886 moltype = length =
SEQUENCE: 886
000

-continued

SEQ ID NO: 887 moltype = length =
SEQUENCE: 887
000

SEQ ID NO: 888 moltype = length =
SEQUENCE: 888
000

SEQ ID NO: 889 moltype = length =
SEQUENCE: 889
000

SEQ ID NO: 890 moltype = length =
SEQUENCE: 890
000

SEQ ID NO: 891 moltype = length =
SEQUENCE: 891
000

SEQ ID NO: 892 moltype = length =
SEQUENCE: 892
000

SEQ ID NO: 893 moltype = length =
SEQUENCE: 893
000

SEQ ID NO: 894 moltype = length =
SEQUENCE: 894
000

SEQ ID NO: 895 moltype = length =
SEQUENCE: 895
000

SEQ ID NO: 896 moltype = length =
SEQUENCE: 896
000

SEQ ID NO: 897 moltype = length =
SEQUENCE: 897
000

SEQ ID NO: 898 moltype = length =
SEQUENCE: 898
000

SEQ ID NO: 899 moltype = length =
SEQUENCE: 899
000

SEQ ID NO: 900 moltype = length =
SEQUENCE: 900
000

SEQ ID NO: 901 moltype = length =
SEQUENCE: 901
000

SEQ ID NO: 902 moltype = length =
SEQUENCE: 902
000

SEQ ID NO: 903 moltype = length =
SEQUENCE: 903
000

SEQ ID NO: 904 moltype = length =
SEQUENCE: 904
000

SEQ ID NO: 905 moltype = length =
SEQUENCE: 905
000

SEQ ID NO: 906 moltype = length =
SEQUENCE: 906

000

SEQ ID NO: 907 moltype = length =
SEQUENCE: 907
000

SEQ ID NO: 908 moltype = length =
SEQUENCE: 908
000

SEQ ID NO: 909 moltype = length =
SEQUENCE: 909
000

SEQ ID NO: 910 moltype = length =
SEQUENCE: 910
000

SEQ ID NO: 911 moltype = length =
SEQUENCE: 911
000

SEQ ID NO: 912 moltype = length =
SEQUENCE: 912
000

SEQ ID NO: 913 moltype = length =
SEQUENCE: 913
000

SEQ ID NO: 914 moltype = length =
SEQUENCE: 914
000

SEQ ID NO: 915 moltype = length =
SEQUENCE: 915
000

SEQ ID NO: 916 moltype = length =
SEQUENCE: 916
000

SEQ ID NO: 917 moltype = length =
SEQUENCE: 917
000

SEQ ID NO: 918 moltype = length =
SEQUENCE: 918
000

SEQ ID NO: 919 moltype = length =
SEQUENCE: 919
000

SEQ ID NO: 920 moltype = length =
SEQUENCE: 920
000

SEQ ID NO: 921 moltype = length =
SEQUENCE: 921
000

SEQ ID NO: 922 moltype = length =
SEQUENCE: 922
000

SEQ ID NO: 923 moltype = length =
SEQUENCE: 923
000

SEQ ID NO: 924 moltype = length =
SEQUENCE: 924
000

SEQ ID NO: 925 moltype = length =
SEQUENCE: 925
000

SEQ ID NO: 926 moltype = length =

SEQUENCE: 926
000

SEQ ID NO: 927 moltype = length =
SEQUENCE: 927
000

SEQ ID NO: 928 moltype = length =
SEQUENCE: 928
000

SEQ ID NO: 929 moltype = length =
SEQUENCE: 929
000

SEQ ID NO: 930 moltype = length =
SEQUENCE: 930
000

SEQ ID NO: 931 moltype = length =
SEQUENCE: 931
000

SEQ ID NO: 932 moltype = length =
SEQUENCE: 932
000

SEQ ID NO: 933 moltype = length =
SEQUENCE: 933
000

SEQ ID NO: 934 moltype = length =
SEQUENCE: 934
000

SEQ ID NO: 935 moltype = length =
SEQUENCE: 935
000

SEQ ID NO: 936 moltype = length =
SEQUENCE: 936
000

SEQ ID NO: 937 moltype = length =
SEQUENCE: 937
000

SEQ ID NO: 938 moltype = length =
SEQUENCE: 938
000

SEQ ID NO: 939 moltype = length =
SEQUENCE: 939
000

SEQ ID NO: 940 moltype = length =
SEQUENCE: 940
000

SEQ ID NO: 941 moltype = length =
SEQUENCE: 941
000

SEQ ID NO: 942 moltype = length =
SEQUENCE: 942
000

SEQ ID NO: 943 moltype = length =
SEQUENCE: 943
000

SEQ ID NO: 944 moltype = length =
SEQUENCE: 944
000

SEQ ID NO: 945 moltype = length =
SEQUENCE: 945
000

-continued

SEQ ID NO: 946 moltype = length =
SEQUENCE: 946
000

SEQ ID NO: 947 moltype = length =
SEQUENCE: 947
000

SEQ ID NO: 948 moltype = length =
SEQUENCE: 948
000

SEQ ID NO: 949 moltype = length =
SEQUENCE: 949
000

SEQ ID NO: 950 moltype = length =
SEQUENCE: 950
000

SEQ ID NO: 951 moltype = length =
SEQUENCE: 951
000

SEQ ID NO: 952 moltype = length =
SEQUENCE: 952
000

SEQ ID NO: 953 moltype = length =
SEQUENCE: 953
000

SEQ ID NO: 954 moltype = length =
SEQUENCE: 954
000

SEQ ID NO: 955 moltype = length =
SEQUENCE: 955
000

SEQ ID NO: 956 moltype = length =
SEQUENCE: 956
000

SEQ ID NO: 957 moltype = length =
SEQUENCE: 957
000

SEQ ID NO: 958 moltype = length =
SEQUENCE: 958
000

SEQ ID NO: 959 moltype = length =
SEQUENCE: 959
000

SEQ ID NO: 960 moltype = length =
SEQUENCE: 960
000

SEQ ID NO: 961 moltype = length =
SEQUENCE: 961
000

SEQ ID NO: 962 moltype = length =
SEQUENCE: 962
000

SEQ ID NO: 963 moltype = length =
SEQUENCE: 963
000

SEQ ID NO: 964 moltype = length =
SEQUENCE: 964
000

SEQ ID NO: 965 moltype = length =
SEQUENCE: 965
000

-continued

SEQ ID NO: 966 moltype = length =
SEQUENCE: 966
000

SEQ ID NO: 967 moltype = length =
SEQUENCE: 967
000

SEQ ID NO: 968 moltype = length =
SEQUENCE: 968
000

SEQ ID NO: 969 moltype = length =
SEQUENCE: 969
000

SEQ ID NO: 970 moltype = length =
SEQUENCE: 970
000

SEQ ID NO: 971 moltype = length =
SEQUENCE: 971
000

SEQ ID NO: 972 moltype = length =
SEQUENCE: 972
000

SEQ ID NO: 973 moltype = length =
SEQUENCE: 973
000

SEQ ID NO: 974 moltype = length =
SEQUENCE: 974
000

SEQ ID NO: 975 moltype = length =
SEQUENCE: 975
000

SEQ ID NO: 976 moltype = length =
SEQUENCE: 976
000

SEQ ID NO: 977 moltype = length =
SEQUENCE: 977
000

SEQ ID NO: 978 moltype = length =
SEQUENCE: 978
000

SEQ ID NO: 979 moltype = length =
SEQUENCE: 979
000

SEQ ID NO: 980 moltype = length =
SEQUENCE: 980
000

SEQ ID NO: 981 moltype = length =
SEQUENCE: 981
000

SEQ ID NO: 982 moltype = length =
SEQUENCE: 982
000

SEQ ID NO: 983 moltype = length =
SEQUENCE: 983
000

SEQ ID NO: 984 moltype = length =
SEQUENCE: 984
000

SEQ ID NO: 985 moltype = length =
SEQUENCE: 985

000

SEQ ID NO: 986 moltype = length =
SEQUENCE: 986
000

SEQ ID NO: 987 moltype = length =
SEQUENCE: 987
000

SEQ ID NO: 988 moltype = length =
SEQUENCE: 988
000

SEQ ID NO: 989 moltype = length =
SEQUENCE: 989
000

SEQ ID NO: 990 moltype = length =
SEQUENCE: 990
000

SEQ ID NO: 991 moltype = length =
SEQUENCE: 991
000

SEQ ID NO: 992 moltype = length =
SEQUENCE: 992
000

SEQ ID NO: 993 moltype = length =
SEQUENCE: 993
000

SEQ ID NO: 994 moltype = length =
SEQUENCE: 994
000

SEQ ID NO: 995 moltype = length =
SEQUENCE: 995
000

SEQ ID NO: 996 moltype = length =
SEQUENCE: 996
000

SEQ ID NO: 997 moltype = length =
SEQUENCE: 997
000

SEQ ID NO: 998 moltype = length =
SEQUENCE: 998
000

SEQ ID NO: 999 moltype = length =
SEQUENCE: 999
000

SEQ ID NO: 1000 moltype = DNA length = 1182
FEATURE Location/Qualifiers
source 1..1182
mol_type = genomic DNA
organism = Brevibacterium aurantiacum
SEQUENCE: 1000
atgacgagcc ttcaccccga aactttaatg gtgcacgggg gtatgaaggg attgacagag 60
gcgggtgttc acgtcccggc gatcgacctg tcgacaacga atcctgttaa tgacgtagcg 120
acagggggtg attcttacga atggcttgca acgggtcaca cgttgaagga tggtgattct 180
gctgtttacc agcgtttatg gcagcccggt gtagctcgtt tcgagacggc tctggctggg 240
ctggagcacg cggaggaggc tgtagctttc gccacgggta tggccgccat gaccgcggcc 300
ttattggcag cagtatcagc tggcacgcct catatcgtcg cagtccgccc attatacggc 360
ggttcagacc atcttttaga gactggttta ctggggacaa ctgtcacgtg ggcgaaagaa 420
gctgacatcg ccagtgcaat ccaagacgat acagggttag tgatcgtgga gacgccagcc 480
aatcctagtc ttgatctggt agacctggat tctgtcgtgt cagcggcagg gaacgtccct 540
gtccttgtag ataatacgtt ttgtactcct gtccttcagc aacctatctc gcacggcgcc 600
gcacttgtat tacattcggc aacaaagtat ttagggggc atggggacgc catgggcggg 660
atcatcgcga ctaatgctga ttgggctatg cgcctgcgtc aggtccgtgc gatcactggt 720
gcattactgc atccgatggg cgcgtacttg ttacaccgcg gtttgcgtac tctggctgtt 780
cgcatgcgtg ccgctcagac aactgctggt gagcttgctg agcgcttaga cgctcatccc 840
gctatttcag ttgtgcacta cccaggattg aaggggcaag atcctcgtgg attgttaggc 900

```
cgtcagatga gtggaggtgg ggcaatgatt gctatggagc tggcaggggg attcgatgcg  960
gcacgctcct ttgttgagca ttgtaacttg gtcgtgcatg ccgtatcact tgggggagca  1020
gacacattaa ttcaacatcc ggcaagtttg acacaccgcc cggtcgcagc aaccgccaag  1080
cctggtgatg gtttgatccg cttgagcgtg gggcttgagc acgttgacga cttggccgat  1140
gacttgatcg ctgctttgga cgcctctcgc gctgctgcat ga                    1182

SEQ ID NO: 1001        moltype = DNA  length = 1197
FEATURE                Location/Qualifiers
source                 1..1197
                       mol_type = genomic DNA
                       organism = Citrobacter freundii
SEQUENCE: 1001
atgtctgatt gtcgtgccta cggctttaac acacagatcg tccacgccgg acaacaaccg  60
gacccaagca ctggtgcatt gtcgacgcca atctttcaga cttctacttt cgttttcgat  120
tcggcagaac agggggccgc acgtttcgcg ttggaggaac cgggatacat ctatacgcgc  180
ttgggcaatc caactactga tgcgcttgaa aagaaacttg cagtgctgga acgtggggac  240
gcggcgttag ccacagcgag cggcatctcc gctattacca caagtcttct tactctttgc  300
cagcaagggg accatatcgt atcagctagt gcaatctacg gttgcactca cgcattctta  360
agtcattcgc ttcctaaatt tggcattaac gtttcattcg tcgacgcagc gaagcccgaa  420
gaaatccgcg ccgccatgcg tccagagaca aaagtggtat atatcgagac gcccgcgaac  480
cctactttat ccttagtgga tattgagact gttgctggaa tcgcgcacca gcaaggagcc  540
ttgttagtcg tggacaacac ttttatgtct ccgtattgtc aacaaccatt actgctgggt  600
gctgacatcg tggtccatag tgttaccaag tacattaacg ggcatgggga tgttattggc  660
ggtgtcatcg taggtaaaca ggagttcatc gaccaagcac gctttgtggg attaaaggac  720
attacgggcg gatgcatgag ccccttttaat gcatggctga cacttcgcgg ggtaaagacg  780
ttagggatcc gtatggagcg tcattgcgaa aacgcattga aaatcgcgcg ttttcttgag  840
ggccatcctg ctattacacg tgtctattat cctggattgc cgtcacaccc ccaatacgaa  900
cttgggaagc gccaaatgtc gcttcctggg ggaatcattt cgtttgaaat tgctggtggc  960
cttgaagcag gtcgccgtat gattaacagc gtggagttat gtttgctggc agttagctta  1020
ggtgatacgg agacgttgat tcagcatccg gcgagcatga cacattcccc tgttgctccc  1080
gaggagcgtc tgaaggctgg catcactgat ggactgatcc gtttgtccgt cggccttgaa  1140
gatccggaag acatcattaa cgacctggag cacgccattc gcaaggcaac gttttaa     1197

SEQ ID NO: 1002        moltype = DNA  length = 1200
FEATURE                Location/Qualifiers
source                 1..1200
                       mol_type = genomic DNA
                       organism = Porphyromonas gingivalis
SEQUENCE: 1002
atgaagaaag aggacttaat gcgttcgggg ttcgcaactc gtgctattca tggtggagcc  60
atcgaaaatg cttttgggtg cctggccacc cccatctacc aaacttcaac gtttgttttc  120
gatacggctg aacagggtgg acgtcgcttt gcgggtgaag aagatgggta catttacact  180
cgcttaggaa acccgaactg tacccaggtt gaggagaagc tggcgatgtt agaaggaggg  240
gaagcagcgg cctccgcaag tagtggtatc ggagcgatct cttcagctat ctgggtgtgc  300
gtcaaggcgg gagatcatat tgtagcggga aaaactttgt acggttgcac gtttgcgttc  360
ttgacccacg gactttctcg ctatggagtt gaggtcacct tggtggacac gcgccatcca  420
gaagaggttg aggccgctat tcgtccaaac actaagttgg tctatttgga aactcccgca  480
aaccctaaca tgtaccttac tgatatcaaa gctgtgtgtg atatcgcgca caagcatgag  540
ggtgttcgcg tcatggtgga taatacctac tgtacacctt acatctgtcg cccactggag  600
ttaggtgctg atattgttgt ccattccgcc acaaaatatc tgaacggaca tggagatgtt  660
atcgctgggt ttgtagtagg gaaagaggat tacatcaagg aggtcaaatt ggttggtgtt  720
aaggacttga caggagccaa tatgtcaccc ttcgacgcat accttattag tcgtggtatg  780
aagacgttac aaatccgtat ggaacaacat tgccgtaacg cacaaacagt tgctgagttt  840
ctggagaagc atcctgcggt tgaggcggtg tacttcccgg gcttgccttc attcccgcaa  900
tatgagttgg ccaagaagca gatggcactt ccgggagcga tgattgcgtt tgaagttaag  960
ggaggctgcg aagccggtaa gaaacttatg aacaatcttc atctgtgttc cttagccgtc  1020
tccttaggcg ataccgagac tttaatccaa cacccggcct caatgacgca ctcgccctat  1080
acgcccgagg aacgcgccgc aagcgacatc tcggaggggc ttgtacgcct ttctgttgga  1140
ttggaaaatg ttgaggatat tatcgcggac ctgaagcatg gcctggatag tcttatctaa  1200

SEQ ID NO: 1003        moltype = DNA  length = 1674
FEATURE                Location/Qualifiers
source                 1..1674
                       mol_type = genomic DNA
                       organism = Streptomyces sp.
SEQUENCE: 1003
atgtccccga cggcgtttcc agcggccgaa acagctactg cccctgcaac tgccgtcgat  60
cctgggccag aactggacgg cggagatttc gcccttccag agggcgggct ggatgacgat  120
cgtcgcttac gtgcattgga cgcagttgac gagtatttga cccgcaagcg caagcatttg  180
gttgggtacc aagctaccca ggatatgcag ggaacggcct tggatttagc ccgtttcatg  240
cccaacaaca tcaacaacct gggagatcct ttccagtcgg gtgggtataa accaaatacg  300
aaagtcgttg agcgtgccgt actggactac tatgcaaaat tgtggcacgc agaacgtcca  360
cacgacccag ctgacccaga aagctactgg ggttacatgt tatcgatggg ctcaactgag  420
ggcaacatgt acgccctgtg gaatgcacgt gactacctgt cgggtaaggc tttgattcag  480
cctcccacgg caccatttga cgctgttcgc tacgtgaagg ctgaccccga tcgccgcaat  540
cctaacgcac accacccagt cgcattctac tcggaggata cccactattc ttttgctaaa  600
gccgttgcgg tgctgggtgt cgaaactttc cacgctgtgg gtctggagaa atacgctgac  660
gagtgcccct tggtggatcc agtaaccggc cttcgtacct ggccgaccga agttccatcg  720
cgcccggggc cgtcgggttt aagctgggac ggccctggtg agattgatgt tgatgcgctt  780
```

```
gcagtactgg tcgagttctt cgcagcgaag ggtcaccccg tcttcgtcaa ccttaacttg  840
gggtctacat ttaaaggagc acatgatgac gtacgtgcgg tatgtgaacg cttattacca  900
atcttcgagc gccatggctt agtacaacgt gaagttgtat atgggagctg tccccaaacc  960
ggccgcccct tagtggatgt acgtcgcgga ttttggatcc acgtagatgg ggcacttggg  1020
gcggggtatg ccccttttct gcgtcttgcc gccgaagacc cggaaggtta tggttggacc  1080
cctgaggcag aattacctga gttcgacttc ggcttacgtt tgccgacggc ggggcatgga  1140
gaagttgata tggttagcag catcgccatg agtggacata agtgggcagg cgcgccgtgg  1200
ccatgcggca tctatatgac gaaagtgaaa tatcagatta gtccaccgtc acagcccgat  1260
tatattggtg ctcctgacac aacatttgcc ggttcccgta acggcttttc gccgttaatt  1320
ttgtgggatc atttatcgcg ctactcgtac cgcgaccagg tagagcgcat ccgcgaagca  1380
caggagcttg cagcatattt ggaacgccgc cttaccgcta tggagcgcga gctgggagtg  1440
gaactttggc cagcccgcac accgggtgct gtaaccgtac gttttcgcaa accctctgct  1500
gagctggttg cgaagtggtc cttgtcgtcg caggatgttt taatggtgcc gggtgatgaa  1560
actacgcgtc gtagttacgt tcatgtgttc gtgatgcctt ctgttgatcg tgcaaagtta  1620
gatgcgttgc tggcagaatt ggccgaagat cccgtcatct tgggtgcgcc ttaa        1674

SEQ ID NO: 1004        moltype = DNA  length = 1032
FEATURE                Location/Qualifiers
source                 1..1032
                       mol_type = genomic DNA
                       organism = Escherichia coli
SEQUENCE: 1004
atgataaaac tttcgaatat caccaaagtg ttccaccagg gcacccgcac catccaggcg  60
ttgaacaacg tcagcctgca tgtgccagct ggacaaattt atggcgttat cggtgcctca  120
ggcgcgggta agagtacgct tatacgttgt gtaaacctgc tggagcgccc aaccgagggt  180
agcgtgctgg tcgatggcca ggaactgacc acgctgtcag aatccgagtt gaccaaagct  240
cgtcgccaga ttggtatgat tttccagcat tttaacctgc tctcttcgcg tactgttttt  300
ggcaacgtgg ctctgccgct ggagctggac aacacaccga aagacgagat caaacgtcgc  360
gtgacggaat tgctgtcatt ggttggtctt ggcgataagc atgatagcta cccgtcgaat  420
ctttccggtg ggcagaaaca acgtgtggcg attgcccgtg cattagccag caatcccaaa  480
gtattgctgt gtgatgaagc caccagcgcg ctggacccgg caacgacacg ttctattctc  540
gaactgctga aagacatcaa ccgccgtctg ggtttgacga ttctgttgat cactcacgaa  600
atggacgttg tgaagcgcat ttgtgattgc gtggcggtca tcagcaatgg cgaactgatc  660
gagcaggaca cggtaagtga agtgttctcg catccgaaaa cgccgctggc gcagaagttt  720
attcagtcga ccctgcatct ggatatcccg gaagattacc aggaacgtct gcaagcggag  780
ccatttactg actgcgtgcc gatgctgcgt ctggagttta ccggtcaatc ggtcgatgcc  840
ccactgcttt ctgaaaccgc gcgtcgtttc aacgtcaaca acaacattat tagcgcgcag  900
atggattacg ccggtggcgt taagttcggc atcatgctga ctgaaatgca cggcacacaa  960
caagatacgc aagccgccat tgcctggctg caggaacacc atgtaaaagt agaggtactg  1020
ggttatgtct ga                                                    1032

SEQ ID NO: 1005        moltype = DNA  length = 654
FEATURE                Location/Qualifiers
source                 1..654
                       mol_type = genomic DNA
                       organism = Escherichia coli
SEQUENCE: 1005
atgtctgagc cgatgatgtg gctgctggtt cgtggcgtat gggaaacgct ggcaatgacc  60
ttcgtatccg gtttttttgg ctttgtgatt ggtctgccgg ttggcgttct gctttatgtc  120
acgcgtccgg ggcaaattat tgctaacgcg aagttgtatc gtaccatttc tgcgattgtg  180
aacattttcc gttccatccc gttcattatc ttgctggtat ggatgattcc gtttacccgc  240
gttattgtcg gtacatcgat tggattgcag gcagcgattg ttccgttaac cgttggtgca  300
gcaccgttta ttgcccgtat ggtcgagaac gctctgctgg agatcccaac cgggttaatt  360
gaagcttccc gcgcaatggg ggccacgcca atgcagatcg tccgtaaagt gctgttaccg  420
gaagcgttgc cgggtctggt gaatgcggca actatcaccc tgattaccct ggttggttat  480
tccgcgatgg gtggtgcagt cggtgccggt ggtttaggtc agattggcta tcagtatggc  540
tacatcggct acaacgcgac ggtgatgaat acggtactgg tattgctggt cattctggtt  600
tatttaattc agttcgcagg cgaccgcatc gtccgggctg tcactcgcaa gtaa        654

SEQ ID NO: 1006        moltype = DNA  length = 816
FEATURE                Location/Qualifiers
source                 1..816
                       mol_type = genomic DNA
                       organism = Escherichia coli
SEQUENCE: 1006
atggcgttca aattcaaaac ctttgcggca gtgggagccc tgattggatc actggcactg  60
gtaggctgcg gtcaggatga aaaagatcca aaccacatta aagtcggcgt gattgttggt  120
gccgaacagc aggttgcaga agtcgcgcag aaagttgcga aagacaaata tggcctggac  180
gttgagctgg taaccttcaa cgactatgtt ctgccaaacg aagcattgag caaaggcgat  240
atcgacgcca acgccttcca gcataaaccg taccttgatc agcaactgaa agatcgtggc  300
tacaaactgg tcgcagtagg caacacattt gtttatccga ttgctggtta ctccaagaaa  360
atcaaatcac tggatgaact gcaggatggt tcgcaggttg ccgtgccaaa cgacccaact  420
aaccttggtc gttcactgct gctgctgcaa aaagtgggct tgatcaaact gaaagatggc  480
gttggcctgc tgccgaccgt tcttgatgtt gttgagaacc caaaaaatct gaaaattgtt  540
gaactggaag caccgcagct accgcgctct ctggacgacg cgcaaatcgc tctggcagtt  600
atcaatacca cctatgccag ccagattggc ctgactccag cgaaagacgg tatctttgtc  660
gaagataaag agtccccgta cgtaaacctg atcgtaacgc gtgaagacaa caaagacgcc  720
gaaaacgtga agaaattcgt tcaggcttat cagtctgacg aagtttacga agcagcaaac  780
aaagtgttta acggcggcgc tgttaaaggc tggtaa                           816
```

```
SEQ ID NO: 1007        moltype = AA  length = 393
FEATURE                Location/Qualifiers
source                 1..393
                       mol_type = protein
                       organism = Brevibacterium aurantiacum
SEQUENCE: 1007
MTSLHPETLM VHGGMKGLTE AGVHVPAIDL STTNPVNDVA TGGDSYEWLA TGHTLKDGDS  60
AVYQRLWQPG VARFETALAG LEHAEEAVAF ATGMAAMTAA LLAAVSAGTP HIVAVRPLYG  120
GSDHLLETGL LGTTVTWAKE ADIASAIQDD TGLVIVETPA NPSLDLVDLD SVVSAAGNVP  180
VLVDNTFCTP VLQQPISHGA ALVLHSATKY LGGHGDAMGG IIATNADWAM RLRQVRAITG  240
ALLHPMGAYL LHRGLRTLAV RMRAAQTTAG ELAERLDAHP AISVVHYPGL KGQDPRGLLG  300
RQMSGGGAMI AMELAGGFDA ARSFVEHCNL VVHAVSLGGA DTLIQHPASL THRPVAATAK  360
PGDGLIRLSV GLEHVDDLAD DLIAALDASR AAA                               393

SEQ ID NO: 1008        moltype = AA  length = 398
FEATURE                Location/Qualifiers
source                 1..398
                       mol_type = protein
                       organism = Citrobacter freundii
SEQUENCE: 1008
MSDCRAYGFN TQIVHAGQQP DPSTGALSTP IFQTSTFVFD SAEQGAARFA LEEPGYIYTR  60
LGNPTTDALE KKLAVLERGD AALATASGIS AITTSLLTLC QQGDHIVSAS AIYGCTHAFL  120
SHSLPKFGIN VSFVDAAKPE EIRAAMRPET KVVYIETPAN PTLSLVDIET VAGIAHQQGA  180
LLVVDNTFMS PYCQQPLLLG ADIVVHSVTK YINGHGDVIG GVIVGKQEFI DQARFVGLKD  240
ITGGCMSPFN AWLTLRGVKT LGIRMERHCE NALKIARFLE GHPAITRVYY PGLPSHPQYE  300
LGKRQMSLPG GIISFEIAGG LEAGRRMINS VELCLLAVSL GDTETLIQHP ASMTHSPVAP  360
EERLKAGITD GLIRLSVGLE DPEDIINDLE HAIRKATF                          398

SEQ ID NO: 1009        moltype = AA  length = 399
FEATURE                Location/Qualifiers
source                 1..399
                       mol_type = protein
                       organism = Porphyromonas gingivalis
SEQUENCE: 1009
MKKEDLMRSG FATRAIHGGA IENAFGCLAT PIYQTSTFVF DTAEQGGRRF AGEEDGYIYT  60
RLGNPNCTQV EEKLAMLEGG EAAASASSGI GAISSAIWVC VKAGDHIVAG KTLYGCTFAF  120
LTHGLSRYGV EVTLVDTRHP EEVEAAIRPN TKLVYLETPA NPNMYLTDIK AVCDIAHKHE  180
GVRVMVDNTY CTPYICRPLE LGADIVVHSA TKYLNGHGDV IAGFVVGKED YIKEVKLVGV  240
KDLTGANMSP FDAYLISRGM KTLQIRMEQH CRNAQTVAEF LEKHPAVEAV YFPGLPSFPQ  300
YELAKKQMAL PGAMIAFEVK GGCEAGKKLM NNLHLCSLAV SLGDTETLIQ HPASMTHSPY  360
TPEERAASDI SEGLVRLSVG LENVEDIIAD LKHGLDSLI                         399

SEQ ID NO: 1010        moltype = AA  length = 557
FEATURE                Location/Qualifiers
source                 1..557
                       mol_type = protein
                       organism = Streptomyces sp.
SEQUENCE: 1010
MSPTAFPAAE TATAPATAVD PGPELDGGDF ALPEGGLDDD RRLRALDAVD EYLTRKRKHL  60
VGYQATQDMQ GTALDLARFM PNNINNLGDP FQSGGYKPNT KVVERAVLDY YAKLWHAERP  120
HDPADPESYW GYMLSMGSTE GNMYALWNAR DYLSGKALIQ PPTAPFDAVR YVKADPDRRN  180
PNAHHPVAFY SEDTHYSFAK AVAVLGVETF HAVGLEKYAD ECPLVDPVTG LRTWPTEVPS  240
RPGPSGLSWD GPGEIDVDAL AVLVEFFAAK GHPVFVNLNL GSTFKGAHDD VRAVCERLLP  300
IFERHGLVQR EVVYGSCPQT GRPLVDVRRG FWIHVDGALG AGYAPFLRLA AEDPEGYGWT  360
PEAELPEFDF GLRLPTAGHG EVDMVSSIAM SGHKWAGAPW PCGIYMTKVK YQISPPSQPD  420
YIGAPDTTFA GSRNGFSPLI LWDHLSRYSY RDQVERIREA QELAAYLERR LTAMERELGV  480
ELWPARTPGA VTVRFRKPSA ELVAKWSLSS QDVLMVPGDE TTRRSYVHVF VMPSVDRAKL  540
DALLAELAED PVILGAP                                                 557

SEQ ID NO: 1011        moltype = AA  length = 343
FEATURE                Location/Qualifiers
source                 1..343
                       mol_type = protein
                       organism = Escherichia coli
SEQUENCE: 1011
MIKLSNITKV FHQGTRTIQA LNNVSLHVPA GQIYGVIGAS GAGKSTLIRC VNLLERPTEG  60
SVLVDGQELT TLSESELTKA RRQIGMIFQH FNLLSSRTVF GNVALPLELD NTPKDEIKRR  120
VTELLSLVGL GDKHDSYPSN LSGGQKQRVA IARALASNPK VLLCDEATSA LDPATTRSIL  180
ELLKDINRRL GLTILLITHE MDVVKRICDC VAVISNGELI EQDTVSEVFS HPKTPLAQKF  240
IQSTLHLDIP EDYQERLQAE PFTDCVPMLR LEFTGQSVDA PLLSETARRF NVNNNIISAQ  300
MDYAGGVKFG IMLTEMHGTQ QDTQAAIAWL QEHHVKVEVL GYV                     343

SEQ ID NO: 1012        moltype = AA  length = 217
FEATURE                Location/Qualifiers
source                 1..217
                       mol_type = protein
                       organism = Escherichia coli
SEQUENCE: 1012
```

-continued

```
MSEPMMWLLV RGVWETLAMT FVSGFFGFVI GLPVGVLLYV TRPGQIIANA KLYRTISAIV  60
NIFRSIPFII LLVWMIPFTR VIVGTSIGLQ AAIVPLTVGA APFIARMVEN ALLEIPTGLI  120
EASRAMGATP MQIVRKVLLP EALPGLVNAA TITLITLVGY SAMGGAVGAG GLGQIGYQYG  180
YIGYNATVMN TVLVLLVILV YLIQFAGDRI VRAVTRK                           217

SEQ ID NO: 1013        moltype = AA  length = 271
FEATURE                Location/Qualifiers
source                 1..271
                       mol_type = protein
                       organism = Escherichia coli
SEQUENCE: 1013
MAFKFKTFAA VGALIGSLAL VGCGQDEKDP NHIKVGVIVG AEQQVAEVAQ KVAKDKYGLD  60
VELVTFNDYV LPNEALSKGD IDANAFQHKP YLDQQLKDRG YKLVAVGNTF VYPIAGYSKK  120
IKSLDELQDG SQVAVPNDPT NLGRSLLLLQ KVGLIKLKDG VGLLPTVLDV VENPKNLKIV  180
ELEAPQLPRS LDDAQIALAV INTTYASQIG LTPAKDGIFV EDKESPYVNL IVTREDNKDA  240
ENVKKFVQAY QSDEVYEAAN KVFNGGAVKG W                                 271

SEQ ID NO: 1014        moltype = DNA  length = 1257
FEATURE                Location/Qualifiers
source                 1..1257
                       mol_type = genomic DNA
                       organism = Escherichia coli
SEQUENCE: 1014
atgagtggac tcaaacaaga actggggctg gcccagggca tcggcctact atcgacgtca  60
ttattaggca ctggcgtgtt tgccgttcct gcgttagctg cgctagtagc aggcaataac  120
agcctgtggg cgtggcccgt tttgattatc ttagtgttcc cgattgcgat tgtgtttgcg  180
attctgggtc gccactatcc cagcgcaggc ggcgtcgcac acttcgtcgg tatggcgttt  240
ggttcgcggc ttgagcgagt caccggctgg ttgtttttat cggtcattcc cgtgggtttg  300
cctgccgcgc tacaaattgc tgccggattc ggccaggcaa tgtttggctg gcatagcggg  360
caactgttgt tggcagaact cggtacgctg gcgctggtgt ggtatatcgg tactcgaggt  420
gccagttcca gtgctaatct acaaacagtt attgccgggc ttatcgtcgc actgattgtc  480
gctatctggt gggcgggcga tatcaaacct gcgaatatcc ccttccctgc gccaggaaat  540
atcgaactta ccgggttatt cgctgcgtta tcagtgatgt tctggtgttt tgtcggtctg  600
gaagcatttg cccatcttgc ctcggaattt aaaaatccag agcgtgattt tcctcgtgct  660
ttgatgattg gcctgctgct ggcaggatta gtctattggg gctgtacggt agtcgtctta  720
cacttcgacg cctatggtga acaaatggcg gcggcagcat cgcttcccaa aattgtagtg  780
cagttattcg gtgtaggagc gttatggatt gcctgcgtaa ttggctatct ggcctgcttt  840
gccagtctca acatttatat acagagcttc gcccgcctgg tctggtcgca ggcgcaacat  900
aatcctgacc attacctggc acgcctctct tctcgccata ttccgaataa tgccctcaat  960
gcggtgctcg gctgctgcgt ggtgagcacg ttggtgattc atgctttaga gatcaatctg  1020
gacgctctta ttatttatgc caatggcatc tttattatga tttatctgtt atgcatgctg  1080
gcaggctgta aattattgca aggacgttat cgactactgg cagtggttgg cgggctatta  1140
tgcgttctgt tactggcaat ggtcggctgg aaaagtctct acgcgctgat catgctggcg  1200
gggttatggc tgtttctgcc aaaacgaaaa acgccggaaa atggcataac cacataa     1257

SEQ ID NO: 1015        moltype = DNA  length = 1197
FEATURE                Location/Qualifiers
source                 1..1197
                       mol_type = genomic DNA
                       organism = Citrobacter freundii
SEQUENCE: 1015
atgtctgact gtcgtgctta cggattcaat acccagatcg ttcatgcggg ccaacaaccc  60
gacccttcca ctggcgcgct cagtacgcct attttccaga cgtcaacctt cgtttttgac  120
agtgccgaac agggcgccgc ccgctttgcg cttgaagaac ccggctacat ctatacgcgc  180
cttggaaacc ccaccaccga cgcgctggag aaaaagctgg ctgtgctgga aagaggcgat  240
gccgcgctgg caactgcatc cggtatttca gccatcacca cctcgttgct gaccctttgc  300
cagcagggcg accatatcgt ttccgccagt gccatttacg gctgcactca cgcttttctg  360
tcacacagcc tgccgaagtt cggcattaac gtcagcttcg tcgacgccgc caagccggaa  420
gaaatccgcg cggccatgcg cccggaaacc aaagtggtgt atatcgaaac accagcaaac  480
ccaacgctct cgctggttga tattgaaacg gtcgccggga tcgcccatca gcaaggcgca  540
ttgctggtcg tggataacac ctttatgtca ccctactgcc agcaacctct gctgttaggt  600
gccgacatcg tggtgcacag cgtgaccaag tacatcaacg gccacgggga cgtgattggc  660
ggtgtgattg ttggcaagca ggaatttatc gaccaggcac gattcgtcgg gctgaaagat  720
atcaccggcg gctgcatgag tccgttcaac gcctggctga cgctgcgcgg cgtgaaaacg  780
ctgggcatcc gaatggagcg ccattgtgaa aacgcgttaa aaattgcccg cttcctggaa  840
gggcatccgg ccattacccg cgtgtattac cctggcttgc cttcacatcc gcagtatgag  900
ctgggtaaac gtcagatgag cctgccggga ggaattatca gcttcgaaat cgccggcggc  960
ctcgaggctg gcagacggat gatcaattct gtagaattgt gcctcctcgc ggtcagtctc  1020
ggtgacaccg aaaccctcat tcagcaccca gcgtctatga cacattcgcc cgttgcgcca  1080
gaggaacggc ttaaagcagg tattaccgac ggacttatcc gtctttctgt tggtcttgaa  1140
gatccagaag atattattaa cgaccttgaa cacgccatca gaaaggcaac attctga     1197

SEQ ID NO: 1016        moltype = DNA  length = 1200
FEATURE                Location/Qualifiers
source                 1..1200
                       mol_type = genomic DNA
                       organism = Porphyromonas gingivalis
SEQUENCE: 1016
atgaaaaaag aagaccttat gcgtagtggc tttgccacac gtgccatcca tggaggcgct  60
```

atcgagaacg ccttcggctg cttagccact cccatctacc aaacatcgac tttcgttttt 120
gacactgccg aacagggagg ccgccgcttt gccggagagg aagacggata catctatacc 180
cgtctgggca accccaactg cacccaagtg gaagagaaac tggccatgct cgagggcgga 240
gaagccgccg catcggcctc atccggtatc ggagccatca gctctgccat ctgggtatgc 300
gtgaaggccg gcgaccatat cgtagccggc aagacgctct acggctgcac cttcgccttc 360
ctcacccacg gactgagccg ctacggtgtg gaagtcaccc tcgtggatac ccgccatccg 420
gaagaggtgg aggctgccat tcgcccgaat acgaagctcg tctatctgga gactccggcc 480
aaccccaata tgtacctgac cgacatcaag gcagtctgcg acatcgctca taagcacgaa 540
ggcgtacgcg tcatggtgga caatacctac tgcacgccct atatctgccg tccgctggag 600
ctgggtgccg acatcgtggt acacagcgcg accaagtacc tgaacggaca tggcgacgtc 660
atcgccggat tcgtcgttgg taaagaggac tacatcaagg aggtgaagct cgtcggcgtc 720
aaggacctca cgggggccaa tatgagtccg ttcgatgctt atctgatcag ccgcggcatg 780
aagacgctgc agatacgtat ggagcagcac tgccgcaatg ctcagaccgt agccgaattc 840
ctcgaaaagc atccggccgt agaagcagtt tatttccccg gacttccgag cttcccccaa 900
tacgaattgg ccaagaagca gatggcactg cccggagcca tgatcgcctt cgaagtgaag 960
ggcggttgcg aagccggtaa gaagctgatg aacaacctgc acctctgctc cctcgccgtg 1020
agcttgggcg atacggaaac cctcatccag catccggcca gcatgaccca ctcgccctac 1080
acacccgaag agcgtgctgc cagcgacata tccgaaggac tggtacgcct gtccgtgggt 1140
ctggagaacg tggaggacat catcgccgac ctcaaacacg gtctggacag cctgatctaa 1200

SEQ ID NO: 1017 moltype = DNA length = 1182
FEATURE Location/Qualifiers
source 1..1182
mol_type = genomic DNA
organism = Brevibacterium aurantiacum
SEQUENCE: 1017
atgacctcac tgcacccaga aacgctcatg gtccacggcg gaatgaaagg cctcaccgag 60
gcaggagtcc acgtaccggc catcgacctc tcgaccacca acccagtcaa cgatgtcgcc 120
accggcggtg actcctacga atggctcgcc accggccata cgctcaagga cggcgactcg 180
gccgtctacc agcgcctctg gcagcccggt gtcgcacgct tcgagaccgc gctggccggg 240
ctcgaacacg ctgaggaagc agtcgccttc gccacgggca tggccgcaat gactgccgca 300
cttctcgcgg ccgtcagcgc aggaacaccc cacatcgtcg cagtgcgtcc cctctatggc 360
ggaagcgacc acctcctcga aaccggactg ctggggacaa cagtcacatg ggcaaaggaa 420
gccgacatcg cctcggcgat ccaagatgac accggactcg tcattgtcga gaccccggca 480
aaccccagcc tggaccttgt tgatctcgac agtgtcgtct cagccgccgg caacgtgcct 540
gtgctggtgg acaacacatt ctgcacacct gttctccagc agcccatctc ccacggagcg 600
gccctcgtac tgcacagcgc gacaaaatac ctcggcggtc atggcgatgc catgggcggc 660
atcatcgcca ccaacgccga ctgggcgatg cgcctgcgac aggtccgagc catcacagga 720
gccctgctcc accccatggg cgcgtatctc cttcatcggg gcttgcgcac tctggccgtg 780
cgcatgcgcg cggctcagac caccgccggt gagctcgctg agcgcctgga cgcgcaccct 840
gccatctccg tcgtccacta cccgggactg aaaggccagg acccacgcgg actgctcgga 900
cgccaaatgt ccggtggtgg tgcgatgatc gcgatggagc tcgccggtgg attcgacgcc 960
gcccgcagct tcgtcgaaca ctgcaacctc gtcgtccacg cggtgtccct gggcggcgct 1020
gacactctca tccagcatcc ggcgtcactg actcacaggc cagttgcggc cacggcgaag 1080
cccggcgatg gtctcatccg actctctgtg ggactcgaac acgtcgatga cctggcagac 1140
gatctcatcg ctgccctcga cgcgagtcgg gccgctgcct ga 1182

SEQ ID NO: 1018 moltype = DNA length = 1674
FEATURE Location/Qualifiers
source 1..1674
mol_type = genomic DNA
organism = Streptomyces sp.
SEQUENCE: 1018
atgagcccga ccgccttccc cgccgccgag accgcgaccg cgcccgcgac cgccgtcgat 60
cccggtccgg agctggacgg cggtgacttc gccctccccg agggcggcct ggacgacgac 120
cggcggctgc gcgcgctcga cgccgtggac gagtacctga cccgcaagcg caagcacctg 180
gtcggctacc aggccaccca ggacatgcag ggcaccgcac tggacctcgc ccggttcatg 240
ccgaacaaca tcaacaacct cggcgacccg ttccagagcg gcggatacaa gcccaacacc 300
aaggtcgtcg agcgggccgt gctcgactac tacgcgaagc tctggcacgc cgagcgcccg 360
cacgacccgg ccgacccgga gtcgtactgg ggctacatgc tgtccatggg ctcgaccgag 420
ggcaacatgt acgccctctg gaacgccagg gactacctga gcggcaaggc gctgatccag 480
ccgccgaccg ccccctcga cgcggtgcgc tacgtcaagg ccgaccccga ccgacggaac 540
ccgaacgccc accacccggt ggccttctac tccgaggaca cccactactc cttcgccaag 600
gccgtggccg tcctcggcgt ggagaccttc cacgccgtcg gcctggagaa gtacgccgac 660
gagtgcccgc tggtcgaccc ggtgaccggg ctgcgcacct ggcccaccga ggtgccctcc 720
cgcccgggtc cgtccggcct gtcctgggac ggccccggcg agatagacgt cgacgccctc 780
gccgtactcg tcgagttctt cgccgccaag ggtcacccgg tcttcgtcaa cctcaacctc 840
ggcagcacct tcaagggcgc ccacgacgac gtccgcgccg tctgcgagcg cttgctgccg 900
atcttcgagc ggcacgggct cgtccagcgc gaggtggtct acggcagctg cccgcagacc 960
ggccggccgc tggtggacgt gcgccgcggc ttctggatcc acgtggacgg cgcgctcggc 1020
gccggctacg cgccgttcct gcggctggcc gccgaggacc cggaagggta cggctggacg 1080
cccgaggcgg agctgcccga gttcgacttc ggcctgcggc tgcccaccgc cgggcacggc 1140
gaggtggaca tggtctcctc gatcgcgatg agcggccaca agtgggccgg cgcgccgtgg 1200
ccgtgcggca tctacatgac caaggtgaag taccagatct cgccgccgtc ccagccggac 1260
tacatcggcg ccccggacac caccttcgcc ggctcccgca acggcttctc cccgctgatc 1320
ctctgggacc acctgtcccg gtactcctac cgggaccagg tggagcggat ccgcgaggcc 1380
caggagctgg ccgcctacct ggagcggcgg ctgaccgcca tggagcgcga actcggcgtc 1440
gagctctggc cggcccgtac cccgggcgcc gtcaccgtac ggttccgcaa gccgagcgcc 1500
gagctggtgg ccaagtggtc gctgtcctcc caggacgtgc tgatggtccc gggcgacgag 1560

```
accacccggc gcagctacgt gcacgtcttc gtgatgccct cggtcgaccg ggccaagctg  1620
gacgcgctgc tcgccgaact cgccgaggac ccggtgatcc tgggcgcacc gtag        1674

SEQ ID NO: 1019        moltype = DNA  length = 4141
FEATURE                Location/Qualifiers
source                 1..4141
                       mol_type = other DNA
                       organism = synthetic construct
SEQUENCE: 1019
cgaggcagtt ccataggatg gcaagatcct ggtatcggtc tgcgattccg actcgtccaa  60
catcaataca acctattaat ttcccctcgt caaaaataag gttatcaagt gagaaatcac  120
catgagtgac gactgaatcc ggtgagaatg gcaaaagctt atgcatttct ttccagactt  180
gttcaacagg ccagccatta cgctcgtcat caaaatcact cgcatcaacc aaaccgttat  240
tcattcgtga ttgcgcctga gcgagacgaa atacgcgatc gctgttaaaa ggacaattac  300
aaacaggaat cgaatgcaac cggcgcagga acactgccag cgcatcaaca atattttcac  360
ctgaatcagg atattcttct aatacctgga atgctgtttt cccggggatc gcagtggtga  420
gtaaccatgc atcatcagga gtacggataa aatgcttgat ggtcggaaga ggcataaatt  480
ccgtcagcca gtttagtctg accatctcat ctgtaacatc attggcaacg ctacctttgc  540
catgtttcag aaacaactct ggcgcatcgg gcttcccata caatcgatag attgtcgcac  600
ctgattgccc gacattatcg cgagcccatt tatacccata taaatcagca tccatgttgg  660
aatttaatcg cggcctcgag caagacgttt cccgttgaat atggctcata acaccccttg  720
tattactgtt tatgtaagca gacagtttta ttgttcatga tgatatattt ttatcttgtg  780
caatgtaaca tcagagattt tgagacacaa cgtggctttg ttgaataaat cgaacttttg  840
ctgagttgaa ggatcagatc acgcatcttc ccgacaacgc agaccgttcc gtggcaaagc  900
aaaagttcaa aatcaccaac tggtccacct acaacaaagc tctcatcaac cgtggctccc  960
tcactttctg gctggatgat ggggcgattc aggcctggta tgagtcagca acaccttctt  1020
cacgaggcag acctcagcgc tagcggagtg tatactggct tactatgttg gcactgatga  1080
gggtgtcagt gaagtgcttc atgtggcagg agaaaaaagg ctgcaccggt gcgtcagcag  1140
aatatgtgat acaggatata ttccgcttcc tcgctcactg actcgctacg ctcggtcgtt  1200
cgactgcggc gagcggaaat ggcttacgaa cggggcggag atttcctgga agatgccagg  1260
aagatactta acagggaagt gagagggccg cggcaaagcc gtttttccat aggctccgcc  1320
cccctgacaa gcatcacgaa atctgacgct caaatcagtg gtggcgaaac ccgacaggac  1380
tataaagata ccaggcgttt ccccctggcgg ctccctcgtg cgctctcctg ttcctgcctt  1440
tcggtttacc ggtgtcattc cgctgttatg gccgcgtttg tctcattcca cgcctgacac  1500
tcagttccgg gtaggcagtt cgctccaagc tggactgtat gcacgaaccc cccgttcagt  1560
ccgaccgctg cgccttatcc ggtaactatc gtcttgagtc caacccggaa agacatgcaa  1620
aagcaccact ggcagcagcc actggtaatt gatttagagg agttagtctt gaagtcatgc  1680
gccggttaag gctaaactga aaggacaagt tttggtgact gcgctcctcc aagccagtta  1740
cctcggttca aagagttggt agctcagaga accttcgaaa aaccgccctg caaggcggtt  1800
ttttcgtttt cagagcaaga gattacgcgc agaccaaaac gatctcaaga agatcatctt  1860
attaaggggt ctgacgctca gtggaacggt gcaccctgca gggctagctg ataaagcgtt  1920
cgcgctgcat tcggcagttt aagacccact ttcacattta agttgttttt ctaatccgca  1980
tatgatcaat tcaaggccga ataagaaggc tggctctgca ccttggtgat caaataattc  2040
gatagcttgt cgtaataatg gcggcatact atcagtagta ggtgtttccc tttcttcttt  2100
agcgacttga tgctcttgat cttccaatac gcaacctaaa gtaaaatgcc ccacagcgct  2160
gagtgcatat aatgcattct ctagtgaaaa accttgttgg cataaaaagg ctaattgatt  2220
ttcgagagtt tcatactgtt tttctgtagg ccgtgtacct aaatgtactt ttgctccatc  2280
gcgatgactt agtaaagcac atctaaaact tttagcgtta ttacgtaaaa aatcttgcca  2340
gctttcccct tctaaagggc aaaagtgagt atggtgccta tctaacatct caatggctaa  2400
ggcgtcgagc aaagcccgct tattttttac atgccaatac aatgtaggct gctctacacc  2460
tagcttctgg gcgagtttac gggttgttaa accttcgatt ccgacctcat taagcagctc  2520
taatgcgctg ttaatcactt tacttttatc taatctagac atcattaatt cctaattttt  2580
gttgacactc tatcattgat agagttattt taccactccc tatcagtgat agagaaaagt  2640
gaatctacga ctcttgacga cgaggaggaa ataaatgacg agccttcacc ccgaaacttt  2700
aatggtgcac gggggtatga agggattgac agaggcgggt gttcacgtcc cggcgatcga  2760
cctgtcgaca acgaatcctg ttaatgacgt agcgacaggg ggtgattctt acgaatggct  2820
tgcaacgggt cacacgttga aggatggtga ttctgctgtt taccagcgtt tatggcagcc  2880
cggtgtagct cgtttcgaga cggctctggc tgggctggag cacgcggagg aggctgtagc  2940
tttcgccacg ggtatggccg ccatgaccgc ggccttattg gcagcagtat cagctggcac  3000
gcctcatatc gtcgcagtcc gcccattata cggcggttca gaccatcttt tagagactgg  3060
tttactgggg acaactgtca cgtgggcgaa agaagctgac atcgccagtg caatccaaga  3120
cgatacaggg ttagtgatcg tggagacgcc agccaatcct agtcttgatc tggtagacct  3180
ggattctgtc gtgtcagcgg cagggaacgt ccctgtcctt gtagataata cgttttgtac  3240
tcctgtcctt cagcaaccta tctcgcacgg cgccgcactt gtattacatt cggcaacaaa  3300
gtatttaggg gggcatgggg acgccatggg cgggatcatc gcgactaatg ctgattgggc  3360
tatgcgcctg cgtcaggtcc gtgcgatcac tggtgcatta ctgcatccga tgggcgcgta  3420
cttgttacac cgcggtttgc gtactctggc tgttcgcatg cgtgccgctc agacaactgc  3480
tggtgagctt gctgagcgct tagacgctca tcccgctatt tcagttgtgc actacccagg  3540
attgaagggg caagatcctc gtggattgtt aggccgtcag atgagtggag gtggggcaat  3600
gattgctatg gagctggcag ggggattcga tgcggcacgc tcctttgttg agcattgtaa  3660
cttggtcgtg catgccgtat cacttggggg agcagacaca ttaattcaac atccggcaag  3720
tttgacacac cgcccggtcg cagcaaccgc caagcctggt gatggtttga tccgcttgag  3780
cgtggggctt gagcacgttg acgacttggc cgatgacttg atcgctgctt tggacgcctc  3840
tcgcgctgct gcatgaggag gaacgattgg taaacccggt gaacgcatga gaaagccccc  3900
ggaagatcac cttccggggg ctttttttatt gcgcggacca aaacgaaaaa agacgctcga  3960
aagcgtctct tttctggaat ttggtaccga ggcgtaatgc tctgccagtg ttacaaccaa  4020
ttaaccaatt ctgattagaa aaactcatcg agcatcaaat gaaactgcaa tttattcata  4080
tcaggattat caataccata tttttgaaaa agccgtttct gtaatgaagg agaaaactca  4140
c                                                                  4141
```

```
SEQ ID NO: 1020        moltype = DNA  length = 4156
FEATURE                Location/Qualifiers
source                 1..4156
                       mol_type = other DNA
                       organism = synthetic construct
SEQUENCE: 1020
cgaggcagtt ccataggatg gcaagatcct ggtatcggtc tgcgattccg actcgtccaa  60
catcaataca acctattaat ttcccctcgt caaaaataag gttatcaagt gagaaatcac  120
catgagtgac gactgaatcc ggtgagaatg gcaaaagctt atgcatttct ttccagactt  180
gttcaacagg ccagccatta cgctcgtcat caaaatcact cgcatcaacc aaaccgttat  240
tcattcgtga ttgcgcctga gcgagacgaa atacgcgatc gctgttaaaa ggacaattac  300
aaacaggaat cgaatgcaac cggcgcagga acactgccag cgcatcaaca atattttcac  360
ctgaatcagg atattcttct aatacctgga atgctgtttt cccggggatc gcagtggtga  420
gtaaccatgc atcatcagga gtacggataa aatgcttgat ggtcggaaga ggcataaatt  480
ccgtcagcca gtttagtctg accatctcat ctgtaacatc attggcaacg ctacctttgc  540
catgtttcag aaacaactct ggcgcatcgg gcttcccata caatcgatag attgtcgcac  600
ctgattgccc gacattatcg cgagcccatt tatacccata taaatcagca tccatgttgg  660
aatttaatcg cggcctcgag caagacgttt cccgttgaat atggctcata acaccccttg  720
tattactgtt tatgtaagca gacagtttta ttgttcatga tgatatattt ttatcttgtg  780
caatgtaaca tcagagattt tgagacacaa cgtggctttg ttgaataaat cgaacttttg  840
ctgagttgaa ggatcagatc acgcatcttc ccgacaacgc agaccgttcc gtggcaaagc  900
aaaagttcaa aatcaccaac tggtccacct acaacaaagc tctcatcaac cgtggctccc  960
tcactttctg gctggatgat ggggcgattc aggcctggta tgagtcagca acaccttctt  1020
cacgaggcag acctcagcgc tagcggagtg tatactggct tactatgttg gcactgatga  1080
gggtgtcagt gaagtgcttc atgtggcagg agaaaaaagg ctgcaccggt gcgtcagcag  1140
aatatgtgat acaggatata ttccgcttcc tcgctcactg actcgctacg ctcggtcgtt  1200
cgactgcggc gagcggaaat ggcttacgaa cggggcggag atttcctgga agatgccagg  1260
aagatactta acagggaagt gagagggccg cggcaaagcc gtttttccat aggctccgcc  1320
cccctgacaa gcatcacgaa atctgacgct caaatcagtg gtggcgaaac ccgacaggac  1380
tataaagata ccaggcgttt ccccctggcg gctccctcgtg cgctctcctg ttcctgcctt  1440
tcggtttacc ggtgtcattc cgctgttatg gccgcgtttg tctcattcca cgcctgacac  1500
tcagttccgg gtaggcagtt cgctccaagc tggactgtat gcacgaaccc cccgttcagt  1560
ccgaccgctg cgccttatcc ggtaactatc gtcttgagtc caacccggaa agacatgcaa  1620
aagcaccact ggcagcagcc actggtaatt gatttagagg agttagtctt gaagtcatgc  1680
gccggttaag gctaaactga aaggacaagt tttggtgact gcgctcctcc aagccagtta  1740
cctcggttca aagagttggt agctcagaga accttcgaaa aaccgccctg caaggcggtt  1800
ttttcgtttt cagagcaaga gattacgcgc agaccaaaac gatctcaaga agatcatctt  1860
attaaggggt ctgacgctca gtggaacggt gcaccctgca gggctagctg ataaagcgtt  1920
cgcgctgcat tcggcagttt aagacccact ttcacattta agttgttttt ctaatccgca  1980
tatgatcaat tcaaggccga ataagaaggc tggctctgca ccttggtgat caaataattc  2040
gatagcttgt cgtaataatg gcggcatact atcagtagta ggtgtttccc tttcttcttt  2100
agcgacttga tgctcttgat cttccaatac gcaacctaaa gtaaaatgcc ccacagcgct  2160
gagtgcatat aatgcattct ctagtgaaaa accttgttgg cataaaaagg ctaattgatt  2220
ttcgagagtt tcatactgtt tttctgtagg ccgtgtacct aaatgtactt ttgctccatc  2280
gcgatgactt agtaaagcac atctaaaact tttagcgtta ttacgtaaaa aatcttgcca  2340
gctttcccct tctaaagggc aaaagtgagt atggtgccta tctaacatct caatggctaa  2400
ggcgtcgagc aaagcccgct tattttttac atgccaatac aatgtaggct gctctacacc  2460
tagcttctgg gcgagtttac gggttgttaa accttcgatt ccgacctcat taagcagctc  2520
taatgcgctg ttaatcactt tacttttatc taatctagac atcattaatt cctaattttt  2580
gttgacactc tatcattgat agagttattt taccactccc tatcagtgat agagaaaagt  2640
gaacggtctt tcaacaacca caggaggtat taatatgtct gattgtcgtg cctacggctt  2700
taacacacag atcgtccacg ccggacaaca accggaccca agcactggtg cattgtcgac  2760
gccaatcttt cagacttcta ctttcgtttt cgattcggca gaacaggggg ccgcacgttt  2820
cgcgttggag gaaccgggat acatctatac gcgcttgggc aatccaacta ctgatgcgct  2880
tgaaaagaaa cttgcagtgc tggaacgtgg ggacgcggcg ttagccacag cgagcggcat  2940
ctccgctatt accacaagtc ttcttactct ttgccagcaa ggggaccata tcgtatcagc  3000
tagtgcaatc tacggttgca ctcacgcatt cttaagtcat tcgcttccta aatttggcat  3060
taacgtttca ttcgtcgacg cagcgaagcc cgaagaaatc cgcgccgcca tgcgtccaga  3120
gacaaaagtg gtatatatcg agacgcccgc gaaccctact ttatccttag tggatattga  3180
gactgttgct ggaatcgcgc accagcaagg agccttgtta gtcgtggaca acacttttat  3240
gtctccgtat tgtcaacaac cattactgct gggtgctgac atcgtggtcc atagtgttac  3300
caagtacatt aacgggcatg gggatgttat tggcggtgtc atcgtaggta aacaggagtt  3360
catcgaccaa gcacgctttg tgggattaaa ggacattacg ggcggatgca tgagcccctt  3420
taatgcatgg ctgacacttc gcggggtaaa gacgttaggg atccgtatgg agcgtcattg  3480
cgaaaacgca ttgaaaatcg cgcgttttct tgagggccat cctgctatta cacgtgtcta  3540
ttatcctgga ttgccgtcac acccccaata cgaacttggg aagcgccaaa tgtcgcttcc  3600
tgggggaatc atttcgtttg aaattgctgg tggccttgaa gcaggtcgcc gtatgattaa  3660
cagcgtggag ttatgtttgc tggcagttag cttaggtgat acggagacgt tgattcagca  3720
tccggcgagc atgacacatt cccctgttgc tcccgaggag cgtctgaagg ctggcatcac  3780
tgatggactg atccgtttgt ccgtcggcct tgaagatccg gaagacatca ttaacgacct  3840
ggagcacgcc attcgcaagg caacgtttta aggaggaacg attggtaaac ccggtgaacg  3900
catgagaaag cccccggaag atcaccttcc gggggctttt ttattgcgcg gaccaaaacg  3960
aaaaaagacg ctcgaaagcg tctcttttct ggaatttggt accgaggcgt aatgctctgc  4020
cagtgttaca accaattaac caattctgat tagaaaaact catcgagcat caaatgaaac  4080
tgcaatttat tcatatcagg attatcaata ccatattttt gaaaaagccg tttctgtaat  4140
gaaggagaaa actcac                                                  4156

SEQ ID NO: 1021        moltype = DNA  length = 4156
```

-continued

```
FEATURE                 Location/Qualifiers
source                  1..4156
                        mol_type = other DNA
                        organism = synthetic construct
SEQUENCE: 1021
cgaggcagtt ccataggatg gcaagatcct ggtatcggtc tgcgattccg actcgtccaa  60
catcaataca acctattaat ttcccctcgt caaaaataag gttatcaagt gagaaatcac  120
catgagtgac gactgaatcc ggtgagaatg gcaaaagctt atgcatttct ttccagactt  180
gttcaacagg ccagccatta cgctcgtcat caaaatcact cgcatcaacc aaaccgttat  240
tcattcgtga ttgcgcctga gcgagacgaa atacgcgatc gctgttaaaa ggacaattac  300
aaacaggaat cgaatgcaac cggcgcagga acactgccag cgcatcaaca atattttcac  360
ctgaatcagg atattcttct aatacctgga atgctgtttt cccggggatc gcagtggtga  420
gtaaccatgc atcatcagga gtacggataa aatgcttgat ggtcggaaga ggcataaatt  480
ccgtcagcca gtttagtctg accatctcat ctgtaacatc attggcaacg ctacctttgc  540
catgtttcag aaacaactct ggcgcatcgg gcttcccata caatcgatag attgtcgcac  600
ctgattgccc gacattatcg cgagcccatt tatacccata taaatcagca tccatgttgg  660
aatttaatcg cggcctcgag caagacgttt cccgttgaat atggctcata acaccccttg  720
tattactgtt tatgtaagca gacagtttta ttgttcatga tgatatattt ttatcttgtg  780
caatgtaaca tcagagattt tgagacacaa cgtggctttg ttgaataaat cgaacttttg  840
ctgagttgaa ggatcagatc acgcatcttc ccgacaacgc agaccgttcc gtggcaaagc  900
aaaagttcaa aatcaccaac tggtccacct acaacaaagc tctcatcaac cgtggctccc  960
tcactttctg gctggatgat ggggcgattc aggcctggta tgagtcagca acaccttctt  1020
cacgaggcag acctcagcgc tagcggagtg tatactggct tactatgttg gcactgatga  1080
gggtgtcagt gaagtgcttc atgtggcagg agaaaaaagg ctgcaccggt gcgtcagcag  1140
aatatgtgat acaggatata ttccgcttcc tcgctcactg actcgctacg ctcggtcgtt  1200
cgactgcggc gagcggaaat ggcttacgaa cggggcggag atttcctgga agatgccagg  1260
aagatactta acagggaagt gagagggccg cggcaaagcc gtttttccat aggctccgcc  1320
cccctgacaa gcatcacgaa atctgacgct caaatcagtg gtggcgaaac ccgacaggac  1380
tataaagata ccaggcgttt ccccctggcg ctccctcgtg cgctctcctg ttcctgcctt  1440
tcggtttacc ggtgtcattc cgctgttatg gccgcgtttg tctcattcca cgcctgacac  1500
tcagttccgg gtaggcagtt cgctccaagc tggactgtat gcacgaaccc cccgttcagt  1560
ccgaccgctg cgccttatcc ggtaactatc gtcttgagtc caacccggaa agacatgcaa  1620
aagcaccact ggcagcagcc actggtaatt gatttagagg agttagtctt gaagtcatgc  1680
gccggttaag gctaaactga aaggacaagt tttggtgact gcgctcctcc aagccagtta  1740
cctcggttca aagagttggt agctcagaga accttcgaaa aaccgccctg caaggcggtt  1800
ttttcgtttt cagagcaaga gattacgcgc agaccaaaac gatctcaaga agatcatctt  1860
attaaggggt ctgacgctca gtggaacggt gcaccctgca gggctagctg ataaagcgtt  1920
cgcgctgcat tcggcagttt aagacccact ttcacattta agttgttttt ctaatccgca  1980
tatgatcaat tcaaggccga ataagaaggc tggctctgca ccttggtgat caaataattc  2040
gatagcttgt cgtaataatg gcggcatact atcagtagta ggtgtttccc tttcttcttt  2100
agcgacttga tgctcttgat cttccaatac gcaacctaaa gtaaaatgcc ccacagcgct  2160
gagtgcatat aatgcattct ctagtgaaaa accttgttgg cataaaaagg ctaattgatt  2220
ttcgagagtt tcatactgtt tttctgtagg ccgtgtacct aaatgtactt ttgctccatc  2280
gcgatgactt agtaaagcac atctaaaact tttagcgtta ttacgtaaaa aatcttgcca  2340
gctttcccct tctaaagggc aaaagtgagt atggtgccta tctaacatct caatggctaa  2400
ggcgtcgagc aaagcccgct tattttttac atgccaatac aatgtaggct gctctacacc  2460
tagcttctgg gcgagtttac gggttgttaa accttcgatt ccgacctcat taagcagctc  2520
taatgcgctg ttaatcactt tacttttatc taatctagac atcattaatt cctaattttt  2580
gttgacactc tatcattgat agagttattt taccactccc tatcagtgat agagaaaagt  2640
gaaagggtat tattgtcgta aggaggaatc tatgaagaaa gaggacttaa tgcgttcggg  2700
gttcgcaact cgtgctattc atggtggagc catcgaaaat gcttttgggt gcctggccac  2760
ccccatctac caaacttcaa cgtttgtttt cgatacggct gaacagggtg gacgtcgctt  2820
tgcgggtgaa gaagatgggt acatttacac tcgcttagga aacccgaact gtacccaggt  2880
tgaggagaag ctggcgatgt tagaaggagg ggaagcagcg gcctccgcaa gtagtggtat  2940
cggagcgatc tcttcagcta tctgggtgtg cgtcaaggcg ggagatcata ttgtagcggg  3000
aaaaactttg tacggttgca cgtttgcgtt cttgacccac ggactttctc gctatggagt  3060
tgaggtcacc ttggtggaca cgcgccatcc agaagaggtt gaggccgcta ttcgtccaaa  3120
cactaagttg gtctatttgg aaactcccgc aaaccctaac atgtacctta ctgatatcaa  3180
agctgtgtgt gatatcgcgc acaagcatga gggtgttcgc gtcatggtgg ataataccta  3240
ctgtacacct tacatctgtc gcccactgga gttaggtgct gatattgttg tccattccgc  3300
cacaaaatat ctgaacggac atggagatgt tatcgctggg tttgtagtag ggaaagagga  3360
ttacatcaag gaggtcaaat tggttggtgt taaggacttg acaggagcca atatgtcacc  3420
cttcgacgca taccttatta gtcgtggtat gaagacgtta caaatccgta tggaacaaca  3480
ttgccgtaac gcacaaacag ttgctgagtt tctggagaag catcctgcgg ttgaggcggt  3540
gtacttcccg ggcttgcctt cattcccgca atatgagttg gccaagaagc agatggcact  3600
tccgggagcg atgattgcgt ttgaagttaa gggaggctgc gaagccggta agaaacttat  3660
gaacaatctt catctgtgtt ccttagccgt ctccttaggc gataccgaga ctttaatcca  3720
acacccggcc tcaatgacgc actcgcccta tacgcccgag gaacgcgccg caagcgacat  3780
ctcggagggg cttgtacgcc tttctgttgg attggaaaat gttgaggata ttatcgcgga  3840
cctgaagcat ggcctggata gtcttatcta aggaggaacg attggtaaac ccggtgaacg  3900
catgagaaag cccccggaag atcaccttcc gggggctttt ttattgcgcg gaccaaaacg  3960
aaaaaagacg ctcgaaagcg tctcttttct ggaatttggt accgaggcgt aatgctctgc  4020
cagtgttaca accaattaac caattctgat tagaaaaact catcgagcat caaatgaaac  4080
tgcaatttat tcatatcagg attatcaata ccatattttt gaaaaagccg tttctgtaat  4140
gaaggagaaa actcac                                                  4156

SEQ ID NO: 1022         moltype = DNA  length = 4630
FEATURE                 Location/Qualifiers
source                  1..4630
```

mol_type = other DNA
organism = synthetic construct
SEQUENCE: 1022
cgaggcagtt ccataggatg gcaagatcct ggtatcggtc tgcgattccg actcgtccaa 60
catcaataca acctattaat ttcccctcgt caaaaataag gttatcaagt gagaaatcac 120
catgagtgac gactgaatcc ggtgagaatg gcaaaagctt atgcatttct ttccagactt 180
gttcaacagg ccagccatta cgctcgtcat caaaatcact cgcatcaacc aaaccgttat 240
tcattcgtga ttgcgcctga gcgagacgaa atacgcgatc gctgttaaaa ggacaattac 300
aaacaggaat cgaatgcaac cggcgcagga acactgccag cgcatcaaca atattttcac 360
ctgaatcagg atattcttct aatacctgga atgctgtttt cccggggatc gcagtggtga 420
gtaaccatgc atcatcagga gtacggataa aatgcttgat ggtcggaaga ggcataaatt 480
ccgtcagcca gtttagtctg accatctcat ctgtaacatc attggcaacg ctacctttgc 540
catgtttcag aaacaactct ggcgcatcgg gcttcccata caatcgatag attgtcgcac 600
ctgattgccc gacattatcg cgagcccatt tatacccata taaatcagca tccatgttgg 660
aatttaatcg cggcctcgag caagacgttt cccgttgaat atggctcata acaccccttg 720
tattactgtt tatgtaagca gacagtttta ttgttcatga tgatatattt ttatcttgtg 780
caatgtaaca tcagagattt tgagacacaa cgtggctttg ttgaataaat cgaacttttg 840
ctgagttgaa ggatcagatc acgcatcttc ccgacaacgc agaccgttcc gtggcaaagc 900
aaaagttcaa aatcaccaac tggtccacct acaacaaagc tctcatcaac cgtggctccc 960
tcactttctg gctggatgat ggggcgattc aggcctggta tgagtcagca acaccttctt 1020
cacgaggcag acctcagcgc tagcggagtg tatactggct tactatgttg gcactgatga 1080
gggtgtcagt gaagtgcttc atgtggcagg agaaaaaagg ctgcaccggt gcgtcagcag 1140
aatatgtgat acaggatata ttccgcttcc tcgctcactg actcgctacg ctcggtcgtt 1200
cgactgcggc gagcggaaat ggcttacgaa cggggcggag atttcctgga agatgccagg 1260
aagatactta acagggaagt gagagggccg cggcaaagcc gtttttccat aggctccgcc 1320
cccctgacaa gcatcacgaa atctgacgct caaatcagtg gtggcgaaac ccgacaggac 1380
tataaagata ccaggcgttt ccccctggcgg ctccctcgtg cgctctcctg ttcctgcctt 1440
tcggtttacc ggtgtcattc cgctgttatg gccgcgtttg tctcattcca cgcctgacac 1500
tcagttccgg gtaggcagtt cgctccaagc tggactgtat gcacgaaccc cccgttcagt 1560
ccgaccgctg cgccttatcc ggtaactatc gtcttgagtc caacccggaa agacatgcaa 1620
agcaccactg gcagcagcca ctggtaattg atttagagga gttagtcttg aagtcatgcg 1680
ccggttaagg ctaaactgaa aggacaagtt ttggtgactg cgctcctcca agccagttac 1740
ctcggttcaa agagttggta gctcagagaa ccttcgaaaa accgccctgc aaggcggttt 1800
tttcgttttc agagcaagag attacgcgca gaccaaaacg atctcaagaa gatcatctta 1860
ttaaggggtc tgacgctcag tggaacggtg caccctgcag ggctagctga taaagcgttc 1920
gcgctgcatt cggcagttta agacccactt tcacatttaa gttgtttttc taatccgcat 1980
atgatcaatt caaggccgaa taagaaggct ggctctgcac cttggtgatc aaataattcg 2040
atagcttgtc gtaataatgg cggcatacta tcagtagtag gtgtttccct ttcttcttta 2100
gcgacttgat gctcttgatc ttccaatacg caacctaaag taaaatgccc cacagcgctg 2160
agtgcatata atgcattctc tagtgaaaaa ccttgttggc ataaaaaggc taattgattt 2220
tcgagagttt catactgttt ttctgtaggc cgtgtaccta aatgtacttt tgctccatcg 2280
cgatgactta gtaaagcaca tctaaaactt ttagcgttat tacgtaaaaa atcttgccag 2340
ctttcccctt ctaaagggca aaagtgagta tggtgcctat ctaacatctc aatggctaag 2400
gcgtcgagca aagcccgctt attttttaca tgccaataca atgtaggctg ctctacacct 2460
agcttctggg cgagtttacg ggttgttaaa ccttcgattc cgacctcatt aagcagctct 2520
aatgcgctgt taatcacttt acttttatct aatctagaca tcattaattc ctaatttttg 2580
ttgacactct atcattgata gagttatttt accactccct atcagtgata gagaaaagtg 2640
aacaccagta gttcaaaagg aggtagaaca gatgtccccg acggcgtttc cagcggccga 2700
aacagctact gcccctgcaa ctgccgtcga tcctgggcca gaactggacg gcggagattt 2760
cgcccttcca gagggcgggc tggatgacga tcgtcgctta cgtgcattgg acgcagttga 2820
cgagtatttg acccgcaagc gcaagcattt ggttgggtac caagctaccc aggatatgca 2880
gggaacggcc ttggatttag cccgtttcat gcccaacaac atcaacaacc tgggagatcc 2940
tttccagtcg ggtgggtata aaccaaatac gaaagtcgtt gagcgtgccg tactggacta 3000
ctatgcaaaa ttgtggcacg cagaacgtcc acacgaccca gctgacccag aaagctactg 3060
gggttacatg ttatcgatgg gctcaactga gggcaacatg tacgccctgt ggaatgcacg 3120
tgactacctg tcgggtaagg ctttgattca gcctcccacg gcaccatttg acgctgttcg 3180
ctacgtgaag gctgaccccg atcgccgcaa tcctaacgca caccacccag tcgcattcta 3240
ctcggaggat acccactatt cttttgctaa agccgttgcg gtgctgggtg tcgaaacttt 3300
ccacgctgtg ggtctggaga aatacgctga cgagtgcccc ttggtggatc cagtaaccgg 3360
ccttcgtacc tggccgaccg aagttccatc gcgcccgggg ccgtcgggtt taagctggga 3420
cggccctggt gagattgatg ttgatgcgct tgcagtactg gtcgagttct tcgcagcgaa 3480
gggtcacccc gtcttcgtca accttaactt ggggtctaca tttaaaggag cacatgatga 3540
cgtacgtgcg gtatgtgaac gcttattacc aatcttcgag cgccatggct tagtacaacg 3600
tgaagttgta tatgggagct gtccccaaac cggccgccct ttagtggatg tacgtcgcgg 3660
attttggatc cacgtagatg gggcacttgg ggcggggtat gccccttttc tgcgtcttgc 3720
cgccgaagac ccggaaggtt atggttggac ccctgaggca gaattacctg agttcgactt 3780
cggcttacgt ttgccgacgg cggggcatgg agaagttgat atggttagca gcatcgccat 3840
gagtggacat aagtgggcag gcgcgccgtg gccatgcggc atctatatga cgaaagtgaa 3900
atatcagatt agtccaccgt cacagcccga ttatattggt gctcctgaca caacatttgc 3960
cggttcccgt aacggctttt cgccgttaat tttgtgggat catttatcgc gctactcgta 4020
ccgcgaccag gtagagcgca tccgcgaagc acaggagctt gcagcatatt tggaacgccg 4080
ccttaccgct atggagcgcg agctgggagt ggaactttgg ccagcccgca caccgggtgc 4140
tgtaaccgta cgttttcgca aaccctctgc tgagctggtt gcgaagtggt ccttgtcgtc 4200
gcaggatgtt ttaatggtgc cgggtgatga aactacgcgt cgtagttacg ttcatgtgtt 4260
cgtgatgcct tctgttgatc gtgcaaagtt agatgcgttg ctggcagaat tggccgaaga 4320
tcccgtcatc ttgggtgcgc cttaaggagg aacgattggt aaacccggtg aacgcatgag 4380
aaagccccg gaagatcacc ttccgggggc ttttttattg cgcggaccaa aacgaaaaaa 4440
gacgctcgaa agcgtctctt ttctggaatt tggtaccgag gcgtaatgct ctgccagtgt 4500
tacaaccaat taaccaattc tgattagaaa aactcatcga gcatcaaatg aaactgcaat 4560

-continued ttattcatat caggattatc aataccatat ttttgaaaaa gccgtttctg taatgaagga 4620
gaaaactcac 4630

SEQ ID NO: 1023 moltype = DNA length = 7482
FEATURE Location/Qualifiers
source 1..7482
mol_type = other DNA
organism = synthetic construct
SEQUENCE: 1023
gtaaaacgac ggccagtgaa ttcgttaaga cccactttca catttaagtt gtttttctaa 60
tccgcatatg atcaattcaa ggccgaataa gaaggctggc tctgcacctt ggtgatcaaa 120
taattcgata gcttgtcgta ataatggcgg catactatca gtagtaggtg tttccctttc 180
ttctttagcg acttgatgct cttgatcttc caatacgcaa cctaaagtaa aatgccccac 240
agcgctgagt gcatataatg cattctctag tgaaaaacct tgttggcata aaaaggctaa 300
ttgattttcg agagtttcat actgtttttc tgtaggccgt gtacctaaat gtacttttgc 360
tccatcgcga tgacttagta aagcacatct aaaactttta gcgttattac gtaaaaaatc 420
ttgccagctt tccccttcta aagggcaaaa gtgagtatgg tgcctatcta acatctcaat 480
ggctaaggcg tcgagcaaag cccgcttatt ttttacatgc caatacaatg taggctgctc 540
tacacctagc ttctgggcga gtttacgggt tgttaaacct tcgattccga cctcattaag 600
cagctctaat gcgctgttaa tcactttact tttatctaat ctagacatca ttaattccta 660
atttttgttg acactctatc attgatagag ttattttacc actccctatc agtgatagag 720
aaaagtgaac tctaggttcc aggcattcga aatgccacga ctaacttaat gacgataata 780
aataatcaat gataaaactt tcgaatatca ccaaagtgtt ccaccagggc acccgcacca 840
tccaggcgtt gaacaacgtc agcctgcatg tgccagctgg acaaatttat ggcgttatcg 900
gtgcctcagg cgcgggtaag agtacgctta tacgttgtgt aaacctgctg gagcgcccaa 960
ccgagggtag cgtgctggtc gatggccagg aactgaccac gctgtcagaa tccgagttga 1020
ccaaagctcg tcgccagatt ggtatgattt tccagcattt taacctgctc tcttcgcgta 1080
ctgtttttgg caacgtggct ctgccgctgg agctggacaa cacaccgaaa gacgagatca 1140
aacgtcgcgt gacggaattg ctgtcattgg ttggtcttgg cgataagcat gatagctacc 1200
cgtcgaatct ttccggtggg cagaaacaac gtgtggcgat tgcccgtgca ttagccagca 1260
atcccaaagt attgctgtgt gatgaagcca ccagcgcgct ggacccggca acgacacgtt 1320
ctattctcga actgctgaaa gacatcaacc gccgtctggg tttgacgatt ctgttgatca 1380
ctcacgaaat ggacgttgtg aagcgcattt gtgattgcgt ggcggtcatc agcaatggcg 1440
aactgatcga gcaggacacg gtaagtgaag tgttctcgca tccgaaaacg ccgctggcgc 1500
agaagtttat tcagtcgacc ctgcatctgg atatcccgga agattaccag gaacgtctgc 1560
aagcggagcc atttactgac tgcgtgccga tgctgcgtct ggagtttacc ggtcaatcgg 1620
tcgatgcccc actgcttttct gaaaccgcgc gtcgtttcaa cgtcaacaac aacattatta 1680
gcgcgcagat ggattacgcc ggtggcgtta agttcggcat catgctgact gaaatgcacg 1740
gcacacaaca agatacgcaa gccgccattg cctggctgca ggaacaccat gtaaaagtag 1800
aggtactggg ttatgtctga gccgatgatg tggctgctgg ttcgtggcgt atgggaaacg 1860
ctggcaatga ccttcgtatc cggttttttt ggctttgtga ttggtctgcc ggttggcgtt 1920
ctgctttatg tcacgcgtcc ggggcaaatt attgctaacg cgaagttgta tcgtaccatt 1980
tctgcgattg tgaacatttt ccgttccatc ccgttcatta tcttgctggt atggatgatt 2040
ccgtttaccc gcgttattgt cggtacatcg attggattgc aggcagcgat tgttccgtta 2100
accgttggtg cagcaccgtt tattgcccgt atggtcgaga acgctctgct ggagatccca 2160
accgggttaa ttgaagcttc ccgcgcaatg gggggccacgc caatgcagat cgtccgtaaa 2220
gtgctgttac cggaagcgtt gccgggtctg gtgaatgcgg caactatcac cctgattacc 2280
ctggttggtt attccgcgat gggtggtgca gtcggtgccg gtggtttagg tcagattggc 2340
tatcagtatg gctacatcgg ctacaacgcg acggtgatga atacggtact ggtattgctg 2400
gtcattctgg tttatttaat tcagttcgca ggcgaccgca tcgtccgggc tgtcactcgc 2460
aagtaacgtt caacacaaca taaataattg aagaaggaat aaggtatggc gttcaaattc 2520
aaaacctttg cggcagtggg agccctgatt ggatcactgg cactggtagg ctgcggtcag 2580
gatgaaaaag atccaaacca cattaaagtc ggcgtgattg ttggtgccga acagcaggtt 2640
gcagaagtcg cgcagaaagt tgcgaaagac aaatatggcc tggacgttga gctggtaacc 2700
ttcaacgact atgttctgcc aaacgaagca ttgagcaaag gcgatatcga cgccaacgcc 2760
ttccagcata aaccgtacct tgatcagcaa ctgaaagatc gtggctacaa actggtcgca 2820
gtaggcaaca catttgttta tccgattgct ggttactcca agaaaatcaa atcactggat 2880
gaactgcagg atggttcgca ggttgccgtg ccaaacgacc caactaacct tggtcgttca 2940
ctgctgctgc tgcaaaaagt gggcttgatc aaactgaaag atggcgttgg cctgctgccg 3000
accgttcttg atgttgttga gaacccaaaa aatctgaaaa ttgttgaact ggaagcaccg 3060
cagctaccgc gctctctgga cgacgcgcaa atcgctctgg cagttatcaa taccacctat 3120
gccagccaga ttggcctgac tccagcgaaa gacggtatct ttgtcgaaga taaagagtcc 3180
ccgtacgtaa acctgatcgt aacgcgtgaa gacaacaaag acgccgaaaa cgtgaagaaa 3240
ttcgttcagg cttatcagtc tgacgaagtt tacgaagcag caaacaaagt gtttaacggc 3300
ggcgctgtta aaggctggta atgaagatat aatccgcatt gcggatgcaa ttattaatga 3360
tcaacttcct ctgccagaaa tcatgctgga agaataagct tggcgtaatc atggtcatag 3420
ctgtttcctg tgtgaaattg ttatccgctc acaattccac acaacatacg agccggaagc 3480
ataaagtgta aagcctgggg tgcctaatga gtgagctaac tcacattaat tgcgttgcgc 3540
tcactgcccg ctttccagtc gggaaacctg tcgtgccagc tgcattaatg aatcggccaa 3600
cgcgcgggga gaggcggttt gcgtattggg cgctcttccg cttcctcgct cactgactcg 3660
ctgcgctcgg tcgttcggct gcggcgagcg gtatcagctc actcaaaggc ggtagtacgg 3720
gttttgctgc ccgcaaacgg gctgttctgg tgttgctagt ttgttatcag aatcgcagat 3780
ccggcttcag gtttgccggc tgaaagcgct atttcttcca gaattgccat gatttttttcc 3840
ccacgggagg cgtcactggc tcccgtgttg tcggcagctt tgattcgata agcagcatcg 3900
cctgtttcag gctgtctatg tgtgactgtt gagctgtaac aagttgtctc aggtgttcaa 3960
tttcatgttc tagttgcttt gttttactgg tttcacctgt tctattaggt gttacatgct 4020
gttcatctgt tacattgtcg atctgttcat ggtgaacagc tttaaatgca ccaaaaactc 4080
gtaaaagctc tgatgtatct atcttttttta caccgttttc atctgtgcat atggacagtt 4140
ttccctttga tatctaacgg tgaacagttg ttctactttt gtttgttagt cttgatgctt 4200

-continued

```
cactgataga tacaagagcc ataagaacct cagatccttc cgtatttagc cagtatgttc  4260
tctagtgtgg ttcgttgttt ttgcgtgagc catgagaacg aaccattgag atcatgctta  4320
ctttgcatgt cactcaaaaa ttttgcctca aaactggtga gctgaatttt tgcagttaaa  4380
gcatcgtgta gtgtttttct tagtccgtta cgtaggtagg aatctgatgt aatggttgtt  4440
ggtattttgt caccattcat ttttatctgg ttgttctcaa gttcggttac gagatccatt  4500
tgtctatcta gttcaacttg gaaaatcaac gtatcagtcg ggcggcctcg cttatcaacc  4560
accaatttca tattgctgta agtgtttaaa tctttactta ttggtttcaa aacccattgg  4620
ttaagccttt taaactcatg gtagttattt tcaagcatta acatgaactt aaattcatca  4680
aggctaatct ctatatttgc cttgtgagtt ttcttttgtg ttagttcttt taataaccac  4740
tcataaatcc tcatagagta tttgttttca aaagacttaa catgttccag attatatttt  4800
atgaattttt ttaactggaa aagataaggc aatatctctt cactaaaaac taattctaat  4860
ttttcgcttg agaacttggc atagtttgtc cactggaaaa tctcaaagcc tttaaccaaa  4920
ggattcctga tttccacagt tctcgtcatc agctctctgg ttgctttagc taatacacca  4980
taagcatttt ccctactgat gttcatcatc tgagcgtatt ggttataagt gaacgatacc  5040
gtccgttctt tccttgtagg gttttcaatc gtggggttga gtagtgccac acagcataaa  5100
attagcttgg tttcatgctc cgttaagtca tagcgactaa tcgctagttc atttgctttg  5160
aaaacaacta attcagacat acatctcaat tggtctaggt gattttaatc actataccaa  5220
ttgagatggg ctagtcaatg ataattacta gtccttttcc tttgagttgt gggtatctgt  5280
aaattctgct agacctttgc tggaaaactt gtaaattctg ctagaccctc tgtaaattcc  5340
gctagacctt tgtgtgtttt ttttgtttat attcaagtgg ttataattta tagaataaag  5400
aaagaataaa aaaagataaa aagaatagat cccagccctg tgtataactc actactttag  5460
tcagttccgc agtattacaa aaggatgtcg caaacgctgt ttgctcctct acaaaacaga  5520
ccttaaaacc ctaaaggctt aagtagcacc ctcgcaagct cgggcaaatc gctgaatatt  5580
ccttttgtct ccgaccatca ggcacctgag tcgctgtctt tttcgtgaca ttcagttcgc  5640
tgcgctcacg gctctggcag tgaatggggg taaatggcac tacaggcgcc ttttatggat  5700
tcatgcaagg aaactaccca taatacaaga aaagcccgtc acgggcttct cagggcgttt  5760
tatggcgggt ctgctatgtg gtgctatctg actttttgct gttcagcagt tcctgccctc  5820
tgattttcca gtctgaccac ttcggattat cccgtgacag gtcattcaga ctggctaatg  5880
cacccagtaa ggcagcggta tcatcaacag gcttacccgt cttactgtct tttctacggg  5940
gtctgacgct cagtggaacg aaaactcacg ttaagggatt ttggtcatga gattatcaaa  6000
aaggatcttc acctagatcc ttttaaatta aaaatgaagt tttaaatcaa tctaaagtat  6060
atatgagtaa acttggtctg acagttacca atgcttaatc agtgaggcac ctatctcagc  6120
gatctgtcta tttcgttcat ccatagttgc ctgactcccc gtcgtgtaga taactacgat  6180
acgggagggc ttaccatctg gccccagtgc tgcaatgata ccgcgagacc cacgctcacc  6240
ggctccagat ttatcagcaa taaaccagcc agccggaagg gccgagcgca gaagtggtcc  6300
tgcaacttta tccgcctcca tccagtctat taattgttgc cgggaagcta gagtaagtag  6360
ttcgccagtt aatagtttgc gcaacgttgt tgccattgct acaggcatcg tggtgtcacg  6420
ctcgtcgttt ggtatggctt cattcagctc cggttcccaa cgatcaaggc gagttacatg  6480
atcccccatg ttgtgcaaaa aagcggttag ctccttcggt cctccgatcg ttgtcagaag  6540
taagttggcc gcagtgttat cactcatggt tatggcagca ctgcataatt ctcttactgt  6600
catgccatcc gtaagatgct tttctgtgac tggtgagtac tcaaccaagt cattctgaga  6660
atagtgtatg cggcgaccga gttgctcttg cccggcgtca atacgggata ataccgcgcc  6720
acatagcaga actttaaaag tgctcatcat tggaaaacgt tcttcggggc gaaaactctc  6780
aaggatctta ccgctgttga gatccagttc gatgtaaccc actcgtgcac ccaactgatc  6840
ttcagcatct tttactttca ccagcgtttc tgggtgagca aaaacaggaa ggcaaaatgc  6900
cgcaaaaaag ggaataaggg cgacacggaa atgttgaata ctcatactct tcctttttca  6960
atattattga agcatttatc agggttattg tctcatgagc ggatacatat ttgaatgtat  7020
ttagaaaaat aaacaaatag gggttccgcg cacatttccc cgaaaagtgc cacctgacgt  7080
ctaagaaacc attattatca tgacattaac ctataaaaat aggcgtatca cgaggccctt  7140
tcgtctcgcg cgtttcggtg atgacggtga aaacctctga cacatgcagc tcccggagac  7200
ggtcacagct tgtctgtaag cggatgccgg gagcagacaa gcccgtcagg gcgcgtcagc  7260
gggtgttggc gggtgtcggg gctggcttaa ctatgcggca tcagagcaga ttgtactgag  7320
agtgcaccat atgcggtgtg aaataccgca cagatgcgta aggagaaaat accgcatcag  7380
gcgccattcg ccattcaggc tgcgcaactg ttgggaaggg cgatcggtgc gggcctcttc  7440
gctattacgc cagctggcga aagggggatg tgctgcaagg cg                     7482

SEQ ID NO: 1024        moltype = AA  length = 393
FEATURE                Location/Qualifiers
source                 1..393
                       mol_type = protein
                       organism = synthetic construct
SEQUENCE: 1024
MTSLHPETLM VHGGMKGLTE AGVHVPAIDL STTNPVNDVA TGGDSYEWLA TGHTLKDGDS  60
AVYQRLWQPG VARFETALAG LEHAEEAVAF ATGMAAMTAA LLAAVSAGTP HIVAVRPLYG  120
GSDHLLETGL LGTTVTWAKE ADIASAIQDD TGLVIVETPA NPSLDLVDLD SVVSAAGNVP  180
VLVDNTFCTP VLQQPISHGA ALVLHSATKY LGGHGDAMGG IIATNADWAM RLRQVRAITG  240
ALLHPMGAYL LHRGLRTLAV RMRAAQTTAG ELAERLDAHP AISVVHYPGL KGQDPRGLLG  300
RQMSGGGAMI AMELAGGFDA ARSFVEHCNL VVHAVSLGGA DTLIQHPASL THRPVAATAK  360
PGDGLIRLSV GLEHVDDLAD DLIAALDASR AAA                               393

SEQ ID NO: 1025        moltype = AA  length = 398
FEATURE                Location/Qualifiers
source                 1..398
                       mol_type = protein
                       organism = synthetic construct
SEQUENCE: 1025
MSDCRAYGFN TQIVHAGQQP DPSTGALSTP IFQTSTFVFD SAEQGAARFA LEEPGYIYTR  60
LGNPTTDALE KKLAVLERGD AALATASGIS AITTSLLTLC QQGDHIVSAS AIYGCTHAFL  120
SHSLPKFGIN VSFVDAAKPE EIRAAMRPET KVVYIETPAN PTLSLVDIET VAGIAHQQGA  180
```

-continued

```
LLVVDNTFMS PYCQQPLLLG ADIVVHSVTK YINGHGDVIG GVIVGKQEFI DQARFVGLKD  240
ITGGCMSPFN AWLTLRGVKT LGIRMERHCE NALKIARFLE GHPAITRVYY PGLPSHPQYE  300
LGKRQMSLPG GIISFEIAGG LEAGRRMINS VELCLLAVSL GDTETLIQHP ASMTHSPVAP  360
EERLKAGITD GLIRLSVGLE DPEDIINDLE HAIRKATF                          398

SEQ ID NO: 1026         moltype = AA  length = 399
FEATURE                 Location/Qualifiers
source                  1..399
                        mol_type = protein
                        organism = synthetic construct
SEQUENCE: 1026
MKKEDLMRSG FATRAIHGGA IENAFGCLAT PIYQTSTFVF DTAEQGGRRF AGEEDGYIYT  60
RLGNPNCTQV EEKLAMLEGG EAAASASSGI GAISSAIWVC VKAGDHIVAG KTLYGCTFAF  120
LTHGLSRYGV EVTLVDTRHP EEVEAAIRPN TKLVYLETPA NPNMYLTDIK AVCDIAHKHE  180
GVRVMVDNTY CTPYICRPLE LGADIVVHSA TKYLNGHGDV IAGFVVGKED YIKEVKLVGV  240
KDLTGANMSP FDAYLISRGM KTLQIRMEQH CRNAQTVAEF LEKHPAVEAV YFPGLPSFPQ  300
YELAKKQMAL PGAMIAFEVK GGCEAGKKLM NNLHLCSLAV SLGDTETLIQ HPASMTHSPY  360
TPEERAASDI SEGLVRLSVG LENVEDIIAD LKHGLDSLI                         399

SEQ ID NO: 1027         moltype = AA  length = 557
FEATURE                 Location/Qualifiers
source                  1..557
                        mol_type = protein
                        organism = synthetic construct
SEQUENCE: 1027
MSPTAFPAAE TATAPATAVD PGPELDGGDF ALPEGGLDDD RRLRALDAVD EYLTRKRKHL  60
VGYQATQDMQ GTALDLARFM PNNINNLGDP FQSGGYKPNT KVVERAVLDY YAKLWHAERP  120
HDPADPESYW GYMLSMGGSTE GNMYALWNAR DYLSGKALIQ PPTAPFDAVR YVKADPDRRN  180
PNAHHPVAFY SEDTHYSFAK AVAVLGVETF HAVGLEKYAD ECPLVDPVTG LRTWPTEVPS  240
RPGPSGLSWD GPGEIDVDAL AVLVEFFAAK GHPVFVNLNL GSTFKGAHDD VRAVCERLLP  300
IFERHGLVQR EVVYGSCPQT GRPLVDVRRG FWIHVDGALG AGYAPFLRLA AEDPEGYGWT  360
PEAELPEFDF GLRLPTAGHG EVDMVSSIAM SGHKWAGAPW PCGIYMTKVK YQISPPSQPD  420
YIGAPDTTFA GSRNGFSPLI LWDHLSRYSY RDQVERIREA QELAAYLERR LTAMERELGV  480
ELWPARTPGA VTVRFRKPSA ELVAKWSLSS QDVLMVPGDE TTRRSYVHVF VMPSVDRAKL  540
DALLAELAED PVILGAP                                                 557

SEQ ID NO: 1028         moltype = AA  length = 207
FEATURE                 Location/Qualifiers
source                  1..207
                        mol_type = protein
                        organism = synthetic construct
SEQUENCE: 1028
MSRLDKSKVI NSALELLNEV GIEGLTTRKL AQKLGVEQPT LYWHVKNKRA LLDALAIEML  60
DRHHTHFCPL EGESWQDFLR NNAKSFRCAL LSHRDGAKVH LGTRPTEKQY ETLENQLAFL  120
CQQGFSLENA LYALSAVGHF TLGCVLEDQE HQVAKEERET PTTDSMPPLL RQAIELFDHQ  180
GAEPAFLFGL ELIICGLEKQ LKCESGS                                      207

SEQ ID NO: 1029         moltype = AA  length = 343
FEATURE                 Location/Qualifiers
source                  1..343
                        mol_type = protein
                        organism = synthetic construct
SEQUENCE: 1029
MIKLSNITKV FHQGTRTIQA LNNVSLHVPA GQIYGVIGAS GAGKSTLIRC VNLLERPTEG  60
SVLVDGQELT TLSESELTKA RRQIGMIFQH FNLLSSRTVF GNVALPLELD NTPKDEIKRR  120
VTELLSLVGL GDKHDSYPSN LSGGQKQRVA IARALASNPK VLLCDEATSA LDPATTRSIL  180
ELLKDINRRL GLTILLITHE MDVVKRICDC VAVISNGELI EQDTVSEVFS HPKTPLAQKF  240
IQSTLHLDIP EDYQERLQAE PFTDCVPMLR LEFTGQSVDA PLLSETARRF NVNNNIISAQ  300
MDYAGGVKFG IMLTEMHGTQ QDTQAAIAWL QEHHVKVEVL GYV                    343

SEQ ID NO: 1030         moltype = AA  length = 217
FEATURE                 Location/Qualifiers
source                  1..217
                        mol_type = protein
                        organism = synthetic construct
SEQUENCE: 1030
MSEPMMWLLV RGVWETLAMT FVSGFFGFVI GLPVGVLLYV TRPGQIIANA KLYRTISAIV  60
NIFRSIPFII LLVWMIPFTR VIVGTSIGLQ AAIVPLTVGA APFIARMVEN ALLEIPTGLI  120
EASRAMGATP MQIVRKVLLP EALPGLVNAA TITLITLVGY SAMGGAVGAG GLGQIGYQYG  180
YIGYNATVMN TVLVLLVILV YLIQFAGDRI VRAVTRK                           217

SEQ ID NO: 1031         moltype = AA  length = 271
FEATURE                 Location/Qualifiers
source                  1..271
                        mol_type = protein
                        organism = synthetic construct
SEQUENCE: 1031
MAFKFKTFAA VGALIGSLAL VGCGQDEKDP NHIKVGVIVG AEQQVAEVAQ KVAKDKYGLD  60
VELVTFNDYV LPNEALSKGD IDANAFQHKP YLDQQLKDRG YKLVAVGNTF VYPIAGYSKK  120
```

-continued

```
IKSLDELQDG SQVAVPNDPT NLGRSLLLLQ KVGLIKLKDG VGLLPTVLDV VENPKNLKIV  180
ELEAPQLPRS LDDAQIALAV INTTYASQIG LTPAKDGIFV EDKESPYVNL IVTREDNKDA  240
ENVKKFVQAY QSDEVYEAAN KVFNGGAVKG W                                 271

SEQ ID NO: 1032        moltype = AA  length = 316
FEATURE                Location/Qualifiers
source                 1..316
                       mol_type = protein
                       organism = synthetic construct
SEQUENCE: 1032
MSELVVFKAN ELAISRYDLT EHETKLILCC VALLNPTIEN PTRKERTVSF TYNQYAQMMN  60
ISRENAYGVL AKATRELMTR TVEIRNPLVK GFEIFQWTNY AKFSSEKLEL VFSEEILPYL  120
FQLKKFIKYN LEHVKSFENK YSMRIYEWLL KELTQKKTHK ANIEISLDEF KFMLMLENNY  180
HEFKRLNQWV LKPISKDLNT YSNMKLVVDK RGRPTDTLIF QVELDRQMDL VTELENNQIK  240
MNGDKIPTTI TSDSYLRNGL RKTLHDALTA KIQLTSFEAK FLSDMQSKHD LNGSFSWLTQ  300
KQRTTLENIL AKYGRI                                                  316

SEQ ID NO: 1033        moltype = AA  length = 286
FEATURE                Location/Qualifiers
source                 1..286
                       mol_type = protein
                       organism = synthetic construct
SEQUENCE: 1033
MSIQHFRVAL IPFFAAFCLP VFAHPETLVK VKDAEDQLGA RVGYIELDLN SGKILESFRP  60
EERFPMMSTF KVLLCGAVLS RIDAGQEQLG RRIHYSQNDL VEYSPVTEKH LTDGMTVREL  120
CSAAITMSDN TAANLLLTTI GGPKELTAFL HNMGDHVTRL DRWEPELNEA IPNDERDTTM  180
PVAMATTLRK LLTGELLTLA SRQQLIDWME ADKVAGPLLR SALPAGWFIA DKSGAGERGS  240
RGIIAALGPD GKPSRIVVIY TTGSQATMDE RNRQIAEIGA SLIKHW                 286

SEQ ID NO: 1034        moltype = DNA  length = 1674
FEATURE                Location/Qualifiers
source                 1..1674
                       mol_type = other DNA
                       organism = synthetic construct
SEQUENCE: 1034
atgtccccga cggcgtttcc agcggccgaa acagctactg cccctgcaac tgccgtcgat  60
cctgggccag aactggacgg cggagatttc gcccttccag agggcgggct ggatgacgat  120
cgtcgcttac gtgcattgga cgcagttgac gagtatttga cccgcaagcg caagcatttg  180
gttgggtacc aagctaccca ggatatggac ggaacggcct tggatttagc ccgtttcatg  240
ccccacaaca tcaacaacct gggagatcct ttccagtcgg gtgggtataa accaaatacg  300
aaagtcgttg agcgtgccgt actggactac tatgcaaaat tgtggcacgc agaacgtcca  360
cacgacccag ctgacccaga aagctactgg ggttacatgt tatcgatggg ctcaactgag  420
ggcaacatgt acgccctgtg gaatgcacgt gactacctgt cgggtaaggc tttgattcag  480
cctcccacgg caccatttga cgctgttcgc tacgtgaagg ctgaccccga tcgccgcaat  540
cctaacgcac accacccagt cgcattctac tcggaggata cccactattc ttttgctaaa  600
gccgttgcgg tgctgggtgt cgaaactttc cacgctgtgg gtctggagaa atacgctgac  660
gagtgcccct tggtggatcc agtaaccggc cttcgtacct ggccgaccga agttccatcg  720
cgcccggggc cgtcgggttt aagctgggac ggccctggtg agattgatgt tgatgcgctt  780
gcagtactgg tcgagttctt cgcagcgaag ggtcaccccg tcttcgtcaa ccttaacttg  840
gggtctacat ttaaaggagc acatgatgac gtacgtgcgg tatgtgaacg cttattacca  900
atcttcgagc gccatggctt agtacaacgt gaagttgtat atgggagctg tccccaaacc  960
ggccgcccctt tagtggatgt acgtcgcgga ttttggatcc acgtagatgg ggcacttggg  1020
gcggggtatg cccctttttct gcgtcttgcc gccgaagacc cggaaggtta tggttggacc  1080
cctgaggcag aattacctga gttcgacttc ggcttacgtt tgccgacggc ggggcatgga  1140
gaagttgata tggttagcag catcgccatg agtggacata agtgggcagg cgcgccgtgg  1200
ccatgcggca tctatatgac gaaagtgaaa tatcagatta gtccaccgtc acagcccgat  1260
tatattggtg ctcctgacac aacatttgcc ggttcccgta acggcttttc gccgttaatt  1320
ttgtgggatc atttatcgcg ctactcgtac cgcgaccagg tagagcgcat ccgcgaagca  1380
caggagcttg cagcatattt ggaacgccgc cttaccgcta tggagcgcga gctgggagtg  1440
gaactttggc cagcccgcac accgggtgct gtaaccgtac gttttcgcaa accctctgct  1500
gagctggttg cgaagtggtc cttgtcgtcg caggatgttt taatggtgcc gggtgatgaa  1560
actacgcgtc gtagttacgt tcatgtgttc gtgatgcctt ctgttgatcg tgcaaagtta  1620
gatgcgttgc tggcagaatt ggccgaagat cccgtcatct tgggtgcgcc ttaa        1674

SEQ ID NO: 1035        moltype = DNA  length = 1674
FEATURE                Location/Qualifiers
source                 1..1674
                       mol_type = other DNA
                       organism = synthetic construct
SEQUENCE: 1035
atgtccccga cggcgtttcc agcggccgaa acagctactg cccctgcaac tgccgtcgat  60
cctgggccag aactggacgg cggagatttc gcccttccag agggcgggct ggatgacgat  120
cgtcgcttac gtgcattgga cgcagttgac gagtatttga cccgcaagcg caagcatttg  180
gttgggtacc aagctaccca ggatatgcag ggaacggcct tggatttagc ccgtttcatg  240
cccaacaaca tcaacaacct gggagatcct ttccagtcgg gtgggtataa accaaatacg  300
aaagtcgttg agcgtgccgt actggactac tatgcaaaat tgtggcacgc agaacgtcca  360
cacgacccag ctgacccaga aagctactgg ggttacatgt tatcgatggg ctcaactgag  420
ggcaacatgt acgccctgtg gaatgcacgt gactacctgt cgggtaaggc tttgattcag  480
cctcccacgg caccatttga cgctgttcgc tacgtgaagg ctgaccccga tcgccgcaat  540
```

```
cctaacgcac accacccagt cgcattctac tcggaggata cccactattc ttttgctaaa  600
gccgttgcgg tgctgggtgt cgaaactttc cacgctgtgg gtctggagaa atacgctgac  660
gagtgcccct tggtggatcc agtaaccggc cttcgtacct ggccgaccga agttccatcg  720
cgcccggggc cgtcgggttt aagctgggac ggccctggtg agattgatgt tgatgcgctt  780
gcagtactgg tcgagttctt cgcagcgaag ggtcaccccg tcttcgtcaa ccttaacttg  840
gggtctacat ttaaaggagc acatgatgac gtacgtgcgg tatgtgaacg cttattacca  900
atcttcgagc gccatggctt agtacaacgt gaagttgtat atgggagctg tccccaaacc  960
ggccgccctt tagtggatgt acgtcgcgga ttttggatcc acgtagatgg ggcacttggg  1020
gcggggtatg cccctttttct gcgtcttgcc gccgaagacc cggaaggtta tggttggacc  1080
cctgaggcag aattacctga gttcgacttc ggcttacgtt tgccgacggc ggggcatgga  1140
gaagttgata tggttagcag catcgccatg agtggacata agtgggcagg cgcgccgtgg  1200
ccatgcggca tctatatgac gaaagtgaaa tatcagatta gtccaccgtc acagcccgat  1260
tatattggtg ctcctgacac aacatttgcc ggttcccgta acggcttttc gccgttaatt  1320
ttgtgggatc atttatcgcg ctactcgtac cgcgaccagg tagagcgcat ccgcgaagca  1380
caggagcttg cagcatattt ggaacgccgc cttaccgcta tggagcgcga gctgggagtg  1440
gaactttggc cagcccgcac accgggtgct ctgaccgtac gttttcgcaa accctctccg  1500
gagctggttg cgaagtggtc cttgtcgtcg caggatgttt taatggtgcc gggtgatgaa  1560
actacgcgtc gtagttacgt tcatgtgttc gtgatgcctt ctgttgatcg tgcaaagtta  1620
gatgcgttgc tggcagaatt ggccgaagat cccgtcatct tgggtgcgcc ttaa        1674

SEQ ID NO: 1036        moltype = DNA  length = 1674
FEATURE                Location/Qualifiers
source                 1..1674
                       mol_type = other DNA
                       organism = synthetic construct
SEQUENCE: 1036
atgtccccga cggcgtttcc agcggccgaa acagctactg cccctgcaac tgccgtcgat  60
cctgggccag aactggacgg cggagatttc gcccttccag agggcgggct ggatgacgat  120
cagcgcttac gtgcattgga cgcagttgac gagtatttga cccgcaagcg caagcatttg  180
gttgggtacc aagctaccca ggatatggac ggaacggcct tggatttagc ccgtttcatg  240
cccaacaaca tcaacaacct gggagatcct ttccagtcgg gtgggtataa accaaatacg  300
aaagtcgttg agcgtgccgt actggactac tatgcaaaat tgtggcacgc agaacgtcca  360
cacgacccag ctgacccaga aagctactgg ggttacatgt tatcgatggg ctcaactgag  420
ggcaacatgt acgccctgtg gaatgcacgt gactacctgt cgggtaaggc tttgattcag  480
cctcccacgg caccatttga cgctgttcgc tacgtgaagg ctgaccccga tcgccgcaat  540
cctaacgcac accacccagt cgcattctac tcggaggata cccactattc ttttgctaaa  600
gccgttgcgg tgctgggtgt cgaaactttc cacgctgtgg gtctggagaa atacgctgac  660
gagtgcccct tggtggatcc agtaaccggc cttcgtacct ggccgaccga agttccatcg  720
cgcccggggc cgtcgggttt aagctgggac ggccctggtg agattgatgt tgatgcgctt  780
gcagtactgg tcgagttctt cgcagcgaag ggtcaccccg tcttcgtcaa ccttaacttg  840
gggtctacat ttaaaggagc acatgatgac gtacgtgcgg tatgtgaacg cttattacca  900
atcttcgagc gccatggctt agtacaacgt gaagttgtat atgggagctg tccccaaacc  960
ggccgccctt tagtggatgt acgtcgcgga ttttggatcc acgtagatgg ggcacttggg  1020
gcggggtatg cccctttttct gcgtcttgcc gccgaagacc cggaaggtta tggttggacc  1080
cctgaggcag aattacctga gttcgacttc ggcttacgtt tgccgacggc ggggcatgga  1140
gaagttgata tggttagcag catcgccatg agtggacata agtgggcagg cgcgccgtgg  1200
ccatgcggca tctatatgac gaaagtgaaa tatcagatta gtccaccgtc acagcccgat  1260
tatattggtg ctcctgacac aacatttgcc ggttcccgta acggcttttc gccgttaatt  1320
ttgtgggatc atttatcgcg ctactcgtac cgcgaccagg tagagcgcat ccgcgaagca  1380
caggagcttg cagcatattt ggaacgccgc cttaccgcta tggagcgcga gctgggagtg  1440
gaactttggc cagcccgcac accgggtgct gtaaccgtac gttttcgcaa accctctgct  1500
gagctggttg cgaagtggtc cttgtcgtcg caggatgttt taatggtgcc gggtgatgaa  1560
actacgcgtc gtagttacgt tcatgtgttc gtgatgcctt ctgttgatcg tgcaaagtta  1620
gatgcgttgc tggcagaatt ggccgaagat cccgtcatct tgggtgcgcc ttaa        1674

SEQ ID NO: 1037        moltype = DNA  length = 1674
FEATURE                Location/Qualifiers
source                 1..1674
                       mol_type = unassigned DNA
                       organism = unidentified
SEQUENCE: 1037
atggggttcc agttactgtc taaacataag ctgtcagccg aggatcaaca gaaacttgac  60
cgcttttatc gtgatattca gacagaagca gaacgattcc tgggttaccc atgtaacgaa  120
ctctttgact actccccctt gttccggttc ctgcaatatc cgctgaataa cgtcggcgac  180
ccgtacctgc cgagtaacta ccacctgaac acgcacaact ttgagtgcga agtactggaa  240
atcttccgta ccctgaccga ggctactgaa ggttcgactt ggggctacgt gaccaacggc  300
ggtacggaag gtaatcatta tggtcttttc ctggcgagag agctgctgcc tgaaggcctt  360
gtttactatt ctcaggatgc gcactactcg atcgataaaa tcctgaggtg cctcaacctc  420
cgtagcataa tgattcgcag ccacgacgac ggacgcatgg acctggatga tctgcgtgaa  480
actctgcgta tccatcgcga cttgccgccg atcgtttgcg ctaccattgg tactacaatg  540
aagggcgctg tagatgacat cgcaggcatt aaaaagatct tcaaagatct ggcaatacac  600
cgtcactata tccatgctga cgcggcccta ggtggcatga ttttaccgtt cctggataac  660
tccccaccgt ggaattttaa agctggaatc gactctatcg ctatctccgg tcacaaaatg  720
gtgggcagtc ctatcccgtg tggggttgtc ctggctaaaa agtcgaacgt tgaacgtatt  780
gcacagagcg tggaatacat tggtactctg gataccaccc tgtctggctc ccgtaacgcc  840
ttgactccgt tatttctgtg gtacgcgttc cacaccgttg gtatcgaagg tttcaaacgt  900
atcatcccgg catgcttaaa aatggcggac tatgccatcg ctcagctgaa caaaattaac  960
cgcaatgcgt ggcgctaccc ttacagcaac acggtagtct tcgatcgccc aagccccgaa  1020
gtgactcgtt attggcagct ggcttgtcag ggcaacctga gccacctaat caccatgcca  1080
```

```
cacgttacat ctactcaaat tgatcatctg gttgctgaca tcatcgcttc tgagccgata  1140
ccgccgctgc cgaccctgtc agttactccg gcatgcgaac tgctgacttc taccccggac  1200
caggatatta cgctgatcgg caccgctaat cataatctgc tctccgaagt atctaccgcc  1260
ctggctgccg agggtctgtc aattgaaaac ctggctgctg tggcggtaga aagcgaggac  1320
gttgaagttg taaggctccg cgttaacaac cgtgagcgtg cactgcaaat cctgaaccag  1380
aacctggata tcggtcgttg ctacggtcag gctcgaccct ttggcaacga agaagcgacg  1440
caggtactgt cccagctgga atatcaaagc gtgggggagg atgcactact ggtccagctt  1500
gacgattgcc ctggcagcct ggcggagctg ttgaaggatt gccgcaacga agcggtaaaa  1560
atccgtaata tccgactgct ttggcgtggg cacggtaagg gcgtcgtagc aattgctacc  1620
acttctccag atgcgctgaa aacgctgctg aaagaccgta ttcttttgag ctaa        1674

SEQ ID NO: 1038        moltype = DNA  length = 1278
FEATURE                Location/Qualifiers
source                 1..1278
                       mol_type = genomic DNA
                       organism = Mus musculus
SEQUENCE: 1038
atgtccacac ctagtgaagt aaagaaggat ttgctgggtg cagcagggtc attatggccg  60
tcggagccca ttacgctggg tccaggtgaa agtgcttggc agctggtatt gaagaagatc  120
caagagttga gtgacagcgg tcatcaagac ccgttcatgg ttgcagacct tgatgtcctt  180
gtgtctcgtc atcagacgtt ctgtcaagca ctgcctagag tacaaccctt ctatgcagta  240
aagtgcaata gtaacccatg ggtgttacgg gtgttggcag ctcttggcac gggatttgat  300
tgtgcttctc agggagaatt ggagcaagtt ttgggcttgg gtgtagcgcc gtcacggata  360
atcttcgcaa atccctgtaa agcagtcagc cacattcagt ttgcagctcg gtgcggtgtg  420
caattgttga cattcgacag cgaagaggag ttaatcaagg ttgcgcagta ccatccaggc  480
gcacggttgg tgcttcggat tcaaacccag gactcacaat caacgttccc actttccacc  540
aagttcggtg cttctttaga agcatgtgga caccttctgc aggttgccag agagctgggt  600
cttgccgtgg taggtgctag ctttcatgta ggaagcgact gccacacacc tcagagtttt  660
cgtcaggcca tcgcagattg tcatcgtgtg ttcgagatgg gccgtaaggc aggtcatgat  720
atgtcgcttc ttgatttggg tggagggttc ccaggtgtgg aaggttccga ggcgaagttt  780
gaggagatgg caagagtaat caatgccgct cttgctcagt actttccgga agagactggc  840
atcgaggtga tcgcggaacc tggtcgtttc tacgctgggt cggtgtgcac tgcagctgtg  900
aacatcatcg cgaagaagtc tgtcttggaa ccaggtggtc atcgtaagct tatgtactac  960
cttaatgaag gacattacgg ttctttcaga ttgttcttgc gtgatccagt gcctcgtatt  1020
cccatcgtgg tgaaagagtt cccatccgaa ccaccactgt ttccttgcac tttgtacggt  1080
cccacatgtg acgcctatga tcggttgttt tccgaagagg tacaattgcc agagctggat  1140
gttggagatt ggttgatctt cccagatatg ggtgcctata cctcctcaat gtcctcgacc  1200
ttcaacggat ttccaccggc caccgtgtat tgcgcaatgt caccgcagtt acgctccctg  1260
ttggagactg taccataa                                                1278

SEQ ID NO: 1039        moltype = DNA  length = 1278
FEATURE                Location/Qualifiers
source                 1..1278
                       mol_type = genomic DNA
                       organism = Mus musculus
SEQUENCE: 1039
atgaacacac ctagtgaagt aaagaaggat ttgctgggtg ttgcagaaca tttacgtccg  60
tcggagccca ttacgctggg tccaggtgcg agtgcttggc agctggtatt gaagaagatc  120
aaggagttga gtattagcgg tcgtcaagac gctttcatgg ttgcagacct tgatgtcctt  180
gtgtctcgtc atcggacgtt cttacaagca ctgcctagag tacaaccctt ctatgcagta  240
aagtgcaata gtaacccatg ggtgttactt gtgttggcag ctcttggcac gggatttgat  300
tgtgcttctc agggagaatt ggagcaagtt ttgggcttgg gtgtagcgcc gtcacggata  360
atcttcgcaa atccctgtaa agcagtcagc cacattcagt ttgcagctcg gtgcggtgtg  420
caattgttga cattcgacaa tgaagaggag ttaatcaagt tagcgcgtta ccatccacgt  480
gcacggttgg tgcttcggat tcaaaccctg gactcacaat caacgttccc acttagcacc  540
aagttcggtg ctcacttaga agcatgtgga caccttctgc aggttgccag agagctgggt  600
cttgccgtgg taggtgctag ctttcatgta ggaagcgact gccacacacc tgagagttac  660
cgtcaggcca tcgcagattg tcatcgtgtg ttcgagatgg gctgtaaggc aggtcatcac  720
atgtcgcttc ttgatttggg tggagggttc ccaggtgtga aaggttccga ggcgaagttt  780
gaggaggttg caagagtaat caataccgct cttgctcagt actttccgga agagactggc  840
atcgaggtga tcgcggaacc tggtcgtttc tacgctgggt cggtgtgcac tgcagctgtg  900
aacatcatcg ccaagaagtc tagtttggac ccaggtggtc atcgtaagct tgcttactac  960
cttaatgaag gacattacgg tgtattcaga ttgttcttgc gtgatccagt gcctcgtatt  1020
cccatcgtgg tgaaagagtt cccatccgaa ccaccactgt ttccttgcac tttgtacggt  1080
cccacatgtg acgcctatga tcggttgttt tccaccgagg tacaattgcc agagctggat  1140
gttggagatt ggttgatctt cccagatatg ggtgcctatt cgtcctcaat gtcctcgacc  1200
ttcaacggat ttccaatagc caccgtgtat gatgcaatgt caccgcagtt acgctccctg  1260
ttggagactg taccataa                                                1278

SEQ ID NO: 1040        moltype = DNA  length = 1242
FEATURE                Location/Qualifiers
source                 1..1242
                       mol_type = genomic DNA
                       organism = Entamoeba histolytica
SEQUENCE: 1040
atgaaacaaa cgtcccttga ggtgaaggaa tttgccttga atctcatttc tcagttcgaa  60
ccagaaaacc agcctctggg tttctggata ttcgacaccg aaggcgttga gaaagcggta  120
gaacgctgga aaaagaacat gccgactgtc cgtccctgtt ttgcagttaa atgcaacccg  180
gagccgcacc tggtgaaatt actgggggaa ctgggttgcg gcttcgattg cgctagcctg  240
```

-continued

```
aacgaaatca aagaggtact ggacttgggt tttaatccgg aagatatcac ttatagtcag  300
accttcaaac cgtacaacca gttaattgaa gcttcgcatc tgggcatcaa ccacacgatc  360
gttgattcaa tcgacgaagt tcaaaaaatt gctaaatacg cgcctaagat gggtatcatg  420
attcggatca tggaaaatga cacaagcgca ggccacgtct ttggagagaa attcggtctg  480
catgatgatg aagttgagat cgtactgaag gaaattaaag acaaaggtct gaacctggac  540
ggcgttcatt tccacgttgg ctctgattcc cacaacagcg aagtgtttac taaggcactg  600
accaaagctc gtaacactgt aaccctggcc gaacagttcg gcatgaaacc gtacctgatc  660
gacattggtg gcgggttctc tcaggttgcg ccgttcgaag aatttgctgc taccatcgaa  720
aaaactataa aggaactgga atttccagag cgaactcgtt tcattgcaga gccgggtcgc  780
tatatggcat caaatgcctt tcaccttgtc tcttcgctgc atggtaaaag ggtgcgcatc  840
cagaacggta agaaacagat cgaatacacc agcggcgatg ggctgcacgg ctccttcggc  900
tgttgcatct ggttcgaaaa acagaagtct tgcgaatgta taacacaaaa agtaaacgag  960
aacaccaaaa tgtatgaaag catcatctac ggcccatctt gcaacggttc ggacaaagtg  1020
gccacgcagg agttgccgga aatggagccg ggtaaagatt ggctgctgtt ccccaatatg  1080
ggtgcttaca ctatttccat ggcgaccaac tttaacggct tcgaagaacg taaccatgta  1140
atctatacgt taccactcaa aagtactaaa ataattcaga tccctaaaag cattgaatgc  1200
aactccgttc cgtctttaaa cggaatccca cactacgcgt aa                    1242

SEQ ID NO: 1041        moltype = DNA  length = 1509
FEATURE                Location/Qualifiers
source                 1..1509
                       mol_type = genomic DNA
                       organism = Flavobacterium segetis
SEQUENCE: 1041
atggggacca ttaacacgaa gatctataaa tacatgagca tctggaaaac aaaacctctg  60
tccgtgctct tgtctgaagc aactgaggat gaaaaaggcc tgaagcgcac tctgtcggcc  120
cgttcacttg ttgcgctggg tgtcggtgct attatcggcg ctggtttatt ctctctgacc  180
ggcatagctg cggcagacaa tgctggaccg gcagtaaccc tgagctttat cctggcctcc  240
gttggttgcg cgttcgctgg cctgtgttac gcagaatttg cttctatgat tccagttgcg  300
ggtagcgcct acacttatag ttatgctacc atgggcgagt tcgtggcgtg gatcatcggt  360
tgggatctgg tactcgaata cgcattgggc gcagctactg ttgccgttag ctggtcccag  420
tacgtggaca aattcttgca aaactacggc atccatattc cgaactctat cctccacggg  480
ccgtgggata ccacccccgg tattatcaat ttaccgtcga tatttatcat ctgcctgctg  540
agcgtgctgc tgattcgtgg tactaaagaa tctgctctga tcaacaacat tctggtaatc  600
ctgaaagtca cggttgtcat cgtgttcatt ggcctgggct gggggttcat gaactccgca  660
aaccacacgc cctttatccc ggttaacgaa ggtgaggctc tactgtcttc tggtgaaatg  720
agtttcctca actttttcag cagtgactac tttggacact acggatggtc cggtattctt  780
cgcggcgctg gtgtagtatt cttcgcattt atcggcttcg acgcggtgag cactgcggca  840
caggaggcca aggatccgca gaaaggcatg ccaatcggta ttctgggctc actgatcatt  900
tgcaccgttc tgtacgtgct tttcgctttc gttctgaccg gtctggaaaa ctatctaaac  960
ttcaaaggtg acgcttctcc tgtcaccact gcatttgcca aaacaggcta ctttcctg  1020
aatagcggtc tgacgatcgc tatcatagcg ggctacacat ccgttatgct ggtaatgttg  1080
atgggtcagt cccgtgtctt ttatagtatg tctgtggatg gcctgcttcc gaagtttttc  1140
tcgaccctgc ataccaaaaa caggactccg tacaaaacta atttgctgtt catggttttc  1200
gtaagcctgt tcgctggctt tgttccggtc agcgacctgg gccatatggt atccatcggt  1260
accctcttcg ctttctgcct ggtgtgtatc ggcgttatcg ttatgcgaaa aaccaaccca  1320
gacgccgttc gcggttttcg tgttcctttt gtaccggttt tcccgattat cggtgtagtt  1380
atttgtctgg ttctaatggc gggcctgccg attgaatctt gggaacgtct ggcgatctgg  1440
atgattctgg gtgtcgtgat ctacttcttc tactctaaaa agaactctaa actgaataac  1500
cccgaataa                                                         1509

SEQ ID NO: 1042        moltype = DNA  length = 1481
FEATURE                Location/Qualifiers
source                 1..1481
                       mol_type = genomic DNA
                       organism = Flavobacterium frigoris
SEQUENCE: 1042
atggggacga tcaatactaa gaccaacaaa tatatgagca tttggaaaac caaaccgttg  60
tctgtactgt taaacgaggc ctcagaagat gaaaagggcc tgaaaaggac tctgtcctct  120
cgttccctcg tggctctggg tgtcggtgcg atcattggcg caggtctgtt tagcctaaca  180
ggcatcgcag ctgcggaaca tgctggtcca gcggttactc tgagtttcat actggccgct  240
gttggttgtg ctttcgcagg cctgtgctac gcggagtttg cgtcgatgat ccctgtggct  300
gggtctgctt acacctatag ctacgcaacc atgggcgaat ttatggcgtg gatcattggc  360
tgggaccttg tactggaata cgctctgggt gcagcgactg ttggtgtatc ctggtcccgt  420
tacttactgg aattgctgaa caaatatggt gttcacctga acccgaaatt catctgctct  480
ccgtgggaga cacttaccct gggcgacggc actattatcg atggcgggta catcaatctg  540
ccggcaattc tgatcgtgag cgccctcagc ttgctgctga ttagaggtac ccaggaatct  600
gcttctatta acaacatcct ggttgtgctg aaagtaatag tcgtgatcat gttcatcgtt  660
ttaggatggg actatatcga tcccgcaaat tactcacctt acatcccgga aaacaccggc  720
gtaaagggcc aattcggttg gtcgggtatc gctgcgggtg ctggtacggt tttctttgcc  780
ttcattggtt tcgacgccgt ttccactgcg gctcaggagg ctaaaaaccc gcagaaaggc  840
atgccaattg gcatcctggg gtctttggta atttgtacga tcctgtacgt cctttttgcc  900
cacgttatga cgggcctggt gccgtattat aagttcgctg gagatgctaa acccgctgcg  960
acagcattcg cagtcaccgg ttacagtttt ctgcaaactg gactgattgt tgcgatcctg  1020
gctggctata ctagcgttat gctggtcatg ctgatggggc agagtcgtgt tttctacacc  1080
atgagcaaag acggtctgct accaccgctg ttcggtcaga tccattcgaa atttcgcact  1140
ccgtacaaga ctaacctgtt ctttatggta ttcgtttctt tattcgcggg tttcgtgccg  1200
gttagcgacc tcggccacat ggtcagcatc ggtaccctcc tggcgtttgt tcttgtgtgc  1260
ataggtgtgc tggtgatgcg aaaaaagatg ccagatgctc cgcgttcttt caaaaccccg  1320
```

-continued

```
ttcgttccgt atgtacccat cgcaggcgtc ctggtgtgca cttacctgat gtactccctc  1380
ccttacgaat cctggattcg cttagtgctt tggatggcta tcggcgtagc cctgtacttc  1440
gtgtatggaa aaaagcactc aaaactgaac aatccggata a                      1481

SEQ ID NO: 1043        moltype = DNA  length = 2533
FEATURE                Location/Qualifiers
source                 1..2533
                       mol_type = genomic DNA
                       organism = Escherichia coli
SEQUENCE: 1043
atgataaaac tttcgaatat caccaaagtg ttccaccagg gcacccgcac catccaggcg  60
ttgaacaacg tcagcctgca tgtgccagct ggacaaattt atggcgttat cggtgcctca  120
ggcgcgggta agagtacgct tatacgttgt gtaaacctgc tggagcgccc aaccgagggt  180
agcgtgctgg tcgatggcca ggaactgacc acgctgtcag aatccgagtt gaccaaagct  240
cgtcgccaga ttggtatgat tttccagcat tttaacctgc tctcttcgcg tactgttttt  300
ggcaacgtgg ctctgccgct ggagctggac aacacaccga aagacgagat caaacgtcgc  360
gtgacggaat tgctgtcatt ggttggtctt ggcgataagc atgatagcta cccgtcgaat  420
ctttccggtg ggcagaaaca acgtgtggcg attgcccgtg cattagccag caatcccaaa  480
gtattgctgt gtgatgaagc caccagcgcg ctggacccgg caacgacacg ttctattctc  540
gaactgctga aagacatcaa ccgccgtctg ggtttgacga ttctgttgat cactcacgaa  600
atggacgttg tgaagcgcat ttgtgattgc gtggcggtca tcagcaatgg cgaactgatc  660
gagcaggaca cggtaagtga agtgttctcg catccgaaaa cgccgctggc gcagaagttt  720
attcagtcga ccctgcatct ggatatcccg gaagattacc aggaacgtct gcaagcggag  780
ccatttactg actgcgtgcc gatgctgcgt ctggagttta ccggtcaatc ggtcgatgcc  840
ccactgcttt ctgaaaccgc gcgtcgtttc aacgtcaaca acaacattat tagcgcgcag  900
atggattacg ccggtggcgt taagttcggc atcatgctga ctgaaatgca cggcacacaa  960
caagatacgc aagccgccat tgcctggctg caggaacacc atgtaaaagt agaggtactg  1020
ggttatgtct gagccgatga tgtggctgct ggttcgtggc gtatgggaaa cgctggcaat  1080
gaccttcgta tccggttttt ttggctttgt gattggtctg ccggttggcg ttctgcttta  1140
tgtcacgcgt ccggggcaaa ttattgctaa cgcgaagttg tatcgtacca tttctgcgat  1200
tgtgaacatt ttccgttcca tcccgttcat tatcttgctg gtatggatga ttccgtttac  1260
ccgcgttatt gtcggtacat cgattggatt gcaggcagcg attgttccgt taaccgttgg  1320
tgcagcaccg tttattgccc gtatggtcga gaacgctctg ctggagatcc caaccgggtt  1380
aattgaagct tcccgcgcaa tgggggccac gccaatgcag atcgtccgta aagtgctgtt  1440
accggaagcg ttgccgggtc tggtgaatgc ggcaactatc accctgatta ccctggttgg  1500
ttattccgcg atgggtggtg cagtcggtgc cggtggttta ggtcagattg gctatcagta  1560
tggctacatc ggctacaacg cgacggtgat gaatacggta ctggtattgc tggtcattct  1620
ggtttattta attcagttcg caggcgaccg catcgtccgg gctgtcactc gcaagtaacg  1680
ttcaacacaa cataaataat tgaagaagga ataaggtatg gcgttcaaat tcaaaacctt  1740
tgcggcagtg ggagccctga ttggatcact ggcactggta ggctgcggtc aggatgaaaa  1800
agatccaaac cacattaaag tcggcgtgat tgttggtgcc gaacagcagg ttgcagaagt  1860
cgcgcagaaa gttgcgaaag acaaatatgg cctggacgtt gagctggtaa ccttcaacga  1920
ctatgttctg ccaaacgaag cattgagcaa aggcgatatc gacgccaacg ccttccagca  1980
taaaccgtac cttgatcagc aactgaaaga tcgtggctac aaactggtcg cagtaggcaa  2040
cacatttgtt tatccgattg ctggttactc caagaaaatc aaatcactgg atgaactgca  2100
ggatggttcg caggttgccg tgccaaacga cccaactaac cttggtcgtt cactgctgct  2160
gctgcaaaaa gtgggcttga tcaaactgaa agatggcgtt ggcctgctgc cgaccgttct  2220
tgatgttgtt gagaacccaa aaaatctgaa aattgttgaa ctggaagcac cgcagctacc  2280
gcgctctctg gacgacgcgc aaatcgctct ggcagttatc aataccacct atgccagcca  2340
gattggcctg actccagcga aagacggtat ctttgtcgaa gataaagagt ccccgtacgt  2400
aaacctgatc gtaacgcgtg aagacaacaa agacgccgaa aacgtgaaga aattcgttca  2460
ggcttatcag tctgacgaag tttacgaagc agcaaacaaa gtgtttaacg gcggcgctgt  2520
taaaggctgg taa                                                     2533

SEQ ID NO: 1044        moltype = DNA  length = 666
FEATURE                Location/Qualifiers
source                 1..666
                       mol_type = genomic DNA
                       organism = Bacillus subtilis
SEQUENCE: 1044
atgtttgaga agtattttcc aaatgttgac ttgaccgagt tatggaatgc cacatatgaa  60
actctgtata tgacattgat ttccttactg tttgccttcg taatcggcgt catcctggga  120
ttgctgttat tcttaacatc taaggggtct ctttggcaaa ataaagcagt aaattccgtt  180
atcgcagccg ttgtcaacat ctttcgttca attcccttcc ttattttaat catcctgctt  240
cttggtttca ctaaattctt agtgggaaca attttgggac caaatgcggc tcttcccgcg  300
ttagtcatcg gtagtgctcc cttttatgct cgtctggtcg aaatcgcact tcgtgaagtg  360
gacaaaggag tgattgaggc ggcgaaatcg atgggggcta agacgagcac tattattttt  420
aaggttctta tccccgagtc catgcccgcg ctgatttccg gaattacagt gactgcgatt  480
gcattgatcg ggtcaaccgc catcgcagga gctattggtt ctggtggatt gggaaactta  540
gcatacgttg aaggctatca atcgaataat gcggatgtga ccttcgtggc cacagttttc  600
atcctgatta ttgttttcat cattcagatc attggtgacc ttattaccaa catcatcgat  660
aaacgc                                                             666

SEQ ID NO: 1045        moltype = DNA  length = 2533
FEATURE                Location/Qualifiers
source                 1..2533
                       mol_type = other DNA
                       organism = synthetic construct
SEQUENCE: 1045
```

```
atgataaaac tttcgaatat caccaaagtg ttccaccagg gcacccgcac catccaggcg  60
ttgaacaacg tcagcctgca tgtgccagct ggacaaattt atggcgttat cggtgcctca  120
ggcgcgggta agagtacgct tatacgttgt gtaaacctgc tggagcgccc aaccgagggt  180
agcgtgctgg tcgatggcca ggaactgacc acgctgtcag aatccgagtt gaccaaagct  240
cgtcgccaga ttggtatgat tttccagcat tttaacctgc tctcttcgcg tactgttttt  300
ggcaacgtgg ctctgccgct ggagctggac aacacaccga aagacgagat caaacgtcgc  360
gtgacggaat tgctgtcatt ggttggtctt ggcgataagc atgatagcta cccgtcgaat  420
ctttccggtg ggcagaaaca acgtgtggcg attgcccgtg cattagccag caatcccaaa  480
gtattgctgt gtgatgaagc caccagcgcg ctggacccgg caacgacacg ttctattctc  540
gaactgctga aagacatcaa ccgccgtctg ggtttgacga ttctgttgat cactcacgaa  600
atggacgttg tgaagcgcat ttgtgattgc gtggcggtca tcagcaatgg cgaactgatc  660
gagcaggaca cggtaagtga agtgttctcg catccgaaaa cgccgctggc gcagaagttt  720
attcagtcga ccctgcatct ggatatcccg gaagattacc aggaacgtct gcaagcggag  780
ccatttactg actgcgtgcc gatgctgcgt ctggagttta ccggtcaatc ggtcgatgcc  840
ggcctgcttt ctgaaaccgc gcgtcgtttc aacgtcaaca acaacattat tagcgcgcag  900
atggattacg ccggtggcgt taagttcggc atcatgctga ctgaaatgca cggcacacaa  960
caagatacgc aagccgccat tgcctggctg caagaacacc atgtaaaagt agaggtactg  1020
ggttatgtct gagccgatga tgtggctgct ggttcgtggc gtatgggaaa cgctggcaat  1080
gaccttcgta tccggttttt ttggctttgt gattggtctg ccggttggcg ttctgcttta  1140
tgtcacgcgt ccggggcaaa ttattgctaa cgcgaagttg tatcgtacca tttctgcgat  1200
tgtgaacatt ttccgttcca tcccgttcat tatcttgctg gtatggatga ttccgtttac  1260
ccgcgttatt gtcggtacat cgattggatt gcaggcagcg attgttccgt taaccgttgg  1320
tgcagcaccg tttattgccc gtatggtcga gaacgctctg ctggagatcc caaccgggtt  1380
aattgaagct tcccgcgcaa tgggggccac gccaatgcag atcgtccgta aagtgctgtt  1440
accggaagcg ttgccgggtc tggtgaatgc ggcaactatc accctgatta ccctggttgg  1500
ttattccgcg atgggtggtg cagtcggtgc cggtggttta ggtcagattg gctatcagta  1560
tggctacatc ggctacaacg cgacggtgat gaatacggta ctggtattgc tggtcattct  1620
ggtttattta attcagttcg caggcgaccg catcgtccgg gctgtcactc gcaagtaacg  1680
ttcaacacaa cataaataat tgaagaagga ataaggtatg gcgttcaaat tcaaaacctt  1740
tgcggcagtg ggagccctga ttggatcact ggcactggta ggctgcggtc aggatgaaaa  1800
agatccaaac cacattaaag tcggcgtgat tgttggtgcc gaacagcagg ttgcagaagt  1860
cgcgcagaaa gttgcgaaag acaaatatgg cctggacgtt gagctggtaa ccttcaacga  1920
ctatgttctg ccaaacgaag cattgagcaa aggcgatatc gacgccaacg ccttccagca  1980
taaaccgtac cttgatcagc aactgaaaga tcgtggctac aaactggtcg cagtaggcaa  2040
cacatttgtt tatccgattg ctggttactc caagaaaatc aaatcactgg atgaactgca  2100
agatggttcg caggttgccg tgccaaacga cccaactaac cttggtcgtt cactgctgct  2160
gctgcaaaaa gtgggcttga tcaaactgaa agatggcgtt ggcctgctgc cgaccgttct  2220
tgatgttgtt gagaacccaa aaaatctgaa aattgttgaa ctggaagcac cgcagctacc  2280
gcgctctctg gacgacgcgc aaatcgctct ggcagttatc aataccacct atgccagcca  2340
gattggcctg actccagcga aagacggtat ctttgtcgaa gataaagagt ccccgtacgt  2400
aaacctgatc gtaacgcgtg aagacaacaa agacgccgaa aacgtgaaga aattcgttca  2460
ggcttatcag tctgacgaag tttacgaagc agcaaacaaa gtgtttaacg gcggcgctgt  2520
taaaggctgg taa                                                     2533
```

```
SEQ ID NO: 1046        moltype = DNA  length = 2533
FEATURE                Location/Qualifiers
source                 1..2533
                       mol_type = other DNA
                       organism = synthetic construct
SEQUENCE: 1046
atgataaaac tttcgaatat caccaaagtg ttccaccagg gcacccgcac catccaggcg  60
ttgaacaacg tcagcctgca tgtgccagct ggacaaattt atggcgttat cggtgcctca  120
ggcgcgggta agagtacgct tatacgttgt gtaaacctgc tggagcgccc aaccgagggt  180
agcgtgctgg tcgatggcca ggaactgacc acgctgtcag aatccgagtt gaccaaagct  240
cgtcgccaga ttggtatgat tttccagcat tttaacctgc tctcttcgcg tactgttttt  300
ggcaacgtgg ctctgccgct ggagctggac aacacaccga aagacgagat caaacgtcgc  360
gtgacggaat tgctgtcatt ggttggtctt ggcgataagc atgatagcta cccgtcgaat  420
ctttccggtg ggcagaaaca acgtgtggcg attgcccgtg cattagccag caatcccaaa  480
gtattgctgt gtgatgaagc caccagcgcg ctggacccgg caacgacacg ttctattctc  540
gaactgctga aagacatcaa ccgccgtctg ggtttgacga ttctgttgat cactcacgaa  600
atggacgttg tgaagcgcat ttgtgattgc gtggcggtca tcagcaatgg cgaactgatc  660
gagcaggaca cggtaagtga agtgttctcg catccgaaaa cgccgctggc gcagaagttt  720
attcagtcga ccctgcatct ggatatcccg gaagattacc aggaacgtct gcaagcggag  780
ccatttactg actgcgtgcc gatgctgcgt ctggagttta ccggtcaatc ggtcgatgcc  840
ccactgcttt ctgaaaccgc gcgtcgtttc aacgtcaaca acaacattat tagcgcgcag  900
atggattacg ccggtggcgt taagttcggc atcatgctga ctgaaatgca cggcacacaa  960
caagatacgc aagccgccat tgcctggctg caagaacacc atgtaaaagt agaggtactg  1020
ggttatgtct gagccgatga tgtggctgct ggttcgtggc gtatgggaaa cgctggcaat  1080
gaccttcgta tccggttttt ttggctttgt gattggtctg ccggttggcg ttctgcttta  1140
tgtcacgcgt ccggggcaaa ttattgctaa cgcgaagttg tatcgtacca tttctgcgat  1200
tgtgaacatt ttccgttcca tcccgttcat tatcttgctg gtatggatga ttccgtttac  1260
ccgcgttatt gtcggtacat cgattggatt gcaggcagcg attgttccgt taaccgttgg  1320
tgcagcaccg tttattgccc gtatggtcga gaacgctctg ctggagatcc caaccgggtt  1380
aattgaagct tcccgcgcaa tgggggccac gccaatgcag atcgtccgta aagtgctgtt  1440
accggaagcg ttgccgggtc tggtgaatgc ggcaactatc accctgatta ccctggttgg  1500
ttattccgcg atgggtggtg cagtcggtgc cggtggttta ggtcagattg gctatcagta  1560
tggctacatc ggctacaacg cgacggtgat gaatacggta ctggtattgc tggtcattct  1620
ggtttattta attcagttcg caggcgaccg catcgtccgg gctgtcactc gcaagtaacg  1680
ttcaacacaa cataaataat tgaagaagga ataaggtatg gcgttcaaat tcaaaacctt  1740
```

```
tgcggcagtg ggagccctga ttggatcact ggcactggta ggctgcggtc aggatgaaaa  1800
agatccaaac cacattaaag tcggcgtgat tgttggtgcc gaacagcagg ttgcagaagt  1860
cgcgcagaaa gttgcgaaag acaaatatgg cctggacgtt gagctggtaa ccttcaacga  1920
ctatgttctg ccaaacgaag cattgagcaa aggcgatatc gacgccaacg ccttccagca  1980
taaaccgtac cttgatcagc aactgaaaga tcgtggctac aaactggtcg cagtaggcaa  2040
cacatttgtt tatccgattg ctggttactc caagaaaatc aaatcactgg atgaactgca  2100
agatggttcg caggttgccg tgccaaacga cccaactaac cttggtcgtt cactgctgct  2160
gctgcaaaaa gtgggcttga tcaaactgaa agatggcgtt ggcctgctgc cgaccgttct  2220
tgatgttgtt gagaacccaa aaaatctgaa aattgttgaa ctggaagcac cgcagctacc  2280
gcgctctctg gacgacgcgc aaatcgctct ggcagttatc aataccacct atgccagcca  2340
gattggcctg actccagcga aagacggtat ctttgtcgaa gataaagagt ccccgtacgt  2400
aaacctgatc gtaacgcgtg aagacaacaa agacgccgaa aacgtgaaga aattcgttca  2460
ggcttatcag tctgacgaag tttacgaagc agcaaacaaa gtgtttaacg gcggcgctgt  2520
taaaggctgg taa                                                     2533

SEQ ID NO: 1047        moltype = DNA  length = 2533
FEATURE                Location/Qualifiers
source                 1..2533
                       mol_type = other DNA
                       organism = synthetic construct
SEQUENCE: 1047
atgataaaac tttcgaatat caccaaagtg ttccaccagg gcacccgcac catccaggcg  60
ttgaacaacg tcagcctgca tgtgccagct ggacaaattt atggcgttat cggtgcctca  120
ggcgcgggta agagtacgct tatacgttgt gtaaacctgc tggagcgccc aaccgagggt  180
agcgtgctgg tcgatggcca ggaactgacc acgctgtcag aatccgagtt gaccaaagct  240
cgtcgccaga ttggtatgat tttccagcat tttaacctgc tctcttcgcg tactgttttt  300
ggcaacgtgg ctctgccgct ggagctggac aacacaccga aagacgagat caaacgtcgc  360
gtgacggaat tgctgtcatt ggttggtctt ggcgataagc atgatagcta cccgtcgaat  420
ctttccggtg ggcagaaaca acgtgtggcg attgcccgtg cattagccag caatcccaaa  480
gtattgctgt gtgatgaagc caccagcgcg ctggacccgg caacgacacg ttctattctc  540
gaactgctga aagacatcaa ccgccgtctg ggtttgacga ttctgttgat cactcacgaa  600
atggacgttg tgaagcgcat ttgtgattgc gtggcggtca tcagcaatgg cgaactgatc  660
gagcaggaca cggtaagtga agtgttctcg catccgaaaa cgccgctggc gcagaagttt  720
attcagtcga ccctgcatct ggatatcccg gaagattacc aggaacgtct gcaagcggag  780
ccatttactg actgcgtgcc gatgctgcgt ctggagttta ccggtcaatc ggtcgatgcc  840
tccctgcttt ctgaaaccgc gcgtcgtttc aacgtcaaca acaacattat tagcgcgcag  900
atggattacg ccggtggcgt taagttcggc atcatgctga ctgaaatgca cggcacacaa  960
caagatacgc aagccgccat tgcctggctg caagaacacc atgtaaaagt agaggtactg  1020
ggttatgtct gagccgatga tgtggctgct ggttcgtggc gtatgggaaa cgctggcaat  1080
gaccttcgta tccggttttt ttggctttgt gattggtctg ccggttggcg ttctgcttta  1140
tgtcacgcgt ccggggcaaa ttattgctaa cgcgaagttg tatcgtacca tttctgcgat  1200
tgtgaacatt ttccgttcca tcccgttcat tatcttgctg gtatggatga ttccgtttac  1260
ccgcgttatt gtcggtacat cgattggatt gcaggcagcg attgttccgt taaccgttgg  1320
tgcagcaccg tttattgccc gtatggtcga gaacgctctg ctggagatcc caaccgggtt  1380
aattgaagct tcccgcgcaa tgggggccac gccaatgcag atcgtccgta aagtgctgtt  1440
accggaagcg ttgccgggtc tggtgaatgc ggcaactatc accctgatta ccctggttgg  1500
ttattccgcg atgggtggtg cagtcggtgc cggtggttta ggtcagattg gctatcagta  1560
tggctacatc ggctacaacg cgacggtgat gaatacggta ctggtattgc tggtcattct  1620
ggtttattta attcagttcg caggcgaccg catcgtccgg gctgtcactc gcaagtaacg  1680
ttcaacacaa cataaataat tgaagaagga ataaggtatg gcgttcaaat tcaaaacctt  1740
tgcggcagtg ggagccctga ttggatcact ggcactggta ggctgcggtc aggatgaaaa  1800
agatccaaac cacattaaag tcggcgtgat tgttggtgcc gaacagcagg ttgcagaagt  1860
cgcgcagaaa gttgcgaaag acaaatatgg cctggacgtt gagctggtaa ccttcaacga  1920
ctatgttctg ccaaacgaag cattgagcaa aggcgatatc gacgccaacg ccttccagca  1980
taaaccgtac cttgatcagc aactgaaaga tcgtggctac aaactggtcg cagtaggcaa  2040
cacatttgtt tatccgattg ctggttactc caagaaaatc aaatcactgg atgaactgca  2100
agatggttcg caggttgccg tgccaaacga cccaactaac cttggtcgtt cactgctgct  2160
gctgcaaaaa gtgggcttga tcaaactgaa agatggcgtt ggcctgctgc cgaccgttct  2220
tgatgttgtt gagaacccaa aaaatctgaa aattgttgaa ctggaagcac cgcagctacc  2280
gcgctctctg gacgacgcgc aaatcgctct ggcagttatc aataccacct atgccagcca  2340
gattggcctg actccagcga aagacggtat ctttgtcgaa gataaagagt ccccgtacgt  2400
aaacctgatc gtaacgcgtg aagacaacaa agacgccgaa aacgtgaaga aattcgttca  2460
ggcttatcag tctgacgaag tttacgaagc agcaaacaaa gtgtttaacg gcggcgctgt  2520
taaaggctgg taa                                                     2533

SEQ ID NO: 1048        moltype = AA  length = 557
FEATURE                Location/Qualifiers
source                 1..557
                       mol_type = protein
                       organism = synthetic construct
SEQUENCE: 1048
MSPTAFPAAE TATAPATAVD PGPELDGGDF ALPEGGLDDD RRLRALDAVD EYLTRKRKHL  60
VGYQATQDMD GTALDLARFM PHNINNLGDP FQSGGYKPNT KVVERAVLDY YAKLWHAERP  120
HDPADPESYW GYMLSMGSTE GNMYALWNAR DYLSGKALIQ PPTAPFDAVR YVKADPDRRN  180
PNAHHPVAFY SEDTHYSFAK AVAVLGVETF HAVGLEKYAD ECPLVDPVTG LRTWPTEVPS  240
RPGPSGLSWD GPGEIDVDAL AVLVEFFAAK GHPVFVNLNL GSTFKGAHDD VRAVCERLLP  300
IFERHGLVQR EVVYGSCPQT GRPLVDVRRG FWIHVDGALG AGYAPFLRLA AEDPEGYGWT  360
PEAELPEFDF GLRLPTAGHG EVDMVSSIAM SGHKWAGAPW PCGIYMTKVK YQISPPSQPD  420
YIGAPDTTFA GSRNGFSPLI LWDHLSRYSY RDQVERIREA QELAAYLERR LTAMERELGV  480
```

-continued

```
ELWPARTPGA VTVRFRKPSA ELVAKWSLSS QDVLMVPGDE TTRRSYVHVF VMPSVDRAKL  540
DALLAELAED PVILGAP                                                557

SEQ ID NO: 1049        moltype = AA  length = 557
FEATURE                Location/Qualifiers
source                 1..557
                       mol_type = protein
                       organism = Streptomyces sp.
SEQUENCE: 1049
MSPTAFPAAE TATAPATAVD PGPELDGGDF ALPEGGLDDD RRLRALDAVD EYLTRKRKHL  60
VGYQATQDMQ GTALDLARFM PNNINNLGDP FQSGGYKPNT KVVERAVLDY YAKLWHAERP  120
HDPADPESYW GYMLSMGSTE GNMYALWNAR DYLSGKALIQ PPTAPFDAVR YVKADPDRRN  180
PNAHHPVAFY SEDTHYSFAK AVAVLGVETF HAVGLEKYAD ECPLVDPVTG LRTWPTEVPS  240
RPGPSGLSWD GPGEIDVDAL AVLVEFFAAK GHPVFVNLNL GSTFKGAHDD VRAVCERLLP  300
IFERHGLVQR EVVYGSCPQT GRPLVDVRRG FWIHVDGALG AGYAPFLRLA AEDPEGYGWT  360
PEAELPEFDF GLRLPTAGHG EVDMVSSIAM SGHKWAGAPW PCGIYMTKVK YQISPPSQPD  420
YIGAPDTTFA GSRNGFSPLI LWDHLSRYSY RDQVERIREA QELAAYLERR LTAMERELGV  480
ELWPARTPGA VTVRFRKPSA ELVAKWSLSS QDVLMVPGDE TTRRSYVHVF VMPSVDRAKL  540
DALLAELAED PVILGAP                                                557

SEQ ID NO: 1050        moltype = AA  length = 557
FEATURE                Location/Qualifiers
source                 1..557
                       mol_type = protein
                       organism = synthetic construct
SEQUENCE: 1050
MSPTAFPAAE TATAPATAVD PGPELDGGDF ALPEGGLDDD RRLRALDAVD EYLTRKRKHL  60
VGYQATQDMQ GTALDLARFM PNNINNLGDP FQSGGYKPNT KVVERAVLDY YAKLWHAERP  120
HDPADPESYW GYMLSMGSTE GNMYALWNAR DYLSGKALIQ PPTAPFDAVR YVKADPDRRN  180
PNAHHPVAFY SEDTHYSFAK AVAVLGVETF HAVGLEKYAD ECPLVDPVTG LRTWPTEVPS  240
RPGPSGLSWD GPGEIDVDAL AVLVEFFAAK GHPVFVNLNL GSTFKGAHDD VRAVCERLLP  300
IFERHGLVQR EVVYGSCPQT GRPLVDVRRG FWIHVDGALG AGYAPFLRLA AEDPEGYGWT  360
PEAELPEFDF GLRLPTAGHG EVDMVSSIAM SGHKWAGAPW PCGIYMTKVK YQISPPSQPD  420
YIGAPDTTFA GSRNGFSPLI LWDHLSRYSY RDQVERIREA QELAAYLERR LTAMERELGV  480
ELWPARTPGA LTVRFRKPSP ELVAKWSLSS QDVLMVPGDE TTRRSYVHVF VMPSVDRAKL  540
DALLAELAED PVILGAP                                                557

SEQ ID NO: 1051        moltype = AA  length = 557
FEATURE                Location/Qualifiers
source                 1..557
                       mol_type = protein
                       organism = synthetic construct
SEQUENCE: 1051
MSPTAFPAAE TATAPATAVD PGPELDGGDF ALPEGGLDDD QRLRALDAVD EYLTRKRKHL  60
VGYQATQDMD GTALDLARFM PNNINNLGDP FQSGGYKPNT KVVERAVLDY YAKLWHAERP  120
HDPADPESYW GYMLSMGSTE GNMYALWNAR DYLSGKALIQ PPTAPFDAVR YVKADPDRRN  180
PNAHHPVAFY SEDTHYSFAK AVAVLGVETF HAVGLEKYAD ECPLVDPVTG LRTWPTEVPS  240
RPGPSGLSWD GPGEIDVDAL AVLVEFFAAK GHPVFVNLNL GSTFKGAHDD VRAVCERLLP  300
IFERHGLVQR EVVYGSCPQT GRPLVDVRRG FWIHVDGALG AGYAPFLRLA AEDPEGYGWT  360
PEAELPEFDF GLRLPTAGHG EVDMVSSIAM SGHKWAGAPW PCGIYMTKVK YQISPPSQPD  420
YIGAPDTTFA GSRNGFSPLI LWDHLSRYSY RDQVERIREA QELAAYLERR LTAMERELGV  480
ELWPARTPGA VTVRFRKPSA ELVAKWSLSS QDVLMVPGDE TTRRSYVHVF VMPSVDRAKL  540
DALLAELAED PVILGAP                                                557

SEQ ID NO: 1052        moltype = AA  length = 557
FEATURE                Location/Qualifiers
source                 1..557
                       mol_type = protein
                       organism = unidentified
SEQUENCE: 1052
MGFQLLSKHK LSAEDQQKLD RFYRDIQTEA ERFLGYPCNE LFDYSPLFRF LQYPLNNVGD  60
PYLPSNYHLN THNFECEVLE IFRTLTEATE GSTWGYVTNG GTEGNHYGLF LARELLPEGL  120
VYYSQDAHYS IDKILRCLNL RSIMIRSHDD GRMDLDDLRE TLRIHRDLPP IVCATIGTTM  180
KGAVDDIAGI KKIFKDLAIH RHYIHADAAL GGMILPFLDN SPPWNFKAGI DSIAISGHKM  240
VGSPIPCGVV LAKKSNVERI AQSVEYIGTL DTTLSGSRNA LTPLFLWYAF HTVGIEGFKR  300
IIPACLKMAD YAIAQLNKIN RNAWRYPYSN TVVFDRPSPE VTRYWQLACQ GNLSHLITMP  360
HVTSTQIDHL VADIIASEPI PPLPTLSVTP ACELLTSTPD QDITLIGTAN HNLLSEVSTA  420
LAAEGLSIEN LAAVAVESED VEVVRLRVNN RERALQILNQ NLDIGRCYGQ ARPFGNEEAT  480
QVLSQLEYQS VGEDALLVQL DDCPGSLAEL LKDCRNEAVK IRNIRLLWRG HGKGVVAIAT  540
TSPDALKTLL KDRILLS                                                557

SEQ ID NO: 1053        moltype = AA  length = 425
FEATURE                Location/Qualifiers
source                 1..425
                       mol_type = protein
                       organism = Mus musculus
SEQUENCE: 1053
MSTPSEVKKD LLGAAGSLWP SEPITLGPGE SAWQLVLKKI QELSDSGHQD PFMVADLDVL  60
VSRHQTFCQA LPRVQPFYAV KCNSNPWVLR VLAALGTGFD CASQGELEQV LGLGVAPSRI  120
```

```
IFANPCKAVS HIQFAARCGV QLLTFDSEEE LIKVAQYHPG ARLVLRIQTQ DSQSTFPLST  180
KFGASLEACG HLLQVARELG LAVVGASFHV GSDCHTPQSF RQAIADCHRV FEMGRKAGHD  240
MSLLDLGGGF PGVEGSEAKF EEMARVINAA LAQYFPEETG IEVIAEPGRF YAGSVCTAAV  300
NIIAKKSVLE PGGHRKLMYY LNEGHYGSFR LFLRDPVPRI PIVVKEFPSE PPLFPCTLYG  360
PTCDAYDRLF SEEVQLPELD VGDWLIFPDM GAYTSSMSST FNGFPPATVY CAMSPQLRSL  420
LETVP                                                             425

SEQ ID NO: 1054        moltype = AA  length = 425
FEATURE                Location/Qualifiers
source                 1..425
                       mol_type = protein
                       organism = Mus musculus
SEQUENCE: 1054
MNTPSEVKKD LLGVAEHLRP SEPITLGPGA SAWQLVLKKI KELSISGRQD AFMVADLDVL  60
VSRHRTFLQA LPRVQPFYAV KCNSNPWVLL VLAALGTGFD CASQGELEQV LGLGVAPSRI  120
IFANPCKAVS HIQFAARCGV QLLTFDNEEE LIKLARYHPR ARLVLRIQTL DSQSTFPLST  180
KFGAHLEACG HLLQVARELG LAVVGASFHV GSDCHTPESY RQAIADCHRV FEMGCKAGHH  240
MSLLDLGGGF PGVKGSEAKF EEVARVINTA LAQYFPEETG IEVIAEPGRF YAGSVCTAAV  300
NIIAKKSSLD PGGHRKLAYY LNEGHYGVFR LFLRDPVPRI PIVVKEFPSE PPLFPCTLYG  360
PTCDAYDRLF STEVQLPELD VGDWLIFPDM GAYSSSMSST FNGFPIATVY DAMSPQLRSL  420
LETVP                                                             425

SEQ ID NO: 1055        moltype = AA  length = 413
FEATURE                Location/Qualifiers
source                 1..413
                       mol_type = protein
                       organism = Entamoeba histolytica
SEQUENCE: 1055
MKQTSLEVKE FALNLISQFE PENQPLGFWI FDTEGVEKAV ERWKKNMPTV RPCFAVKCNP  60
EPHLVKLLGE LGCGFDCASL NEIKEVLDLG FNPEDITYSQ TFKPYNQLIE ASHLGINHTI  120
VDSIDEVQKI AKYAPKMGIM IRIMENDTSA GHVFGEKFGL HDDEVEIVLK EIKDKGLNLD  180
GVHFHVGSDS HNSEVFTKAL TKARNTVTLA EQFGMKPYLI DIGGGFSQVA PFEEFAATIE  240
KTIKELEFPE RTRFIAEPGR YMASNAFHLV SSLHGKRVRI QNGKKQIEYT SGDGLHGSFG  300
CCIWFEKQKS CECITQKVNE NTKMYESIIY GPSCNGSDKV ATQELPEMEP GKDWLLFPNM  360
GAYTISMATN FNGFEERNHV IYTLPLKSTK IIQIPKSIEC NSVPSLNGIP HYA         413

SEQ ID NO: 1056        moltype = AA  length = 502
FEATURE                Location/Qualifiers
source                 1..502
                       mol_type = protein
                       organism = Flavobacterium segetis
SEQUENCE: 1056
MGTINTKIYK YMSIWKTKPL SVLLSEATED EKGLKRTLSA RSLVALGVGA IIGAGLFSLT  60
GIAAADNAGP AVTLSFILAS VGCAFAGLCY AEFASMIPVA GSAYTYSYAT MGEFVAWIIG  120
WDLVLEYALG AATVAVSWSQ YVDKFLQNYG IHIPNSILHG PWDTTPGIIN LPSIFIICLL  180
SVLLIRGTKE SALINNILVI LKVTVVIVFI GLGWGFMNSA NHTPFIPVNE GEALLSSGEM  240
SFLNFFSSDY FGHYGWSGIL RGAGVVFFAF IGFDAVSTAA QEAKDPQKGM PIGILGSLII  300
CTVLYVLFAF VLTGLENYLN FKGDASPVTT AFAKTGYTFL NSGLTIAIIA GYTSVMLVML  360
MGQSRVFYSM SVDGLLPKFF STLHTKNRTP YKTNLLFMVF VSLFAGFVPV SDLGHMVSIG  420
TLFAFCLVCI GVIVMRKTNP DAVRGFRVPF VPVFPIIGVV ICLVLMAGLP IESWERLAIW  480
MILGVVIYFF YSKKNSKLNN PE                                          502

SEQ ID NO: 1057        moltype = AA  length = 493
FEATURE                Location/Qualifiers
source                 1..493
                       mol_type = protein
                       organism = Flavobacterium frigoris
SEQUENCE: 1057
MGTINTKTNK YMSIWKTKPL SVLLNEASED EKGLKRTLSS RSLVALGVGA IIGAGLFSLT  60
GIAAAEHAGP AVTLSFILAA VGCAFAGLCY AEFASMIPVA GSAYTYSYAT MGEFMAWIIG  120
WDLVLEYALG AATVGVSWSR YLLELLNKYG VHLNPKFICS PWETLTLGDG TIIDGGYINL  180
PAILIVSALS LLLIRGTQES ASINNILVVL KVIVVIMFIV LGWDYIDPAN YSPYIPENTG  240
VKGQFGWSGI AAGAGTVFFA FIGFDAVSTA AQEAKNPQKG MPIGILGSLV ICTILYVLFA  300
HVMTGLVPYY KFAGDAKPAA TAFAVTGYSF LQTGLIVAIL AGYTSVMLVM LMGQSRVFYT  360
MSKDGLLPPL FGQIHSKFRT PYKTNLFFMV FVSLFAGFVP VSDLGHMVSI GTLLAFVLVC  420
IGVLVMRKKM PDAPRSFKTP FVPYVPIAGV LVCTYLMYSL PYESWIRLVL WMAIGVALYF  480
VYGKKHSKLN NPD                                                    493

SEQ ID NO: 1058        moltype = AA  length = 343
FEATURE                Location/Qualifiers
source                 1..343
                       mol_type = protein
                       organism = synthetic construct
SEQUENCE: 1058
MIKLSNITKV FHQGTRTIQA LNNVSLHVPA GQIYGVIGAS GAGKSTLIRC VNLLERPTEG  60
SVLVDGQELT TLSESELTKA RRQIGMIFQH FNLLSSRTVF GNVALPLELD NTPKDEIKRR  120
VTELLSLVGL GDKHDSYPSN LSGGQKQRVA IARALASNPK VLLCDEATSA LDPATTRSIL  180
ELLKDINRRL GLTILLITHE MDVVKRICDC VAVISNGELI EQDTVSEVFS HPKTPLAQKF  240
IQSTLHLDIP EDYQERLQAE PFTDCVPMLR LEFTGQSVDA PLLSETARRF NVNNNIISAQ  300
```

```
MDYAGGVKFG IMLTEMHGTQ QDTQAAIAWL QEHHVKVEVL GYV                   343

SEQ ID NO: 1059        moltype = AA  length = 217
FEATURE                Location/Qualifiers
source                 1..217
                       mol_type = protein
                       organism = synthetic construct
SEQUENCE: 1059
MSEPMMWLLV RGVWETLAMT FVSGFFGFVI GLPVGVLLYV TRPGQIIANA KLYRTISAIV  60
NIFRSIPFII LLVWMIPFTR VIVGTSIGLQ AAIVPLTVGA APFIARMVEN ALLEIPTGLI  120
EASRAMGATP MQIVRKVLLP EALPGLVNAA TITLITLVGY SAMGGAVGAG GLGQIGYQYG  180
YIGYNATVMN TVLVLLVILV YLIQFAGDRI VRAVTRK                           217

SEQ ID NO: 1060        moltype = AA  length = 271
FEATURE                Location/Qualifiers
source                 1..271
                       mol_type = protein
                       organism = synthetic construct
SEQUENCE: 1060
MAFKFKTFAA VGALIGSLAL VGCGQDEKDP NHIKVGVIVG AEQQVAEVAQ KVAKDKYGLD  60
VELVTFNDYV LPNEALSKGD IDANAFQHKP YLDQQLKDRG YKLVAVGNTF VYPIAGYSKK  120
IKSLDELQDG SQVAVPNDPT NLGRSLLLLQ KVGLIKLKDG VGLLPTVLDV VENPKNLKIV  180
ELEAPQLPRS LDDAQIALAV INTTYASQIG LTPAKDGIFV EDKESPYVNL IVTREDNKDA  240
ENVKKFVQAY QSDEVYEAAN KVFNGGAVKG W                                 271

SEQ ID NO: 1061        moltype = AA  length = 222
FEATURE                Location/Qualifiers
source                 1..222
                       mol_type = protein
                       organism = Bacillus subtilis
SEQUENCE: 1061
MFEKYFPNVD LTELWNATYE TLYMTLISLL FAFVIGVILG LLLFLTSKGS LWQNKAVNSV  60
IAAVVNIFRS IPFLILIILL LGFTKFLVGT ILGPNAALPA LVIGSAPFYA RLVEIALREV  120
DKGVIEAAKS MGAKTSTIIF KVLIPESMPA LISGITVTAI ALIGSTAIAG AIGSGGLGNL  180
AYVEGYQSNN ADVTFVATVF ILIIVFIIQI IGDLITNIID KR                     222

SEQ ID NO: 1062        moltype = AA  length = 343
FEATURE                Location/Qualifiers
source                 1..343
                       mol_type = protein
                       organism = synthetic construct
SEQUENCE: 1062
MIKLSNITKV FHQGTRTIQA LNNVSLHVPA GQIYGVIGAS GAGKSTLIRC VNLLERPTEG  60
SVLVDGQELT TLSESELTKA RRQIGMIFQH FNLLSSRTVF GNVALPLELD NTPKDEIKRR  120
VTELLSLVGL GDKHDSYPSN LSGGQKQRVA IARALASNPK VLLCDEATSA LDPATTRSIL  180
ELLKDINRRL GLTILLITHE MDVVKRICDC VAVISNGELI EQDTVSEVFS HPKTPLAQKF  240
IQSTLHLDIP EDYQERLQAE PFTDCVPMLR LEFTGQSVDA GLLSETARRF NVNNNIISAQ  300
MDYAGGVKFG IMLTEMHGTQ QDTQAAIAWL QEHHVKVEVL GYV                   343

SEQ ID NO: 1063        moltype = AA  length = 343
FEATURE                Location/Qualifiers
source                 1..343
                       mol_type = protein
                       organism = synthetic construct
SEQUENCE: 1063
MIKLSNITKV FHQGTRTIQA LNNVSLHVPA GQIYGVIGAS GAGKSTLIRC VNLLERPTEG  60
SVLVDGQELT TLSESELTKA RRQIGMIFQH FNLLSSRTVF GNVALPLELD NTPKDEIKRR  120
VTELLSLVGL GDKHDSYPSN LSGGQKQRVA IARALASNPK VLLCDEATSA LDPATTRSIL  180
ELLKDINRRL GLTILLITHE MDVVKRICDC VAVISNGELI EQDTVSEVFS HPKTPLAQKF  240
IQSTLHLDIP EDYQERLQAE PFTDCVPMLR LEFTGQSVDA SLLSETARRF NVNNNIISAQ  300
MDYAGGVKFG IMLTEMHGTQ QDTQAAIAWL QEHHVKVEVL GYV                   343

SEQ ID NO: 1064        moltype = DNA  length = 9687
FEATURE                Location/Qualifiers
source                 1..9687
                       mol_type = genomic DNA
                       organism = Escherichia coli
SEQUENCE: 1064
aatcgccggt gtactccgcg tcagaaaggt atacagccac ggcagggaga tcctgctctt  60
caagaaaaac agggcgcccg tcaaaccagg tgaccgtgtc ggtgatctcg gctttcagtt  120
tggccagaat ggctgcacga attgcgctgt gtctgttcat cgcttcaggt ggatcctcag  180
ttggtttttc agggctgcgg aaagttcttt gggcatatcg ctttcaataa ggcgctttga  240
aatagcggtg aaggccacgg tgagcggtgt ctcaagagga actttgacca catcaatcgg  300
ataacgggcc tgacctacgc gccgcatgac ctgccagcgc ccgttcgcaa gctgttggat  360
aaaagcgtta cgaaaggtat agggcccgat tttaaggacg ctgcccgctc cgtttctggc  420
cccttttta cgcgagagcc tgacgcgcgc cgtgccgagc tttatcgcag gaagattacc  480
gcggttgatt tttatcgacg cgaccgggcg atcgtgacgg gccttgcgca gacgggaacg  540
ctggcggacc agacgaaccg gaagccccctt tttccggtta tcatcaactg ttgcttcttt  600
cgctacagct ttgctcccct ggcttatcgt tcttctggcc accctgttaa gtgcttttgc  660
```

-continued

```
ggttgcctca ggaacgatta accggctgag gctgttcagg ttctgaatag ccctttccag  720
tcctttcaca gacatagcgc ctcctcattc gagatggatg cggggttttc cgttgaacat  780
gtcatagcgg gtaacgatca ggttcttacc gtcgtagtcg acgctgtcgt ttcggcgtgg  840
ctggtaaagc tcagagaaaa ccaccagcga agtacctgtt cccgacaatg gccccatttc  900
ctcgagttgc tcggcgggaa caacgtcata gctgctgcca ttgatgatcg ctgtctttcc  960
catctttttt atagtggccg cgtccatgcg cgccgccatc cggtcaaagg agttaggcat  1020
tgatcttaac ttcaacaacg gtggtgtttg cccctgcatc ttcccaggcg atgcccgcgg  1080
caacggcgtc cgtttcttcg atcgtgattt tgccgtcctt cagatacacc tgcgccccgg  1140
cagtaaccgc atctgcggat acttttggca ggaggaaaac accctcagta aaaccgtccc  1200
cggtatcgcc agccgggata tcggtaattg ccaccgcgat aagttttcca acaacaaccg  1260
ggtcgccgct gtgaacatcg gttgcaccac tgtttaccag agggatcgtt ttcccgtcct  1320
gcgcatagtt cttagccata acttctccat tcagcccctt tcgaggctgg tttcaggtat  1380
aaaaaaagcc cttacgggcg tctgtttgtc aggactgttt tttactgacc agaggatttg  1440
gtcatgccgc gatagtccag cggcgccacg ccagcatcaa tacgcacttt cgtggcgata  1500
ccatcagtgg tgaagccttc ctgctgatcg atgtatggcg tgtcgacgcc gttgagataa  1560
gcgacctcaa tggtgtcggt gcccttcgcg gcagccagat accaggcttt cgcatcagct  1620
tcatccagac gtggttcggc aatgacttct gcaaagttct ggatagggtt aacgatcccg  1680
gcattgatgt ctgcaccttt aacactggcc gacttgatgg tctgatttgc cagagtttcc  1740
agggcgacgg gcaccagcat gtaggccgga cggatattca gggttcgctc cccctccttc  1800
tgcagacgca tcagcttgcg cgattcgtcc aggctggcca cagaaattgc acccgagctc  1860
aggttcttgt gatcggcatg gaacagcgcc tttccgtctg agagtttcgg gtttttggtc  1920
agaatggcgt aaaccagatc gccaatcgtt gctttcgccg cgcgccccat cttcatcggt  1980
acgtcggtaa gctggttcag atcgtcgttg atgatcgcct ggcgagttac tgagaagatt  2040
tcaccatacg tggcaagcgc gatggtttcg cctttgtcac tggtagtgat gtacttgtac  2100
tcagcccctt cgcgaacctg tcgcagagaa gggaacccac ccataccgac acgatgcgcc  2160
gttttgaagt ccgacagctg gcctttttg gtccactgct cgaaggtttc ctgcgcctcg  2220
tcccagccct gaatcagcgc tttgttcgca acatcaagca gaatgttgcc aaagtcagag  2280
gtgctgtggg tcagcgccag gccaaccatc tgcatcgggt tgtagctggc cacgccgata  2340
ccttttctg tcagggccat acgcgcatac tcgcgcagcg tcataccgtt ataaacgtta  2400
tcccgctcct gaccttcgaa cccggcacgc gccatcagtg cctggcgaat accatccgcg  2460
acgaagttac cgttgcccgc atgaatatgc ggctgagtgg ttttattgga cggcgtggcc  2520
gttttaccga gttctgccag cagcaaatct ttcgccttat cgacggagca atcagggtcg  2580
gccacacact gattctgcag ttccatgtgc ttattaccga acatggcaaa gagatcgccg  2640
atagcgttaa cacgggtttt ctgctcagcc aacacctgcg cgcggatcgc attttcatcc  2700
ggtgccgggt ctgtttttgc ctgcggtgcc tgaggctggg taataaccgg gtcacgctgg  2760
gtagtgttgc gcggcggggt gatcatgttg cgaatgcttt ttggcatttt ttcaaattcc  2820
tcaatacgtt ttgaatgaat acaggccata gcctgaaggg atggtgtcac ctggtcggca  2880
aaacccagtt caaggcactc gctgccgttc atccaggttt cgtcctccag cattaccgca  2940
atttcttcgg tggattttcc ggttttctgt gcataagccg ggataagaac ggattcaacc  3000
ttgtcgagaa gatccgcata gtcgcgcata tcgctcgcgt caccaccagc aaacccccag  3060
ggcttatgga tcatcatcat cgtgttttca ggcatgatga ccggattgcc taccatcgca  3120
atcaccgagg ccatggaggc cgccagaccg tcgatatgta cggtaatcgc cgcgccgtgg  3180
tgcttcagcg cgttataaat agcaattccg tcgaagacat caccaccggg cgagttgata  3240
taaaggttga tgtgggtgac gtccccaagt gcccggagat cattgacgaa ctgtttcgcc  3300
gttacgcccc agtacccgat ttcgtcataa ataaaaatgt cggcctcact gttattgctg  3360
gcctgcatgc ggaaccacga attacttttt gcgctggctt tcggacggtg gcgcgcccgg  3420
ttctttggct tcggcactgg tgcctccttt atcattggcg gggtcggtgt caaacaccag  3480
gccctgttca cggttctcgt caacctcagc tttacggcgt gacttaacat catccgggtt  3540
gcgaccgctg gcacgtatcc agtcggattc agtagcagca ccgccgcgga tctgcgtttt  3600
ccaggcattc gcttctttaa cgggatcaat ccacggcata acgggccccg aataaaccgc  3660
gttataaagc gagtccatat caatgcctct cggcagcttg atttctccgg cagcaatagc  3720
catcttgagc caggctcggt acatgggccg ggtcactgaa ccgatgaacc agtcctgaag  3780
aatcagatag ccgtcggttg actcgacaag ctcctgccgc tgggcactgt acgttccgtt  3840
gtagtttctg gatgtgctgg aaaagctgag gcgactgccg gcggacacgg cacgcagctg  3900
tccgttacga aaagattcga ggttagggtt cgggcgatcg gatttaatca tcccgatttc  3960
ttccccggcc tgcagttcgt catagagcat accgggctga atcatcagct cgcggtcatc  4020
gctgcttgaa tcagaatcga agctctgtcc gtcgcctttt ttgatataca tgccgagtgc  4080
cgcagcaatt ctggcagcag taagctccga gtcctcgtat tctttcagcg cgctcagacg  4140
catcagaaca ccagacaaaa gagacgttcc gcgggtctgg tgcaggcgtc gggtgaattt  4200
gagatgcagc atgttctctg catctatctc tttggtatca aactgacgcc cggatactgg  4260
caggctttta tagacctgat attttttcgg gcgtccccag ttatcgacaa aaacgccctg  4320
attgagctgg gtggcagcat cgctgttcat cggcacaaag tccggctcca gcgcttccag  4380
ccagaacggc acgccagcaa ccggctgaag accatttccg gtaccgcgaa ccagctgagc  4440
aaatacctca ccgtcccgga gccacgttcg cagcatcagc cgctccagca ttgggcgggt  4500
aaactgggtt gtgacatctg gccttacgga ccattcgccc cactttcggc ggatatcagt  4560
ggccagcttt ttagcgatct tcccgttact cagcatcgga tgcggttcaa ctatgatgcc  4620
cttcgcaccc accacccttt cttccagctt gtcgaaaacg ccgatcacca gatcgtggtt  4680
gttatccagc cagcgcgcct gctgcctcag cgaaaccgcc cccatctggc tgagctgatc  4740
ggctgaacga ttttccttct gggctttgtg ggtacgcgtt tgctttaccg cctcatacgc  4800
tttaataact gcgcgggcac gcaggcgtga ggctttccag cctggtgaaa acaggccaat  4860
cgcatcatct aaaaaactca tccaaacctc gccagcctgt agccgggtcg cccacggcgt  4920
ttgttattga gcgttgccag tcgtcgctcc cattcctgac ggccttttct gatttccgac  4980
aggttttcga gcgtcatctg ctgcccgttg aaagtgattg atttcccctc cagaacagac  5040
agctcggctg cagcatagcg gtcgatcatg ttttgaatat ctgctggatt cacacccaac  5100
ctcctgacga agaccacgga ttagcctgct cggttacggg cttctcacgt tttggttttg  5160
gtttagattt cggcgcaggc ggcggggatg gcatttcgcc agcttccgtc tgcgtgtcct  5220
cgatccacgt ttcccgccgt gcccactcag gagctgacgg ccatttgatt ttttcgtaac  5280
cactaaggat ggcgagcgcg tcggcataaa cgagcaggtc aaatgcttcg tttgcgcccc  5340
ggccgggctt actccatttc ccttcattcg agcgttcctc atacgtcagt tcgtcataga  5400
```

-continued accagctgcc cagccaggcg gggaaatgca catagccagg gccgggtgaa tcacgccaca 5460
gcgcattatt cacccggtct ttaagggcat cggtctggag aagataaaga ggcacatcac 5520
cagtcgcctg tgcgcggcgc gttgatctgc ccgtgttgtc gggaaacgtt cgctggataa 5580
gtttgctgcg cctgacgctg tcccctttga agagatagat acgcttaccc agcccctcac 5640
ggcgacatct gcgccagaac ttgtaggcat tatccgtcac gccatcttcg ccccctgagt 5700
ccacggccat cgacatcagc cgcatgccct ttgatgggtc agctgcgagc ggccacgttt 5760
tatcaaagac gtcagtgagt aaaagatccc agtcctccgg atagctcgcc ggatccacct 5820
gaatgctttc accgttgccg tcgcagcgca gcgaatgccg gatgttgtaa cggtcaacta 5880
tccagcgctc acccatactt ccataacccg taatctgcac aacaaagcgc cggttgcgcc 5940
cggcctgcac gtccacggtc gcagtgagaa actgcacgcc gttcggtacc gaacgttttg 6000
ggacgtcttc ggcacgctgc tcgagcaatt cacttttacg ctgctccatg ctggctcgcg 6060
gcaaataggg cctgccgaaa tcggtgttga tcaccgtctt cagggtttct tcgctgcgcg 6120
tggattcata ttcctgctcg gcggtcagaa acttataaat aagctgcgcc caggtctggt 6180
aagcagctgc cggaccttcc atccagaagg aggcaatacg ggaacgacgg ccatcaccgc 6240
taaccaggcc tttcctgtcg atggtttgcc cgtcccggag ccagacacat ttcatgttaa 6300
gcgcacgctt catgtccggt gtgatcctgc ctttacaggc agggcactga agaaacgccg 6360
cttcgctggc aagcacagga tcgctgctgt cgcggtatcc ggtcatattg tccatttccg 6420
gctggaaata ttcgccgcaa tgcgggcatg gccagtaaag acgacggcgg tcaccacggt 6480
tatagagcga taaaattccg gtggtcggag gggcttcatg gggcgtggag cgccgccatt 6540
ttgtgtctct gatatccctc ccgggcgagc tctcaaccag cgtcatcccg gaggacatga 6600
atgtcgtggt tcgtttcgat gccagtgaaa aagcatcccc ctccccgtcg atatcttccg 6660
gaaagcggtc ataatccgtc agcgccacac ttttatagtc cgaggacgac atgatattga 6720
cggatggcca gcccagcttc agatagttac cggcgcggaa tgtacggtcg tagacgttgt 6780
tatcgttacg tcttgggctt agccgggttt taacttcagg gctacagcga aaagtacggt 6840
ccaggcgttt tttggaatgc tcgcgcgctt tttcctcaga tacctgaatt acaagcatat 6900
ctgccggatc gcagacaatg ttataaacga tccagccgtc aatcagcccg atggttttac 6960
ccgttcgcgc tgggcccaca aacacaaccg catcgtattc acgcgatgcc agacagttca 7020
tcggctcaat cacatagggt gccagatccg gatcccacgg aactgagttt cccgcccccca 7080
ttggcacgcg catataagta ctgaccgcat cggccaccgg catacgacgc ggggctcgta 7140
aaataccgga aacatcgcgg cggatgtccc tggcggatgc ccgctttgcc atcagtcctc 7200
ctcaggctgc tcctcctctt ttccagcgtc ctgcaccttc tccgccatct ggtcgcgcag 7260
atcatcgata acgctttgca cacgaactac cgcagcaggc gttaaagcac agtcgcgctc 7320
gagcacatcc gggagggttt caagtaccat gacgacggct ttcgccatca atgagaattc 7380
tcgcgccact tcatctgcgg gtattaactg ccccgtatcc tgttcgaact tcagcctctc 7440
gttctctgct ttccagtggg acagcctgtc agaagggggc atatcgtcga tgttggccga 7500
aacggtaggg atcatcagtt cggtcagaat gtcggtcacc agatagagct ttaacttgct 7560
attgctgcct ggagcaggtt caacattttt cagtctcgcg gcaaccgtct gacggtgtac 7620
gccggttatc cctgccagct ggttgatatt gagttttaaa gtggcaattt cctggtccat 7680
gatggtgaac actttttgaa cgattcgaca tgttgcgaaa atggcctcta attaaatcaa 7740
agacctgcgc acatgatgat gatgaccctg gatccgaaaa actagccgtt tcccgcgagc 7800
acgccgcccc gtggcagggt ccccctccgg gagtaccttt tgataataat tatcaattgc 7860
acactatcga cggcactgct gccagataac accaccgggg aaacattcca tcatgatggc 7920
cgtgcggaca taggaagcca gttcatccat cgctttcttg tctgctgcca tttgctttgt 7980
gacatccagc gccgcacatt cagcagcgtt tttcagcgcg ttttcgatca acgtttcaat 8040
gttggtatca acaccaggtt taactttgaa cttatcggca ctgacggtta ccttgttctg 8100
cgctggctca tcacgctgga taccaaggct gatgttgtag atattggtca ccggctgagg 8160
tgtttcgatt gccgctgcgt ggatagcacc atttgcgata gcggcgtcct tgatgaatga 8220
cactccattg cgaataagtt cgaaggagac ggtgtcacga atgcgctggt ccagctcgtc 8280
gattgccttt tgtgcagcag aggtatcaat ctcaacgcca agcgtcatcg aagcgcaata 8340
ttgctgctca ccaaaacgcg tattgaccag gtgttcaacg gcaaatttct gcccttctga 8400
tgtcagaaag gtaaagtgat ttctttctg gtattcagtt gctgtgtgtc tggtttcagc 8460
aaaaccaagc tcgcgcaatt cggctgtgcc agatttagaa ggcagatcac cagacagcaa 8520
cgcgccacgg aaaaacagcg cataaagcac ttcattagca gcgccagata gcgtaatgat 8580
tttgttactc atggaatatt tccttttagg cgtgagcctg tcgcacggca atgccgcccg 8640
agaggtaaac gcaacctaac ggcatcaccc aggctcacta ctgaaagact ctctttgatg 8700
tgcgcgtgcg atgcgcgtag aagactgatt tatcaacctg tctttatatc aggattcatt 8760
acctgactat ttgtgggtaa agttcgtagt gcgctgatcg tgcaaaatga ttttagttgg 8820
gaacagttcg caactctgtc ccataaaaat cagcatattc ccatctatcc catatccagc 8880
gcattgacca tcgggatact gaagggagat tccatcatct cttagaaaga tcaccatctc 8940
ttttgtttca atttgcatat agctacctgg aggatttatg aatgcaagga ttttcatgga 9000
ctattaccat gagattgatt ttccatcttt attcgcgaga gcagtggaaa gcgatgacga 9060
tgtgggtact acattgcgca ttcacctact ttgtgagcgc atggtcgaag catggatatg 9120
cgcatgctgt gactgccaag atctctttgg aagagataaa aacaaacttt taatcgaatg 9180
taatactaaa atatccatgg cgggaaacct gggaatcccc ccggaactta tgaaatcact 9240
taaaaccatc aactcaatgc gtaatgacct tgcacacaat ccatcaatac aaagcattgc 9300
tgattcaagg atccagagcc tgaaggatac tctgactgaa tactttaaac agcatccaac 9360
ggaacccagc atggaagaat caaaactggg tatttttaac gccgagaatc aattaaccga 9420
agaagtttcc ttagatagtg acagttcaaa aaacagactt aagttaatct tgctgttcag 9480
caagttaatg caggcgttaa tgcaattagt tgcagctaat cataatgggc gctgggataa 9540
ccaatttagc caattcgttt accatgtgac catgaacgca acaaagagat aaatccaagc 9600
ccgttttgta cgggctgttg cattatcaca ggcactcagt gaatgcctgc tgtaatgccg 9660
ctagtcgtcg agttgcaaca caccgtg 9687

SEQ ID NO: 1065 moltype = DNA length = 735
FEATURE Location/Qualifiers
source 1..735
mol_type = genomic DNA
organism = Escherichia coli

SEQUENCE: 1065

```
atgaggattg atatattaat tggacatact agttttttttc atcaaaccag tagagataac  60
ttccttcact atctcaatga ggaagaaata aaacgctatg atcagtttca ttttgtgagt  120
gataaagaac tctatatttt aagccgtatc ctgctcaaaa cagcactaaa aagatatcaa  180
cctgatgtct cattacaatc atggcaattt agtacgtgca aatatggcaa accatttata  240
gtttttcctc agttggcaaa aaagattttt tttaaccttt cccatactat agatacagta  300
gccgttgcta ttagttctca ctgcgagctt ggtgtcgata ttgaacaaat aagagattta  360
gacaactctt atctgaatat cagtcagcat tttttactc cacaggaagc tactaacata  420
gtttcacttc ctcgttatga aggtcaatta ctttttgga aaatgtggac gctcaaagaa  480
gcttacatca aatatcgagg taaaggccta tctttaggac tggattgtat tgaatttcat  540
ttaacaaata aaaaactaac ttcaaaatat agaggttcac ctgtttattt ctctcaatgg  600
aaaatatgta actcatttct cgcattagcc tctccactca tcacccctaa aataactatt  660
gagctatttc ctatgcagtc ccaactttat caccacgact atcagctaat tcattcgtca  720
aatgggcaga attga                                                  735
```

```
SEQ ID NO: 1066        moltype = DNA  length = 9621
FEATURE                Location/Qualifiers
source                 1..9621
                       mol_type = genomic DNA
                       organism = Escherichia coli
SEQUENCE: 1066
atggataata cctctggaga ttttccatgt aataagatgg acacgcgtaa gcagttaccg  60
ctaacaccaa gtcaacaggg gtttttattc cattccttaa aggataagaa aaggagtaac  120
taccatgagc attttacatg catttttttct cagcatgtag atagcgccca cttcaagtgg  180
gcgctggaaa cgttatttcg aaagcatgag tgttttcgca ctgattataa ctgggagatt  240
gatgagcgcc cttgtcaggt ggtgaagacc gatgtgttgc cggatatata tgtgttagac  300
tgtgagcaag aggaaatacg ttttctacta gctaatgatg acattatcat tcctgtcccg  360
caggatgacg gtattgatgc tataattcct caactgctac aggctgattt aaaataccca  420
ttttccttga aaacgatccc agtccgggcc taccttattc agtcaacgaa agaaaagtgct  480
tttatactat cataccatca tattgtgatg gatggctgga gcttatccct tttcattaaa  540
cagttgctcc aactctatgg agcggctgtg gtcagtggtg tgagggatga tagcgccatt  600
atcccctcat ctctgaaacc ccttgtagac acactgtcgg cccgacgtca cacctttcag  660
cacgactatt gggctgcata tcttcgggag ggaacaccaa cttgtatcgt gccgctgtca  720
caatatcaca cagatactga agccgagaac aattcttacg ttaatcaaac aaatcatgtg  780
gagatcaatt tgtctccgga tgtgtgtcag aaaatacaga cgctatgcag cgattatcgt  840
atcacccccg cagtaatctt ctatgtggcc tggggcatcc tgctacaacg ttggtgctat  900
gctgacgatg tgttattcgg cgcgacaata tcagggcgaa atataccaat tgatggtata  960
gaagaaacac tagggctatt tattaacacg ttgccgctgc gtctgcgtga tgatggggcg  1020
acactgttgc aacacttaca acgtatgcac caaacactaa tagctcacta cagcaatgaa  1080
catgatgcct tagccagcat acaacggttg gtacataaag aaggtcatgc tggggatctt  1140
tttaatacct tagtggtgtt ggagaattat cccgttgata tgacattatt gtcatgcgcg  1200
tcgcccgtgg caattcgcca tctcagtgta catgaacaaa cgcactatcc gctgaccttg  1260
accatcactc aacagaaggg attccgtttc agtattgcat atgcccttaa ctacctgacc  1320
aacaacatgg cgcaagcgtt gctgatgcac ctgagttatc tgcttgaaca actggtggac  1380
aatccgcagc gccccattgc tgcgttggta aacttgtccc catgccagca ggcgcaggta  1440
cttcaaccct atctggaacg catggcatgc cgggattggg atagtcaatc caacgtcatc  1500
gaacaatttc atcaagttgc tgcgacttcg ccagcacagg tcgcagtggt tgatgaattg  1560
tgcgcgttga cctattcgga gttggcagca caagctgagc agctcgcggc ttatttggta  1620
cagcagggtg ttatggttgg cgatactgta ggcataatta gcgaacgccg ggtaaacacc  1680
gtggttgcca tcatcgccat catgttgatc ggggctgctt atgtgcccat cagcccccgac  1740
tacccagtgg gtaggatgca ggaaattatt gatgacagcg gcttggcgct gttgctggta  1800
catggcaaac cgctagatgc attaaacgtt gcgcagagtg acctctgtgc atttcccgtc  1860
gcgccctcgg tggtatttcc ggttatcaca ccagattctc gcgcttatgt gatttattca  1920
tcggggtcga cgggtaagcc aaaaggtatc gcggtggcgc accgcggttt attgcgcctg  1980
atacaaggcg acagcccgct gaaggtggag agcggtgaga caacgctgct gacctgccca  2040
tttgagtttg atgtttcggt gtttgagatg tggtctacct tgctcaacca cggcaaacta  2100
gtattactca gcaaacaggc attacttgat atcaatcaca ttcgccgcac gatcgctgat  2160
gaacaggtgg cgcgcgcctg gtttacctca tccttgttta actcctatgt ggcagaaggt  2220
gccgatttct tcggtatgtt acaacacatt acggtgggcg gcgaagcagt atctgcgtgg  2280
catgtcaacg acgtgatgca aaaatacccg catctggtgg tgacaaacgg ttatgggccg  2340
acggaaaaca ctatttttac caccgcatat cgtttcaacg ggttgcaacc cgcccgagtc  2400
ccgataggat acgcggtacc gggcacctcg ctctacatta ccgatctcca tgggcatttg  2460
ttgcctatcg gtgccaccgg tgaactagtg gcgggtggag tgggggtcgc catcggctat  2520
cagaacaacc cggcgctaag tgcgacggtt tttgtccctg atccttttat tcccggcggt  2580
atgatgtaca aaactggcga ttatgcccgg ttgctggatg atggctgtgt tgactgtttt  2640
gggcgtaaag acggtcaaat taagatcaat ggacaacgaa ttgaaaccgg agagatcgag  2700
cagcgcctgc tggagtgctc cggcattatc gaggcggtag tggttcctta ccgcgtacgt  2760
gaaacgctgc atattgcggc agtggtctgc gtcaatgata gctatgatga ggtggaagtt  2820
cgagggcaat tggctgacag attgccgcca ttcgctattc cggaatcctt ggtggtggtg  2880
acggagattg caaaaagcca tagtggcaag gccgacttgg cgcagttgcg gtatctcctg  2940
cccgcaactc agtgcaacgc cgtgtccacc acgatatcag aggtgcatag tgacatggaa  3000
catgcgctgc atgctatctg gcaacgcgta cttgatagac aagacattga tagcaatgcc  3060
tcctttttcg ccctcggtgg cacctcattg gataccatca gggttaaagg ggatattaag  3120
cggcaacttg gcttggagat tgatattacc gatctcttta agtacccaac gctcacggcg  3180
ttagcacatt ttctcgatac tgccgtatcg ccggaggatg caattccaac gcgtgctgtt  3240
gtctacagcg acatgccggt ggcgattgtc ggtatggcgg gacgtttccc cggtgcggcg  3300
aatattgcag cgttgtggac gctggttgta ggaggggaat cgggattaac actgttcagt  3360
gatgaagagt tgcgcgcgca tggtgtgaca cctgacacgc ttaaacaagc gaattatata  3420
aaaaccaaag ggattgttga tgatcacgaa tggtttgatg cggatttctt tggttatact  3480
cccaacgagg cggaatgtat ggatccgcaa attcgcttat tgcatcagtg ctgctggcaa  3540
```

-continued

```
actctggaac acgctgggtg cgatcctgcc acctttactg gtgcgattgg catttatgcc  3600
ggactgctga catcccccca ctggcttaat gcggtaatgc aagacactac cgactctacc  3660
gccctgtaca aggccagtat cctgaatatc cattccgtca cagcattgat tgcccatgcg  3720
cttaacctca ccggccctgc cgtgacgctt gacaccgcct gctccacttc ggcagtggct  3780
atccaccagg cctgcatcgc actacgtaac cgggattgcg atgcggcatt ggcgggcggc  3840
gtttctatcg agatgcctgc gtaccggggc tatgaatatc atgaaggcat gatcaatgcg  3900
cgagatggtg tctgtcgtcc tttcgatagc caagcctctg gcacagtcac cggtgatggc  3960
ttaggaatgc tgctgctaaa acgtctggac gacgcgctgg cggatcggga ctgcatctat  4020
ggtgtgatca aaggttcggc ggtcaataat gatggcaata acaaaatcgg ctataccgcg  4080
ccgagtgtga tcgggcaatc aacggtaatc cgcaccagtt tgcgccgtgc cggttttgat  4140
agcgacagta tcggattggt ggaagcgcac ggcaccggta cggtgctggg tgatcctatt  4200
gagttacgtg cgcttaatga ggtgtttggc ccaacacctg ttccgttttg tgtggtttca  4260
gcgctgaaaa gtaatattgg ccacctcaac tccgctgcgg gagtggcggg cgtcatcaaa  4320
acaacgctcg ccctgcatca tcaagtgttg ccaccaacag cgcactttcg ccaactcaat  4380
cctgctatag atctatcgcg ttctgcattg tacgttaacc agcaagtcca accgtggccg  4440
tcgacgcgtc ctcgtcgtgc actggtgagc tccttcggca tcggcggcac caatgccagc  4500
atcgcactag aagcacatca acatgaggac gacccttcag cgacgggggt acgcgacagc  4560
tatctgttgt tgttctccgc taaaacaccc gctgcgttag agttgcgcgt ggcctccaca  4620
ctggaatatg tcaagcatgg agtaggggtg cgcctgccgg atgtggctta tacattgcaa  4680
actggacgca cagcctttga ccatcggcgg gcttatttgg tgagtcgtgg gtcgaaaatc  4740
gatctctcct gtgccacgat attgcaagcg gaaatcttca atggtcagcg cacgacagcg  4800
gagatctgct tcatgtttcc tggtcaaggt agccaatatc acggcatggc cagcgcgctc  4860
tatgctcatc aacccatgtt tcgccagcac atggatcgct gctttgctgc attccaacgc  4920
tattcgacgg tcgatctcaa ggcgttgttg tttgacgatg aggatacgcg ggatattgat  4980
caaacgcagt tcacacaacc ggcgttgttc tgtgtcgaat acagcctagc gcgcaccttg  5040
attgatctgg ggattacgcc ggacagtatg atcgggcaca gtctgggcga gtatgttgcg  5100
gcctgtattg ctggcgtatt tactcttgag gatgcgctgc acgtcattga ggcgcgcgga  5160
cgtttgatgc agtccatgcg tcccggtagc atgatggcgg tctaccttag tcgcgaacag  5220
ttgaccccat ggctagctgc agaacggggt attgaactgg cagctaataa tagcgcgcat  5280
ttttgcgtag tcgcgggcga gcaggcggcc atttcccgtt tgagcacacg cttagtcgag  5340
ggcgggatac agcacaggcg cctgaaaacc tctcacgcat tccactcggc catgatgacg  5400
ccgatgctgc acgattttgc acagttgctg gggcaaatcc cgatgcacgc gccgcacaag  5460
cgctttatat ctaatgtaag cggtacatgg attactgagg agcaagctac ctcgccggat  5520
tactgggtgc agcaagtgcg caacgcggtg ctgtttagcg aaggtgcggc gcaactgttg  5580
gtacaaccca cgctgtttat cgaatgtggg ccgggtaata cgctctctac ctttattcaa  5640
ggacataacc aatacagcga tcagccgacc ctgttgacgc tacgcaaagc caacgcggcg  5700
atcgatgatg agcacatgtt gcatcgtacg ctggcggcgc tgtgggtcag gggggagaat  5760
attgattgga gacgctttaa ccagacggca ctcggcaagc acattccatt gccggattac  5820
cccttcgaac agacttatta ctatcgctat ggtgctgcac tttccggtta tcgccagtat  5880
ccaaatcctc tgcgccgtcc gcaagatgag tggctccagc gtgtgctgtg gcggatgcac  5940
gacacatcct tgcgggaggc gttctatgcg ccgggcgaat tgatcatcat tattagtgct  6000
gacggcgaca agttacagca gacgctgatg agtagtggtg tcgacagcat cacaatgccg  6060
ctgccgatat cgtcagagga cgacgtgtgg gataatgacc gtattctgac gcatttccac  6120
gacatctgcg cacttttagc acacaaaacc taccgacagt tacattgctt gtatgctccc  6180
ggtgcggagg caggatcatc gttgacacag tcgctctcgg gactttatcg tgttgctcgc  6240
tggtgtatgc acagcaccac gccgctggcg tccttaacag tattgaccca tggtgcgttt  6300
cgcgtacagg aagaggataa tcccgaaccg acgctggcag cgttgtcggg cgcagtaaac  6360
gtgtttgccc aagagctgca cccgaccgaa gtacgattga tcgatatcga tgcgcagagc  6420
agtgatgaga atctgaactt gctaacccag cgtctggccc cgaaacaaga aacggtaatg  6480
gcgctcaggc aggggatgct ttacctgcga cgctttatcc cgacacggct gttggcgcac  6540
ttacccccctc aaacagggtg tataccgggc aacgtactgt ggattatcgg cggtgaaaag  6600
gggattggcc gcatgatcgg cgaagcgctt gctcagcgtg agggagtccg tgtggtactg  6660
agcagccgca caggttatca ccatgaagcg gtgcagcagg acgcattaga cgttatccac  6720
tgcgacgtga cgcaggcgga ggcggttaga gcttgtctgg caactctgct cgaacgctat  6780
ggacggttgg atggcgtgat ttttgctgcc gacgctacca ccacattgac actgcatcaa  6840
ttgagcgaat ctgcgctacg cgacacgcta acggtgaaag aacggggtac tgctaatgtg  6900
ctgcatgcgt tagcgcaacg gaatctgctg gatgagcgtc tgctactgct gttctgtaac  6960
tcgttggctg ccgtgaatgc ggagattggc cagacaggct atgctaccgc cagcgcctat  7020
ttggatgcac tggcacagca actgcgtacc cgctacaagg tgaatgcgct cagtatcggg  7080
ttggatgcat tgcgtgagca gggcatgttg ttggatgcta taaacggcag tgaatacgat  7140
gtcttgcgtg gactgcgccc attgatgacg ggaacgttgc tacaggctta taaacaacaa  7200
ggggctgaca ccagctacta cgcgcgatta tcccccgagt ccgattggct gctggatgag  7260
caccggatat ccggtatcgc cacgctgccg ggaaccggct atctggcgct ggcgtatgaa  7320
gctctgcgcc attactttgt gcaagaccaa atctgcattg atgaattggt ctttttggca  7380
ccgttgactg tgatggacaa ctgcagtgtt gacgtttttg ttgacatttc acctaacggg  7440
caaggagtta gtgtcgaggt gaaatcaatg acggagcgct ttagtggcac gttaacaacc  7500
catgccagag gcagggcgac gcgtctgatg gtagacgata atgttgtgtg cgatctcacg  7560
gggctgatgc gcgagatgca cactatcact cctccaacaa aggaattatc gagcacgcac  7620
ttccactatg ggccgcgctg gcacagcgta caacaactgt atggcaatac cgcccagact  7680
caggttttcg caacgctggc cctgcccacc gttgccgcta atgatacgat cgcactgcac  7740
cctgcgctgt tggacatcgc cagcagtgtt gtcgaacaac tgcctggttt tcatactgat  7800
tcggtacctt tcctttatca ggatttacgc ctgtaccgcc cgttgccgaa caccttacat  7860
gtggcgctga ctgtcaatcg gcacgatgag gagggtgaca gctacgcttt cacgctctac  7920
gacatggcag gcgagatggt tgcccgctgt gcggcaatgg tgaagcgcaa ggtacagctc  7980
cacatacaag atgtcgatga cgacacgcga ctgcgcgtgc ccagtgccga taactaccaa  8040
ctgcggctgg ccgctgaggg ggagggggca ggaaagctag cgttgtgccc tacgccgcgc  8100
ttagcgctgg gggattcaca agtagagatt gaggtactgg ccaccggact gaactttaag  8160
gatgtgctgt tcaccacggg attgctccgg cagcagccgg gtgaggctcc gctgcaattg  8220
ggactggagt gcgccggacg cattactcgc gtgggtaaaa atgtcactga atttgccccg  8280
```

```
ggagaggatg ttatggcggt gctaaacggt ggttttgtcc agtacgcacg ggtagaaagc  8340
gattgcgtag tgagaaaacc agcccattgt cgcatcgaac aggcggctgc gctgcctatc  8400
gcatacctca ccgcctatta cgcactggtg gtgcgcgcta atttgcaacc cggagaacga  8460
gtattgatcc acagtgcggc ggggggcgtt ggcttggctg cgctacatat tgccaaacgc  8520
tgcggagcac agattttcgc cacagcaggt agcgagcaga aacgcgatta cttgctttcg  8580
ctaggcgtac atgccgtagc tgattcacac gacgaacagt tcgctgccac tctgctgacc  8640
gcatcggacg gacaggggat ggatgtgatc cttaactccc tcacaggccg tctgcttgac  8700
gctagcctcg cgctgctggc accgctgggc cgttttcttg agctgggcag caaggacatt  8760
gtggaagaca aagcgctacc gatgcgtttc ttcgcccaag gcggcacctt tattccgatt  8820
aattttcacg cggcgcatgg tgcgtttagt cgctacctgc aacagattgt cgcttggata  8880
gatgataaca cgctaccgct ccttccatgc aaatccgtac cattgcccga ggttgcacgc  8940
gccttcgcca ccctgaccac gccgcagcat attggcaagg tggtggtaac gcatcgcact  9000
gcggcaggca tggaccggct gaacgccatg atagcagaaa ggcgcctcgg cggctatgcg  9060
ctcagcatga gcaatgccga ggtgatgcgc caattgtggc cgatactgaa cactcgcagt  9120
ccgtgggcgc aactgctgct ctcacctcgg gcgatcgata gattagcgcg gggcaaccgg  9180
gtggatcgcg gtgtaccgtc tgccgctaac gatacgatta ctcagcagac agtgaaaaag  9240
cggccccgtc cggaaattgg cgtgccttac agccccgcga cacgtgaagt ggaacgcgtg  9300
ctctgccaaa tcctggaaga gtatctgggt ctggatagag taggcattga cgacaactat  9360
gccgaattag gggcaacctc actcgatatg gtgcaactga gtgggcaaat ggcgcgtcac  9420
tatccgcaag tgagcgtggt gtcgctgtac aaccacgcca ccgtgcgcca gctggcgacg  9480
ttttgccagc ccccggaggg cgagtcaaat gcgccatcac cacagcctgc agtacagacg  9540
aatacgcgcg cgaatcagat agcaaaacgt gctttgcaaa ttgcgaaaaa tactgcgcgc  9600
agtcacacgt ctttgcatta a                                              9621
```

```
SEQ ID NO: 1067        moltype = DNA  length = 2601
FEATURE                Location/Qualifiers
source                 1..2601
                       mol_type = genomic DNA
                       organism = Escherichia coli
SEQUENCE: 1067
atggaatacg caagcgaaat gaacggcatg gaaatcgcca ttattggtat ggcggtccgt  60
ttcccgcagt cccggacgtt acacgaattc tggcataaca tcgttcaggg taaagagtgc  120
gtcaccttct ttagcgagga ggagttgctg gccgaaggcg tcgaacagag tactctggac  180
aacccggcct atgtacgggc caagccctat atcgagggca tatgcgactt tgatgctgca  240
tttttcggtt acagtcacaa agaggcgcag actctggatc cgaaatcccg cgtattacat  300
gaagttgcct accatgcgct ggaagatgca ggctatgccc aacgtaccag cgatctgatc  360
accggggtat tcgtgggggc gtcagaagat gtggattggc tacggcgttc gctgtcacag  420
attggcggcg atgcgctgaa tcgttttgag tctggcatct atggtcataa ggatctgctc  480
gcacatctca ttgcctacag tctcaatctc aacggtccgg tgtatagtct ctacaccagt  540
tgttcgactt ctctgagtgc aacgcatatc gcttgccgca gcttgttgtt tggcgaatgt  600
gatctggcgt tggcgggtgg aattactatc gatttaccgc agaagtcagg ctacttctgt  660
caacagggca tgatccactc caccgatggc cactgccgtc cttttgacag tcaggcttct  720
ggcaccctgt ttggcgatgg cgcgggtgtg gttgtgcttc ggcgtttgga agatgctctg  780
gcagcgggcg atcgcatcta tgcggtgatc cggggtagcg cggtcaacaa tgacggtaaa  840
caaaaaatcg gttttgtcgc gcctggtcat gagggacaga aggcggtcat ttgtgcggcc  900
tgtcatctgg cagaagtaag cccagaaagc atcggctacg ttgaaaccca cggtaccggc  960
acccgtattg gcgatcctat cgagttcgct gcgttgacgg aggcgttcga tacttcacac  1020
cgccaatact gtgcactagg ggctgtaaag gcgaatattg gccacaccca cgcggcggcg  1080
ggcgtggctg ggttaatcaa gacggcgctg gtacttcatc accggaccat tccgccgctc  1140
gccaactatc aaatgcctaa ctcgaagctg gatctggcgc attcaccgtt ttatatcccg  1200
atacagccgc aggagtggcc cgcatcgcgg atgccgcccc gcgctggcgt cagttctttt  1260
ggcattggcg gtactaatgt gcatatgatt ttggaagggc tgaatcctgc ggtgcgcgat  1320
gaccatgacc aagtgcgagc accggtgttt atccctctct ccgcgccgtc tttcgagcag  1380
ttggatgagc tgacgcaaca gcttaccccg ttgctggcta cccttgatgc gtcaacgcta  1440
gcctacacac aacaagtggc gcgccccgtg tttgattgcc gccgagtgat acaagtggaa  1500
aacgatggta cgcaagcgat gctggcatcg ctggataacc taatgcccga cgctccttgg  1560
ggcctacact gtccagatct acgtactacg aacgattgta cttacgcaca gtggctggcg  1620
cattcggcac attatcaacg cgaagcgact gctctgacgg cattactcga cggcatgaat  1680
attccacccg cttattgcca cgctgaaacg tgggcggcac aagcgaacag cagcctgcta  1740
atcagaggct gccagactat cgccgcgcta aaaacctgga tgaacctgct accgacatta  1800
acactgctgt cgggtgctgg aacaggcctt ttgcctgccg ctgcagccag tggcatgatt  1860
gcgacgcaag acgtgttgca tttgctgtgg gaaatggagc aaaaggcgct tcatctctgg  1920
cttcctgagc gccatgaacc tatccccggc tacgtgctgg cttggcaagg aaatcccatc  1980
accgatgcac agcgtaacga cagagggttt tggagtgaag cgctgttggc agatacccga  2040
gaactggggg agggcgttca cagtatcaac tgggttaggc tgccgccgga aataagagaa  2100
gacgttgatg tattgcgcta cgtggcgcaa ctgtggtgtg caggtatcaa tgtggattgg  2160
gccgtgtggt acggcactcc gctgccgcaa cgcgggagcg catcagcata tcccttcgca  2220
cacaaccact acccattgcc tggacgggta atgggtagtg tggagaccca acccgaagca  2280
ggacccgaaa cgcaccaccc ttatcaggca cgtcccgtgt taagcgtacc tttcgtagcc  2340
gcacactcgc ggggtatgca gtatatcaca ggtctgatgg aactgttgct ggaaatatcg  2400
ccggtcgggg tggacgacga ctttttttgaa ttaggcgggc attcgctgct ggtgacgcaa  2460
ttgacctccc gtttagaacg cgatttcaac gtacatatcg atcttttgac cctgatggaa  2520
aaccccaatc cgcgcaatat ctacgcgcat atcgcggcgc aactgggggg cgaagacaac  2580
ctcgaaatag cctgtcagta a                                              2601
```

```
SEQ ID NO: 1068        moltype = DNA  length = 870
FEATURE                Location/Qualifiers
source                 1..870
                       mol_type = genomic DNA
```

```
                         organism = Escherichia coli
SEQUENCE: 1068
atgatgaacg tggcggtaat aggtgcagga gtaatgggaa ctggcgtcgc tcataacatg  60
gcgcaatacg gcatatcaac taacgttgtg gatatttctc aatctcagtt ggataaatgc  120
cgacagatga tcgaagcgaa cttacgctta tataattttc acccgcagca taaaaaaaag  180
acgcatagca cagcggagat aatggaaaat atccgtttca caactgagtt ggacgacatt  240
gtagaatgtg atttggtgat tgagaatatt actgaggata tagagaaaaa aaatgcacta  300
tacacacgga tgaatacgat ctgcggcgcg tcgacagtgt ttggtgttaa tacgtccgcc  360
atatctatca ctgcgttgtc aaaattaatg cgacatccgg agaatgtagt cggcgtccat  420
tttatgaacc cggtaccgct gatgcacacc gtcgaattaa tccgtggtgt acatactgca  480
gagcgtacac tgaacatatt tcaccactta tttgctcagt tgaataaaac cggcatcgtg  540
gtcaatgatt ctccgggctt tgtcactaat cgtgccatga tgatttttgt taacgaagcc  600
atatttatgg tgcaggagca gatcgcccgt gctgaggata tcgatacgtt gtttaaaacc  660
tgcttcgggc acaagatggg gccactacaa actgccgatt tgattggctt ggatacgatt  720
ttgcaatcgt tgcaggtgct atatgaaagt tttaatgatg ataagtatcg ccccagcttt  780
ttattaaaga aaatggtcga tgcagggtat ttgggcgtga aatcagggca ggggttttat  840
cgctatcaac agacgtacgc cgagcagtga                                   870

SEQ ID NO: 1069          moltype = DNA  length = 249
FEATURE                  Location/Qualifiers
source                   1..249
                         mol_type = genomic DNA
                         organism = Escherichia coli
SEQUENCE: 1069
atgaaaaagc aagatatgaa agccgccatt cgggaatttc tttcacgctc attacgtggg  60
catacgttga acgatgatga cgatattttt tctctcgggc ttgtccattc gttatttact  120
gtgcaaatca tactgtttat agaaaaaaat tttcaggttg agctggaagt gagtgagttg  180
aaaacagaac agattgctac cgtcaataaa atagtggagc tcattcagcg acaaacaggc  240
ctggagtaa                                                          249

SEQ ID NO: 1070          moltype = DNA  length = 1131
FEATURE                  Location/Qualifiers
source                   1..1131
                         mol_type = genomic DNA
                         organism = Escherichia coli
SEQUENCE: 1070
atgtgcactg aaaattatga gctggctcag caagaggcag tcctgtttgc caaacaacat  60
ctcgccctgg ctgcacagaa tattgaacgt cagcagttta ttgtgccaga cattatttct  120
tgcgtggcgc aggccgggta cttaggtgcg tcaatccccc aaaaatatgg cggacgaggt  180
tacgattctt atcaactgtg cgctttgcat gaagtgatgg ctggggttca cggttcgtta  240
gaaaatctca taacagtgac tggcatggtc agcacgctgc tgcaacgcgt gggcagcgca  300
gcgcaaaaag cccattattt gccaaagctg gcaacggggg aattgatcgg cgcgattgcc  360
ctcacagagc cgaatatcgg cagtgactta gtgaacgtgg aaacagaatt acagcaggat  420
ggcgacggtt ggcggctgaa cgggaaaaag aaatggatca cgctagggca gattgctgat  480
tttttttattg ttttaatcca ctgtggtaat caattagcga cagtgcttat cgatcgcaat  540
accgacggct ttactatcac tccactcaac gacatgttgg ggttacgcgg caatatgttg  600
gcagagctgc attttaatga ctgccgcctg aaggaggatg cattgctcgg tccgctcacc  660
cctggggtac cgctggcggt gaattttgcg ctcaatgaag ggcggttcac caccgcttgt  720
ggcagcctag gattatgtcg ggccgctgtg gatgtggcag cgcgctacat ccgccagcgt  780
aaacagttca agcggcggtt attttctcat ggcattgttc agcacttgtt tgccacaatg  840
ctgacccaaa cgcgcagtgc gcaactaatg tgcttcagcg cggcggaata ccgcgaaacg  900
ctgcacccgg ccatgataaa ccaaatcctg atggcgaagt atgtcgcttc caaagctgcg  960
gtggacgtgg ccgggaaggc ggtgcaactg ctcggtgcga atggttgcca tgccgattat  1020
gccgtcgaac gttactaccg cgacgccaaa atcatggaaa tcatcgaagg gacatcgcaa  1080
attcatgaaa tccaaattgc gatgaattac atgatgggga gtgaagcatg a           1131

SEQ ID NO: 1071          moltype = DNA  length = 1269
FEATURE                  Location/Qualifiers
source                   1..1269
                         mol_type = genomic DNA
                         organism = Escherichia coli
SEQUENCE: 1071
atgacgaagg atgtcgcact gatgttccct ggctccggtt cgcaatatgt aggcatggca  60
cggtggctgt atgagcgtta tccgcaggtg cgtactctgt ttgatgaagc tagccagatc  120
acggaacggg acatggcagc gctgtgcctg tcgggtactt tggtacaact tgctgagccg  180
acggcaatgg cgctggctat ctataccacc agcgtggccc actttgtcgc gtggcagcag  240
tttttggcgc aaaccggtgt ccatgtcaac ctacgttata tgttgggtca tagtttgggc  300
gaatatgctg cgctgacctg tagtggtgcg ctgagctttt cccaagcact ggcgctggtg  360
gcgatgcgta gccgtttagc cagtgagatc gcccgcgaaa tggacgcgag taccactatc  420
atcaagcaag ggaatcaggc actggtggca gcggcgtgcg aggtggcgga gcgtgaaacc  480
cgacagcagg tcggtattgc ctgcttcaat tcgccgcaac agtttatgtt atccggacaa  540
aactcggcca ttatcgccgc cgagcaatac ctgctggatc atgatcgcca agtcgaagta  600
gtgccgctga ttggtggtgt tccttaccac agcccactat tgaaaccttg cggacagcaa  660
ttgcgcaagg cgctggatcg ctgcgaatgg cgacgtccgt gctgcccagt gatctccaat  720
gtcaacgctc aaccctatcc cgatacggtc acgccagtcc agtggctaga acaacagctc  780
tctcagccag tgcagtggca gcgctctctc acctacctga caggacactt gtcaccgatc  840
gcgatagaga tcggtccgca aagtgtgctg aaaaacctgc tgctggagaa tcgctatcca  900
gcaccagttt acgcatttga caatcgtcat gatcgtgcgc aactagcatt ggtgctgggg  960
gataacatgg cggtgaagac cgatccggaa gccgtgcgcc gccaacgcat cacgctgctc  1020
```

-continued

```
actaacgccc tgacagccac acgccatcac cgcgccgccg atgtggctgc cagtgcgcaa  1080
ttgaaagaat tgctcagtcg tttttttgag cgcatccagc agattgagca gcgcggcaca  1140
tccagcgaag aggacattgc ttttttgcat gagcttcttg aacagggatt tcaactcaaa  1200
ggcagtagtc aggcagaaat cgacgcctgc cacgcgcggt tggcttccga caacggcgga  1260
caggcgtaa                                                          1269

SEQ ID NO: 1072        moltype = DNA  length = 4797
FEATURE                Location/Qualifiers
source                 1..4797
                       mol_type = genomic DNA
                       organism = Escherichia coli
SEQUENCE: 1072
atggaacagc aagggattat gagacagttg cctaccgacg accaaacgat agtcgactat  60
ttgtatcgta tcgccggaga atatggggaa aaagccgctg tattgatggg ggacgcggcg  120
ctgagctatc acgatcttaa tgcacgctct aaccaactgg cgcattatct gcgtgggctg  180
gggatcggcg aggatcgtgt ggtagctatc cgcctgccgc gcggcatggc aatgctgatt  240
gccattttcg ctattgtaaa agctggtggt gcctatttac cgctggcgta caatgcaccg  300
cgcagccgca ttgaaaatat actgagcaac agcggcgctg tttgtctgat cggtactgac  360
gatggtgatc gctggccgat tcctcgcgtc gaaatcgaca gcgcggcggt cagtgccatg  420
ccaacgacgg atctgcgtta ccgaccacat gcgcggcaac tggcgtatat tatttacacc  480
tccggttcca ccggtgtccc taaaggggtg gcgacggaac atgcagcgct gctaaaccga  540
attgtctgga tgcagaacgc ttatcctatc agttctcagg acgtgctgtt tcagaagacg  600
gtgtacacct ttgacgtctc tgtctgggag atgttctggt gggcgatgta cggcgcatct  660
gtagtgctgt taccgtccgg actggagagc gatccgcgaa ccttggctcg actgattcag  720
cgtcaccgcg tgtcggttgt gcactttgtc ccttcgatgc tgaacctgtt tgtcgagtat  780
ctggagatga aacaggatcc tcgtttgacc gcctcattgc gattagtgtt ttccagcggt  840
gagaaactca cggtccacag tgtggctcgc ttttatcaat cggtggcgca gggtgatctt  900
ataaatctct atggcccgac cgaagcagca atcgatgtca gtcatcaccg ctgcctgcgc  960
gggtacgact acgacgatat ccctatcggt caagcgattg acggttgccg actctatgtg  1020
ctggatgacc atggtaatcc ggtagcagac ggcgaagagg gcgaactgta tctcgctggt  1080
atcgggctgg cacgtggcta tctcaacaac gtggcgttaa ctgatcgctg ttttactata  1140
catccaactt tgcgccattt agggaaaccg gagcggctgt ataaaactgg agatctggtg  1200
tggcgcgacg gggaaagcca acaaattcat tacattggcc gtaatgattt tcagattaaa  1260
attagagggt tgcgcgttga attgggagaa atcgaagccc atgcgatgcg tttcccgggg  1320
gtacagcagg cagtcgtggt ggcggatcag gatgatcccg acaatcagtt gatttacgct  1380
tttgtcgtca gtagcgtgcc gctcaatttg gcggccttaa tggacgcact gtccaaaaac  1440
ttgcctgcct acatgctgcc gaaccgtttg ttggcaatgt cagagttacc actctccgac  1500
aatggcaagt gctgtcgtaa aacgttgctc gacttggcgc gggcgtactc agccagtcgc  1560
gtcgatttac gtgaaactcc cgccgtgcgc tacctaccgt tgtcatcggc tcaatcgtcg  1620
atgtggttta tgcaacaatt ggcgccgcat actgcactat acaataaccc caccgccttg  1680
ctgcttgaag gagaactgga tcgcacgcgg atggacggcg cgattcgtca attgatgagt  1740
cggcatactc tgttacgtgc tatggcggaa acccacaatg gacaaccagt attggcggtg  1800
cctcagtgcg tatcgtcgca ggcgttgctg accatagtgc cactcccctc ggtgagtgat  1860
gataacgcgc tacaggcgat gatcaaccag cgtgcggcac accccatgcc cttaacgtca  1920
ggcacaccgc tgtgccggtt tgaactgttg acgctcgatg acgatcgtag cgtattgttg  1980
attcatctgc accacatcat cagtgatggc tggtcgaaag gcgttttgtt acgcgaattg  2040
caggccgcat ataacggtga atcgctgacg ccagaaccgt tgttggagta tgccgactac  2100
atggagtacc aagaagagtg gcgtcagagt gacgcctatc aggacgcgat gcgttactgg  2160
caaaataccc tggcggggac gttgccgatt cttgatatcc ccaccgatca accgcgtcag  2220
aaggtggcac gttaccaagg cgcgtttgtt gccttcgcat tgtctgccaa cacatgcgag  2280
cgagtgttgg cggcggcgcg tgcgcagcgc gtgtcgttgt ataactatct gctgaccgcc  2340
ttcgtcctcc tgctgcatcg taatgcgcgt caacaggaat acatcgtcgg tatgccgatt  2400
gctgcgcggc tgacgaaaga acaggagcat atgatcgcgc cgctggtcaa cgtactaccg  2460
ctgcgcttac ctcttgacga agcggcatcg ttttccgagt tagtacagac gatcagaggt  2520
attctgtttg ccgctttcag gcaccagcgt ctcgaattta ccgacatagt gcgcgcagtg  2580
aatgtggatc gcagcgccgg acatttccca atatatcagt gcatgttcca actcgacaat  2640
atgcctctgg cgagcccgac actaaacggt gtcaacgtta caccattatt gttggatacc  2700
agtgcatctc aggtggatat ttcgctaagt atgcagcata tcgatgggcg catcaccggc  2760
actttcgaat acgacgctgg gttatacagt gcggatcgta ttcagcacct ggtggcgcag  2820
tggagagaac tgctagatga ggccagcagc caacccacgc agttagtccg cgatttgatt  2880
cgtttcaccc ctcgagagca cgcttggctg gcgcggcaca acgccactga agttgctctg  2940
ccgcccgtag ataacctgct ggcgctagtg ttaccgcact gccagcagcg ccctacacag  3000
gtggctttgc gccacgctga cgacgccatg acctatggcg aattgcaaca ggccacgatg  3060
cagatgtgta cttggctgcg tgcgcaaggc gtaaaacgcg gagaatctgt cgcactgcaa  3120
ctgccttttt gtttcgaatt gattatcgca caattggcga tcctctcttt gggggcgagc  3180
tatgtgccgc tggatggtaa cgcgccagcg gcccgcaatg ccctgatctt ggcgcaggca  3240
acgccgtgca tgctgctggt ggcgcaaccg ctggaatccc ctcatgggct gacgatacct  3300
tgggtgctag tgcctgactg gcgtagcctg ctgacagaaa taccgaacct gccagttagt  3360
gttgcgccag atgctttaga ttgcgatgcg gtggtgatct ttacctccgg tactaccggg  3420
cagcccaaag gcgtccgact cagccaacgt aatctggtca acttaaccgc atcctttata  3480
tccagctatc aagtgacgca tcaggatgtt ttgctaccca ttacctcagt cgcgtctgct  3540
agctttgtcg gggaggtact gccgctgctc gccgctggcg gtaccttagt attggcgcaa  3600
aaagcgcaga gtttggatag tgatgcgctc attgcgctgc tggcatctca gcgggtgact  3660
atcctgagca ccaccccatc gctttctgcc agcctctctg tgctggctca gtcgatggga  3720
tcgctgcgct tgtttctgtg cggtggtgaa gcgttagagt atgagcagat agcgccgctt  3780
ctgccgcaca tggcagtggt taacggttat ggcctgaccg aaagcggtat ctgctcgacc  3840
tactttcctg tcgcaaagcg tagggagcaa gaaacgggag cattgcccat tggccgcccg  3900
attcagaaca cccaagctta tgtggtggat gcatataatc gtttggtacc gccaggtgcc  3960
tgtggagaac tctgtttctc tggtctgggc atttcgcccg gctaccttga tgcacgacag  4020
```

-continued

```
gatcccgagc gctttgtcga gttgccggaa taccctggcg ttcgggtgct gaaaactggc  4080
gatcgtgctc gttgggcaac cgacgggatg ttgttctatc tcggcagaca agatcgccaa  4140
gtgcagatcc gtggataccg agttgaactg ggcgacatcg aaagcctact gaaacagcat  4200
ccggatattg ctgatgcgtg ggtcgatgtg cgacgcaatg cggcggcaac gccgctacta  4260
gtggccttct attgcagcgt caacggcgtt gcgctggatg ctcagcaatt gcgcgtatgg  4320
ctcagcctgc ggcttccgtt gcatatgctg ccgttgctct acgtgccgct gagcgccatg  4380
ccgctaggtg taaacggcaa aatcgatccc cagtgcctgc cgctggtcga tctgcggcag  4440
ttggaagggc cgggcgagta tgtccctccg gcaaccgaac tggaacagcg tctggcggag  4500
atctggcagc agttgcttgg cctggagcgt gtcggcacca ccacaaattt cttcgatctc  4560
ggtggacact cacttctgct agtacagatg cagcaataca tcgggcagca gtgcggtcag  4620
cacgtggcgt tggttgacct gctgcgcttc actaccatca aacgcttggc ggaatttctg  4680
ctggcccccgg acgcagcgca agggaccaca ggagatcaga cacaactgcg tgcggcgaag  4740
cagcgtttgg cctttggtca cacgcgctgg gcagccacaa ccgacagtca tcactga     4797
```

```
SEQ ID NO: 1073        moltype = DNA  length = 3033
FEATURE                Location/Qualifiers
source                 1..3033
                       mol_type = genomic DNA
                       organism = Escherichia coli
SEQUENCE: 1073
atggcagaga atgattttgg tatagctatc attgggatgg cggggcgttt ccctcaagcc  60
gatacggtac aggcgttttg ggaaaatctt ctggcaagcc gagagtgcat ttcctttac   120
agcgatgagg aactgctggc gatgggaatc agtcctgaat ttgttcagca cccagattac  180
gtcaaggcca aaggggaggt agctgacatc gataaatttg atgctgcttt cttcggtatc  240
gcaccccgag aggcggagct gatggatcct cagcaccgtg tcctgttgga aaccgcgtgg  300
gcagccttcg aagatgcggg ctatgtggct gccgattatc cgggggatgt gggtattttt  360
gctggcaaaa gcatggattc ctatttgatg ctgaacttga tgccgcactt taaacgcgtt  420
ttctcttctg gcagtttgca ggcggccatt ggtaacgaca aagacagtat cactactacc  480
atcgcctatc acctcaacct gcgcggcccg gcgatcacgg tgcagacttc ctcatcgaca  540
tccttggtgg cggtgtgcgt ggcatgccaa agtctgttga cttggcagtg tgacatggcg  600
attgctggcg gagtaacgct ggggccacca gcaaaaaccg gctacttgtc gcaggaaggt  660
gggatcaccg ccgccgatgg ccactgtcgg gcgttttccg ataacagcag cggatttgtg  720
cccggcaccg gcgcggggct ggtggtgtta aagcgtgttg atgaagcgct gcgtgatggc  780
gataacatct atgcggtcat caaaggattt gccgtcaaca acgacggttc ggagaagatc  840
agttataccg cgccgagcgt ggatgcccaa gcgcgcgcca ttgctcaggc acagcggttg  900
gcaggtttga caccgcagga tatcacttat gtggaagccc acggtaccgg tacgcgtttg  960
ggcgatccgg ttgagttttc tgcgctaagc caagcctttg cgggcgcgtc acaaaagcag  1020
tactgtgcgc tggggtcggt aaaaaccaat atcggccatt tggatacggc agcgggcgtc  1080
gcagggttga taaaaaccgc gctggcagtg cagcagggaa taattcccgc aacattgcac  1140
tttgaacggc ccaatgcaca gatcgatctg accaatagtc cgttttacat caacactacc  1200
tgtcaaccgt ggcaaccgga aagcggcatc cgtcgcgcgg gcgtcacctc gcttggcatg  1260
ggcggcacca atgcccatgt tgtgctggaa caagcgccag ccgttgactt gcaagcgcga  1320
gcgcctgtac ctgcctacag tattttgccg ttttctgcca agaccgacag tgccttatcc  1380
tcggggctgg cgcgttttgc cgattttctg caacatgaat cgctgccgga taggcgggat  1440
ctggcgtgga cactctcaca gggacgtaaa gccttcgcac atcgcgccgc gctcgtaacc  1500
agagatctac atgctgccgg gacgctgttg cagcaggccg cgacagcgcc gtttgctcgt  1560
ggtgtagcgc agacacagct cgggctgggg ctgttgtttt ccgggcaggg tagccaatat  1620
cagcgcatgg gccatcagct ctatcaggtt tggccggcct acgccgatgc cttcgaccgt  1680
tgcgcgacgt tactcgagcg tgaataccaa ctggatatcc gccatgagtt gttcagagca  1740
gaagtctcgt tagcccaagg cgaacgcctt gcgcaaacct gcctcacaca accgctgctg  1800
ttcagcgtcg agtatgcctt agcccaattg tggctcagtt ggggaatcac gccaacggta  1860
atgattggtc attcgctggg cgaatgggtg gcagcgacgt tggcaggcgt gttctcttta  1920
gaggatgcgt tgcgcttggt ggcgcgtcga gcagagctga tgcatcaggc accaagcggt  1980
gccatgttga tggtggcgct gcccgaagca cagattcgcg cactgattac cgccccgctg  2040
gcgattgccg ctgttaacgc ccctgactat tcggttatcg ccgggcctac gtcggagatc  2100
ctcgccgtca gccagcgtct gacggagcag aacatcatca acaaacgatt gcatacctct  2160
catgccttcc actctagcat gatgcaagat gcggcgcagg cgctacgtca ggcatttgag  2220
aatgtacgac tgaacccgcc gacgctcacc atcatctcta ccgtaaccgg cgcgcacgtc  2280
agtgccgaca ctctcaccac accggactac tggattgaac agatgctgat gcctgtgcag  2340
ttctccgctg cactgcaaga ggcgcaagct acatttgatg tcgattttct ggaaatcggg  2400
ccaggtgcca ccctgaccca gctgaccaac ggtcatgcat taggtgatcg tctcgcgttc  2460
agctcgctgc cagcaggtgc ccgcagcagc gatgagcaca aacatatctt agataccgtg  2520
gcagcgcttt gggtgcgagg gcataacatc gatttgtctg cgtttgcagg tgagcaaccg  2580
cgccgtgtct ctctaccgac ctacgccttt gacaaaatcc gttactgggt cgacagtcca  2640
gaagaacaga ggagcgccgt aacgccggtg gcggacgcgg gaagtgtcat ccctagcgaa  2700
ccgtcggtgc gccgtcagcc gcgtccggcg ttttcggtgc cttacgcggc tccagagagc  2760
aaaacgcagc gcggcttagt ggcgatttgt gaagcattgc tgggaattga cggcttgggc  2820
attgacgaca acttcttcga agctggcgga cattcattga tgctgggcat gttgctggcg  2880
caggtacagg aacggttcgc cgtcactctt tcctttttcg acgtgatgga ggatgccagc  2940
gtgcgcgcgt tagcgcagtt ggtcgagcag gagcagcagg atgatggagg gtccgcactt  3000
gccgtgctag ttaacgacat gattaatgag tga                                3033
```

```
SEQ ID NO: 1074        moltype = DNA  length = 6501
FEATURE                Location/Qualifiers
source                 1..6501
                       mol_type = genomic DNA
                       organism = Escherichia coli
SEQUENCE: 1074
atgacgatac atcatgccgc attggcgcga atgttaccgg cggaaaaaaa ggaaaagcta  60
```

-continued

```
ttacgacagt tggcgcaatc aggcgtgtcg cccagccgca ttcccatcat caaagcggat  120
ccggcgcagg caatcccgct gtcgtttaat caggagcggt tgtggttttt gcaaaaatac  180
gacagtaccg ccactaacta caacctttat gtggtgtatc gtttgcatgg cgtggtggat  240
atgccgatgc tcacggaggc attgcgccat gtgcaagcac gccacgccat cttgcgtacc  300
cgtatcatag tacgtaacga tcggccttgc caggtgatag atgatgcgtc ttcgttagtt  360
ctcgatacgg tcacgctggc agcgcaggcc ccaacttcag cgctagatgc ggtaattcag  420
caggtgataa acacccggtt cgatctggca cgcggtcctc tgtgggggt aactcagatt  480
attcaacccg atcaaggttg tcatttggtg ttttgcgcgc accatatcat catcgacggt  540
atctcgttac ggctattgtt cgatgagtta cagcagcagt atgctcgatt gcatgctggt  600
aatgaaacgt cgctgcctcc gccgccgctg caatatgccg attatgcctt ctggcagcgc  660
gaatggttcc aggatacctt gctggcgaac gaacttgcct actggcgtgc gcgtttgcaa  720
gacgcgcctc tgctgtcgac atttccatcg ctgcacccgc gcccggcaca accctctaca  780
catggttccc ggttcagcat caccctggat gaaacattaa gcctcgcgtt gaaacacgta  840
gcccgcacgc aggaaacaac gccgttcgtg ctgatgctga ctgccttcca actggtgctg  900
atgcgttacg ctcagcaaca gcgattggtg ataggcatgc cagtatcggg gcgcattcgc  960
ccggaattgc agagtagcat tggttattat gccagcactg cggttatcta caccgatttt  1020
aatggggttg aggtagggcg cgaggcgctc cagcgtgtga aggccagcgt gaaagagacg  1080
caggggcgcc agcaactgcc gtttgaaaac ttggtgaata tgctggatct ccctcgcagc  1140
ctttcccatt caccgttgtt ccagatcctc tatatctacc ataaccacgt gaccccacgc  1200
gcttttacct tggctggtgc gtattgggag caggtgacgt atcacaatca gaccgtcaaa  1260
tacgacatga cagtcgaggt gttccaaaac gacgccacgt tcgacgtctc ctttgagtac  1320
gatttggggt tatacgatgc tgatgtggtg aagcagattg ccgaggcgct gcgtcagcac  1380
tgcttatcgt tgacatcatc actggagacc ccgatagggg cgatccctct gcatgcaccg  1440
gagaccgcaa cgccgcggcg tgatccgctc aacgccacta acgtcccgtg gctcgggccg  1500
caggatgtgc tgcgtatcat tgaacagcgc tgtgtgcagc acccaaagca actggcaata  1560
cagcagcatg acggcacact gacctacgct gagctctggg cgcgtgtgca gttcatcgcg  1620
atgcgttttc gagcgcatgg catacaaccg ggcgatcgta ttggcgtgct gttgccacgt  1680
cacagggatg tgattgcaac catgttggcg acgtggtttg tgggggcgtg ctacgtgccg  1740
ttcgatattc atcagcctgc cgcgcgtttg caacgcctta tgcaacgcgc gcgtttggtc  1800
tgtctggtgg tccgtcagcc gggagagtgg ggtgaaattg tacaactgtc gttgccggaa  1860
ttgatgcagg acatgtcgaa tgcgatccgg tattctacac cttgcgcgct gttgccggat  1920
atgcaggcct acctgttgtt tacctccggc agtaccggtg aacctaaagg cgtgtgcgtt  1980
gttcaccgcg ggttgctgaa cttgttgttg gatatgcagc gtacctttgc ggttggctcg  2040
caagaccggc tgctctcggt gacgacgcca acatttgata tctcattctt ggagtatctg  2100
ttgccgctga tctccggtgc gagtctctat ctgacagagg cggaacgcgc cgcagacagc  2160
ttccgtatga ttccgctgat tgccgactat cgaccaacgc tgatgcaggc gacgccctcg  2220
ttctggcacg ggctgttgat ggcgggttgg cgtggcgacc cggaactatg tgtgctggca  2280
ggcggtgaag cgctgccaac gaaagtggcg gaagaactgt tgcgctgttg tggttcattg  2340
tggaacctct acggtcccac cgaaacaacc atttggtcgc tgaaatcgca gataacccaa  2400
gcggaaaaca tcaccctcgg cgctcccatt gccaataccc gtatatacat tctggacaat  2460
gagggccatc cagtgccgca aggcgttgac ggcgagcttt acatcgccgg ggatggtgtg  2520
gcgcaagggt atgatgggca gcctgagttg aacgcacagt tcttcttgtc agaaccaggg  2580
gtccccggtg gcaggatgtt ccgcactggc gatctggtca ggagtgatgc gcaggggcag  2640
ttgtttttg ttgggcgcaa agatagccag atcaaactgc gcggttatcg tattgagtta  2700
ggcgaaattg aacggacgtt ggcacggcat ccgcatgtgg acgccgcggt ggtggcctgt  2760
attgaaagag caccgttaca caaagcactg gcagcattca tcatcaccag tgagcctccc  2820
tcgctattcg agcaactgaa aaacgagctt cggcagcaac tgccagacta tatggtgcca  2880
acgctgtggc agagggtggc cgacttcccg aacactgaca acggtaaaat cgatcgtaag  2940
cggttagcgg aaaatttcgt tgccgatagc tcccttgtgt cgccgcagac gcaagcgctg  3000
agcgacacgg aacagatgtt gctggcgctg tggatgcgct atttgccgat aaaaaacgtc  3060
gatcctgagt gcgatttctt tcgcttgggg ggacattcgc tgttggcggt aacgttggta  3120
gcagagatca accgcacttt tcactgcgcc ttgaccctga aggacatttt ccactactcc  3180
acactacggg cactgagtgc gcgtattgca cagcaatcta tcacggacgc tgccgcgtct  3240
caggatgact gggtgatagt gcacgaccct gagcatcgtc atcaaccgtt cccattgacg  3300
gatgttcagc gcgcctactg gcttggacga cagacgggtg ctacctcgat cgcgacccac  3360
atctaccatg aatttgacgt agaacacttt aatgttacgc gttttaccca tgcggtgaat  3420
gcgctgatcg ctcgccatga aatgctacgt gcgcgggtac tccccgacgg tactcagcag  3480
attctggcgc aagtgccggc gtatcagtta gagcagcgcg atctgagtgc tttgtcccct  3540
aacgcacgaa acgatgcctt gatggcgatc cgcgatcggc tgtcgcatca tgtgcatccc  3600
gcagatcgtt ggccgctgtt tgatttcagt tattcggctt gcacggcgca acatggccgc  3660
ttgcatttca gtctcgatct gctgattgcc gatgctctga gtatgcgcac gctacagcag  3720
gagttgatga tgctgtaccg tgagccccat gtgtcactgc cgttgctacc gttctctttt  3780
cgtgactacg tgcaggcgct gttggtagag caggcgagtg aagcctatgc acgcgatcag  3840
gcctattggc aacgggcgct gccgcagctg tatggcccac caacgctgcc cgtacagggc  3900
gatttggcgc aactgtctgc gatcaggttc gtacgtcgcc gtcatcggct gtcagcccac  3960
aactggggag tgctgagcgc gctggcccaa cgcacacgta tcaccaagac ggcattgttg  4020
ttgacagtct ttagccaagt gctggcacgt tggagcctta gcccgacgtt tacgctcaat  4080
ctgacgttgt tcaaccgccc gcagggttac cccaacgcag aggcagttat tggtgatttt  4140
accgctgtca gcttgctgaa tgtttgttac gacagccagc actcttatgc ccacaacgct  4200
cagcgtattc aggtgcaact gtgggaagat ctcgaacatc gtcgtttcag tgggatccgc  4260
gccagcgagg cgctgatcca tagcggtcgt ttccatgcgc cgatgccggt ggtattcact  4320
agtatgttgg atatcgacgg ggagacgact gcgcaagacc ctcgggacac aacccgtttt  4380
actctgtgtc cggacgccaa tattacccaa acaccgcagg tgtggctcga tcaccaggtg  4440
atcgagttgg ctggggagtt gcatttcaac tgggacgcgg tcgagcaact gtttgatacc  4500
acgctgctgg atcagatgtt tggtgcttat tgtcatgcgc tgcaggcgct ggttgccatg  4560
ccgcaaagtt ggtgggggt aaatagttct ctggcgctgc ccaccgttag tgcaccggtc  4620
acgcaggctc ctgcacctac ggccttgttg caccatggat tactgcgtca ggcagcactg  4680
acgccacagg aaactgcgct gatcagtcct atccgtgaat tgacctatcg ccaactgtcg  4740
acggcggcgg atcatgtggc ccgcgccctg ttagcgctgg gcgtgcagca tggcgaccgc  4800
```

```
gtggcggtgg tgatggaaaa aggctggcag cagattgccg ccgtacacgg cattttacga  4860
ctgggtgcgg tctatctgcc agtggatccg gtgctaccgc cacagcgtcg ccagcttttg  4920
ctgacggtgg gcgaggtgcg ggtacaagta acgcagccgg gtctcacgca attggagccg  4980
tcgctgcccg tgctgatcat cgacgacgga atgctggaca cgcctgctgc gccgttgcct  5040
gaagtggctg ggatgtcac  ggatctggcc tatatcattt tcacttccgg ctccaccggt  5100
accccgaaag gagtgatgat cgaccaccgt gcggccatga acacgctgga agacatcaac  5160
gaacgctttg gcctcaatgc gcaggatagg gtgttcgggc tgtcatcatt gagctttgac  5220
ctgtcggttt acgatgcctt tgcgcctttt atggtgggtg cagcgctggt actgccggaa  5280
gcaggacggg aaaaagatcc gcgtcattgg cagacagtta tggcacacgg tcatgtaagc  5340
gtctggaatg cagtgcccgc actgatgcag atgctgtgcg aataccacag cggcgatcgg  5400
atgagttatc cgacgttgcg tctggcactg ttgagcggcg actggatccc gctaacgtta  5460
ccggagcaga tgcgcgagcg gctcaatgaa acgatggaca tcatcagtct gggtggagcg  5520
accgagtgcg ccatctggtc ggtctactac ccgataggtg aggtggaatc gacgtggacc  5580
agtattccct acggtcgggg cctgcgcaac cagccagtat acgtgctaaa tgcgcaactg  5640
gaggaatgtc cggtcggggt ggaaggagag atttgcattg gcgggatggg gctggcacaa  5700
ggctacctga acgacgcaga gaaaacggcg gcgagctttg tctggcgcga agcgagtggt  5760
gagcgaattt accgcactgg ggatcgcggg cgctactttg ctgacgggca agtcgccttt  5820
ttggggcgca acgataccca agtgaaggtg aatggttacc gtatcgaact gggggaagtc  5880
aaaagccacc ttgaacagct cgacagcgta gggagtgccg ccgtggtgtg ccaccaggga  5940
cagctgtatg cctttatcac tgccgcagaa aacctgcatc ctgacgatac tgacgccctg  6000
ttagcgcgtg ttcgtgctca gttagccgtg cagttgccgt attacctgct gccccaacat  6060
ttctttcttc tcaaggtgct gccgatgaca ggcaacggca aaattgatca ggcggcaatg  6120
gttcaagagg ttatccaacg tatgtcgcaa tctacatcac agaagtcgag ggccctcgcg  6180
cacgcctcgc cctatgaaca gcaggtggcc gctctctggt gcgaggtact acaacgagaa  6240
cagatcggac tgaatgacaa cttttttgaa gcgggggcgg gctcaatcca gatcgtgctg  6300
ttgcatcgcc gtattgagga gatttttaag gttacggtac ctattgctga gctatttcgc  6360
ttaaccaccg tgaaaagaat tgccggttat ttgcaggcta tgcaggacaa tgcacgggcg  6420
gtgaatcaaa cacagcagcg tgatgcttcc cgatcccgcg cccagcaacg acttgtacgt  6480
cgtcaccagc gtcagcgtta a                                              6501

SEQ ID NO: 1075        moltype = DNA  length = 6465
FEATURE                Location/Qualifiers
source                 1..6465
                       mol_type = genomic DNA
                       organism = Escherichia coli
SEQUENCE: 1075
atgacttaca gtgaaagcga tattgccatt gttggcatga actgccggta ccccggcgtg  60
cacagcgttg cggcattcga aacggtgctt cgcaccggat gcaacatttt ggaccccaaa  120
gtgaccccga gcaacggcca caatcacatt acgctgaaca acgtctatga gcacatggcg  180
gagttcgatg ccaacttttt tggctacagc cgtgcagaag cagaaatcat ggatccacag  240
cagcgcgtat ttctgacctg tgcttgggag atgtttgaac aaagcggtta caacccgaag  300
cagcacgatg cgcgcgtcgg cctatatgcg ggcgtgagta ccagcttcta tttgcttact  360
cacctgatga acaacccaga caagcttgca caactcggtg gtctccaaat catggtcggc  420
aatgacaaag atcatttgac gtcccaactg gcttaccgcc tgaatattac cggcccttgc  480
gtgacggttc aggccagttg tgccacctcg ctggtggcag tgcatctggc ctgcgaaggg  540
ctgctgagcg gtcagtgcga tatggcgcta gcgggtggcg tcacgtttcg catggaggag  600
cagcgcagct atgaatcgca cggtgatggg ctgcaagcag aggatggcct gattcatact  660
tttgatgcgc aggcgagcgg tacggtctac agcagtggtt tgggcatggt gctgctcaaa  720
cgggctacag acgcgcaggt gcaaggggat aacatccttg ccgtcatcaa gggaagcgcc  780
atcaacaatg atggcggtgc gcgcagtggt tataccgtgc cgggtgttga tggtcaggaa  840
gctgtgatga ttgaggcgca tagcttggcg gaggtgacgc cgcagcaaat tcagtatcta  900
gaactgcatg gcagcggcac gccgttgggt gacgctatcg aattcgcggc catcaaacgt  960
gtgtttggga cgccagcgcc gaatgcgaca ccgtggcgtc tgggggctgt gaaacctaac  1020
gtgggtcacg tagaaatggc atctggcatc accagtctca taaaaacggt gctgagtctt  1080
actaaccggg tgttttaccc tacgctgaat tttcaacggg ctaatccgca actggggttg  1140
gaggacagcc cgtttgaagt ggtgtcccgt ttaacgcctt ggccggaggg caccacgcca  1200
cgcaccgctg gtgtgagtgc gttcggattg ggcggcacca acgcacatct ggtggtacaa  1260
gcgccgttat cgacgccgca ggcgagggcg cagcagatgg ggccttgtgt cgttgtactc  1320
tcggcaaaaa accacaatgc cctggaacag atgcaaaacg ccctgctggc gaaactggcc  1380
gcacatccag agatacgctt acaggacgtg gcttacaccc tgcgtcacgg gcgtttctcc  1440
gccccggtac gtaagtgtgt catcgcagag aattgcaccc agctagcccg acaactccgc  1500
gacgcaccga tggtggaggc aaccacgggt tgcacgatct actggagatt ggggcaccgt  1560
ttcgttgttg cactcgagac gcttagtgac tggctggcgt gctctgaggt gttgtcacag  1620
gcggtgggac aactgctcga gcattttccg ctcgaaccag cctgtctgca agatctctcc  1680
cctgcgcaac ggacgtttat cagccagtat gcgctgatcg cgttgattga cgaacgggaa  1740
acgttgaatg tggtgctatg cggcgacggt gatggtggct atgctgccgc cgtactacga  1800
ggagactgca cactagagca agcatggcac aggttgaatg cgggccaacc gtttgatgat  1860
gtgccgacga atcccctctt gcagcccgat gtctgctctt tgatgctgga cgacgcggcg  1920
agtgatgcca atcgcaccgc gctagaggcg ttagggcagt tatggttggc tggcgtcagc  1980
ctagattggc gctgggtgga tgcggcggag cgtatgttgg gcagtcaacg catcgccctg  2040
ccggggaccg tttttacacc gcagcgctat tgggtcgagg ccgtacggcc tgccacgttc  2100
tcccacgaat cgtcgaataa tctcttatcc cgcgcaacaa aatccgatat tattgcagtg  2160
gtgacggaga tatgggaacg cacgcttggt gtcagcattg atgatcacca cgccagcttc  2220
ttcgaactgg gtgggcattc gctgttagcg tcaaccattt tatatgatat tcagcaacgt  2280
tacggcatca cctgtacgct aagcgcattc tttgccgatc ccaccatcga gggattaagt  2340
tgctatctgc tcgaacaagg cggcagtgag acagcggttt cagcattgcc tgatacggtc  2400
tttgcccctg accagcagca cctacctttt ccgctgactg acgtgcaaca ggcctattgg  2460
gttgggcggc gaaaatcctt gggattgggc aatatttcca cccatatcta tgtggaatat  2520
gaactacagg ggctagatga aacagcgttc aaccgcgcgc tcaatgcggt gattgcgcgg  2580
```

-continued

```
cacagcatgt tgcgtgcaat tgtcaacgat gacggtatgc agcagatatt gccaaacgtg  2640
ccggaatacc acgttgcctt ctataccacc cagtgcgagg atgcgtttca acagcgttgc  2700
cgtgagctgc gtgacaccct ctcacatcag atgattgatt gtagtcgctg gcctctgttt  2760
cagatggagg tcgtggttga tccgcagcaa aaagcccggc tacatgtatc tatcgacctg  2820
ctgatagccg atgcatggag tctggagttg ttcattcggg aactagctta tcactaccgc  2880
catccgcagg cggcattgcc tacattgacg tacagtttcc gcgactatgt gctgacctta  2940
aaatcctacg agaaaacgcc gcagtttgaa cgggcacgtg actactggcg cgcccgcatc  3000
gaaactctgc cgccggggcc acgattgccg ctgcgtaccg accccacgaa gctggaaaac  3060
cccacattcg tgcgccgtag ctattgtcta tctcgtgcta tctggcagcg cttgaaaacg  3120
caggcgggtc agatgagtat cacgcctact acactgctgc tcacggggtt tgctcaggtg  3180
ttggcgcgct ttagttcctc gccgcacttt agccttaacc tgacgctgtt taatcgtctg  3240
ccgttgcacg cagatatcaa tcacttaatt ggcgatttta ctgcactgac gttgctggag  3300
attgatatgt cgcagggaga aacccttgcag gcgcgggcaa acgtgatcca ctctcaactg  3360
tggcgcgatt tggataaccg cttgtttggc ggtatccagg tctctcgact gctggtacaa  3420
actcaccgcg atccggcgaa atcggtgatt cctatcgtgt tcaccagctt gctcaatcaa  3480
tatgaggcga gctgggaaac ggatgatacg ctgttcaacc aaccgcagga tgatctgtac  3540
agtatttcac agacaccgca ggtgtggctc gatcatcagg taatggagcg taacggggaa  3600
ttgcacttta attgggacgt ggtggaacaa ttgtttgaac cggcgctaat ggatcagatg  3660
ttccagtgtt attgccaact cctgcacgcc ctagcccagc gaccacagct ctggcatgag  3720
actcaagatg tgctggcgct gcccaccgtt agtgcaccgg tcacgcaggc tcctgcacct  3780
acggccttgt tgcaccatgg gttactgcgt caggcagcac tgacgccaca ggaaactgcg  3840
ctgatcagtc ctatccgtga attgacctat cgccaactgt cgacggcggc ggatcatgtg  3900
gcccgcgccc tgttagcgct gggcgtgcag catggcgacc gcgtggcggt ggtgatggaa  3960
aaaggctggc agcagattgc cgccgtacac ggcattttac gactgggtgc ggtctatctg  4020
ccagtggatc cggtgctacc gccacagcgt cgccagcttt tgctgacggt gggcgaggtg  4080
cgggtacaag taacgcagcc gggtctcacg caattggagc cgtcgctgcc cgtgctgatc  4140
atcgacgacg gaatgctgga cacgcctgct gcgccgttgc ctgaagtggc tggggatgtc  4200
acggatctgg cctatatcat tttcacttcc ggctccaccg gtaccccgaa aggagtgatg  4260
atcgaccacc gtgcggccat gaacacactg gaagacatca acgaacgctt tggcctcaat  4320
gcgcaggata gggtgttcgg gctgtcatca ttgagctttg acctgtcggt ttacgatgcc  4380
tttgcgcctt ttatggtggg tgcagcgctg gtactgccgg aagcaggacg ggaaaaagat  4440
ccgcgtcatt ggcagacagt tatggcacac ggtcatgtaa gcgtctggaa tgcagtgccc  4500
gcactgatgc agatgctgtg cgaataccac agcggcgatc ggatgagtta tccgacgttg  4560
cgtctggcac tgttgagcgg cgactggatc ccgctaacgt taccggagca gatgcgcgag  4620
cggctcaatg aaacgatgga catcatcagt ctgggtggag cgaccgagtg cgccatctgg  4680
tcggtctact acccgatagg tgaggtggaa tcgacgtgga ccagtattcc ctacggtcgg  4740
ggcctgcgca accagccagt atacgtgcta aatgcgcaac tggaggaatg tccggtcggg  4800
gtggaaggag agatttgcat tggcgggatg gggctggcac aaggctacct gaacgacgca  4860
gagaaaacgg cggcgagctt tgtctggcgc gaagcgagtg gtgagcgaat ttaccgcact  4920
ggggatcgcg ggcgctactt tgctgacggg caagtcgcct ttttggggcg caacgatacc  4980
caagtgaagg tgaatggtta ccgtatcgaa ctgggggaaa tcgagcgctg cattgcgcga  5040
catcccgatg tggagcagtc agtggtggtg gcagtgggta attctcaaca tcgtcggctg  5100
gtcgcttttg ccaaactgca cgatcgccac caggcgcagg cattgcaagc taaggaagcg  5160
gaggcggcgg cactggcgca gggtattatt gtgaatccgg cacagcgtct agcgttcaaa  5220
ctcaaggagc cacatattcg cgcgctggat ggtctgggca ttgcactgac ggcaccggcg  5280
gatagcacac gttacatcaa acgccgcagc tatcgtcatt tcagcgcgca aaaaaccacg  5340
ctggcacagt tggggcaatt gctgtcggc ttggggcaga tgcgtctacc cggtctacct  5400
tttgccaagt atgcctatgc gtccgccggg gggctatacc cggtgcaaac ctacgtgtac  5460
ctgcatccag acaagatcga agagggagta tccggtattt actacttcga cccgcgacag  5520
agctgtctta tgccggtagc accagaagtc gagctgaaca gtggttttca tgccggacct  5580
aatcagtcta ttgccgatcg ggcggcattc acgctgttta tggtggctga tatggcggtg  5640
atctcgccat tctatgggca agaggcagct tggcacttct cggtgatgga agcaggtact  5700
ctctgccatt tactggaaga agatgcgccg cgctacggat tggggctgtg ccaacttggg  5760
atggcagact tttccgctgt ggcatcgcat tttcaattgt cgccacatca tcgctatgtc  5820
cattgcaccg tggggggcgc gatagggcaa gaggcggcaa gtgctgcagc attgctgcgc  5880
gatttctcca cctatgagaa accgaaggaa accgctgcgc cgctggacat gcagagctac  5940
aaagatgcca tgctgcgcgg cctgcgtcag caactgcctg actatatggt gccgagtgat  6000
ctgatgttag cgaccgattt tccgttaacc gctaacggca agctagatcg gcaaaaatta  6060
cagctgcagg gcgaacaaat tgcccaccag cgtgacggcg tgggtccaat ccaggtggac  6120
agtgcgttac aacagcggct ggtggcgctc tggcaggagg tactcggcgt gagccacgtg  6180
tcggccgaag acgatttctt ctcgctgggg ggcagttcta tagaattggt gcgtattcag  6240
caggcacttg aggcgattat cggcaggag attcccattg tcgatctgtt ccgtctgcca  6300
accatcgcgg atgtggcgcg ttaccttgat gagcaactgc acaatctacc cgccgcccac  6360
gatatcgtat tagcgcaggc tgaggtttcg caggtcagcg ctgcgcgcga gaatctggcg  6420
ttgcggcgta aacgtgccca acagggagaa aagggcgatg agtga                  6465
```

```
SEQ ID NO: 1076          moltype = DNA  length = 1464
FEATURE                  Location/Qualifiers
source                   1..1464
                         mol_type = genomic DNA
                         organism = Escherichia coli
SEQUENCE: 1076
atgagtgagc agagctatcg tagcgcaggg acactgttgg cacagttggc gtccggagaa  60
accacctcag tggcgttggt gaatcactat ttttcacgta tggcgcagtt taacaagccg  120
ttgaatgcgg tggtgcagca gcactatgcg ttggcgttgg aggccgccgc gcgcgccgat  180
cgtgagcgac tggaggggcg cgcaaggggc gtgttgcacg gattaccttg tactgttaag  240
gagtcgtttg acgtgcaagg gtggttaacc acgtccggtg cccattatct gaaagataac  300
cgggcgacgc aggatgctcc ttccatcgca cgcttacgcg ctgccggggc gatcctgatg  360
ggaaaaacca atgtgccgat gatgactgcc gattggcaaa cctataacga tctgtatggc  420
```

```
accacccata acctgtggga taggcaacgt tcacccggcg gatcgtccgg aggagcggcg  480
gtggcggtgg cggcggattt cacccccgtg gaatttggca gcgatttgtt tggctcactg  540
cgcattcccg cacactacac aggtgtctat gcccatcgtt gtagcttggg gttgatgtcg  600
gtcagaggac atgtgcccgg tggtggtccg caagcgactg atgagccgga tctctcgacg  660
gcgggcccca tggcgcgcag cgcggcggat ctgcgtctga tgatgcgcgc attgagcaca  720
ttctgggtgg aaccgccgcg tattcccgat tttagccgtt atcaggccaa agcaaactac  780
cgcgtgtgca cgtggtttag tgcgccccac catgagatag atcaacagat cgcacagcgt  840
tttcaatcgt ttatcgacaa gttacgcgca cagcctggcg tggaggttga tgatgctatg  900
cccgccgata tcgatcccga cgcactgttt gatatagcag tcaaactcag tggtcggctg  960
gtaagtacgg cgctcaatgg acgccagcgt cttacagccg ggctggctgc gctgggcttc  1020
aggcttgtgg gcaagctggc ggatgtgcct gaggggataa cgagctatta ccagggcatg  1080
ctgaaagaca gtggcgaaca gcggaataca gacaaactcc gccacgaata cagccgggtg  1140
atagaaaccc ttttcgcgcg ttatgacgtg ttgttgacac ctgtcagccc ggtgctggcg  1200
tttgcgcaca tgcagcagcc ggtgcgtaag cgcaagctta tcgtcaatgg cgaaccgcaa  1260
gattacaacg aacatttgtt ctggaacatg ttagcaacgg tttttggttt gcctgccacc  1320
gtttacccat tggcgaaaac gatggatgag cttccgtgcg gcatacagat catttccggg  1380
cattttcacg atgatgtgac gattaacttt gctgagttct gcgaaagcat cagtggcgga  1440
ttcacggtac cggaagggta ctag                                         1464

SEQ ID NO: 1077        moltype = DNA  length = 1440
FEATURE                Location/Qualifiers
source                 1..1440
                       mol_type = genomic DNA
                       organism = Escherichia coli
SEQUENCE: 1077
atgacggtga ataagcttga gccagacaac ggcacgccga acgatgagct gttcacggtg  60
gcgggtatgt ttgacggctc gctgtataaa ttactcctgc gcatggcgtt gccgatgttt  120
gtcggtatgt taacgcaggt gacctatgcc atcgccgata ttttttggct gagccacatt  180
gatgtcacca acagcggcat cattgccggt gtggggctgg ttttccccgt tggaatgggg  240
ttatttgcca tcgccaacgg cattcaaatc ggtatgggat ctttgctgtc ccgcgccatc  300
ggcatgcagc ggttggatcg tgcacagcgg attttgtcgg tcggtatcat catcgcgcta  360
ttctttgcga tcgtgatcac cgtacttggc tatgtttatg cccagccgct attgcgctca  420
ctgggggcca cgaagagcat catcggctac gcaacggagt tctattatta ttcgctgctg  480
accgtgttca gcatcatgtt gattggcgtc atgatggggc tgtttcaagg cgcgggtaag  540
atcatggtca tcatgaaggc ctcattgttg gggggcgttgg taaatattat gctcgatcca  600
atcatgatct ttgtattcga ttttggtgtg aaaggggtgg cattggcgtc gtttctggcg  660
caactgagta tggtcgccta tttcatctac acattgatgg gattacatat cgggttgagt  720
atacgcatcg cgttacgccc attctcctgg aaaatctacc gagagtttct ctccgtcggc  780
atggcgcaga tgctgatgca actgatcatt gcggtcggca tagtgattta taattttttt  840
atcgtcaggc tggacgtaaa cgcgatggca gcgtttacgc tcactggtcg catcgactat  900
ttcatcatca cgccgatgct ggctatcgcg accgcgttgc tgactgtggt ggggcaaaac  960
tggggacacg gaaatgtcac ccgcacgctg aatgcctatt gggccgccgt cgcgctggcc  1020
ttctctattg tgctggtgtt agccgttatg catattgtac tggcaccctg gatgtatccc  1080
ctgtttactc gtgttgttgc cgtgagtgac tatgcggtac tgcaaacccg tatcatggca  1140
ctggcactac cctttgtcgc tatcagcctg ttagcaagtg aatattatca ggccattggt  1200
aagccttggt attcggtgtt gttgacgctg atgcgtcacg tgtttatatc tgtccctgtc  1260
gtatacctgc tggcgattgt gttagagatg cgtattaccg gcgtctattt tggggcgatg  1320
agcggcactt ttgtggctgc gttgttggcg tggcgtctgc tgcgtctttc acctcgtctg  1380
ctgcgatgga atcaggaggc ggtgcgctcc caacacttgg atatggaggt ggcaccatga  1440

SEQ ID NO: 1078        moltype = DNA  length = 4368
FEATURE                Location/Qualifiers
source                 1..4368
                       mol_type = genomic DNA
                       organism = Escherichia coli
SEQUENCE: 1078
atgatgtcgg gcaatccgtt gtcgtggcca caggaacagt gccacatcat tgatcaactg  60
tatccttaca gtgccgtaaa catcattggt ggtgtggtca ccattgaggg aattgtcgat  120
ctgccccgac tacacgcggc catccagtcc gccattcggc aatttgatgc gttgcgtatg  180
tggtttgtga tgggagagga gagtgaagtg gtcagccaag tgcagcctta tcactggcgc  240
gatatccgcc atttgacttt ttccccagat tatgacaagg agaacctacg cccagcggcg  300
atcgaaacat ttgttgatga gtggttccgg cagcccttta ccctgctggc gcacgatttg  360
ttcgagtttg tcacctttac gtgcggtgaa caatacagcg gttatttatt taaagcccat  420
cacggcattg ctgatggttg gtcaatggcg ttgttgtcaa accatgtcaa gcgagcatac  480
gaacagcagg acgtaccaga tgatgcgtca ccagcctata gcgcatttct ggcgcagcag  540
caatcttatc aggcgtcaac gcgctttgcc gttgatcgtg gctggtggcg tgactatatc  600
gacgaatacc gcgactgctt tccagacagt tcccccatcg ttactactga gggcatcagt  660
tgttccactt ggcttgagcc agccatgatt aaccgtctct acaggttgtg taatcgttat  720
ggctgtacgc ttaatacgct gtttattgca ctcttcgctc tctatcgcgc cagagtatgg  780
ggggaggaaa aaggcgtaat aggcgtgccg ttagccaatc ggcatactcg cgaggcgcgg  840
cgttgctttg gcatgtttac taatcaattg ccgctggcct atcgactggt gcgcacggaa  900
cgattctgtg aacgggtggc ctttttccag cgcgaactga aacgcggttt taaacacagc  960
aaatatccca ttaccttatt caaccaggat ttggcggaac agggggggagg gaagttgcgg  1020
gcgttcgatt attgcgttaa ttattataac tttacctatg aacgccacat tgcaggtgcc  1080
gcgcaacgcg tggagagtta ctacagcggc gagcagtcct ataagctaca gattgttttg  1140
caaactgtta ataatcataa agaaagcctt aggttgagtc tggaggcgct gcgtagcgct  1200
ttcactccgc accaactgac agcgatgaaa aatgggctgt tggatttagt cactgcattg  1260
gatcggcaac ctgacgctcg tctaggcgat ctcgaagtct atcctgcgcc gcacgtcgca  1320
ttggcatgtg gctcactcaa accctcattt acttcccgat ttgcagcgca agttgtggag  1380
```

-continued

```
catggtgatc gcacagcact aattgataat gaacagtctt tgacttatcg gcagttggat  1440
gacgctgttg agcgggttgc gcgttatctg cgccaacagg ggatcggacg cggtcaagtg  1500
gttgggatta tcgctgagca tagcgctcaa acggtgatgg ttatttatgg tattttgcgc  1560
tgcggcgcgg catttctgcc gctaaatccc gcgttgccaa cgacccgcct ttacgccatg  1620
tgtcgtaaag cgcaggtagc gcatatcctt tacgatccgg cgatgcatga attgacgcag  1680
gcgctggcgt ttcccgcgtc cagcttgctc caggccttag ccacttcggc gcttgctaga  1740
gaacccttggc cagctattga accgcaggat ctggcatatg tgctgtttac ctccggatcg  1800
accggcgagc ctaagggcgt gcaagtctct catggcaatc tggctaacta tctccatttc  1860
gccgccgaac gttactttac agcgcaggac cgggctgcgc tctactcttc gctgtccttc  1920
gatttgacca tcactacgct gttcgccccc ttatgtgtgg gcgctagcat cagcgtttgt  1980
cggcacgccg agagcgaaac attgctgcgc atggccgtgg ttgatcagcc caacacagtg  2040
atcaaactga cgcctgcaca cctgcggttg ttgtgtgcgg ctggcataag cagtgagcag  2100
attcgtacct tggtggttgg cggggaggat ttcaagcggg atctggcgcg taaggcggct  2160
gctctctttc ctcaggccgt gatctataac gaatatgggc cgacagaggc caccgttggt  2220
tgcatgatct atcgctacac cgggcaagaa acgctgcctt cattgcccat cggtatggcg  2280
atcgacggtt gccaggtagc aatttgctcc ccttggggct gtccggtacc ggaaggcgaa  2340
actggtgaat tggtgattta tggcgcgtca gtgacgcagg gctatatcga tgcgccgcaa  2400
caaacggccg ccgcctacct taaagatacc aatggggtga tgattggcta tcgcagcggt  2460
gatattggct acgccatcgc tcctaatacg ctggtttatc agggacgtaa agacgatcag  2520
gtcaaaatta atggctatcg tattgagctg tgcgaaatcg aacaagcgtt gttgagcgca  2580
cctcaggtag aaagtgcggc ggtggcggtg attgatgatg tgcaggggca gcacagcggg  2640
ttgctagcct gcgtgacacc gtcatctgtt gatgtagcta ccgtaatgca acatctgcgt  2700
cagcaattac ccacctacat gcaacccaag cagtgctgtg ctatcgccca actgccgcta  2760
tcgcacaatg gcaaggtgga cgtgcgtcag atggtcgcaa cggtccgaaa caccgcgcct  2820
gcatcgggta gcgagcggct gggagatgcg gcgataaggc attcagttcg ggtatgtgtg  2880
gaaggggcgc tggagcaaac tgagtttgat gataacgaaa atctttatgt cttggggttg  2940
gactccatca agagtatcca gattgcagcg cagctcaggc accacggctg gacgatgtca  3000
gcggtgcagg tgatggagtg tggaacagtg aacgccatct gtgagtttct cgctagtcat  3060
acaacggtgt cacagctcgc gcagtatgct cataacaccc gtatcgatct acccgcattg  3120
cgttggttta cgcagttggc gttgccagtg cccaatgttt ataaccatgt cattgtgctg  3180
aaagtgttgc cgggctgccc gctcgagcag ttacacaaca ggctgcatac attaatccag  3240
cagcagccag ctttgcacag tgcgctggac gctgaggggc ggttgctagt atgcgaccct  3300
aatgtgtgtt atcccaacga ggtgctcacg gaatattcga cggcgcagtg gacgttggca  3360
gaggtgatcg ctcagtgcaa tagcatgctt gacgtgacaa atggtcgagt ctttacggca  3420
gctctgttac acgccccgca gcctgcgtct agcacgctgg tactctgtgc ccatcacttg  3480
tgcgtcgata tgcactcttg gtatttaatc ctcagcacgc tggacgccgt cagcactgtc  3540
aatggcacca gcaacagcgg actgcatcgc tggaatgact atctggcgag caaaacggta  3600
gattccgcca cacacgaaag ctggcgcaca gtatgtcaaa cgctaccgct gcatttccca  3660
cccgtgtcat tgccagatga ctcattacct cgtacgcgcg cttggcgtga agactttcgc  3720
catccttgcg tcaggaggtt gtttgaatcc agtggtaata ccgcgtacag cgccgaaacc  3780
tatgtgctaa cggcattggc gctggtgctg cgttactaca gcgaagagcc ttggtgtcgc  3840
atcgagatgg aaggcatggg acgcggctgc tggcccgatg agcctgacgt tgcggatacg  3900
gtcgggtggt ttactctatt ttatccttgg gcgatccctc tgcatggcga tatggcgaca  3960
ctgttatctg cgatcgcttc cgatttggca aaacgcacgc atggtggggg agattacggt  4020
ctgctgcaaa tgcggcatgc accggaagac tctcttgcgc aagggatccg aatgaattac  4080
atcggtgtgc aggcgcaacc ttcactccgc tattttcata ttgatcactt taatagtgat  4140
atctataccg cgcctgaaaa cgcgctcggc tgcgtgctgg agtttaatat tgcgcgctcg  4200
gcagctgatg gtctctcctt ccactgccgt ttcgatccca cgcgcattgc gctgaatgat  4260
gtgcaactcc tgctggcgcg ctacaagaac agcctcactg atctggatgc ctggctgtgc  4320
caacacagcg ccacgctgac gggcgcgccg actttgtgga cactataa              4368
```

```
SEQ ID NO: 1079          moltype = DNA  length = 2460
FEATURE                  Location/Qualifiers
source                   1..2460
                         mol_type = genomic DNA
                         organism = Escherichia coli
SEQUENCE: 1079
atggcaaagg atgattttac ctgtggctca ctggatattg ccattattgg catgagcggg  60
cgtttttccg gtgcggaatc ggtgcccgag tggtgggata agttgctggc gggtgaggag  120
ttcactcaac cgacatgcac agaagacgat aatgggaacc cttggattag gctgcgcaat  180
ataatcaccg ctccctatga cttcgatgct gcatttttca atattccgcc tggcgaagcc  240
ctgttgatgg atccgcaaca acgaatattt cttgaatgct gctacaacgc tcttgagcat  300
gcgggctata ttcccacgca acttaagcga gtcggcgtct atggggcgac ctacgccaat  360
aactatttta tcgatcgcgt ctatccatac ctgaagatga gcggcgatca ccattatctt  420
caggcgcaga ttggtaacga aaaggattac ttgtgtgctc aggttgccta caagttgggg  480
tttaccggac ccgctgtgag tgtacagacc gcctgttcca gttcgttggt ggcagcatat  540
ttagcatgcg aggggttatt gacttttcaa gccgatgttg cgttggcagg tggggtcacc  600
ttgggttttt tacaggcgca cggctacagt ccgcaaggtg ataagctggt atcgcaagac  660
ggacactgcg ccccgtttag cgctgaggcg accggcacgg tatacagcag cggtgcggga  720
gttgtggtgc taaaacgtct tgaggatgca ctacgcgacc aagacagagt gtatgcggtg  780
attaaaggag gtgcggtaaa taacgacggc gggcgtcggc tggggtttgt cgcccccagc  840
gtagaaggac aggtagaagc gatcaatacg gcgcttgccg ccgcagaagt cgtaccgact  900
gatatcgcac tgatcgaaac gcacggtacc ggtaccccgt tgggtgatga gattgagctt  960
gaagctctgc accgggtttt cgcaccggca tgtgcgccgc acagcattca attgggtgcg  1020
gtaaaagcca acttgggtca cctgggagtc gcttccggta tcgtcagctt aatgaaaacc  1080
gcactgacgc tatatactgg tttagttccc ccgcagatca acctagtaaa taaacataaa  1140
aaactgttgc agccagcctc gccattttat ctcagtgatg tagtgacttc tgtcccacaa  1200
acgaaaagga tccatgccac cgttagttcg tttgggctgg gagggaccaa tgctcatttg  1260
gttctgcaaa actggtgcga gacgcctgcg caagcggtgc aagaaaatga gcgccgcctg  1320
```

-continued

```
tttttcttca gcgccaaaac gccattagcc cttagacaac agttggatgc tcattatcac  1380
gctctggcga cctatgcgga agcagataaa gatcgtatcg cctatactct cgcgcaacgc  1440
cgggcacatt tcccgtatcg ctgtgcgctg gcggcagaca gtgtggtagc gttgcgtgca  1500
agtttggcga aactgcggga tgctgacatg tcttttaccc ctatcaatat ggaaactacc  1560
ttggtgttcc tatatccgga ccgggacgat aagctggaga gtgccctgac gcatttgctg  1620
gcttgtcaac ctaacttgcg ccagcggcac cagcgcctgt ctcaggatgt tgcacaaatc  1680
tgcgaaccag ccgattggac gccagcattg cgtcagttta tccagcaggt gagtcttagt  1740
gaatggctga tcgaacaaag tatctcgcct gtgcagcaca tcggttacct gacgggggct  1800
gcagcagcgc agtatgttgc gcgcatcatc tcactggaaa acgctgttca gcaggtgatt  1860
gtggctgaaa cgacaccgga gcagacgctg gccggcaaca gtgaactgag cgaaatattg  1920
gctaatctgg cggtgacgga gggaacgctg atgctggaaa tcggtcgcgc ggggacgttt  1980
tccatattgt atcaccagca tgcgcagtgg gttgggcaaa cagtattttc ccccatgctg  2040
aatacggata cgcctgagga catcctgccg ctgttgggca ctctttggca acgaggagtg  2100
actatttgtt taccggaaat gccagccgtg cagactatag gcttacccgg ttattcgttt  2160
gatcgcgtcc ggtatgaaat tcagtccagt gatgcgagag agaacgctat gttaccagtg  2220
agttatttgt cggtcagcga ctttgtggag aaaacctggc gttcattgtt atgcatcgat  2280
cattatgacg aacacgcggt tattttcgaa tacggagcga cctcgatgca cgttatctct  2340
ttcgtcgaca gctgtaacca catttataaa atcggactga ctgccgccga tatttatgcc  2400
agacccgcta tccgtgagca cagtgaattt atctccgaat gtgttgatgg tattttatga  2460
```

```
SEQ ID NO: 1080        moltype = DNA  length = 1515
FEATURE                Location/Qualifiers
source                 1..1515
                       mol_type = genomic DNA
                       organism = Escherichia coli
SEQUENCE: 1080
atgacaataa tggaacacgt tagcattaaa acattatatc atctcctgtg ctgtatgctg  60
ctctttattt ccgctatgtg cgctttggcg caagaacatg agcctatcgg ggcgcaagat  120
gagcgcctgt cgacattaat tcaccaacgg atgcaggagg ccaaggtccc agccctttcc  180
gtaagtgtga ccattaaggg ggtacgtcag cgatttgtct acggtgttgc cgatgtggct  240
agtcagaaag cgaatactct agacacagtt tacgagctgg gatcgatgag taaggcgttt  300
accggacttg tggtgcaaat actgattcag gaaggcagac tccggcaagg ggatgatatc  360
attacctatc tgccggaaat gcgcttgaat tatcagggaa aacctgcttc cctgaccgtg  420
gctgatttcc tttatcatac atcaggattg cctttttcaa cactggctcg gctggaaaac  480
cctatgcctg ggagcgctgt ggcacagcaa ctgcgcaacg agaatctgct gtttgcgccg  540
ggtgcgaagt ttagctatgc ctccgccaat tatgatgtgt tgggcgcggt gattgaaaat  600
gtgacgggaa aaacctttac agaggtcatt gcggaacgac tcacgcagcc gctgggcatg  660
tcggcgactg tggcagttaa gggggatgag attattgtca acaaggcaag cggctataaa  720
ctgggattcg gcaaacccgt tctgtttcat gcgcctctgg cccggaacca tgttcctgcc  780
gcctatatcc atagcactct gcctgatatg gaaatatgga tagacgcctg gttgcacaga  840
aaggctttgc cggcaacgct gcgtgaggcg atgagtaaca gttggcgtgg taatagtgat  900
gttccgcttg ccgcagacaa tcgtatcctc tatgccagcg gttggtttat cgaccagaat  960
caaggccctt acatcagtca cggtgggcag aatccaaact tttcttcttg cattgcgttg  1020
cgaccggatc agcagattgg cattgttgcg ctggcaaata tgaattcgaa tctgatacta  1080
cagctttgcg cggatatcga taattatctg cgcattggca aatatgctga cggcgctggt  1140
gatgcaatta cagccaccga taccctttttc gtctacctca cgttgttgct gtgtttttgg  1200
ggggcggtgg ttgtagtgcg cggtgctttc cgtgtttatc gcgcaacggc gcatggccct  1260
ggaaaacagc agaggttacg tttacgcgta cgtgactata tcatcgcctt ggcggttcct  1320
gggctcgtgg ccgccatgct ctatgtcgca ccgggtatac tatctccagg acttgactgg  1380
cgttttatct tggtatgggg tccatcgagc gtgttggcga taccgttcgg aattatcctg  1440
ttagctttcg ttctgacatt aaatcatcaa attaaacgaa ttctattaca caacaaggag  1500
tgggacgatg agtaa                                                  1515
```

```
SEQ ID NO: 1081        moltype = DNA  length = 723
FEATURE                Location/Qualifiers
source                 1..723
                       mol_type = genomic DNA
                       organism = Escherichia coli
SEQUENCE: 1081
atgagtaata tcagtttgta ttgtttgcca tattcaggtg gttctgccgc catgtattat  60
aaatggcgta gcgtgctgtc ggacaatatt actttgcggc ctttagaacc tgcggggagg  120
ggaactagaa tacgccagcc gctgtgtctt acgatggtgg atgccgtcgc tgacctttat  180
caacaatttg tgaaacacta cacaggtgga gactacgcca tttttgggca tagtctcgga  240
gggatcatgg ccttcgaact ggtgcattat attctcgatc atggacatga catgccatgc  300
gcgctgtttt tttccggctg tcgcccaccc gatcgggcct ctcatgaagt aatactgcat  360
accttgcccg atcaggcgtt tatggaagag atcgtcaagc tgggcggaac tccggttgat  420
gtctttcgta ataaagagtt aatgacaatt ttcaccccca tcattaaaaa cgattatcgg  480
ctctatgagc agtatgtatt tcaggccaag gcgcgcacat taacctgtcc gatcgtgcta  540
tttcatggcg atgctgacaa tctggtaatg caggatgaat tacttgcatg ggaaaaattc  600
accacacgaa agacgcggac tattatattt cctgctgccg atcatttttt tgtcgataag  660
cattttgaac aggtggtagg ttatgtgaac cagacgattg aatcactcga aatagtaggg  720
tag                                                               723
```

```
SEQ ID NO: 1082        moltype = DNA  length = 213
FEATURE                Location/Qualifiers
source                 1..213
                       mol_type = genomic DNA
                       organism = Escherichia coli
SEQUENCE: 1082
```

```
atggataagt tcaaagaaaa aaacccgtta tctctgcgtg aaagacaagt attgcgcatg  60
ctggcacaag gtgatgagta ctctcaaata tcacataatc ttaacatatc aataaacaca  120
gtaaagtttc atgtgaaaaa catcaaacat aaaatacaag ctcggaatac gaatcacgct  180
atacacattg ctaacaggaa tgagattatc taa                              213

SEQ ID NO: 1083        moltype = DNA  length = 513
FEATURE                Location/Qualifiers
source                 1..513
                       mol_type = genomic DNA
                       organism = Escherichia coli
SEQUENCE: 1083
atggctgttc catcatcaaa agaagagtta attaaagcta ttaatagtaa tttttcttta  60
ttaaataaga agctagaatc tattacgccc caactcgcct ttgaacctct attggaaggg  120
cacgcgaagg ggactacgat tagcgtagcg aatctggttt cctatctgat tggctgggga  180
gagctggtgt tacactggca tgaccaagag gcaaaaggaa aaactattat ttttcctgag  240
gaaggattta aatggaatga attggggcgt ttagcacaga aattctaccg tgactatgag  300
gatattacag agtacgaagt tttattggca cggttaaagg aaaataagca gcaactcgtg  360
gctttgattg aacgattcag taacgacgag ctttacggta aaccttggta taataaatgg  420
acccgaggtc gtatgattca atttaatacc gcctcgcctt ataaaaatgc ttcggggagg  480
ttaaataaac tgcagaaatg tcttgcagaa tag                              513

SEQ ID NO: 1084        moltype = AA  length = 244
FEATURE                Location/Qualifiers
source                 1..244
                       mol_type = protein
                       organism = Escherichia coli
SEQUENCE: 1084
MRIDILIGHT SFFHQTSRDN FLHYLNEEEI KRYDQFHFVS DKELYILSRI LLKTALKRYQ  60
PDVSLQSWQF STCKYGKPFI VFPQLAKKIF FNLSHTIDTV AVAISSHCEL GVDIEQIRDL  120
DNSYLNISQH FFTPQEATNI VSLPRYEGQL LFWKMWTLKE AYIKYRGKGL SLGLDCIEFH  180
LTNKKLTSKY RGSPVYFSQW KICNSFLALA SPLITPKITI ELFPMQSQLY HHDYQLIHSS  240
NGQN                                                               244

SEQ ID NO: 1085        moltype = AA  length = 3206
FEATURE                Location/Qualifiers
source                 1..3206
                       mol_type = protein
                       organism = Escherichia coli
SEQUENCE: 1085
MDNTSGDFPC NKMDTRKQLP LTPSQQGFLF HSLKDKKRSN YHEHFTCIFS QHVDSAHFKW  60
ALETLFRKHE CFRTDYNWEI DERPCQVVKT DVLPDIYVLD CEQEEIRFLL ANDDIIIPVP  120
QDDGIDAIIP QLLQADLKYP FSLKTIPVRA YLIQSTKESA FILSYHHIVM DGWSLSLFIK  180
QLLQLYGAAV VSGVRDDSAI IPSSLKPLVD TLSARRHTFQ HDYWAAYLRE GTPTCIVPLS  240
QYHTDTEAEN NSYVNQTNHV EINLSPDVCQ KIQTLCSDYR ITPAVIFYVA WGILLQRWCY  300
ADDVLFGATI SGRNIPIDGI EETLGLFINT LPLRLRDDGA TLLQHLQRMH QTLIAHYSNE  360
HDALASIQRL VHKEGHAGDL FNTLVVLENY PVDMTLLSCA SPVAIRHLSV HEQTHYPLTL  420
TITQQKGFRF SIAYALNYLT NNMAQALLMH LSYLLEQLVD NPQRPIAALV NLSPCQQAQV  480
LQPYLERMAC RDWDSQSNVI EQFHQVAATS PAQVAVVDEL CALTYSELAA QAEQLAAYLV  540
QQGVMVGDTV GIISERRVNT VVAIIAIMLI GAAYVPISPD YPVGRMQEII DDSGLALLLV  600
HGKPLDALNV AQSDLCAFPV APSVVFPVIT PDSRAYVIYS SGSTGKPKGI AVAHRGLLRL  660
IQGDSPLKVE SGETTLLTCP FEFDVSVFEM WSTLLNHGKL VLLSKQALLD INHIRRTIAD  720
EQVARAWFTS SLFNSYVAEG ADFFGMLQHI TVGGEAVSAW HVNDVMQKYP HLVVTNGYGP  780
TENTIFTTAY RFNGLQPARV PIGYAVPGTS LYITDLHGHL LPIGATGELV AGGVGVAIGY  840
QNNPALSATV FVPDPFIPGG MMYKTGDYAR LLDDGCVDCF GRKDGQIKIN GQRIETGEIE  900
QRLLECSGII EAVVVPYRVR ETLHIAAVVC VNDSYDEVEV RGQLADRLPP FAIPESLVVV  960
TEIAKSHSGK ADLAQLRYLL PATQCNAVST TISEVHSDME HALHAIWQRV LDRQDIDSNA  1020
SFFALGGTSL DTIRVKGDIK RQLGLEIDIT DLFKYPTLTA LAHFLDTAVS PEDAIPTRAV  1080
VYSDMPVAIV GMAGRFPGAA NIAALWTLVV GGESGLTLFS DEELRAHGVT PDTLKQANYI  1140
KTKGIVDDHE WFDADFFGYT PNEAECMDPQ IRLLHQCCWQ TLEHAGCDPA TFTGAIGIYA  1200
GLLTSPHWLN AVMQDTTDST ALYKASILNI HSVTALIAHA LNLTGPAVTL DTACSTSAVA  1260
IHQACIALRN RDCDAALAGG VSIEMPAYRG YEYHEGMINA RDGVCRPFDS QASGTVTGDG  1320
LGMLLLKRLD DALADRDCIY GVIKGSAVNN DGNNKIGYTA PSVIGQSTVI RTSLRRAGFD  1380
SDSIGLVEAH GTGTVLGDPI ELRALNEVFG PTPVPFCVVS ALKSNIGHLN SAAGVAGVIK  1440
TTLALHHQVL PPTAHFRQLN PAIDLSRSAL YVNQQVQPWP STRPRRALVS SFGIGGTNAS  1500
IALEAHQHED DPSATGVRDS YLLLFSAKTP AALELRVAST LEYVKHGVGV RLPDVAYTLQ  1560
TGRTAFDHRR AYLVSRGSKI DLSCATILQA EIFNGQRTTA EICFMFPGQG SQYHGMASAL  1620
YAHQPMFRQH MDRCFAAFQR YSTVDLKALL FDDEDTRDID QTQFTQPALF CVEYSLARTL  1680
IDLGITPDSM IGHSLGEYVA ACIAGVFTLE DALHVIEARG RLMQSMRPGS MMAVYLSREQ  1740
LTPWLAAERG IELAANNSAH FCVVAGEQAA ISRLSTRLVE GGIQHRRLKT SHAFHSAMMT  1800
PMLHDFAQLL GQIPMHAPHK RFISNVSGTW ITEEQATSPD YWVQQVRNAV LFSEGAAQLL  1860
VQPTLFIECG PGNTLSTFIQ GHNQYSDQPT LLTLRKANAA IDDEHMLHRT LAALWVRGEN  1920
IDWRRFNQTA LGKHIPLPDY PFEQTYYYRY GAALSGYRQY PNPLRRPQDE WLQRVLWRMH  1980
DTSLREAFYA PGELIIIISA DGDKLQQTLM SSGVDSITMP LPISSEDDVW DNDRILTHFH  2040
DICALLAHKT YRQLHCLYAP GAEAGSSLTQ SLSGLYRVAR WCMHSTTPLA SLTVLTHGAF  2100
RVQEEDNPEP TLAALSGAVN VFAQELHPTE VRLIDIDAQS SDENLNLLTQ RLAPKQETVM  2160
ALRQGMLYLR RFIPTRLLAH LPPQTGCIPG NVLWIIGGEK GIGRMIGEAL AQREGVRVVL  2220
SSRTGYHHEA VQQDALDVIH CDVTQAEAVR ACLATLLERY GRLDGVIFAA DATTTLTLHQ  2280
LSESALRDTL TVKERGTANV LHALAQRNLL DERLLLLFCN SLAAVNAEIG QTGYATASAY  2340
LDALAQQLRT RYKVNALSIG LDALREQGML LDAINGSEYD VLRGLRPLMT GTLLQAYKQQ  2400
```

-continued

```
GADTSYYARL SPESDWLLDE HRISGIATLP GTGYLALAYE ALRHYFVQDQ ICIDELVFLA  2460
PLTVMDNCSV DVFVDISPNG QGVSVEVKSM TERFSGTLTT HARGRATRLM VDDNVVCDLT  2520
GLMREMHTIT PPTKELSSTH FHYGPRWHSV QQLYGNTAQT QVFATLALPT VAANDTIALH  2580
PALLDIASSV VEQLPGFHTD SVPFLYQDLR LYRPLPNTLH VALTVNRHDE EGDSYAFTLY  2640
DMAGEMVARC AAMVKRKVQL HIQDVDDDTR LRVPSADNYQ LRLAAEGEGA GKLALCPTPR  2700
LALGDSQVEI EVLATGLNFK DVLFTTGLLR QQPGEAPLQL GLECAGRITR VGKNVTEFAP  2760
GEDVMAVLNG GFVQYARVES DCVVRKPAHC RIEQAAALPI AYLTAYYALV VRANLQPGER  2820
VLIHSAAGGV GLAALHIAKR CGAQIFATAG SEQKRDYLLS LGVHAVADSH DEQFAATLLT  2880
ASDGQGMDVI LNSLTGRLLD ASLALLAPLG RFLELGSKDI VEDKALPMRF FAQGGTFIPI  2940
NFHAAHGAFS RYLQQIVAWI DDNTLPLLPC KSVPLPEVAR AFATLTTPQH IGKVVVTHRT  3000
AAGMDRLNAM IAERRLGGYA LSMSNAEVMR QLWPILNTRS PWAQLLLSPR AIDRLARGNR  3060
VDRGVPSAAN DTITQQTVKK RPRPEIGVPY SPATREVERV LCQILEEYLG LDRVGIDDNY  3120
AELGATSLDM VQLSGQMARH YPQVSVVSLY NHATVRQLAT FCQPPEGESN APSPQPAVQT  3180
NTRANQIAKR ALQIAKNTAR SHTSLH                                       3206

SEQ ID NO: 1086        moltype = AA  length = 866
FEATURE                Location/Qualifiers
source                 1..866
                       mol_type = protein
                       organism = Escherichia coli
SEQUENCE: 1086
MEYASEMNGM EIAIIGMAVR FPQSRTLHEF WHNIVQGKEC VTFFSEEELL AEGVEQSTLD  60
NPAYVRAKPY IEGICDFDAA FFGYSHKEAQ TLDPKSRVLH EVAYHALEDA GYAQRTSDLI  120
TGVFVGASED VDWLRRSLSQ IGGDALNRFE SGIYGHKDLL AHLIAYSLNL NGPVYSLYTS  180
CSTSLSATHI ACRSLLFGEC DLALAGGITI DLPQKSGYFC QQGMIHSTDG HCRPFDSQAS  240
GTLFGDGAGV VVLRRLEDAL AAGDRIYAVI RGSAVNNDGK QKIGFVAPGH EGQKAVICAA  300
CHLAEVSPES IGYVETHGTG TRIGDPIEFA ALTEAFDTSH RQYCALGAVK ANIGHTHAAA  360
GVAGLIKTAL VLHHRTIPPL ANYQMPNSKL DLAHSPFYIP IQPQEWPASR MPPRAGVSSF  420
GIGGTNVHMI LEGLNPAVRD DHDQVRAPVF IPLSAPSFEQ LDELTQQLTP LLATLDASTL  480
AYTQQVARPV FDCRRVIQVE NDGTQAMLAS LDNLMPDAPW GLHCPDLRTT NDCTYAQWLA  540
HSAHYQREAT ALTALLDGMN IPPAYCHAET WAAQANSSLL IRGCQTIAAL KTWMNLLPTL  600
TLLSGAGTGL LPAAAASGMI ATQDVLHLLW EMEQKALHLW LPERHEPIPG YVLAWQGNPI  660
TDAQRNDRGF WSEALLADTR ELGEGVHSIN WVRLPPEIRE DVDVLRYVAQ LWCAGINVDW  720
AVWYGTPLPQ RGSASAYPFA HNHYPLPGRV MGSVETQPEA GPETHHPYQA RPVLSVPFVA  780
AHSRGMQYIT GLMELLLEIS PVGVDDDFFE LGGHSLLVTQ LTSRLERDFN VHIDLLTLME  840
NPNPRNIYAH IAAQLGGEDN LEIACQ                                       866

SEQ ID NO: 1087        moltype = AA  length = 289
FEATURE                Location/Qualifiers
source                 1..289
                       mol_type = protein
                       organism = Escherichia coli
SEQUENCE: 1087
MMNVAVIGAG VMGTGVAHNM AQYGISTNVV DISQSQLDKC RQMIEANLRL YNFHPQHKKK  60
THSTAEIMEN IRFTTELDDI VECDLVIENI TEDIEKKNAL YTRMNTICGA STVFGVNTSA  120
ISITALSKLM RHPENVVGVH FMNPVPLMHT VELIRGVHTA ERTLNIFHHL FAQLNKTGIV  180
VNDSPGFVTN RAMMIFVNEA IFMVQEQIAR AEDIDTLFKT CFGHKMGPLQ TADLIGLDTI  240
LQSLQVLYES FNDDKYRPSF LLKKMVDAGY LGVKSGQGFY RYQQTYAEQ             289

SEQ ID NO: 1088        moltype = AA  length = 82
FEATURE                Location/Qualifiers
source                 1..82
                       mol_type = protein
                       organism = Escherichia coli
SEQUENCE: 1088
MKKQDMKAAI REFLSRSLRG HTLNDDDDIF SLGLVHSLFT VQIILFIEKN FQVELEVSEL  60
KTEQIATVNK IVELIQRQTG LE                                           82

SEQ ID NO: 1089        moltype = AA  length = 376
FEATURE                Location/Qualifiers
source                 1..376
                       mol_type = protein
                       organism = Escherichia coli
SEQUENCE: 1089
MCTENYELAQ QEAVLFAKQH LALAAQNIER QQFIVPDIIS CVAQAGYLGA SIPQKYGGRG  60
YDSYQLCALH EVMAGVHGSL ENLITVTGMV STLLQRVGSA AQKAHYLPKL ATGELIGAIA  120
LTEPNIGSDL VNVETELQQD GDGWRLNGKK KWITLGQIAD FFIVLIHCGN QLATVLIDRN  180
TDGFTITPLN DMLGLRGNML AELHFNDCRL KEDALLGPLT PGVPLAVNFA LNEGRFTTAC  240
GSLGLCRAAV DVAARYIRQR KQFKRRLFSH GIVQHLFATM LTQTRSAQLM CFSAAEYRET  300
LHPAMINQIL MAKYVASKAA VDVAGKAVQL LGANGCHADY AVERYYRDAK IMEIIEGTSQ  360
IHEIQIAMNY MMGSEA                                                  376

SEQ ID NO: 1090        moltype = AA  length = 422
FEATURE                Location/Qualifiers
source                 1..422
                       mol_type = protein
                       organism = Escherichia coli
SEQUENCE: 1090
MTKDVALMFP GSGSQYVGMA RWLYERYPQV RTLFDEASQI TERDMAALCL SGTLVQLAEP  60
```

```
TAMALAIYTT SVAHFVAWQQ FLAQTGVHVN LRYMLGHSLG EYAALTCSGA LSFSQALALV  120
AMRSRLASEI AREMDASTTI IKQGNQALVA AACEVAERET RQQVGIACFN SPQQFMLSGQ  180
NSAIIAAEQY LLDHDRQVEV VPLIGGVPYH SPLLKPCGQQ LRKALDRCEW RRPCCPVISN  240
VNAQPYPDTV TPVQWLEQQL SQPVQWQRSL TYLTGHLSPI AIEIGPQSVL KNLLLENRYP  300
APVYAFDNRH DRAQLALVLG DNMAVKTDPE AVRRQRITLL TNALTATRHH RAADVAASAQ  360
LKELLSRFFE RIQQIEQRGT SSEEDIAFLH ELLEQGFQLK GSSQAEIDAC HARLASDNGG  420
QA                                                                 422

SEQ ID NO: 1091        moltype = AA  length = 2310
FEATURE                Location/Qualifiers
source                 1..2310
                       mol_type = protein
                       organism = Escherichia coli
SEQUENCE: 1091
MEQQGIMRQL PTDDQTIVDY LYRIAGEYGE KAAVLMGDAA LSYHDLNARS NQLAHYLRGL  60
GIGEDRVVAI RLPRGMAMLI AIFAIVKAGG AYLPLAYNAP RSRIENILSN SGAVCLIGTD  120
DGDRWPIPRV EIDSAAVSAM PTTDLRYRPH ARQLAYIIYT SGSTGVPKGV ATEHAALLNR  180
IVWMQNAYPI SSQDVLFQKT VYTFDVSVWE MFWWAMYGAS VVLLPSGLES DPRTLARLIQ  240
RHRVSVVHFV PSMLNLFVEY LEMKQDPRLT ASLRLVFSSG EKLTVHSVAR FYQSVAQGDL  300
INLYGPTEAA IDVSHHRCLR GYDYDDIPIG QAIDGCRLYV LDDHGNPVAD GEEGELYLAG  360
IGLARGYLNN VALTDRCFTI HPTLRHLGKP ERLYKTGDLV WRDGESQQIH YIGRNDFQIK  420
IRGLRVELGE IEAHAMRFPG VQQAVVVADQ DDPDNQLIYA FVVSSVPLNL AALMDALSKN  480
LPAYMLPNRL LAMSELPLSD NGKCCRKTLL DLARAYSASR VDLRETPAVR YLPLSSAQSS  540
MWFMQQLAPH TALYNNPTAL LLEGELDRTR MDGAIRQLMS RHTLLRAMAE THNGQPVLAV  600
PQCVSSQALL TIVPLPSVSD DNALQAMINQ RAAHPMPLTS GTPLCRFELL TLDDDRSVLL  660
IHLHHIISDG WSKGVLLREL QAAYNGESLT PEPLLEYADY MEYQEEWRQS DAYQDAMRYW  720
QNTLAGTLPI LDIPTDQPRQ KVARYQGAFV AFALSANTCE RVLAAARAQR VSLYNYLLTA  780
FVLLLHRNAR QQEYIVGMPI AARLTKEQEH MIAPLVNVLP LRLPLDEAAS FSELVQTIRG  840
ILFAAFRHQR LEFTDIVRAV NVDRSAGTPC ALLPDMQAYL LFTSGSTGEP KGVCVVHRGL  900
LNLLLDMQRT FAVGSQDRLL SVTTPTFDIS FLEYLLPLIS GASLYLTEAE RAADSFRMIP  960
LIADYRPTLM QATPSFWHGL LMAGWRGDPE LCVLAGGEAL PTKVAEELLR CCGSLWNLYG  1020
PTETTIWSLK SQITQAENIT LGAPIANTRI YILDNEGHPV PQGVDGELYI AGDGVAQGYD  1080
GQPELNAQFF LSEPGVPGGR MFRTGDLVRS DAQGQLFFVG RKDSQIKLRG YRIELGEIER  1140
TLARHPHVDA AVVACIERAP LHKALAAFII TSEPPSLFEQ LKNELRQQLP DYMVPTLWQR  1200
VADFPNTDNG KIDRKRLAEN FVADSSLVSP QTQALSDTEQ MLLALWMRYL PIKNVDPECD  1260
FFRLGGHSLL AVTLVAEINR TFHCALTLKD IFHYSTLRAL SARIAQQSIT DAAASQDDWV  1320
IVHDPEHRHQ PFPLTDVQRA YWLGRQTGAT SIATHIYHEF DVEHFNVTRF THAVNALIAR  1380
HEMLRARVLP DGTQQILAQV PAYQLEQRDL SALSPNARND ALMAIRDRLS HHVHPADRWP  1440
LFDFSYSACT AQHGRLHFSL DLLIADALSM RTLQQELMML YREPHVSLPL LPFSFRDYVQ  1500
ALLVEQASEA YARDQAYWQR ALPQLYGPPT LPVQGDLAQL SAIRFVRRRH RLSAHNWGVL  1560
SALAQRTRIT KTALLLTVFH FPIYQCMFQL DNMPLASPTL NGVNVTPLLL DTSASQVDIS  1620
LSMQHIDGRI TGTFEYDAGL YSADRIQHLV AQWRELLDEA SSQPTQLVRD LIRFTPREHA  1680
WLARHNATEV ALPPVDNLLA LVLPHCQQRP TQVALRHADD AMTYGELQQA TMQMCTWLRA  1740
QGVKRGESVA LQLPFCFELI IAQLAILSLG ASYVPLDGNA PAARNALILA QATPCMLLVA  1800
QPLESPHGLT IPWVLVPDWR SLLTEIPNLP VSVAPDALDC DAVVIFTSGT TGQPKGVRLS  1860
QRNLVNLTAS FISSYQVTHQ DVLLPITSVA SASFVGEVLP LLAAGGTLVL AQKAQSLDSD  1920
ALIALLASQR VTILSTTPSL SASLSVLAQS MGSLRLFLCG GEALEYEQIA PLLPHMAVVN  1980
GYGLTESGIC STYFPVAKRR EQETGALPIG RPIQNTQAYV VDAYNRLVPP GACGELCFSG  2040
LGISPGYLDA RQDPERFVEL PEYPGVRVLK TGDRARWATD GMLFYLGRQD RQVQIRGYRV  2100
ELGDIESLLK QHPDIADAWV DVRRNAAATP LLVAFYCSVN GVALDAQQLR VWLSLRLPLH  2160
MLPLLYVPLS AMPLGVNGKI DPQCLPLVDL RQLEGPGEYV PPATELEQRL AEIWQQLLGL  2220
ERVGTTTNFF DLGGHSLLLV QMQQYIGQQC GQHVALVDLL RFTTIKRLAE FLLAPDAAQG  2280
TTGDQTQLRA AKQRLAFGHT RWAATTDSHH                                   2310

SEQ ID NO: 1092        moltype = AA  length = 1010
FEATURE                Location/Qualifiers
source                 1..1010
                       mol_type = protein
                       organism = Escherichia coli
SEQUENCE: 1092
MAENDFGIAI IGMAGRFPQA DTVQAFWENL LASRECISFY SDEELLAMGI SPEFVQHPDY  60
VKAKGEVADI DKFDAAFFGI APREAELMDP QHRVLLETAW AAFEDAGYVA ADYPGDVGIF  120
AGKSMDSYLM LNLMPHFKRV FSSGSLQAAI GNDKDSITTT IAYHLNLRGP AITVQTSSST  180
SLVAVCVACQ SLLTWQCDMA IAGGVTLGPP AKTGYLSQEG GITAADGHCR AFSDNSSGFV  240
PGTGAGLVVL KRVDEALRDG DNIYAVIKGF AVNNDGSEKI SYTAPSVDAQ ARAIAQAQRL  300
AGLTPQDITY VEAHGTGTRL GDPVEFSALS QAFAGASQKQ YCALGSVKTN IGHLDTAAGV  360
AGLIKTALAV QQGIIPATLH FERPNAQIDL TNSPFYINTT CQPWQPESGI RRAGVTSLGM  420
GGTNAHVVLE QAPAVDLQAR APVPAYSILP FSAKTDSALS SGLARFADFL QHESLPDRRD  480
LAWTLSQGRK AFAHRAALVT RDLHAAGTLL QQAATAPFAR GVAQTQLGLG LLFSGQGSQY  540
QRMGHQLYQV WPAYADAFDR CATLLEREYQ LDIRHELFRA EVSLAQGERL AQTCLTQPLL  600
FSVEYALAQL WLSWGITPTV MIGHSLGEWV AATLAGVFSL EDALRLVARR AELMHQAPSG  660
AMLMVALPEA QIRALITAPL AIAAVNAPDY SVIAGPTSEI LAVSQRLTEQ NIINKRLHTS  720
HAFHSSMMQD AAQALRQAFE NVRLNPPTLT IISTVTGAHV SADTLTTPDY WIEQMLMPVQ  780
FSAALQEAQA TFDVDFLEIG PGATLTQLTN GHALGDRLAF SSLPAGARSS DEHKHILDTV  840
AALWVRGHNI DLSAFAGEQP RRVSLPTYAF DKIRYWVDSP EEQRSAVTPV ADAGSVIPSE  900
PSVRRQPRPA FSVPYAAPES KTQRGLVAIC EALLGIDGLG IDDNFFEAGG HSLMLGMLLA  960
QVQERFAVTL SFFDVMEDAS VRALAQLVEQ EQQDDGGSAL AVLVNDMINE             1010

SEQ ID NO: 1093        moltype = AA  length = 1454
```

```
FEATURE                Location/Qualifiers
source                 1..1454
                       mol_type = protein
                       organism = Escherichia coli
SEQUENCE: 1093
MTIHHAALAR MLPAEKKEKL LRQLAQSGVS PSRIPIIKAD PAQAIPLSFN QERLWFLQKY  60
DSTATNYNLY VVYRLHGVVD MPMLTEALRH VQARHAILRT RIIVRNDRPC QVIDDASSLV  120
LDTVTLAAQA PTSALDAVIQ QVINTRFDLA RGPLWGVTQI IQPDQGCHLV FCAHHIIIDG  180
ISLRLLFDEL QQQYARLHAG NETSLPPPPL QYADYAFWQR EWFQDTLLAN ELAYWRARLQ  240
DAPLLSTFPS LHPRPAQPST HGSRFSITLD ETLSLALKHV ARTQETTPFV LMLTAFQLVL  300
MRYAQQQRLV IGMPVSGRIR PELQSSIGYY ASTAVIYTDF NGVEVGREAL QRVKASVKET  360
QGRQQLPFEN LVNMLDLPRS LSHSPLFQIL YIYHNHVTPR AFTLAGAYWE QVTYHNQTVK  420
YDMTVEVFQN DATFDVSFEY DLGLYDADVV KQIAEALRQH CLSLTSSLET PIGAIPLHAP  480
ETATPRRDPL NATNVPWLGP QDVLRIIEQR CVQHPKQLAI QQHDGTLTYA ELWARVQFIA  540
MRFRAHGIQP GDRIGVLLPR HRDVIATMLA TWFVGACYVP FDIHQPAARL QRLMQRARLV  600
CLVVRQPGEW GEIVQLSLPE LMQDMSNAIR YSSQVLARWS LSPTFTLNLT LFNRPQGYPN  660
AEAVIGDFTA VSLLNVCYDS QHSYAHNAQR IQVQLWEDLE HRRFSGIRAS EALIHSGRFH  720
APMPVVFTSM LDIDGETTAQ DPRDTTRFTL CPDANITQTP QVWLDHQVIE LAGELHFNWD  780
AVEQLFDTTL LDQMFGAYCH ALQALVAMPQ SWWGVNSSLA LPTVSAPVTQ APAPTALLHH  840
GLLRQAALTP QETALISPIR ELTYRQLSTA ADHVARALLA LGVQHGDRVA VVMEKGWQQI  900
AAVHGILRLG AVYLPVDPVL PPQRRQLLLT VGEVRVQVTQ PGLTQLEPSL PVLIIDDGML  960
DTPAAPLPEV AGDVTDLAYI IFTSGSTGTP KGVMIDHRAA MNTLEDINER FGLNAQDRVF  1020
GLSSLSFDLS VYDAFAPFMV GAALVLPEAG REKDPRHWQT VMAHGHVSVW NAVPALMQML  1080
CEYHSGDRMS YPTLRLALLS GDWIPLTLPE QMRERLNETM DIISLGGATE CAIWSVYYPI  1140
GEVESTWTSI PYGRGLRNQP VYVLNAQLEE CPVGVEGEIC IGGMGLAQGY LNDAEKTAAS  1200
FVWREASGER IYRTGDRGRY FADGQVAFLG RNDTQVKVNG YRIELGEVKS HLEQLDSVGS  1260
AAVVCHQGQL YAFITAAENL HPDDTDALLA RVRAQLAVQL PYYLLPQHFF LLKVLPMTGN  1320
GKIDQAAMVQ EVIQRMSQST SQKSRALAHA SPYEQQVAAL WCEVLQREQI GLNDNFFEAG  1380
GGSIQIVLLH RRIEEIFKVT VPIAELFRLT TVKRIAGYLQ AMQDNARAVN QTQQRDASRS  1440
RAQQRLVRRH QRQR                                                   1454

SEQ ID NO: 1094        moltype = AA  length = 2154
FEATURE                Location/Qualifiers
source                 1..2154
                       mol_type = protein
                       organism = Escherichia coli
SEQUENCE: 1094
MTYSESDIAI VGMNCRYPGV HSVAAFETVL RTGCNILDPK VTPSNGHNHI TLNNVYEHMA  60
EFDANFFGYS RAEAEIMDPQ QRVFLTCAWE MFEQSGYNPK QHDARVGLYA GVSTSFYLLT  120
HLMNNPDKLA QLGGLQIMVG NDKDHLTSQL AYRLNITGPC VTVQASCATS LVAVHLACEG  180
LLSGQCDMAL AGGVTFRMEE QRSYESHGDG LQAEDGLIHT FDAQASGTVY SSGLGMVLLK  240
RATDAQVQGD NILAVIKGSA INNDGGARSG YTVPGVDGQE AVMIEAHSLA EVTPQQIQYL  300
ELHGSGTPLG DAIEFAAIKR VFGTPAPNAT PWRLGAVKPN VGHVEMASGI TSLIKTVLSL  360
TNRVFYPTLN FQRANPQLGL EDSPFEVVSR LTPWPEGTTP RTAGVSAFGL GGTNAHLVVQ  420
APLSTPQARA QQMGPCVVVL SAKNHNALEQ MQNALLAKLA AHPEIRLQDV AYTLRHGRFS  480
APVRKCVIAE NCTQLARQLR DAPMVEATTG CTIYWRLGHR FVVALETLSD WLACSEVLSQ  540
AVGQLLEHFP LEPACLQDLS PAQRTFISQY ALIALIDERE TLNVVLCGDG DGGYAAAVLR  600
GDCTLEQAWH RLNAGQPFDD VPTNPLLQPD VCSLMLDDAA SDANRTALEA LGQLWLAGVS  660
LDWRWVDAAE RMLGSQRIAL PGTVFTPQRY WVEAVRPATF SHESSNNLLS RATKSDIIAV  720
VTEIWERTLG VSIDDHHASF FELGGHSLLA STILYDIQQR YGITCTLSAF FADPTIEGLS  780
CYLLEQGGSE TAVSALPDTV FAPDQQHLPF PLTDVQQAYW VGRRKSLGLG NISTHIYVEY  840
ELQGLDETAF NRALNAVIAR HSMLRAIVND DGMQQILPNV PEYHVAFYTT QCEDAFQQRC  900
RELRDTLSHQ MIDCSRWPLF QMEVVVDPQQ KARLHVSIDL LIADAWSLEL FIRELAYHYR  960
HPQAALPTLT YSFRDYVLTL KSYEKTPQFE RARDYWRARI ETLPPGPRLP LRTDPTKLEN  1020
PTFVRRSYCL SRAIWQRLKT QAGQMSITPT TLLLTGFAQV LARFSSSPHF SLNLTLFNRL  1080
PLHADINHLI GDFTALTLLE IDMSQGETLQ ARANVIHSQL WRDLDNRLFG GIQVSRLLVQ  1140
THRDPAKSVI PIVFTSLLNQ YEASWETDDT LFNQPQDDLY SISQTPQVWL DHQVMERNGE  1200
LHFNWDVVEQ LFEPALMDQM FQCYCQLLHA LAQRPQLWHE TQDVLALPTV SAPVTQAPAP  1260
TALLHHGLLR QAALTPQETA LISPIRELTY RQLSTAADHV ARALLALGVQ HGDRVAVVME  1320
KGWQQIAAVH GILRLGAVYL PVDPVLPPQR RQLLLTVGEV RVQVTQPGLT QLEPSLPVLI  1380
IDDGMLDTPA APLPEVAGDV TDLAYIIFTS GSTGTPKGVM IDHRAAMNTL EDINERFGLN  1440
AQDRVFGLSS LSFDLSVYDA FAPFMVGAAL VLPEAGREKD PRHWQTVMAH GHVSVWNAVP  1500
ALMQMLCEYH SGDRMSYPTL RLALLSGDWI PLTLPEQMRE RLNETMDIIS LGGATECAIW  1560
SVYYPIGEVE STWTSIPYGR GLRNQPVYVL NAQLEECPVG VEGEICIGGM GLAQGYLNDA  1620
EKTAASFVWR EASGERIYRT GDRGRYFADG QVAFLGRNDT QVKVNGYRIE LGEIERCIAR  1680
HPDVEQSVVV AVGNSQHRRL VAFAKLHDRH QAQALQAKEA EAAALAQGII VNPAQRLAFK  1740
LKEPHIRALD GLGIALTAPA DSTRYIKRRS YRHFSAQKTT LAQLGQLLSG LGQMRLPGLP  1800
FAKYAYASAG GLYPVQTYVY LHPDKIEEGV SGIYYFDPRQ SCLMPVAPEV ELNSGFHAGP  1860
NQSIADRAAF TLFMVADMAV ISPFYGQEAA WHFSVMEAGT LCHLLEEDAP RYGLGLCQLG  1920
MADFSAVASH FQLSPHHRYV HCTVGGAIGQ EAASAAALLR DFSTYEKPKE TAAPLDMQSY  1980
KDAMLRGLRQ QLPDYMVPSD LMLATDFPLT ANGKLDRQKL QLQGEQIAHQ RDGVGPIQVD  2040
SALQQRLVAL WQEVLGVSHV SAEDDFFSLG GSSIELVRIQ QALEAIIGQE IPIVDLFRLP  2100
TIADVARYLD EQLHNLPAAH DIVLAQAEVS QVSAARENLA LRRKRAQQGE KGDE        2154

SEQ ID NO: 1095        moltype = AA  length = 487
FEATURE                Location/Qualifiers
source                 1..487
                       mol_type = protein
                       organism = Escherichia coli
```

```
SEQUENCE: 1095
MSEQSYRSAG TLLAQLASGE TTSVALVNHY FSRMAQFNKP LNAVVQQHYA LALEAAARAD  60
RERLEGRARG VLHGLPCTVK ESFDVQGWLT TSGAHYLKDN RATQDAPSIA RLRAAGAILM  120
GKTNVPMMTA DWQTYNDLYG TTHNLWDRQR SPGGSSGGAA VAVAADFTPV EFGSDLFGSL  180
RIPAHYTGVY AHRCSLGLMS VRGHVPGGGP QATDEPDLST AGPMARSAAD LRLMMRALST  240
FWVEPPRIPD FSRYQAKANY RVCTWFSAPH HEIDQQIAQR FQSFIDKLRA QPGVEVDDAM  300
PADIDPDALF DIAVKLSGRL VSTALNGRQR LTAGLAALGF RLVGKLADVP EGITSYYQGM  360
LKDSGEQRNT DKLRHEYSRV IETLFARYDV LLTPVSPVLA FAHMQQPVRK RKLIVNGEPQ  420
DYNEHLFWNM LATVFGLPAT VYPLAKTMDE LPCGIQIISG HFHDDVTINF AEFCESISGG  480
FTVPEGY                                                            487

SEQ ID NO: 1096         moltype = AA  length = 479
FEATURE                 Location/Qualifiers
source                  1..479
                        mol_type = protein
                        organism = Escherichia coli
SEQUENCE: 1096
MTVNKLEPDN GTPNDELFTV AGMFDGSLYK LLLRMALPMF VGMLTQVTYA IADIFWLSHI  60
DVTNSGIIAG VGLVFPVGMG LFAIANGIQI GMGSLLSRAI GMQRLDRAQR ILSVGIIIAL  120
FFAIVITVLG YVYAQPLLRS LGATKSIIGY ATEFYYYSLL TVFSIMLIGV MMGLFQGAGK  180
IMVIMKASLL GALVNIMLDP IMIFVFDFGV KGVALASFLA QLSMVAYFIY TLMGLHIGLS  240
IRIALRPFSW KIYREFLSVG MAQMLMQLII AVGIVIYNFF IVRLDVNAMA AFTLTGRIDY  300
FIITPMLAIA TALLTVVGQN WGHGNVTRTL NAYWAAVALA FSIVLVLAVM HIVLAPWMYP  360
LFTRVVAVSD YAVLQTRIMA LALPFVAISL LASEYYQAIG KPWYSVLLTL MRHVFISVPV  420
VYLLAIVLEM RITGVYFGAM SGTFVAALLA WRLLRLSPRL LRWNQEAVRS QHLDMEVAP   479

SEQ ID NO: 1097         moltype = AA  length = 1455
FEATURE                 Location/Qualifiers
source                  1..1455
                        mol_type = protein
                        organism = Escherichia coli
SEQUENCE: 1097
MMSGNPLSWP QEQCHIIDQL YPYSAVNIIG GVVTIEGIVD LPRLHAAIQS AIRQFDALRM  60
WFVMGEESEV VSQVQPYHWR DIRHLTFSPD YDKENLRPAA IETFVDEWFR QPFTLLAHDL  120
FEFVTFTCGE QYSGYLFKAH HGIADGWSMA LLSNHVKRAY EQQDVPDDAS PAYSAFLAQQ  180
QSYQASTRFA VDRGWWRDYI DEYRDCFPDS SPIVTTEGIS CSTWLEPAMI NRLYRLCNRY  240
GCTLNTLFIA LFALYRARVW GEEKGVIGVP LANRHTREAR RCFGMFTNQL PLAYRLVRTE  300
RFCERVAFFQ RELKRGFKHS KYPITLFNQD LAEQGGGKLR AFDYCVNYYN FTYERHIAGA  360
AQRVESYYSG EQSYKLQIVL QTVNNHKESL RLSLEALRSA FTPHQLTAMK NGLLDLVTAL  420
DRQPDARLGD LEVYPAPHVA LACGSLKPSF TSRFAAQVVE HGDRTALIDN EQSLTYRQLD  480
DAVERVARYL RQQGIGRGQV VGIIAEHSAQ TVMVIYGILR CGAAFLPLNP ALPTTRLYAM  540
CRKAQVAHIL YDPAMHELTQ ALAFPASSLL QALATSALAR EPWPAIEPQD LAYVLFTSGS  600
TGEPKGVQVS HGNLANYLHF AAERYFTAQD RAALYSSLSF DLTITTLFAP LCVGASISVC  660
RHAESETLLR MAVVDQPNTV IKLTPAHLRL LCAAGISSEQ IRTLVVGGED FKRDLARKAA  720
ALFPQAVIYN EYGPTEATVG CMIYRYTGQE TLPSLPIGMA IDGCQVAICS PWGCPVPEGE  780
TGELVIYGAS VTQGYIDAPQ QTAAAYLKDT NGVMIGYRSG DIGYAIAPNT LVYQGRKDDQ  840
VKINGYRIEL CEIEQALLSA PQVESAAVAV IDDVQGQHSG LLACVTPSSV DVATVMQHLR  900
QQLPTYMQPK QCCAIAQLPL SHNGKVDVRQ MVATVRNTAP ASGSERLGDA AIRHSVRVCV  960
EGALEQTEFD DNENLYVLGL DSIKSIQIAA QLRHHGWTMS AVQVMECGTV NAICEFLASH  1020
TTVSQLAQYA HNTRIDLPAL RWFTQLALPV PNVYNHVIVL KVLPGCPLEQ LHNRLHTLIQ  1080
QQPALHSALD AEGRLLVCDP NVCYPNEVLT EYSTAQWTLA EVIAQCNSML DVTNGRVFTA  1140
ALLHAPQPAS STLVLCAHHL CVDMHSWYLI LSTLDAVSTV NGTSNSGLHR WNDYLASKTV  1200
DSATHESWRT VCQTLPLHFP PVSLPDDSLP RTRAWREDFR HPCVRRLFES SGNTAYSAET  1260
YVLTALALVL RYYSEEPWCR IEMEGMGRGC WPDEPDVADT VGWFTLFYPW AIPLHGDMAT  1320
LLSAIASDLA KRTHGGGDYG LLQMRHAPED SLAQGIRMNY IGVQAQPSLR YFHIDHFNSD  1380
IYTAPENALG CVLEFNIARS AADGLSFHCR FDPTRIALND VQLLLARYKN SLTDLDAWLC  1440
QHSATLTGAP TLWTL                                                   1455

SEQ ID NO: 1098         moltype = AA  length = 819
FEATURE                 Location/Qualifiers
source                  1..819
                        mol_type = protein
                        organism = Escherichia coli
SEQUENCE: 1098
MAKDDFTCGS LDIAIIGMSG RFSGAESVPE WWDKLLAGEE FTQPTCTEDD NGNPWIRLRN  60
IITAPYDFDA AFFNIPPGEA LLMDPQQRIF LECCYNALEH AGYIPTQLKR VGVYGATYAN  120
NYFIDRVYPY LKMSGDHHYL QAQIGNEKDY LCAQVAYKLG FTGPAVSVQT ACSSSLVAAY  180
LACEGLLTFQ ADVALAGGVT LGFLQAHGYS PQGDKLVSQD GHCAPFSAEA TGTVYSSGAG  240
VVVLKRLEDA LRDQDRVYAV IKGGAVNNDG GRRLGFVAPS VEGQVEAINT ALAAAEVVPT  300
DIALIETHGT GTPLGDEIEL EALHRVFAPA CAPHSIQLGA VKANLGHLGV ASGIVSLMKT  360
ALTLYTGLVP PQINLVNKHK KLLQPASPFY LSDVVTSVPQ TKRIHATVSS FGLGGTNAHL  420
VLQNWCETPA QAVQENERRL FFFSAKTPLA LRQQLDAHYH ALATYAEADK DRIAYTLAQR  480
RAHFPYRCAL AADSVVALRA SLAKLRDADM SFTPINMETT LVFLYPDRDD KLESALTHLL  540
ACQPNLRQRH QRLSQDVAQI CEPADWTPAL RQFIQQVSLS EWLIEQSISP VQHIGYLTGA  600
AAAQYVARII SLENAVQQVI VAETTPEQTL AGNSELSEIL ANLAVTEGTL MLEIGRAGTF  660
SILYHQHAQW VGQTVFSPML NTDTPEDILP LLGTLWQRGV TICLPEMPAV QTIGLPGYSF  720
DRVRYEIQSS DARENAMLPV SYLSVSDFVE KTWRSLLCID HYDEHAVIFE YGATSMHVIS  780
FVDSCNHIYK IGLTAADIYA RPAIREHSEF ISECVDGIL                         819
```

-continued

```
SEQ ID NO: 1099        moltype = AA  length = 504
FEATURE                Location/Qualifiers
source                 1..504
                       mol_type = protein
                       organism = Escherichia coli
SEQUENCE: 1099
MTIMEHVSIK TLYHLLCCML LFISAMCALA QEHEPIGAQD ERLSTLIHQR MQEAKVPALS  60
VSVTIKGVRQ RFVYGVADVA SQKANTLDTV YELGSMSKAF TGLVVQILIQ EGRLRQGDDI  120
ITYLPEMRLN YQGKPASLTV ADFLYHTSGL PFSTLARLEN PMPGSAVAQQ LRNENLLFAP  180
GAKFSYASAN YDVLGAVIEN VTGKTFTEVI AERLTQPLGM SATVAVKGDE IIVNKASGYK  240
LGFGKPVLFH APLARNHVPA AYIHSTLPDM EIWIDAWLHR KALPATLREA MSNSWRGNSD  300
VPLAADNRIL YASGWFIDQN QGPYISHGGQ NPNFSSCIAL RPDQQIGIVA LANMNSNLIL  360
QLCADIDNYL RIGKYADGAG DAITATDTLF VYLTLLLCFW GAVVVVRGAF RVYRATAHGP  420
GKQQRLRLRV RDYIIALAVP GLVAAMLYVA PGILSPGLDW RFILVWGPSS VLAIPFGIIL  480
LAFVLTLNHQ IKRILLHNKE WDDE                                         504

SEQ ID NO: 1100        moltype = AA  length = 240
FEATURE                Location/Qualifiers
source                 1..240
                       mol_type = protein
                       organism = Escherichia coli
SEQUENCE: 1100
MSNISLYCLP YSGGSAAMYY KWRSVLSDNI TLRPLEPAGR GTRIRQPLCL TMVDAVADLY  60
QQFVKHYTGG DYAIFGHSLG GIMAFELVHY ILDHGHDMPC ALFFSGCRPP DRASHEVILH  120
TLPDQAFMEE IVKLGGTPVD VFRNKELMTI FTPIIKNDYR LYEQYVFQAK ARTLTCPIVL  180
FHGDADNLVM QDELLAWEKF TTRKTRTIIF PAADHFFVDK HFEQVVGYVN QTIESLEIVG  240

SEQ ID NO: 1101        moltype = AA  length = 70
FEATURE                Location/Qualifiers
source                 1..70
                       mol_type = protein
                       organism = Escherichia coli
SEQUENCE: 1101
MDKFKEKNPL SLRERQVLRM LAQGDEYSQI SHNLNISINT VKFHVKNIKH KIQARNTNHA  60
IHIANRNEII                                                        70

SEQ ID NO: 1102        moltype = AA  length = 170
FEATURE                Location/Qualifiers
source                 1..170
                       mol_type = protein
                       organism = Escherichia coli
SEQUENCE: 1102
MAVPSSKEEL IKAINSNFSL LNKKLESITP QLAFEPLLEG HAKGTTISVA NLVSYLIGWG  60
ELVLHWHDQE AKGKTIIFPE EGFKWNELGR LAQKFYRDYE DITEYEVLLA RLKENKQQLV  120
ALIERFSNDE LYGKPWYNKW TRGRMIQFNT ASPYKNASGR LNKLQKCLAE             170

SEQ ID NO: 1103        moltype =   length =
SEQUENCE: 1103
000

SEQ ID NO: 1104        moltype =   length =
SEQUENCE: 1104
000

SEQ ID NO: 1105        moltype = DNA  length = 1083
FEATURE                Location/Qualifiers
source                 1..1083
                       mol_type = other DNA
                       organism = synthetic construct
SEQUENCE: 1105
tcactgcccg ctttccagtc gggaaacctg tcgtgccagc tgcattaatg aatcggccaa  60
cgcgcgggga gaggcggttt gcgtattggg cgccagggtg gtttttcttt tcaccagtga  120
gactggcaac agctgattgc ccttcaccgc ctggccctga gagagttgca gcaagcggtc  180
cacgctggtt tgccccagca ggcgaaaatc ctgtttgatg gtggttaacg gcgggatata  240
acatgagcta tcttcggtat cgtcgtatcc cactaccgag atatccgcac caacgcgcag  300
cccggactcg gtaatggcgc gcattgcgcc cagcgccatc tgatcgttgg caaccagcat  360
cgcagtggga acgatgccct cattcagcat ttgcatggtt tgttgaaaac cggacatggc  420
actccagtcg ccttcccgtt ccgctatcgg ctgaatttga ttgcgagtga gatatttatg  480
ccagccagcc agacgcagac gcgccgagac agaacttaat gggcccgcta acagcgcgat  540
ttgctggtga cccaatgcga ccagatgctc cacgcccagt cgcgtaccgt cctcatggga  600
gaaaataata ctgttgatgg gtgtctggtc agagacatca agaaataacg ccggaacatt  660
agtgcaggca gcttccacag caatggcatc ctggtcatcc agcggatagt taatgatcag  720
cccactgacg cgttgcgcga gaagattgtg caccgccgct ttacaggctt cgacgccgct  780
tcgttctacc atcgacacca ccacgctggc acccagttga tcggcgcgag atttaatcgc  840
cgcgacaatt tgcgacggcg cgtgcagggc cagactggag gtggcaacgc caatcagcaa  900
cgactgtttg cccgccagtt gttgtgccac gcggttggga atgtaattca gctccgccat  960
cgccgcttcc actttttccc gcgttttcgc agaaacgtgg ctggcctggt tcaccacgcg  1020
ggaaacggtc tgataagaga caccggcata ctctgcgaca tcgtataacg ttactggttt  1080
cat                                                               1083
```

```
SEQ ID NO: 1106        moltype = AA  length = 360
FEATURE                Location/Qualifiers
source                 1..360
                       mol_type = protein
                       organism = synthetic construct
SEQUENCE: 1106
MKPVTLYDVA EYAGVSYQTV SRVVNQASHV SAKTREKVEA AMAELNYIPN RVAQQLAGKQ  60
SLLIGVATSS LALHAPSQIV AAIKSRADQL GASVVVSMVE RSGVEACKAA VHNLLAQRVS  120
GLIINYPLDD QDAIAVEAAC TNVPALFLDV SDQTPINSII FSHEDGTRLG VEHLVALGHQ  180
QIALLAGPLS SVSARLRLAG WHKYLTRNQI QPIAEREGDW SAMSGFQQTM QMLNEGIVPT  240
AMLVANDQMA LGAMRAITES GLRVGADISV VGYDDTEDSS CYIPPLTTIK QDFRLLGQTS  300
VDRLLQLSQG QAVKGNQLLP VSLVKRKTTL APNTQTASPR ALADSLMQLA RQVSRLESGQ  360

SEQ ID NO: 1107        moltype = DNA  length = 20
FEATURE                Location/Qualifiers
source                 1..20
                       mol_type = other DNA
                       organism = synthetic construct
SEQUENCE: 1107
aattgtgagc gctcacaatt                                             20

SEQ ID NO: 1108        moltype = DNA  length = 60
FEATURE                Location/Qualifiers
source                 1..60
                       mol_type = other DNA
                       organism = synthetic construct
SEQUENCE: 1108
ttgacaatta atcatcggct cgtataatgt gtggaattgt gagcgctcac aattagctgt  60

SEQ ID NO: 1109        moltype = DNA  length = 72
FEATURE                Location/Qualifiers
source                 1..72
                       mol_type = other DNA
                       organism = synthetic construct
SEQUENCE: 1109
gaccagaggt aaggaggtaa caaccatgcg agtgttgaag aaacatctta atcatgctgc  60
ggagggtttc ta                                                     72

SEQ ID NO: 1110        moltype =   length =
SEQUENCE: 1110
000

SEQ ID NO: 1111        moltype = DNA  length = 17
FEATURE                Location/Qualifiers
source                 1..17
                       mol_type = other DNA
                       organism = synthetic construct
SEQUENCE: 1111
taacaccgtg cgtgttg                                                17

SEQ ID NO: 1112        moltype = DNA  length = 17
FEATURE                Location/Qualifiers
source                 1..17
                       mol_type = other DNA
                       organism = synthetic construct
SEQUENCE: 1112
tacctctggc ggtgata                                                17

SEQ ID NO: 1113        moltype = DNA  length = 48
FEATURE                Location/Qualifiers
source                 1..48
                       mol_type = other DNA
                       organism = synthetic construct
SEQUENCE: 1113
ccgggcgcta tcatgccata ccgcgaaagg ttttgcgcca ttcgatgg              48

SEQ ID NO: 1114        moltype = DNA  length = 1157
FEATURE                Location/Qualifiers
source                 1..1157
                       mol_type = other DNA
                       organism = synthetic construct
SEQUENCE: 1114
tcactgcccg ctttccagtc gggaaacctg tcgtgccagc tgcattaatg aatcggccaa  60
cgcgcgggga gaggcggttt gcgtattggg cgccagggtg gtttttcttt tcaccagtga  120
gactggcaac agctgattgc ccttcaccgc ctggccctga gagagttgca gcaagcggtc  180
cacgctggtt tgccccagca ggcgaaaatc ctgtttgatg gtggttaacg gcgggatata  240
acatgagcta tcttcggtat cgtcgtatcc cactaccgag atatccgcac caacgcgcag  300
cccggactcg gtaatggcgc gcattgcgcc cagcgccatc tgatcgttgg caaccagcat  360
```

```
cgcagtggga acgatgccct cattcagcat ttgcatggtt tgttgaaaac cggacatggc  420
actccagtcg ccttcccgtt ccgctatcgg ctgaatttga ttgcgagtga gatatttatg  480
ccagccagcc agacgcagac gcgccgagac agaacttaat gggcccgcta acagcgcgat  540
ttgctggtga cccaatgcga ccagatgctc cacgcccagt cgcgtaccgt cctcatggga  600
gaaaataata ctgttgatgg gtgtctggtc agagacatca agaaataacg ccggaacatt  660
agtgcaggca gcttccacag caatggcatc ctggtcatcc agcggatagt taatgatcag  720
cccactgacg cgttgcgcga gaagattgtg caccgccgct ttacaggctt cgacgccgct  780
tcgttctacc atcgacacca ccacgctggc acccagttga tcggcgcgag atttaatcgc  840
cgcgacaatt tgcgacggcg cgtgcagggc cagactggag gtggcaacgc caatcagcaa  900
cgactgtttg cccgccagtt gttgtgccac gcggttggga atgtaattca gctccgccat  960
cgccgcttcc actttttccc gcgttttcgc agaaacgtgg ctggcctggt tcaccacgcg  1020
ggaaacggtc tgataagaga caccggcata ctctgcgaca tcgtataacg ttactggttt  1080
catattcacc accctgaatt gactctcttc cgggcgctat catgccatac cgcgaaaggt  1140
tttgcgccat tcgatgg                                                 1157

SEQ ID NO: 1115        moltype = DNA  length = 29
FEATURE                Location/Qualifiers
source                 1..29
                       mol_type = other DNA
                       organism = synthetic construct
SEQUENCE: 1115
ttgacaatta atcatcggct cgtataatg                                    29

SEQ ID NO: 1116        moltype = DNA  length = 60
FEATURE                Location/Qualifiers
source                 1..60
                       mol_type = other DNA
                       organism = synthetic construct
SEQUENCE: 1116
cgcgccgctt cgtcaggcca catagctttc ttgttctgat cggaacgatc gttggctgtg  60

SEQ ID NO: 1117        moltype = DNA  length = 26
FEATURE                Location/Qualifiers
source                 1..26
                       mol_type = other DNA
                       organism = synthetic construct
SEQUENCE: 1117
attcaccacc ctgaattgac tctctt                                       26

SEQ ID NO: 1118        moltype = DNA  length = 1641
FEATURE                Location/Qualifiers
source                 1..1641
                       mol_type = other DNA
                       organism = synthetic construct
SEQUENCE: 1118
ttgacaatta atcatcggct cgtataatgt gtggaattgt gagcgctcac aattagctgt  60
gaccagaggt aaggaggtaa caaccatgcg agtgttgaag aaacatctta atcatgctgc  120
ggagggtttc taatggggac cattaacacg aagatctata aatacatgag catctggaaa  180
acaaaacctc tgtccgtgct cttgtctgaa gcaactgagg atgaaaaagg cctgaagcgc  240
actctgtcgg cccgttcact tgttgcgctg ggtgtcggtg ctattatcgg cgctggttta  300
ttctctctga ccggcatagc tgcggcagac aatgctggac cggcagtaac cctgagcttt  360
atcctggcct ccgttggttg cgcgttcgct ggcctgtgtt acgcagaatt tgcttctatg  420
attccagttg cgggtagcgc ctacacttat agttatgcta ccatgggcga gttcgtggcg  480
tggatcatcg gttgggatct ggtactcgaa tacgcattgg gcgcagctac tgttgccgtt  540
agctggtccc agtacgtgga caaattcttg caaaactacg gcatccatat tccgaactct  600
atcctccacg ggccgtggga taccaccccc ggtattatca atttaccgtc gatatttatc  660
atctgcctgc tgagcgtgct gctgattcgt ggtactaaag aatctgctct gatcaacaac  720
attctggtaa tcctgaaagt cacggttgtc atcgtgttca ttggcctggg ctgggggttc  780
atgaactccg caaaccacac gcccttatc ccggttaacg aaggtgaggc tctactgtct  840
tctggtgaaa tgagtttcct caactttttc agcagtgact actttggaca ctacggatgg  900
tccggtattc ttcgcggcgc tggtgtagta ttcttcgcat ttatcggctt cgacgcggtg  960
agcactgcgg cacaggaggc caaggatccg cagaaaggca tgccaatcgg tattctgggc  1020
tcactgatca tttgcaccgt tctgtacgtg cttttcgctt tcgttctgac cggtctggaa  1080
aactatctaa acttcaaagg tgacgcttct cctgtcacca ctgcatttgc caaaacaggc  1140
tatactttcc tgaatagcgg tctgacgatc gctatcatag cgggctacac atccgttatg  1200
ctggtaatgt tgatgggtca gtcccgtgtc ttttatagta tgtctgtgga tggcctgctt  1260
ccgaagtttt tctcgaccct gcataccaaa aacaggactc cgtacaaaac taatttgctg  1320
ttcatggttt tcgtaagcct gttcgctggc tttgttccgg tcagcgacct gggccatatg  1380
gtatccatcg gtaccctctt cgctttctgc ctggtgtgta tcggcgttat cgttatgcga  1440
aaaaccaacc cagacgccgt tcgcggtttt cgtgttcctt ttgtaccggt tttcccgatt  1500
atcggtgtag ttatttgtct ggttctaatg gcgggcctgc cgattgaatc ttgggaacgt  1560
ctggcgatct ggatgattct gggtgtcgtg atctacttct tctactctaa aaagaactct  1620
aaactgaata accccgaata a                                            1641

SEQ ID NO: 1119        moltype = DNA  length = 1766
FEATURE                Location/Qualifiers
source                 1..1766
                       mol_type = other DNA
                       organism = synthetic construct
```

-continued

```
SEQUENCE: 1119
ttgacaatta atcatcggct cgtataatgt gtggaattgt gagcgctcac aattaagtga  60
attgccaata acaattacta aggaggtttt ttatgtcccc gacggcgttt ccagcggccg  120
aaacagctac tgcccctgca actgccgtcg atcctgggcc agaactggac ggcggagatt  180
tcgcccttcc agagggcggg ctggatgacg atcgtcgctt acgtgcattg gacgcagttg  240
acgagtattt gacccgcaag cgcaagcatt tggttgggta ccaagctacc caggatatgg  300
acggaacggc cttggattta gcccgtttca tgccccacaa catcaacaac ctgggagatc  360
ctttccagtc gggtgggtat aaaccaaata cgaaagtcgt tgagcgtgcc gtactggact  420
actatgcaaa attgtggcac gcagaacgtc cacacgaccc agctgaccca gaaagctact  480
ggggttacat gttatcgatg ggctcaactg agggcaacat gtacgccctg tggaatgcac  540
gtgactacct gtcgggtaag gctttgattc agcctcccac ggcaccattt gacgctgttc  600
gctacgtgaa ggctgacccc gatcgccgca atcctaacgc acaccaccca gtcgcattct  660
actcggagga tacccactat tcttttgcta aagccgttgc ggtgctgggt gtcgaaactt  720
tccacgctgt gggtctggag aaatacgctg acgagtgccc cttggtggat ccagtaaccg  780
gccttcgtac ctggccgacc gaagttccat cgcgcccggg gccgtcgggt ttaagctggg  840
acggccctgg tgagattgat gttgatgcgc ttgcagtact ggtcgagttc ttcgcagcga  900
agggtcaccc cgtcttcgtc aaccttaact tggggtctac atttaaagga gcacatgatg  960
acgtacgtgc ggtatgtgaa cgcttattac caatcttcga gcgccatggc ttagtacaac  1020
gtgaagttgt atatgggagc tgtccccaaa ccggccgccc tttagtggat gtacgtcgcg  1080
gattttggat ccacgtagat ggggcacttg ggcggggta tgcccctttt ctgcgtcttg  1140
ccgccgaaga cccggaaggt tatggttgga cccctgaggc agaattacct gagttcgact  1200
tcggcttacg tttgccgacg gcggggcatg gagaagttga tatggttagc agcatcgcca  1260
tgagtggaca taagtgggca ggcgcgccgt ggccatgcgg catctatatg acgaaagtga  1320
aatatcagat tagtccaccg tcacagcccg attatattgg tgctcctgac acaacatttg  1380
ccggttcccg taacggcttt tcgccgttaa ttttgtggga tcatttatcg cgctactcgt  1440
accgcgacca ggtagagcgc atccgcgaag cacaggagct tgcagcatat ttggaacgcc  1500
gccttaccgc tatggagcgc gagctgggag tggaactttg gccagcccgc acaccgggtg  1560
ctgtaaccgt acgttttcgc aaaccctctg ctgagctggt tgcgaagtgg tccttgtcgt  1620
cgcaggatgt tttaatggtg ccgggtgatg aaactacgcg tcgtagttac gttcatgtgt  1680
tcgtgatgcc ttctgttgat cgtgcaaagt tagatgcgtt gctggcagaa ttggccgaag  1740
atcccgtcat cttgggtgcg ccttaa                                      1766

SEQ ID NO: 1120        moltype = DNA  length = 328
FEATURE                Location/Qualifiers
source                 1..328
                       mol_type = other DNA
                       organism = synthetic construct
SEQUENCE: 1120
aatgtgaatg gcacgattat gcgggatact tacaccaccg acggaatatg aaaatcaata  60
ttatcgacgg ctcagaagtg tctagattat ccgtggcgat ctgacatggg aattagccat  120
ggtccatatg aatatcctcc ttagttccta ttccgaagtt cctattctct agaaagtata  180
ggaacttcga agcagctcca gcctacacaa tcgctcaaga cgtgtaattc cggcgtttcg  240
acattaatcc tggcgatcgt ctttatgatc aaggcggtcg cggtcatcat cctttcgctg  300
gtactcacca tcaaaagtat taccgcca                                    328

SEQ ID NO: 1121        moltype = AA  length = 418
FEATURE                Location/Qualifiers
source                 1..418
                       mol_type = protein
                       organism = Escherichia coli
SEQUENCE: 1121
MSGLKQELGL AQGIGLLSTS LLGTGVFAVP ALAALVAGNN SLWAWPVLII LVFPIAIVFA  60
ILGRHYPSAG GVAHFVGMAF GSRLERVTGW LFLSVIPVGL PAALQIAAGF GQAMFGWHSG  120
QLLLAELGTL ALVWYIGTRG ASSSANLQTV IAGLIVALIV AIWWAGDIKP ANIPFPAPGN  180
IELTGLFAAL SVMFWCFVGL EAFAHLASEF KNPERDFPRA LMIGLLLAGL VYWGCTVVVL  240
HFDAYGEQMA AAASLPKIVV QLFGVGALWI ACVIGYLACF ASLNIYIQSF ARLVWSQAQH  300
NPDHYLARLS SRHIPNNALN AVLGCCVVST LVIHALEINL DALIIYANGI FIMIYLLCML  360
AGCKLLQGRY RLLAVVGGLL CVLLLAMVGW KSLYALIMLA GLWLFLPKRK TPENGITT    418

SEQ ID NO: 1122        moltype = DNA  length = 32
FEATURE                Location/Qualifiers
source                 1..32
                       mol_type = other DNA
                       organism = synthetic construct
SEQUENCE: 1122
attgccaata acaattacta aggaggtttt tt                               32
```